(12) United States Patent
Albrecht et al.

(10) Patent No.: US 10,035,801 B2
(45) Date of Patent: Jul. 31, 2018

(54) PYRAZOLO COMPOUNDS AND USES THEREOF

(71) Applicants: CONSTELLATION PHARMACEUTICALS, INC., Cambridge, MA (US); GENENTECH, INC., South San Francisco, CA (US)

(72) Inventors: Brian K. Albrecht, Cambridge, MA (US); Steven F. Bellon, Wellesley, MA (US); Victor S. Gehling, Somerville, MA (US); Jean-Christophe Harmange, Andover, MA (US); Kwong Wah Lai, Shanghai (CN); Jun Liang, South San Francisco, CA (US); Peter Dragovich, South San Francisco, CA (US); Daniel F. Ortwine, South San Francisco, CA (US); Sharada Labadie, South San Francisco, CA (US); Birong Zhang, South San Francisco, CA (US); James Richard Kiefer, South San Francisco, CA (US)

(73) Assignees: GENENTECH, INC., South San Francisco, CA (US); CONSTELLATION PHARMACEUTICALS INC., Cambridge, MA (US)

(*) Notice: Subject to any disclaimer, the term of this patent is extended or adjusted under 35 U.S.C. 154(b) by 93 days.

(21) Appl. No.: 14/775,405

(22) PCT Filed: Mar. 13, 2014

(86) PCT No.: PCT/CN2014/000262
§ 371 (c)(1),
(2) Date: Sep. 11, 2015

(87) PCT Pub. No.: WO2014/139326
PCT Pub. Date: Sep. 18, 2014

(65) Prior Publication Data
US 2016/0060267 A1 Mar. 3, 2016

Related U.S. Application Data

(60) Provisional application No. 61/778,759, filed on Mar. 13, 2013.

(51) Int. Cl.
| | |
|---|---|
| *C07D 487/04* | (2006.01) |
| *A61K 31/519* | (2006.01) |
| *A61K 45/06* | (2006.01) |
| *A61K 31/5377* | (2006.01) |
| *A61K 31/337* | (2006.01) |
| *A61K 31/517* | (2006.01) |
| *A61K 31/437* | (2006.01) |
| *C12N 9/99* | (2006.01) |
| *C07D 498/04* | (2006.01) |
| *C07D 487/14* | (2006.01) |

(52) U.S. Cl.
CPC ......... *C07D 487/04* (2013.01); *A61K 31/337* (2013.01); *A61K 31/437* (2013.01); *A61K 31/517* (2013.01); *A61K 31/519* (2013.01); *A61K 31/5377* (2013.01); *A61K 45/06* (2013.01); *C07D 487/14* (2013.01); *C07D 498/04* (2013.01); *C12N 9/99* (2013.01)

(58) Field of Classification Search
None
See application file for complete search history.

(56) References Cited

U.S. PATENT DOCUMENTS

| | | |
|---|---|---|
| 4,950,585 A | 8/1990 | Tachibana et al. |
| 4,992,442 A | 2/1991 | Tsujitani et al. |
| 6,096,490 A | 8/2000 | Tosaka et al. |
| 6,995,163 B2 | 2/2006 | Hibi et al. |
| 7,816,365 B2 | 10/2010 | Schiemann et al. |
| 2006/0178371 A1 | 8/2006 | Guzi et al. |
| 2012/0277224 A1 | 11/2012 | McCall et al. |
| 2014/0171432 A1 | 6/2014 | Kanouni et al. |
| 2014/0275092 A1 | 9/2014 | Albrecht et al. |
| 2016/0060267 A1 | 3/2016 | Albrecht et al. |

FOREIGN PATENT DOCUMENTS

| | | | |
|---|---|---|---|
| CN | 101573359 A | 11/2009 | |
| CN | 101627019 A | 1/2010 | |
| CN | 102241678 A | 11/2011 | |
| EP | 0297490 A1 | 1/1989 | |
| EP | 0369145 A2 * | 5/1990 | ........... C07D 487/14 |
| EP | 0976754 A1 | 2/2000 | |
| JP | 05255337 A | 10/1993 | |
| JP | 2000153671 A | 6/2000 | |

(Continued)

OTHER PUBLICATIONS

CAS Registry 1310145-35-7 published Jun. 23, 2011.*
CAS Registry 1310091-70-3 published Jun. 23, 2011.*
CAS Registry 1310091-59-8 published Jun. 23, 2011.*
CAS Registry 1310083-43-2 published Jun. 23, 2011.*
CAS Registry 1279890-78-6 published Apr. 14, 2011.*
CAS Registry 879588-57-5 published Apr. 7, 2006.*

(Continued)

*Primary Examiner* — Jeffrey S Lundgren
*Assistant Examiner* — Michael J Schmitt
(74) *Attorney, Agent, or Firm* — Viksnins Harris Padys Malen LLP

(57) ABSTRACT

Provided are compounds useful as inhibitors of one or more histone demethylases, such as KDM5. The invention also provides pharmaceutically acceptable compositions comprising compounds of the present invention and methods of using the present composition in the treatment of various disorders.

15 Claims, No Drawings

(56) References Cited

FOREIGN PATENT DOCUMENTS

| | | |
|---|---|---|
| JP | 2002326462 A | 11/2002 |
| JP | 2005008581 A | 1/2005 |
| JP | 2006045156 A | 2/2006 |
| WO | 7900733 A1 | 10/1979 |
| WO | 199808847 A1 | 3/1998 |
| WO | 2003101993 A1 | 12/2003 |
| WO | 2004017908 A2 | 3/2004 |
| WO | 2004022062 A1 | 3/2004 |
| WO | 2004022559 A1 | 3/2004 |
| WO | 2004022560 A1 | 3/2004 |
| WO | 2005103052 A1 | 11/2005 |
| WO | 2006068954 A2 | 6/2006 |
| WO | 2007044410 A1 | 4/2007 |
| WO | 2009076593 A1 | 6/2009 |
| WO | 2009086303 A2 | 7/2009 |
| WO | WO 2011135491 A1 * | 11/2011 ............ A01N 43/90 |
| WO | 2012041817 A1 | 4/2012 |
| WO | 2012149157 A2 | 11/2012 |
| WO | 2013174930 A2 | 11/2013 |
| WO | 2013174931 A1 | 11/2013 |
| WO | 2014066795 A1 | 5/2014 |
| WO | 2014009752 A1 | 8/2014 |
| WO | 2014144850 A1 | 9/2014 |
| WO | 2015035062 A1 | 3/2015 |

OTHER PUBLICATIONS

Deeb, et al., "Synthesis of substituted pyrazolo[1,5-a]pyrimidines", Chinese Journal of Chemistry 9(5), 474-480 (1991).

Eadsforth, et al., "Assessment of Pseudomonas aeruginosa N 5,N10-Methylenetetrahydrofolate Dehydrogenase Cyclohydrolase as a Potential Antibacterial Drug Target", PLoS One 7(5), 1-11 (2012).

Pandit, et al., "Studies on the Vilsmeier-Haack Reaction: Part V—Reaction of 2-Methyl-4-quinazolone Derivatives & a New Synthesis of Pyrazolo[5,1-b]quinazolones", Indian Journal of Chemistry 11, 532-537 (1973).

US Registry [Online], STN Search Report, Registry, Columbus, Ohio, 1-9 (2017).

Chemical Abstract, Activate Scientific GmbH, Database accession No. 1273577-70-0, XP002760082, 1 pg, (Apr. 1, 2011).

Chemical Abstract, Database accession No. 500310-82-7, XP002760084, 1 pg, (Mar. 24, 2003).

Chemical Abstract, Database accession No. 500694-98-4, XP002760083, 1 pg, (Mar. 26, 2003).

Lubbers, et al., "Design, Synthesis, and Structure-Activity Relationship Studies of ATP Analogues as DNA Gyrase Inhibitors", Bioorganic & Medicinal Chemistry Letters, vol. 10, No. 8, 821-826 (2000).

Nie, et al., "Structure-based design, synthesis, and study of pyrazolo [1,5-a][1,3,5]triazine derivatives as potent inhibitors of protein kinase CK2", Bioorganic & Medicinal Chemistry Letters, vol. 17, No. 15, 4191-4195 (2007).

Soliman, et al., "Synthesis of Some Novel Imidazopyrazole and Pyrazolopyrimidine Derivatives", Journal of Heterocyclic Chemistry, vol. 51, No. 5, 1476-1481 (2014).

Sun, et al., "Fragment-based approach to the design of 5-chlorouracil-linked-pyrazolo[1,5-a][1,3,5]triazines as thymidine phosphorylase inhibitors", European Journal of Medicinal Chemistry, Editions Scientifique Elsevier, Paris, Fr. vol. 70, 400-410 (2013).

U.S. Appl. No. 14/209,449, 2014-0275092.

Data for GSK J4 HCl supplied by BPS Bioscience, downloaded from the internet at http://bpsbioscience.com/gsk-j4-hcl, 2 pages (Dec. 30, 2016).

CA Registry, No. 736964-77-5, entered into the Registry File on Sep. 1, 2004, supplied by Vitas-M Chemical Library, 1 page.

Namiki, et al., Chemical Abstract vol. 129, No. 189339 (Abstract for WO 98/35968, Aug. 20, 1998), 2 pages (1998).

Vitas-M Laboratory, Source of Chemical Reagents for Research and Development, 2 pages retrieved from the Internet at http://www.vitasmlab.com/ Jul. 4, 2016.

CA Registry, No. 1087532-74-8, entered into the Registry File on Dec. 21, 2008, supplied by ChemBridge Corp. Chemical Library.

CA Registry, No. 1118787-65-7, entered into the Registry File Mar. 11, 2009, supplied by Enamine Chemical Library.

CA Registry, No. 693796-29-1, entered into the Registry File on Jun. 16, 2004, supplied by ChemBridge Corp. Chemical Library.

Chembridge, Screening Libraries: Key Facts, 2 pages retrieved from the Internet at http://www.chembridge.com/screening_libraries (Jan. 2, 2016).

Chemical Abstract, vol. 124, No. 146184 (Abstract for JP 07242670 Sep. 19, 1996) (1996).

Chemical Abstract, vol. 129, No. 164224 (Abstract for JP 05262774 Oct. 12, 1993) (1994).

Enaminestore, 1 page retrieved from the Internet at http://www.enamine.net/index.php?option=com_content&task=view&id=22 (Jan. 9, 2015).

Hamada, et al., "Design, Synthesis, Enzyme-Inhibitory Activity, and Effect on Human Cancer Cells of a Novel Series of Jumonji Domain-Containing Protein 2 Histone Demethylase Inhibitors", J. Med. Chem. 53, 5629-5638 (2010).

Lohse, et al., "Inhibitors of histone demethylases", Bioorganic & Medicinal Chemistry 19, 3625-3636 (2011).

Mukoyama, et al., English Translation of JP 2005-008581 (Jan. 2005).

Patent Cooperation Treaty, International Searching Authority, Search Report and Written Opinion for PCT/CN2014/000262, 19 pages, dated Jun. 13, 2014.

Rotili, et al., "Pan-Histone Demethylase Inhibitors Simultaneously Targeting Jumonji C and Lysine-Specific Demethylases Display High Anticancer Activities", Journal Med. Chem. 57, 42-55 (2014).

Sharma, et al., "A chromatin-mediated reversible drug-tolerant state in cancer cell subpopulations", Cell 141 (1), 69-80 (2010).

Spannhoff, et al., "The Emerging Therapeutic Potential of Histone Methyltransferase and Demethylase Inhibitors", Chem Med Chem 4, 1568-1582 (2009).

Suzuki, et al., "Lysine Demethylases Inhibitors", Journal of Med. Chem., 15 pages. (2011).

Wang, et al., "A small molecule modulates Jumonji histone demethylase activity and selectively inhibits cancer growth", Nature Communications 4, 1-13 (2013).

* cited by examiner

PYRAZOLO COMPOUNDS AND USES THEREOF

TECHNICAL FIELD OF THE INVENTION

The present invention relates to compounds useful as inhibitors of histone demethylases.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as neurodegenerative disorders, metabolic diseases, inflammation, and cancer. Thus, therapeutic agents directed against this emerging class of gene regulatory enzymes promise new approaches to the treatment of human diseases.

Additionally, the relatively rapid acquisition of resistance to cancer drugs remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways and epigenetic alterations. Rare, stochastic, resistance-conferring genetic alterations have been found within a tumor cell population selected during drug treatment. See Sharma et al., *Cell* 141(1):69-80 (2010). The KDM5/JARID1 family of histone demethylases was found to play a role in cancer resistance. The KDM5/JARID1 family of demethylases in humans contains four members, KDM5A, KDM5B, KDM5C and KDM5D. KDM5 family members contain five conserved domains: JmjN, ARID, JmjC, PHD and a $C_5HC_2$ zinc finger. Amino acid sequences of KDM5A, KDM5B, KDM5C and KDM5D are known and are publicly available, e.g., see UniProtKB/Swiss-Prot (see e.g., KDM5A (e.g., P29375-1 and P29375-2), KDM5B (e.g., Q9UGL1-1 and Q9UGL1-2), KDM5C (e.g., P41229-1, P41229-2, P41229-3 and P41229-4) and KDM5D (e.g., Q9BY66-1, Q9BY66-2 and Q9BY66-3). There is currently a need for compounds that inhibit of KDM5 demethylases for treating hyperproliferative diseases, preventing drug resistance, and/or for improving the efficacy of other cancer treatments (e.g. targeted therapies, chemotherapies, and radiotherapies.

SUMMARY OF THE INVENTION

It has now been found that compounds of this invention, and pharmaceutically acceptable compositions thereof, are effective as inhibitors of histone demethylases, including 2-oxoglutarate dependent enzymes such as Jumonji domain containing proteins, members of the H3K4 (histone 3 K4) demethylase family of proteins, and/or members of the JARID subfamily of histone demethylases. Such compounds are of formula I:

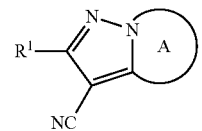

or a pharmaceutically acceptable salt thereof, wherein $R^1$ and Ring A are as defined and described herein.

Provided compounds, and pharmaceutically acceptable compositions thereof, are useful for treating a variety of diseases, disorders or conditions associated with abnormal cellular responses triggered by events mediated by histone demethylases such as 2-oxoglutarate dependent enzymes, Jumonji domain containing proteins, members of the H3K4 (histone 3 K4) demethylase family of proteins, and/or members of the JARID subfamily of enzymes. Such diseases, disorders, or conditions include those described herein.

Provided compounds are also useful for the study of histone demethylases, such as 2-oxoglutarate dependent enzymes, Jumonji domain containing proteins, members of the H3K4 (histone 3 K4) demethylase family of proteins, and/or members of the JARID subfamily of enzymes in biological and pathological phenomena, the study of intracellular signal transduction pathways mediated by such histone demethylases, and the comparative evaluation of new inhibitors of these and other histone demethylases.

Another aspect includes a composition, comprising a compound of formula (I) or a pharmaceutically acceptable salt thereof, and a pharmaceutically acceptable adjuvant, carrier, or vehicle.

Another aspect includes compounds and compositions for treating diseases, disorders or conditions associated with KDM5 activity. Such diseases, disorders, or conditions include those described herein.

Another aspect includes a compound of formula (I) and salts thereof.

Another aspect includes a pharmaceutical composition comprising a compound of formula (I) or a salt thereof.

Another aspect includes a method of treating a disease associated with KDM5 activity, comprising administering a therapeutically effective amount of a compound of formula (I), or a pharmaceutically acceptable salt thereof, to a patient in need thereof.

Another aspect includes the use of a compound of formula (I), or a pharmaceutically acceptable salt thereof, in therapy. Another aspect includes the use of a pharmaceutical composition comprising a compound of formula (I), or a pharmaceutically acceptable salt thereof, in therapy.

Another aspect includes the use of a compound of formula (I), or a pharmaceutically acceptable salt thereof, in treating a disease associated with KDM5 activity. Another aspect includes the use of a pharmaceutical composition comprising a compound of formula (I), or a pharmaceutically acceptable salt thereof, in treating a disease associated with KDM5 activity.

Another aspect includes the use of a compound of formula (I), or a pharmaceutically acceptable salt thereof, in the manufacture of a medicament for the treatment of a disease associated with KDM5 activity. Another aspect includes the use of a pharmaceutical composition comprising a compound of formula (I), or a pharmaceutically acceptable salt thereof, in the manufacture of a medicament for the treatment of a disease associated with KDM5 activity.

Another aspect includes a method of increasing the efficacy of a cancer treatment comprising a cancer therapy agent, comprising administering to a patient (a) an effective amount of a compound of formula (I) or a pharmaceutically acceptable salt thereof, and (b) an effective amount of the cancer therapy agent.

Another aspect includes a method of treating an individual with cancer who has an increased likelihood of developing resistance to a cancer therapy agent comprising administering to the individual (a) an effective amount of a compound of formula (I) or a pharmaceutically acceptable salt thereof, and (b) an effective amount of the cancer therapy agent.

Another aspect includes compounds for the study of histone demethylases, such as KDM5, the study of intracellular signal transduction pathways mediated by such histone demethylases, and the comparative evaluation of modulators of these demethylases.

Another aspect includes a process for preparing a compound of formula I or a salt thereof.

Another aspect includes a novel synthetic intermediate disclosed herein that is useful for preparing a compound of formula I or a salt thereof.

DETAILED DESCRIPTION OF CERTAIN EMBODIMENTS

General Description of Compounds of the Invention

In certain embodiments, the present invention provides a compound of formula I:

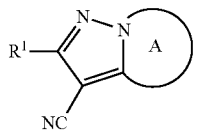

or a pharmaceutically acceptable salt thereof, wherein:

$R^1$ is —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$;

each R is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-3 heteroatoms independently selected from nitrogen, oxygen, or sulfur, a 4-7 membered saturated or partially unsaturated heterocyclic ring having 1-2 heteroatoms independently selected from nitrogen, oxygen, or sulfur, a 7-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

each R' is independently —R, —C(O)R, —CO$_2$R, or two R' on the same nitrogen are taken together with their intervening atoms to form a 4-7 membered heterocyclic ring having 1-2 heteroatoms independently selected from nitrogen, oxygen, and sulfur;

Ring A is

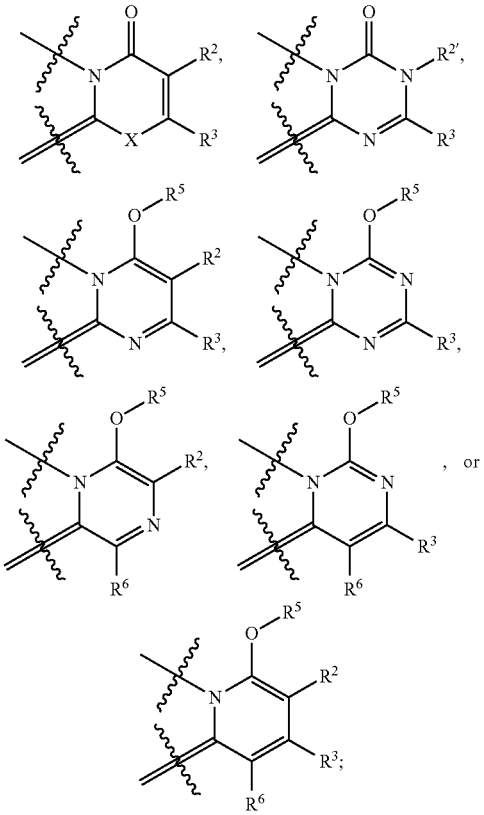

$R^2$ and $R^3$ are independently —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; or:

$R^2$ and $R^3$ are taken together with their intervening atoms to form an optionally substituted 5-7 membered partially unsaturated or aromatic fused ring having 0-4 heteroatoms independently selected from nitrogen, oxygen, and sulfur;

$R^{2'}$ is —R, —OR, —SR, —N(R')$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; or:

$R^{2'}$ and $R^3$ are taken together with their intervening atoms to form an optionally substituted 5-7 membered partially unsaturated or aromatic fused ring having 1-4 heteroatoms independently selected from nitrogen, oxygen, and sulfur;

X is —N(R$^4$)—, —O—, or —S—;

$R^4$ is —R, —C(O)R, —CO$_2$R, or —S(O)$_2$R; or:

$R^4$ and $R^3$ are taken together with their intervening atoms to form an optionally substituted 5-7 membered saturated, partially unsaturated, or aromatic fused ring having 1-4 heteroatoms independently selected from nitrogen, oxygen, and sulfur;

$R^5$ is R, —C(O)R, —CO$_2$R, —C(O)N(R')$_2$, —C(O)C(O)R, or —C(O)CH$_2$C(O)R; or:

$R^5$ and $R^2$ are taken together with their intervening atoms to form an optionally substituted 5-7 membered partially unsaturated or aromatic fused ring having 1-4 heteroatoms independently selected from nitrogen, oxygen, and sulfur; and $R^6$ is —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; or:

$R^6$ and $R^3$ are taken together with their intervening atoms to form an optionally substituted 5-7 membered partially unsaturated or aromatic fused ring having 0-4 heteroatoms independently selected from nitrogen, oxygen, and sulfur.

In some embodiments, the present invention provides a compound of formula I other than any one of the following:

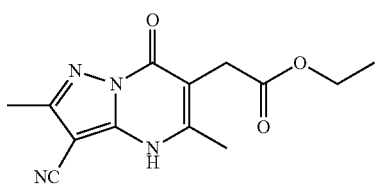 [SMILES: CCOC(=O)Cc1c(C)[nH]c2c(C#N)c(C)nn2c1=O]

I-1

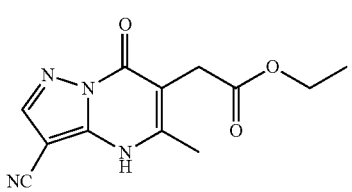 [SMILES: CCOC(=O)Cc1c(C)[nH]c2c(C#N)cnn2c1=O]

I-2

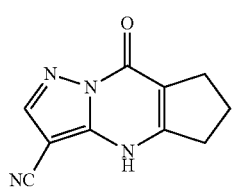 [SMILES: N#Cc1cnn2c(=O)c3c([nH]c12)CCC3]

I-3

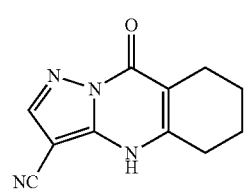 [SMILES: N#Cc1cnn2c(=O)c3c([nH]c12)CCCC3]

I-4

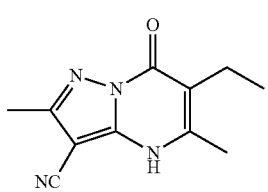 [SMILES: CCc1c(C)[nH]c2c(C#N)c(C)nn2c1=O]

I-5

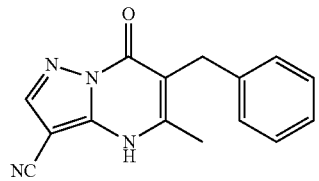 [SMILES: Cc1[nH]c2c(C#N)cnn2c(=O)c1Cc1ccccc1]

I-6

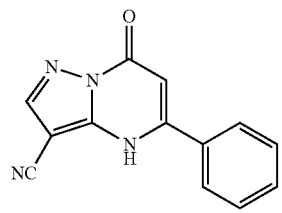 [SMILES: N#Cc1cnn2c(=O)cc(-c3ccccc3)[nH]c12]

I-7

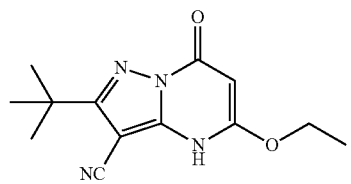 [SMILES: CCOc1cc(=O)n2nc(C(C)(C)C)c(C#N)c2[nH]1]

I-8

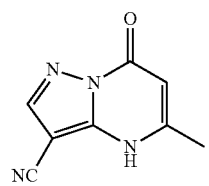

I-9

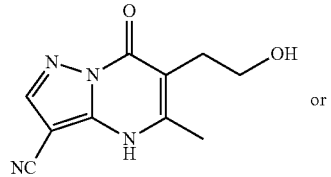

I-10 or

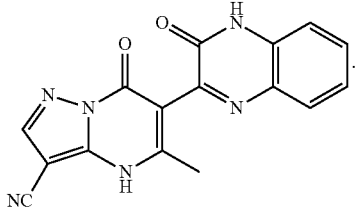

I-11

Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

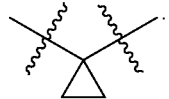

In other embodiments, a cycloalkylene group is a 1,2-cycloalkylene group or a 1,3-cycloalkylene group. Exemplary 1,2-cycloalkylene groups include

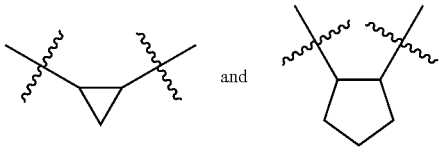

and

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$;

—CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}C(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}C(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}S(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include—R$^†$, —NR$^†_2$, —C(O)R$^†$, —C(O)OR$^†$, —C(O)C(O)R$^†$, —C(O)$CH_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits the target 2-oxoglutarated dependent enzyme with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of at least one 2-oxoglutarate dependent enzyme between a sample comprising a provided compound, or composition thereof, and at least one 2-oxoglutarate dependent enzyme, and an equivalent sample comprising at least one 2-oxoglutarate dependent enzyme, in the absence of said compound, or composition thereof.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, aralphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

Description of Exemplary Compounds

In certain embodiments, the present invention provides a compound of formula I,

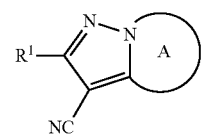

I or a pharmaceutically acceptable salt thereof, wherein $R^1$ and Ring A are as defined and described herein.

As defined generally above, $R^1$ is —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined above and described herein. In some embodiments, $R^1$ is hydrogen. In some embodiments, $R^1$ is optionally substituted $C_{1-6}$ aliphatic. In certain embodiments, $R^1$ is optionally substituted $C_{1-6}$ alkyl, $C_{1-6}$ alkenyl, or $C_{1-6}$ alkynyl. In certain embodiments, $R^1$ is optionally substituted $C_{1-6}$ alkyl. In certain embodiments, $R^1$ is methyl. In certain other embodiments, $R^1$ is ethyl or tert-butyl. In some embodiments, $R^1$ is —OR, —SR, or —N(R')$_2$. In certain embodiments, $R^1$ is —SR. In certain embodiments, $R^1$ is —NH$_2$. In certain embodiments, $R^1$ is —CN or —NO$_2$. In some embodiments, $R^1$ is halogen. In certain embodiments, $R^1$ is fluoro, chloro, bromo, or iodo. In certain embodiments, $R^1$ is fluoro. In some embodiments, $R^1$ is —C(O)R, —CO$_2$R, —C(O)SR, —C(O)N(R')$_2$, —C(O)C(O)R, or —C(O)CH$_2$C(O)R. In certain embodiments, $R^1$ is —C(S)OR or —C(S)N(R')$_2$. In other embodiments, $R^1$ is —S(O)R, —SO$_2$R, or —SO$_2$N(R')$_2$. In some embodiments, $R^1$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain embodiments, $R^1$ is —N(R')N(R')$_2$. In some embodiments, $R^1$ is —C=NN(R')$_2$, —C=NOR, —C(=N(R'))N(R')$_2$, —OC(O)R, or —OC(O)N(R')$_2$.

As defined generally above, Ring A is

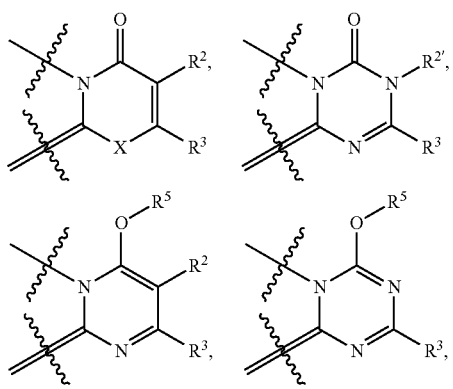

-continued

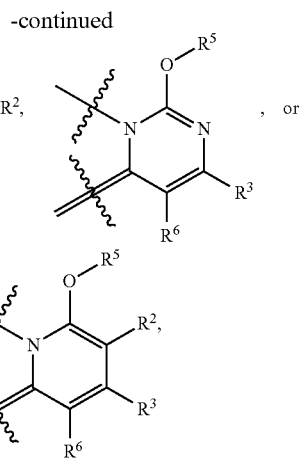

wherein X, R², R²′, R³, R⁵, and R⁶ are as defined above and described herein. Thus, in certain embodiments, a compound of the invention is of one of the following formulae:

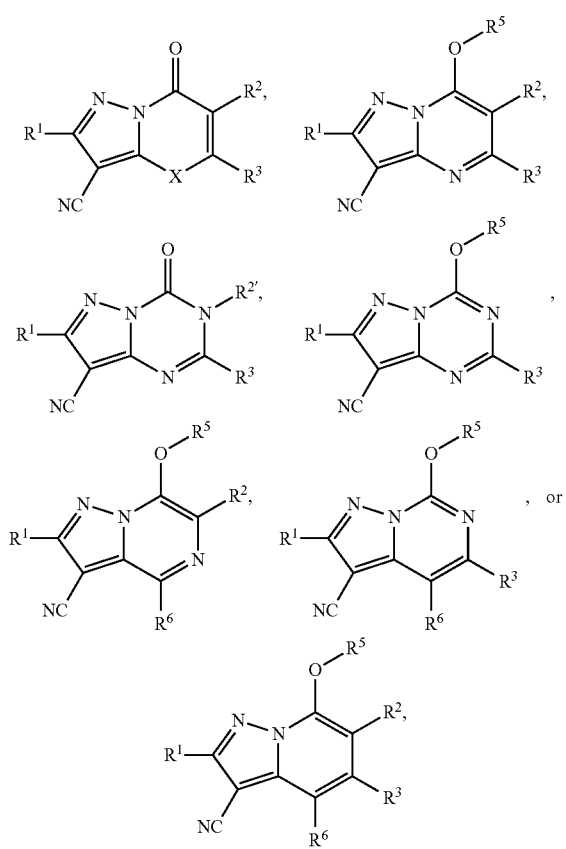

wherein R¹, R², R²′, R³, R⁵, R⁶, and X are as defined above and described herein.

As defined generally above, R² is —R, halogen, —OR, —SR, —N(R')₂, —CN, —NO₂, —C(O)R, —CO₂R, —C(O)N(R')₂, —C(O)SR, —C(O)C(O)R, —C(O)CH₂C(O)R, —C(S)N(R')₂, —C(S)OR, —S(O)R, —SO₂R, —SO₂N(R')₂, —N(R')C(O)R, —N(R')C(O)N(R')₂, —N(R')SO₂R, —N(R')SO₂N(R')₂, —N(R')N(R')₂, —N(R')C(=N(R'))N(R')₂, —C=NN(R')₂, —C=NOR, —C(=N(R'))N(R')₂, —OC(O)R, or —OC(O)N(R')₂, wherein R and R' are as defined above and described herein. In some embodiments, R² is hydrogen. In some embodiments, R² is optionally substituted C₁₋₆ aliphatic. In certain embodiments, R² is optionally substituted C₁₋₆ alkyl, C₁₋₆ alkenyl, or C₁₋₆ alkynyl. In certain embodiments, R² is optionally substituted C₁₋₆ alkyl. In certain embodiments, R² is ethyl. In certain other embodiments, R² is methyl, propyl, isopropyl, butyl, or isobutyl. In some embodiments, R² is C₁₋₆ alkyl substituted with an —OH or —OC₁₋₆alkyl group. In certain embodiments, R² is —CH₂CH₂OH or —CH₂CH₂OCH₃. In some embodiments, R² is cycloalkyl. In certain embodiments, R² is cyclopropyl, cyclobutyl, cyclopentyl, or cyclohexyl. In some embodiments, R² is optionally substituted C₁₋₆ alkenyl. In certain embodiments, R² is allyl. In some embodiments, R² is optionally substituted C₁₋₆ alkynyl. In certain embodiments, R² is 2-propynyl. In some embodiments, R² is optionally substituted benzyl. In certain embodiments, R² is unsubstituted benzyl. In certain other embodiments, R² is substituted benzyl. In some embodiments, R² is C₁₋₆ alkyl substituted with an ester group. In certain embodiments, R² is —CH₂CO₂C₁₋₆alkyl or —CH₂CO₂aryl. In certain embodiments, R² is —CH₂CO₂CH₂CH₃. In some embodiments, R² is —OR, —SR, or —N(R')₂. In certain embodiments, R² is —CN or —NO₂. In some embodiments, R² is halogen. In certain embodiments, R² is fluoro, chloro, bromo, or iodo. In some embodiments, R² is —C(O)R, —CO₂R, —C(O)SR, —C(O)N(R')₂, —C(O)C(O)R, or —C(O)CH₂C(O)R. In certain embodiments, R² is —C(S)OR or —C(S)N(R')₂. In other embodiments, R² is —S(O)R, —SO₂R, or —SO₂N(R')₂. In some embodiments, R² is —N(R')C(O)R, —N(R')C(O)N(R')₂, —N(R')SO₂R, —N(R')SO₂N(R')₂, —N(R')N(R')₂, or —N(R')C(=N(R'))N(R')₂. In some embodiments, R² is —C=NN(R')₂, —C=NOR, —C(=N(R'))N(R')₂, —OC(O)R, or —OC(O)N(R')₂.

As defined generally above, R²′ is —R, —OR, —SR, —N(R')₂, —C(O)R, —CO₂R, —C(O)N(R')₂, —C(O)SR, —C(O)C(O)R, —C(O)CH₂C(O)R, —C(S)N(R')₂, —C(S)OR, —S(O)R, —SO₂R, —SO₂N(R')₂, —N(R')C(O)R, —N(R')C(O)N(R')₂, —N(R')SO₂R, —N(R')SO₂N(R')₂, —N(R')N(R')₂, —N(R')C(=N(R'))N(R')₂, —C=NN(R')₂, —C=NOR, —C(=N(R'))N(R')₂, —OC(O)R, or —OC(O)N(R')₂, wherein R and R' are as defined above and described herein. In some embodiments, R²′ is hydrogen. In some embodiments, R²′ is optionally substituted C₁₋₆ aliphatic. In certain embodiments, R²′ is optionally substituted C₁₋₆ alkyl, C₁₋₆ alkenyl, or C₁₋₆ alkynyl. In certain embodiments, R²′ is optionally substituted C₁₋₆ alkyl. In certain embodiments, R²′ is ethyl. In certain other embodiments, R²′ is methyl, propyl, isopropyl, butyl, or isobutyl. In some embodiments, R²′ is C₁₋₆ alkyl substituted with an —OH or —OC₁₋₆alkyl group. In certain embodiments, R²′ is —CH₂CH₂OH or —CH₂CH₂OCH₃. In some embodiments, R²′ is cycloalkyl. In certain embodiments, R²′ is cyclopropyl, cyclobutyl, cyclopentyl, or cyclohexyl. In some embodiments, R²′ is optionally substituted C₁₋₆ alkenyl. In certain embodiments, R²′ is allyl. In some embodiments, R²′ is optionally substituted C₁₋₆ alkynyl. In certain embodiments, R²′ is 2-propynyl. In some embodiments, R²′ is optionally substituted benzyl. In certain embodiments, R²′ is unsubstituted benzyl. In certain other embodiments, R²′ is substituted benzyl. In some embodiments, R²′ is C₁₋₆ alkyl substituted with an ester group. In certain embodiments, R²′ is —CH₂CO₂C₁₋₆alkyl or —CH₂CO₂aryl. In certain embodiments, R²′ is —CH₂CO₂CH₂CH₃. In some embodiments, R²′ is —OR, —SR, or —N(R')₂. In some embodiments, R²′ is —C(O)R, —CO₂R, —C(O)SR, —C(O)N(R')₂, —C(O)C(O)R, or —C(O)CH$_2$C(O)R. In certain embodiments, R$^{2'}$ is —C(S) OR or —C(S)N(R')$_2$. In other embodiments, R$^{2'}$ is —S(O)R, —SO$_2$R, or —SO$_2$N(R')$_2$. In some embodiments, R$^{2'}$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In some embodiments, R$^{2'}$ is —C=NN(R')$_2$, —C=NOR, —C(=N(R'))N(R')$_2$, —OC(O)R, or —OC(O)N(R')$_2$.

As defined generally above, R$^3$ is —R, halogen, —OR, —SR, —N(R')$_2$, —CN, —NO$_2$, —C(O)R, —CO$_2$R, —C(O)N(R')$_2$, —C(O)C(O)R, —C(O)CH$_2$C(O)R, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —C=NN(R')$_2$, —C=NOR, —OC(O)R, or —OC(O)N(R')$_2$, wherein R and R' are as defined above and described herein. In some embodiments, R$^3$ is hydrogen. In some embodiments, R$^3$ is optionally substituted C$_{1-6}$ aliphatic. In certain embodiments, R$^3$ is optionally substituted C$_{1-6}$ alkyl, C$_{1-6}$ alkenyl, or C$_{1-6}$ alkynyl. In certain embodiments, R$^3$ is optionally substituted C$_{1-6}$ alkyl. In certain embodiments, R$^3$ is methyl. In certain other embodiments, R$^3$ is ethyl, propyl, isopropyl, butyl, or isobutyl. In certain embodiments, R$^3$ is —CF$_3$. In some embodiments, R$^3$ is C$_{1-6}$ alkyl substituted with an —OH or —OC$_{1-6}$alkyl group. In certain embodiments, R$^3$ is —CH$_2$OH, —CH$_2$CH$_2$OH, —CH$_2$CH$_2$CH$_2$OH, —CH$_2$OCH$_2$CH$_3$, —CH$_2$OCH$_3$, —CH$_2$CH$_2$CH$_2$OCH$_3$, —CH(OH)CH$_3$, or —CH$_2$CH$_2$OCH$_3$. In some embodiments, R$^3$ is C$_{1-6}$ alkyl substituted with an —NHC$_{1-6}$alkyl or —N(C$_{1-6}$alkyl)$_2$ group. In certain embodiments, R$^3$ is —CH$_2$NHC$_{1-6}$alkyl. In certain embodiments, R$^3$ is —CH$_2$NHCH$_3$. In some embodiments, R$^3$ is C$_{1-6}$ alkyl substituted with an aryl, heteroaryl, carbocyclyl, or heterocyclyl ring. In some embodiments, R$^3$ is optionally substituted benzyl. In certain embodiments, R$^3$ is unsubstituted benzyl. In certain other embodiments, R$^3$ is substituted benzyl. In certain embodiments, R$^3$ is —C(R°)$_2$Ph. In certain embodiments, R$^3$ is —C(R°)$_2$Ph, wherein R° is hydrogen or methyl. In certain embodiments, R$^3$ is trifluoromethylbenzyl. In certain embodiments, R$^3$ is —C(R°)$_2$(heteroaryl). In certain embodiments, R$^3$ is —C(R°)$_2$(heteroaryl), wherein the heteroaryl is pyridyl, pyrimidyl, pyrazinyl, pyridazinyl, triazinyl, pyridinonyl, pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl. In certain embodiments, R$^3$ is —CH$_2$(heteroaryl), wherein the heteroaryl is pyridyl, pyrimidyl, pyrazinyl, pyridazinyl, triazinyl, pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl. In certain embodiments, R$^3$ is —C(R°)$_2$(carbocyclyl). In certain embodiments, R$^3$ is —C(R°)$_2$(carbocyclyl), wherein the carbocyclyl is cyclopropyl, cyclobutyl, cyclopentyl, cyclohexyl, or cycloheptyl. In certain embodiments, R$^3$ is —CH$_2$(carbocyclyl), wherein the carbocyclyl is cyclopropyl, cyclobutyl, cyclopentyl, cyclohexyl, or cycloheptyl. In certain embodiments, R$^3$ is —C(R°)$_2$(heterocyclyl). In certain embodiments, R$^3$ is —C(R°)$_2$(heterocyclyl), wherein the heterocyclyl is tetrahydrofuranyl, tetrahydrothienyl, tetrahydropyranyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In certain embodiments, R$^3$ is —CH$_2$(heterocyclyl), wherein the heterocyclyl is tetrahydrofuranyl, tetrahydrothienyl, tetrahydropyranyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. In some embodiments, R$^3$ is optionally substituted C$_{1-6}$ alkenyl. In certain embodiments, R$^3$ is allyl. In some embodiments, R$^3$ is optionally substituted C$_{1-6}$ alkynyl. In certain embodiments, R$^3$ is propargyl. In some embodiments, R$^3$ is an optionally substituted aryl or heteroaryl group. In certain embodiments, R$^3$ is phenyl. In certain embodiments, R$^3$ is substituted phenyl. In certain embodiments, R$^3$ is toluyl. In certain other embodiments, R$^3$ is a 5-6 membered heteroaryl ring having 1-3 heteroatoms selected from nitrogen, oxygen, and sulfur. In certain embodiments, R$^3$ is pyridyl, pyrimidyl, pyrazinyl, pyridazinyl, triazinyl, pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl. In some embodiments, R$^3$ is —OR, —SR, or —N(R')$_2$. In some embodiments, R$^3$ is halogen. In certain embodiments, R$^3$ is fluoro, chloro, bromo, or iodo. In some embodiments, R$^3$ is —C(O)R, —CO$_2$R, —C(O)N(R')$_2$, —C(O)SR, —C(O)C(O)R, or —C(O)CH$_2$C(O)R. In certain embodiments, R$^3$ is optionally substituted —CO$_2$C$_{1-6}$alkyl. In certain embodiments, R$^3$ is —CO$_2$Et or —CO$_2$Bn. In certain embodiments, R$^3$ is —CONHC$_{1-6}$alkyl. In certain embodiments, R$^3$ is —CONHCH$_3$ or —CONHCH$_2$CH$_3$. In certain embodiments, R$^3$ is —C(S)OR or —C(S)N(R')$_2$. In other embodiments, R$^3$ is —S(O)R, —SO$_2$R, or —SO$_2$N(R')$_2$. In some embodiments, R$^3$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In some embodiments, R$^3$ is —C=NN(R')$_2$, —C=NOR, —C(=N(R'))N(R')$_2$, —OC(O)R, or —OC(O)N(R')$_2$.

In some embodiments, R$^2$ and R$^3$ are taken together with their intervening atoms to form an optionally substituted 5-7 membered partially unsaturated or aromatic fused ring having 0-4 heteroatoms independently selected from nitrogen, oxygen, and sulfur. In certain embodiments, R$^2$ and R$^3$ are taken together with their intervening atoms to form a 5-membered fused ring. In certain embodiments, R$^2$ and R$^3$ are taken together with their intervening atoms to form a fused cyclopentene ring. In certain embodiments, R$^2$ and R$^3$ are taken together with their intervening atoms to form a 6-membered fused ring. In certain embodiments, R$^2$ and R$^3$ are taken together with their intervening atoms to form a fused cyclohexene ring. In certain embodiments, R$^2$ and R$^3$ are taken together with their intervening atoms to form a fused benzene ring. In certain embodiments, R$^2$ and R$^3$ are taken together with their intervening atoms to form a 5-7 membered partially unsaturated fused ring having 1-4 heteroatoms independently selected from nitrogen, oxygen, and sulfur. In certain embodiments, R$^2$ and R$^3$ are taken together with their intervening atoms to form a 5-7 membered aromatic fused ring having 1-4 heteroatoms independently selected from nitrogen, oxygen, and sulfur.

In some embodiments, R$^{2'}$ and R$^3$ are taken together with their intervening atoms to form an optionally substituted 5-7 membered partially unsaturated or aromatic fused ring having 1-4 heteroatoms independently selected from nitrogen, oxygen, and sulfur. In certain embodiments, R$^{2'}$ and R$^3$ are taken together with their intervening atoms to form a 5-membered fused ring. In certain embodiments, R$^{2'}$ and R$^3$ are taken together with their intervening atoms to form a 6-membered fused ring. In certain embodiments, R$^{2'}$ and R$^3$ are taken together with their intervening atoms to form a fused pyridine ring. In certain embodiments, R$^{2'}$ and R$^3$ are taken together with their intervening atoms to form a 5-7 membered partially unsaturated fused ring having 1-4 heteroatoms independently selected from nitrogen, oxygen, and sulfur. In certain embodiments, $R^{2'}$ and $R^3$ are taken together with their intervening atoms to form a 5-7 membered aromatic fused ring having 1-4 heteroatoms independently selected from nitrogen, oxygen, and sulfur.

As defined generally above, X is —N($R^4$)—, —O—, or —S—, wherein $R^4$ is as defined above and described herein. In certain embodiments, X is —O— or —S—. In some embodiments, X is —N($R^4$)—. In certain embodiments, X is —NH—. In certain embodiments, X is —N(CH$_3$)—.

As defined generally above, $R^4$ is —R, —C(O)R, —CO$_2$R, or —S(O)$_2$R, or $R^4$ and $R^3$ are taken together with their intervening atoms to form an optionally substituted 5-7 membered saturated, partially unsaturated, or aromatic fused ring having 1-4 heteroatoms independently selected from nitrogen, oxygen, and sulfur. In certain embodiments, $R^4$ is hydrogen. In some embodiments, $R^4$ is optionally substituted C$_{1-6}$ alkyl. In certain embodiments, $R^4$ is optionally substituted C$_{1-3}$ alkyl. In certain embodiments, $R^4$ is methyl. In certain embodiments, $R^4$ is substituted C$_{1-6}$ alkyl. In certain embodiments, $R^4$ is benzyl. In certain embodiments, $R^4$ is —CH$_2$CH$_2$N(CH$_3$)$_2$. In some embodiments, $R^4$ is aryl or heteroaryl. In certain embodiments, $R^4$ is phenyl. In some embodiments, $R^4$ is —C(O)R, —CO$_2$R, or —S(O)$_2$R.

In some embodiments, $R^4$ and $R^3$ are taken together with their intervening atoms to form an optionally substituted 5-7 membered saturated, partially unsaturated, or aromatic fused ring having 1-4 heteroatoms independently selected from nitrogen, oxygen, and sulfur. In certain embodiments, $R^4$ and $R^3$ are taken together with their intervening atoms to form a 5-membered fused ring. In certain embodiments, $R^4$ and $R^3$ are taken together with their intervening atoms to form a fused pyrrolidine ring. In certain embodiments, $R^4$ and $R^3$ are taken together with their intervening atoms to form a 6-membered fused ring. In certain embodiments, $R^4$ and $R^3$ are taken together with their intervening atoms to form a fused piperidine ring. In certain embodiments, $R^4$ and $R^3$ are taken together with their intervening atoms to form a 5-7 membered partially unsaturated fused ring having 1-4 heteroatoms independently selected from nitrogen, oxygen, and sulfur. In certain embodiments, $R^4$ and $R^3$ are taken together with their intervening atoms to form a 5-7 membered aromatic fused ring having 1-4 heteroatoms independently selected from nitrogen, oxygen, and sulfur.

As defined generally above, $R^5$ is R, —C(O)R, —CO$_2$R, —C(O)N(R')$_2$, —C(O)C(O)R, or —C(O)CH$_2$C(O)R, or $R^5$ and $R^2$ are taken together with their intervening atoms to form an optionally substituted 5-7 membered partially unsaturated or aromatic fused ring having 1-4 heteroatoms independently selected from nitrogen, oxygen, and sulfur. In some embodiments, $R^5$ is hydrogen. In some embodiments, $R^5$ is optionally substituted C$_{1-6}$ alkyl. In certain embodiments, $R^5$ is methyl. In certain embodiments, $R^5$ is substituted C$_{1-6}$ alkyl. In certain embodiments, $R^5$ is C$_{1-6}$ alkyl substituted with an —OH or —OC$_{1-6}$alkyl group. In certain embodiments, $R^5$ is —CH$_2$CH$_2$OCH$_3$. In some embodiments, $R^4$ is —C(O)R, —CO$_2$R, —C(O)N(R')$_2$, —C(O)C(O)R, or —C(O)CH$_2$C(O)R.

As defined generally above, $R^6$ is —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined above and described herein. In some embodiments, $R^6$ is hydrogen. In some embodiments, $R^6$ is optionally substituted C$_{1-6}$ aliphatic. In certain embodiments, $R^6$ is optionally substituted C$_{1-6}$ alkyl, C$_{1-6}$ alkenyl, or C$_{1-6}$ alkynyl. In certain embodiments, $R^6$ is optionally substituted C$_{1-6}$ alkyl. In certain embodiments, $R^6$ is ethyl. In certain other embodiments, $R^6$ is methyl, propyl, isopropyl, butyl, or isobutyl. In some embodiments, $R^6$ is C$_{1-6}$ alkyl substituted with an —OH or —OC$_{1-6}$alkyl group. In certain embodiments, $R^6$ is —CH$_2$CH$_2$OH or —CH$_2$CH$_2$OCH$_3$. In some embodiments, $R^6$ is cycloalkyl. In certain embodiments, $R^6$ is cyclopropyl, cyclobutyl, cyclopentyl, or cyclohexyl. In some embodiments, $R^6$ is optionally substituted C$_{1-6}$ alkenyl. In certain embodiments, $R^6$ is allyl. In some embodiments, $R^6$ is optionally substituted C$_{1-6}$ alkynyl. In certain embodiments, $R^6$ is 2-propynyl. In some embodiments, $R^6$ is optionally substituted benzyl. In certain embodiments, $R^6$ is unsubstituted benzyl. In certain other embodiments, $R^6$ is substituted benzyl. In some embodiments, $R^6$ is C$_{1-6}$ alkyl substituted with an ester group. In certain embodiments, $R^6$ is —CH$_2$CO$_2$C$_{1-6}$alkyl or —CH$_2$CO$_2$aryl. In certain embodiments, $R^6$ is —CH$_2$CO$_2$CH$_2$CH$_3$. In some embodiments, $R^6$ is —OR, —SR, or —N(R')$_2$. In certain embodiments, $R^6$ is —CN or —NO$_2$. In some embodiments, $R^6$ is halogen. In certain embodiments, $R^6$ is fluoro, chloro, bromo, or iodo. In some embodiments, $R^6$ is —C(O)R, —CO$_2$R, —C(O)SR, —C(O)N(R')$_2$, —C(O)C(O)R, or —C(O)CH$_2$C(O)R. In certain embodiments, $R^6$ is —C(S)OR or —C(S)N(R')$_2$. In other embodiments, $R^6$ is —S(O)R, —SO$_2$R, or —SO$_2$N(R')$_2$. In some embodiments, $R^6$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In some embodiments, $R^6$ is —C=NN(R')$_2$, —C=NOR, —C(=N(R'))N(R')$_2$, —OC(O)R, or —OC(O)N(R')$_2$.

In some embodiments, $R^6$ and $R^3$ are taken together with their intervening atoms to form an optionally substituted 5-7 membered partially unsaturated or aromatic fused ring having 0-4 heteroatoms independently selected from nitrogen, oxygen, and sulfur. In certain embodiments, $R^6$ and $R^3$ are taken together with their intervening atoms to form a 5-membered fused ring. In certain embodiments, $R^6$ and $R^3$ are taken together with their intervening atoms to form a fused cyclopentene ring. In certain embodiments, $R^6$ and $R^3$ are taken together with their intervening atoms to form a 6-membered fused ring. In certain embodiments, $R^6$ and $R^3$ are taken together with their intervening atoms to form a fused cyclohexene ring. In certain embodiments, $R^6$ and $R^3$ are taken together with their intervening atoms to form a fused benzene ring. In certain embodiments, $R^6$ and $R^3$ are taken together with their intervening atoms to form a 5-7 membered partially unsaturated fused ring having 1-4 heteroatoms independently selected from nitrogen, oxygen, and sulfur. In certain embodiments, $R^6$ and $R^3$ are taken together with their intervening atoms to form a 5-7 membered aromatic fused ring having 1-4 heteroatoms independently selected from nitrogen, oxygen, and sulfur.

As defined generally above, each R is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-3 heteroatoms independently selected from nitrogen, oxygen, or sulfur, a 4-7 membered saturated or partially unsaturated heterocyclic ring having 1-2 heteroatoms independently selected from nitrogen, oxygen, or sulfur, a 7-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, R is hydrogen. In some embodiments, R is optionally substituted $C_{1-6}$ alkyl, alkenyl, or alkynyl. In certain embodiments, R is optionally substituted $C_{1-6}$ alkyl. In certain embodiments, R is unsubstituted $C_{1-6}$ alkyl. In certain embodiments, R is substituted $C_{1-6}$ alkyl. In certain embodiments, R is methyl, ethyl, propyl, butyl, isopropyl, isobutyl, allyl, or benzyl.

In some embodiments, R is a 3-7 membered saturated or partially unsaturated carbocyclic ring. In certain embodiments, R is a 3-4 membered saturated carbocyclic ring. In other embodiments, R is a 5-7 membered saturated or partially unsaturated carbocyclic ring. In certain embodiments, R is cyclopropyl, cyclobutyl, cyclopentyl, cyclopentenyl, cyclohexyl, cyclohexenyl, cycloheptyl, or cycloheptenyl.

In some embodiments, R is a 4-7 membered saturated or partially unsaturated heterocyclic ring having 1-2 heteroatoms independently selected from nitrogen, oxygen, or sulfur. In certain embodiments, R is a 4-7 membered saturated heterocyclic ring. In other embodiments, R is a 5-7 membered partially unsaturated heterocyclic ring. In certain embodiments, R is tetrahydrofuranyl, tetrahydrothienyl, tetrahydropyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, R is an 8-10 membered bicyclic saturated or partially unsaturated carbocylic ring or a 7-10 membered bicyclic saturated or partially unsaturated heterocyclic ring having 1-4 heteroatoms independently selected from nitrogen, oxygen, or sulfur. In certain embodiments, R is decahydronaphthyl, tetrahydronaphthyl, or decalin. In certain other embodiments, R is tetrahydroquinolinyl, tetrahydroisoquinolinyl, or decahydroquinolinyl. In some embodiments, R is a heterocyclyl ring is fused to an aryl or heteroaryl ring. In certain embodiments, R is indolinyl, 3H-indolyl, chromanyl, phenanthridinyl, 2-azabicyclo[2.2.1]heptanyl, octahydroindolyl, or tetrahydroquinolinyl.

In some embodiments, R is phenyl or a 5-6 membered heteroaryl ring having 1-3 heteroatoms independently selected from nitrogen, oxygen, or sulfur. In certain embodiments, R is phenyl. In certain other embodiments, R is a 5-membered heteroaryl ring having 1-3 heteroatoms selected from nitrogen, oxygen, or sulfur. In yet other embodiments, R is a 6-membered heteroaryl ring having 1-3 nitrogens. In certain embodiments, R is phenyl, pyridyl, pyrimidyl, pyrazinyl, pyridazinyl, or triazinyl. In certain other embodiments, R is pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl.

In some embodiments, R is bicyclic aromatic ring. In certain embodiments, R is naphthyl. In other embodiments, R is an 8-10 membered bicyclic heteroaryl ring having 1-4 heteroatoms independently selected from nitrogen, oxygen, or sulfur. In certain embodiments, R is quinolinyl, quinoxalinyl, quinazolinyl, pyridopyrazinyl, or pyridopyrimidyl. In certain other embodiments, R is indolyl, benzimidazolyl, benzothiazolyl, benzofuranyl, benzotriazolyl, benzoxazolyl, benzothiophenyl, indazolyl, imidazopyridyl, imidazopyrimidyl, imidazopyrazinyl, imidazopyridazinyl, pyrazolopyridyl, pyrazolopyrimidyl, pyrazolopyrazinyl, pyrazolopyridazinyl, pyrrolothiazolyl, imidazothiazolyl, thiazolopyridyl, thiazolopyrimidyl, thiazolopypyrazinyl, thiazolopyridazinyl, oxazolopyridyl, oxazolopyrimidyl, oxazolopyrazinyl, or oxazolopyridazinyl.

As defined generally above, each R' is independently —R, —C(O)R, —CO$_2$R, or two R' on the same nitrogen are taken together with the intervening nitrogen to form a 4-7 membered heterocyclic ring having 1-2 heteroatoms independently selected from nitrogen, oxygen, and sulfur. In certain embodiments, R' is R as defined and described above. In certain embodiments, R' is —C(O)R or —CO$_2$R. In some embodiments, two R' on the same nitrogen are taken together with their intervening atoms to form a 4-7 membered heterocyclic ring having 1-2 heteroatoms independently selected from nitrogen, oxygen, and sulfur. In certain embodiments, two R' on the same nitrogen are taken together with their intervening atoms to form an azetidine, pyrrolidine, piperidine, morpholine, piperazine, homopiperidine, or homopiperazine ring.

According to one aspect, a provided compound is of formula II:

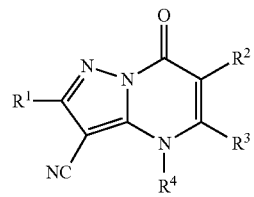

II or a pharmaceutically acceptable salt thereof, wherein $R^1$, $R^2$, $R^3$, and $R^4$ are as defined and described herein. In certain embodiments, a compound of formula II has one of the following formulae:

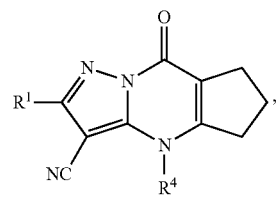

II-a

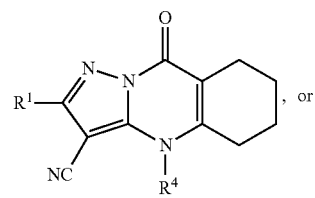

II-b

, or

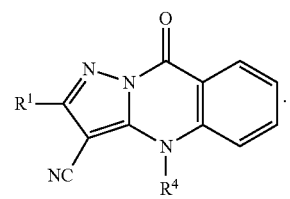

II-c

.

According to another aspect, a provided compound is of formula III:

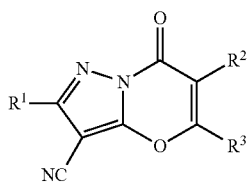

III or a pharmaceutically acceptable salt thereof, wherein $R^1$, $R^2$, $R^3$, and $R^4$ are as defined and described herein. In certain embodiments, a compound of formula II has one of the following formulae:

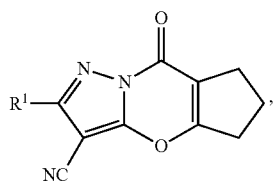

III-a

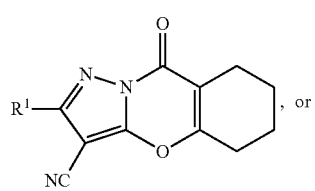

III-b, or

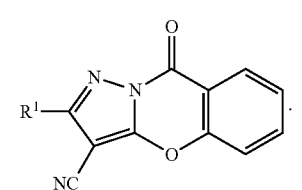

III-c

According to another aspect, a provided compound is of formula IV:

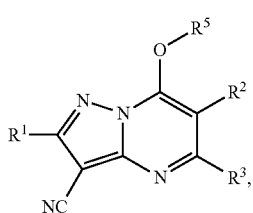

IV or a pharmaceutically acceptable salt thereof, wherein $R^1$, $R^2$, $R^3$, and $R^5$ are as defined and described herein. In certain embodiments, $R^5$ is optionally substituted $C_{1-6}$ aliphatic. In certain embodiments, $R^5$ is methyl. In some embodiments, $R^5$ is optionally substituted $C_{1-6}$ alkyl. In certain embodiments, $R^5$ is substituted $C_{1-6}$ alkyl. In certain embodiments, $R^5$ is $C_{1-6}$ alkyl substituted with —OH or —OC$_{1-6}$alkyl. In certain embodiments, $R^5$ is —CH$_2$CH$_2$OMe.

According to another aspect, a provided compound is of formula V:

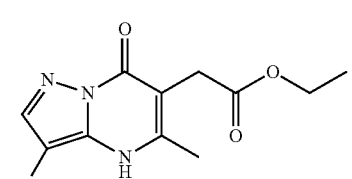

V or a pharmaceutically acceptable salt thereof, wherein $R^1$, $R^{2'}$, and $R^3$ are as defined and described herein.

Exemplary compounds of formula I are set forth in Table 1 below.

TABLE 1

Exemplary Compounds of Formula I

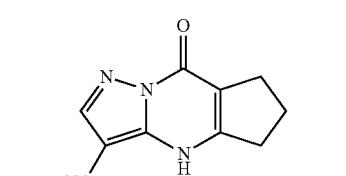

I-1

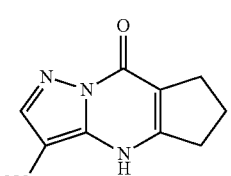

I-2

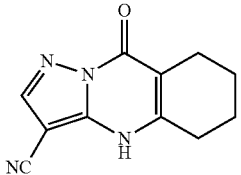

I-3

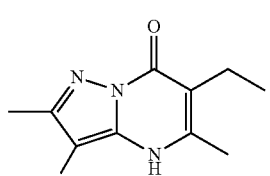

I-4

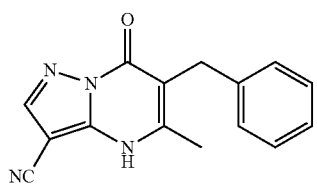

I-5

I-6

TABLE 1-continued
Exemplary Compounds of Formula I
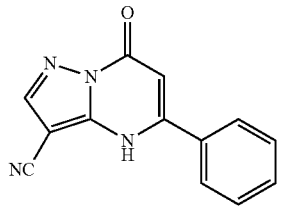

TABLE 1-continued
Exemplary Compounds of Formula I
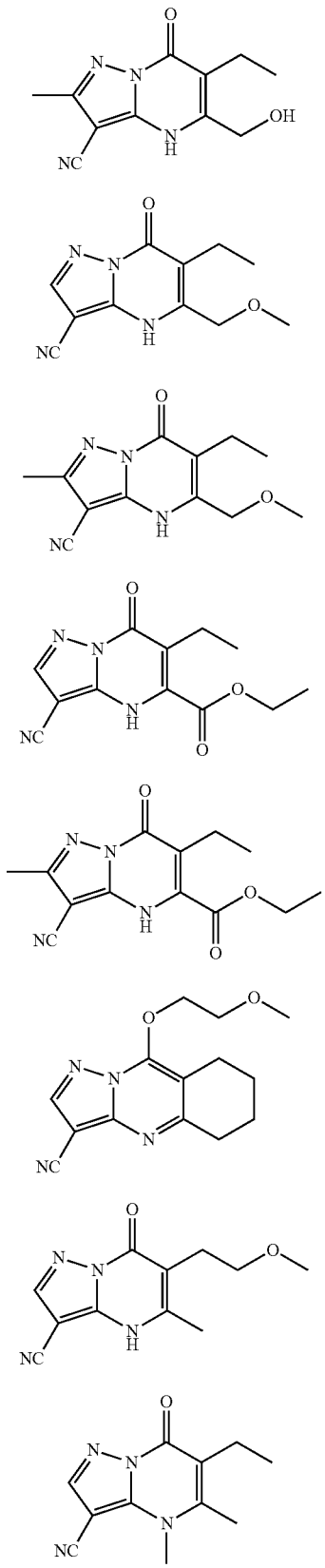
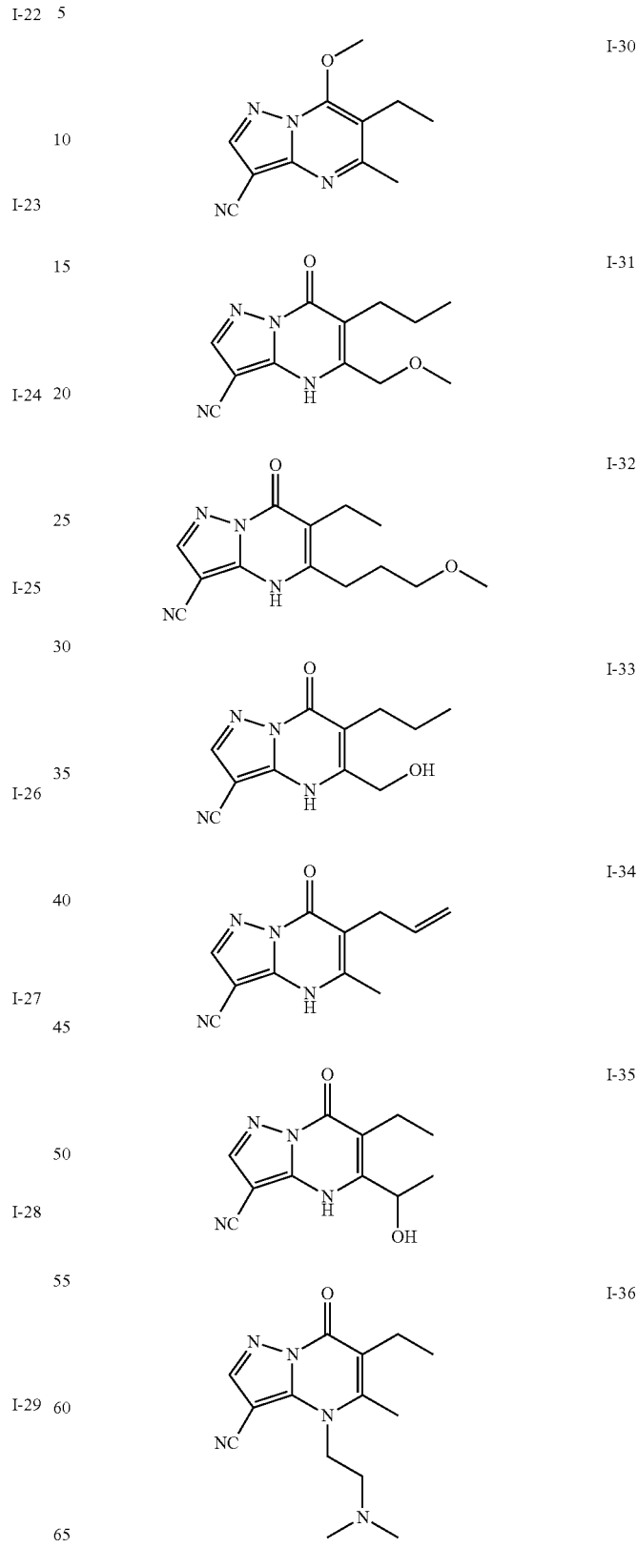

TABLE 1-continued
Exemplary Compounds of Formula I
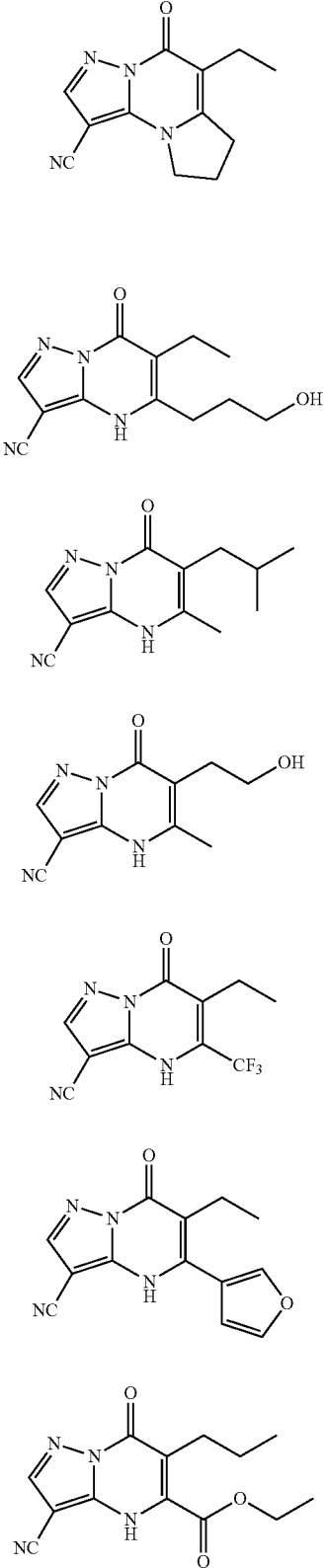
I-37
I-38
I-39
I-40
I-41
I-42
I-43
TABLE 1-continued
Exemplary Compounds of Formula I
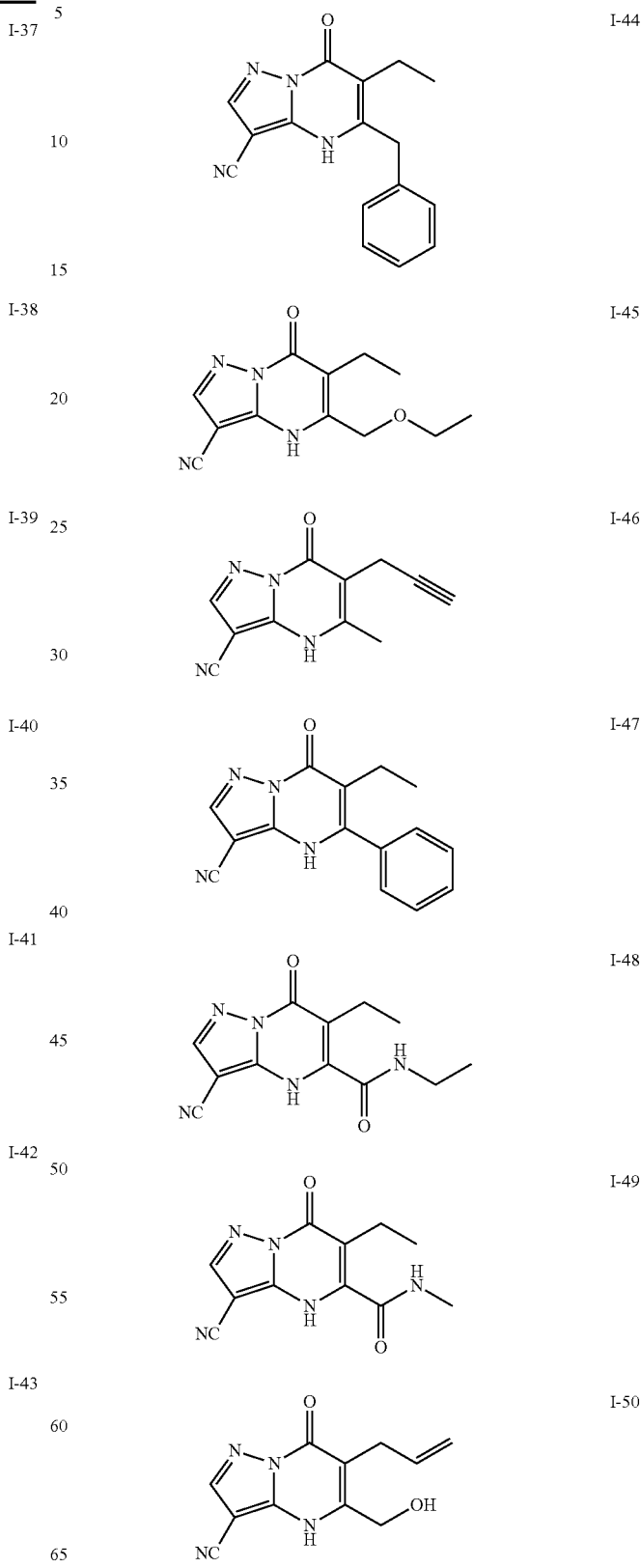
I-44
I-45
I-46
I-47
I-48
I-49
I-50

TABLE 1-continued
Exemplary Compounds of Formula I
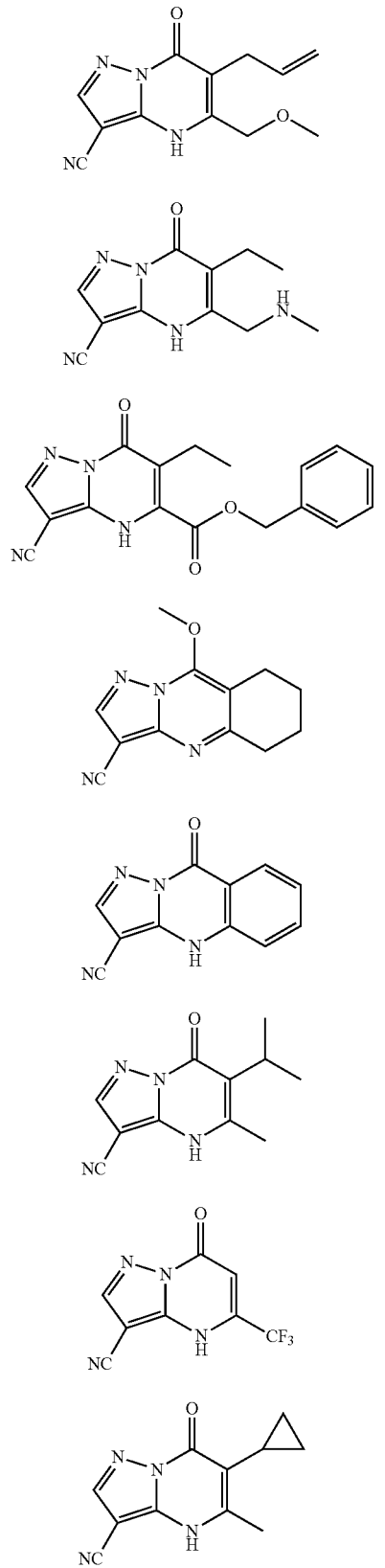
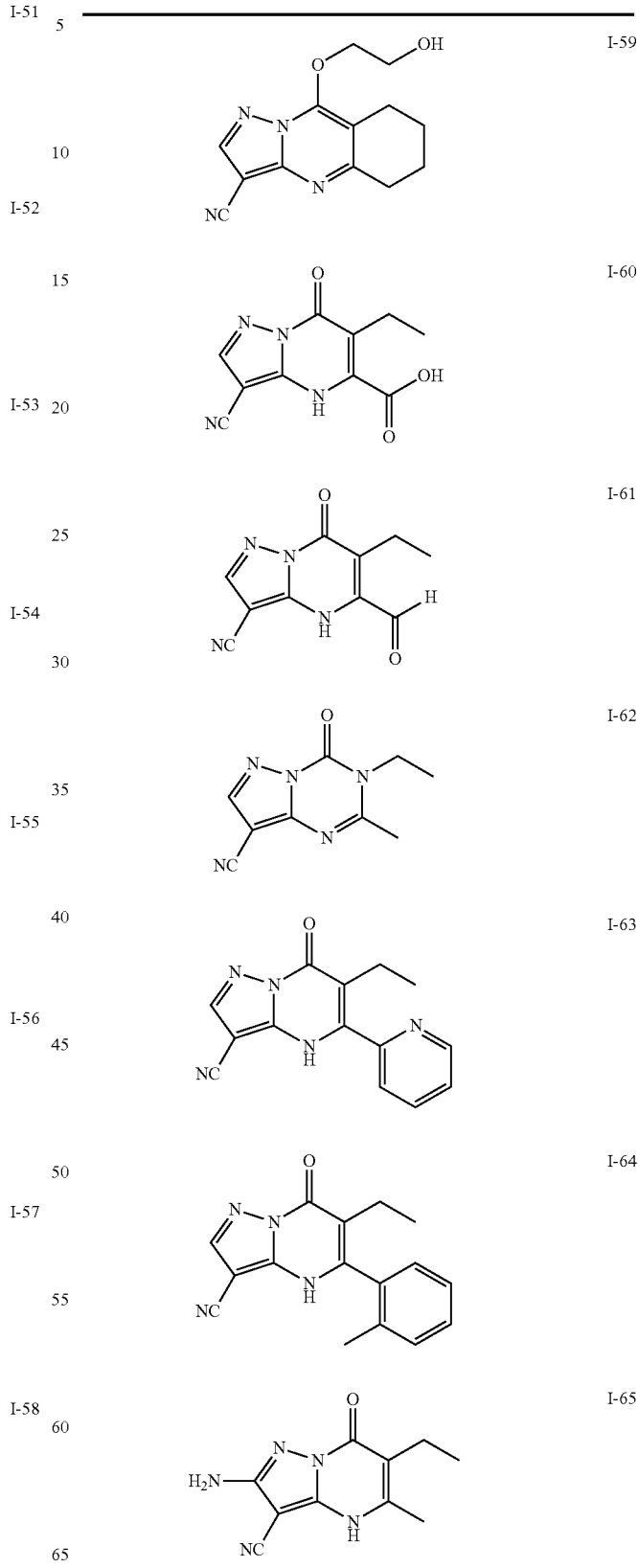

TABLE 1-continued

Exemplary Compounds of Formula I

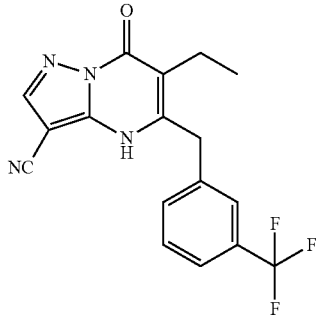 [SMILES: CCc1c(Cc2cccc(C(F)(F)F)c2)[nH]c2c(C#N)cnn2c1=O]
I-66

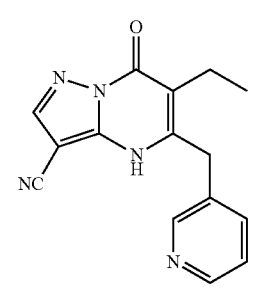 [SMILES: CCc1c(Cc2cccnc2)[nH]c2c(C#N)cnn2c1=O]
I-67

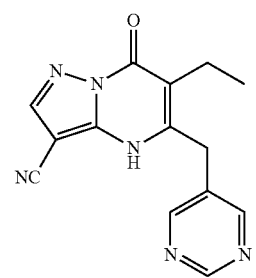
I-68

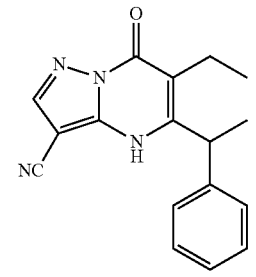
I-69

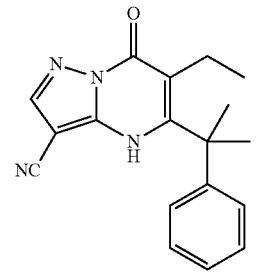 [SMILES: CCc1c(C(C)(C)c2ccccc2)[nH]c2c(C#N)cnn2c1=O]
I-70

TABLE 1-continued

Exemplary Compounds of Formula I

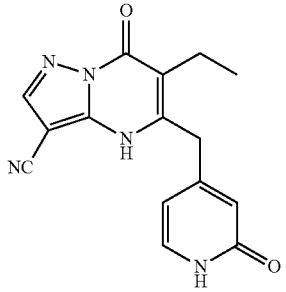 [SMILES: CCc1c(Cc2cc[nH]c(=O)c2)[nH]c2c(C#N)cnn2c1=O]
I-71

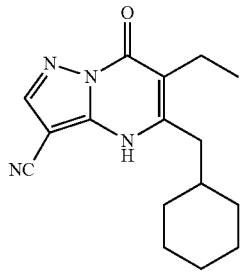 [SMILES: CCc1c(CC2CCCCC2)[nH]c2c(C#N)cnn2c1=O]
I-72

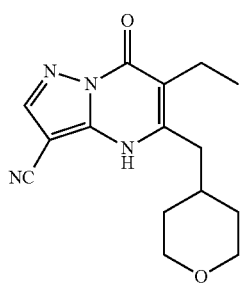 [SMILES: CCc1c(CC2CCOCC2)[nH]c2c(C#N)cnn2c1=O]
I-73

In certain embodiments, the present invention provides any compound depicted in Table 1, above, or a pharmaceutically acceptable salt thereof.

In some embodiments, the present invention provides a compound set forth in Table 1-a below.

TABLE 1-a

Compounds of Formula I

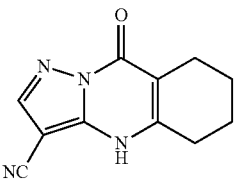 [SMILES: N#Cc1cnn2c(=O)c3c([nH]c12)CCCC3]
I-4

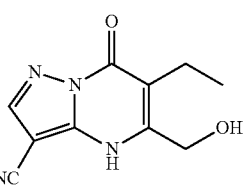
I-21

TABLE 1-a-continued

Compounds of Formula I

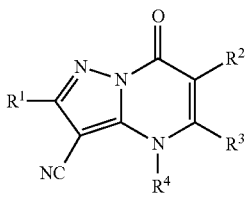

In certain embodiments, the present invention provides any compound depicted in Table 1-a, above, or a pharmaceutically acceptable salt thereof.

In certain embodiments, the present invention provides a compound of formula (I), which is a compound of formula (II):

or a salt thereof, wherein:
$R^1$ is H, $C_{1-6}$alkyl, trifluoromethyl, 3-6 membered carbocyclyl, 6 membered aryl, 3-6 membered heterocyclyl, 5-6 membered heteroaryl, halo, —$OR^f$, —$SR^f$, —$N(R^f)_2$, —CN, or —$NO_2$, wherein said alkyl, carbocyclyl, aryl, heteroaryl, and heterocyclyl are optionally substituted with one or more groups independently selected from oxo, halo, $C_{1-3}$alkoxy and $C_{1-3}$alkyl;

$R^2$ and $R^3$ are each independently H, $C_{1-12}$alkyl, $C_{2-12}$alkenyl, $C_{2-12}$alkynyl, carbocyclyl, aryl, heterocyclyl, heteroaryl, halo, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2R^a$, —$N(R^a)SO_2N(R^a)_2$, —$N(R^a)N(R^a)_2$, —$N(R^a)C(=N(R^a))N(R^a)_2$, —$C(=N)N(R^a)_2$, —$C=NOR^a$, —$C(=N(R^a))N(R^a)_2$, —$OC(O)R^a$, or —$OC(O)N(R^a)_2$, wherein each $C_{1-12}$alkyl, $C_{2-12}$alkenyl, $C_{2-12}$alkynyl, carbocyclyl, aryl, heteroaryl, and heterocyclyl of $R^2$ and $R^3$ is independently optionally substituted with one or more groups $R^x$; and wherein $R^2$ and $R^3$ are not each H; or $R^2$ and $R^3$ taken together with the atoms to which they are attached form a 4, 5, 6, 7, or 8 membered carbocyclyl or aryl, which carbocyclyl or aryl is optionally substituted with one or more groups $R^x$;

$R^4$ is H, $C_{1-12}$alkyl, $C_{2-12}$alkenyl, $C_{2-12}$alkynyl, carbocyclyl, aryl, heteroaryl, and heterocyclyl, wherein each $C_{1-12}$alkyl, $C_{2-12}$alkenyl, $C_{2-12}$alkynyl, carbocyclyl, aryl, heteroaryl, and heterocyclyl is optionally substituted with one or more groups independently selected from oxo, $C_{1-12}$ alkyl, $C_{1-12}$haloalkyl, carbocyclyl, aryl, heterocyclyl, heteroaryl, halo, —CN, —$NO_2$, —$NR^mR^m$, —$OR^m$, —$C(=O)OR^m$, and —$OC(=O)R^m$; or $R^4$ and $R^3$ taken together with the atoms to which they are attached form a heterocyclyl;

each $R^a$ is independently selected from H, $C_{1-6}$alkyl, $C_{2-6}$alkenyl, $C_{2-6}$alkynyl, carbocyclyl, aryl, heteroaryl, and heterocyclyl, wherein each $C_{1-6}$alkyl, $C_{3-6}$alkenyl, $C_{3-6}$alkynyl, carbocyclyl, aryl, heteroaryl, and heterocyclyl is optionally substituted with one or more groups $R^x$;

each $R^f$ is independently selected from H, $C_{1-3}$alkyl, trifluoromethyl, 3-6 membered carbocyclyl, 6 membered aryl, 3-6 membered heterocyclyl, and 5-6 membered heteroaryl, or two $R^f$ groups together with the nitrogen to which they are attached form a 3-6 membered heterocycle;

each $R^g$ is independently selected from H, $C_{1-6}$alkyl, $C_{2-6}$alkenyl, $C_{2-6}$alkynyl, $C_{3-8}$carbocyclyl, aryl, heteroaryl, and heterocyclyl, wherein each $C_{1-6}$alkyl, $C_{3-6}$alkenyl, $C_{3-6}$alkynyl, $C_{3-8}$carbocyclyl, aryl, heteroaryl, and heterocyclyl is optionally substituted with one or more groups $R^x$; or two $R^g$ groups together with the nitrogen to which they are attached form a 3-6 membered heterocycle or a 5-6 membered heteroaryl;

each $R^m$ is independently selected from H, $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, and benzyl, wherein any $C_{1-6}$alkyl, $C_{2-6}$alkenyl, $C_{2-6}$alkynyl, $C_{1-6}$ haloalkyl, carbocyclyl, $C_{1-6}$ alkanoyl, phenyl, or benzyl is optionally substituted with one or more groups independently selected from halo, —CN, —$NO_2$, —$NR^yR^z$, and —$OR^w$; or two $R^m$ groups together with the nitrogen to which they are attached form a 3-6 membered heterocycle;

each $R^v$ is independently hydrogen, $C_{1-6}$alkyl, $C_{2-6}$alkenyl, $C_{2-6}$alkynyl, carbocyclyl, aryl, heteroaryl, and heterocyclyl, wherein each $C_{1-6}$alkyl, $C_{2-6}$alkenyl, $C_{2-6}$alkynyl, carbocyclyl, aryl, heteroaryl, and heterocyclyl is optionally substituted with one or more groups independently selected from oxo, halo, amino, hydroxyl, aryl, carbocyclyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from H, $C_{1-4}$alkyl, $C_{1-4}$alkanoyl, phenyl, benzyl, and phenethyl;

each $R^x$ is independently selected from oxo, $C_{1-6}$alkyl, $C_{2-6}$alkenyl, $C_{2-6}$alkynyl, carbocyclyl, aryl, heteroaryl, heterocycle, —F, —Cl, —Br, —I, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —S(O)$_2$—N(R$^v$)$_2$, —N(R$^v$)—C(O)—R$^v$, —N(R$^v$)—S(O)—R$^v$, —N(R$^v$)—S(O)$_2$—R$^v$, —N(R$^v$)—S(O)—N(R$^v$)$_2$, and —N(R$^v$)—S(O)$_2$—N(R$^v$)$_2$, wherein any $C_{1-6}$alkyl, $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —S(O)$_2$—N(R$^v$)$_2$, —N(R$^v$)—C(O)—R$^v$, —N(R$^v$)—C(O)—OR$^v$, —N(R$^v$)—S(O)—R$^v$, —N(R$^v$)—S(O)$_2$—R$^v$, and $C_{1-6}$alkyl that is optionally substituted with one or more groups independently selected from oxo and halo;

each $R^y$ and $R^z$ is independently selected from H, $C_{1-4}$alkyl, $C_{1-4}$alkanoyl, $C_{1-4}$alkoxycarbonyl, phenyl, benzyl, and phenethyl, or $R^y$ and $R^z$ together with the nitrogen to which they are attached form a heterocyclyl;

each $R^{xa}$ is independently selected from aryl, heteroaryl, heterocycle, and carbocycle, wherein any aryl, heteroaryl, heterocycle, and carbocycle is optionally substituted with one or more groups independently selected from $C_{1-6}$alkyl, $C_{2-6}$alkenyl, $C_{2-6}$alkynyl, —F, —Cl, —Br, —I, —NO$_2$, —N(R$^v$)$_2$, —CN, carbocycle, aryl, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —O—C(O)—O—R$^v$, —C(O)—R$^v$, —C(O)—O—R$^v$, —S(O)—R$^v$, —S(O)$_2$—R$^v$, —O—C(O)—N(R$^v$)$_2$, —N(R$^v$)—C(O)—OR$^v$, —N(R$^v$)—C(O)—N(R$^v$)$_2$, —S(O)$_2$—N(R$^v$)$_2$, —N(R$^v$)—C(O)—R$^v$, —N(R$^v$)—S(O)—R$^v$, —N(R$^v$)—S(O)$_2$—R$^v$, and —N(R$^v$)—S(O)—N(R$^v$)$_2$, wherein any $C_{1-6}$alkyl, $C_{2-6}$alkenyl, and $C_{2-6}$alkynyl is optionally substituted with one or more groups independently selected from oxo, halo, —NO$_2$, —N(R$^v$)$_2$, —CN, —C(O)—N(R$^v$)$_2$, —S(O)—N(R$^v$)$_2$, —S(O)$_2$—N(R$^v$)$_2$, —O—R$^v$, —S—R$^v$, —O—C(O)—R$^v$, —C(O)—R$^v$, —C(O)—O—R$^v$, —S(O)—R$^v$, —S(O)$_2$—R$^v$, —C(O)—N(R$^v$)$_2$, —S(O)$_2$—N(R$^v$)$_2$, —N(R$^v$)—C(O)—R$^v$, —N(R$^v$)—S(O)—R$^v$, and —N(R$^v$)—S(O)$_2$—R$^v$.

In certain embodiments, $R^1$ is H, $C_{1-6}$alkyl, trifluoromethyl, 3-6 membered carbocyclyl, 6 membered aryl, 3-6 membered heterocyclyl, 5-6 membered heteroaryl, halo, —OR$^f$, —SR$^f$, —N(R$^f$)$_2$, —CN, or —NO$_2$, wherein said alkyl, carbocyclyl, aryl, heteroaryl, and heterocyclyl are optionally substituted with one or more groups independently selected from oxo, halo, $C_{1-3}$alkoxy and $C_{1-3}$alkyl.

In certain embodiments, $R^1$ is H, methyl, or ethyl.

In certain embodiments, $R^1$ is H.

In certain embodiments, $R^2$ is H.

In certain embodiments, $R^2$ is $C_{1-12}$alkyl, $C_{2-12}$alkenyl, $C_{2-12}$alkynyl, carbocyclyl, aryl, heterocyclyl, heteroaryl, halo, —OR$^a$, —SR$^a$, —N(R$^a$)$_2$, —CN, —NO$_2$, —C(O)R$^a$, —CO$_2$R$^a$, —C(O)N(R$^a$)$_2$, —C(O)SR$^a$, —C(O)C(O)R$^a$, —C(O)CH$_2$C(O)R$^a$, —C(S)N(R$^a$)$_2$, —C(S)OR$^a$, —S(O)R$^a$, —SO$_2$R$^a$, —SO$_2$N(R$^a$)$_2$, —N(R$^a$)C(O)R$^a$, —N(R$^a$)C(O)N(R$^a$)$_2$, —N(R$^a$)SO$_2$R$^a$, —N(R$^a$)SO$_2$N(R$^a$)$_2$, —N(R$^a$)N(R$^a$)$_2$, —N(R$^a$)C(=N(R$^a$))N(R$^a$)$_2$, —C(=N)N(R$^a$)$_2$, —C=NOR$^a$, —C(=N(R$^a$))N(R$^a$)$_2$, —OC(O)R$^a$, or —OC(O)N(R$^a$)$_2$, wherein each $C_{1-12}$alkyl, $C_{2-12}$alkenyl, $C_{2-12}$alkynyl, carbocyclyl, aryl, heteroaryl, and heterocyclyl of $R^2$ is independently optionally substituted with one or more groups $R^x$.

In certain embodiments, $R^2$ and $R^3$ taken together with the atoms to which they are attached form a 4, 5, 6, 7, or 8 membered carbocyclyl or aryl, which carbocyclyl or aryl is optionally substituted with one or more groups $R^x$.

In certain embodiments, $R^2$ is H, $C_{1-6}$alkyl, $C_{2-12}$alkenyl, $C_{2-12}$alkynyl, carbocyclyl, aryl, heteroaryl, halo, —CN, —SR$^a$, —N(R$^a$)$_2$, and —CO$_2$R$^a$, wherein any $C_{1-6}$alkyl, carbocyclyl and aryl is optionally substituted with one or more groups independently selected from $C_{1-3}$alkyl, carbocyclyl, halo, —CN, —N(R$^v$)—C(O)—R$^v$, and —O—R$^v$.

In certain embodiments, $R^2$ is H, isopropyl, ethyl, tert-butyl, 2,2-difluoroethyl, cyclobutyl, 2-propyn-1-yl, bromo, chloro, 2-furyl, vinyl, phenyl, 2-chlorophenylthio, 2-fluoroethyl, 2-propenyl, 1-methylvinylcyclopropyl, 4-pyridyl, 2-buten-1-yl, iodo, 1-methyl-2-propyn-1-yl, 1-methylprop-1-yl, 1-(cyclopropyl)ethyl, methoxycarbonyl, 2-butynyl, 2-hydroxy-1-methylethyl, 4-(methylcarbonylamino)butyl, 3-(methylcarbonylamino)propyl, 4-aminobutyl, 1-methyl-2-propenyl, 1-methylcyclobutyl, propyl, 2-methoxyethyl, and 2-methylpropyl.

In certain embodiments, $R^3$ is H.

In certain embodiments, $R^3$ is $C_{1-12}$alkyl, $C_{2-12}$alkenyl, $C_{2-12}$alkynyl, carbocyclyl, aryl, heterocyclyl, heteroaryl, halo, —OR$^a$, —SR$^a$, —N(R$^a$)$_2$, —CN, —NO$_2$, —C(O)R$^a$, —CO$_2$R$^a$, —C(O)N(R$^a$)$_2$, —C(O)SR$^a$, —C(O)C(O)R$^a$, —C(O)CH$_2$C(O)R$^a$, —C(S)N(R$^a$)$_2$, —C(S)OR$^a$, —S(O)R$^a$, —SO$_2$R$^a$, —SO$_2$N(R$^a$)$_2$, —N(R$^a$)C(O)R$^a$, —N(R$^a$)C(O)N(R$^a$)$_2$, —N(R$^a$)SO$_2$R$^a$, —N(R$^a$)SO$_2$N(R$^a$)$_2$, —N(R$^a$)N(R$^a$)$_2$, —N(R$^a$)C(=N(R$^a$))N(R$^a$)$_2$, —C(=N)N(R$^a$)$_2$, —C=NOR$^a$, —C(=N(R$^a$))N(R$^a$)$_2$, —OC(O)R$^a$, or —OC(O)N(R$^a$)$_2$, wherein each $C_{1-12}$alkyl, $C_{2-12}$alkenyl, $C_{2-12}$alkynyl, carbocyclyl, aryl, heteroaryl, and heterocyclyl of $R^3$ is independently optionally substituted with one or more groups $R^x$.

In certain embodiments, $R^3$ is H, $C_{1-12}$alkyl, $C_{2-12}$alkenyl, $C_{2-12}$alkynyl, aryl, heterocyclyl, heteroaryl, halo, —OR$^a$, —N(R$^a$)$_2$, —C(O)R$^a$, —CO$_2$R$^a$, —C(O)N(R$^a$)$_2$, or —N(R$^a$)C(O)R$^a$, wherein each $C_{1-12}$alkyl, $C_{2-12}$alkenyl, $C_{2-12}$alkynyl, aryl, heteroaryl, and heterocyclyl of $R^3$ is independently optionally substituted with one or more groups $R^x$.

In certain embodiments, $R^3$ is H, methyl, chloro, bromo, carboxy, formyl, aminocarbonyl, furan-3-yl, phenyl, benzyl, phenethyl, phenoxy, 1H-pyrazol-4-yl, 1-(cyclopropylmethyl)-1H-pyrazol-4-yl, 1-(1-methylcyclopropyl)-1H-pyrazol-4-yl, 5-fluoro-1H-pyrazol-4-yl, 1-(2-phenylpropan-2-yl)-1H-pyrazol-4-yl, 1-(pyridin-3-yl)-1H-pyrazol-4-yl, 1-(pyridin-4-yl)-1H-pyrazol-4-yl, 1-(pyridin-2-yl)-1H-pyrazol-4-yl, 1-[1-(N-methylaminocarbonyl)-1,1-dimethylmethyl]-1H-pyrazol-4-yl, 5-fluoro-1-isopropyl-1H-pyrazol-4-yl, 1-(cyclopropylmethyl)-1H-pyrazol-5-yl, 1-(cyclopropylmethyl)-1H-pyrazol-3-yl, 1-(tetrahydro-2H-thiopyran-4-yl)-1H-pyrazol-4-yl, 1-(1,1-dioxidotetrahydro-2H-thiopyran-4-yl)-1H-pyrazol-4-yl, 1-((6-(3-oxobut-1-en-1-yl)pyridin-2-yl)methyl)-1H-pyrazol-4-yl, 3-iodophenyl, methylaminocarbonyl, 3-methyl-1,2,4-oxadiazol-5-yl, 5-methyl-1,3,4-oxadiazol-2-yl, 1H-imidazol-2-yl, N-(benzoylmethyl)aminocarbonyl, 5-phenyloxazol-2-yl, 1-cyclohexylpyrazol-4-yl, 1-isopropylpyrazol-4-yl, biphenyl-3-yl, 3-((4-fluorophenyl)amino)phenyl, 3-(2-oxopyrrolidin-1-yl)phenyl, 3-(methylcarbonylamino)-5-phenylphenyl, phenylamino, piperidin-1-yl, methoxymethyl, ethoxymethyl, ethoxycarbonyl, 3-methoxypropyl, benzyloxycarbonyl, trifluoromethyl, 3-furyl, ethylaminocarbonyl, hydroxymethyl, 3-hydroxypropyl, 2-hydroxyethyl, methylaminomethyl, benzofuran-3-yl, 1-phenyl-1H-pyrazol-3-yl, 5-cyclopropylfuran-2-yl, 2-methylfuran-3-yl, 1-phenyl-1H-pyrazol-4-yl, 1-ethyl-1H-pyrazol-4-yl, 1-methyl-6-oxo-1,6-dihydropyridin-3-yl, furan-2-yl, 5-phenylfuran-2-yl, 1-isopropyl-1H-pyrazol-4-yl, pyrimidin-5-yl, 5-methylpyridin-3-yl, 1-methyl-1H-pyrazol-3-yl, 4-phenylfuran-2-yl, 2-fluorophenyl, 4-cyanophenyl, 4-methoxyphenyl, 4-(trifluoromethyl)phenyl, 4-fluorophenyl, 1-benzyl-1H-pyrazol-4-yl, 5-chloropyridin-3-yl, 5-fluoropyridin-3-yl, prop-1-en-2-yl, vinyl, 1-methyl-1H-pyrazol-5-yl, 4-(hydroxymethyl)furan-2-yl, 3-cyanophenyl, 1H-pyrazol-5-yl, 2,5-dihydrofuran-3-yl, thiophen-3-yl, thiophen-2-yl, 1-methyl-1H-pyrazol-4-yl, 5-methylfuran-2-yl, 5-(hydroxymethyl)furan-2-yl, 3-(trifluoromethyl)phenyl, 3-methoxyphenyl, 3-fluorophenyl, pyridin-3-yl, 1-(methylsulfonyl)-1H-pyrazol-4-yl, 1-cyclopentyl-1H-pyrazol-4-yl, 1-(thiophen-3-ylmethyl)-1H-pyrazol-4-yl, 4-chloro-3-(morpholine-4-carbonyl)phenyl, 3-chloro-4-(cyclopropylaminocarbonyl)phenyl, 1-(1-hydroxy-2-methylpropan-2-yl)-1H-pyrazol-4-yl, 1-(3-methoxybenzyl)-1H-pyrazol-4-yl, 1-(pyridin-4-ylmethyl)-1H-pyrazol-4-yl, 1-(2-chlorobenzyl)-1H-pyrazol-4-yl, 1-(3-phenoxybenzyl)-1H-pyrazol-4-yl, 1-(4-phenoxybenzyl)-1H-pyrazol-4-yl, 1-cyclohexyl-1H-pyrazol-4-yl, 1-(1-phenylethyl)-1H-pyrazol-4-yl, 1-cyclobutyl-1H-pyrazol-4-yl, 1-(sec-butyl)-1H-pyrazol-4-yl, 4-fluoro-3-(pyrrolidine-1-carbonyl)phenyl, 1-(cyclopropylsulfonyl)-1H-pyrazol-3-yl, 1-(cyclopropanecarbonyl)-1H-pyrazol-3-yl, 1-(2-cyclopropylethyl)-1H-pyrazol-4-yl, 1-([1,1'-biphenyl]-3-ylmethyl)-1H-pyrazol-4-yl, 1-phenethyl-1H-pyrazol-4-yl, 1-(2-methoxybenzyl)-1H-pyrazol-4-yl, 1-(4-methoxybenzyl)-1H-pyrazol-4-yl, 1-(tert-butyl)-1H-pyrazol-4-yl, 3,4-dimethylphenyl, 3-chloro-4-ethoxyphenyl, 4-methoxy-3-methylphenyl, 2-methylbenzo[d]thiazol-5-yl, 1-(2-phenoxybenzyl)-1H-pyrazol-4-yl, 1-(phenylsulfonyl)-1H-pyrazol-4-yl, 1-benzoyl-1H-pyrazol-4-yl, 1-benzhydryl-1H-pyrazol-4-yl, 1-([1,1'-biphenyl]-2-ylmethyl)-1H-pyrazol-4-yl, 1-(cyclohexylmethyl)-1H-pyrazol-4-yl, 1-(pyridin-3-ylmethyl)-1H-pyrazol-4-yl, benzofuran-2-yl, (E)-styryl, 5-ethylfuran-2-yl, 1-(2-methoxyethyl)-1H-pyrazol-4-yl, 1-(naphthalen-1-ylmethyl)-1H-pyrazol-4-yl, 1-([1,1'-biphenyl]-4-ylmethyl)-1H-pyrazol-4-yl, 3-phenoxyphenyl, phenylethynyl, 3,4-dichlorophenyl, 3-chloro-4-methoxyphenyl, 3-methoxy-4-methylphenyl, 1-(thiazol-4-ylmethyl)-1H-pyrazol-4-yl, 1H-indazol-5-yl, 3,4-dimethoxyphenyl, 4-methoxy-3,5-dimethylphenyl, 1-(oxetan-3-yl)-1H-pyrazol-4-yl, 1-(2-fluorobenzyl)-1H-pyrazol-4-yl, 1-(4-fluorobenzyl)-1H-pyrazol-4-yl, 1-(methoxycarbonylmethyl)-1H-pyrazol-4-yl, 1-(2-(dimethylamino)ethyl)-1H-pyrazol-4-yl, 3-cyano-4-methylphenyl, benzo[d][1,3]dioxol-5-yl, 2,3-dihydrobenzofuran-5-yl, 1-(3-fluorobenzyl)-1H-pyrazol-4-yl, 1-(thiophen-2-ylmethyl)-1H-pyrazol-4-yl, 1-(2,2,2-trifluoroethyl)-1H-pyrazol-4-yl, 1-(3-chlorobenzyl)-1H-pyrazol-4-yl, 1-isobutyl-1H-pyrazol-4-yl, 1-(3,3,3-trifluoropropyl)-1H-pyrazol-4-yl, 1-(difluoromethyl)-1H-pyrazol-4-yl, 1-(2-cyanoethyl)-1H-pyrazol-4-yl, 4-cyclopropylfuran-2-yl, 1H-pyrrol-3-yl, 2,2-difluorobenzo[d][1,3]dioxol-5-yl, 3-fluoro-4-(aminocarbonyl)phenyl, 3-fluoro-4-(methylsulfonyl)phenyl, 3-chloro-4-(trifluoromethoxy)phenyl, 5-fluoro-3-(aminocarbonyl)phenyl, 3-(hydroxymethyl)-4-methoxyphenyl, 1-(methylsulfonyl)-1H-pyrrol-3-yl, 1-methyl-1H-pyrrol-3-yl, 1H-indol-2-yl, cyclopropylcarbonylamino, benzoylamino, 3-bromophenyl, 3-(1-methylpyrazol-4-yl)phenyl, 3-(1-isopropylpyrazol-4-yl)phenyl, 4-phenylphenyl, 4-(4-fluoroanilino)phenyl, 3-(tert-butoxycarbonylamino)phenyl, 1-acetyl-1,2,3,6-tetrahydropyridin-4-yl, 1-propionyl-1,2,3,6-tetrahydropyridin-4-yl, 1-acryloyl-1,2,3,6-tetrahydropyridin-4-yl, 1-methyl-1,2,3,6-tetrahydropyridin-4-yl, 1-((2-methylthiazol-4-yl)methyl)-1H-pyrazol-4-yl, 1-(2-(acetylamino)ethyl)-1H-pyrazol-4-yl, 3,5-dichlorophenyl, 2-fluoro-4-(methylsulfonyl)phenyl, 1-(tert-pentyl)-1H-pyrazol-4-yl, 3-(2-morpholinoethyl)phenyl, 3-(2-(dimethylamino)ethyl)phenyl, 1-(1-(thiazol-4-yl)ethyl)-1H-pyrazol-4-yl, 1-(tetrahydro-2H-pyran-4-yl)-1H-pyrazol-4-yl, 3-methoxy-4-(trifluoromethyl)phenyl, 3-methoxycarbonyl-4-chlorophenyl, 4-(trifluoromethoxy)phenyl, 3-methyl-4-(trifluoromethoxy)phenyl, 4-cyclopropyl-3-(trifluoromethyl)phenyl, 2,2-dimethyl-2,3-dihydrobenzofuran-5-yl, 3,5-dimethoxyphenyl, 3,4-difluorophenyl, 4-biphenyl, 3-chloro-5-fluorophenyl, 3,5-bis(trifluoromethyl)phenyl, 3-fluoro-5-methoxyphenyl, 3-(aminocarbonyl)phenyl, 4-(cyclopropylmethoxy)phenyl, 2-fluoro-5-(benzyloxycarbonyl)phenyl, 3-(1H-pyrazol-1-yl)phenyl, 1-(2-hydroxycyclopentyl)-1H-pyrazol-4-yl, 3-(N-methylaminosulfonyl)phenyl, 4-(2-hydroxypropan-2-yl)phenyl, 2-(trifluoromethyl)pyridin-4-yl, 6-phenoxypyridin-3-yl, 2-methoxypyridin-4-yl, 4-methyl-2-phenylthiazol-5-yl, 3-amino-5-cyanophenyl, 1-(tetrahydrofuran-3-yl), 3-(N-ethylaminocarbonyl)phenyl, 3-(aminocarbonylmethyl)phenyl, 6-phenylpyridin-3-yl, 1-(tetrahydro-2H-pyran-3-yl)-1H-pyrazol-4-yl, 1-(1-methoxypropan-2-yl)-1H-pyrazol-4-yl, 1-(2-ethoxyethyl)-1H-pyrazol-4-yl, 1-acetyl-2,5-dihydro-1H-pyrrol-3-yl, 1-acetyl-1,2,5,6-tetrahydropyridin-3-yl, 1-propionyl-1,2,5,6-tetrahydropyridin-3-yl, 1-propionyl-2,5-dihydro-1H-pyrrol-3-yl, 1-((1S,3S)-3-hydroxycyclobutyl)-1H-pyrazol-4-yl, 2,5-dihydro-1H-pyrrol-3-yl, 1,2,5,6-tetrahydropyridin-3-yl, 1-methyl-1,2,5,6-tetrahydropyridin-3-yl, 1-acryloyl-1,2,5,6-tetrahydropyridin-3-yl, 1-acryloyl-2,5-dihydro-1H-pyrrol-3-yl, 4-chloro-3,5-dimethylphenyl, 4-cyano-3-methylphenyl, 1-oxo-2,3-dihydro-1H-inden-5-yl, 3,4-bis(trifluoromethyl)phenyl, 3-methyl-4-(trifluoromethyl)phenyl, 1-(benzo[b]thiophen-7-ylmethyl)-1H-pyrazol-4-yl, 4-fluoro-3-(N-cyclohexylaminocarbonyl)phenyl, 4-morpholinophenyl, 4-(4-(tert-butoxycarbonyl)piperazin-1-yl)phenyl, 3-chloro-5-methylphenyl, 3-(methylsulfonyl)phenyl, 4-(methylsulfonylamino)phenyl, 4-(morpholinophenyl, 3-morpholinophenyl, 1-(2-(vinylcarbonylamino)ethyl)-1H-pyrazol-4-yl, 1-(2-aminoethyl)-1H-pyrazol-4-yl, 3-cyclopropyl-4-methylphenyl, 3-ethoxyphenyl, 3-(hydroxymethyl)phenyl, 1-(2-(tert-butoxycarbonylamino)ethyl)-1H-pyrazol-4-yl, 3-phenethoxyphenyl, 1,2,3,6-tetrahydropyridin-4-yl, 1-(2-(vinylsulfonylamino)ethyl)-1H-pyrazol-4-yl, 4-(phenylamino)phenyl, 3-methyl-1H-pyrazol-4-yl, 4-(benzyloxy)phenyl, 3,5-difluorophenyl, 3-fluoro-5-trifluoromethylphenyl, 3-(ethylsulfonyl)phenyl, 3-(trifluoromethoxy)phenyl, 1-(thiazol-5-ylmethyl)-1H-pyrazol-4-yl, p-tolyl, 4-cyclopropylphenyl, 4-(ethylsulfonyl)phenyl, 1-(6-vinylpyridin-2-yl)methyl)-1H-pyrazol-4-yl, 6-(benzyloxy)pyridin-3-yl, 1-(tert-butoxycarbonyl)-2,5-dihydro-1H-pyrrol-3-yl, 1-(2-hydroxy-1-phenylethyl)-1H-pyrazol-4-yl, 1-(2-cyano-1-phenylethyl)-1H-pyrazol-4-yl, 6-cyclopropylpyridin-3-yl, 4-cyano-3-methoxyphenyl, 4-methoxy-3-(trifluoromethyl)phenyl, 4-chlorophenyl, 1-(3,4-difluorobenzyl)-1H-pyrazol-4-yl, 4-methyl-3-(trifluoromethyl)phenyl, 4-(pyrrolidine-1-carbonyl)phenyl, 4-(isopropylaminocarbonyl)phenyl, 4-(4-methylpiperazin-1-yl)phenyl, 3-chloro-5-cyanophenyl, 3-(pyrrolidine-1-carbonyl)phenyl, 3-(methylsulfonylaminomethyl)phenyl, 3-(1H- pyrazol-5-yl)phenyl, 4-(methylsulfonyl)phenyl, 4-(cyclopropylaminocarbonyl)phenyl, 1-(2-fluoroethyl)-1H-pyrazol-4-yl, 3-(cyclopropylmethoxy)phenyl, 3-(benzyloxy)phenyl, 3-(morpholinomethyl)phenyl, 3-(phenoxymethyl)phenyl, 1-(3-fluorophenyl)-1H-pyrazol-4-yl, 2-cyclopropylvinyl, 6-(trifluoromethyl)pyridin-3-yl, 1-(4-fluorophenyl)-1H-pyrazol-4-yl, 2,4-dimethylthiazol-5-yl, 1-propyl-1H-pyrazol-4-yl, 1-butyl-1H-pyrazol-4-yl, 1-(2-(phenylamino)ethyl)-1H-pyrazol-4-yl, 4-(aminocarbonyl)phenyl, 4-(N-methylaminocarbonyl)phenyl, 3-fluoro-4-(N-methylaminocarbonyl)phenyl, 1-(2-(3,3-difluoroazetidin-1-yl)ethyl)-1H-pyrazol-4-yl, 1-(2-(3,3-difluoropyrrolidin-1-yl)ethyl)-1H-pyrazol-4-yl, 1-(2-((2,2,2-trifluoroethyl)amino)ethyl)-1H-pyrazol-4-yl, 1-propenyl, 3-(methylcarbonylamino)phenyl, 4-(methylsulfonylamino)phenyl, 4-(morpholine-4-carbonyl)phenyl, 4-(4-acetylpiperazin-1-yl)phenyl, 1-(2,2-difluoroethyl)-1H-pyrazol-4-yl, 5-isopropylfuran-2-yl, 1-(3,3-difluorocyclopentyl)-1H-pyrazol-4-yl, 141S,3R)-3-hydroxycyclopentyl)-1H-pyrazol-4-yl, 1-((1S,3S)-3-hydroxycyclopentyl)-1H-pyrazol-4-yl, 3-(1H-pyrazol-4-yl)phenyl, 5-bromofuran-2-yl, 3-(phenylamino)phenyl, 2-methylthiazol-5-yl, 3-(phenylethynyl)phenyl, 3-phenethylphenyl, 1-(3-fluorocyclopentyl)-1H-pyrazol-4-yl, 1-(1-methoxy-2-methylpropan-2-yl)-1H-pyrazol-4-yl, 1-(1-acryloylazetidin-3-yl)-1H-pyrazol-4-yl, 1-(1-propionylazetidin-3-yl)-1H-pyrazol-4-yl, 6-oxo-1,6-dihydropyridin-3-yl, 4-(piperazin-1-yl)phenyl, 1-(1-fluoro-2-methylpropan-2-yl)-1H-pyrazol-4-yl, 3-(trifluoromethyl)-1H-pyrazol-4-yl, 3,5-dimethylphenyl, 4-(morpholinosulfonyl)phenyl, 3-(4-methylpiperazine-1-carbonyl)phenyl, 3-(2-hydroxypropan-2-yl)phenyl, 1-isopropyl-3-methyl-1H-pyrazol-4-yl, 1-isopropyl-5-methyl-1H-pyrazol-4-yl, 3-cyclopropyl-1H-pyrazol-5-yl, 5-methoxycarbonylpyrrol-3-yl, 3-cyclopropyl-1-isopropyl-1H-pyrazol-5-yl, 5-cyclopropyl-1-isopropyl-1H-pyrazol-3-yl, 1-isopropyl-5-(methoxycarbonyl)pyrrol-3-yl, 1-methyl-3-(trifluoromethyl)-1H-pyrazol-5-yl, 1-isopropyl-1H-pyrazol-3-yl, 1-cyclopentyl-5-cyclopropyl-1H-pyrazol-3-yl, 1-cyclopentyl-3-cyclopropyl-1H-pyrazol-5-yl, 1-cyclopentyl-1H-pyrazol-3-yl, 1-isopropyl-1H-pyrazol-5-yl, 1-isopropyl-5-(N-methylaminocarbonyl)pyrrol-3-yl, 1-isopropyl-5-(N,N-dimethylaminocarbonyl)pyrrol-3-yl, 1-(2-cyclopropylethyl)-1H-pyrazol-3-yl, 1-(2-cyclopropylethyl)-1H-pyrazol-5-yl, 1-ethyl-1H-pyrazol-3-yl, 3-(3,3-dimethyl-2-oxopyrrolidin-1-yl)phenyl, 3-(2-oxo-3-phenylpyrrolidin-1-yl)phenyl, 3-((E)-styryl)phenyl, 3-(3-cyanophenyl)phenyl, 3-(3-(methylsulfonylamino)phenyl)phenyl, 3-(4-(methylsulfonylamino)phenyl)phenyl, or 3-(4-(N-methylaminosulfonyl)phenyl)phenyl.

In certain embodiments, $R^3$ is 1H-pyrazol-4-yl, 1-(cyclopropylmethyl)-1H-pyrazol-4-yl, 1-(1-methylcyclopropyl)-1H-pyrazol-4-yl, 5-fluoro-1H-pyrazol-4-yl, 1-(2-phenylpropan-2-yl)-1H-pyrazol-4-yl, 1-(pyridin-3-yl)-1H-pyrazol-4-yl, 1-(pyridin-4-yl)-1H-pyrazol-4-yl, 1-(pyridin-2-yl)-1H-pyrazol-4-yl, 1-[1-(N-methylaminocarbonyl)-1,1-dimethylmethyl]-1H-pyrazol-4-yl, 5-fluoro-1-isopropyl-1H-pyrazol-4-yl, 1-(cyclopropylmethyl)-1H-pyrazol-5-yl, 1-(cyclopropylmethyl)-1H-pyrazol-3-yl, 1-(tetrahydro-2H-thiopyran-4-yl)-1H-pyrazol-4-yl, 1-(1,1-dioxidotetrahydro-2H-thiopyran-4-yl)-1H-pyrazol-4-yl, 1-((6-(3-oxobut-1-en-1-yl)pyridin-2-yl)methyl)-1H-pyrazol-4-yl, 3-iodophenyl, 3-methyl-1,2,4-oxadiazol-5-yl, 5-methyl-1,3,4-oxadiazol-2-yl, 1H-imidazol-2-yl, 5-phenyloxazol-2-yl, 1-cyclohexylphenyl, 4-isopropylpyrazol-4-yl, biphenyl-3-yl, 3-((4-fluorophenyl)amino)phenyl, 3-(2-oxopyrrolidin-1-yl)phenyl, 3-(methylcarbonylamino)-5-phenylphenyl, 3-furyl, benzofuran-3-yl, 1-phenyl-1H-pyrazol-3-yl, 5-cyclopropylfuran-2-yl, 2-methylfuran-3-yl, 1-phenyl-1H-pyrazol-4-yl, 1-ethyl-1H-pyrazol-4-yl, 1-methyl-6-oxo-1,6-dihydropyridin-3-yl, furan-2-yl, 5-phenylfuran-2-yl, 1-isopropyl-1H-pyrazol-4-yl, pyrimidin-5-yl, 5-methylpyridin-3-yl, 1-methyl-1H-pyrazol-3-yl, 4-phenylfuran-2-yl, 2-fluorophenyl, 4-cyanophenyl, 4-methoxyphenyl, 4-(trifluoromethyl)phenyl, 4-fluorophenyl, 1-benzyl-1H-pyrazol-4-yl, 5-chloropyridin-3-yl, 5-fluoropyridin-3-yl, 1-methyl-1H-pyrazol-5-yl, 4-(hydroxymethyl)furan-2-yl, 3-cyanophenyl, 2,5-dihydrofuran-3-yl, thiophen-3-yl, thiophen-2-yl, 1-methyl-1H-pyrazol-4-yl, 5-methylfuran-2-yl, 5-(hydroxymethyl)furan-2-yl, 3-(trifluoromethyl)-phenyl, 3-methoxyphenyl, 3-fluorophenyl, pyridin-3-yl, 1-(methylsulfonyl)-1H-pyrazol-4-yl, 1-cyclopentyl-1H-pyrazol-4-yl, 1-(thiophen-3-ylmethyl)-1H-pyrazol-4-yl, 4-chloro-3-(morpholine-4-carbonyl)phenyl, 3-chloro-4-(cyclopropylaminocarbonyl)phenyl, 1-(1-hydroxy-2-methylpropan-2-yl)-1H-pyrazol-4-yl, 1-(3-methoxybenzyl)-1H-pyrazol-4-yl, 1-(pyridin-4-ylmethyl)-1H-pyrazol-4-yl, 1-(2-chlorobenzyl)-1H-pyrazol-4-yl, 1-(3-phenoxybenzyl)-1H-pyrazol-4-yl, 1-(4-phenoxybenzyl)-1H-pyrazol-4-yl, 1-cyclohexyl-1H-pyrazol-4-yl, 1-(1-phenylethyl)-1H-pyrazol-4-yl, 1-cyclobutyl-1H-pyrazol-4-yl, 1-(sec-butyl)-1H-pyrazol-4-yl, 4-fluoro-3-(pyrrolidine-1-carbonyl)phenyl, 1-(cyclopropylsulfonyl)-1H-pyrazol-3-yl, 1-(cyclopropanecarbonyl)-1H-pyrazol-3-yl, 1-(2-cyclopropylethyl)-1H-pyrazol-4-yl, 1-([1,1'-biphenyl]-3-ylmethyl)-1H-pyrazol-4-yl, 1-phenethyl-1H-pyrazol-4-yl, 1-(2-methoxybenzyl)-1H-pyrazol-4-yl, 1-(4-methoxybenzyl)-1H-pyrazol-4-yl, 1-(tert-butyl)-1H-pyrazol-4-yl, 3,4-dimethylphenyl, 3-chloro-4-ethoxyphenyl, 4-methoxy-3-methylphenyl, 2-methylbenzo[d]thiazol-5-yl, 1-(2-phenoxybenzyl)-1H-pyrazol-4-yl, 1-(phenylsulfonyl)-1H-pyrazol-4-yl, 1-benzoyl-1H-pyrazol-4-yl, 1-benzhydryl-1H-pyrazol-4-yl, 1-([1,1'-biphenyl]-2-ylmethyl)-1H-pyrazol-4-yl, 1-(cyclohexylmethyl)-1H-pyrazol-4-yl, 1-(pyridin-3-ylmethyl)-1H-pyrazol-4-yl, benzofuran-2-yl, 5-ethylfuran-2-yl, 1-(2-methoxyethyl)-1H-pyrazol-4-yl, 1-(naphthalen-1-ylmethyl)-1H-pyrazol-4-yl, 1-([1,1'-biphenyl]-4-ylmethyl)-1H-pyrazol-4-yl, 3-phenoxyphenyl, 3,4-dichlorophenyl, 3-chloro-4-methoxyphenyl, 3-methoxy-4-methylphenyl, 1-(thiazol-4-ylmethyl)-1H-pyrazol-4-yl, 1H-indazol-5-yl, 3,4-dimethoxyphenyl, 4-methoxy-3,5-dimethylphenyl, 1-(oxetan-3-yl)-1H-pyrazol-4-yl, 1-(2-fluorobenzyl)-1H-pyrazol-4-yl, 1-(4-fluorobenzyl)-1H-pyrazol-4-yl, 1-(methoxycarbonylmethyl)-1H-pyrazol-4-yl, 1-(2-(dimethylamino)ethyl)-1H-pyrazol-4-yl, 3-cyano-4-methylphenyl, benzo[d][1,3]dioxol-5-yl, 2,3-dihydrobenzofuran-5-yl, 1-(3-fluorobenzyl)-1H-pyrazol-4-yl, 1-(thiophen-2-ylmethyl)-1H-pyrazol-4-yl, 1-(2,2,2-trifluoroethyl)-1H-pyrazol-4-yl, 1-(3-chlorobenzyl)-1H-pyrazol-4-yl, 1-isobutyl-1H-pyrazol-4-yl, 1-(3,3,3-trifluoropropyl)-1H-pyrazol-4-yl, 1-(difluoromethyl)-1H-pyrazol-4-yl, 1-(2-cyanoethyl)-1H-pyrazol-4-yl, 4-cyclopropylfuran-2-yl, 2,2-difluorobenzo[d][1,3]dioxol-5-yl, 3-fluoro-4-(aminocarbonyl)phenyl, 3-fluoro-4-(methylsulfonyl)phenyl, 3-chloro-4-(trifluoromethoxy)phenyl, 5-fluoro-3-(aminocarbonyl)phenyl, 3-(hydroxymethyl)-4-methoxyphenyl, 1-(methylsulfonyl)-1H-pyrrol-3-yl, 1-methyl-1H-pyrrol-3-yl, 3-bromophenyl, 3-(1-methylpyrazol-4-yl)phenyl, 3-(1-isopropylpyrazol-4-yl)phenyl, 4-phenylphenyl, 4-(4-fluoroanilino)phenyl, 3-(tert-butoxycarbonylamino)phenyl, 1-acetyl-1,2,3,6-tetrahydropyridin-4-yl, 1-propionyl-1,2,3,6-tetrahydropyridin-4-yl, 1-acryloyl-1,2,3,6-tetrahydropyridin-4-yl, 1-methyl-1,2,3,6-tetrahydropyridin-4-yl, 1-((2-methylthiazol-4-yl)methyl)-1H-pyrazol-4-yl, 1-(2-(acetylamino)ethyl)-1H-pyrazol-4-yl, 3,5-dichlorophenyl, 2-fluoro-4-(methylsulfonyl)phenyl, 1-(tert-pentyl)-1H-pyrazol-4-yl, 3-(2-morpholinoethyl)phenyl, 3-(2-(dimethylamino)ethyl)phenyl, 1-(1-(thiazol-4-yl)ethyl)-1H-pyrazol-4-yl, 1-(tetrahydro-2H-pyran-4-yl)-1H-pyrazol-4-yl, 3-methoxy-4-(trifluoromethyl)phenyl, 3-methoxycarbonyl-4-chlorophenyl, 4-(trifluoromethoxy)phenyl, 3-methyl-4-(trifluoromethoxy)phenyl, 4-cyclopropyl-3-(trifluoromethyl)phenyl, 2,2-dimethyl-2,3-dihydrobenzofuran-5-yl, 3,5-dimethoxyphenyl, 3,4-difluorophenyl, 4-biphenyl, 3-chloro-5-fluorophenyl, 3,5-bis(trifluoromethyl)phenyl, 3-fluoro-5-methoxyphenyl, 3-(aminocarbonyl)phenyl, 4-(cyclopropylmethoxy)phenyl, 2-fluoro-5-(benzyloxycarbonyl)phenyl, 3-(1H-pyrazol-1-yl)phenyl, 1-(2-hydroxycyclopentyl)-1H-pyrazol-4-yl, 3-(N-methylaminosulfonyl)phenyl, 4-(2-hydroxypropan-2-yl)phenyl, 2-(trifluoromethyl)pyridin-4-yl, 6-phenoxypyridin-3-yl, 2-methoxypyridin-4-yl, 4-methyl-2-phenylthiazol-5-yl, 3-amino-5-cyanophenyl, 1-(tetrahydrofuran-3-yl, 3-(N-ethylaminocarbonyl)phenyl, 3-(aminocarbonylmethyl)phenyl, 6-phenylpyridin-3-yl, 1-(tetrahydro-2H-pyran-3-yl)-1H-pyrazol-4-yl, 1-(1-methoxypropan-2-yl)-1H-pyrazol-4-yl, 1-(2-ethoxyethyl)-1H-pyrazol-4-yl, 1-acetyl-2,5-dihydro-1H-pyrrol-3-yl, 1-acetyl-1,2,5,6-tetrahydropyridin-3-yl, 1-propionyl-1,2,5,6-tetrahydropyridin-3-yl, 1-propionyl-2,5-dihydro-1H-pyrrol-3-yl, 1-((1S,3S)-3-hydroxycyclobutyl)-1H-pyrazol-4-yl, 2,5-dihydro-1H-pyrrol-3-yl, 1,2,5,6-tetrahydropyridin-3-yl, 1-methyl-1,2,5,6-tetrahydropyridin-3-yl, 1-acryloyl-1,2,5,6-tetrahydropyridin-3-yl, 1-acryloyl-2,5-dihydro-1H-pyrrol-3-yl, 4-chloro-3,5-dimethylphenyl, 4-cyano-3-methylphenyl, 1-oxo-2,3-dihydro-1H-inden-5-yl, 3,4-bis(trifluoromethyl)phenyl, 3-methyl-4-(trifluoromethyl)phenyl, 1-(benzo[b]thiophen-7-ylmethyl)-1H-pyrazol-4-yl, 4-fluoro-3-(N-cyclohexylaminocarbonyl)phenyl, 4-morpholinophenyl, 4-(4-(tert-butoxycarbonyl)piperazin-1-yl)phenyl, 3-chloro-5-methylphenyl, 3-(methylsulfonyl)phenyl, 4-(methylsulfonylamino)-phenyl, 4-(morpholinomethyl)phenyl, 3-morpholinophenyl, 1-(2-(vinylcarbonylamino)ethyl)-1H-pyrazol-4-yl, 1-(2-aminoethyl)-1H-pyrazol-4-yl, 3-cyclopropyl-4-methylphenyl, 3-ethoxyphenyl, 3-(hydroxymethyl)phenyl, 1-(2-(tert-butoxycarbonylamino)ethyl)-1H-pyrazol-4-yl, 3-phenethoxyphenyl, 1,2,3,6-tetrahydropyridin-4-yl, 1-(2-(vinylsulfonylamino)ethyl)-1H-pyrazol-4-yl, 4-(phenylamino)phenyl, 3-methyl-1H-pyrazol-4-yl, 4-(benzyloxy)phenyl, 3,5-difluorophenyl, 3-fluoro-5-trifluoromethylphenyl, 3-(ethylsulfonyl)phenyl, 3-(trifluoromethoxy)-phenyl, 1-(thiazol-5-ylmethyl)-1H-pyrazol-4-yl, p-tolyl, 4-cyclopropylphenyl, 4-(ethylsulfonyl)-phenyl, 1-(6-vinylpyridin-2-yl)methyl)-1H-pyrazol-4-yl, 6-(benzyloxy)pyridin-3-yl, 1-(tert-butoxycarbonyl)-2,5-dihydro-1H-pyrrol-3-yl, 1-(2-hydroxy-1-phenylethyl)-1H-pyrazol-4-yl, 1-(2-cyano-1-phenylethyl)-1H-pyrazol-4-yl, 6-cyclopropylpyridin-3-yl, 4-cyano-3-methoxyphenyl, 4-methoxy-3-(trifluoromethyl)phenyl, 4-chlorophenyl, 1-(3,4-difluorobenzyl)-1H-pyrazol-4-yl, 4-methyl-3-(trifluoromethyl)phenyl, 4-(pyrrolidine-1-carbonyl)phenyl, 4-(isopropylamino-carbonyl)phenyl, 4-(4-methylpiperazin-1-yl)phenyl, 3-chloro-5-cyanophenyl, 3-(pyrrolidine-1-carbonyl)phenyl, 3-(methylsulfonylaminomethyl)phenyl, 3-(1H-pyrazol-5-yl)phenyl, 4-(methylsulfonyl)phenyl, 4-(cyclopropylaminocarbonyl)phenyl, 1-(2-fluoroethyl)-1H-pyrazol-4-yl, 3-(cyclopropylmethoxy)phenyl, 3-(benzyloxy)phenyl, 3-(morpholinomethyl)phenyl, 3-(phenoxymethyl)phenyl, 1-(3-fluorophenyl)-1H-pyrazol-4-yl, 2-cyclopropylvinyl, 6-(trifluoromethyl)pyridin-3-yl, 1-(4-fluorophenyl)-1H-pyrazol-4-yl, 2,4-dimethylthiazol-5-yl, 1-propyl-1H-pyrazol-4-yl, 1-butyl-1H-pyrazol-4-yl, 1-(2-(phenylamino)ethyl)-1H-pyrazol-4-yl, 4-(aminocarbonyl)phenyl, 4-(N-methylaminocarbonyl)phenyl, 3-fluoro-4-(N-methylamino-carbonyl)phenyl, 1-(2-(3,3-difluoroazetidin-1-yl)ethyl)-1H-pyrazol-4-yl, 1-(2-(3,3-difluoropyrrolidin-1-yl)ethyl)-1H-pyrazol-4-yl, 1-(2-(2,2,2-trifluoroethyl)amino)ethyl)-1H-pyrazol-4-yl, 1-propenyl, 3-(methylcarbonylamino)phenyl, 4-(methylsulfonylamino)phenyl, 4-(morpholine-4-carbonyl)phenyl, 4-(4-acetylpiperazin-1-yl)phenyl, 1-(2,2-difluoroethyl)-1H-pyrazol-4-yl, 5-isopropylfuran-2-yl, 1-(3,3-difluorocyclopentyl)-1H-pyrazol-4-yl, 141S,3R)-3-hydroxycyclopentyl)-1H-pyrazol-4-yl, 1-((1S,3S)-3-hydroxycyclopentyl)-1H-pyrazol-4-yl, 3-(1H-pyrazol-4-yl)phenyl, 5-bromofuran-2-yl, 3-(phenylamino)phenyl, 2-methylthiazol-5-yl, 3-(phenylethynyl)phenyl, 3-phenethylphenyl, 1-(3-fluorocyclopentyl)-1H-pyrazol-4-yl, 1-(1-methoxy-2-methylpropan-2-yl)-1H-pyrazol-4-yl, 1-(1-acryloylazetidin-3-yl)-1H-pyrazol-4-yl, 1-(1-propionylazetidin-3-yl)-1H-pyrazol-4-yl, 6-oxo-1,6-dihydropyridin-3-yl, 4-(piperazin-1-yl)phenyl, 1-(1-fluoro-2-methylpropan-2-yl)-1H-pyrazol-4-yl, 3-(trifluoromethyl)-1H-pyrazol-4-yl, 3,5-dimethylphenyl, 4-(morpholinosulfonyl)phenyl, 3-(4-methylpiperazine-1-carbonyl)phenyl, 3-(2-hydroxypropan-2-yl)phenyl, 1-isopropyl-3-methyl-1H-pyrazol-4-yl, 1-isopropyl-5-methyl-1H-pyrazol-4-yl, 3-cyclopropyl-1H-pyrazol-5-yl, 5-methoxycarbonylpyrrol-3-yl, 3-cyclopropyl-1-isopropyl-1H-pyrazol-5-yl, 5-cyclopropyl-1-isopropyl-1H-pyrazol-3-yl, 1-isopropyl-5-(methoxycarbonyl)pyrrol-3-yl, 1-methyl-3-(trifluoromethyl)-1H-pyrazol-5-yl, 1-isopropyl-1H-pyrazol-3-yl, 1-cyclopentyl-5-cyclopropyl-1H-pyrazol-3-yl, 1-cyclopentyl-3-cyclopropyl-1H-pyrazol-5-yl, 1-cyclopentyl-1H-pyrazol-3-yl, 1-isopropyl-1H-pyrazol-5-yl, 1-isopropyl-5-(N-methylaminocarbonyl)pyrrol-3-yl, 1-isopropyl-5-(N,N-dimethylaminocarbonyl)-pyrrol-3-yl, 1-(2-cyclopropylethyl)-1H-pyrazol-3-yl, 1-(2-cyclopropylethyl)-1H-pyrazol-5-yl, 1-ethyl-1H-pyrazol-3-yl, 3-(3,3-dimethyl-2-oxopyrrolidin-1-yl)phenyl, 3-(2-oxo-3-phenylpyrrolidin-1-yl)phenyl, 3-((E)-styryl)phenyl, 3-(3-cyanophenyl)phenyl, 3-(3-(methylsulfonylamino)phenyl)phenyl, 3-(4-(methylsulfonylamino)phenyl)phenyl, or 3-(4-(N-methylaminosulfonyl)phenyl)phenyl.

In certain embodiments, $R^3$ is aryl or heteroaryl, wherein each aryl and heteroaryl is optionally substituted with one or more groups $R^x$; provided $R^3$ is not phenyl, fluorophenyl, chlorophenyl, pyridyl, nitrophenyl, or propylisoxazole.

In certain embodiments, $R^3$ is pyrazol-4-yl, optionally substituted with $R^x$.

In certain embodiments, $R^x$ is $C_{1-6}$alkyl, that is substituted with one or more groups independently selected from $R^{xa}$, oxo, halo, —$NO_2$, —$N(R^v)_2$, —CN, —C(O)—$N(R^v)_2$, —S(O)—$N(R^v)_2$, —$S(O)_2$—$N(R^v)_2$, —O—$R^v$, —S—$R^v$, —O—C(O)—$R^v$, —C(O)—$R^v$, —C(O)—O—$R^v$, —S(O)—$R^v$, —$S(O)_2$—$R^v$, —C(O)—$N(R^v)_2$, —$S(O)_2$—$N(R^v)_2$, —$N(R^v)$—C(O)—$R^v$, —$N(R^v)$—C(O)—$OR^v$, —$N(R^v)$—S(O)—$R^v$, and —$N(R^v)$—$S(O)_2$—$R^v$.

In certain embodiments, $R^x$ is $C_{1-6}$alkyl that is optionally substituted with $R^{xa}$.

In certain embodiments, $R^3$ is pyrazol-4-yl, substituted with $R^x$.

In certain embodiments, $R^3$ is phenyl that is substituted with oxo, $C_{1-6}$alkyl, $C_{2-6}$alkenyl, $C_{2-6}$alkynyl, carbocyclyl, aryl, heteroaryl, heterocycle, —$N(R^v)_2$, —CN, —C(O)—N$(R^v)_2$, —S(O)—$N(R^v)_2$, —$S(O)_2$—$N(R^v)_2$, —O—$R^v$, —S—$R^v$, —O—C(O)—$R^v$, —O—C(O)—O—$R^v$, —C(O)—$R^v$, —C(O)—O—$R^v$, —S(O)—$R^v$, —$S(O)_2$—$R^v$, —O—C(O)—$N(R^v)_2$, —$N(R^v)$—C(O)—$OR^v$, —$N(R^v)$—C(O)—$N(R^v)_2$, —$S(O)_2$—$N(R^v)_2$, —$N(R^v)$—C(O)—$R^v$, —$N(R^v)$—S(O)—$R^v$, —$N(R^v)$—$S(O)_2$—$R^v$, —$N(R^v)$—S(O)—$N(R^v)_2$, or —$N(R^v)$—$S(O)_2$—$N(R^v)_2$, wherein any $C_{1-6}$alkyl, $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, —N(R$^\nu$)—S(O)$_2$—R$^\nu$, or $C_{1-6}$alkyl that is optionally substituted with one or more groups independently selected from oxo and halo.

In certain embodiments, $R^x$ is $C_{2-6}$alkenyl or $C_{2-6}$alkynyl, wherein any $C_{2-6}$alkenyl and $C_{2-6}$alkynyl is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, and —N(R$^\nu$)—S(O)$_2$—R$^\nu$ In certain embodiments, $R^x$ is selected from $C_{2-6}$alkenyl, $C_{2-6}$alkynyl, carbocyclyl, aryl, heteroaryl, heterocycle, —F, —Cl, —Br, —I, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —O—C(O)—O—R$^\nu$, —C(O)—R$^\nu$, —C(O)—O—R$^\nu$, —S(O)—R$^\nu$, —S(O)$_2$—R$^\nu$, —O—C(O)—N(R$^\nu$)$_2$, —N(R$^\nu$)—C(O)—OR$^\nu$, —N(R$^\nu$)—C(O)—N(R$^\nu$)$_2$, —S(O)$_2$—N(R$^\nu$)$_2$, —N(R$^\nu$)—C(O)—R$^\nu$, —N(R$^\nu$)—S(O)—R$^\nu$, —N(R$^\nu$)—S(O)$_2$—R$^\nu$, —N(R$^\nu$)—S(O)—N(R$^\nu$)$_2$, and —N(R$^\nu$)—S(O)$_2$—N(R$^\nu$)$_2$, wherein any $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, —N(R$^\nu$)—S(O)$_2$—R$^\nu$, and $C_{1-6}$alkyl that is optionally substituted with one or more groups independently selected from oxo and halo.

In certain embodiments, $R^3$ is heteroaryl that is substituted with oxo, $C_{1-6}$alkyl, $C_{2-6}$alkenyl, $C_{2-6}$alkynyl, carbocyclyl, aryl, heteroaryl, heterocycle, —F, —Cl, —Br, —I, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —O—C(O)—O—R$^\nu$, —C(O)—R$^\nu$, —C(O)—O—R$^\nu$, —S(O)—R$^\nu$, —S(O)$_2$—R$^\nu$, —O—C(O)—N(R$^\nu$)$_2$, —N(R$^\nu$)—C(O)—OR$^\nu$, —N(R$^\nu$)—C(O)—N(R$^\nu$)$_2$, —S(O)$_2$—N(R$^\nu$)$_2$, —N(R$^\nu$)—C(O)—R$^\nu$, —N(R$^\nu$)—S(O)—R$^\nu$, —N(R$^\nu$)—S(O)$_2$—R$^\nu$, —N(R$^\nu$)—S(O)—N(R$^\nu$)$_2$, or —N(R$^\nu$)—S(O)$_2$—N(R$^\nu$)$_2$; wherein any $C_{1-6}$alkyl is substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, and —N(R$^\nu$)—S(O)$_2$—R$^\nu$; and wherein any $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, —N(R$^\nu$)—S(O)$_2$—R$^\nu$, and $C_{1-6}$alkyl that is optionally substituted with one or more groups independently selected from oxo and halo.

In certain embodiments, $R^3$ is a 5-membered heteroaryl that is substituted with oxo, $C_{1-6}$alkyl, $C_{2-6}$alkenyl, $C_{2-6}$alkynyl, carbocyclyl, aryl, heteroaryl, heterocycle, —F, —Cl, —Br, —I, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —O—C(O)—O—R$^\nu$, —C(O)—R$^\nu$, —C(O)—O—R$^\nu$, —S(O)—R$^\nu$, —S(O)$_2$—R$^\nu$, —O—C(O)—N(R$^\nu$)$_2$, —N(R$^\nu$)—C(O)—OR$^\nu$, —N(R$^\nu$)—C(O)—N(R$^\nu$)$_2$, —S(O)$_2$—N(R$^\nu$)$_2$, —N(R$^\nu$)—C(O)—R$^\nu$, —N(R$^\nu$)—S(O)—R$^\nu$, —N(R$^\nu$)—S(O)$_2$—R$^\nu$, —N(R$^\nu$)—S(O)—N(R$^\nu$)$_2$, or —N(R$^\nu$)—S(O)$_2$—N(R$^\nu$)$_2$; wherein any $C_{1-6}$alkyl, is substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, and —N(R$^\nu$)—S(O)$_2$—R$^\nu$; and wherein any $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, —N(R$^\nu$)—S(O)$_2$—R$^\nu$, and $C_{1-6}$alkyl that is optionally substituted with one or more groups independently selected from oxo and halo.

In certain embodiments, $R^3$ is phenyl that is substituted with oxo, $C_{1-6}$alkyl, $C_{2-6}$alkenyl, $C_{2-6}$alkynyl, carbocyclyl, aryl, heteroaryl, heterocycle, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —O—C(O)—O—R$^\nu$, —C(O)—R$^\nu$, —C(O)—O—R$^\nu$, —S(O)—R$^\nu$, —S(O)$_2$—R$^\nu$, —O—C(O)—N(R$^\nu$)$_2$, —N(R$^\nu$)—C(O)—OR$^\nu$, —N(R$^\nu$)—C(O)—N(R$^\nu$)$_2$, —S(O)$_2$—N(R$^\nu$)$_2$, —N(R$^\nu$)—C(O)—R$^\nu$, —N(R$^\nu$)—S(O)—R$^\nu$, —N(R$^\nu$)—S(O)$_2$—R$^\nu$, —N(R$^\nu$)—S(O)—N(R$^\nu$)$_2$, or —N(R$^\nu$)—S(O)$_2$—N(R$^\nu$)$_2$; wherein any $C_{1-6}$alkyl, is substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, and —N(R$^\nu$)—S(O)$_2$—R$^\nu$; and wherein any $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —NO$_2$, —N(R$^\nu$)$_2$, —CN, —C(O)—N(R$^\nu$)$_2$, —S(O)—N(R$^\nu$)$_2$, —S(O)$_2$—N(R$^\nu$)$_2$, —O—R$^\nu$, —S—R$^\nu$, —O—C(O)—R$^\nu$, —C(O)—R$^\nu$, —C(O)—O—R$^\nu$, —S(O)—R$^\nu$, —S(O)$_2$—R$^\nu$, —C(O)—N(R$^\nu$)$_2$, —S(O)$_2$—N(R$^\nu$)$_2$, —N(R$^\nu$)—C(O)—R$^\nu$, —N(R$^\nu$)—C(O)—OR$^\nu$, —N(R$^\nu$)—S(O)—R$^\nu$, —N(R$^\nu$)—S(O)$_2$—R$^\nu$, and $C_{1-6}$alkyl that is optionally substituted with one or more groups independently selected from oxo and halo.

In certain embodiments, $R^2$ and $R^3$ taken together with the atoms to which they are attached form a cyclohexyl ring, which is optionally substituted with one or more groups $R^x$.

In certain embodiments, $R^2$ and $R^3$ taken together with the atoms to which they are attached form a phenyl ring, which is optionally substituted with one or more groups $R^x$.

In certain embodiments, $R^4$ is H, methyl, ethyl, propyl, cyclopropylmethyl, 2-hydroxyethyl, 2-(dimethylamino)ethyl, phenyl, benzyl, or 2-methoxyethyl.

In certain embodiments, $R^4$ and $R^3$ taken together with the atoms to which they are attached form a heterocyclyl.

In certain embodiments, the present invention provides a compound of formula (I) as described in any one of Examples 1-432 or a salt thereof.

In certain embodiments, the present invention provides a compound formula (I) as described in any one of Examples 1-457 or a salt thereof.

In certain embodiments, the compound is other than any one of the following:

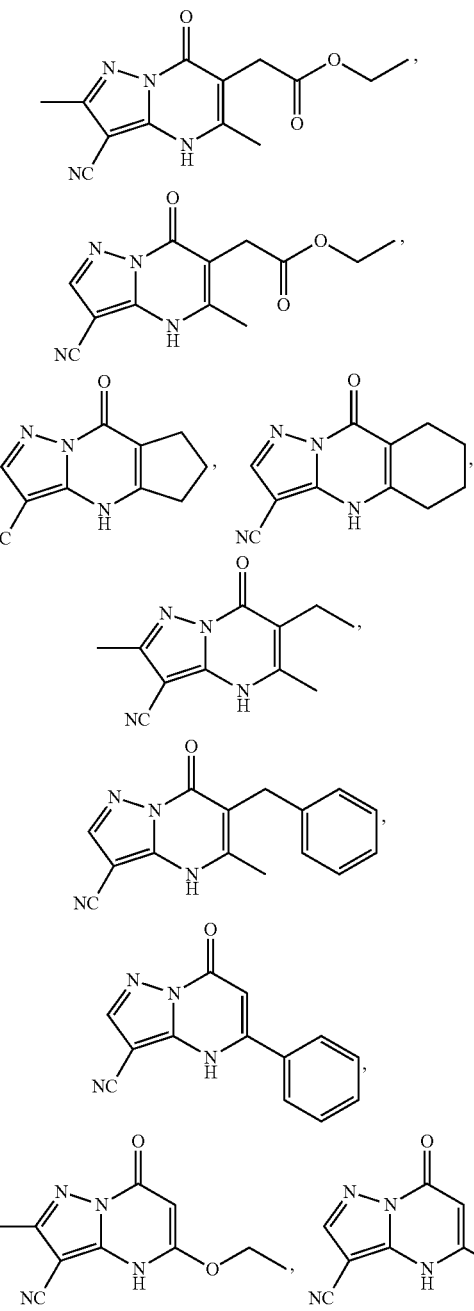

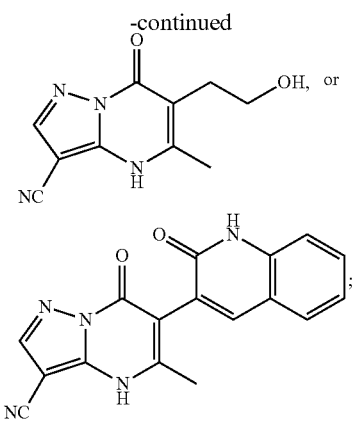

In certain embodiments, the compound is not a compound of formula (II):

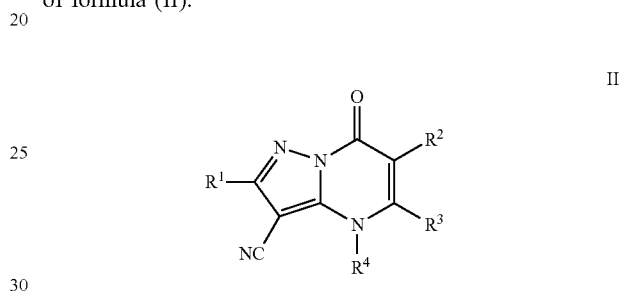

wherein:

$R^1$ is 3-(methylamino)propyl, when $R^2$ is ethoxycarbonyl, and $R^3$ is H;

$R^1$ is H, when $R^2$ is H, and $R^3$ is 2,3-dihydro-1,4-benzodioxin-6-yl;

$R^1$ is methoxy, when $R^2$ is H, and $R^3$ is 4-chlorophenyl;

$R^1$ is hydroxy, when $R^2$ is H, and $R^3$ is 4-chlorophenyl;

$R^1$ is H, when $R^2$ is ethyl, ethoxycarbonylmethyl, 2-hydroxypropyl, 2-(acyloxy)propyl, 2-(acyloxy)ethyl, 2-(2-(N-benzyloxycarbonylamino)propanoyloxy)propyl, 2-chloropropyl, 1-(ethoxycarbonyl)ethyl, ethoxycarbonylmethyl, 1-(carboxy)ethyl, 1-(1-(methoxycarbonylethyl)ethoxycarbonyl)ethyl, 2-hydroxy-1-methylethyl, 2-hydroxyethyl, or 4-(trifluoromethylthio)benzyl, and $R^3$ is methyl;

$R^1$ is H, when $R^2$ is H, and $R^3$ is phenyl, tetrahydropyran-4-ylmethyl, chloromethyl, methoxycarbonyl, ethoxycarbonylmethyl, benzyl, or 1-(2-fluorophenyl)cyclopropyl;

$R^1$ is H, when $R^2$ is H, 4-benzyloxyphenyl, 3,4-dihydro-6,7-dimethyl-3-oxo-2-quinoxalinyl, or indol-3-yl, 3-pyrazolyl, ethoxycarbonyl, cyano, 3,4-dihydro-3-oxo-2-quinoxalinyl, or carboxy, and $R^3$ is H;

$R^1$ is 3-aminopiperidino, when $R^2$ is H, and $R^3$ is trifluoromethyl;

$R^1$ is H, methyl, phenyl, N-(4-fluorophenyl)amino, N-phenylamino, N-benzylamino, N-(3,5-dimethoxyphenyl)amino, N-(3-methoxyphenyl)amino, N-(4-methoxyphenyl)amino, N-(3,4-dimethoxyphenyl)amino, N-(4-methylphenyl)amino N-(2-methoxyphenyl)amino, 4,5,6,7-tetrahydro-1H-indol-2-yl, N-(4-fluorophenyl)amino or N-(4-propylphenyl)amino, when $R^2$ is H, and $R^3$ is methyl;

$R^1$ is phenylamino, when $R^2$ is H, and $R^3$ is isopropyl;

$R^1$ is N-(3,5-dimethoxyphenyl)amino, when $R^2$ is H, and $R^3$ is phenyl, 2-fluorophenyl, 2-chlorophenyl, or chloromethyl;

$R^1$ is N-(3,5-dimethoxyphenyl)amino, when $R^2$ is chloro, and $R^3$ is methyl;

R¹ is methyl, N-(4-morpholinophenyl)amino, N-(3-methoxy-4-(2-morpholinoethoxy)phenyl)amino, N-(3,5-dimethoxyphenyl)amino, or N-(4-propylphenyl)amino, when R² is H, and R³ is ethyl;

R¹ is N-(3-methoxy-5-(2-morpholinoethoxy)phenyl) amino, N-(3,5-dimethoxyphenyl)amino, phenylamino, N-(4-bromophenyl)amino, or N-(4-morpholinophenyl) amino, when R² is H, and R³ is cyclopropyl;

R¹ is N-(3,5-dimethoxyphenyl)amino, when R² is H, and R³ is isopropyl;

R¹ is N-(3,5-dimethoxyphenyl)amino, when R² is methyl, and R³ is methyl;

R¹ is N-(3,5-dimethoxyphenyl)amino, when R² is fluoro, and R³ is methyl;

R¹ is N-(3,5-dimethoxyphenyl)amino, when R² is H, and R³ is methoxymethyl;

R¹ is N-(3,5-dimethoxyphenyl)amino, when R² is H, and R³ is methoxycarbonylmethyl;

R¹ is H, methyl or N-(3,5-dimethoxyphenyl)amino, when R² is H, and R³ is propyl;

R¹ is H, methyl or N-(3,5-dimethoxyphenyl)amino, when R² is benzyl, and R³ is methyl;

R¹ is H or methyl, when R² is benzyl, and R³ is H;

R¹ is N-(3,5-dimethoxyphenyl)amino, when R² is H, and R³ is phenyl, 2-pyridyl, or N,N-dimethylaminomethyl;

R¹ is H, when R² is 2-hydroxyethyl, 2-chloroethyl, 2-(acyloxy)ethyl, and R³ is ethoxycarbonyl;

R¹ is H, when R² is 2-hydroxyethyl, and R³ is hydroxy;

R¹ is H, when R² is 2-(acyloxy)ethyl, and R³ is benzyloxymethyl;

R¹ is 2-pyrrolyl, when R² is H, and R³ is H;

R¹ is N-(4-ethoxyphenyl)amino, when R² is 3,4-dihydro-6,7-dimethyl-3-oxo-2-quinoxalinyl, and R³ is H;

R¹ is H, when R² is 2-(acyloxy)ethyl, and R³ is methoxymethyl;

R¹ is H, when R² is cyano, and R³ is phenyl or 4-chlorophenyl;

R¹ is methyl, when R² is 3,4-dihydro-3-oxo-2-quinoxalinyl, and R³ is H;

R¹ is H, when R² and R³ taken together form a fused benzo ring;

R¹ is H, when R² is 3-methoxybenzyl, and R³ is propyl;

R¹ is methyl, when R² is H, ethyl, ethoxycarbonylmethyl, or 3-chlorobenzyl, and R³ is methyl;

R¹ is pyrrolidino, when R² is H, and R³ is 3-chlorobenzyl, 5-(propyl)isoxazol-3-yl, or 4-nitrophenyl;

R¹ is morpholino, when R² is H, and R³ is tetrahydropyran-2-yl;

R¹ is pyrrolidino, when R² is benzoylamino, and R³ is H;

R¹ is N-(4-methoxyphenyl)amino, when R² is H, and R³ is 4-nitrophenyl;

R¹ is H, when R² is 2-(2,4-dichlorobenzoyloxy)ethyl, 2-(3-methylbenzoyloxy)ethyl, 2-(acetoxy)ethyl or 2-(cyclohexylcarbonyloxy)ethyl, and R³ is methyl;

R¹ is methyl, when R² and R³ taken together form a fused cyclopentyl ring;

R¹ is H, when R² and R³ taken together form a fused cyclohexyl ring;

R¹ is methyl, when R² is H, and R³ is ethoxycarbonylmethyl;

R¹ is phenyl, when R² is H, and R³ is methyl or amino;

R¹ is H, when R² is chloro, and R³ is methyl;

R¹ is methyl, R² is H, and R³ is phenyl;

R¹ is methyl, R² is 2-hydroxyethyl, and R³ is methyl; or

R¹ is methylthio, R² is H, and R³ is phenyl.

In certain embodiments, the compound is other than any one of the following:

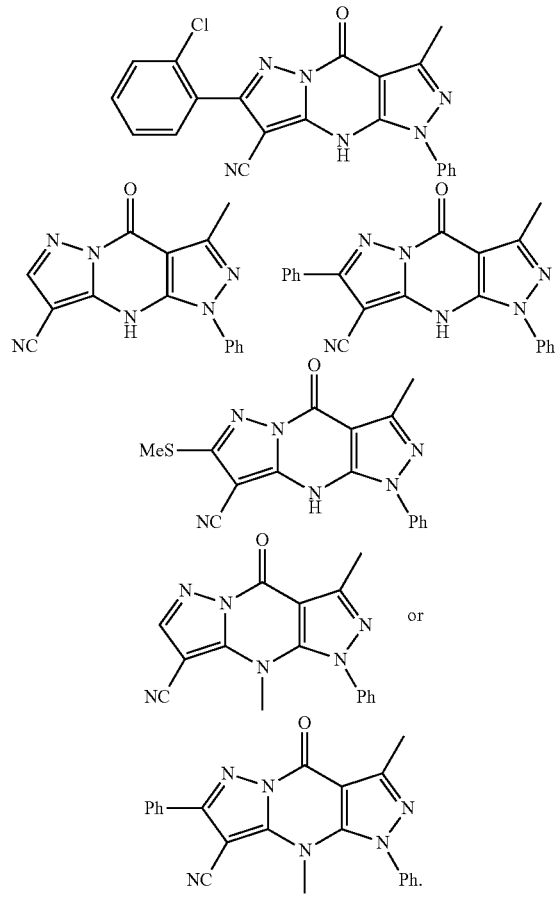

Uses, Formulation and Administration

Pharmaceutically Acceptable Compositions

According to another embodiment, the invention provides a composition comprising a provided compound or a pharmaceutically acceptable derivative thereof and a pharmaceutically acceptable carrier, adjuvant, or vehicle. The amount of compound in compositions of this invention is such that is effective to measurably inhibit a histone demethylase, or a mutant thereof, in a biological sample or in a patient. In some embodiments, the histone demethylase is a 2-oxoglutarate dependent enzyme. In some embodiments, the histone demethylase is a Jumonji domain containing protein. In some embodiments, the histone demethylase is a member of the H3K4 (histone 3 K4) demethylase family. In certain embodiments, the histone demethylase is a JARID subfamily of enzymes. In some embodiments, the histone demethylase is selected from JARID1A, JARID1B, or a mutant thereof.

In certain embodiments, the amount of compound in compositions of this invention is such that is effective to measurably inhibit a 2-oxoglutarate dependent enzyme, or a mutant thereof, in a biological sample or in a patient. In certain embodiments, the 2-oxoglutarate dependent enzyme is a Jumonji domain containing protein. In certain embodiments, the Jumonji domain containing protein is a member of the JMJD2 subfamily. In certain embodiments, the member of the JMJD2 subfamily is GASC1.

In certain embodiments, the amount of compound in compositions of this invention is such that is effective to measurably inhibit a member of the H3K4 (histone 3 K4)

demethylase family of proteins, or a mutant thereof, in a biological sample or in a patient. In certain embodiments, the amount of compound in compositions of this invention is such that is effective to measurably inhibit a member of the JARID subfamily of proteins, or a mutant thereof, in a biological sample or in a patient. In some embodiments, the amount of compound in compositions of this invention is such that is effective to measurably inhibit JARID1A, JARID1B, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a histone demethylase enzyme, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided by the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions provided by the invention may be formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 95-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Compounds and compositions described herein are generally useful for the inhibition of activity of one or more enzymes involved in epigenetic regulation.

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, demethylation, is catalyzed by histone lysine demethylases (HKDM) or histone arginine demethylases. The Jumonji domain containing family of 2-oxoglutarate dependent oxygenases represents a major class of histone demethylases that are involved in epigenetic regulation. Almost all Jumonji domain containing proteins described to date are histone lysine demethylases, though JMJD6 has been found to be a histone arginine demethylase. An important class of Jumonji domain containing proteins is the JMJD2 (jumonji domain containing 2) subfamily of JMJC-type lysine demethylases.

GASC1 (also known as JMJD2C) is a 2-oxoglutarate dependent histone lysine demethylase in the JMJD2 subfamily. GASC1 demethylases trimethylated lysine 9 and lysine 36 on histone H3 (i.e., H3K9me3 and H3K36me3) (Whetstine, et al. (2006) *Cell* 125: 467-481). Trimethylation on lysine 9 of histone H3 is associated with heterochromatin formation and transcriptional repression (Cloos, et al. (2006) *Nature* 442: 307-311). GASC1 is also known to bind to H3K4me3 and H4K20me3 (Huang, et al. (2006) *Science* 312: 748-751).

In some embodiments, enzymes that are inhibited by the compounds and compositions described herein and against which the methods described herein are useful include 2-oxoglutarate dependent enzymes or an isoform or mutant thereof. In some embodiments, the 2-oxoglutarate dependent enzyme is a Jumonji domain containing protein. In certain embodiments, the Jumonji domain containing protein is a member of the JMJD2 subfamily. In certain embodiments, the member of the JMJD2 subfamily is GASC1.

The activity of a provided compound as an inhibitor of a 2-oxoglutarate dependent enzyme (e.g. Jumonji domain containing protein, e.g. JMJD2, e.g. GASC1) or an isoform or mutant thereof, may be assayed in vitro, in vivo or in a cell line.

In vitro assays include assays that determine inhibition of GASC1 or a mutant thereof. In some embodiments, inhibitor binding may be determined by running a competition experiment where new inhibitors are incubated with GASC1 bound to known radioligands. Detailed conditions for assaying a provided compound as an inhibitor of GASC1 or a mutant thereof are set forth in the Examples below.

In some embodiments, detection of GASC1 activity is achieved with in vitro histone lysine demethylase (HKDM) assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes. 2-Oxoglutarate, a cofactor necessary for GASC1 function, can also be employed in a competitive binding assay. Mass spectrometry and Western blot analysis can also be used to detect GASC1 activity; see for example Whetstine, et al. *Cell* 125: 467-481 (2006). For examples of HKDM screening assays, see WO 2007/104314 and WO 2008/089883. It will be understood that the assays described herein can be used for other HKDM proteins in addition to GASC1. In certain embodiments, a provided compound is competitive with 2-oxoglutarate.

GASC1 is implicated in proliferative diseases. The GASC1 gene was first identified in esophageal squamous cell carcinoma cell lines, resulting in its designation as gene amplified in squamous cell carcinoma 1 (GASC1) (Yang, et al. (2000) *Cancer Res*. 60: 4735-4739). Down regulation of GASC1 expression inhibits cell proliferation, and histone methylation regulation is implicated in tumorigenesis (Whetstine, et al. (2006) *Cell* 125: 467-481). GASC1 interacts with androgen receptor and another histone demethylase, LSD1, in vitro and in vivo and increases androgen receptor-dependent gene expression in prostate cells, implicating GASC1 in prostate cancer (Wissmann, et al. (2007) *Nat. Cell Biol*. 9: 347-353). Furthermore, the GASC1 gene is amplified in basal like breast tumors and in lung sarcomatoid carcinoma and is translocated in MALT lymphomas (Han, et al. (2008) *Genes Chromosomes Cancer* 47: 490-499; Helias, et al. (2008) *Cancer Genet. Cytogenet*. 180: 51-55; Italiano, et al. (2006) *Cancer Genet. Cytogenet*. 167: 122-130; Vinatzer, et al. (2008) *Clin Cancer Res* 14: 6426-6431). GASC1 plays an important role in cancer and other proliferative diseases.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In certain embodiments, provided compounds inhibit one or more 2-oxoglutarate dependent enzymes. In certain embodiments, provided compounds inhibit one or more Jumonji domain containing enzymes. In certain embodiments, provided compounds inhibit one or more JMJD2 proteins. In certain embodiments, provided compounds inhibit GASC1. Provided compounds are inhibitors of 2-oxoglutarate dependent enzymes (e.g. GASC1) and are therefore useful for treating one or more disorders associated with activity of a 2-oxoglutarate dependent enzyme (e.g. GASC1). In certain embodiments, the present invention provides a method for treating a GASC1-mediated disorder comprising the step of administering to a patient in need thereof a provided compound, or a pharmaceutically acceptable composition thereof.

As used herein, the term "GASC1-mediated" disorder or condition means any disease or other deleterious condition in which GASC1, or a mutant thereof, is known to play a role. Accordingly, another embodiment of the present invention relates to treating or lessening the severity of one or more diseases in which GASC1, or a mutant thereof, is known to play a role.

Diseases and conditions treatable according to the methods of this invention include, but are not limited to, cancer and other proliferative disorders. In one embodiment, a human patient is treated with a compound of the current invention and a pharmaceutically acceptable carrier, adjuvant, or vehicle, wherein said compound of is present in an amount to measurably inhibit activity of a 2-oxoglutarate dependent enzyme (e.g. Jumonji domain containing protein, e.g. JMJD2, e.g. GASC1).

Another important class of Jumonji domain containing proteins is the H3K4 (histone 3 K4) demethylases which are involved in tissue development, cancer, and stem cell biology. (Roesch, et al. (2010) *Cell* 141:283-594). Such H3K4 demethylases include the JARID subfamily of histone demethylases (e.g., JARID1A and JARID1B).

JARID1A (also known as KDM5A) is highly expressed in the hematopoietic system. JARID1B (also known as KDM5B, PLU-1, and RBP2-H1) is a member of the family of jumonji/ARID1 (JARID1) histone 3 K4 demethylases. In normal cells, JARID is marginally expressed. However, JARID1B is highly expressed in regenerative tissues such as testis and bone marrow. In cancer, JARID1B functions as a transcriptional regulator of oncogenes, for example BRCA1 in breast cancer (Yamane et al., (2007) *Molecular Cell* 25:801-812). Indeed, JARID1B is overexpressed in breast cancer. It was also reported that JARID1B is highly expressed in slow-cycling melanoma cells. Accordingly, inhibition of JARID1B is an important target for eradicating all melanoma cells (rapidly proliferating and slow-cycling) (Roesch, et al. (2010) *Cell* 141:283-594).

In some embodiments, enzymes that are inhibited by the compounds and compositions described herein and against which the methods described herein are useful include 2-oxoglutarate dependent enzymes or an isoform or mutant thereof. In some embodiments, the 2-oxoglutarate dependent enzyme is a Jumonji domain containing protein. In certain embodiments, the Jumonji domain containing protein is a member of the JMJD2 subfamily. In certain embodiments, the member of the JMJD2 subfamily is GASC1. In some embodiments, the enzyme is a member of the JARID subfamily. In certain embodiments, the enzyme is JARID1A, PLU-1, or JMJD2B.

The activity of a provided compound as an inhibitor of a histone demethylase enzyme (e.g. Jumonji domain containing protein, e.g. JMJD2, JMJD2B, JARID1A, JARID1B, PLU-1, or GASC1) or an isoform or mutant thereof, may be assayed in vitro, in vivo or in a cell line.

In vitro assays include assays that determine inhibition of an enzyme or a mutant thereof. In some embodiments, inhibitor binding may be determined by running a competition experiment where new inhibitors are incubated with the enzyme bound to known radioligands. Detailed conditions for assaying a provided compound as an inhibitor of enzyme or a mutant thereof are set forth in the Examples below.

In some embodiments, detection of histone demethylase (e.g. Jumonji domain containing protein, e.g. JMJD2, JMJD2B, JARID1A, JARID1B, PLU-1, or GASC1) activity is achieved with in vitro histone lysine demethylase (HKDM) assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes. 2-Oxoglutarate, a cofactor necessary for GASC1 function, can also be employed in a competitive binding assay. Mass spectrometry and Western blot analysis can also be used to detect GASC1 activity; see for example Whetstine, et al. *Cell* 125: 467-481 (2006). For examples of HKDM screening assays, see WO 2007/104314 and WO 2008/089883. It will be understood that the assays described herein can be used for other HKDM proteins in addition to GASC1. In certain embodiments, a provided compound is competitive with 2-oxoglutarate.

In certain embodiments, provided compounds inhibit one or more 2-oxoglutarate dependent enzymes. In certain embodiments, provided compounds inhibit one or more Jumonji domain containing enzymes. In certain embodiments, provided compounds inhibit one or more JMJD2 proteins. In certain embodiments, provided compounds inhibit GASC1. In some embodiments, provided compounds inhibit one or more of JARID1A, JARID1B, PLU-1, and/or JMJD2B. Provided compounds are inhibitors of such histone demethylases and are therefore useful for treating one or more disorders associated with activity of one or more of JARID1A, JARID1B, PLU-1, and/or JMJD2B. In certain embodiments, the present invention provides a method for treating a JARID1A-, JARID1B-, PLU-1-, and/or JMJD2B-mediated disorder comprising the step of administering to a patient in need thereof a provided compound, or a pharmaceutically acceptable composition thereof.

As used herein, the term "JARID1A-mediated" disorder or condition means any disease or other deleterious condition in which JARID1A, or a mutant thereof, is known to play a role. Accordingly, another embodiment of the present invention relates to treating or lessening the severity of one or more diseases in which JARID1A, or a mutant thereof, is known to play a role.

As used herein, the term "JARID1B-mediated" disorder or condition means any disease or other deleterious condition in which JARID1B, or a mutant thereof, is known to play a role. Accordingly, another embodiment of the present invention relates to treating or lessening the severity of one or more diseases in which JARID1B, or a mutant thereof, is known to play a role.

As used herein, the term "PLU-1-mediated" disorder or condition means any disease or other deleterious condition in which PLU-1, or a mutant thereof, is known to play a role. Accordingly, another embodiment of the present invention relates to treating or lessening the severity of one or more diseases in which PLU-1, or a mutant thereof, is known to play a role.

As used herein, the term "JMJD2B-mediated" disorder or condition means any disease or other deleterious condition in which JMJD2B, or a mutant thereof, is known to play a role. Accordingly, another embodiment of the present invention relates to treating or lessening the severity of one or more diseases in which JMJD2B, or a mutant thereof, is known to play a role.

Another aspect includes the use of a compound of formula (I) or a salt thereof for the inhibition of KDM5. Compounds of formula (I) may also be used to inhibit the removal of methyl marks on histone lysine residues, including inhibiting the removal of methyl marks from mono-, di- or tri-methylation of histones H1, H2A, H2B, H3 and H4, such as H3K4 (including for example the KDM5 substrate H3K4me3), thereby altering interactions of these histone proteins with DNA and/or other proteins, and altering certain subsequent genetic or protein expression. Compounds of formula (I) may also be used to inhibit KDM5 and reduce drug-tolerant cells, thereby treating or preventing drug-resistant diseases, such as drug-resistant cancer. In certain embodiments, the disease can be treated using compounds of formula (I) to prevent resistance from forming, for example before targets of chemotherapies become mutated to confer resistance to such chemotherapies.

In certain embodiments, the binding or inhibition activity of a compound of formula (I) may be determined by running a competition experiment where a compound of formula (I) is incubated with the KDM5 enzyme bound to known radioligands. Detailed conditions for assaying a compound of formula (I) as an inhibitor of KDM5 or a mutant thereof are set forth in the Examples below.

In certain embodiments, detection of KDM5 activity is achieved with in vitro assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes.

Another aspect includes a method of treating or preventing a disease responsive to the inhibition of KDM5 activity in a patient. The method includes administering a therapeutically effective amount of a compound of formula (I) or a salt thereof to a patient in need thereof.

Another aspect includes the use of a compound of formula (I), or a pharmaceutically acceptable salt thereof, in therapy. Another aspect includes the use of a pharmaceutical composition comprising a compound of formula (I), or a pharmaceutically acceptable salt thereof, in therapy.

Another aspect includes the use of a compound of formula (I), or a pharmaceutically acceptable salt thereof, in treating a disease associated with KDM5 activity. Another aspect includes the use of a pharmaceutical composition comprising a compound of formula (I), or a pharmaceutically acceptable salt thereof, in treating a disease associated with KDM5 activity.

Another aspect includes the use of a compound of formula (I), or a pharmaceutically acceptable salt thereof, in the manufacture of a medicament for the treatment of a disease associated with KDM5 activity. Another aspect includes the use of a pharmaceutical composition comprising a compound of formula (I), or a pharmaceutically acceptable salt thereof, in the manufacture of a medicament for the treatment of a disease associated with KDM5 activity.

In certain embodiments, the disease or condition is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Another aspect includes a method for treating, ameliorating or preventing cancer, drug-resistant cancer or another proliferative disorder by administration of an effective amount of a compound of formula (I) or salt thereof to a mammal, for example a human, in need of such treatment. In certain embodiments, the disease to be treated is cancer or drug resistant cancer.

The invention further relates to a method for treating, ameliorating or preventing cancer or another proliferative disorder by administration of an effective amount of a compound according to this invention to a mammal, in particular a human in need of such treatment. In some aspects of the invention, the disease to be treated by the methods of the present invention may be cancer. Examples of cancers that may be treated using the compounds and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, androgen dependent cancer, angioimmunoblastic T-cell lymphoma, angiomyolipoma, angiosarcoma, astrocytoma, atypical teratoid rhabdoid tumor, B-cell chronic lymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method for the treatment of benign proliferative disorder. Examples of benign proliferative disorders treated with compounds according to the present invention include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Another embodiment includes a therapeutic method useful for modulating protein methylation, gene expression, cell proliferation, cell differentiation and/or apoptosis in vivo in diseases mentioned above, in particular cancer, comprising administering to a patient in need of such therapy a pharmacologically active and therapeutically effective amount of one or more of the compounds of formula (I).

Another embodiment includes a method for regulating endogenous or heterologous promoter activity by contacting a cell with a compound of formula (I).

Another embodiment includes the use of a compound of formula I or salt thereof for the production of pharmaceutical compositions which are employed for the treatment and/or prophylaxis and/or amelioration of the diseases, disorders, illnesses and/or conditions as mentioned herein.

Another embodiment includes the use of a compound of formula I or salt thereof for the production of pharmaceutical compositions which are employed for the treatment and/or prophylaxis of diseases and/or disorders responsive or sensitive to the inhibition of histone demethylases, particularly those diseases mentioned above, such as e.g. cancer.

The invention further provides a method for the treatment a subject, such as a human, suffering from one of the abovementioned conditions, illnesses, disorders or diseases. The method comprises administering a therapeutically effective amount of one or more of the compounds according to this invention, which function by inhibiting one or more 2-oxoglutarate dependent enzymes (e.g. Jumonji domain containing protein, e.g. JMJD2, e.g. GASC1) and, in general, by modulating protein methylation, to induce various cellular effects, in particular induction or repression of gene expression, arresting cell proliferation, inducing cell differentiation and/or inducing apoptosis, to a subject in need of such treatment.

The invention further provides a therapeutic method useful for modulating protein methylation, gene expression, cell proliferation, cell differentiation and/or apoptosis in vivo in diseases mentioned above, in particular cancer, comprising administering to a subject in need of such therapy a pharmacologically active and therapeutically effective amount of one or more of the compounds according to this invention.

The invention further provides a method for regulating endogenous or heterologous promoter activity by contacting a cell with a compound according to this invention.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of histone demethylases, particularly those diseases mentioned above, such as e.g. cancer.

Provided compounds or compositions may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and, in certain embodiments, from about 1 mg/kg to about 25 mg/kg, of subject body weight per day, one or more times a day, to obtain the desired therapeutic effect.

According to one embodiment, the invention relates to a method of inhibiting one or more histone demethylase (e.g. Jumonji domain containing protein, e.g. JMJD2, JMJD2B, JARID1A, JARID1B, PLU-1 e.g. GASC1) activity in a biological sample comprising the step of contacting said biological sample with a provided compound, or a composition comprising said compound.

According to another embodiment, the invention relates to a method of inhibiting a histone demethylase (e.g. Jumonji domain containing protein, e.g. JMJD2, JMJD2B, JARID1A, JARID1B, PLU-1 e.g. GASC1), or a mutant thereof, activity in a biological sample comprising the step of contacting said biological sample with a provided compound, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of activity of a histone demethylase (e.g. Jumonji domain containing protein, e.g. JMJD2, JMJD2B, JARID1A, JARID1B, PLU-1 e.g. GASC1) or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of a histone demethylase (e.g. Jumonji domain containing protein, e.g. JMJD2, JMJD2B, JARID1A, JARID1B, PLU-1 e.g. GASC1), or a mutant thereof, in a patient comprising the step of administering to said patient a provided compound, or a composition comprising said compound. In certain embodiments, the present invention provides a method for treating a disorder mediated by a histone demethylase (e.g. Jumonji domain containing protein, e.g. JMJD2, JMJD2B, JARID1A, JARID1B, PLU-1 e.g. GASC1), or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition may also be present in the compositions of this invention or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Example of epigenetic regulators include the histone demethylase (e.g. Jumonji domain containing protein, e.g. JMJD2, JMJD2B, JARID1A, JARID1B, PLU-1 e.g. GASC1) already described, as well as other histone demethylases, histone lysine methyl transferases, histone arginine methyl transferases, histone deacetylases, histone acetylases, histone methylases, and DNA methyltransferases. Histone deacetylase inhibitors include, but are not limited to, vorinostat.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams &

Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone), panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033,2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, camptothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention may also be combined with include, without limitation: treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Additionally, chemotherapeutic agents include pharmaceutically acceptable salts, acids or derivatives of any of chemotherapeutic agents, described herein, as well as combinations of two or more of them.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In certain embodiments, in such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. In certain embodiments, the amount of additional therapeutic agent in the presently disclosed compositions will range from about 50% to 100% of the amount normally present in a composition comprising that agent as the only therapeutically active agent.

Another aspect includes treating or preventing drug resistance in a patient using a compound of formula (I) or a pharmaceutically acceptable salt thereof. For example, a method of treating or preventing drug resistant cancer in a patient comprises administering a therapeutically effective amount of a compound of formula (I) to the patient alone or in combination with a cytotoxic agent. In certain embodiments, the individual is selected for treatment with a cytotoxic agent (e.g., targeted therapies, chemotherapies, and/or radiotherapies). In certain embodiments, the individual starts treatment comprising administration of a compound of formula (I) or a pharmaceutically acceptable salt thereof prior to treatment with the cytotoxic agent. In certain embodiments, the individual concurrently receives treatment comprising the compound of formula (I) or a pharmaceutically acceptable salt thereof and the cytotoxic agent. In certain embodiments, the compound of formula (I) or the pharmaceutically acceptable salt thereof increases the period of cancer sensitivity and/or delays development of cancer resistance.

In particular, provided herein are methods of treating cancer in an individual comprising administering to the individual (a) a compound of formula (I) or a pharmaceutically acceptable salt thereof and (b) a cytotoxic agent (e.g., targeted therapy, chemotherapy, and/or radiotherapy). In certain embodiments, the respective amounts of the compound of formula (I) or a pharmaceutically acceptable salt thereof and the cytotoxic agent are effective to increase the period of cancer sensitivity and/or delay the development of cancer cell resistance to the cancer therapy agent. In certain embodiments, the respective amounts of the compound of formula (I) or a pharmaceutically acceptable salt thereof and the cytotoxic agent are effective to increase efficacy of a cancer treatment comprising the cancer therapy agent. For example, in certain embodiments, the respective amounts of the compound of formula (I) or a pharmaceutically acceptable salt thereof and the cytotoxic agent are effective to increase efficacy compared to a treatment (e.g., standard of care treatment) (e.g., standard of care treatment) comprising administering an effective amount of the cancer therapy agent without (in the absence of) the compound of formula (I) or a pharmaceutically acceptable salt thereof. In certain embodiments, the respective amounts of the compound of formula (I) or a pharmaceutically acceptable salt thereof and cytotoxic agent are effective to increase response (e.g., complete response) compared to a treatment (e.g., standard of care treatment) comprising administering an effective amount of cytotoxic agent without (in the absence of) the compound of formula (I) or a pharmaceutically acceptable salt thereof.

Also provided herein are methods of increasing efficacy of a cancer treatment comprising a cytotoxic agent in an individual comprising administering to the individual (a) an effective amount of a compound of formula (I) or a pharmaceutically acceptable salt thereof and (b) an effective amount of the cytotoxic agent.

Provided herein are methods of treating cancer in an individual wherein cancer treatment comprising administering to the individual (a) an effective amount of a compound of formula (I) or a pharmaceutically acceptable salt thereof and (b) an effective amount of a cytotoxic agent, wherein the cancer treatment has increased efficacy compared to a treatment (e.g., standard of care treatment) comprising administering an effective amount of cytotoxic agent without (in the absence of) the compound of formula (I) or a pharmaceutically acceptable salt thereof.

In addition, provided herein are methods of delaying and/or preventing development of cancer resistant to a cancer therapy agent in an individual, comprising administering to the individual (a) an effective amount of a compound of formula (I) or a pharmaceutically acceptable salt thereof and (b) an effective amount of the cytotoxic agent.

Provided herein are methods of treating an individual with cancer who has an increased likelihood of developing resistance to a cancer therapy agent comprising administering to the individual (a) an effective amount of a compound of formula (I) or a pharmaceutically acceptable salt thereof and (b) an effective amount of the cytotoxic agent.

Further provided herein are methods of increasing sensitivity to a cancer therapy agent in an individual with cancer comprising administering to the individual (a) an effective amount of a compound of formula (I) or a pharmaceutically acceptable salt thereof and (b) an effective amount of the cytotoxic agent.

Provided herein are also methods of extending the period of a cancer therapy agent sensitivity in an individual with cancer comprising administering to the individual (a) an effective amount of a compound of formula (I) or a pharmaceutically acceptable salt thereof and (b) an effective amount of the cytotoxic agent.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

Provided herein is a compound of formula (I), or a pharmaceutically acceptable salt thereof, for use in medical therapy.

Provided herein is a compound of formula (I), or a pharmaceutically acceptable salt thereof, for the prophylactic or therapeutic treatment of a proliferative disorder.

Provided herein is a compound of formula (I), or a pharmaceutically acceptable salt thereof, for inhibiting activity of a 2-oxoglutarate dependent enzyme, or a mutant thereof.

Provided herein is a compound of formula (I), or a pharmaceutically acceptable salt thereof, for treating a GASC1-mediated disorder.

Provided herein is a compound of formula (I), or a pharmaceutically acceptable salt thereof, for inhibiting activity of a JARID family enzyme.

Provided herein is a compound of formula (I), or a pharmaceutically acceptable salt thereof, for treating a JARID-mediated disorder.

Provided herein is a compound of formula (I), or a pharmaceutically acceptable salt thereof, for increasing efficacy of a cancer treatment comprising a cytotoxic.

Provided herein is a compound of formula (I), or a pharmaceutically acceptable salt thereof, for treating an individual with cancer who has an increased likelihood of developing resistance to a cytotoxic agent.

Provided herein is a compound of formula (I), or a pharmaceutically acceptable salt thereof, for treating cancer.

Provided herein is a compound of formula (I), or a pharmaceutically acceptable salt thereof, for increasing efficacy of a cancer treatment.

Provided herein is a compound of formula (I), or a pharmaceutically acceptable salt thereof, for delaying and/or preventing development of cancer resistant to a cytotoxic agent.

Provided herein is a compound of formula (I), or a pharmaceutically acceptable salt thereof, for increasing sensitivity to a cytotoxic agent.

Provided herein is a compound of formula (I), or a pharmaceutically acceptable salt thereof, for extending the period of a cancer therapy agent sensitivity.

Provided herein is a compound of formula (I), or a pharmaceutically acceptable salt thereof, for extending the duration of response to a cancer therapy.

Provided herein is the use of a compound of formula (I), or a pharmaceutically acceptable salt thereof, to prepare a medicament useful for inhibiting activity of a 2-oxoglutarate dependent enzyme, or a mutant thereof.

Provided herein is the use of a compound of formula (I), or a pharmaceutically acceptable salt thereof, to prepare a medicament useful for treating a GASC1-mediated disorder.

Provided herein is the use of a compound of formula (I), or a pharmaceutically acceptable salt thereof, to prepare a medicament useful for inhibiting activity of a JARID family enzyme.

Provided herein is the use of a compound of formula (I), or a pharmaceutically acceptable salt thereof, to prepare a medicament useful for treating a JARID-mediated disorder.

Provided herein is the use of a compound of formula (I), or a pharmaceutically acceptable salt thereof, to prepare a medicament useful for increasing efficacy of a cancer treatment comprising a cytotoxic.

Provided herein is the use of a compound of formula (I), or a pharmaceutically acceptable salt thereof, to prepare a medicament useful for treating an individual with cancer who has an increased likelihood of developing resistance to a cytotoxic agent.

Provided herein is the use of a compound of formula (I), or a pharmaceutically acceptable salt thereof, to prepare a medicament useful for treating cancer.

Provided herein is the use of a compound of formula (I), or a pharmaceutically acceptable salt thereof, to prepare a medicament useful for increasing efficacy of a cancer treatment.

Provided herein is the use of a compound of formula (I), or a pharmaceutically acceptable salt thereof, to prepare a medicament useful for delaying and/or preventing development of cancer resistant to a cytotoxic agent.

Provided herein is the use of a compound of formula (I), or a pharmaceutically acceptable salt thereof, to prepare a medicament useful for increasing sensitivity to a cytotoxic agent.

Provided herein is the use of a compound of formula (I), or a pharmaceutically acceptable salt thereof, to prepare a medicament useful for extending the period of a cancer therapy agent sensitivity.

Provided herein is the use of a compound of formula (I), or a pharmaceutically acceptable salt thereof, to prepare a medicament useful for extending the duration of response to a cancer therapy.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkaloid. In certain embodiments, the vinca alkaloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

In certain embodiments of any of the methods, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising an inhibitor of a histone demethylase (e.g. Jumonji domain containing protein, e.g. JMJD2, JMJD2B, JARID1A, JARID1B, PLU-1 e.g. GASC1). Implantable devices coated with a compound of this invention are another embodiment of the present invention.

Exemplification

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The general synthetic methods illustrated in Schemes 1-4 and the general LCMS isolations procedures identified as LCMS Method A-LCMS Method F were used to prepare the compounds of Examples 1-432 as detailed below.

General Synthetic Methods

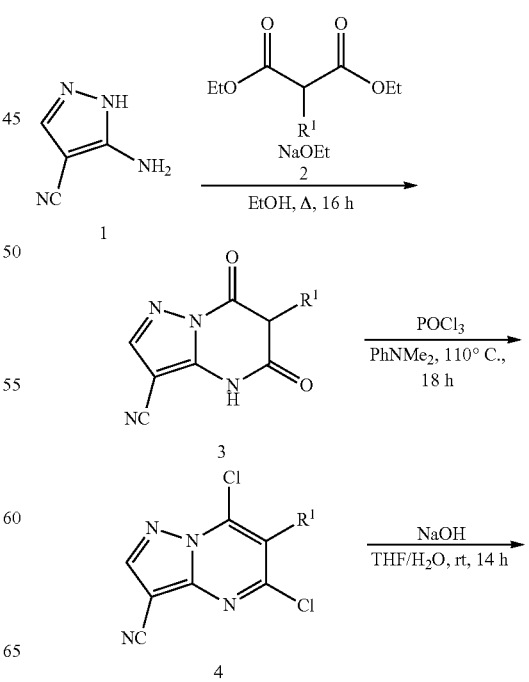

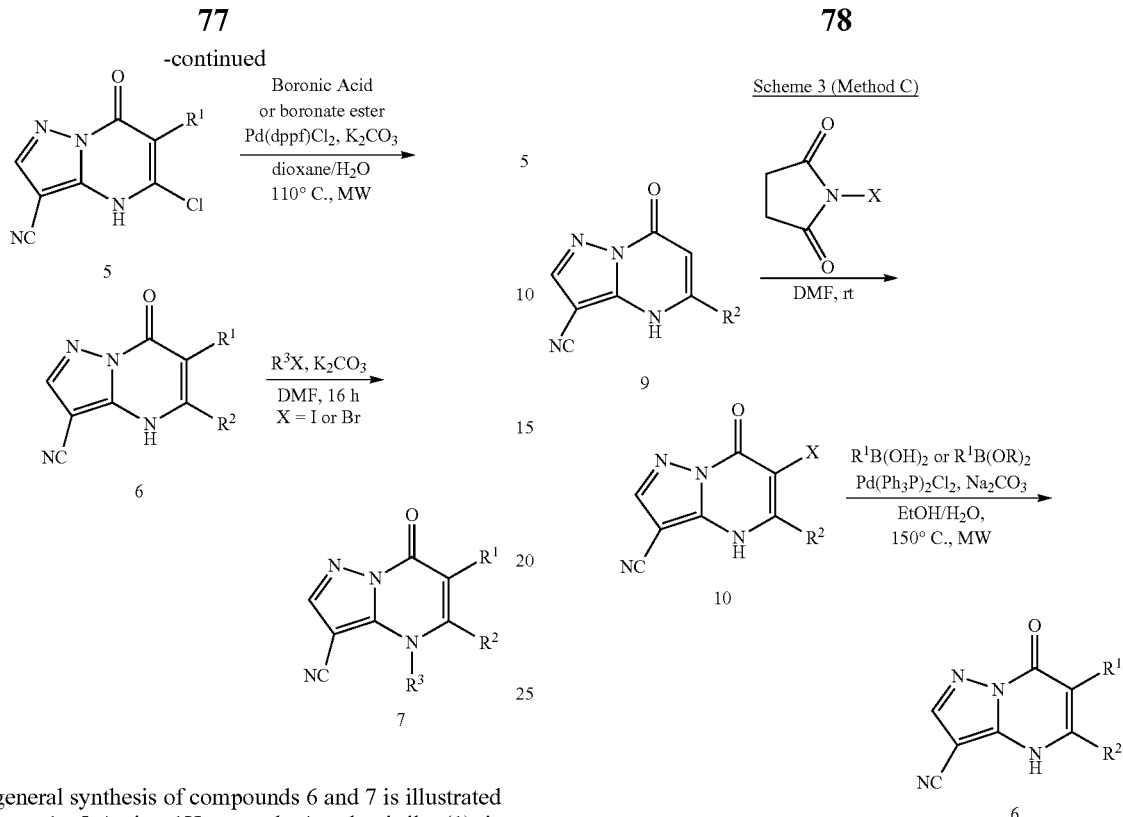

The general synthesis of compounds 6 and 7 is illustrated in Scheme 1. 5-Amino-1H-pyrazole-4-carbonitrile (1) is condensed with alkyl malonate in refluxing EtOH using NaOEt as base to give intermediate 3. This is followed by reaction with phosphorous oxychloride that leads to dichloro intermediate 4, which was selectively hydrolysed using sodium hydroxide to afford the common chloride intermediate 5. Subsequent Suzuki cross-coupling with boronic acid or boronate ester resulted in compound 6, which could be further N-alkylated with a halide $R^3X$ to afford compound 7.

X = Cl, or Br, or I

An alternative synthesis of compound 6 (Method C) is shown in Scheme 3. Compound 9 was treated with N-halogen succinamide in DMF to give halide 10. Subsequent Suzuki coupling of compound 10 with a boronic acid or boronate ester also provided compound 6.

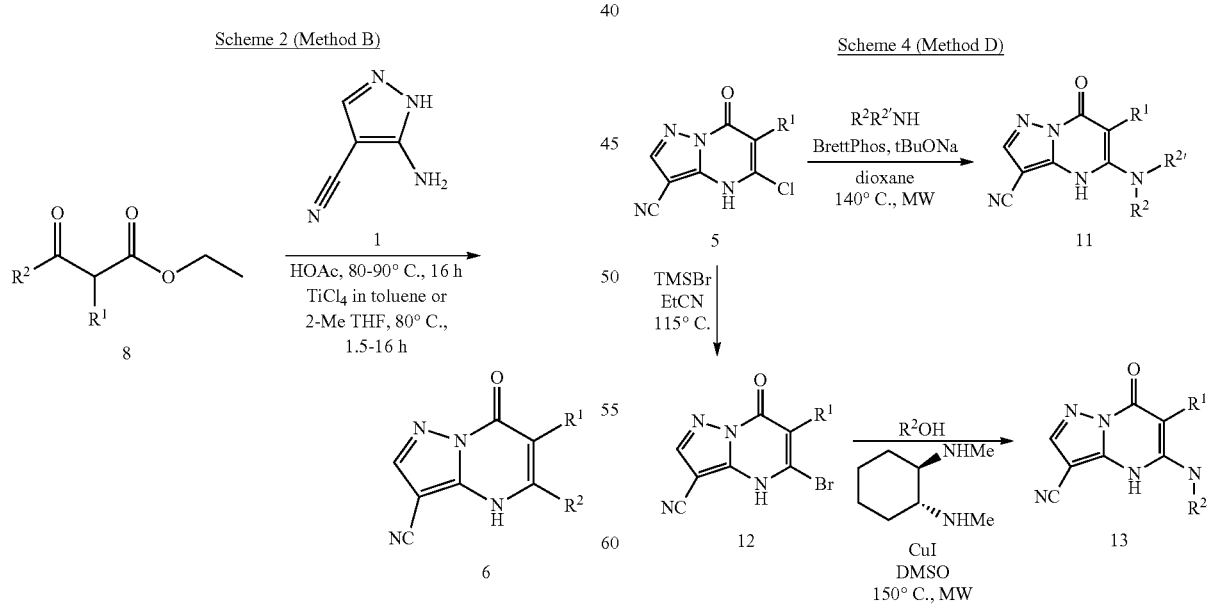

An alternative synthesis (Method B) of compound 6 is outlined in Scheme 2. 5-Amino-1H-pyrazole-4-carbonitrile (1) was condensed with ketoester 8 in the presence of acetic acid or titanium tetrachloride to afford compound 6.

Under Pd-catalyzed conditions, chloride 5 could also be coupled with an amine to give compound 11. The chloride in compound 5 could be further transformed to bromide 12, in the presence of TMSBr. Subsequent coupling reaction of bromide 12 with an alcohol provided compound 13.

General LCMS Procedures

LCMS Method A (Agilent 10-80 AB, ELSD, 2 min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting with 10% A and 90% B, going to 20% A and 80% B within 0.9 min, then holding at 20% A and 80% B for 0.6 min. Total run time was 2 min.

LCMS Method B (Agilent 0-30 AB, ELSD, 2 min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting at 100% A, going to 30% A and 70% B within 0.9 min, then holding at 30% A and 70% B for 0.6 min. Total run time was 2 min.

LCMS Method C (Agilent 0-60 AB, ELSD, 2 min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting with 100% A and going to 40% A and 60% B within 0.9 min, then holding at 40% A and 60% B for 0.6 min. Total run time was 2 min.

LCMS Method D (Agilent 30-90 AB, ELSD, 2 min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting with 30% A and 70% B, going to 10% A and 90% B within 0.9 min, then holding at 10% A and 90% B for 0.6 min. Total run time was 2 min.

LCMS Method E (SHIMADZU, 5-95 AB, ELSD, 1.5 min)

Experiments were performed on a SHIMADZU 20A HPLC (with a PDA detector) with SHIMADZU 2010EV MSD mass spectrometer using ESI as ionization source using an Merk RP-18e 2×25 mm column and a 1.5 mL/min flow rate. Solvent A was water containing 0.038% TFA, and solvent B was acetonitrile containing 0.02% TFA. A gradient was run: starting with 95% A and 5% B, going to 5% A and 95% B over the next 0.7 min. This solvent ratio was maintained for 0.4 min before returning to 95% A and 5% B over the next 0.4 min. Total run time was 1.5 min.

LCMS Method F (Agilent 5-95 AB, ELSD, 10 min)

Experiments were performed on an Agilent 6140 quadrupole LC/MS system linked to a HPLC Agilent 1200 system with a UV detector monitoring at 254 nm, and mass spectrometry scanning 90-1300 amu in ESI+ ionization mode. This system uses an Agilent SB C18 (1.8 um 30×2.1 mm) column, maintained at 25° C. and a 0.4 mL/min flow rate. Solvent A was water containing 0.05% TFA, and solvent B was acetonitrile containing 0.05% TFA. A gradient was run: starting with 95% A and 5% B for the first 0.3 min, going to 5% A and 95% B over the next 6.5 min. This solvent ratio was maintained for 1.5 min before returning to 95% A and 5% B over the next 0.1 min. Total run time was 10 min.

EXAMPLES

Example 1(Method A)

Step 1

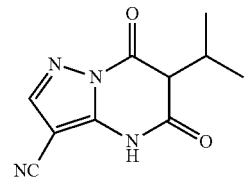 [SMILES: CC(C)C1C(=O)Nc2c(C#N)cnn2C1=O]

6-isopropyl-5,7-dioxo-4,5,6,7-tetrahydropyrazolo[1,5-a]pyrimidine-3-carbonitrile Sodium (9.0 g, 391 mmol) was added slowly to EtOH (400 mL), and the mixture was stirred at 26° C. for 1.5 hours until sodium was consumed completely. To the resultant NaOEt solution was added 5-amino-1H-pyrazole-4-carbonitrile (20 g, 185 mmol), followed by diethyl 2-isopropylmalonate (37.5 g, 185 mmol). The reaction mixture was refluxed for 16 hours. Then the reaction mixture was cooled to room temperature and diluted with MTBE (200 mL). The precipitate was collected by filtration and dissovled in water. The solution was acidified with concentrated HCl to pH 2-3 to afford an off-white precipitate, which was filtered and dried under reduced pressure to afford the desired product as a white solid (30 g, 74% yield). $^1$H NMR (400 MHz, DMSO-d$_6$) δ 8.23 (s, 1H), 3.23 (q, J=6.8 Hz, 1H), 1.20 (d, J=6.8 Hz, 6H).

Step 2

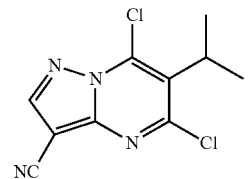 [SMILES: CC(C)c1c(Cl)nc2c(C#N)cnn2c1Cl]

5,7-dichloro-6-isopropylpyrazolo[1,5-a]pyrimidine-3-carbonitrile

6-Isopropyl-5,7-dioxo-4,5,6,7-tetrahydropyrazolo[1,5-a]pyrimidine-3-carbonitrile (30 g, 137 mmol) was added to POCl$_3$ (100 mL) in five portions, followed by N,N-dimethylaniline (17 g, 137 mmol). The reaction mixture was heated to 110° C. and stirred for 16 hours. After being cooled to room temperature, POCl$_3$ was removed under reduced pressure and the residue was diluted with water (200 mL), extracted with EtOAc (200 mL×3). Combined organics were dried over anhydrous Na$_2$SO$_4$, and concentrated. The crude residue was re-crystallized from EtOAc and hexanes (1:5) to afford the desired product as a white solid (25 g, 71% yield). $^1$H NMR (400 MHz, DMSO-d$_6$) δ 8.86 (s, 1H), 3.73-3.68 (m, 1H), 1.41 (d, J=7.2 Hz, 6H). LCMS (ESI) m/z 255.1 [M+H]$^+$, RT=1.12 min (LCMS Method A).

Step 3

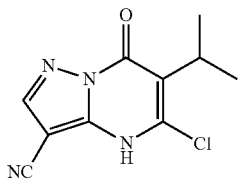 [SMILES: CC(C)c1c(Cl)[nH]c2c(C#N)cnn2c1=O]

5-chloro-6-isopropyl-7-oxo-4,7-dihydropyrazolo[1,5-a]pyrimidine-3-carbonitrile

To a solution of 5,7-dichloro-6-isopropylpyrazolo[1,5-a]pyrimidine-3-carbonitrile (10 g, 39.2 mmol) in THF (100 mL) was added aqueous NaOH solution (100 mL, 2 M). The mixture was stirred at 26° C. for 16 hours when reaction went to completion. After acidification with 1M aqueous HCl to pH=1, the mixture was extracted with EtOAc (500 mL×3). The combined organic layers were dried over anhydrous $Na_2SO_4$, and concentrated via rotavap. The crude residue was recrystallized from EtOAc/hexanes (1:5) to afford the desired product as a white solid (6.8 g, 73% yield). $^1$H NMR (400 MHz, DMSO-$d_6$) δ 8.29 (s, 1H), 3.30-3.23 (m, 1H), 1.30 (d, J=7.2 Hz, 6H). LCMS (ESI) m/z 237.2 $[M+H]^+$, RT=1.11 min (LCMS Method C).

Example 2

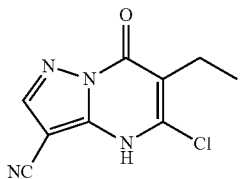

5-chloro-6-ethyl-7-oxo-4,7-dihydropyrazolo[1,5-a]pyrimidine-3-carbonitrile

In a similar procedure as shown in Example 1, the title compound was prepared in 36% yield from 5-amino-1H-pyrazole-4-carbonitrile and diethyl 2-ethylmalonate. $^1$H NMR (400 MHz, MeOH-$d_4$) δ 8.09 (s, 1H), 2.70 (q, J=7.6 Hz, 2H), 1.12 (t, J=7.6 Hz, 3H); LCMS (ESI) m/z 223.1 $[M+H]^+$, RT=1.02 min (LCMS method C).

Example 3

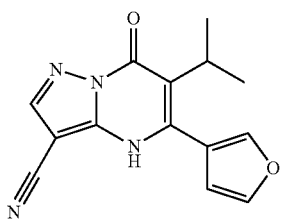

5-(furan-3-yl)-6-isopropyl-7-oxo-4,7-dihydropyrazolo[1,5-a]pyrimidine-3-carbonitrile To a solution of 5-chloro-6-isopropyl-7-oxo-4,7-dihydropyrazolo[1,5-a]pyrimidine-3-carbonitrile (200 mg, 0.845 mmol), furan-3-ylboronic acid (104 mg, 0.93 mmol) and $K_2CO_3$ (233 mg, 1.69 mmol) in dioxane: $H_2O$ (5:1, 3 mL) was added Pd(dppf)$Cl_2$ (70 mg, 0.085 mmol). The reaction vessel was sealed and heated in microwave at 110° C. for 30 minutes. After cooling to room temperature, the reaction mixture was concentrated and the residue was purified by flash column chromatography on silica gel eluting with 0-10% MeOH in DCM to give crude product, which was further purified by preparative HPLC to afford the desired product as white solid (40 mg, 18% yield). $^1$H NMR (400 MHz, DMSO-$d_6$) δ 13.26 (s, 1H), 8.35 (s, 1H), 8.09 (s, 1H), 7.88 (s, 1H), 6.74 (s, 1H), 2.90-2.85 (m, 1H), 1.26 (d, J=6.4 Hz, 6H). LCMS (ESI) m/z 269.1 $[M+H]^+$, RT=0.95 min (LCMS Method A).

Example 4

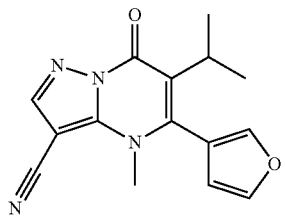

5-(furan-3-yl)-6-isopropyl-4-methyl-7-oxo-4,7-dihydropyrazolo[1,5-a]pyrimidine-3-carbonitrile To a solution of 5-(furan-3-yl)-6-isopropyl-7-oxo-4,7-dihydropyrazolo[1,5-a]pyrimidine-3-carbonitrile (320 mg, 1.19 mmol) and $K_2CO_3$ (330 mg, 2.39 mmol) in DMF (3 mL) was added MeI (0.12 mL, 1.79 mmol). After being stirred at room temperature for 6 hours, the mixture was partitioned between EtOAc (30 mL) and $H_2O$ (30 mL) and the two layers were separated. The aqueous layer was extracted with EtOAc (30 mL). The combined organic layers were washed with brine (50 mL), dried over anhydrous $Na_2SO_4$, filtered and concentrated, and the residue was purified by preparative HPLC to give the desired product as white solid (15 mg, 4% yield). $^1$H NMR (400 MHz, DMSO-$d_6$) δ 8.47 (s, 1H), 8.00 (s, 1H), 7.98 (s, 1H), 6.71 (s, 1H), 3.60 (s, 1H), 2.65-2.60 (m, 1H), 1.22 (d, J=7.2 Hz, 6H). LCMS (ESI) m/z 283.1 $[M+H]^+$, RT=1.01 min (LCMS Method A).

Example 5

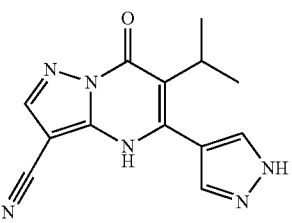

6-Isopropyl-7-oxo-5-(1H-pyrazol-4-yl)-4,7-dihydropyrazolo[1,5-a]pyrimidine-3-carbonitrile To a solution of 5-chloro-6-ethyl-7-oxo-4,7-dihydropyrazolo[1,5-a]pyrimidine-3-carbonitrile (10 g, 42.26 mmol), 4-(4,4,5,5-tetramethyl-1,3,2-dioxaborolan-2-yl)-1H-pyrazole (10.66 mg, 54.93 mmol) and Na$_2$CO$_3$ (8.96 g, 84.51 mmol) in DME: H$_2$O (2:1, 150 mL) was added Pd(dppf)Cl$_2$ (3.1 g, 4.23 mmol) under nitrogen atmosphere. The reaction mixture was heated at 110° C. for 16 hours. After being cooled to room temperature, the reaction mixture was concentrated and the residue was purified by flash column chromatography on silica gel eluting with 0-10% MeOH in DCM to provide the desired product as a brown solid (7.0 g, 62% yield). $^1$H NMR (400 MHz, DMSO-d$_6$) δ 13.42 (s, 1H), 13.09 (s, 1H), 8.36 (s, 1H), 8.17 (s, 1H), 7.78 (s, 1H), 2.97 (m, 1H), 1.29 (d, J=7.2 Hz, 6H). LCMS (ESI): m/z 269.2 [M+H]$^+$, RT=1.02 min (LCMS Method C).

Example 6

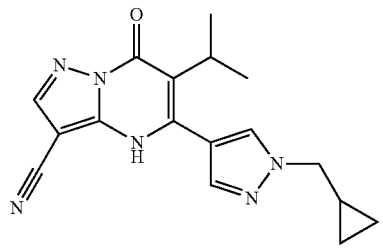 [SMILES: CC(C)c1c(-c2cnn(CC3CC3)c2)[nH]c2c(C#N)cnn2c1=O]

5-(1-(Cyclopropylmethyl)-1H-pyrazol-4-yl)-6-isopropyl-7-oxo-4,7-dihydropyrazolo[1,5-a]pyrimidine-3-carbonitrile To the mixture of 6-isopropyl-7-oxo-5-(1H-pyrazol-4-yl)-4,7-dihydropyrazolo[1,5-a]pyrimidine-3-carbonitrile (100 mg, 0.372 mmol) and (bromomethyl)cyclopropane (50 mg, 0.372 mmol) in DMF (2 mL) was added Cs$_2$CO$_3$ (364 mg, 1.12 mmol). The reaction mixture was stirred at room temperature for 16 hours. The reaction mixture was filtered and the filtrate was purified by preparative HPLC to afford the desired product (20 mg, 17% yield) as an off-white solid. $^1$H NMR (400 MHz, CD$_3$OD) δ 8.20 (s, 1H), 8.12 (s, 1H), 7.76 (s, 1H), 4.11 (d, J=7.2 Hz, 2H), 3.10-3.03 (m, 1H), 1.37 (d, J=7.2 Hz, 6H), 1.37 (m, 1H), 0.68-0.63 (m, 2H), 0.47-0.43 (m, 2H); LCMS (ESI) m/z 269.1 [M+H]$^+$, RT=0.73 min (LCMS Method E).

Example 7

Step 1

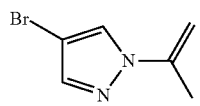

4-Bromo-1-(prop-1-en-2-yl)-1H-pyrazole

A solution of Cu(OAc)$_2$ (6.18 g, 34.02 mmol) and 2,2'-bipyridine (5.31 g, 68.04 mmol) in DCE (30 mL) was heated to 70° C. for 15 min. Then this mixture was transferred to a suspension of 4-bromo-1H-pyrazole (5 g, 34.02 mmol), potassium trifluoro(prop-1-en-2-yl)borate (10.07 g, 68.04 mmol), and Na$_2$CO$_3$ (7.21 g, 68.04 mmol) in DCE (20 mL). The mixture was stirred at 70° C. for 8 hours before being partitioned between EtOAc and 1 N HCl. The aqueous layer was extracted with EtOAc (20 mL×2) and the combined organic layers were washed with brine, dried over Na$_2$SO$_4$ and concentrated to afford crude product which was purified by flash column chromatography on silica gel (hexanes/EA=200/1) to give the desired product (4.0 g, 66% yield) as colorless oil. $^1$H NMR (400 MHz, CDCl$_3$) δ 7.70 (s, 1H), 7.54 (s, 1H), 5.28 (d, J=4.4 Hz, 1H), 4.72 (s, 1H), 2.45 (s, 3H).

Step 2

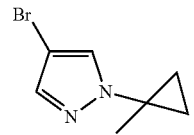

4-Bromo-1-(1-methylcyclopropyl)-1H-pyrazole

A solution of TFA (2.38 mL, 32.08 mmol) in DCM (10 mL) was added dropwise to Et$_2$Zn (1 M toluene solution, 32 mmol) in DCM (30 mL) under N$_2$ atmosphere in ice bath. After 20 min, a solution of CH$_2$I$_2$ (8.5 g, 32.08 mmol) in DCM (10 mL) was added dropwise and stirred for another 20 min. Then a solution of 4-bromo-1-(prop-1-en-2-yl)-1H-pyrazole in DCM (5 mL) was added and the ice bath was removed. After stirring at room temperature for 24 hours, the mixture was quenched with saturated NH$_4$Cl solution and extracted by DCM (20 mL×2). Combined organics were dried over anhydrous Na$_2$SO$_4$, filtered and concentrated to give the crude product which was purified by flash column chromatography on silica gel (hexanes/EA=100/1) to give the desired product (490 mg, 15% yield) as yellow oil. $^1$H NMR (400 MHz, DMSO-d$_6$) δ 7.50 (s, 1H), 7.43 (s, 1H), 1.59 (s, 3H) 1.24 (t, J=6.0 Hz, 2H), 0.91 (t, J=6.8 Hz, 2H).

Step 3

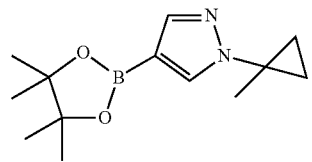 [SMILES: CC1(n2cc(B3OC(C)(C)C(C)(C)O3)cn2)CC1]

1-(1-Methylcyclopropyl)-4-(4,4,5,5-tetramethyl-1,3,2-dioxaborolan-2-yl)-1H-pyrazole A mixture of 4-bromo-1-(1-methylcyclopropyl)-1H-pyrazole (650 mg, 3.23 mmol), 4,4,4',4',5,5,5',5'-octamethyl-2,2'-bi(1,3,2-dioxaborolane) (820 mg, 3.23 mmol), Pd(PPh$_3$)$_2$Cl$_2$ (210 mg, 0.3 mmol) and CH$_3$COOK (792 mg, 8.07 mmol) in dioxane (10 mL) was heated at 100° C. for 5 hours under nitrogen atmosphere. After cooling to room temperature, the mixture was evaporated and the residue was purified by flash column chromatography on silical gel eluting with 0-10% EtOAc in hexanes to give the desired product (160 mg, 20% yield) as a white solid. $^1$H NMR (400 MHz, CDCl$_3$): δ 7.80 (s, 1H), 7.77 (s, 1H), 1.32 (s, 12H), 1.27-1.23 (m, 2H), 0.92-0.89 (m, 2H).

Step 4

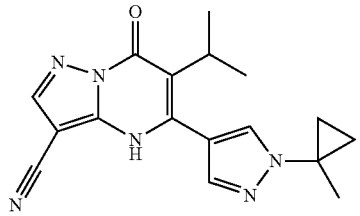 [SMILES: CC(C)c1c(-c2cnn(C3(C)CC3)c2)[nH]c2c(C#N)cnn2c1=O]

6-Isopropyl-5-(1-(1-methylcyclopropyl)-1H-pyrazol-4-yl)-7-oxo-4,7-dihydropyrazolo[1,5-a]pyrimidine-3-carbonitrile To a solution of 5-chloro-6-isopropyl-7-oxo-4,7-dihydropyrazolo[1,5-a]pyrimidine-3-carbonitrile (160 mg, 0.64 mmol), 1-(1-methylcyclopropyl)-4-(4,4,5,5-tetramethyl-1,3,2-dioxaborolan-2-yl)-1H-pyrazole (151 mg, 0.64 mmol) and Na$_2$CO$_3$ (136 mg, 1.28 mmol) in DME/H$_2$O (2/1, 3 mL) was added Pd(dppf)Cl$_2$ (44 mg, 0.06 mmol) under nitrogen atmosphere. The reaction mixture was heated at 110° C. for 30 min under microwave condition. After cooling to room temperature, the reaction mixture was concentrated and the residue was purified by flash column chromatography on silica gel eluting with 50-100% EtOAc in hexanes to give crude product which was further purified by rpHPLC (Gemini C$_{18}$ 150×25 mm×10 um, 35-65% MeCN/H$_2$O) to give the desired product (62 mg, 30% yield) as a white solid. $^1$H NMR (400 MHz, DMSO-d$_6$) δ 13.01 (s, 1H), 8.37 (s, 1H), 8.23 (s, 1H), 7.71 (s, 1H), 2.98-2.92 (m, 1H), 1.64 (s, 6H), 1.29 (d, J=7.2 Hz, 6H), 1.26-1.24 (m, 2H), 1.00-0.97 (m, 2H). LCMS (ESI) m/z 323.1 [M+H]$^+$, RT=1.18 min (LCMS Method C).

Example 8

Step 1

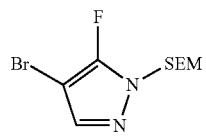

4-Bromo-5-fluoro-1-((2-(trimethylsilyl)ethoxy)methyl)-1H-pyrazole

To a solution of 4-bromo-1((2-(trimethylsilyl)ethoxy)methyl)-1H-pyrazole (5.0 g, 18.0 mmol) in THF (50 mL) at −78° C. was added LDA (18.0 mL, 36.0 mmol, 2 M in THF) dropwise under N$_2$. After stirring at −78° C. for 30 min, the reaction mixture was cooled to −100° C. and N-fluoro-N-(phenylsulfonyl)benzenesulfonamide (11.37 g, 36.0 mmol, dissolved in 50 mL of THF) was added dropwise to the reaction mixture, and the reaction mixture was stirred at −78° C. for 1 hour. The reaction was quenched with sat. NH$_4$Cl (100 mL) and extracted with methyl tert-butyl ether (100 mL). The organic layer was dried over anhydrous Na$_2$SO$_4$, filtered and concentrated to give the crude product which was purified by flash column chromatography on silica gel eluting with 0-2% EtOAc in hexanes to afford 4-bromo-5-fluoro-1-((2-(trimethylsilyl)ethoxy)methyl)-1H-pyrazole as colourless oil (460 mg, 9% yield). $^1$H NMR (400 MHz, CDCl$_3$) δ 7.42 (d, J=2.4 Hz, 1H), 5.37 (s, 2H), 3.63 (d, J=8.4 Hz, 2H), 0.93 (d, J=8.4 Hz, 2H), 0.01 (s, 9H).

Step 2

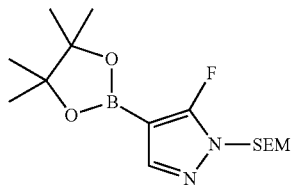 [SMILES: CC1(C)OB(c2cnn(COCC[Si](C)(C)C)c2F)OC1(C)C]

5-Fluoro-4-(4,4,5,5-tetramethyl-1,3,2-dioxaborolan-2-yl)-1-((2-(trimethylsilyl)ethoxy)methyl)-1H-pyrazole To a solution of 4-bromo-5-fluoro-1-((2-(trimethylsilyl)ethoxy)methyl)-1H-pyrazole (460 mg, 1.56 mmol) in THF (10 mL) was added iPrMgBr (4.67 mL, 4.67 mmol, 1 M in THF) at 0° C., and the reaction was allowed to stir at room temperature for 1 hour. 2-methoxy-4,4,5,5-tetramethyl-1,3,2-dioxaborolane (985 mg, 6.23 mmol) was then added, and the mixture was stirred at room temperature for 2 hours. The reaction was quenched with sat. NH$_4$Cl (20 mL) and extracted with methyl tert-butyl ether (50 mL). The organic layer was dried over anhydrous Na$_2$SO$_4$, filtered and concentrated to give the crude target which was purified by flash column chromatography on silica gel eluting with 0-3% EtOAc in hexanes to afford the desired product (360 mg, 68% yield) as colorless oil. $^1$H NMR (400 MHz, CDCl$_3$) δ 7.63 (d, J=3.2 Hz, 1H), 5.35 (s, 2H), 3.62 (d, J=8.0 Hz, 2H), 1.33 (s, 12H), 0.91 (d, J=8.0 Hz, 2H), 0.02 (s, 9H).

Step 3

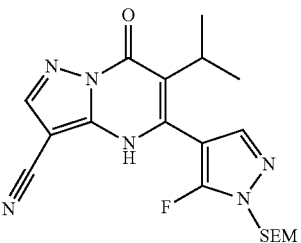 [SMILES: CC(C)c1c(-c2cnn(COCC[Si](C)(C)C)c2F)[nH]c2c(C#N)cnn2c1=O]

5-(5-Fluoro-1-((2-(trimethylsilyl)ethoxy)methyl)-1H-pyrazol-4-yl)-6-isopropyl-7-oxo-4,7-dihydropyrazolo[1,5-a]pyrimidine-3-carbonitrile To a solution of 5-chloro-6-isopropyl-7-oxo-4,7-dihydropyrazolo[1,5-a]pyrimidine-3-carbonitrile (144 mg, 0.61 mmol), 5-fluoro-4-(4,4,5,5-tetramethyl-1,3,2-dioxaborolan-2-yl)-1-((2-(trimethylsilyl)ethoxy)methyl)-1H-pyrazole (260 mg, 0.76 mmol) and Na$_2$CO$_3$ (161 mg, 1.52 mmol) in DME:H$_2$O (2:1, 3 mL) was added Pd(dppf)Cl$_2$ (56 mg, 0.076 mmol) under nitrogen atmosphere. The reaction mixture was heated at 110° C. for 30 min under microwave condition. After being cooled to room temperature, the reaction mixture was concentrated and the residue was purified by flash column chromatography on silica gel eluting with 0-3% MeOH in DCM to provide the desired product (220 mg crude) as a brown solid. LCMS m/z 417.0 [M+H]⁺.

Step 4

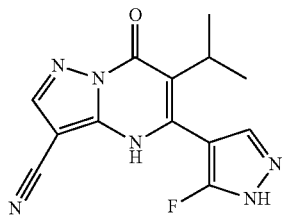 [SMILES: CC(C)c1c(-c2cn[nH]c2F)[nH]c2c(C#N)cnn2c1=O]

5-(5-Fluoro-1H-pyrazol-4-yl)-6-isopropyl-7-oxo-4,7-dihydropyrazolo[1,5-a]pyrimidine-3-carbonitrile To a solution of 5-(5-fluoro-1-((2-(trimethylsilyl)ethoxy)methyl)-1H-pyrazol-4-yl)-6-isopropyl-7-oxo-4,7-dihydropyrazolo[1,5-a]pyrimidine-3-carbonitrile (220 mg crude) in anhydrous DCM (4 mL) was added TFA (2 mL). The reaction mixture was stirred at room temperature for 1 hour. The reaction mixture was concentrated and the residue was redissolved in HCl/dioxane (20 mL). The reaction mixture was stirred at room temperature for 16 hours and concentrated to give crude product (150 mg) which was used directly in next step. LCMS m/z 286.9 [M+H]⁺.

Step 5

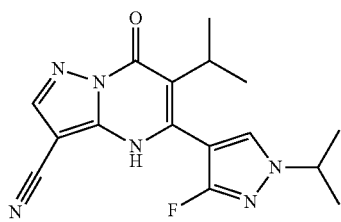 [SMILES: CC(C)c1c(-c2cn(C(C)C)nc2F)[nH]c2c(C#N)cnn2c1=O]

5-(3-Fluoro-1-isopropyl-1H-pyrazol-4-yl)-6-isopropyl-7-oxo-4,7-dihydropyrazolo[1,5-a]pyrimidine-3-carbonitrile To a solution of 5-(5-fluoro-1H-pyrazol-4-yl)-6-isopropyl-7-oxo-4,7-dihydropyrazolo[1,5-a]pyrimidine-3-carbonitrile (150 mg crude, 0.53 mmol) and 2-iodopropane (71 mg, 0.42 mmol) in DMF (3 mL) was added $Cs_2CO_3$ (345 mg, 1.06 mmol). The reaction mixture was stirred at room temperature for 16 hours. The reaction mixture was filtered and purified by rpHPLC (Gemini $C_{18}$ 150×25 mm, ×10 um, 33-63% MeCN/$H_2O$) to give the title compound (25 mg, 18% yield) as a white solid. ¹H NMR (400 MHz, DMSO-$d_6$) δ 13.24 (s, 1H), 8.39 (s, 1H), 8.14 (s, 1H), 4.54-4.73 (m, 1H), 2.84-2.77 (m, 1H), 1.44 (d, J=6.4 Hz, 6H), 1.28 (d, J=7.2 Hz, 6H). LCMS (ESI): m/z 329.1 [M+H]⁺, RT=1.23 min (LCMS Method C).

Example 9

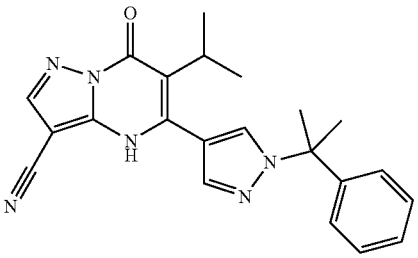 [SMILES: CC(C)c1c(-c2cnn(C(C)(C)c3ccccc3)c2)[nH]c2c(C#N)cnn2c1=O]

6-Isopropyl-7-oxo-5-(1-(2-phenylpropan-2-yl)-1H-pyrazol-4-yl)-4,7-dihydropyrazolo[1,5-a]pyrimidine-3-carbonitrile To a mixture of 6-isopropyl-7-oxo-5-(1H-pyrazol-3-yl)-4,7-dihydropyrazolo[1,5-a]pyrimidine-3-carbonitrile (200 mg, 0.75 mmol) and 2-phenylpropan-2-ol (2 mL) was added concentrated sulfuric acid (41 μL, 0.75 mmol). The reaction was heated to 100° C. for 20 min under microwave irradiation. The reaction was quenched with sat. NaHCO₃ (10 mL) and extracted with ethyl acetate (20 mL). The organic phase was dried over anhydrous $Na_2SO_4$, filtered and concentrated. The residue was purified by rpHPLC (Gemini $C_{18}$ 150×25 mm×10 um, 50-80% MeCN/$H_2O$) to give the desired product (140 mg, 49% yield) as a white solid. ¹H NMR (400 MHz, DMSO-$d_6$) δ 13.06 (s, 1H), 8.38 (s, 1H), 8.31 (s, 1H), 7.81 (s, 1H), 7.35-7.31 (m, 2H), 7.28-7.24 (m, 1H), 7.08 (d, J=7.2 Hz, 2H), 3.02-2.95 (m, 1H), 1.99 (s, 6H), 1.30 (d, J=7.2 Hz, 6H). LCMS (ESI): m/z 387.1 [M+H]⁺, RT=1.12 min (LCMS Method A).

Example 10

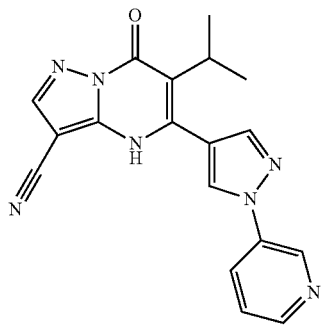 [SMILES: CC(C)c1c(-c2cnn(-c3cccnc3)c2)[nH]c2c(C#N)cnn2c1=O]

6-Isopropyl-7-oxo-5-(1-(pyridin-3-yl)-1H-pyrazol-4-yl)-4,7-dihydropyrazolo[1,5-a]pyrimidine-3-carbonitrile A mixture of 6-isopropyl-7-oxo-5-(1H-pyrazol-4-yl)-4,7-dihydropyrazolo[1,5-a]pyrimidine-3-carbonitrile (200 mg, 0.75 mmol), 3-iodopyridine (306 mg, 1.49 mmol), CuI (7 mg, 0.04 mmol), L-proline (9 mg, 0.075 mmol) and $K_2CO_3$ (103 mg, 0.75 mmol) in DMSO (5 mL) was heated at 120° C. for 16 hours under a nitrogen atmosphere. After cooling, the mixture was filtered and the filtrate was evaporated. The residue was purified by rpHPLC (ASB $C_{18}$ 150*25 mm, 40% MeCN/$H_2O$) to give the desired product as its HCl salt (25 mg, 10% yield) as a white solid. $^1$H NMR (400 MHz, DMSO-$d_6$) δ 13.33 (s, 1H), 9.31 (s, 1H), 9.10 (s, 1H), 8.70 (s, 1H), 8.54 (d, J=8.4 Hz, 1H), 8.42 (s, 1H), 8.16 (s, 1H), 7.80 (dd, J=8.4, 4.8 Hz, 1H), 3.01-2.95 (m, 1H), 1.32 (d, J=7.2 Hz, 6H). LCMS (ESI): m/z 346.0 [M+H]$^+$, RT=1.08 min (LCMS Method C).

Example 11

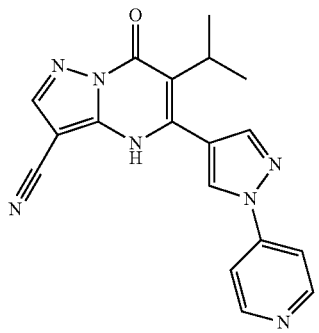 [SMILES: CC(C)c1c(-c2cnn(-c3ccncc3)c2)[nH]c2c(C#N)cnn2c1=O]

6-Isopropyl-7-oxo-5-(1-(pyridin-4-yl)-1H-pyrazol-4-yl)-4,7-dihydropyrazolo[1,5-a]pyrimidine-3-carbonitrile In a similar procedure as shown in Example 10, this compound was prepared in 10% yield from 4-iodopyridine. $^1$H NMR (400 MHz, DMSO-$d_6$): δ 9.36 (s, 1H), 9.01 (brs, 2H), 8.45-8.43 (m, 3H), 8.33 (s, 1H), 2.94-2.90 (m, 1H), 1.32 (d, J=6.8 Hz, 6H). LCMS (ESI): m/z 346.1 [M+H]$^+$, RT=0.95 min (LCMS Method C).

Example 12

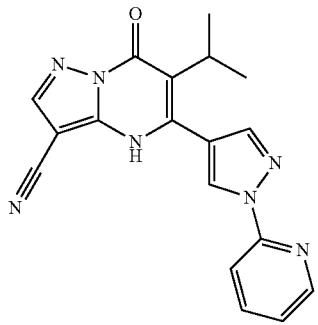 [SMILES: CC(C)c1c(-c2cnn(-c3ccccn3)c2)[nH]c2c(C#N)cnn2c1=O]

6-Isopropyl-7-oxo-5-(1-(pyridin-2-yl)-1H-pyrazol-4-yl)-4,7-dihydropyrazolo[1,5-a]pyrimidine-3-carbonitrile To a solution of 6-isopropyl-7-oxo-5-(1H-pyrazol-4-yl)-4,7-dihydropyrazolo[1,5-a]pyrimidine-3-carbonitrile (200 mg, 0.75 mmol) in DMF (5 mL) was added NaH (60% dispersion in mineral oil, 90 mg, 2.25 mmol) in DMF (5 mL) at 0° C. under $N_2$. After stirring at 0° C. for 30 min, 2-fluoropyridine (109 mg, 1.12 mmol) was added in portions. After addition, the resultant mixture was heated at 70° C. for 5 hours. The reaction was quenched with sat. $NH_4Cl$ (20 mL) and extracted with ethyl acetate (2×20 mL). The organic layers were dried over anhydrous $Na_2SO_4$, filtered and concentrated. The residue was purified by rpHPLC (ASB $C_{18}$ 150×25 mm, 40-70% MeCN/$H_2O$) to give the desired product (35 mg, 14% yield) as a white solid. $^1$H NMR (400 MHz, DMSO-$d_6$) δ 13.29 (s, 1H), 9.01 (s, 1H), 8.55 (d, J=4.4 Hz, 2H), 8.41 (s, 1H), 8.11-8.07 (m, 2H), 8.02 (d, J=8.0 Hz, 1H), 7.47-7.44 (m, 1H), 3.01-2.94 (m, 1H), 1.32 (d, J=7.2 Hz, 6H); LCMS (ESI): m/z 346.0 [M+H]$^+$, RT=1.24 min (LCMS Method C).

Example 13

Step 1

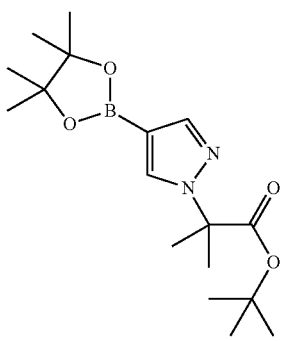 [SMILES: CC(C)(C)OC(=O)C(C)(C)n1cc(B2OC(C)(C)C(C)(C)O2)cn1]

Tert-butyl 2-methyl-2-(4-(4,4,5,5-tetramethyl-1,3,2-dioxaborolan-2-yl)-1H-pyrazol-1-yl)propanoate To a solution of 4-(4,4,5,5-tetramethyl-1,3,2-dioxaborolan-2-yl)-1H-pyrazole (5.0 g, 25.8 mmol) and tert-butyl 2-bromo-2-methylpropanoate (6.32 g, 28.3 mmol) in DMF (50 mL) was added $Cs_2CO_3$ (12.59 g, 38.65 mmol). The reaction mixture was stirred at room temperature for 16 hours. The mixture was filtered and partitioned between methyl tert-butyl ether (100 mL) and $H_2O$ (100 mL). The combined organic layer was separated, washed with brine, dried over anhydrous $Na_2SO_4$ and concentrated to afford crude product which was purified by flash column chromatography on silica gel eluting with 0-10% EtOAc in hexanes to give the desired product (7.0 g, 81% yield) as a white solid. $^1$H NMR (400 MHz, CDCl$_3$) δ 7.87 (s, 1H), 7.84 (s, 1H), 1.81 (s, 6H), 1.39 (s, 9H), 1.37 (s, 12H).

Step 2

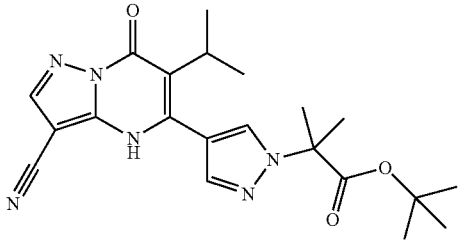 [SMILES: CC(C)c1c(-c2cnn(C(C)(C)C(=O)OC(C)(C)C)c2)[nH]c2c(C#N)cnn2c1=O]

Tert-butyl 2-(4-(3-cyano-6-isopropyl-7-oxo-4,7-dihydropyrazolo[1,5-a]pyrimidin-5-yl)-1H-pyrazol-1-yl)-2-methylpropanoate To a solution of 5-chloro-6-isopropyl-7-oxo-4,7-dihydropyrazolo[1,5-a]pyrimidine-3-carbonitrile (1.0 g, 4.2 mmol), tert-butyl 2-methyl-2-(4-(4,4,5,5-tetramethyl-1,3,2-dioxaborolan-2-yl)-1H-pyrazol-1-yl)propanoate (2.12 g, 6.3 mmol) and $Na_2CO_3$ (890 mg, 8.4 mmol) in DME: $H_2O$ (2/1, 30 mL) was added $Pd(dppf)Cl_2$ (307 mg, 0.042 mmol) under nitrogen atmosphere. The reaction mixture was heated at 110° C. for 16 hours. After being cooled to room temperature, the reaction mixture was concentrated and the residue was purified by flash column chromatography on silica gel eluting with 0-3% MeOH in DCM to provide the crude product which was re-crystallized from TBME/MeOH (5/1, 20 mL) to give the desired product (760 mg, 44% yield) as a brown solid. $^1$H NMR (400 MHz, DMSO-$d_6$) δ 13.16 (brs, 1H), 8.35 (s, 1H), 8.23 (s, 1H), 7.77 (S, 1H), 2.99-2.96 (m, 1H), 1.79 (s, 6H), 1.34 (s, 9H), 1.29 (d, J=6.8 Hz, 2H).
Step 3

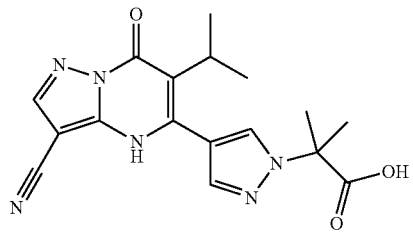 [SMILES: CC(C)c1c(-c2cnn(C(C)(C)C(=O)O)c2)[nH]c2c(C#N)cnn2c1=O]

2-(4-(3-Cyano-6-isopropyl-7-oxo-4,7-dihydropyrazolo[1,5-a]pyrimidin-5-yl)-1H-pyrazol-1-yl)-2-methylpropanoic acid A mixture of tert-butyl 2-(4-(3-cyano-6-isopropyl-7-oxo-4,7-dihydropyrazolo[1,5-a]pyrimidin-5-yl)-1H-pyrazol-1-yl)-2-methylpropanoate (500 mg, 1.22 mmol) in HCl/dioxane (20 mL) was stirred at room temperature for 16 hours. The mixture was evaporated to give crude product as a brown solid which was used directly for next step. $^1$H NMR (400 MHz, DMSO-$d_6$) δ 13.13 (brs, 1H), 8.37 (s, 1H), 8.28 (s, 1H), 7.77 (s, 1H), 3.01-2.94 (m, 1H), 1.81 (s, 6H), 1.30 (d, J=7.2 Hz, 2H).
Step 4

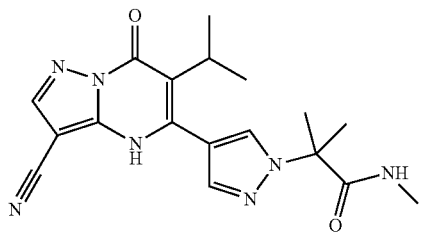 [SMILES: CNC(=O)C(C)(C)n1cc(-c2[nH]c3c(C#N)cnn3c(=O)c2C(C)C)cn1]

2-(4-(3-Cyano-6-isopropyl-7-oxo-4,7-dihydropyrazolo[1,5-a]pyrimidin-5-yl)-1H-pyrazol-1-yl)-N,2-dimethylpropanamide To a solution of 2-(4-(3-cyano-6-isopropyl-7-oxo-4,7-dihydropyrazolo[1,5-a]pyrimidin-5-yl)-1H-pyrazol-1-yl)-2-methylpropanoic acid (100 mg, 0.24 mmol) and methanamine hydrochloride (32 mg, 0.48 mmol) in DMF (2 mL) was added HATU (137 mg, 0.36 mmol) and DIPEA (124 mg, 0.96 mmol). The reaction mixture was stirred at room temperature for 16 hours. The reaction mixture was purified by rpHPLC (Gemini $C_{18}$ 150×25 mm×10 um, 6-36% MeCN/$H_2O$) to give the desired product (28 mg, 32% yield) as a white solid. $^1$H NMR (400 MHz, DMSO-$d_6$) δ 13.02 (brs, 1H), 8.37 (s, 1H), 8.21 (s, 1H), 7.78 (s, 1H), 7.56 (d, J=4.0 Hz, 1H), 3.03-3.00 (m, 1H), 2.61 (d, J=4.8 Hz, 3H), 1.77 (s, 6H), 1.31 (d, J=6.8 Hz, 6H). LCMS (ESI): m/z 368.1 [M+H]$^+$, RT=1.08 min (LCMS Method C).

Example 14

Step 1

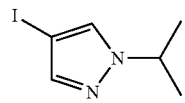

4-Iodo-1-isopropyl-1H-pyrazole

To a stirred solution of 4-iodo-1H-pyrazole (5 g, 25.8 mmol) and $Cs_2CO_3$ (25.2 g, 77.3 mmol) in DMF (50 mL) was added 2-iodopropane (5.26 g, 30.9 mmol). The mixture was stirred at 10° C. for 16 hours. $Cs_2CO_3$ was removed by filtration. The filtrate was diluted with $H_2O$ (50 mL) and extracted with EtOAc (50 mL). The organic layer was washed with water (20 mL×6). The organic was dried over $Na_2SO_4$, concentrated to give the desired product (5.2 g, 85% yield) as colourless oil. $^1$H NMR (400 MHz, $CD_3OD$) δ 7.75 (s, 1H), 7.47 (s, 1H), 4.55-4.48 (m, 1H), 1.45 (d, J=6.8 Hz, 6H).

Step 2

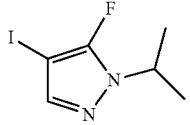

5-Fluoro-4-iodo-1-isopropyl-1H-pyrazole

The solution of 4-iodo-1-isopropyl-1H-pyrazole (2.0 g, 8.47 mmol) in THF (20 mL) was cooled to −78° C. LDA (8.47 mL, 16.94 mmol, 2 M in THF) was added dropwise to the solution at −78° C. and then stirred at −78° C. for 30 min. The reaction mixture was cooled to −100° C. and N-fluoro-N-(phenylsulfonyl)benzenesulfonamide (10.7 g, 33.89 mmol, dissolved in 20 mL THF) was added dropwise to the reaction mixture. The reaction mixture was stirred at −78° C. for 1 hour. Saturated $NH_4Cl$ (50 mL) was added to quench the reaction and then extracted with EtOAc (50 mL×3). Combined organic layers were dried over $Na_2SO_4$, filtered and concentrated to give the crude target which was purified by flash column chromatography on silica gel eluting with 0-2% EtOAc in hexanes to afford the desired crude product as colourless oil.

Step 3

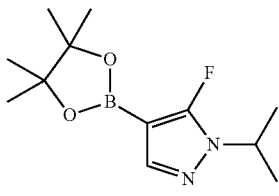 [SMILES: CC(C)n1ncc(B2OC(C)(C)C(C)(C)O2)c1F]

5-Fluoro-1-isopropyl-4-(4,4,5,5-tetramethyl-1,3,2-dioxaborolan-2-yl)-1H-pyrazole A solution of 5-fluoro-4-iodo-1-isopropyl-1H-pyrazole (400 mg, 1.58 mmol) in THF (5 mL) was added 1 M of iPrMgBr (4.7 mL, 4.7 mmol) in THF at 0° C., and the reaction was allowed to stir for 1 hour. 2-methoxy-4,4,5,5-tetramethyl-1,3,2-dioxaborolane (1 g, 6.32 mmol) was then added, and the mixture was stirred at 10° C. for 2 hours. Saturated $NH_4Cl$ (10 mL) was added to quench the reaction. Then the organic solvent was removed in vacuo. The remaining aqueous layer was extracted with DCM (10 mL×3). Combined organic layers were dried over $Na_2SO_4$, filtered and concentrated to give the crude target which was purified by flash column chromatography on silica gel eluting with 0-3% EtOAc in hexanes to afford the desired crude product as colourless oil.

Step 4

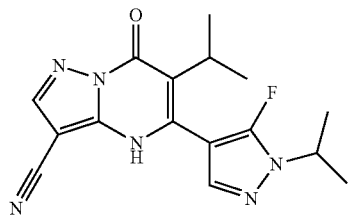

5-(5-Fluoro-1-isopropyl-1H-pyrazol-4-yl)-6-isopropyl-7-oxo-4,7-dihydropyrazolo[1,5-a]pyrimidine-3-carbonitrile In a similar procedure as shown in Example 3, the title compound was prepared in 14% yield from 6-isopropyl-7-oxo-5-(1H-pyrazol-4-yl)-4,7-dihydropyrazolo[1,5-a]pyrimidine-3-carbonitrile and 5-fluoro-1-isopropyl-4-(4,4,5,5-tetramethyl-1,3,2-dioxaborolan-2-yl)-1H-pyrazole as an off white solid. $^1$H NMR (400 MHz, $CD_3OD$) δ 8.09 (s, 1H), 7.55 (d, J=3.2 Hz, 1H), 4.69-4.55 (m, 1H), 2.99-2.93 (m, 1H), 1.51 (d, J=6.8 Hz, 6H), 1.36 (d, J=6.8 Hz, 6H). LCMS (ESI): m/z 329.1 [M+H]$^+$, RT=1.01 min (LCMS method C).

Example 15 and 16

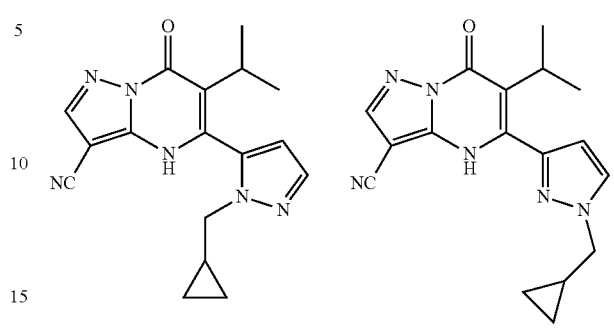

5-(1-(cyclopropylmethyl)-1H-pyrazol-5-yl)-6-isopropyl-7-oxo-4,7-dihydropyrazolo[1,5-a]pyrimidine-3-carbonitrile and 5-(1-(cyclopropylmethyl)-1H-pyrazol-3-yl)-6-isopropyl-7-oxo-4,7-dihydropyrazolo[1,5-a]pyrimidine-3-carbonitrile A mixture of 6-isopropyl-7-oxo-5-(1H-pyrazol-3-yl)-4H-pyrazolo[1,5-a]pyrimidine-3-carbonitrile (0.224 mmol, 60 mg), (iodomethyl)cyclopropane (0.671 mmol, 126 mg) and $Cs_2CO_3$ (0.671 mmol, 219 mg) in DMF (2 mL) was stirred at room temperature for 7 hours. The reaction mixture was filtered and the filtrate was purified by preparative HPLC to afford the desired products as white solids.

1$^{st}$ eluting peak: 5-[2-(cyclopropylmethyl)pyrazol-3-yl]-6-isopropyl-7-oxo-4H-pyrazolo[1,5-a]pyrimidine-3-carbonitrile, 5.6 mg, 7.8% yield. $^1$H NMR (DMSO-d$_6$) δ: 13.63 (s, 1H), 8.37 (s, 1H), 7.67-7.60 (m, 1H), 6.59-6.47 (m, 1H), 3.93 (d, J=7.0 Hz, 2H), 1.37-1.09 (m, 8H), 0.51-0.38 (m, 2H), 0.33-0.18 (m, 2H). LCMS (ESI): m/z 323.2 [M+H]$^+$, RT=4.52 min (LCMS Method F).

2$^{nd}$ eluting peak: 5-[1-(cyclopropylmethyl)pyrazol-3-yl]-6-isopropyl-7-oxo-4H-pyrazolo[1,5-a]pyrimidine-3-carbonitrile, 11.6 mg, 16.1% yield. $^1$H NMR (DMSO-d$_6$) δ: 13.21 (s, 1H), 8.36 (s, 1H), 8.00 (d, J=2.3 Hz, 1H), 6.62 (d, J=2.3 Hz, 1H), 4.10 (d, J=7.1 Hz, 2H), 3.13 (p, J=6.9 Hz, 1H), 1.36-1.29 (m, 1H), 1.28 (d, J=7.0 Hz, 6H), 0.62-0.53 (m, 2H), 0.45-0.38 (m, 2H). LCMS (ESI): m/z 323.2 [M+H]$^+$, RT=4.83 min (LCMS Method F).

Example 17

Step 1

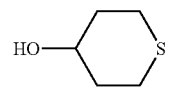

Tetrahydro-2H-thiopyran-4-ol

To the reaction mixture of dihydro-2H-thiopyran-4(3H)-one (2.0 g, 16.92 mmol) in MeOH (20 mL) was added $NaBH_4$ (1.95 g, 51.64 mmol) at 0° C. The reaction mixture was stirred at 10° C. for 1 hour. The reaction was quenched with saturated $NH_4Cl$ (20 mL), extracted with EtOAc (20 mL×3). Combined organic layers were dried over $Na_2SO_4$, filtered and concentrated to give the desired crude product as colourless oil.

Step 2

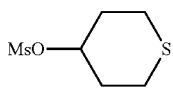

Tetrahydro-2H-thiopyran-4-yl methanesulfonate

To the reaction mixture of tetrahydro-2H-thiopyran-4-ol (2.0 g, 16.92 mmol) and Et$_3$N (3.42 g, 33.84 mmol) in DCM (20 mL) was added MsCl (2.91 g, 25.38 mmol) at 0° C. The reaction mixture was stirred at 10° C. for 2 hours. The reaction mixture was washed with saturated NaHCO$_3$, extracted with EtOAc (20 mL×3). Combined organic layers were dried over Na$_2$SO$_4$, filtered and concentrated to give the desired crude product as white solid.

Step 3

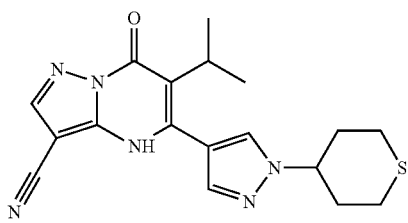 [SMILES: CC(C)c1c(-c2cnn(C3CCSCC3)c2)[nH]c2c(C#N)cnn2c1=O]

6-isopropyl-7-oxo-5-(1-(tetrahydro-2H-thiopyran-4-yl)-1H-pyrazol-4-yl)-4,7-dihydropyrazolo[1,5-a]pyrimidine-3-carbonitrile In a similar procedure as shown in Example 6, the title compound was prepared in 12% yield as an off white solid. $^1$H NMR (400 MHz, CD$_3$OD) δ 8.09 (s, 1H), 7.95 (s, 1H), 7.68 (s, 1H), 4.29-4.24 (m, 1H), 3.16-3.09 (m, 1H), 2.96-2.85 (m, 2H), 2.82-2.71 (m, 2H), 2.48-2.35 (m, 2H), 2.26-2.10 (m, 2H), 1.37 (d, J=6.8 Hz, 6H). LCMS (ESI) m/z 369.1 [M+H]$^+$, RT=1.01 min (LCMS method C).

Example 18

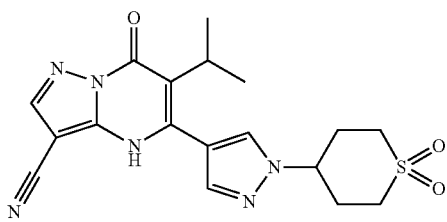 [SMILES: CC(C)c1c(-c2cnn(C3CCS(=O)(=O)CC3)c2)[nH]c2c(C#N)cnn2c1=O]

5-(1-(1,1-Dioxidotetrahydro-2H-thiopyran-4-yl)-1H-pyrazol-4-yl)-6-isopropyl-7-oxo-4,7-dihydropyrazolo[1,5-a]pyrimidine-3-carbonitrile To a solution of 6-isopropyl-7-oxo-5-(1-(tetrahydro-2H-thiopyran-4-yl)-1H-pyrazol-4-yl)-4,7-dihydropyrazolo[1,5-a]pyrimidine-3-carbonitrile (65 mg, 0.176 mmol) in MeOH (6 mL) at 0° C. was added dropwise a solution of oxone (271 mg, 0.441 mmol) in water (6 mL) and the reaction mixture was stirred at 10° C. for 16 hours. The solvent was removed under reduced pressure. The residue was purified by preparative HPLC to afford the desired product (20 mg, 29% yield) as an off-white solid. $^1$H NMR (400 MHz, CD$_3$OD) δ 8.12 (s, 1H), 8.03 (s, 1H), 7.73 (s, 1H), 4.70-4.24 (m, 1H), 3.39-3.36 (m, 4H), 3.13-3.09 (m, 1H), 2.70-2.65 (m, 2H), 2.52-2.48 (m, 2H), 1.37 (d, J=7.2 Hz, 6H). LCMS (ESI): m/z 401.1 [M+H]$^+$, RT=0.85 min (LCMS Method C).

Example 19

Step 1

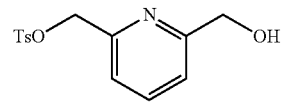 [SMILES: Cc1ccc(S(=O)(=O)OCc2cccc(CO)n2)cc1]

(6-(Hydroxymethyl)pyridin-2-yl)methyl 4-methylbenzenesulfonate

To a solution of pyridine-2,6-diyldimethanol (1 g, 7.19 mmol) in DCM (20 mL) was added Ag$_2$O (2.5 g, 10.78 mmol) and KI (119 mg, 0.72 mmol). The resulting mixture was cooled to −20° C. and was added TsCl (1.51 g, 7.19 mmol) in DCM (10 mL). The resulting mixture was stirred at room temperature for 3 hours. The reaction mixture was concentrated, and purified by flash column chromatography on silica gel (PE/EtOAc=1/1) to give the desired product (800 mg, 40% yield) as white solid.

Step 2

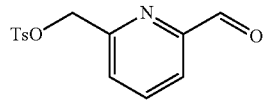

(6-Formylpyridin-2-yl)methyl 4-methylbenzenesulfonate

To a solution of (6-(hydroxymethyl)pyridin-2-yl)methyl 4-methylbenzenesulfonate (800 mg, 2.73 mmol) in DCM (10 mL) was added MnO$_2$ (2.37 g, 27.27 mmol). The resulting mixture was stirred at room temperature for 24 hours. The solid was removed by filtration and the filtrate was concentrated to dryness to give the desired crude product (500 mg, 63% yield) as white solid.

Step 3

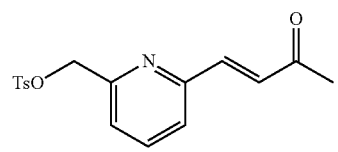 [SMILES: CC(=O)/C=C/c1cccc(COS(=O)(=O)c2ccc(C)cc2)n1]

(E)-(6-(3-oxobut-1-en-1-yl)pyridin-2-yl)methyl 4-methylbenzenesulfonate

To a solution of (6-formylpyridin-2-yl)methyl 4-methylbenzenesulfonate (500 mg, 1.72 mmol) in toluene (20 mL) was added 1-(triphenylphosphoranylidene)propan-2-one (525 mg, 1.65 mmol). The resulting mixture was stirred at 110° C. under N₂ for 16 hours, The reaction mixture was concentrated, and was purified by flash column chromatography on silica gel (PE/EtOAc=3/1) to give the desired product (400 mg, 71% yield) as white solid.

Step 4

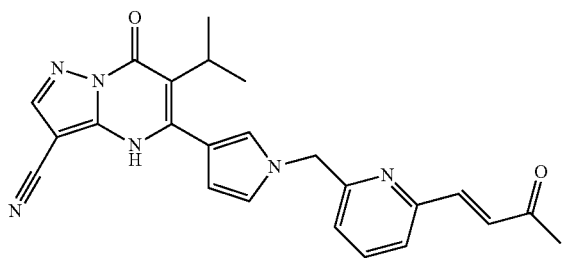 [SMILES: CC(=O)/C=C/c1cccc(Cn2ccc(-c3[nH]c4c(C#N)cnn4c(=O)c3C(C)C)c2)n1]

(E)-6-isopropyl-7-oxo-5-(1-((6-(3-oxobut-1-en-1-yl)pyridin-2-yl)methyl)-1H-pyrazol-4-yl)-4,7-dihydropyrazolo[1,5-a]pyrimidine-3-carbonitrile To a solution of 6-isopropyl-7-oxo-5-(1H-pyrazol-4-yl)-4,7-dihydropyrazolo[1,5-a]pyrimidine-3-carbonitrile (100 mg, 0.3 mmol) in DMF (5 mL) was added (E)-(6-(3-oxobut-1-en-1-yl)pyridin-2-yl)methyl 4-methylbenzenesulfonate (99 mg, 0.3 mmol), KI (5 mg, 0.03 mmol) and Cs₂CO₃ (292 mg, 0.9 mmol). The resulting mixture was stirred at room temperature for 2 hours and was purified by preparative HPLC to afford the desired product (29 mg, 23% yield) as yellow solid. ¹HNMR (400 MHz, DMSO-d₆) δ 13.12 (s, 1H), 8.36 (2s, 2H), 7.91 (m, 1H), 7.81 (m, 1H), 7.71-7.59 (m, 2H), 7.21 (m, 1H), 7.05 (m, 1H), 5.60 (s, 2H), 2.99-2.95 (m, 1H), 2.36 (s, 3H), 1.30 (s, 6H). LCMS (ESI): m/z 428.1 [M+H]⁺, RT=0.78 min (LCMS Method E).

Example 20 (Method B)

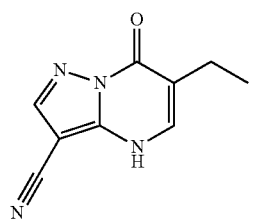

6-Ethyl-7-oxo-4,7-dihydropyrazolo[1,5-a]pyrimidine-3-carbonitrile

A mixture of methyl 2-formylbutanoate (3.2 g, 24.6 mmol) and 5-amino-1H-pyrazole-4-carbonitrile (1.3 g, 12 mmol) in acetic acid (8 mL) was stirred at 80° C. for 16 hours. The reaction mixture was concentrated and the residue was triturated with methyl tert-butyl ether (20 mL) to give the desired product (1.4 g, 63% yield) as white solid; ¹H NMR (400 MHz, DMSO-d₆) δ 13.36 (s, 1H), 8.37 (s, 1H), 7.85 (s, 1H), 2.42-2.48 (q, J=7.6 Hz, 2H), 1.13 (t, J=7.6 Hz, 3H). LCMS (ESI): m/z 189.1 [M+H]⁺, RT=0.86 min (LCMS Method C).

Example 21

Step 1

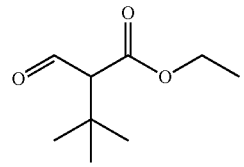

Ethyl 2-formyl-3,3-dimethylbutanoate

To a solution of diethyl 2-(tert-butyl)malonate (500 mg, 2.31 mmol) in anhydrous DCM (5 mL) at −78° C. under nitrogen atmosphere was added DIBAL-H (1.0 M in toluene, 4.62 mL, 4.62 mmol) dropwise. The resulting mixture was stirred at −78° C. for 3 hours. The reaction mixture was quenched with saturated aqueous NH₄Cl solution (10 mL). The cold bath was removed. Aqueous HCl solution (1.0 M, 10 mL) and D,L-tartaric acid (560 mg) were added sequentially and the mixture was warmed up to room temperature with vigorous stirring. The biphase mixture was then partitioned between aqueous HCl solution (1.0 M, 20 mL) and DCM (20 mL). The organic phase was separated, dried over anhydrous Na₂SO₄, filtered, and concentrated to give the crude product, which was used for the next step without further purification.

Step 2

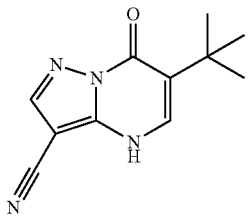 [SMILES: CC(C)(C)c1c[nH]c2c(C#N)cnn2c1=O]

6-(tert-Butyl)-7-oxo-4,7-dihydropyrazolo[1,5-a]pyrimidine-3-carbonitrile

To a solution of ethyl 2-formyl-3,3-dimethylbutanoate (2.0 g crude, 2.31 mmol) in acetic acid (3.0 mL) was added 5-amino-1H-pyrazole-4-carbonitrile (77 mg, 0.7 mmol). The resulting mixture was heated at 90° C. for 16 hours. After being cooled to room temperature, the reaction mixture was concentrated, followed by azeotropic removal of acetic acid residue by toluene (10 mL×2). The resultant residue was washed with methyl tert-butyl ether (10 mL×2) to give the desired product (60 mg, 12% yield over two steps) as white solid. ¹H NMR (400 MHz, DMSO-d₆) δ 8.36 (s, 1H), 7.63 (s, 1H), 1.33 (s, 9H). LCMS (ESI): m/z 217.1 [M+H]⁺, RT=1.06 min (LCMS Method A).

Example 22

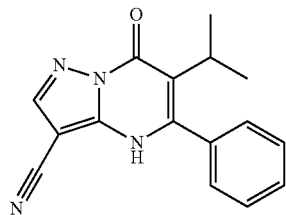 [SMILES: CC(C)c1c(-c2ccccc2)[nH]c2c(C#N)cnn2c1=O]

6-Isopropyl-7-oxo-5-phenyl-4,7-dihydropyrazolo[1,5-a]pyrimidine-3-carbonitrile

To a solution of ethyl 2-benzoyl-3-methylbutanoate (325 mg, 1.39 mmol, 1.5 eq) and 5-amino-1H-pyrazole-4-carbonitrile (100 mg, 0.93 mmol) in 2-methyltetrahydrofuran (2 ml) was added titanium tetrachloride (0.1 mL, 0.87 mmol). The reaction was stirred at room temperature for 20 minutes and then heated at 80° C. for 16 hours. The reaction was cooled to room temperature and diluted with saturated aqueous NaHCO$_3$ (5 mL). The reaction mixture was extracted with EtOAc (20 mL×3) and the combined organic layers were washed with brine (20 mL), dried over anhydrous Na$_2$SO$_4$, filtered and concentrated. The crude residue was purified by flash column chromatography on silica gel eluting with 0-30% EtOAc in hexanes to afford the desired product (107 mg, 42% yield) as a brown solid. $^1$H NMR (400 MHz, CDCl$_3$) δ 13.46 (s, 1H), 8.41 (s, 1H), 7.59-7.58 (m, 3H), 7.53-7.52 (m, 2H), 2.63-2.59 (m, 1H), 1.24 (d, J=6.8 Hz, 6H). LCMS (ESI): m/z 278.9 [M+H]$^+$, RT=1.15 min (LCMS Method A).

Example 23

Step 1

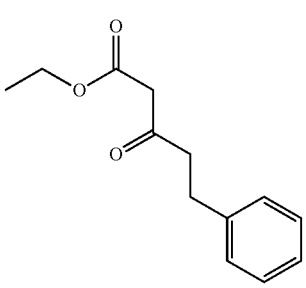 [SMILES: CCOC(=O)CC(=O)CCc1ccccc1]

Ethyl 3-oxo-5-phenylpentanoate

To a solution of ethyl 3-oxobutanoate (8 g, 61.5 mmol) in THF (80 mL) was added NaH (60% suspension in oil, 3 g, 73.8 mmol) portionwise at 0° C. and then stirred for 30 min. Then n-BuLi (29.6 mL, 73.8 mmol) was added via syringe. After being cooled to −25° C., (bromomethyl)benzene (11 g, 64.31 mmol) was added and the mixture was allowed to warm to room temperature and stirred for 2 hours. The mixture was quenched with saturated aqueous NH$_4$Cl (200 mL) and extracted with EtOAc (100 mL). The organic layer was dried over anhydrous Na$_2$SO$_4$, filtered and concentrated to afford the crude product which was purified by flash column chromatography on silica gel eluted with 0-3% EtOAc in hexanes to give the desired product (9.7 g, 72% yield) as yellow oil. $^1$H NMR (400 MHz, CDCl$_3$) δ 7.25-7.29 (m, 2H), 7.16-7.20 (m, 3H), 4.16 (q, J=7.2 Hz, 2H), 3.41 (s, 2H), 2.85-2.94 (m, 4H), 1.25 (t, J=7.2 Hz, 3H).

Step 2

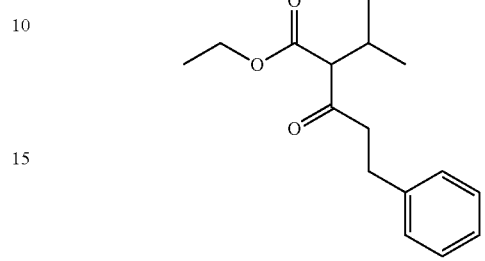

Ethyl 2-isopropyl-3-oxo-5-phenylpentanoate

A mixture of ethyl 3-oxo-5-phenylpentanoate (3 g, 13.62 mmol), 2-iodopropane (2.32 g, 13.62 mmol) and K$_2$CO$_3$ (3 76 g, 27.24 mmol) in DMF (30 mL) was placed in an autoclave and heated to 80° C. for 16 hours. The mixture was filtered, concentrated and the residue was purified by flash column chromatography on silica gel eluting with 0-2% EtOAc in hexanes to give the desired product (400 mg, 11% yield) as colorless liquid. $^1$H NMR (400 MHz, CDCl$_3$) δ 7.15-7.27 (m, 5H), 4.11 (q, J=6.8 Hz, 2H), 3.18 (d, J=9.6 Hz, 1H), 2.78-3.19 (m, 4H), 2.40-2.78 (m, 1H), 1.21 (t, J=6.8 Hz, 3H). 0.93 (d, J=6.8 Hz, 3H), 0.84 (d, J=6.8 Hz, 3H). LCMS (ESI): m/z 263.2 [M+H]$^+$, RT=1.27 min (LCMS Method A).

Step 3

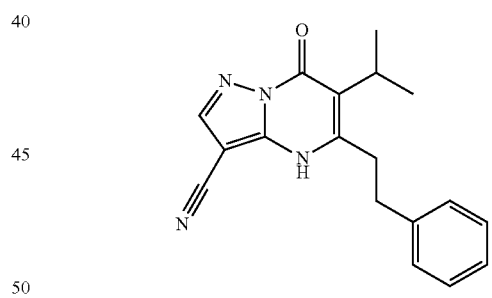

6-isopropyl-7-oxo-5-phenethyl-4,7-dihydropyrazolo[1,5-a]pyrimidine-3-carbonitrile To a solution of ethyl 2-isopropyl-3-oxo-5-phenylpentanoate (700 mg, 2.67 mmol) and 3-amino-1H-pyrazole-4-carbonitrile (433 mg, 4 mmol) in toluene (7 mL) was added titanium tetrachloride (0.2 mL, 1.6 mmol) via syringe under N$_2$ atmosphere and then heated to 80° C. for 16 hours. The mixture was quenched with saturated aqueous NaHCO$_3$ (15 mL) and extracted with EtOAc (50 mL×2). The combined organic layers were washed with brine (10 mL), dried over anhydrous Na$_2$SO$_4$, filtered and concentrated. The residue was purified by prep HPLC to afford the desired product (15 mg, 2% yield) as white solid. $^1$H NMR (400 MHz, CDCl$_3$) δ 8.10 (s, 1H), 7.18-7.32 (m, 5H), 7.10 (s 1H), 3.01 (q, J=6.8

Hz, 1H), 2.85-2.90 (m, 4H), 1.25 (d, J=6.8 Hz, 6H). LCMS (ESI): m/z 307.2 [M+H]+, RT=1.11 min (LCMS Method A).

Example 24

Step 1

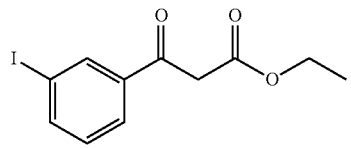

Ethyl 3-(3-iodophenyl)-3-oxopropanoate

To a solution of diethyl carbonate (12.0 g, 101.6 mmol) in anhydrous toluene (100 mL) was added NaH (60% suspension in mineral oil, 3.25 g, 81.3 mmol) portionwise at 0° C. under nitrogen atmosphere. After stirring at 0° C. for 5 minutes, the mixture was warmed up to room temperature and 1-(3-iodophenyl)ethanone (5.0 g, 20.3 mmol) was added dropwise over 10 minutes. The resulting mixture was heated at 110° C. for 16 hours. The reaction was cooled to 0° C. and quenched with $CH_3COOH$ (10 mL). $H_2O$ (50 mL) was added and the mixture was extracted with EtOAc (100 mL×2). The combined organic layers were washed with saturated aqueous $NaHCO_3$ (100 mL), dried over anhydrous $Na_2SO_4$, filtered and concentrated. The residue was purified by flash column chromatography on silical gel (0-5% EtOAc/PE) to afford the desired product as a red oil (4.0 g, 62% yield). $^1$H NMR (400 MHz, $CDCl_3$) δ 8.28 (s, 1H), 7.92 (d, J=8.8 Hz, 1H), 7.90 (d, J=8.0 Hz, 1H), 7.25-7.21 (m, 1H), 4.22 (q, J=7.2 Hz, 2H), 3.95 (s, 1H), 1.27 (t, J=7.2 Hz, 3H). LCMS (ESI): m/z 318.8 [M+H]+, RT=0.93 min (LCMS Method E).

Step 2

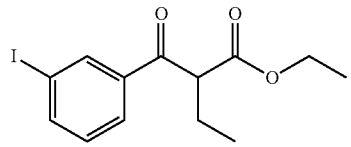 [SMILES: CCOC(=O)C(CC)C(=O)c1cccc(I)c1]

Ethyl 2-(3-iodobenzoyl)butanoate

To a solution of ethyl 3-(3-iodophenyl)-3-oxopropanoate (2.0 g, 6.29 mmol) in acetone (20 mL) in a vial was added $K_2CO_3$ (3.47 g, 25.16 mmol), 2-iodopropane (981 mg, 6.29 mmol). The vial was sealed and heated at 70° C. for 1 day. The reaction was cooled to room temperature and filtered. The filtrate was concentrated and the residue was purified by flash column chromatography on silical gel (0-5% EtOAc/ PE) to afford the desired product as an yellow oil (1.6 g, 73% yield). $^1$H NMR (400 MHz, $CDCl_3$) δ 8.32 (s, 1H), 7.94 (d, J=8.0 Hz, 1H), 7.92 (d, J=8.0 Hz, 1H), 7.27-7.21 (m, 1H), 4.19-4.13 (m, 3H), 2.03 (d, J=7.2 Hz, 2H), 1.20 (t, J=7.2 Hz, 3H), 1.00 (t, J=7.2 Hz, 3H). LCMS (ESI): m/z 346.7 [M+H]+, RT=1.06 min (LCMS Method E).

Step 3

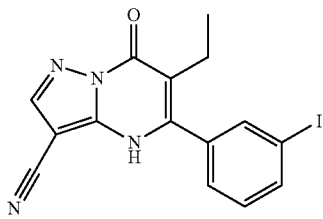 [SMILES: CCc1c(-c2cccc(I)c2)[nH]c2c(C#N)cnn2c1=O]

6-ethyl-5-(3-iodophenyl)-7-oxo-4,7-dihydropyrazolo [1,5-a]pyrimidine-3-carbonitrile To a solution of ethyl 2-(3-iodobenzoyl) butanoate (500 mg, 1.44 mmol) and 5-Amino-1H-pyrazole-4-carbonitrile (234 mg, 2.17 mmol) in anhydrous toluene (10 ml) under nitrogen atmosphere was added $TiCl_4$ (0.1 mL, 0.87 mmol). The reaction was stirred at room temperature for 30 minutes and then heated at 90° C. for 16 hours. The reaction was cooled to room temperature and diluted with saturated aqueous $NaHCO_3$ (20 mL). The reaction mixture was extracted with EtOAc (50 mL×2) and the combined organic layers were washed with brine (20 mL), dried over anhydrous $Na_2SO_4$, filtered and concentrated. The crude residue was purified by preparative HPLC (ASB $C_{18}$ 150×25 mm, 50% MeCN/$H_2O$) to afford the title compound (33 mg, 6% yield) as white solid. $^1$H NMR (400 MHz, $CDCl_3$) δ 8.05 (s, 1H), 7.92 (d, J=8.0 Hz, 1H), 7.86 (s, 1H), 7.48 (d, J=8.0 Hz, 1H), 7.32-7.28 (m, 1H), 2.52 (q, J=7.2 Hz, 2H), 1.14 (t, J=7.2 Hz, 3H). LCMS (ESI): m/z 390.9 [M+H]+, RT=1.09 min (LCMS Method A).

Example 25

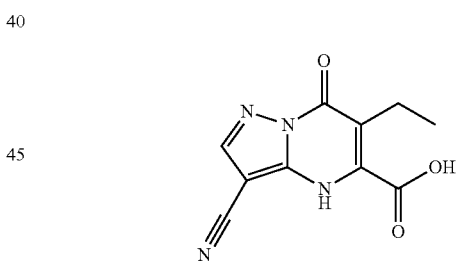

3-cyano-6-ethyl-7-oxo-4,7-dihydropyrazolo[1,5-a] pyrimidine-5-carb oxylic acid

To a suspension of ethyl 3-cyano-6-ethyl-7-oxo-4H-pyrazolo[1,5-a]pyrimidine-5-carboxylate (0.38425 mmol, 100 mg) in THF (1 mL) was added a solution of LiOH (3 M, 0.76 mL). The mixture was stirred at room temperature for 4 hours. The mixture was diluted with water, extracted with EtOAc. The aqueous layer was acidified with 1 N HCl to pH 3, extracted with EtOAc (3×). The combined organics were dried over $Na_2SO_4$, filtered, concentrated and dried to give the title compound (47 mg, 52.7% yield) as a white solid. $^1$H NMR (400 MHz, DMSO-$d_6$) δ 8.40 (s, 1H), 2.67 (q, J=7.33 Hz, 2H), 1.09 (t, J=7.31 Hz, 3H). LCMS (ESI): m/z 233.2 [M+H]+, RT=0.37 min (LCMS Method F).

Example 26

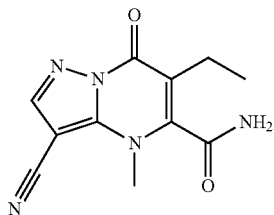 [SMILES: CCc1c(C(N)=O)n(C)c2c(C#N)cnn2c1=O]

3-cyano-6-ethyl-4-methyl-7-oxo-4,7-dihydropyrazolo[1,5-a]pyrimidine-5-carboxamide The mixture of ethyl 3-cyano-6-ethyl-4-methyl-7-oxo-pyrazolo[1,5-a]pyrimidine-5-carboxylate (55 mg, 0.20 mmol) in NH$_4$OH (28% in water, 10 mL) was stirred at room temperature for 48 hours. The mixture was concentrated via rotavap to dryness. The crude product was purified by prep HPLC to give the title compound (24.2 mg, 49.2% yield) as a white solid. $^1$H NMR (400 MHz, DMSO-d$_6$) δ 8.50 (s, 1H), 8.41 (d, J=23.40 Hz, 2H), 3.84 (s, 3H), 2.45 (q, J=7.43 Hz, 2H), 1.10 (t, J=7.37 Hz, 3H). LCMS (ESI): m/z 246.1 [M+H]$^+$, RT=2.31 min (LCMS Method F).

Example 27

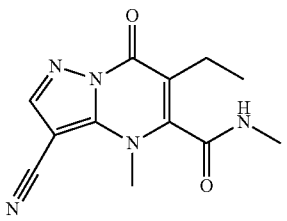 [SMILES: CCc1c(C(=O)NC)n(C)c2c(C#N)cnn2c1=O]

3-cyano-6-ethyl-N,4-dimethyl-7-oxo-4,7-dihydropyrazolo[1,5-a]pyrimidine-5-carboxamide The mixture of 3-cyano-6-ethyl-4-methyl-7-oxo-pyrazolo[1,5-a]pyrimidine-5-carboxylic acid (60 mg, 0.244 mmol), methylamine hydrochloride (49 mg, 0.731 mmol), HATU (189 mg, 0.487 mmol) and DIPEA (157 mg, 1.22 mmol) in DMF (1 mL) was stirred at room temperature for 18 hours. The crude product was purified by prep HPLC (5-50% CH$_3$CN/H$_2$O with 0.1% NH$_4$OH) to give the title compound (6.7 mg, 10.6% yield) as a white solid. $^1$H NMR (400 MHz, DMSO-d$_6$) δ 8.51 (s, 1H), 3.78 (s, 3H), 2.85 (d, J=4.70 Hz, 3H), 2.80 (d, J=4.88 Hz, 2H), 1.07 (t, J=7.37 Hz, 3H). LCMS (ESI): m/z 260.2 [M+H]$^+$, RT=2.98 min (LCMS Method F).

Example 28

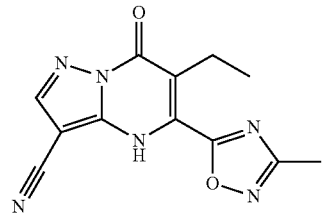 [SMILES: CCc1c(-c2nc(C)no2)[nH]c2c(C#N)cnn2c1=O]

6-ethyl-5-(3-methyl-1,2,4-oxadiazol-5-yl)-7-oxo-4H-pyrazolo[1,5-a]pyrimidine-3-carbonitrile A solution of N-hydroxyacetamidine (60 mg, 0.807 mmol) in THF (1 mL) was treated with NaH (60% suspension in mineral oil, 34 mg, 0.845 mmol) and 4 Å molecular sieves (0.7 g) and heated at 50° C. for 1 hour. Then a solution of ethyl 3-cyano-6-ethyl-7-oxo-4H-pyrazolo[1,5-a]pyrimidine-5-carboxylate (100 mg, 0.384 mmol) in THF (2 mL) was added. The mixture was heated at 50° C. for 4 hours. The mixture was filtered to remove the molecular sieves, and then concentrated to dryness. The crude product was purified by prep HPLC to give the title compound (67 mg, 64% yield) as a white solid. $^1$H NMR (400 MHz, DMSO-d$_6$) δ 8.35 (s, 1H), 2.74 (q, J=7.30 Hz, 2H), 1.09 (t, J=7.31 Hz, 3H). LCMS (ESI): m/z 271.2 [M+H]$^+$, RT=3.87 min (LCMS Method F).

Example 29

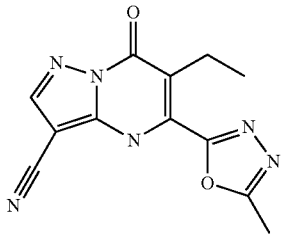 [SMILES: CCc1c(-c2nnc(C)o2)[nH]c2c(C#N)cnn2c1=O]

6-ethyl-5-(5-methyl-1,3,4-oxadiazol-2-yl)-7-oxo-4,7-dihydropyrazolo[1,5-a]pyrimidine-3-carbonitrile To a mixture of 3-cyano-6-ethyl-7-oxo-4H-pyrazolo[1,5-a]pyrimidine-5-carboxylic acid (60 mg, 0.258 mmol) and acetohydrazide (19 mg, 0.258 mmol) in dichloromethane (1 mL) was added 2-chloro-1,3-dimethylimidazolium chloride (90 mg, 0.517 mmol), followed by DIPEA (133 mg, 1.03 mmol) dropwise. The mixture was stirred at room temperature for 18 hours. The mixture was then concentrated, and then purified by prep HPLC (5-50% CH$_3$CN/H$_2$O with 0.1% formic acid) to give the title compound (5.6 mg, 7.2% yield) as an off-white solid. $^1$H NMR (400 MHz, DMSO-d$_6$) δ 8.30 (s, 1H), 2.77 (q, J=7.30 Hz, 2H), 2.64 (s, 3H), 1.10 (t, J=7.26 Hz, 3H). LCMS (ESI): m/z 271.2 [M+H]$^+$, RT=3.29 min (LCMS Method F).

Example 30

Step 1

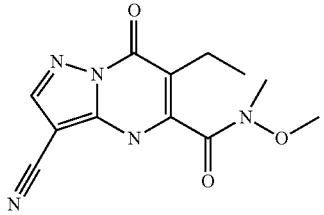 [SMILES: CCc1c(C(=O)N(C)OC)[nH]c2c(C#N)cnn2c1=O]

3-cyano-6-ethyl-N-methoxy-N-methyl-7-oxo-4,7-dihydropyrazolo[1,5-a]pyrimidine-5-carboxamide The mixture of 3-cyano-6-ethyl-7-oxo-4H-pyrazolo[1,5-a]pyrimidine-5-carboxylic acid (200 mg, 0.861 mmol), N-methoxymethanamine hydrochloride (92 mg, 0.947 mmol), DIPEA (267 mg, 2.0672 mmol) and HATU (401 mg, 4.03 mmol) in DMF (4 mL) was stirred at room temperature for 18 hours. The crude product was purified by prep HPLC (5-50% $CH_3CN/H_2O$ with 0.1% formic acid) to give the title compound (171 mg, 72% yield) as a white solid. $^1H$ NMR (400 MHz, $CDCl_3$) δ 8.07 (s, 1H), 3.71 (s, 3H), 3.40 (s, 3H), 2.58 (d, J=7.31 Hz, 2H), 1.23 (t, J=7.38 Hz, 3H). LCMS (ESI) m/z 276 $[M+H]^+$.

Step 2

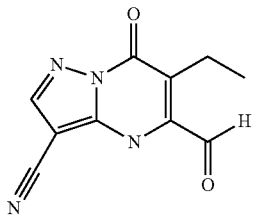 [SMILES: CCc1c(C=O)[nH]c2c(C#N)cnn2c1=O]

6-ethyl-5-formyl-7-oxo-4,7-dihydropyrazolo[1,5-a]pyrimidine-3-carbonitrile

To a solution of 3-cyano-6-ethyl-N-methoxy-N-methyl-7-oxo-4H-pyrazolo[1,5-a]pyrimidine-5-carboxamide (170 mg, 0.618 mmol) in THF (3 mL) at −78° C. was added lithiumaluminum hydride (1 M in THF, 0.678 mL) dropwise. The mixture was stirred at −78° C. for 1 hour, then warmed to 0° C. and kept at that temperature for 2 hours. The reaction was quenched with 25% aqueous solution of Na,K tartrate. The mixture was extracted with EtOAc (6×). The combined organics were dried ($Na_2SO_4$), filtered and concentrated. The crude prod was purified by silica gel column chromatography eluting with 20% MeOH/DCM to give the title compound (54 mg, 40.4% yield) as a yellow solid. LCMS (ESI) m/z 217 $[M+H]^+$.

Step 3

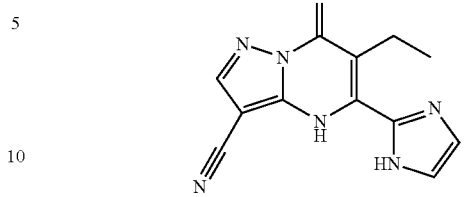

6-ethyl-5-(1H-imidazol-2-yl)-7-oxo-4,7-dihydropyrazolo[1,5-a]pyrimidine-3-carbonitrile To the suspension of 6-ethyl-5-formyl-7-oxo-4H-pyrazolo[1,5-a]pyrimidine-3-carbonitrile (54 mg, 0.25 mmol), $NH_4OH$ (28% in water, 228 mg, 3.75 mmol) and water (0.25 mL) was added glyoxal (40% in water, 181 mg, 1.25 mmol). The mixture was stirred at room temperature for 16 hours. Then the mixture was concentrated to dryness, and the resulting crude product was purified by prep HPLC (5-50% $CH_3CN/H_2O$ with 0.1% formic acid) to give the title compound (36 mg, 56.7% yield) as a yellow solid. $^1H$ NMR (400 MHz, DMSO-$d_6$) δ 8.24 (s, 1H), 7.68 (s, 2H), 2.54 (q, J=7.36 Hz, 2H), 0.94 (t, J=7.33 Hz, 3H). LCMS (ESI): m/z 255.2 $[M+H]^+$, RT=0.62 min (LCMS Method F).

Example 31

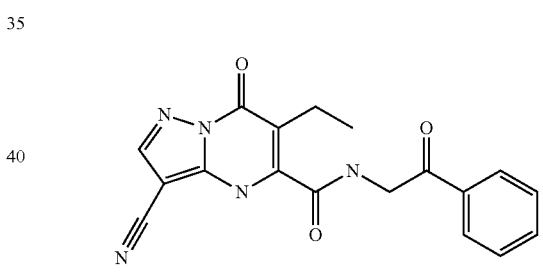

3-cyano-6-ethyl-7-oxo-N-(2-oxo-2-phenylethyl)-4,7-dihydropyrazolo[1,5-a]pyrimidine-5-carboxamide To a solution of 3-cyano-6-ethyl-7-oxo-4H-pyrazolo[1,5-a]pyrimidine-5-carboxylic acid (200 mg, 0.861 mmol) and triethylamine (218 mg, 2.15 mmol) in THF (2 mL) was added isobutyl chloroformate (0.1463 mL). The mixture was stirred at room temperature for 1 hour. Then 2-aminoacetophenone hydrochloride (163 mg, 0.947 mmol) was added. The mixture was stirred at room temperature for 3 hours. The mixture was filtered through celite, washed with EtOAc and concentrated. The crude product was purified by prep HPLC (5-50% $CH_3CN/H_2O$ with 0.1% formic acid) to give the title compound (108 mg, 35.9% yield). $^1H$ NMR (400 MHz, DMSO-$d_6$) δ 9.22 (s, 1H), 8.40 (s, 1H), 8.10-8.03 (m, 2H), 7.74-7.66 (m, 1H), 7.58 (dd, J=7.12, 8.32 Hz, 2H), 4.86 (d, J=5.61 Hz, 2H), 2.61 (q, J=7.26 Hz, 2H), 1.10 (t, J=7.30 Hz, 3H). LCMS (ESI): m/z 350.1 $[M+H]^+$, RT=4.98 min (LCMS Method F).

Example 32

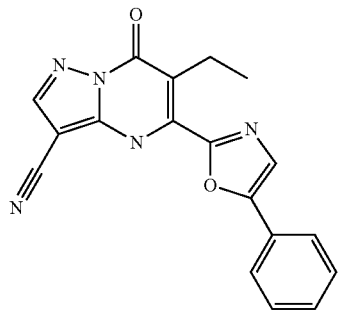 [SMILES: CCc1c(-c2ncc(-c3ccccc3)o2)[nH]c2c(C#N)cnn2c1=O]

6-ethyl-7-oxo-5-(5-phenyloxazol-2-yl)-4,7-dihydro-pyrazolo[1,5-a]pyrimidine-3-carbonitrile To a solution of 3-cyano-6-ethyl-7-oxo-N-phenacyl-4H-pyrazolo[1,5-a]pyrimidine-5-carboxamide (180 mg, 0.515 mmol) in THF (5 mL) was added Burgess reagent (211 mg, 0.859 mmol). The mixture was heated at 120° C. in a microwave for 45 min. The mixture was concentrated and purified by prep HPLC to give the title compound (25 mg, 15% yield) as a pale yellow solid. $^1$H NMR (400 MHz, DMSO-$d_6$) δ 8.42 (s, 1H), 8.12 (s, 1H), 7.94-7.87 (m, 2H), 7.62-7.54 (m, 2H), 7.51-7.44 (m, 1H), 2.91 (q, J=7.27 Hz, 2H), 1.20 (t, J=7.29 Hz, 3H). LCMS (ESI): m/z 332.1 [M+H]$^+$, RT=6.10 min (LCMS Method F).

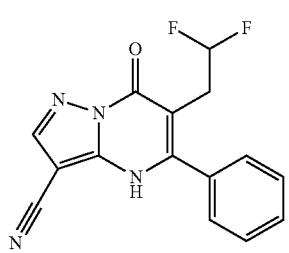

Example 33

6-(2,2-Difluoroethyl)-7-oxo-5-phenyl-4H-pyrazolo[1,5-a]pyrimidine-3-carbonitrile To a solution of ethyl 3-oxo-3-phenyl-propanoate (0.20 g, 1.04 mmol) in 2-methyl THF (5 ml) cooled in ice-bath was added sodium hydride (60% suspension in mineral oil, 0.05 g, 1.2 mmol) and the mixture was stirred for 20 min. To the resulting solution as added 2,2-difluoroethyl trifluoromethanesulfonate (0.24 g, 1.15 mmol). The mixture was then warmed up to room temperature and stirred for 72 hours. The reaction mixture quenched with HCl (1 N) and extracted with ethyl acetate. Combined organics were dried over sodium sulfate, concentrated. The crude product was converted to the desired product (18 mg, 5.8% yield for 2 steps) as described in Example 22. $^1$H NMR (400 MHz, DMSO-$d_6$) δ 8.43 (s, 1H), 7.55 (dq, J=22.2, 3.2 Hz, 5H), 6.34-5.95 (m, 1H), 2.97-2.79 (m, 2H). LCMS (ESI): m/z 301.2 [M+H]$^+$, RT=4.21 min (LCMS Method F).

Example 34

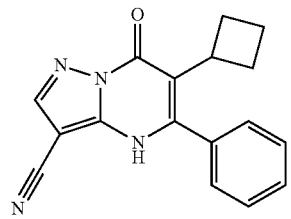 [SMILES: N#Cc1cnn2c(=O)c(C3CCC3)c(-c3ccccc3)[nH]c12]

6-Cyclobutyl-7-oxo-5-phenyl-4H-pyrazolo[1,5-a]pyrimidine-3-carbonitrile

To a solution of ethyl 3-oxo-3-phenyl-propanoate (1.00 g, 5.2 mmol) and cyclobutanone (0.44 g, 6.2 mmol) in 2-MeTHF (50 mL) was added titanium(IV) chloride (11.0 mL 1M in DCM, 11 mmol), followed by pyridine (2.1 mL, 26 mmol). The resulting suspension was stirred at room temperature for 20 hours. The solids were removed by filtration and the filtrate was diluted with ethyl acetate, washed with brine, dried over sodium sulfate and concentrated. The residue obtained after purification on silica gel column chromatography (0-50% EtOAc/heptane) was hydrogenated in the presence of Pd—C (0.20 g, 10% w/w on activated carbon) at ambient temperature for 20 hours in ethyl acetate. The catalyst was removed by filtration and concentration of filtrate afforded ethyl 2-cyclobutyl-3-oxo-3-phenylpropanoate (0.05 g, 3.9% yield over 2 steps). The ketoester was treated with 3-amino-1H-pyrazole-4-carbonitrile as described in Example 22 to obtain the desired product (3 mg, 5.1% yield). $^1$H NMR (400 MHz, CDCl$_3$) δ 7.96 (s, 1H), 7.60-7.49 (m, 3H), 7.47-7.38 (m, 2H), 3.50-3.31 (m, 1H), 2.62-2.46 (m, 2H), 1.99-1.74 (m, 4H). LCMS: (ESI) m/z 291.1 [M+H]$^+$, RT=5.91 min (LCMS Method F).

Example 35

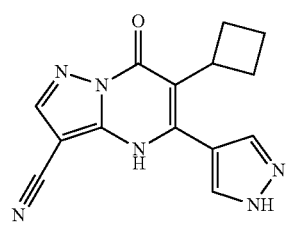 [SMILES: N#Cc1cnn2c(=O)c(C3CCC3)c(-c3cn[nH]c3)[nH]c12]

6-Cyclobutyl-7-oxo-5-(1H-pyrazol-4-yl)-4H-pyrazolo[1,5-a]pyrimidine-3-carbonitrile This compound was prepared similarly as shown in example 34. $^1$H NMR (400 MHz, DMSO-$d_6$) δ 8.36 (s, 1H), 8.12 (s, 1H), 7.82 (s, 1H), 3.65-3.49 (m, 1H), 2.74-2.55 (m, 2H), 2.08-1.89 (m, 2H), 1.90-1.69 (m, 2H). LCMS (ESI): m/z 281.2 [M+H]$^+$, RT=3.88 min (LCMS Method F).

Example 36

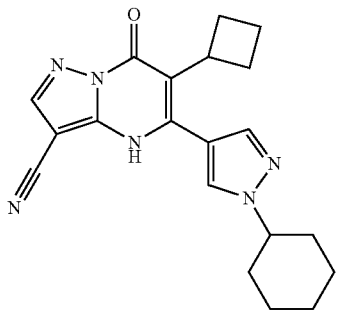 [SMILES: N#Cc1cnn2c(=O)c(C3CCC3)c(-c3cnn(C4CCCCC4)c3)[nH]c12]

6-Cyclobutyl-5-(1-cyclohexylpyrazol-4-yl)-7-oxo-4H-pyrazolo[1,5-a]pyrimidine-3-carbonitrile To a mixture of 6-cyclobutyl-7-oxo-5-(1H-pyrazol-4-yl)-4H-pyrazolo[1,5-a]pyrimidine-3-carbonitrile (40 mg, 0.14 mmol) and bromocyclohexane (46 mg, 0.28 mmol) was added NaH (60% suspension in mineral oil, 11 mg, 0.27 mmol) and the resulting mixture was heated 60° C. for 20 hours. The reaction mixture was cooled, acidified with HCl and extracted with ethyl acetate. The organic layer was washed with brine, dried over sodium sulfate and concentrated. Purification of the crude product by flash column chromatography on silica gel eluting with 0-100% EtOAc/heptane afforded the desired product (5 mg, 10% yield). $^1$H NMR (400 MHz, CDCl$_3$) δ 7.96 (s, 1H), 7.77 (d, J=0.8 Hz, 1H), 7.74 (d, J=0.7 Hz, 1H), 4.27-4.12 (m, 1H), 3.72-3.58 (m, 1H), 2.80-2.64 (m, 2H), 2.23 (d, J=12.3 Hz, 2H), 2.14-2.02 (m, 2H), 1.99-1.90 (m, 3H), 1.81-1.71 (m, 3H), 1.49-1.42 (m, 2H), 1.35-1.15 (m, 2H). LCMS (ESI): m/z 363.2 [M+H]$^+$, RT=5.30 min (LCMS Method F).

Example 37

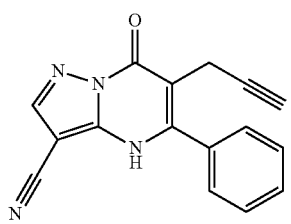

7-Oxo-5-phenyl-6-(prop-2-yn-1-yl)-4,7-dihydropyrazolo[1,5-a]pyrimidine-3-carbonitrile To a solution of 3-amino-1H-pyrazole-4-carbonitrile (0.20 g, 1.8 mmol) and ethyl 2-benzoylpent-4-ynoate (0.63 g 2.7 mmol) in dry 2-Me THF (20 mL) was added titanium tetrachloride (3 mL of 1M solution in toluene, 3 mmol) and the resulting dark orange solution was heated at 80° C. for 2 hours. The resulting reaction mixture was cooled, poured into water (100 mL) and extracted with ethyl acetate. The organic layer was separated, washed with brine, dried over sodium sulfate and concentrated. Purification by flash column chromatography on silica gel (20-100% ethyl acetate/heptane), followed by trituration of the residue with ethyl acetate/heptane afforded the desired product (0.11 g, 21.6% yield). $^1$H NMR (400 MHz, DMSO-d$_6$) δ 13.70 (s, 1H), 8.43 (s, 1H), 7.70-7.47 (m, 5H), 3.17 (d, J=2.7 Hz, 2H), 2.82 (t, J=2.6 Hz, 1H). LCMS (ESI): m/z 275.2 [M+H]$^+$, RT=4.09 min (LCMS Method F).

Example 38

Step 1

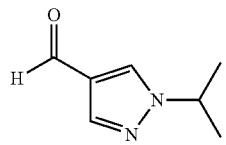

1-isopropyl-1H-pyrazole-4-carbaldehyde

To a solution of 1H-pyrazole-4-carbaldehyde (2.0 g, 21 mmol) and 2-iodopropane (5.32 g, 31.5 mmol) in DMF (10 mL) was added sodium hydride (60% dispersion in mineral oil, 0.83 g, 20.7 mmol) in one portion. The resulting mixture was stirred at room temperature for 2 hours, before being quenched with water and extracted with ethyl acetate. The organic layer was washed with brine, dried over sodium sulfate and concentrated. The residue was purified by flash column chromatography on silica gel eluting with 0-50% EtOAc/heptane to obtain 1-isopropylpyrazole-4-carbaldehyde (1.2 g, 42% yield). $^1$H NMR (400 MHz, CDCl$_3$) δ 9.86 (s, 1H), 7.97 (s, 2H), 4.54 (p, J=6.7 Hz, 1H), 1.55 (d, J=6.7 Hz, 6H).

Step 2

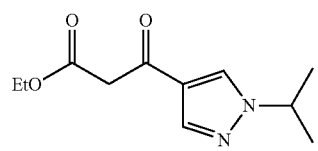 [SMILES: CCOC(=O)CC(=O)c1cnn(C(C)C)c1]

ethyl 3-(1-isopropyl-1H-pyrazol-4-yl)-3-oxopropanoate

To a solution of ethyl acetate (1.28 g, 14.5 mmol) cooled to −78° C. was added LDA (7.24 mL, 2 M solution in THF/heptane/ethylbenzene, 14.4 mmol) and the mixture was stirred at −78° C. for 20 min. To this mixture was added a solution 1-isopropylpyrazole-4-carbaldehyde (1.00 g, 7.24 mmol) in THF (3 mL) and the mixture was stirred for another 20 min. The reaction mixture was quenched with saturated ammonium chloride solution and the mixture was allowed to warm to room temperature. The mixture was extracted with ethyl acetate. The organic layer was washed with brine, dried over sodium sulfate and concentrated. The residue was dissolved in DCM (100 mL) and MnO$_2$ (5.0 g) was added in one portion. The mixture was stirred for 20 hours at room temperature. MnO$_2$ was removed by filtration through a Celite pad and the filtrate was concentrated. Purification of the residue by flash column chromatography on silica gel (0-100% EtOAc/heptane) afforded the desired product (0.70 g, 40% yield). $^1$H NMR (400 MHz, CDCl$_3$) δ

7.99 (d, J=0.6 Hz, 1H), 7.93 (d, J=0.7 Hz, 1H), 4.52 (p, J=6.7 Hz, 1H), 4.20 (q, J=7.1 Hz, 2H), 3.75 (s, 2H), 1.53 (d, J=6.7 Hz, 6H), 1.26 (t, J=7.1 Hz, 3H).

Step 3

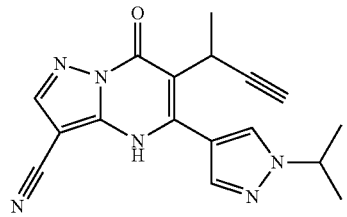 [SMILES: C#CC(C)c1c(-c2cnn(C(C)C)c2)[nH]c2c(C#N)cnn2c1=O]

5-(1-isopropylpyrazol-4-yl)-6-(1-methylprop-2-ynyl)-7-oxo-4H-pyrazolo[1,5-a]pyrimidine-3-carbonitrile A mixture of ethyl 3-(1-isopropylpyrazol-4-yl)-3-oxopropanoate (0.20 g, 0.89 mmol), 3-bromobut-1-yne (0.13 g, 0.98 mmol) and potassium carbonate (0.18 g, 1.33 mmol) in acetone (20 mL) was heated at 50° C. for 20 hours. The reaction mixture was cooled and solid was removed by filtration. The resulting filtrate was concentrated and the crude product was dissolved in ethyl acetate, washed with water and then brine. The organic layer was dried over sodium sulfate and concentrated. The crude product was dissolved in 2-Me THF (10 mL) and 5-amino-1H-pyrazole-4-carbonitrile (0.050 g, 0.5 mmol) was added, followed by titanium tetrachloride (2.6 mL, 1 M solution in toluene). The mixture was heated at 80° C. for 2 hours. The reaction mixture was cooled, diluted with water and ethyl acetate. The organic layer washed with brine, dried over sodium sulfate and concentrated. Purification by flash column chromatography on silica gel (0-100% EtOAc/heptane), followed by trituration of the residue with ethyl acetate afforded the desired product (35 mg, 12% yield for 2 steps). $^1$H NMR (400 MHz, DMSO-d$_6$) δ 8.07 (d, J=19.6 Hz, 1H), 8.02 (s, 1H), 7.69 (s, 1H), 4.58 (p, J=6.7 Hz, 1H), 4.06 (d, J=8.0 Hz, 1H), 2.74 (d, J=2.6 Hz, 1H), 1.51 (d, J=7.1 Hz, 3H), 1.47 (d, J=6.7 Hz, 6H). LCMS (ESI): m/z 321.2 [M+H]$^+$, RT=4.00 min (LCMS Method F).

Example 39

Step 1

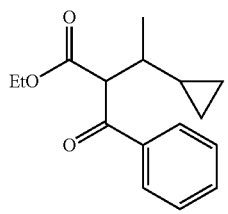

Ethyl 2-benzoyl-3-cyclopropylbutanoate

To a suspension of CuCl (20 mg) in THF (2 mL) cooled in ice-bath was added cyclopropylmagnesium bromide (15 mL, 0.5 M solution in THF) and the suspension was stirred for 10 min. A solution of ethyl 2-benzoylbut-2-enoate (0.50 g, 2.3 mmol) in 5 mL of THF was added dropwise and the reaction mixture stirred for 1 hour at 0° C. The reaction mixture was then quenched with aq. HCl and diluted with ethyl acetate. The organic layer was separated, washed with brine, dried over sodium sulfate and concentrated. Purification by flash column chromatography on silica gel (0-50% EtOAc/heptane) afforded the desired product (0.45 g, 75% yield). $^1$H NMR (400 MHz, CDCl$_3$) δ 8.09-7.96 (m, 2H), 7.62-7.51 (m, 1H), 7.54-7.38 (m, 2H), 4.43-4.28 (m, 1H), 4.22-4.05 (m, 2H), 1.86-1.69 (m, 1H), 1.19 (t, J=7.1 Hz, 3H), 1.09 (dd, J=36.8, 6.7 Hz, 3H), 0.80-0.03 (m, 4H).

Step 2

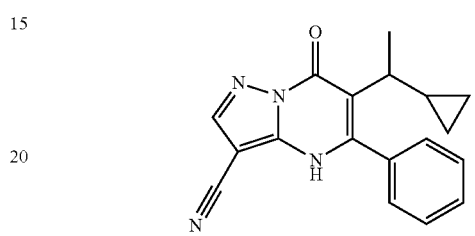

6-(1-cyclopropylethyl)-7-oxo-5-phenyl-4H-pyrazolo[1,5-a]pyrimidine-3-carbonitrile This compound was synthesized using similar procedure was shown for example 37. $^1$H NMR (400 MHz, DMSO-d$_6$) δ 13.47 (s, 1H), 8.40 (s, 1H), 7.64-7.39 (m, 5H), 1.54-1.44 (m, 2H), 1.35-1.31 (m, 3H), 0.43-0.35 (m, 1H), 0.26-0.24 (m, 1H), 0.18-0.15 (m, 1H). LCMS (ESI): m/z 305.2 [M+H]$^+$, RT=4.99 min (LCMS Method F).

Example 40

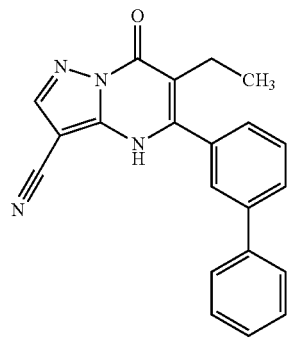

5-([1,1'-Biphenyl]-3-yl)-6-ethyl-7-oxo-4,7-dihydropyrazolo[1,5-a]pyrimidine-3-carbonitrile A mixture of 5-(3-bromophenyl)-6-ethyl-7-oxo-4,7-dihydropyrazolo[1,5-a]pyrimidine-3-carbonitrile (0.060 g, 0.19 mmol), phenylboronic acid (0.030 g, 0.23 mmol), dichlorobis(triphenylphosphine)palladium(II) (0.02 g) and sodium carbonate (0.10 g, mmol) in dioxane/water (2 mL/0.5 mL) was heated at 110° C. for 20 min in a microwave reactor. The reaction mixture was acidified with HCl and extracted with ethyl acetate. The organic layer was washed with brine, dried over sodium sulfate and concentrated. Purification by flash column chromatography on silica gel (20-100%

EtOAc/heptane) and trituration of the residue with ethyl acetate/heptane afforded the desired product (0.01 g, 4% yield). $^1$H NMR (400 MHz, DMSO-d$_6$) δ 8.26 (t, J=1.8 Hz, 1H), 8.12 (s, 1H), 8.03 (dt, J=7.9, 1.4 Hz, 1H), 7.77-7.65 (m, 3H), 7.59-7.46 (m, 3H), 7.47-7.37 (m, 1H), 6.29 (s, 1H). LCMS (ESI): m/z=313.2 [M+H]$^+$, RT=5.35 min (LCMS Method F).

Example 41

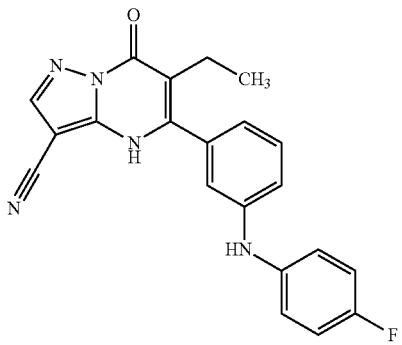 [SMILES: CCc1c(-c2cccc(Nc3ccc(F)cc3)c2)[nH]c2c(C#N)cnn2c1=O]

6-Ethyl-5-(3-((4-fluorophenyl)amino)phenyl)-7-oxo-4,7-dihydropyrazolo[1,5-a]pyrimidine-3-carbonitrile A mixture of 5-(3-bromophenyl)-6-ethyl-7-oxo-4,7-dihydropyrazolo[1,5-a]pyrimidine-3-carbonitrile (0.10 g, 0.29 mmol), 4-fluoroaniline (0.065 mg, 0.50 mmol), Pd$_2$(dba)$_3$ (20 mg) and tert-BuX-Phos (20 mg), cesium carbonate (0.29 g, 0.87 mmol) in dioxane (5 mL) was heated at 110° C. for 5 hours. Only trace amount of the desired product was observed. Therefore, to this mixture was then added (chloro{[BrettPhos][2-(2-aminoethylphenyl]-palladium(II)]}/[BrettPhos] admixture (molar PdP/P=1:1 (40 mg) and heated at 110° C. for another 15 hours. The reaction mixture was acidified with HCl and extracted with ethyl acetate. The organic layer was separated and washed with brine, dried over sodium sulfate and concentrated. Purification by flash column chromatography on silica gel (0-100% DCM/EtOAc) and trituration of the residue with ethyl acetate/heptane afforded the desired product (20 mg, 18.5% yield). $^1$H NMR (400 MHz, DMSO-d$_6$) δ 13.44 (s, 1H), 8.38 (d, J=3.3 Hz, 2H), 7.39 (t, J=7.9 Hz, 1H), 7.19-7.07 (m, 5H), 6.95-6.85 (m, 1H), 2.34 (q, J=7.3 Hz, 2H), 1.01 (t, J=7.3 Hz, 3H). LC/MS (ESI): m/z=374.2 [M+H]$^+$, RT=5.16 min (LCMS Method F).

Example 42

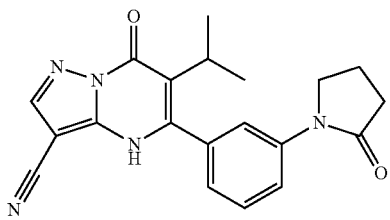 [SMILES: CC(C)c1c(-c2cccc(N3CCCC3=O)c2)[nH]c2c(C#N)cnn2c1=O]

6-isopropyl-7-oxo-5-(3-(2-oxopyrrolidin-1-yl)phenyl)-4,7-dihydropyrazolo[1,5-a]pyrimidine-3-carbonitrile The mixture of 5-(3-bromophenyl)-6-isopropyl-7-oxo-4H-pyrazolo[1,5-a]pyrimidine-3-carbonitrile (0.168 mmol, 60 mg), 2-pyrrolidone (0.588 mmol, 50 mg), BrettPhos (0.0168 mmol, 9.2 mg), BrettPhos Pre-catalyst (0.0168 mmol, 13.7 mg), and Cs$_2$CO$_3$ (0.336 mmol, 109 mg) in 1,4-dioxane (2 mL) in a microwave tube was purged with N$_2$ for 2 min, then sealed and heated at 140° C. in a microwave for 40 min. The mixture was filtered through Celite, washed with EtOAc, concentrated. The crude product was purified by preparative HPLC to afford the desired products as a white solid (29 mg, 47% yield). $^1$H NMR (DMSO-d$_6$) δ: 13.43 (s, 1H), 8.37 (s, 1H), 7.88-7.78 (m, 2H), 7.56 (t, J=7.9 Hz, 1H), 7.25 (d, J=7.5 Hz, 1H), 3.88 (t, J=7.0 Hz, 2H), 2.65 (p, J=6.9 Hz, 1H), 2.57-2.52 (m, 2H), 2.16-2.03 (m, 2H), 1.24 (d, J=6.9 Hz, 6H). LCMS (ESI): m/z 362.2 [M+H]$^+$, RT=4.27 min (LCMS Method F).

Example 43

Step 1

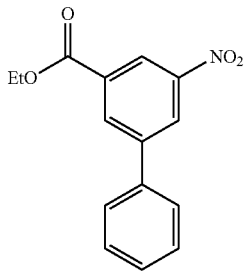 [SMILES: CCOC(=O)c1cc(-c2ccccc2)cc([N+](=O)[O-])c1]

ethyl 5-nitro-[1,1'-biphenyl]-3-carboxylate

A mixture of ethyl 5-bromo-3-nitrobenzoate (5.0 g, 18 mmol), phenylboronic acid (2.7 g, 21 mmol), bis(triphenylphosphine)palladium(II) dichloride (0.63 g, 0.89 mmol) and sodium carbonate (7.6 g, 72 mmol) in a dioxane/water (50:10 mL) was heated at 90° C. for 20 hours. The reaction mixture was cooled, diluted with water and extracted with ethyl acetate. The organic layer was washed with brine, dried over sodium sulfate and concentrated. Purification of the residue by flash column chromatography on silica gel (10-50% EtOAc/heptane) afforded the desire product (4.1 g, 85% yield). $^1$H NMR (400 MHz, CDCl$_3$) δ 8.82 (dd, J=2.2, 1.4 Hz, 1H), 8.67-8.53 (m, 2H), 7.76-7.62 (m, 2H), 7.60-7.41 (m, 3H), 4.48 (q, J=7.2 Hz, 2H), 1.46 (t, J=7.1 Hz, 3H).

Step 2

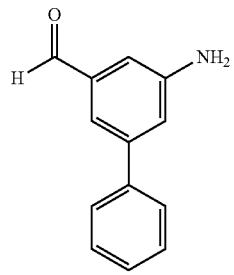 [SMILES: Nc1cc(C=O)cc(-c2ccccc2)c1]

5-amino-[1,1'-biphenyl]-3-carbaldehyde

To a solution of ethyl 3-nitro-5-phenyl-benzoate (1.0 g, 2.1 mmol) in 2-Me THF (20 mL) cooled at 0° C. was added LAH (2.9 mL of 1M solution in THF, 2.9 mmol) and the mixture was allowed to warm to room temperature over 20 min. The reaction mixture was quenched with saturated ammonium chloride. The solid was removed by filtration through a Celite pad and the filtrate was dried over sodium sulfate and was concentrated. The residue was dissolved in DCM (50 ml) and MnO$_2$ (2.0 g) was added in one portion. The mixture was stirred at ambient temperature for 72 hours. The reaction mixture was passed through a Celite pad and the filtrate was concentrated to afford an off-white solid (0.30 g, 34% yield). $^1$H NMR (400 MHz, CDCl$_3$) δ 10.04 (s, 1H), 7.91 (t, J=1.9 Hz, 1H), 7.87 (s, 1H), 7.79 (t, J=1.6 Hz, 1H), 7.65-7.59 (m, 2H), 7.49-7.44 (m, 2H), 7.42-7.36 (m, 1H), 6.70 (s, 1H), 1.56 (s, 9H).

Step 3

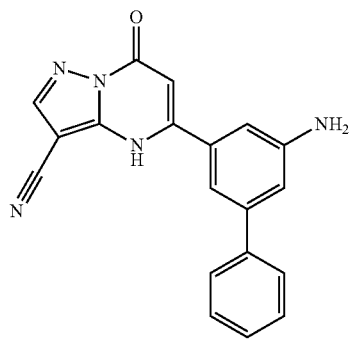 [SMILES: N#Cc1cnn2c(=O)cc(-c3cc(N)cc(-c4ccccc4)c3)[nH]c12]

5-(3-amino-5-phenyl-phenyl)-7-oxo-4H-pyrazolo[1,5-a]pyrimidine-3-carbonitrile

The compound was prepared using procedure that was shown for example 20. $^1$H NMR (400 MHz, DMSO-d$_6$) δ 8.43 (s, 1H), 7.77-7.67 (m, 2H), 7.56-7.45 (m, 2H), 7.44-7.35 (m, 2H), 7.23 (s, 1H), 7.12 (s, 1H), 6.25 (s, 1H). LCMS (ESI): m/z 328.1 [M+H]$^+$, RT=4.19 min (LCMS Method F).

Example 44

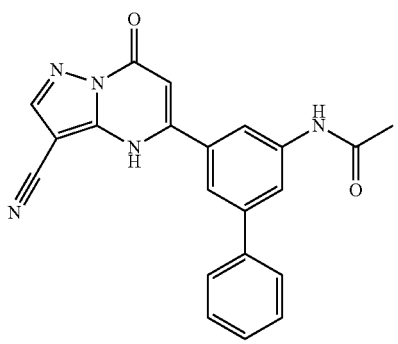 [SMILES: CC(=O)Nc1cc(-c2ccccc2)cc(-c2cc(=O)n3ncc(C#N)c3[nH]2)c1]

N-[3-(3-Cyano-7-oxo-4H-pyrazolo[1,5-a]pyrimidin-5-yl)-5-phenyl-phenyl]acetamide

To a solution of 5-(3-amino-5-phenyl-phenyl)-7-oxo-4H-pyrazolo[1,5-a]pyrimidine-3-carbonitrile (100 mg, 0.30 mmol) in DCM (5 mL) and DIPEA (0.11 mL, 0.61 mmol) was added acetyl chloride (48 mg, 0.61 mmol). The reaction mixture was stirred for 1 hour. The reaction mixture was diluted with DCM and washed with HCl, followed by washing with water and then brine. The organic layer was dried over sodium sulfate and concentrated. Purification of the resulting residue by rpHPLC provided the desired product (15 mg, 13% yield). $^1$H NMR (400 MHz, DMSO-d$_6$) δ 10.28 (s, 1H), 8.35 (d, J=17.1 Hz, 1H), 8.15-8.08 (m, 1H), 8.01 (s, 1H), 7.79-7.68 (m, 3H), 7.56-7.46 (m, 2H), 7.46-7.39 (m, 1H), 6.26 (s, 1H), 2.12 (s, 3H). LCMS (ESI): m/z 370.4 [M+H]$^+$, RT=4.44 min (LCMS Method F).

Example 45 (Method C)

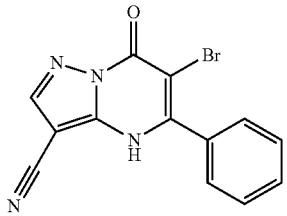

6-Bromo-7-oxo-5-phenyl-4,7-dihydropyrazolo[1,5-a]pyrimidine-3-carbonitrile

To a suspension of 7-oxo-5-phenyl-4,7-dihydropyrazolo[1,5-a]pyrimidine-3-carbonitrile (1.00 g, 4.2 mmol) in DMF (5 mL) was added NBS (0.75 g, 4.2 mmol). The mixture stirred at room temperature for 15 min, and then diluted with water. The precipitate was collected by filtration, washed with water and dried in vacuum oven at 50° C. for 20 hours to afford the desired product (0.70 g, 52% yield). $^1$H NMR (400 MHz, DMSO-d$_6$): δ 8.44 (s, 1H), 7.67-7.51 (m, 5H). LCMS (ESI): m/z 317.1 [M+H]$^+$, RT=3.48 min (LCMS Method F).

Example 46

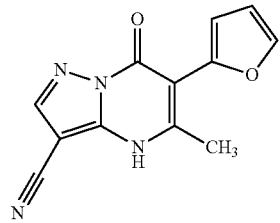 [SMILES: Cc1[nH]c2c(C#N)cnn2c(=O)c1-c1ccco1]

6-(2-Furyl)-5-methyl-7-oxo-4H-pyrazolo[1,5-a]pyrimidine-3-carbonitrile

A mixture of 6-bromo-5-methyl-7-oxo-4H-pyrazolo[1,5-a]pyrimidine-3-carbonitrile (0.10 g, 0.39 mmol), 2-furanyl-boronic acid (0.05 g, 0.47 mmol), dichlorobis(triphenylphosphine)palladium(II) (0.014 g) and sodium carbonate (0.16 g, 1.6 mmol) in a mixture of ethanol/water (2 mL/0.5 mL) was heated to 150° C. for 20 min in a microwave reactor. The reaction mixture was acidified with HCl and extracted with ethyl acetate. The organic layer was separated, washed with brine, dried over sodium sulfate and concentrated. Purification by flash column chromatography on silica gel (20-100% ethyl acetate/heptane) and trituration of the residue with ethyl acetate/heptane afforded the desired product (0.01 g, 11.2% yield). $^1$H NMR (400 MHz, DMSO-$d_6$) δ 8.30 (s, 1H), 8.12 (s, 1H), 7.68-7.61 (m, 1H), 6.60-6.48 (m, 2H), 2.30 (s, 3H). LC/MS (ESI): m/z 241.2 [M+H]$^+$, RT=3.21 min (LCMS Method F).

Example 47 (Method D)

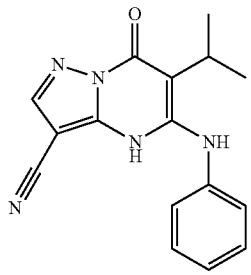 [SMILES: CC(C)c1c(Nc2ccccc2)[nH]c2c(C#N)cnn2c1=O]

6-isopropyl-7-oxo-5-(phenylamino)-4,7-dihydropyrazolo[1,5-a]pyrimidine-3-carbonitrile The mixture of 5-chloro-6-isopropyl-7-oxo-4H-pyrazolo[1,5-a]pyrimidine-3-carbonitrile (60 mg, 0.253 mmol), aniline (71 mg, 0.76 mmol), BrettPhos (14 mg, 0.025 mmol), BrettPhos Pre-catalyst (20 mg, 0.025 mmol), and tBuONa (75 mg, 0.76 mmol) in 1,4-dioxane (2 mL) was purged with N$_2$ for 2 min, then heated at 140° C. in a microwave reactor for 20 min. The mixture was filtered to remove solid. The filter cake was washed with EtOAc. Combined filtrate was concentrated. The crude product was purified by prep HPLC to give the title compound as a white solid (8.2 mg, 11% yield). $^1$H NMR (400 MHz, DMSO-$d_6$) δ 12.93 (s, 1H), 8.56 (s, 1H), 8.21 (s, 1H), 7.30 (t, J=7.76 Hz, 2H), 7.09 (d, J=14.17 Hz, 2H), 6.98 (s, 1H), 3.18-3.00 (m, 1H), 1.29 (d, J=6.87 Hz, 6H). LCMS (ESI): m/z 294.1 [M+H]$^+$, RT=5.3 min (LCMS Method F).

Example 48

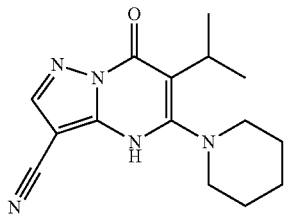 [SMILES: CC(C)c1c(N2CCCCC2)[nH]c2c(C#N)cnn2c1=O]

6-isopropyl-7-oxo-5-(piperidin-1-yl)-4,7-dihydropyrazolo[1,5-a]pyrimidine-3-carbonitrile The mixture of 5-chloro-6-isopropyl-7-oxo-4H-pyrazolo[1,5-a]pyrimidine-3-carbonitrile (160 mg, 0.676 mmol, 20 mg), piperidine (173 mg, 2.03 mmol), RuPhos (32 mg, 0.0676 mmol), RuPhos pre-catalyst (52 mg, 0.0676 mmol), and tBuONa (200 mg, 2.03 mmol) in THF (5 mL) was purged with N$_2$ for 2 min, then heated at 140° C. in a microwave reactor for 15 min. The mixture was filtered to remove solid. The filter cake was washed with EtOAc. Combined filtrate was concentrated. The resulting crude product was purified by prep HPLC to give the title compound as an off-white solid (10.1 mg, 5.2% yield). $^1$H NMR (400 MHz, DMSO-$d_6$) δ 8.10 (s, 1H), 4.22-4.09 (m, 1H), 3.94 (d, J=3.29 Hz, 1H), 3.63 (m, 2H), 3.54-3.42 (m, 1H), 2.17 (m, 1H), 1.73-1.48 (m, 4H), 1.15 (d, J=6.78 Hz, 3H), 0.66 (d, J=6.84 Hz, 3H). LCMS (ESI): m/z 286.2 [M+H]$^+$, RT=5.76 min (LCMS Method F).

Example 49

Step 1

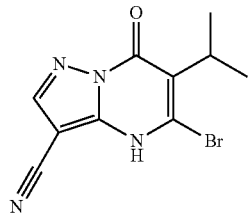 [SMILES: CC(C)c1c(Br)[nH]c2c(C#N)cnn2c1=O]

5-bromo-6-isopropyl-7-oxo-4,7-dihydropyrazolo[1,5-a]pyrimidine-3-carbonitrile

To the suspension of 5-chloro-6-isopropyl-7-oxo-4H-pyrazolo[1,5-a]pyrimidine-3-carbonitrile (200 mg, 0.845 mmol) in EtCN (4 mL) was added TMSBr (1.29 g, 8.45 mmol) dropwise. The mixture was then heated at 115° C. for 17 hours. The reaction was quenched with ice-water, extracted with EtOAc (3×). The combined organics were dried over Na$_2$SO$_4$, filtered and concentrated. The crude product was purified by flash column chromatography on silica gel (0-10% MeOH/DCM with 1% formic acid) to give the title compound (129 mg, 54.3% yield) as an off-white solid. LCMS (ESI) m/z 283.1 [M+H]$^+$.

Step 2

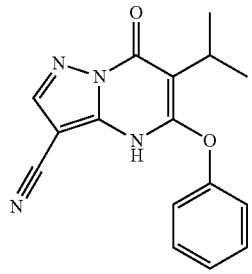 [SMILES: CC(C)c1c(Oc2ccccc2)[nH]c2c(C#N)cnn2c1=O]

6-isopropyl-7-oxo-5-phenoxy-4,7-dihydropyrazolo[1,5-a]pyrimidine-3-carbonitrile

The mixture of 5-bromo-6-isopropyl-7-oxo-4H-pyrazolo[1,5-a]pyrimidine-3-carbonitrile (80 mg, 0.28 mmol), phenol (81 mg, 0.85 mmol), CuI (5 mg, 0.028 mmol), trans-N,N'-dimethylcyclohexane-1,2-diamine (8 mg, 0.056 mmol), and K$_3$PO$_4$ (187 mg, 0.85 mmol) in DMSO (2 mL) was purged with N$_2$ for 2 min, then heated at 150° C. in a microwave reactor for 20 min. The mixture was filtered. The filter cake was washed with EtOAc. Combined filtrate was concentrated. The crude product was purified by prep HPLC (5-50% CH₃CN/H₂O with 0.1% NH₄OH) to give the title compound as an off-white solid (14 mg, 17% yield). $^1$H NMR (400 MHz, DMSO-d$_6$) δ 7.97 (s, 1H), 7.38-7.29 (m, 2H), 7.10-7.06 (m, 2H), 7.02-6.97 (m, 2H), 3.35-3.31 (m, 1H), 1.24 (d, J=6.81 Hz, 6H). LCMS (ESI): m/z 295.2 [M+H]$^+$, RT=5.73 min (LCMS Method F).

Using the General Synthetic Method (Syn. Met.) and the General LCMS Method shown, the following compounds of formula I were also prepared.

| Ex | Structure | Syn. Met. | LCMS (ESI) m/z | LCMS Method | R$_T$ (min) | NMR |
|---|---|---|---|---|---|---|
| 50 | 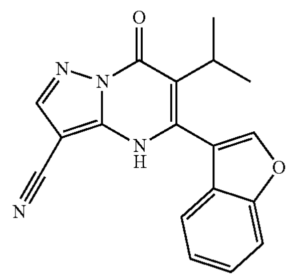 [SMILES: CC(C)c1c(-c2coc3ccccc23)[nH]c2c(C#N)cnn2c1=O] | A | 319.0 | A | 1.08 | $^1$H NMR (400 MHz, CD₃OD) δ 8.28 (s, 1H), 8.19 (s, 1H), 7.68 (d, J = 8.0 Hz, 1H), 7.61 (d, J = 7.6 Hz, 1H), 7.48 (t, J = 8.0 Hz, 1H), 7.40 (t, J = 7.6 Hz, 1H), 2.90-2.84 (m, 1H), 1.36 (d, J = 6.8 Hz, 6H). |
| 51 | 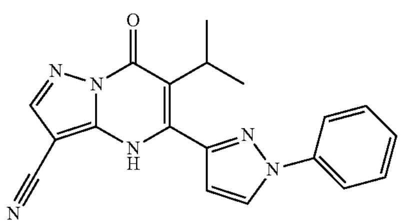 [SMILES: CC(C)c1c(-c2ccn(-c3ccccc3)n2)[nH]c2c(C#N)cnn2c1=O] | A | 345.1 | C | 1.34 | $^1$H NMR (400 MHz, DMSO-d$_6$) δ 13.4 (s, 1H), 8.72 (s, 1H), 8.38 (s, 1H), 7.91 (d, J = 8.0 Hz, 2H), 7.54 (t, J = 7.6 Hz, 2H), 7.37 (t, J = 7.6 Hz, 1H), 6.89 (s, 1H), 2.47-2.45 (m, 1H), 1.28 (d, J = 6.8 Hz, 6H). |
| 52 | 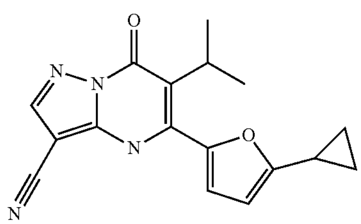 [SMILES: CC(C)c1c(-c2ccc(C3CC3)o2)[nH]c2c(C#N)cnn2c1=O] | A | 309.1 | A | 1.10 | $^1$H NMR (400 MHz, DMSO-d$_6$) δ 13.12 (s, 1H), 8.38 (s, 1H), 6.95 (d, J = 3.2 Hz, 1H), 6.41 (d, J = 3.2 Hz, 1H), 3.12-3.07 (m, 1H), 2.16-2.05 (m, 1H), 1.31 (d, J = 6.8 Hz, 6H), 1.05-0.97 (m, 2H), 0.90-0.83 (m, 2H). |
| 53 | 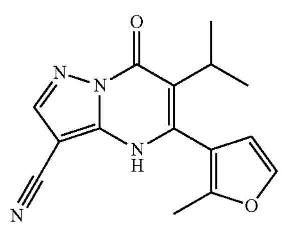 [SMILES: Cc1occc1-c1[nH]c2c(C#N)cnn2c(=O)c1C(C)C] | A | 283.1 | C | 1.20 | $^1$H NMR (400 MHz, CD₃OD) δ 8.21 (s, 1H), 7.55 (d, J = 1.8 Hz, 1H), 6.52 (d, J = 1.8 Hz, 1H), 2.88-2.81 (m, 1H), 2.31 (s, 3H), 1.32 (d, J = 6.8 Hz, 6H). |
| 54 | 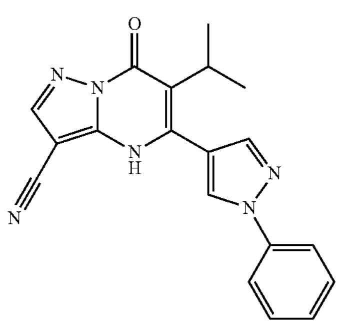 [SMILES: CC(C)c1c(-c2cnn(-c3ccccc3)c2)[nH]c2c(C#N)cnn2c1=O] | A | 345.1 | A | 1.08 | $^1$H NMR (400 MHz, DMSO-d$_6$) δ 13.25 (s, 1H), 8.92 (s, 1H), 8.40 (s, 1H), 8.04 (s, 1H) 7.93 (d, J = 7.6 Hz, 2H), 7.57 (t, J = 7.6 Hz, 2H), 7.40 (t, J = 7.6 Hz, 1H), 3.04-2.97 (m, 1H), 1.32 (d, J = 6.8 Hz, 6H). |

-continued

| Ex | Structure | Syn. Met. | LCMS (ESI) m/z | LCMS Method | R$_T$ (min) | NMR |
|---|---|---|---|---|---|---|
| 55 | 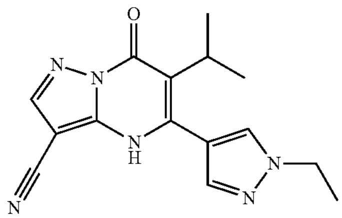 [SMILES: CCn1cc(-c2[nH]c3c(C#N)cnn3c(=O)c2C(C)C)cn1] | A | 296.9 | E | 0.69 | $^1$H NMR (400 MHz, CD$_3$OD) δ 8.21 (s, 1H), 8.06 (s, 1H), 7.76 (s, 1H), 4.30 (q, J = 7.2 Hz, 2H), 3.04-3.10 (m, 1H), 1.53 (t, J = 7.6 Hz, 3H), 1.38 (d, J = 7.2 Hz, 6H). |
| 56 | 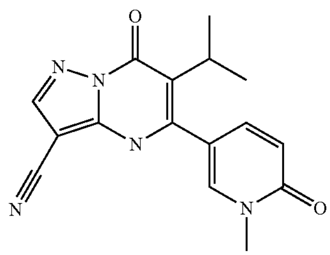 [SMILES: CC(C)c1c(-c2ccc(=O)n(C)c2)[nH]c2c(C#N)cnn2c1=O] | A | 309.9 | E | 0.61 | $^1$H NMR (400 MHz, CD$_3$OD) δ 8.24 (s, 1H), 8.01 (d, J = 2.4 Hz, 1H), 7.61 (dd, J = 9.2, 2.4 Hz, 1H), 6.68 (d, J = 9.2 Hz, 1H), 3.65 (s, 3H), 2.82-2.89 (m, 1H), 1.38 (d, J = 6.8 Hz, 6H). |
| 57 | 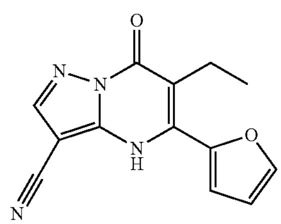 [SMILES: CCc1c(-c2ccco2)[nH]c2c(C#N)cnn2c1=O] | A | 255.0 | C | 1.07 | $^1$H NMR (400 MHz, CD$_3$OD) δ 8.25 (s, 1H), 7.89 (d, J = 1.6 Hz, 1H), 7.17 (d, J = 3.2 Hz, 1H), 6.75 (dd, J = 3.2, 1.6 Hz, 1H), 2.79 (q, J = 7.6 Hz, 2H), 1.22 (t, J = 7.6 Hz, 3H). |
| 58 | 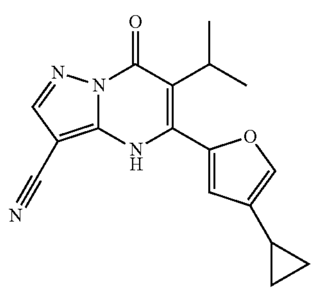 [SMILES: CC(C)c1c(-c2cc(C3CC3)co2)[nH]c2c(C#N)cnn2c1=O] | A | 309.1 | A | 1.10 | $^1$H NMR (400 MHz, DMSO-d$_6$) δ 8.36 (s, 1H), 7.83 (s, 1H), 6.83 (s, 1H), 3.08-3.02 (m, 1H), 1.84-1.73 (m, 1H), 1.27 (d, J = 6.8 Hz, 6H), 0.91-0.84 (m, 2H), 0.64-0.56 (m, 2H). |
| 59 | 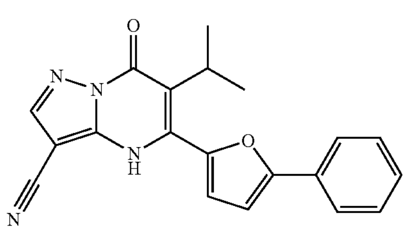 [SMILES: CC(C)c1c(-c2ccc(-c3ccccc3)o2)[nH]c2c(C#N)cnn2c1=O] | A | 345.0 | C | 1.41 | $^1$H NMR (400 MHz, DMSO-d$_6$) δ 8.34 (s, 1H), 7.81 (d, J = 8.0 Hz, 2H), 7.48 (t, J = 7.6 Hz, 2H), 7.36 (t, J = 7.6 Hz, 1H), 7.22 (s, 1H), 7.12 (s, 1H), 2.51-2.49 (m, 1H), 1.54 (d, J = 6.8 Hz, 6H). |
| 60 | 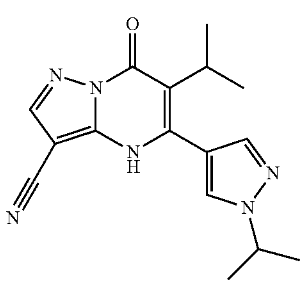 [SMILES: CC(C)c1c(-c2cnn(C(C)C)c2)[nH]c2c(C#N)cnn2c1=O] | A | 310.9 | E | 0.76 | $^1$H NMR (400 MHz, DMSO-d$_6$) δ 13.01 (s, 1H), 8.33 (s, 1H), 8.15 (s, 1H), 7.70 (s, 1H), 4.62-4.56 (m, 1H), 2.98-2.92 (m, 1H), 1.45 (d, J = 6.4 Hz, 6H), 1.26 (d, J = 6.8 Hz, 6H). |

-continued

| Ex | Structure | Syn. Met. | LCMS (ESI) m/z | LCMS Method | R$_T$ (min) | NMR |
|---|---|---|---|---|---|---|
| 61 | 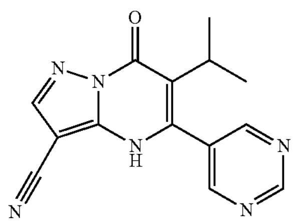 [SMILES: CC(C)c1c(-c2cncnc2)[nH]c2c(C#N)cnn2c1=O] | A | 280.8 | E | 0.64 | $^1$H NMR (400 MHz, DMSO-d$_6$) δ 9.40 (s., 1H), 9.03 (s., 2H), 8.46 (s., 1H), 1.26 (d, J = 6.4 Hz, 6H). |
| 62 | 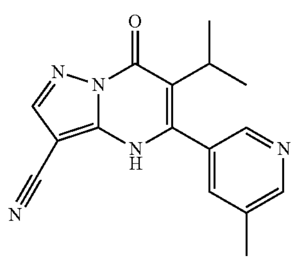 [SMILES: Cc1cncc(-c2[nH]c3c(C#N)cnn3c(=O)c2C(C)C)c1] | A | 294.1 | A | 0.78 | $^1$H NMR (400 MHz, DMSO-d$_6$) δ 8.55 (s, 1H), 8.46 (s, 1H), 8.31 (s, 1H), 7.73 (s, 1H), 2.63-2.56 (m, 1H), 2.39 (s, 3H), 1.25 (d, J = 6.8 Hz, 6H). |
| 63 | 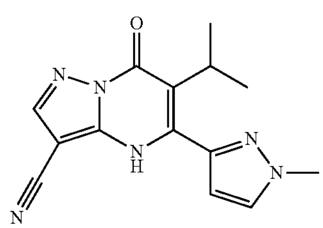 [SMILES: CC(C)c1c(-c2ccn(C)n2)[nH]c2c(C#N)cnn2c1=O] | A | 283.1 | E | 0.70 | $^1$H NMR (400 MHz, DMSO-d$_6$) δ 8.33 (s, 1H), 7.60 (s, 1H), 6.54 (s, 1H), 3.77 (s, 3H), 1.24 (d, J = 7.2 Hz, 6H). |
| 64 | 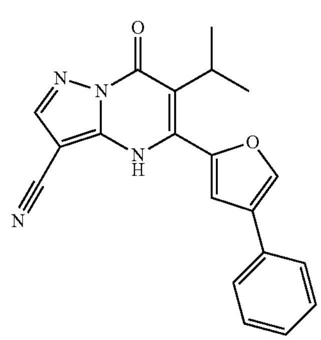 [SMILES: CC(C)c1c(-c2cc(-c3ccccc3)co2)[nH]c2c(C#N)cnn2c1=O] | A | 244.8 | A | 1.12 | $^1$H NMR (400 MHz, DMSO-d$_6$) δ 8.43 (s, 1H), 8.04 (d, J = 1.6 Hz, 1H), 7.47-7.41 (m, 2H), 7.40-7.35 (m, 2H), 7.34-7.20 (m, 1H), 7.11 (d, J = 1.6 Hz, 1H), 0.99 (d, J = 6.8 Hz, 6H). |
| 65 | 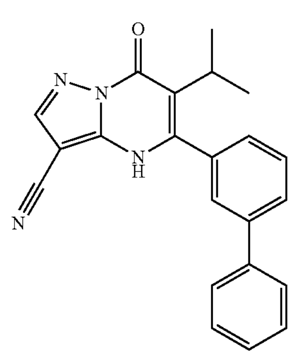 [SMILES: CC(C)c1c(-c2cccc(-c3ccccc3)c2)[nH]c2c(C#N)cnn2c1=O] | A | 355.1 | C | 1.20 | $^1$H NMR (400 MHz, DMSO-d$_6$) δ 13.47 (brs, 1H), 8.36 (brs, 1H), 7.84 (d, J = 7.6 Hz, 1H), 7.77 (brs., 1H), 7.71 (d, J = 7.2 Hz, 2H), 7.66-7.58 (m, 1H), 7.51-7.43 (m, 3H), 7.41-7.35 (m, 1H), 2.66 (m, 1H), 1.23 (d, J = 6.8 Hz, 6H) |

| Ex | Structure | Syn. Met. | LCMS (ESI) m/z | LCMS Method | R_T (min) | NMR |
|---|---|---|---|---|---|---|
| 66 | 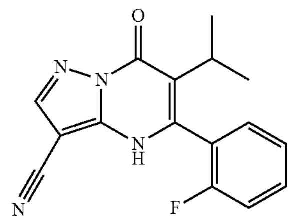 [SMILES: CC(C)c1c(-c2ccccc2F)[nH]c2c(C#N)cnn2c1=O] | A | 297.1 | E | 0.79 | ¹H NMR (400 MHz, DMSO-d₆) δ 8.18 (s, 1H), 7.55-7.44 (m 1H), 7.42-7.33 (m, 1H), 7.30-7.25 (m, 2H), 2.66-2.59 (m, 1H), 1.32 (d, J = 7.2 Hz, 6H). |
| 67 | 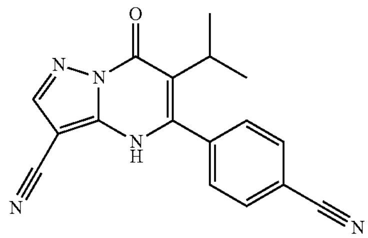 [SMILES: CC(C)c1c(-c2ccc(C#N)cc2)[nH]c2c(C#N)cnn2c1=O] | A | 304.1 | C | 1.22 | ¹H NMR (400 MHz, DMSO-d₆) δ 8.38 (s, 1H), 8.03 (d, J = 8.0 Hz, 2H), 7.71 (d, J = 8.4, 2H), 2.51-2.49 (m, 1H), 1.19 (d, J = 6.8 Hz, 6H). |
| 68 | 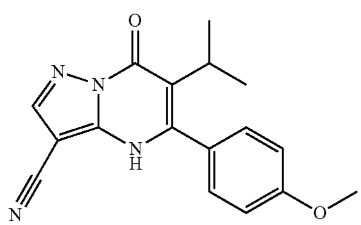 [SMILES: COc1ccc(-c2[nH]c3c(C#N)cnn3c(=O)c2C(C)C)cc1] | A | 309.2 | C | 1.28 | ¹H NMR (400 MHz, DMSO-d₆) δ 13.31 (s, 1H), 8.34 (s, 1H), 7.40 (d, J = 8.4 Hz, 2H), 7.08 (d, J = 8.8 Hz, 2H), 3.81 (s, 3H), 2.66-2.62 (m, 1H), 1.20 (d, J = 6.8 Hz, 6H), |
| 69 | 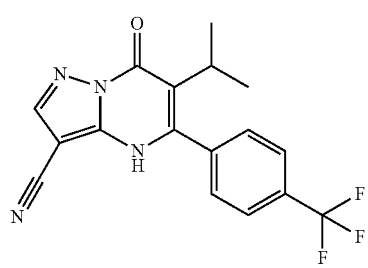 [SMILES: CC(C)c1c(-c2ccc(C(F)(F)F)cc2)[nH]c2c(C#N)cnn2c1=O] | A | 347.10 | A | 1.15 | ¹H NMR (400 MHz, DMSO-d₆) δ 13.48 (s, 1H), 8.38 (s, 1H), 7.95 (d, J = 8.0 Hz, 2H), 7.75 (d, J = 8.0 Hz, 2H), 1.24 (d, J = 6.4 Hz, 6H). |
| 70 | 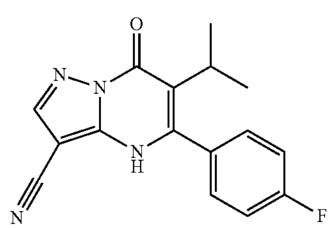 [SMILES: CC(C)c1c(-c2ccc(F)cc2)[nH]c2c(C#N)cnn2c1=O] | A | 296.8 | E | 0.81 | ¹H NMR (400 MHz, DMSO-d₆) δ 13.38 (s, 1H), 8.36 (s, 1H), 7.55 (dd, J = 8.4, 5.6 Hz, 2H), 7.42-7.36 (m, 2H), 2.57-2.51 (m, 1H), 1.21 (d, J = 7.2 Hz, 6H) |
| 71 | 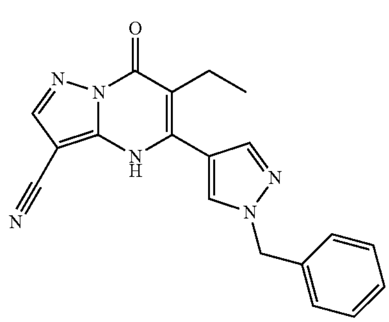 [SMILES: CCc1c(-c2cnn(Cc3ccccc3)c2)[nH]c2c(C#N)cnn2c1=O] | A | 344.8 | E | 0.78 | ¹H NMR (400 MHz, DMSO-d₆) δ 13.09 (s, 1H), 8.35 (d, J = 2.4 Hz, 1H), 7.84 (s, 1H), 7.38-7.28 (m, 5H), 5.44 (s, 2H), 1.07 (t, J = 7.2 Hz, 3H). |

-continued

| Ex | Structure | Syn. Met. | LCMS (ESI) m/z | LCMS Method | $R_T$ (min) | NMR |
|---|---|---|---|---|---|---|
| 72 | 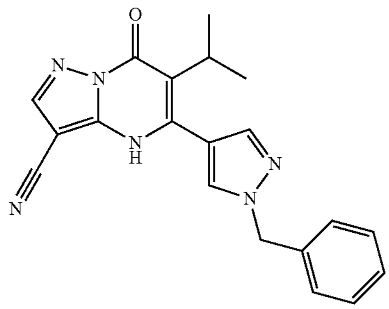 [SMILES: CC(C)c1c(-c2cnn(Cc3ccccc3)c2)[nH]c2c(C#N)cnn2c1=O] | A | 358.8 | E | 0.81 | $^1$H NMR (400 MHz, DMSO-d$_6$) δ 13.07 (s, 1H), 8.33 (s, 1H), 8.28 (s, 1H), 7.75 (s, 1H), 7.38-7.32 (m, 5H), 5.42 (s, 2H), 2.98-2.91 (m, 1H), 1.27 (d, J = 6.8 Hz, 6H). |
| 73 | 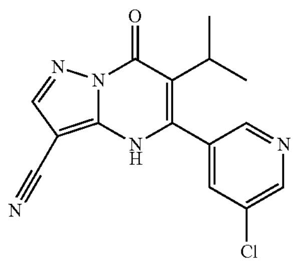 [SMILES: CC(C)c1c(-c2cncc(Cl)c2)[nH]c2c(C#N)cnn2c1=O] | A | 314.1 | C | 1.19 | $^1$H NMR (400 MHz, CD$_3$OD) δ 8.71 (s 1H), 8.59 (s, 1H), 8.19 (s, 1H), 8.04 (s, 1H), 2.72-2.65 (m, 1H), 1.37 (d, J = 7.0 Hz, 6H). |
| 74 | 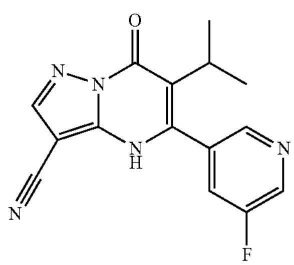 [SMILES: CC(C)c1c(-c2cncc(F)c2)[nH]c2c(C#N)cnn2c1=O] | A | 298.1 | C | 1.13 | $^1$H NMR (400 MHz, CD$_3$OD) δ 8.64 (d, J = 3.0 Hz, 1H), 8.54 (s, 1H), 8.20 (s, 1H), 7.86-7.78 (m, 1H), 2.72-2.65 (m, 1H), 1.37 (d, J = 7.2 Hz, 6H). |
| 75 | 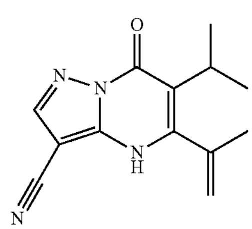 [SMILES: C=C(C)c1[nH]c2c(C#N)cnn2c(=O)c1C(C)C] | A | 243.1 | C | 1.16 | $^1$H NMR (400 MHz, DMSO-d$_6$) δ 13.16 (s, 1H), 8.30 (s, 1H), 5.44 (s, 1H), 5.16 (s, 1H), 2.89-2.82 (m, 1H), 2.07 (s, 3H), 1.25 (d, J = 7.2 Hz, 6H). |
| 76 | 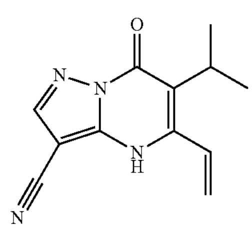 [SMILES: C=Cc1[nH]c2c(C#N)cnn2c(=O)c1C(C)C] | A | 229.1 | C | 1.10 | $^1$H NMR (400 MHz, CD$_3$OD) δ 8.22 (s, 1H), 7.03 (dd, J = 11.6, 17.2 Hz, 1H), 6.07 (d, J = 17.2 Hz, 1H), 5.88 (d, J = 11.6 Hz, 1H), 3.29-3.22 (m, 1H), 1.40 (d, J = 7.2 Hz, 6H). |
| 77 | 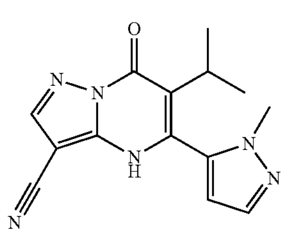 [SMILES: CC(C)c1c(-c2ccnn2C)[nH]c2c(C#N)cnn2c1=O] | A | 282.9 | E | 0.71 | $^1$H NMR (400 MHz, DMSO-d$_6$) δ 8.40 (s, 1H), 7.59 (d, J = 2.0 Hz, 1H), 6.54 (d, J = 2.0 Hz, 1H), 3.75 (s, 3H), 2.53-2.48 (m, 1H), 1.24 (d, J = 7.2 Hz, 6H). |

| Ex | Structure | Syn. Met. | LCMS (ESI) m/z | LCMS Method | R_T (min) | NMR |
|---|---|---|---|---|---|---|
| 78 | 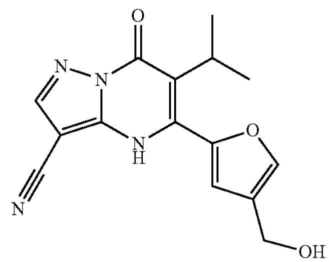 [SMILES: CC(C)c1c(-c2cc(CO)co2)[nH]c2c(C#N)cnn2c1=O] | A | 299.1 | C | 1.08 | $^1$H NMR (400 MHz, CD$_3$OD) δ 8.21 (s, 1H), 7.77 (s, 1H), 6.99 (s, 1H), 4.56 (s, 2H), 3.26-3.20 (m, 1H), 1.39 (d, J = 7.2 Hz, 6H). |
| 79 | 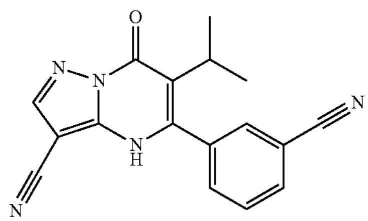 [SMILES: CC(C)c1c(-c2cccc(C#N)c2)[nH]c2c(C#N)cnn2c1=O] | A | 303.8 | E | 0.76 | $^1$H NMR (400 MHz, DMSO-d$_6$) δ 8.30 (s, 1H), 8.00-7.96 (m, 2H), 7.80-7.68 (m, 2H), 2.55-2.50 (m, 1H), 1.21 (d, J = 7.2 Hz, 6H). |
| 80 | 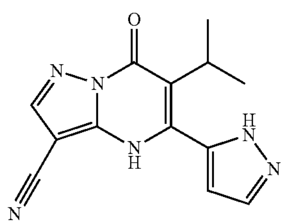 [SMILES: CC(C)c1c(-c2ccn[nH]2)[nH]c2c(C#N)cnn2c1=O] | A | 269.1 | C | 1.03 | $^1$H NMR (400 MHz, CD$_3$OD) δ 8.26 (s, 1H), 7.89 (s, 1H), 6.69 (d, J = 2.4 Hz, 1H), 3.15-3.12 (m, 1H), 1.38 (d, J = 6.8 Hz, 6H). |
| 81 | 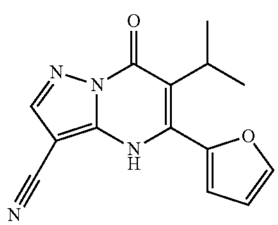 [SMILES: CC(C)c1c(-c2ccco2)[nH]c2c(C#N)cnn2c1=O] | A | 269.1 | A | 0.97 | $^1$H NMR (400 MHz, DMSO-d$_6$) δ 13.34 (s, 1H), 8.40 (s, 1H), 8.06 (d, J = 1.6 Hz, 1H), 7.04 (d, J = 2.8 Hz, 1H), 6.78 (dd, J = 2.8, 1.6 Hz, 1H), 3.12-3.04 (m, 1H), 1.31 (d, J = 6.8 Hz, 6H). |
| 82 | 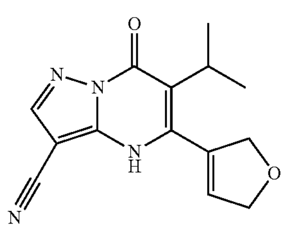 [SMILES: CC(C)c1c(C2=CCOC2)[nH]c2c(C#N)cnn2c1=O] | A | 271.1 | C | 1.07 | $^1$H NMR (400 MHz, DMSO-d$_6$) δ 8.34 (s, 1H), 6.36 (s., 1H), 4.77 (s, 4H), 2.91-284 (m, 1H), 1.28 (d, J = 7.2 Hz, 6H) |
| 83 | 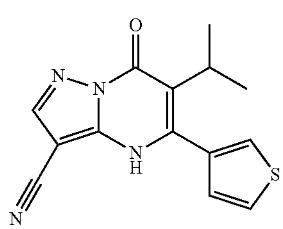 [SMILES: CC(C)c1c(-c2ccsc2)[nH]c2c(C#N)cnn2c1=O] | A | 285.1 | C | 1.22 | $^1$H NMR (400 MHz, DMSO-d$_6$) δ 8.16 (s, 1H), 7.60 (s, 2H), 7.21 (d, J = 4.8 Hz, 1H), 3.00-2.85 (m, 1H), 1.30 (d, J = 6.4 Hz, 6H). |

-continued

| Ex | Structure | Syn. Met. | LCMS (ESI) m/z | LCMS Method | R$_T$ (min) | NMR |
|---|---|---|---|---|---|---|
| 84 | 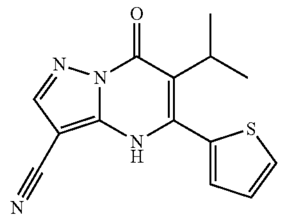 [SMILES: CC(C)c1c(-c2cccs2)[nH]c2c(C#N)cnn2c1=O] | A | 285.1 | C | 1.22 | $^1$H NMR (400 MHz, DMSO-d$_6$) δ 8.11 (s, 1H), 7.63 (d, J = 4.0 Hz, 1H), 7.20 (s, 1H), 7.15-7.09 (m, 1H), 3.24-3.17 (m, 1H), 1.34 (d, J = 6.8 Hz, 6H). |
| 85 | 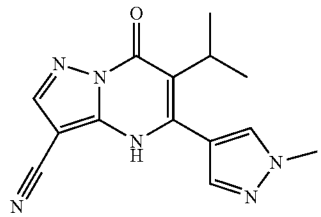 [SMILES: CC(C)c1c(-c2cnn(C)c2)[nH]c2c(C#N)cnn2c1=O] | A | 283.1 | C | 1.06 | $^1$H NMR (400 MHz, DMSO-d$_6$) δ 8.26 (s, 1H), 8.06 (s, 1H), 7.68 (s, 1H), 3.93 (s, 3H), 3.07-3.00 (m, 1H), 1.30 (d, J = 7.2 Hz, 6H). |
| 86 | 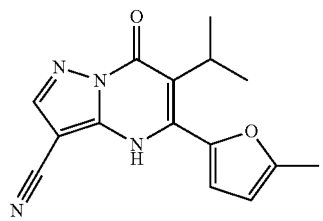 [SMILES: Cc1ccc(-c2[nH]c3c(C#N)cnn3c(=O)c2C(C)C)o1] | A | 283.1 | C | 1.26 | $^1$H NMR (400 MHz, DMSO-d$_6$) δ 8.30 (s, 1H), 6.84 (d, J = 2.4 Hz, 1H), 6.35 (d, J = 2.4 Hz, 1H), 3.16-3.12 (m, 1H), 2.38 (s, 3H), 1.29 (d, J = 6.8 Hz, 6H). |
| 87 | 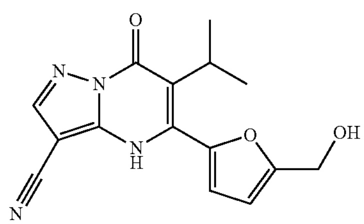 [SMILES: CC(C)c1c(-c2ccc(CO)o2)[nH]c2c(C#N)cnn2c1=O] | A | 298.8 | C | 0.71 | $^1$H NMR (400 MHz, DMSO-d$_6$) δ 8.38 (s, 1H), 6.95 (d, J = 3.2 Hz, 1H), 6.58 (d, J = 3.2 Hz, 1H), 4.52 (s, 2H), 3.17-3.10 (m, 1H), 1.31 (d, J = 6.8 Hz, 6H). |
| 88 | 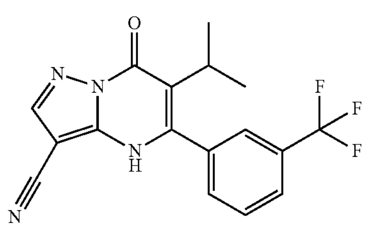 [SMILES: CC(C)c1c(-c2cccc(C(F)(F)F)c2)[nH]c2c(C#N)cnn2c1=O] | A | 347.1 | C | 1.37 | $^1$H NMR (400 MHz, DMSO-d$_6$) δ 13.45 (s, 1H), 8.41 (s, 1H), 7.94-7.88 (m, 2H), 7.84-7.80 (m, 2H), 2.49-2.44 (m, 1H), 1.23 (d, J = 6.4 Hz, 6H). |
| 89 | 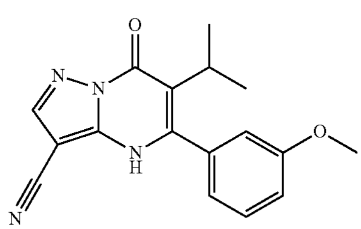 [SMILES: COc1cccc(-c2[nH]c3c(C#N)cnn3c(=O)c2C(C)C)c1] | A | 309.2 | C | 1.27 | $^1$H NMR (400 MHz, DMSO-d$_6$) δ 8.25 (s, 1H), 7.44-7.38 (m, 1H), 7.10-6.98 (m, 3H), 3.81 (s, 3H), 2.70-2.62 (m, 1H), 1.24 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 90 | 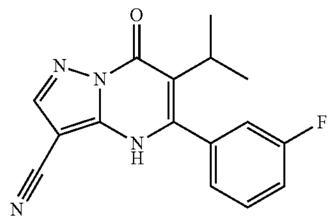 [SMILES: CC(C)c1c(-c2cccc(F)c2)[nH]c2c(C#N)cnn2c1=O] | A | 296.8 | E | 0.80 | $^1$H NMR (400 MHz, DMSO-d$_6$) δ 8.09 (s, 1H), 7.48-7.43 (m, 1H), 7.21-7.11 (m, 3H), 2.79-2.72 (m, 1H), 1.32 (d, J = 7.2 Hz, 6H). |
| 91 | 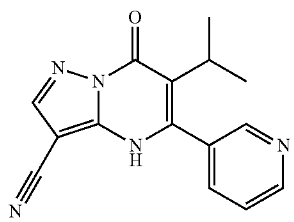 [SMILES: CC(C)c1c(-c2cccnc2)[nH]c2c(C#N)cnn2c1=O] | A | 280.1 | A | 0.99 | $^1$H NMR (400 MHz, DMSO-d$_6$) δ 8.58 (d, J = 4 Hz, 1H), 8.55 (s, 1H), 8.09 (s, 1H), 7.77 (d, J = 7.2 Hz, 1H), 7.46 (t, J = 6.8, Hz, 1H), 2.64-2.56 (m, 1H), 1.23 (d, J = 7.2 Hz, 6H). |
| 92 | 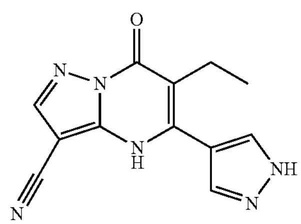 [SMILES: CCc1c(-c2cn[nH]c2)[nH]c2c(C#N)cnn2c1=O] | A | 255.1 | C | 0.93 | $^1$H NMR (400 MHz, CD$_3$OD) δ 8.26 (s, 1H), 8.10-7.98 (m, 2H), 2.66 (q, J = 7.2 Hz, 2H), 1.20 (t, J = 7.2 Hz, 3H). |
| 93 | 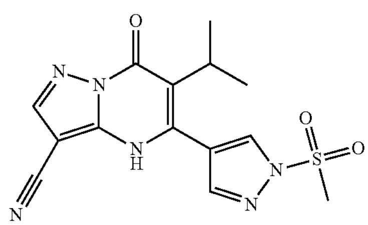 [SMILES: CC(C)c1c(-c2cnn(S(C)(=O)=O)c2)[nH]c2c(C#N)cnn2c1=O] | D | 346.9 | E | 0.73 | $^1$H NMR (400 MHz, DMSO-d$_6$) δ 13.30 (s., 1H), 8.71 (s., 1H), 8.41 (s, 1H), 8.21 (s, 1H), 3.71 (s, 3H), 2.90-2.76 (m, 1H), 1.30 (d, J = 7.2 Hz, 6H). |
| 94 | 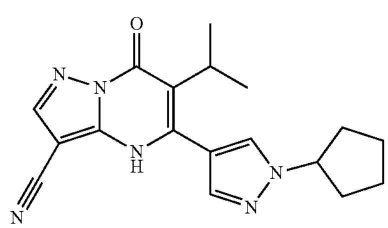 [SMILES: CC(C)c1c(-c2cnn(C3CCCC3)c2)[nH]c2c(C#N)cnn2c1=O] | D | 337.0 | A | 1.05 | $^1$H NMR (400 MHz, DMSO-d$_6$) δ 13.06 (s, 1H), 8.37 (s, 1H), 8.20 (s, 1H), 7.74 (s, 1H), 4.87-4.79 (m, 1H), 3.00-2.94 (m, 1H), 2.20-2.07 (m, 2H), 2.03-1.92 (m, 2H), 1.90-1.78 (m, 2H), 1.73-1.61 (m, 2H), 1.30 (d, J = 6.8 Hz, 6H). |
| 95 | 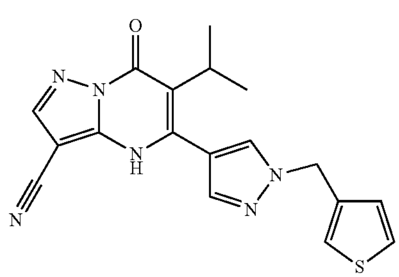 [SMILES: CC(C)c1c(-c2cnn(Cc3ccsc3)c2)[nH]c2c(C#N)cnn2c1=O] | D | 364.9 | A | 1.02 | $^1$H NMR (400 MHz, DMSO-d$_6$) δ 13.07 (s., 1H), 8.36 (s, 1H), 8.25 (s, 1H), 7.76 (s, 1H), 7.55 (dd, J = 4.8, 2.8 Hz, 1H), 7.49 (d, J = 2.8 Hz, 1H), 7.13 (d, J = 4.8 Hz, 1H), 5.44 (s, 2H), 3.00-2.93 (m, 1H), 1.29 (d, J = 7.2 Hz, 6H). |

| Ex | Structure | Syn. Met. | LCMS (ESI) m/z | LCMS Method | R_T (min) | NMR |
|---|---|---|---|---|---|---|
| 96 | 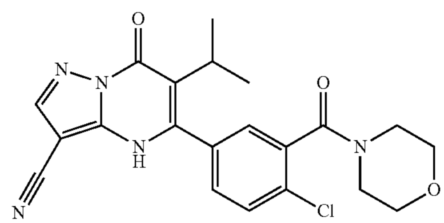 [SMILES: CC(C)c1c(-c2ccc(Cl)c(C(=O)N3CCOCC3)c2)[nH]c2c(C#N)cnn2c1=O] | A | 426.0 | E | 0.76 | $^1$H NMR (400 MHz, DMSO-d$_6$) δ 8.42 (s, 1H), 7.76 (d, J = 8.0 Hz, 1H), 7.60 (dd, J = 8.0, 2.0 Hz, 1H), 7.57 (d, J = 2.0 Hz, 1H), 3.70-3.60 (m, 4H), 3.60-3.52 (m., 2H), 3.25-3.15 (m., 2H), 2.54-2.52 (m, 1H), 1.22 (d, J = 7.2 Hz, 6H). |
| 97 | 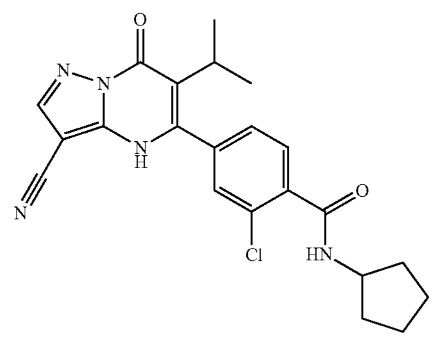 [SMILES: CC(C)c1c(-c2ccc(C(=O)NC3CCCC3)c(Cl)c2)[nH]c2c(C#N)cnn2c1=O] | A | 424.0 | E | 0.83 | $^1$H NMR (400 MHz, DMSO-d$_6$) δ 13.50 (s, 1H), 8.55 (d, J = 7.6 Hz, 1H), 8.42 (s, 1H), 7.71 (s, 1H), 7.58 (d, J = 8.0 Hz, 1H), 7.50 (d, J = 7.6 Hz, 1H), 4.27-4.16 (m, 1H), 2.58-2.55 (m, 1H), 1.90-1.82 (m, 2H), 1.72-1.66 (m, 2H), 1.60-1.49 (m, 4H), 1.25 (d, J = 7.2 Hz, 6H). |
| 98 | 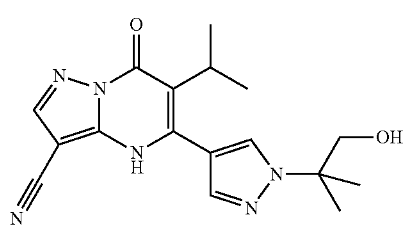 [SMILES: CC(C)c1c(-c2cnn(C(C)(C)CO)c2)[nH]c2c(C#N)cnn2c1=O] | A | 341.1 | A | 0.90 | $^1$H NMR (400 MHz, CD$_3$OD) δ 8.23 (s, 1H), 8.19 (s, 1H), 7.79 (s, 1H), 3.82 (s, 2H), 3.18-3.08 (m, 1H), 1.65 (s, 6H), 1.40 (d, J = 6.8 Hz, 6H). |
| 99 | 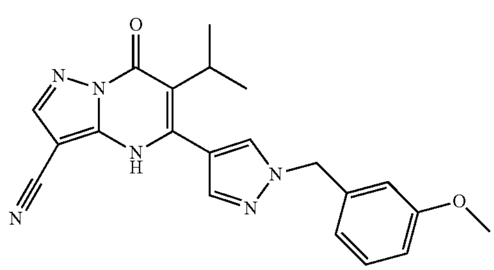 [SMILES: COc1cccc(Cn2cc(-c3[nH]c4c(C#N)cnn4c(=O)c3C(C)C)cn2)c1] | A | 388.9 | E | 0.77 | $^1$H NMR (400 MHz, DMSO-d$_6$) δ 13.12 (br s, 1H), 8.36 (br s, 1H), 8.30 (s, 1H), 7.77 (s, 1H), 7.34-7.23 (m, 1H), 6.90-6.89 (m, 3H), 5.41 (s, 2H), 3.75 (s, 3H), 3.02-2.95 (m, 1H), 1.30 (d, J = 6.8 Hz, 6H). |
| 100 | 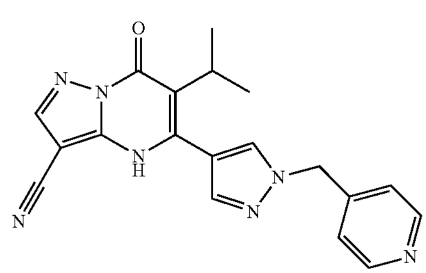 [SMILES: CC(C)c1c(-c2cnn(Cc3ccncc3)c2)[nH]c2c(C#N)cnn2c1=O] | A | 360.1 | E | 0.60 | $^1$H NMR (400 MHz, DMSO-d$_6$) δ 8.58 (d, J = 4.4 Hz, 2H), 8.36 (d, J = 5.6 Hz, 2H), 7.83 (s, 1H), 7.23 (d, J = 4.4 Hz, 2H), 5.54 (s, 2H), 3.08-2.89 (m, 1H), 1.30 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 101 | 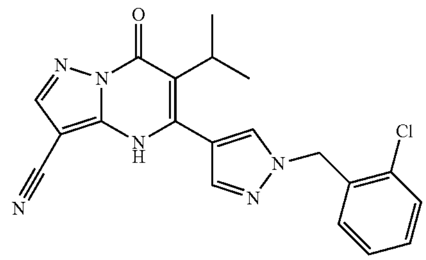 [SMILES: CC(C)c1c(-c2cnn(Cc3ccccc3Cl)c2)[nH]c2c(C#N)cnn2c1=O] | A | 392.9 | E | 0.81 | $^1$H NMR (400 MHz, DMSO-d$_6$) δ 13.12 (br. s, 1H), 8.37 (s, 1H), 8.30 (s, 1H), 7.82 (s, 1H), 7.52 (d, J = 5.6 Hz, 1H), 7.43-7.34 (m, 2H), 7.17 (br. s, 1H), 5.56 (s, 2H), 3.03-2.92 (m, 1H), 1.29 (d, J = 6.4 Hz, 6H). |
| 102 | 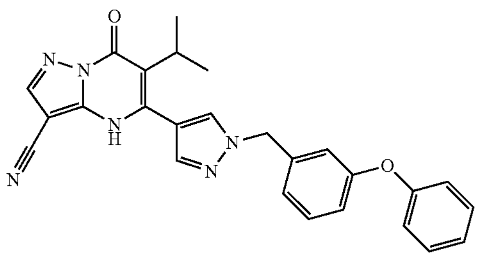 [SMILES: CC(C)c1c(-c2cnn(Cc3cccc(Oc4ccccc4)c3)c2)[nH]c2c(C#N)cnn2c1=O] | A | 451.0 | E | 0.85 | $^1$H NMR (400 MHz, DMSO-d$_6$) δ 8.07 (br. s., 1H), 8.04 (br. s., 1H), 7.62 (s, 1H), 7.41-7.35 (m, 3H), 7.16-7.13 (m, 1H), 7.08-6.96 (m, 4H), 6.93-6.91 (m, 1H), 5.38 (s, 2H), 3.17-2.97 (m, 1H), 1.30 (d, J = 7.2 Hz, 6H). |
| 103 | 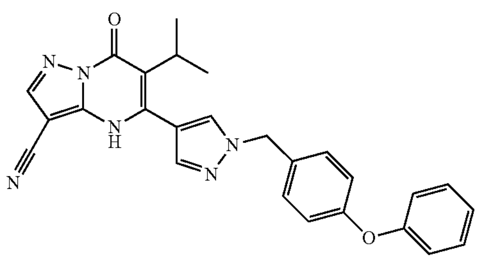 [SMILES: CC(C)c1c(-c2cnn(Cc3ccc(Oc4ccccc4)cc3)c2)[nH]c2c(C#N)cnn2c1=O] | A | 450.9 | E | 0.85 | $^1$H NMR (400 MHz, DMSO-d$_6$) δ 8.17 (br. s, 2H), 7.68 (br. s, 1H), 7.40-7.36 (m, 4H), 7.15-7.12 (m, 1H), 7.01-6.99 (m, 4H), 5.38 (s, 2H), 3.11-2.98 (m, 1H), 1.30 (d, J = 6.8 Hz, 6H). |
| 104 | 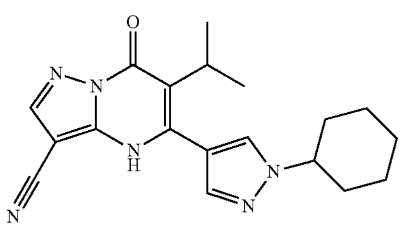 [SMILES: CC(C)c1c(-c2cnn(C3CCCCC3)c2)[nH]c2c(C#N)cnn2c1=O] | A | 350.9 | A | 1.10 | $^1$H NMR (400 MHz, CD$_3$OD) δ 8.21 (s, 1H), 8.09 (s, 1H), 7.75 (s, 1H), 4.29-4.23 (m, 1H), 3.08-3.03 (m, 1H), 2.18-2.15 (m, 2H), 1.96-1.92 (m, 2H), 1.86-1.78 (m, 3H), 1.56-1.46 (m, 2H), 1.37 (d, J = 6.8 Hz, 6H), 1.35-1.28 (m, 1H). |
| 105 | 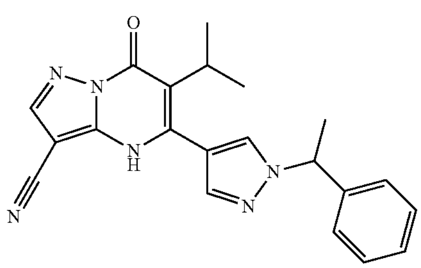 [SMILES: CC(C)c1c(-c2cnn(C(C)c3ccccc3)c2)[nH]c2c(C#N)cnn2c1=O] | A | 372.9 | E | 0.83 | $^1$H NMR (400 MHz, DMSO-d$_6$) δ 13.08 (br. s, 1H), 8.37 (s, 1H), 8.32 (s, 1H), 7.78 (s, 1H), 7.41-7.28 (m, 5H), 5.76 (q, J = 7.2 Hz, 1H), 3.00-2.93 (m, 1H), 1.87 (d, J = 6.8 Hz, 3H), 1.29 (d, J = 6.4 Hz, 6H). |
| 106 | 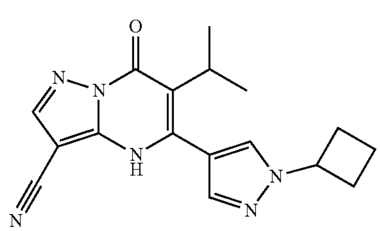 [SMILES: CC(C)c1c(-c2cnn(C3CCC3)c2)[nH]c2c(C#N)cnn2c1=O] | A | 323.0 | A | 1.00 | $^1$H NMR (400 MHz, CD$_3$OD) δ 8.23 (s, 1H), 8.14 (s, 1H), 7.81 (s, 1H), 5.00-4.90 (m, 1H), 3.10-3.04 (m, 1H), 2.71-2.59 (m, 2H), 2.59-2.49 (m, 2H), 2.00-1.90 (m, 2H), 1.40 (d, J = 6.8 Hz, 6H). |

-continued

| Ex | Structure | Syn. Met. | LCMS (ESI) m/z | LCMS Method | R$_T$ (min) | NMR |
|---|---|---|---|---|---|---|
| 107 | 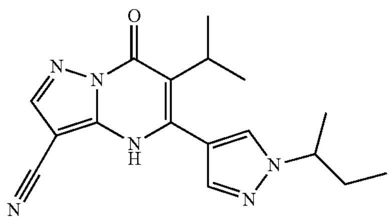 [SMILES: CCC(C)n1cc(-c2[nH]c3c(C#N)cnn3c(=O)c2C(C)C)cn1] | A | 324.9 | A | 1.01 | $^1$H NMR (400 MHz, CD$_3$OD) δ 8.24 (s, 1H), 8.10 (s, 1H), 7.80 (s, 1H), 4.47-4.33 (m, 1H), 3.11-3.05 (m, 1H), 2.05-1.82 (m, 2H), 1.57 (d, J = 6.4 Hz, 3H), 1.40 (d, J = 7.2 Hz, 6H), 0.88 (t, J = 7.2 Hz, 3H) |
| 108 | 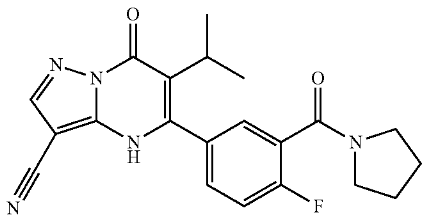 [SMILES: CC(C)c1c(-c2ccc(F)c(C(=O)N3CCCC3)c2)[nH]c2c(C#N)cnn2c1=O] | A | 393.9 | E | 0.78 | $^1$H NMR (400 MHz, CD$_3$OD) δ 8.24 (s, 1H), 7.71-7.57 (m, 2H), 7.47-7.42 (m, 1H), 3.63 (t, J = 6.4 Hz, 2H), 3.39 (t, J = 6.4 Hz, 2H), 2.69 (q, J = 6.8 Hz, 1H), 2.03-1.91 (m, 4H), 1.32 (d, J = 6.8 Hz, 6H). |
| 109 | 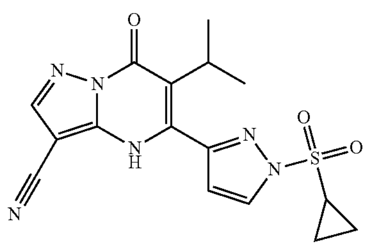 [SMILES: CC(C)c1c(-c2ccn(S(=O)(=O)C3CC3)n2)[nH]c2c(C#N)cnn2c1=O] | A | 372.9 | E | 0.76 | $^1$H NMR (400 MHz, CD$_3$OD) δ 13.34 (s, 1H), 8.73 (s, 1H), 8.42 (s, 1H), 8.22 (s, 1H), 3.30-3.26 (m, 1H), 2.85-2.78 (m, 1H), 1.38-1.36 (m, 2H), 1.31-1.29 (m, 8H). |
| 110 | 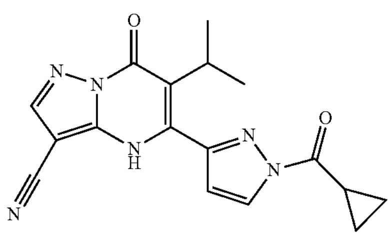 [SMILES: CC(C)c1c(-c2ccn(C(=O)C3CC3)n2)[nH]c2c(C#N)cnn2c1=O] | A | 336.9 | E | 0.80 | $^1$H NMR (400 MHz, DMSO-d$_6$) δ 13.32 (s, 1H), 8.80 (s, 1H), 8.41 (s, 1H), 8.19 (s, 1H), 3.15-3.11 (m, 1H), 2.86-2.81 (m, 1H), 1.31-1.26 (m, 8H), 1.21-1.20 (m, 2H). |
| 111 | 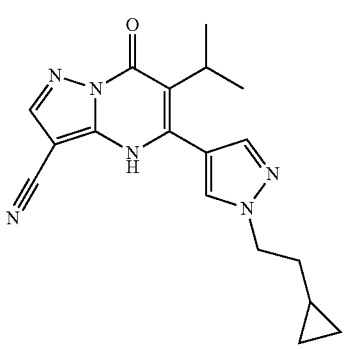 [SMILES: CC(C)c1c(-c2cnn(CCC3CC3)c2)[nH]c2c(C#N)cnn2c1=O] | A | 337.1 | C | 1.26 | $^1$H NMR (400 MHz, CD$_3$OD) δ 8.12 (s, 1H), 7.94 (s, 1H), 7.71 (s, 1H), 4.32 (t, J = 6.4 Hz, 2H), 3.22-3.15 (m, 1H), 1.83-1.78 (m, 2H), 1.40 (d, J = 6.8 Hz, 6H), 0.73-0.71 (m, 1H), 0.49-0.45 (m, 2H), 0.07-0.05 (m, 2H). |
| 112 | 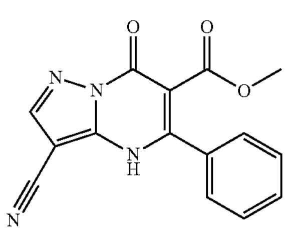 [SMILES: COC(=O)c1c(-c2ccccc2)[nH]c2c(C#N)cnn2c1=O] | B | 295.0 | C | 1.02 | $^1$H NMR (400 MHz, DMSO-d$_6$) δ 8.47 (s, 1H), 7.59-7.54 (m, 5H), 3.52 (s, 3H). |

-continued

| Ex | Structure | Syn. Met. | LCMS (ESI) m/z | LCMS Method | R$_T$ (min) | NMR |
|---|---|---|---|---|---|---|
| 113 | 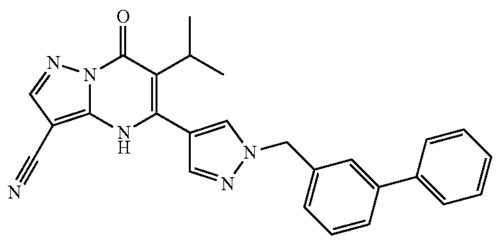 [SMILES: CC(C)c1c(-c2cnn(Cc3cccc(-c4ccccc4)c3)c2)[nH]c2c(C#N)cnn2c1=O] | A | 435.2 | A | 1.18 | $^1$H NMR (400 MHz, DMSO-d$_6$) δ 13.12 (s., 1H), 8.37 (d, J = 4.8 Hz, 2H), 7.79 (s, 1H), 7.63 (d, J = 7.6 Hz, 4H), 7.48 (t, J = 6.8 Hz, 3H), 7.40-7.36 (m, 2H), 5.52 (s., 1H), 3.02-2.95 (m, 1H), 1.29 (d, J = 7.2 Hz, 6H). |
| 114 | 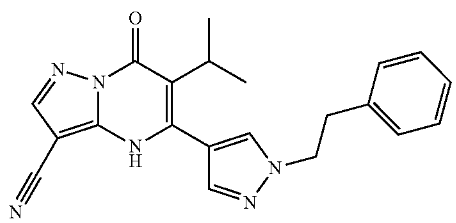 [SMILES: CC(C)c1c(-c2cnn(CCc3ccccc3)c2)[nH]c2c(C#N)cnn2c1=O] | A | 373.2 | E | 0.78 | $^1$H NMR (400 MHz, DMSO-d$_6$) δ 13.08 (s., 1H), 8.36 (s, 1H), 7.91 (s, 1H), 7.77 (s, 1H), 7.48 (t, J = 6.8 Hz, 3H), 7.29-7.22 (m, 3H), 7.17-7.15 (m, 2H), 4.47 (t, J = 6.8 Hz, 2H), 3.15 (t, J = 7.2 Hz, 2H), 2.77-2.71 (m, 1H), 1.22 (d, J = 6.8 Hz, 6H). |
| 115 | 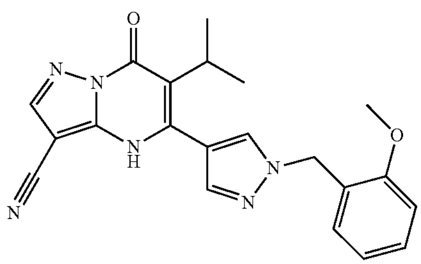 | A | 389.2 | E | 0.78 | $^1$H NMR (400 MHz, DMSO-d$_6$) δ 13.09 (s., 1H), 8.34 (s, 1H), 8.14 (s, 1H), 7.73 (s, 1H), 7.31 (t, J = 7.6 Hz, 1H), 7.05-7.02 (m, 2H), 6.94-6.92 (m, 1H), 5.37 (s, 2H), 3.81 (s, 3H), 2.98-2.92 (m, 1H), 1.27 (d, J = 7.2 Hz, 6H). |
| 116 | 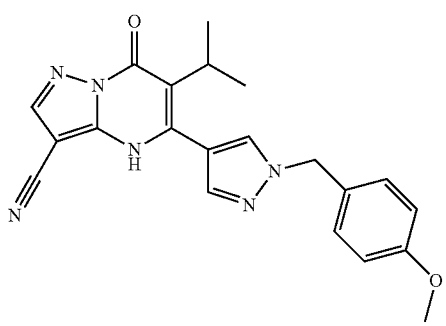 [SMILES: COc1ccc(Cn2cc(-c3[nH]c4c(C#N)cnn4c(=O)c3C(C)C)cn2)cc1] | A | 389.2 | E | 0.77 | $^1$H NMR (400 MHz, DMSO-d$_6$) δ 13.06 (s., 1H), 8.34 (s, 1H), 8.24 (s, 1H), 7.72 (s, 1H), 7.29 (d, J = 8.4 Hz, 2H), 6.91 (d, J = 8.8 Hz, 2H), 5.33 (s, 2H), 3.72 (s, 3H), 2.98-2.90 (m, 1H), 1.26 (d, J = 6.8 Hz, 6H). |
| 117 | 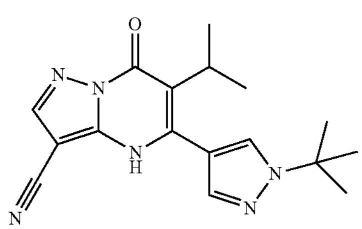 [SMILES: CC(C)c1c(-c2cnn(C(C)(C)C)c2)[nH]c2c(C#N)cnn2c1=O] | A | 325.2 | A | 1.02 | $^1$H NMR (400 MHz, DMSO-d$_6$) δ 13.02 (s., 1H), 8.38 (s, 1H), 8.21 (s, 1H), 7.75 (s, 1H), 3.02-2.95 (m, 1H), 1.60 (s, 9H), 1.30 (d, J = 6.4 Hz, 6H). |
| 118 | 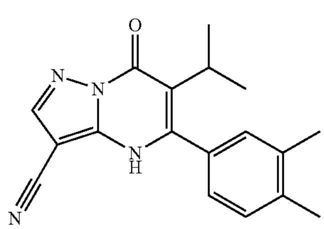 [SMILES: Cc1ccc(-c2[nH]c3c(C#N)cnn3c(=O)c2C(C)C)cc1C] | A | 307.2 | A | 1.13 | $^1$H NMR (400 MHz, DMSO-d$_6$) δ 13.37 (s., 1H), 8.39 (s, 1H), 7.33 (d, J = 8.0 Hz, 1H), 7.28 (s, 1H), 7.21 (d, J = 7.6 Hz, 1H), 2.67-2.63 (m, 1H), 2.31 (s, 6H), 1.23 (d, J = 6.8 Hz, 6H). |

-continued

| Ex | Structure | Syn. Met. | LCMS (ESI) m/z | LCMS Method | $R_T$ (min) | NMR |
|---|---|---|---|---|---|---|
| 119 | 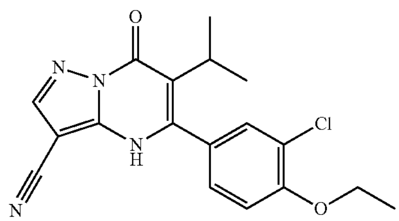 [SMILES: CCOc1ccc(-c2[nH]c3c(C#N)cnn3c(=O)c2C(C)C)cc1Cl] | A | 357.2 | A | 1.15 | $^1$H NMR (400 MHz, DMSO-$d_6$) δ 13.36 (s., 1H), 8.40 (s, 1H), 7.64 (s, 1H), 7.44-7.42 (m, 1H), 7.31 (d, J = 8.4 Hz, 1H), 4.24-4.19 (m, 2H), 2.67-2.60 (m, 1H), 1.40 (t, J = 6.4 Hz, 3H), 1.24 (d, J = 6.8 Hz, 6H). |
| 120 | 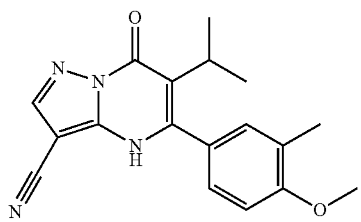 [SMILES: COc1ccc(-c2[nH]c3c(C#N)cnn3c(=O)c2C(C)C)cc1C] | A | 323.1 | A | 1.10 | $^1$H NMR (400 MHz, DMSO-$d_6$) δ 13.31 (s., 1H), 8.39 (s, 1H), 7.31 (d, J = 7.6 Hz, 2H), 7.12 (d, J = 8.0 Hz, 1H), 3.87 (s, 3H), 2.72-2.66 (m, 1H), 2.23 (s, 3H), 1.24 (d, J = 6.8 Hz, 6H). |
| 121 | 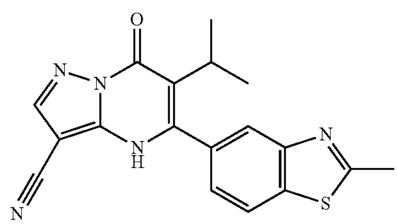 [SMILES: Cc1nc2cc(-c3[nH]c4c(C#N)cnn4c(=O)c3C(C)C)ccc2s1] | A | 350.1 | E | 0.77 | $^1$H NMR (400 MHz, DMSO-$d_6$) δ 13.49 (s., 1H), 8.42 (s, 1H), 8.26 (s, 1H), 8.08 (d, J = 8.8 Hz, 1H), 7.59 (d, J = 8.4 Hz, 1H), 2.86 (s, 3H), 2.64-2.58 (m, 1H), 1.24 (d, J = 6.4 Hz, 6H). |
| 122 | 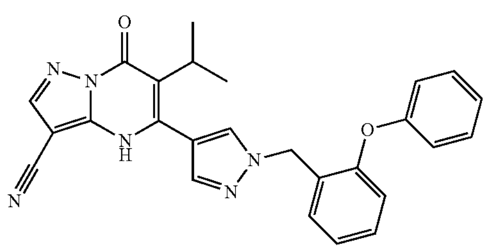 [SMILES: CC(C)c1c(-c2cnn(Cc3ccccc3Oc3ccccc3)c2)[nH]c2c(C#N)cnn2c1=O] | A | 451.2 | A | 1.19 | $^1$H NMR (400 MHz, DMSO-$d_6$) δ 13.08 (s., 1H), 8.15 (s, 1H), 7.67 (s, 1H), 7.39-7.35 (m, 3H), 7.12 (t, J = 7.6 Hz, 1H), 7.05 (d, J = 7.2 Hz, 1H), 6.98 (t, J = 7.6 Hz, 3H), 6.90 (dd, J = 8.4, 2.0 Hz, 1H), 5.38 (s, 2H), 3.00 (m, 1H), 1.27 (d, J = 7.2 Hz, 6H). |
| 123 | 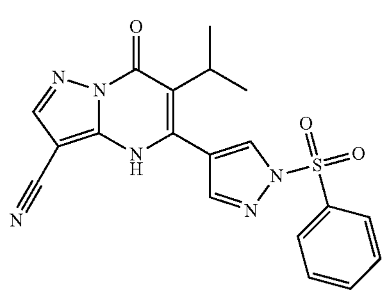 [SMILES: CC(C)c1c(-c2cnn(S(=O)(=O)c3ccccc3)c2)[nH]c2c(C#N)cnn2c1=O] | A | 409.1 | E | 0.82 | $^1$H NMR (400 MHz, DMSO-$d_6$) δ 13.29 (s., 1H), 8.92 (s, 1H), 8.39 (s, 1H), 8.15-8.09 (m, 2H), 7.89-7.85 (m, 1H), 7.77-7.73 (m, 2H), 2.72-2.67 (m, 1H), 1.25 (d, J = 6.4 Hz, 6H). |
| 124 | 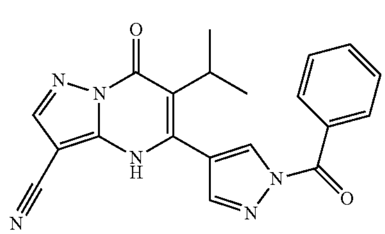 [SMILES: CC(C)c1c(-c2cnn(C(=O)c3ccccc3)c2)[nH]c2c(C#N)cnn2c1=O] | A | 373.1 | E | 0.82 | $^1$H NMR (400 MHz, DMSO-$d_6$) δ 13.39 (s., 1H), 8.97 (s, 1H), 8.41 (s, 1H), 8.21 (s, 1H), 8.09 (d, J = 7.6 Hz, 2H), 7.76 (t, J = 7.2 Hz, 1H), 7.62 (t, J = 7.6 Hz, 2H), 2.92-2.89 (m, 1H), 1.32 (d, J = 7.2 Hz, 6H). |

-continued

| Ex | Structure | Syn. Met. | LCMS (ESI) m/z | LCMS Method | $R_T$ (min) | NMR |
|---|---|---|---|---|---|---|
| 125 | 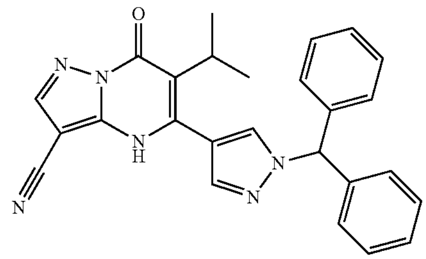 [SMILES: CC(C)c1c(-c2cnn(C(c3ccccc3)c3ccccc3)c2)[nH]c2c(C#N)cnn2c1=O] | A | 435.2 | A | 1.19 | $^1$H NMR (400 MHz, DMSO-d$_6$) δ 13.05 (s., 1H), 8.34 (s, 1H), 8.20 (s, 1H), 7.84 (s, 1H), 7.40-7.32 (m, 8H), 7.26 (d, J = 7.2 Hz, 2H), 7.05 (s, 1H), 2.96-2.85 (m, 1H), 1.25 (d, J = 7.2 Hz, 6H). |
| 126 | 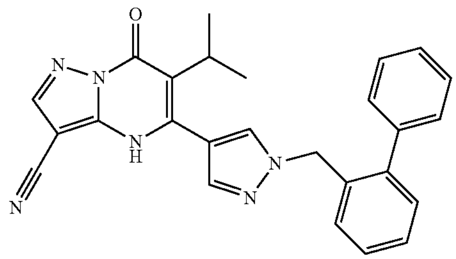 [SMILES: CC(C)c1c(-c2cnn(Cc3ccccc3-c3ccccc3)c2)[nH]c2c(C#N)cnn2c1=O] | A | 435.2 | A | 1.18 | $^1$H NMR (400 MHz, DMSO-d$_6$) δ 13.05 (s., 1H), 8.36 (s, 1H), 7.98 (s, 1H), 7.75 (s, 1H), 7.47-7.40 (m, 7H), 7.30 (d, J = 6.8 Hz, 1H), 7.19 (d, J = 6.0 Hz, 1H), 5.40 (s, 1H), 2.93-2.87 (m, 1H), 1.27 (d, J = 7.2 Hz, 6H). |
| 127 | 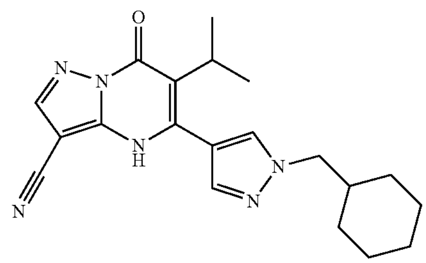 [SMILES: CC(C)c1c(-c2cnn(CC3CCCCC3)c2)[nH]c2c(C#N)cnn2c1=O] | A | 365.0 | E | 0.82 | $^1$H NMR (400 MHz, DMSO-d$_6$) δ 13.06 (s, 1H), 8.36 (s, 1H), 8.11 (s, 1H), 7.34 (s, 1H), 4.05 (d, J = 7.2 Hz, 2H), 3.00-2.95 (m, 1H), 1.86-1.81 (m, 1H), 1.70-1.54 (m, 5H), 1.29 (d, J = 6.8 Hz, 6H), 1.18-1.12 (m, 3H), 0.99-0.96 (m, 2H). |
| 128 | 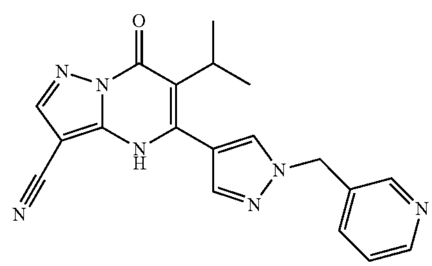 [SMILES: CC(C)c1c(-c2cnn(Cc3cccnc3)c2)[nH]c2c(C#N)cnn2c1=O] | A | 359.9 | E | 0.65 | $^1$H NMR (400 MHz, DMSO-d$_6$) δ 13.08 (s, 1H), 8.58 (s, 1H), 8.54 (d, J = 4.0 Hz, 1H), 8.34 (s, 2H), 7.78-7.74 (m, 2H), 7.42 (dd, J = 8.4, 5.2 Hz, 1H), 5.5 (s, 2H), 3.00-2.94 (m, 1H), 1.29 (d, J = 7.2 Hz, 6H). |
| 129 | 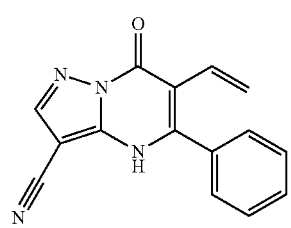 [SMILES: C=Cc1c(-c2ccccc2)[nH]c2c(C#N)cnn2c1=O] | C | 262.9 | E | 0.75 | $^1$H NMR (400 MHz, DMSO-d$_6$) δ 8.13 (s, 1H), 7.46-7.39 (m, 5H), 6.35 (dd, J = 16.8, 11.2 Hz, 1H), 6.24 (dd, J = 17.6, 3.6 Hz, 1H), 4.90 (dd, J = 11.6, 4.0 Hz, 1H). |
| 130 | 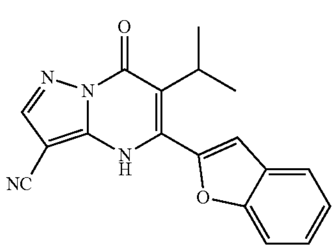 [SMILES: CC(C)c1c(-c2cc3ccccc3o2)[nH]c2c(C#N)cnn2c1=O] | A | 318.1 | E | 0.81 | $^1$H NMR: (400 MHz, CD$_3$OD) δ 8.20 (s, 1H), 7.75 (d, J = 7.6 Hz, 1H), 7.62 (d, J = 8.4 Hz, 1H), 7.44 (t, J = 8.0 Hz, 1H), 7.34 (t, J = 8.0 Hz, 1H), 7.29 (s, 1H), 3.26-3.30 (m, 1H), 1.44 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 131 | 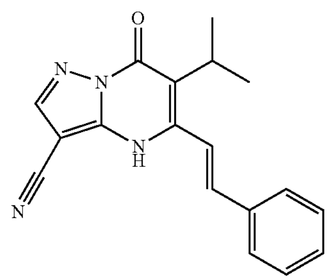 [SMILES: CC(C)c1c(/C=C/c2ccccc2)[nH]c2c(C#N)cnn2c1=O] | A | 304.1 | E | 0.81 | ¹H NMR: (400 MHz, CD₃OD) δ 8.20 (s, 1H), 7.67 (d, J = 7.2 Hz, 2H), 7.32-7.45 (m, 5H), 3.32-3.38 (m, 1H), 1.41 (d, J = 6.8 Hz, 6H). |
| 132 | 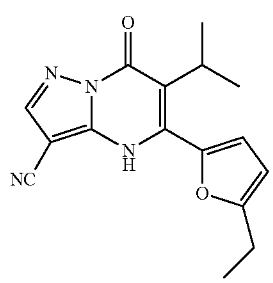 [SMILES: CCc1ccc(-c2[nH]c3c(C#N)cnn3c(=O)c2C(C)C)o1] | A | 296.1 | E | 0.80 | ¹H NMR: (400 MHz, CD₃OD) δ 8.23 (s, 1H), 6.93 (d, J = 3.6 Hz, 1H), 6.36 (d, J = 3.2 Hz, 1H), 3.26-3.31 (m, 1H), 2.81 (q, J = 7.6 Hz, 2H), 1.41 (d, J = 6.8 Hz, 6H), 1.33 (t, J = 8.0 Hz, 3H). |
| 133 | 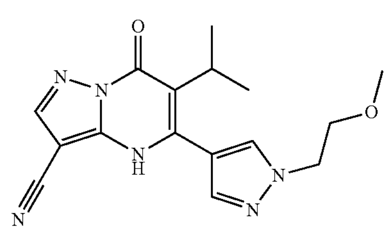 [SMILES: COCCn1cc(-c2[nH]c3c(C#N)cnn3c(=O)c2C(C)C)cn1] | A | 326.15 | E | 0.69 | ¹H NMR: (400 MHz, CD₃OD) δ 8.22 (s, 1H), 8.05 (s, 1H), 7.78 (s, 1H), 4.42 (t, J = 5.2 Hz, 2H), 3.80 (t, J = 5.2 Hz, 2H), 3.35 (s, 3H), 3.04-3.11 (m, 1H), 1.37 (d, J = 6.8 Hz, 6H). |
| 134 | 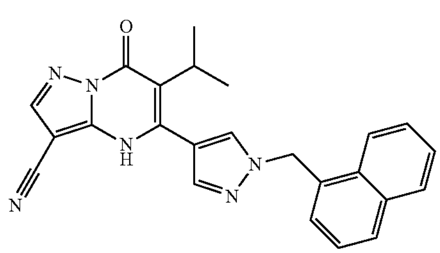 [SMILES: CC(C)c1c(-c2cnn(Cc3cccc4ccccc34)c2)[nH]c2c(C#N)cnn2c1=O] | A | 408.17 | E | 0.86 | ¹H NMR: (400 MHz, CD₃OD) δ 8.16 (s, 1H), 8.10 (d, J = 7.2 Hz, 1H), 7.90-7.95 (m, 3H), 7.80 (s, 1H), 7.47-7.56 (m, 3H), 7.45 (d, J = 5.6 Hz, 1H), 5.93 (s, 2H), 2.90-2.97 (m, 1H), 1.27 (d, J = 6.8 Hz, 6H). |
| 135 | 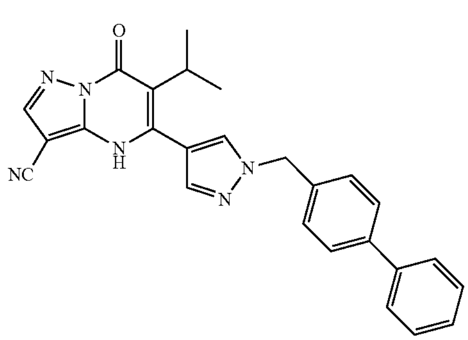 [SMILES: CC(C)c1c(-c2cnn(Cc3ccc(-c4ccccc4)cc3)c2)[nH]c2c(C#N)cnn2c1=O] | A | 434.19 | E | 0.89 | ¹H NMR: (400 MHz, CD₃OD) δ 8.21 (s, 1H), 8.16 (s, 1H), 7.81 (s, 1H), 7.60-7.65 (m, 4H), 7.43-7.46 (m, 4H), 7.34 (t, J = 7.6 Hz, 1H), 5.50 (s, 2H), 3.04-3.11 (m, 1H), 1.38 (d, J = 7.2 Hz, 6H). |

-continued

| Ex | Structure | Syn. Met. | LCMS (ESI) m/z | LCMS Method | $R_T$ (min) | NMR |
|---|---|---|---|---|---|---|
| 136 | 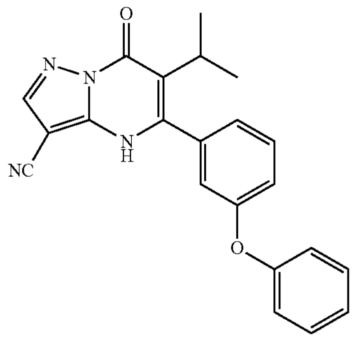 [SMILES: CC(C)c1c(-c2cccc(Oc3ccccc3)c2)[nH]c2c(C#N)cnn2c1=O] | A | 370.14 | E | 0.89 | $^1$H NMR: (400 MHz, CD$_3$OD) δ 8.22 (s, 1H), 7.55 (t, J = 8.0 Hz, 1H), 7.40 (t, J = 8.0 Hz, 2H), 7.15-7.23 (m, 3H), 7.07 (d, J = 7.6 Hz, 3H), 2.72-2.78 (m, 1H), 1.29 (d, J = 7.2 Hz, 6H). |
| 137 | 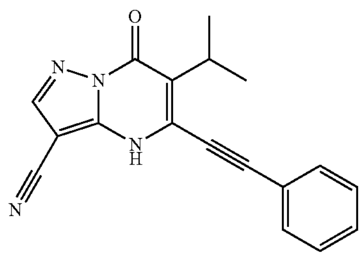 [SMILES: CC(C)c1c(C#Cc2ccccc2)[nH]c2c(C#N)cnn2c1=O] | A | 302.12 | E | 0.85 | $^1$H NMR: (400 MHz, CD$_3$OD) δ 8.23 (s, 1H), 7.66 (d, J = 6.8 Hz, 2H), 7.47-7.67 (m, 3H), 3.53-3.60 (m, 1H), 1.46 (d, J = 7.2 Hz, 6H) |
| 138 | 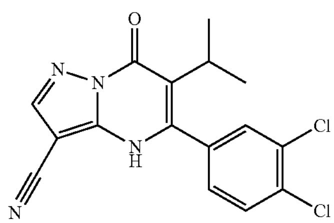 [SMILES: CC(C)c1c(-c2ccc(Cl)c(Cl)c2)[nH]c2c(C#N)cnn2c1=O] | A | 345.9 | E | 0.61 | $^1$H NMR (400 MHz, CD$_3$OD) δ 8.27 (s, 1H), 7.76-7.79 (m, 2H), 7.48 (dd, J = 8.0 Hz, 2.0 Hz, 1H), 2.66-2.73 (m, 1H), 1.35 (d, J = 7.2 Hz, 6H). |
| 139 | 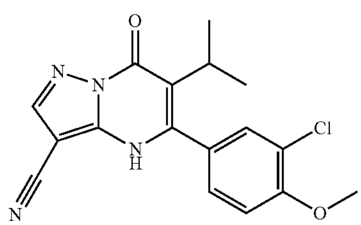 [SMILES: COc1ccc(-c2[nH]c3c(C#N)cnn3c(=O)c2C(C)C)cc1Cl] | A | 342.7 | E | 0.82 | $^1$H NMR (400 MHz, CD$_3$OD) δ 8.24 (s, 1H), 7.57 (d, J = 2.0 Hz, 1H), 7.44 (dd, J = 8.4 Hz, 2.0 Hz, 1H), 7.27 (d, J = 8.6 Hz, 1H), 3.99 (s, 3H), 2.74-2.81 (m, 1H), 1.33 (d, J = 6.8 Hz, 6H). |
| 140 | 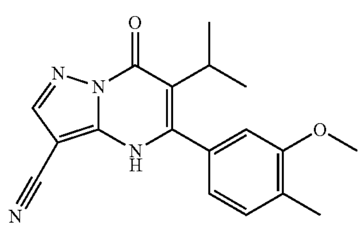 [SMILES: COc1cc(-c2[nH]c3c(C#N)cnn3c(=O)c2C(C)C)ccc1C] | A | 322.9 | E | 0.84 | $^1$H NMR (400 MHz, CD$_3$OD) δ 8.23 (s, 1H), 7.31 (d, J = 7.5 Hz, 1H), 7.03 (s, 1H), 6.97 (d, J = 2.1 Hz, 1H), 3.89 (s, 3H), 2.77-2.84 (m, 1H), 2.28 (s, 3H), 1.33 (d, J = 7.2 Hz, 6H). |
| 141 | 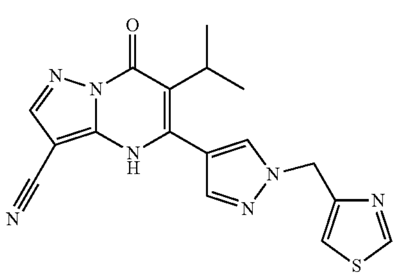 [SMILES: CC(C)c1c(-c2cnn(Cc3cscn3)c2)[nH]c2c(C#N)cnn2c1=O] | D | 365.8 | E | 0.73 | $^1$H NMR: (400 MHz, CD$_3$OD) δ 9.02 (s, 1H), 8.21 (s, 1H), 8.16 (s, 1H), 7.78 (s, 1H), 7.60 (d, J = 1.2 Hz, 1H), 5.60 (s, 2H), 3.02-3.31 (m, 1H), 1.36 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 142 | 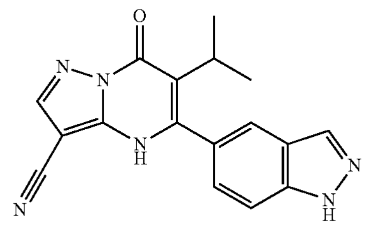 [SMILES: CC(C)c1c(-c2ccc3[nH]ncc3c2)[nH]c2c(C#N)cnn2c1=O] | A | 318.9 | E | 0.71 | $^1$H NMR: (400 MHz, CD$_3$OD) δ 8.25 (s, 1H), 8.21 (s, 1H), 7.98 (s, 1H), 7.74 (d, J = 8.6 Hz, 1H), 7.50 (dd, J = 8.6, 1.2 Hz, 1H), 2.76-2.83 (m, 1H), 1.33 (d, J = 6.8 Hz, 6H). |
| 143 | 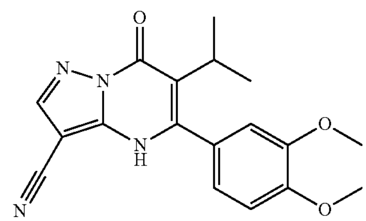 [SMILES: COc1ccc(-c2[nH]c3c(C#N)cnn3c(=O)c2C(C)C)cc1OC] | A | 338.8 | E | 0.78 | $^1$H NMR: (400 MHz, CD$_3$OD) δ 8.23 (s, 1H), 7.06-7.14 (s, 3H), 3.92 (s, 3H), 3.89 (s, 3H), 2.80-2.87 (m, 1H), 1.34 (d, J = 7.1 Hz, 6H) |
| 144 | 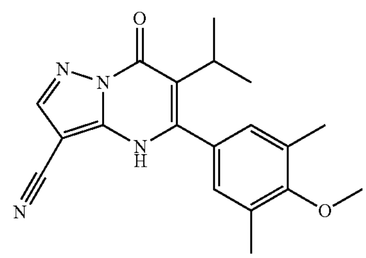 [SMILES: COc1c(C)cc(-c2[nH]c3c(C#N)cnn3c(=O)c2C(C)C)cc1C] | A | 336.9 | E | 0.86 | $^1$H NMR: (400 MHz, CD$_3$OD) δ 8.22 (s, 1H), 7.17 (s, 2H), 3.79 (s, 3H), 2.76-2.83 (m, 1H), 2.36 (s, 6H), 1.32 (d, J = 6.8 Hz, 6H) |
| 145 | 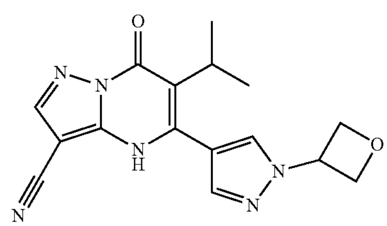 [SMILES: CC(C)c1c(-c2cnn(C3COC3)c2)[nH]c2c(C#N)cnn2c1=O] | A | 325.1 | E | 0.61 | $^1$H NMR: (400 MHz, CD$_3$OD) δ 8.23 (s, 1H), 8.19 (s, 1H), 7.90 (s, 1H), 5.66-5.77 (m, 1H), 5.10 (d, J = 6.8 Hz, 4H), 3.03-3.10 (m, 1H), 1.38 (d, J = 6.8 Hz, 6H) |
| 146 | 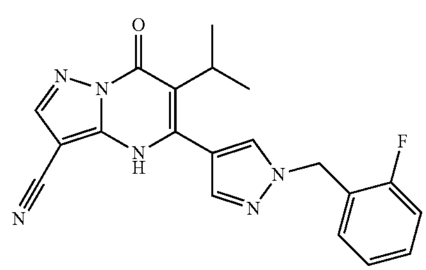 [SMILES: CC(C)c1c(-c2cnn(Cc3ccccc3F)c2)[nH]c2c(C#N)cnn2c1=O] | A | 439.9 | E | 0.80 | $^1$H NMR (400 MHz, DMSO-d$_6$) δ 13.09 (s, 1H), 8.33 (s, 1H), 8.25 (s, 1H), 7.75 (s, 1H), 7.40-7.18 (m, 4H), 5.48 (s, 2H), 2.95-2.95 (m, 1H), 1.26 (d, J = 6.8 Hz, 6H). |
| 147 | 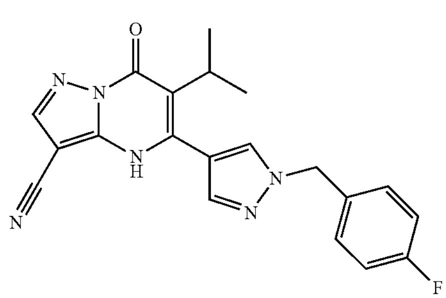 [SMILES: CC(C)c1c(-c2cnn(Cc3ccc(F)cc3)c2)[nH]c2c(C#N)cnn2c1=O] | A | 440.0 | E | 0.78 | $^1$H NMR (400 MHz, DMSO-d$_6$) δ 13.07 (s, 1H), 8.34 (s, 1H), 8.28 (s, 1H), 7.75 (s, 1H), 7.38 (m, 2H), 7.22-7.18 (m, 2H), 5.41 (s, 2H), 2.98-2.90 (m, 1H), 1.26 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 148 | 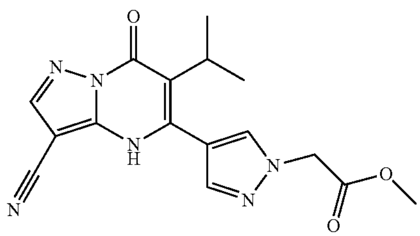 [SMILES: COC(=O)Cn1cc(-c2[nH]c3c(C#N)cnn3c(=O)c2C(C)C)cn1] | A | 403.9 | E | 0.72 | $^1$H NMR (400 MHz, DMSO-d$_6$) δ 13.20 (s, 1H), 8.34 (s, 1H), 8.16 (s, 1H), 7.76 (s, 1H), 5.20 (s, 2H), 3.70 (s, 3H), 2.70-2.92 (m, 1H), 1.26 (d, J = 6.8 Hz, 6H). |
| 149 | 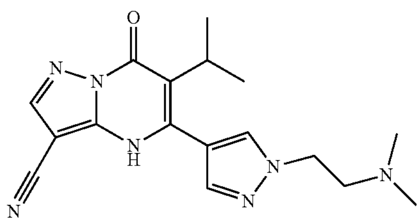 [SMILES: CC(C)c1c(-c2cnn(CCN(C)C)c2)[nH]c2c(C#N)cnn2c1=O] | A | 340.1 | E | 0.60 | $^1$H NMR (400 MHz, DMSO-d$_6$) δ 8.34 (s, 2H), 7.67 (s, 1H), 4.48 (t, J = 6.4 Hz, 2H), 3.08 (t, J = 6.8 Hz, 2H), 2.65 (s, 6H), 1.29 (d, J = 6.8 Hz, 6H). |
| 150 | 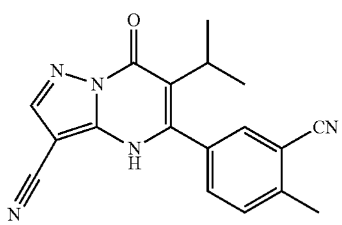 [SMILES: Cc1ccc(-c2[nH]c3c(C#N)cnn3c(=O)c2C(C)C)cc1C#N] | A | 317.9 | C | 1.25 | $^1$H NMR (400 MHz, DMSO-d$_6$) δ 13.40 (s, 1H), 8.40 (s, 1H), 7.90 (s, 1H), 7.71 (d, J = 8.0 Hz, 1H), 7.64 (d, J = 8.0 Hz, 1H), 2.56 (s, 3H), 2.39-2.50 (m, 1H), 1.20 (d, J = 6.8 Hz, 6H). |
| 151 | 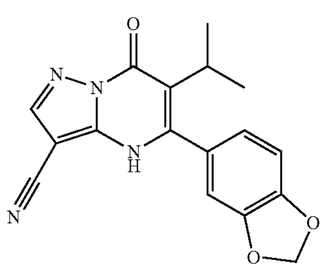 [SMILES: CC(C)c1c(-c2ccc3c(c2)OCO3)[nH]c2c(C#N)cnn2c1=O] | A | 323.0 | E | 0.80 | $^1$H NMR (400 MHz, DMSO-d$_6$) δ 13.33 (s, 1H), 8.36 (s, 1H), 7.09-7.07 (m, 1H), 6.95 (d, J = 8.0 Hz, 1H), 6.11 (s, 2H), 2.68-2.48 (m, 1H), 1.21 (d, J = 6.8 Hz, 6H). |
| 152 | 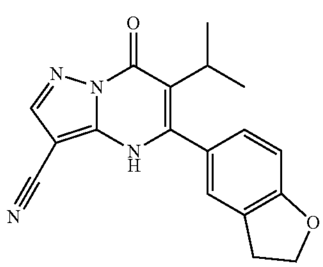 | A | 320.9 | E | 0.81 | $^1$H NMR (400 MHz, DMSO-d$_6$) δ 13.27 (s, 1H), 8.35 (s, 1H), 7.35 (s, 1H), 7.19 (d, J = 8.0 Hz, 1H), 6.90 (d, J = 8.8 Hz, 1H), 4.60 (t, J = 8.8 Hz, 2H), 3.24 (t, J = 8.8 Hz, 2H) 2.72-2.65 (m, 1H), 1.21 (d, J = 6.8 Hz, 6H). |
| 153 | 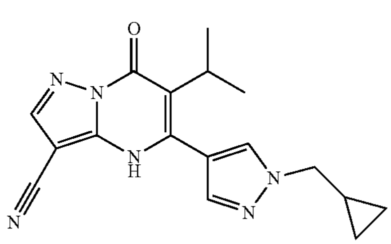 [SMILES: CC(C)c1c(-c2cnn(CC3CC3)c2)[nH]c2c(C#N)cnn2c1=O] | A | 269.1 | E | 0.73 | $^1$H NMR (400 MHz, CD$_3$OD) δ 8.20 (s, 1H), 8.12 (s, 1H), 7.76 (s, 1H), 4.11 (d, J = 7.2 Hz, 2H), 3.10-3.03 (m, 1H), 1.37 (d, J = 7.2 Hz, 6H), 1.37 (m, 1H), 0.68-0.63 (m, 2H), 0.47-0.43 (m, 2H). |

| Ex | Structure | Syn. Met. | LCMS (ESI) m/z | LCMS Method | R$_T$ (min) | NMR |
|---|---|---|---|---|---|---|
| 154 | 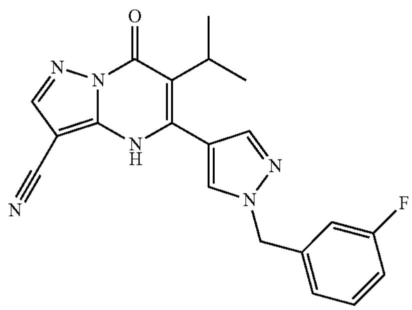 [SMILES: CC(C)c1c(-c2cnn(Cc3cccc(F)c3)c2)[nH]c2c(C#N)cnn2c1=O] | A | 398.9 | E | 0.77 | $^1$H NMR (400 MHz, CD$_3$OD) δ 8.20 (s, 1H), 8.15 (s, 1H), 7.80 (s, 1H), 7.38 (m, 1H), 7.40 (m, J = 8.0 Hz, 2H), 7.08-7.03 (m, 1H), 5.47 (s, 2H), 3.07-3.00 (m, 1H), 1.36 (d, J = 7.2 Hz, 6H). |
| 155 | 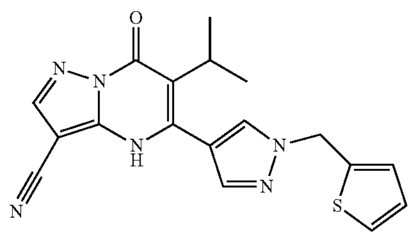 [SMILES: CC(C)c1c(-c2cnn(Cc3cccs3)c2)[nH]c2c(C#N)cnn2c1=O] | A | 364.9 | E | 0.79 | $^1$H NMR (400 MHz, CD$_3$OD) δ 8.19 (s, 1H), 8.10 (s, 1H), 7.78 (s, 1H), 7.40 (dd, J = 4.8, 0.8 Hz, 1H), 7.18 (d, J = 3.2 Hz, 1H), 7.00 (dd, J = 4.8, 3.2 Hz, 1H), 5.63 (s, 1H), 3.06-2.99 (m, 1H), 1.35 (d, J = 7.2 Hz, 6H). |
| 156 | 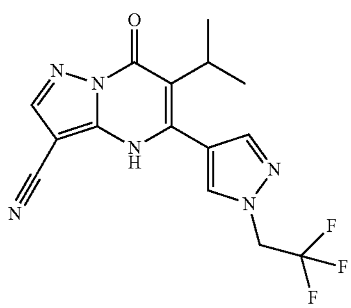 [SMILES: CC(C)c1c(-c2cnn(CC(F)(F)F)c2)[nH]c2c(C#N)cnn2c1=O] | A | 350.9 | A | 0.96 | $^1$H NMR (400 MHz, CD$_3$OD) δ 8.24 (s, 1H), 8.23 (s, 1H), 7.90 (s, 1H), 5.12 (q, J = 8.8 Hz, 2H), 3.06-2.98 (m, 1H), 1.39 (d, J = 6.4 Hz, 6H). |
| 157 | 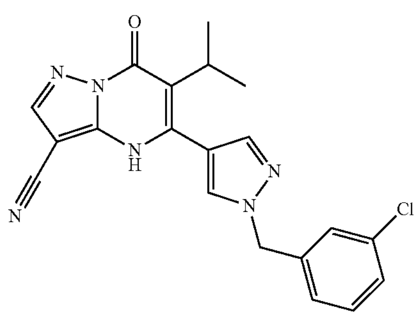 [SMILES: CC(C)c1c(-c2cnn(Cc3cccc(Cl)c3)c2)[nH]c2c(C#N)cnn2c1=O] | A | 392.8 | E | 0.83 | $^1$H NMR (400 MHz, CD$_3$OD) δ 8.20 (s, 1H), 8.17 (s, 1H), 7.81 (s, 1H), 7.38-7.25 (m, 4H), 5.45 (s, 2H), 3.08-2.98 (m, 1H), 1.36 (d, J = 7.2 Hz, 6H). |
| 158 | 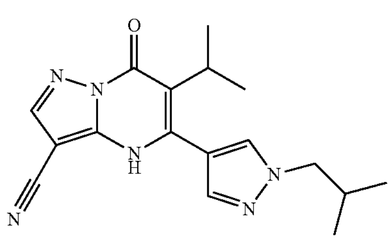 [SMILES: CC(C)Cn1cc(-c2[nH]c3c(C#N)cnn3c(=O)c2C(C)C)cn1] | A | 325.0 | A | 1.02 | $^1$H NMR (400 MHz, CD$_3$OD) δ 8.24 (s, 1H), 8.06 (s, 1H), 7.80 (s, 1H), 4.08 (d, J = 7.2 Hz, 2H), 3.12-3.04 (m, 1H), 2.31-2.24 (m, 1H), 1.39 (d, J = 6.8 Hz, 6H), 0.98 (d, J = 7.2 Hz, 6H). |

| Ex | Structure | Syn. Met. | LCMS (ESI) m/z | LCMS Method | R_T (min) | NMR |
|---|---|---|---|---|---|---|
| 159 | 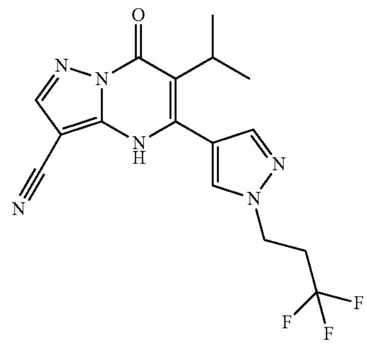 [SMILES: CC(C)c1c(-c2cnn(CCC(F)(F)F)c2)[nH]c2c(C#N)cnn2c1=O] | A | 365.0 | A | 1.00 | ¹H NMR (400 MHz, CD₃OD) δ 8.21 (s, 1H), 8.10 (s, 1H), 7.80 (s, 1H), 4.54 (t, J = 6.8 Hz, 2H), 3.06-3.02 (m, 1H), 2.92-2.84 (m, 2H), 1.35 (d, J = 6.8 Hz, 6H). |
| 160 | 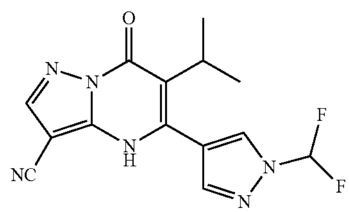 [SMILES: CC(C)c1c(-c2cnn(C(F)F)c2)[nH]c2c(C#N)cnn2c1=O] | A | 319.0 | A | 0.92 | ¹H NMR (400 MHz, CD₃OD) δ 8.50 (s, 1H), 8.22 (s, 1H), 7.98 (s, 1H), 7.62 (t, J = 60.0 Hz, 1H), 2.98-2.90 (m, 1H), 1.37 (d, J = 7.2 Hz, 6H). |
| 161 | 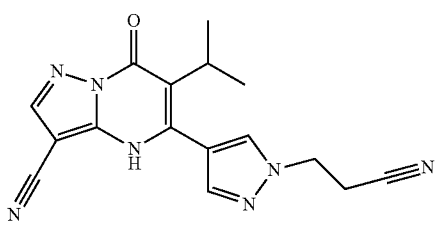 [SMILES: CC(C)c1c(-c2cnn(CCC#N)c2)[nH]c2c(C#N)cnn2c1=O] | A | 322.0 | A | 0.83 | ¹H NMR (400 MHz, CD₃OD) δ 8.21 (s, 1H), 8.14 (s, 1H), 7.84 (s, 1H), 4.55 (t, J = 6.4 Hz, 2H), 3.10 (t, J = 6.4 Hz, 2H), 3.06-3.03 (m, 1H), 1.36 (d, J = 6.8 Hz, 6H). |
| 162 | 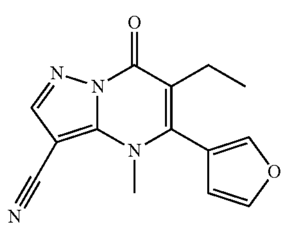 [SMILES: CCc1c(-c2ccoc2)n(C)c2c(C#N)cnn2c1=O] | A | 269.1 | A | 0.92 | ¹H NMR (400 MHz, DMSO-d₆) δ 8.48 (s, 1H), 8.05 (s, 1H), 7.98 (s, 1H), 6.73 (s, 1H), 3.63 (s, 3H), 2.30 (q, J = 7.2 Hz, 2H), 0.96 (t, J = 7.6 Hz, 3H). |
| 163 | 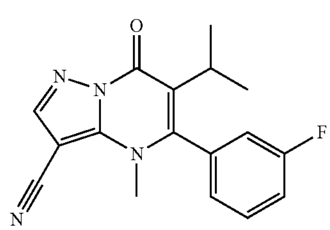 [SMILES: CC(C)c1c(-c2cccc(F)c2)n(C)c2c(C#N)cnn2c1=O] | A | 311.1 | C | 1.33 | ¹H NMR (400 MHz, DMSO-d₆) δ 8.52 (s, 1H), 7.70-7.66 (m, 1H), 7.49-7.39 (m, 2H), 7.29 (d, J = 7.6 Hz, 1H), 3.45 (s, 3H), 2.32-2.25 (m, 1H), 1.18 (d, J = 6.8 Hz, 6H). |
| 164 | 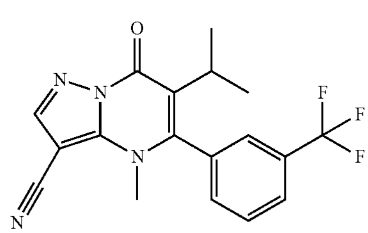 [SMILES: CC(C)c1c(-c2cccc(C(F)(F)F)c2)n(C)c2c(C#N)cnn2c1=O] | A | 360.8 | E | 0.86 | ¹H NMR (400 MHz, DMSO-d₆) δ 8.52 (s, 1H), 8.03-7.98 (m, 1H), 7.93-7.85 (m, 2H), 7.83-7.80 (m, 1H), 3.44 (s, 3H), 2.24-2.16 (m, 1H), 1.18 (d, J = 6.8 Hz, 6H). |

| Ex | Structure | Syn. Met. | LCMS (ESI) m/z | LCMS Method | $R_T$ (min) | NMR |
|---|---|---|---|---|---|---|
| 165 | 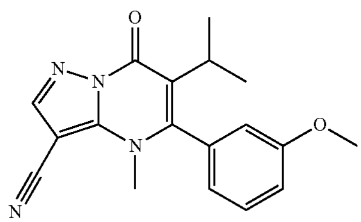 [SMILES: COc1cccc(-c2c(C(C)C)c(=O)n3ncc(C#N)c3n2C)c1] | A | 322.8 | E | 0.82 | $^1$H NMR (400 MHz, DMSO-d$_6$) δ 8.50 (s, 1H), 7.58-7.52 (m, 1H), 7.18-7.14 (m, 1H), 7.05-6.98 (m, 2H), 3.82 (s, 3H), 3.47 (s, 3H), 2.40-2.32 (m, 1H), 1.19 (d, J = 6.8 Hz, 6H). |
| 166 | 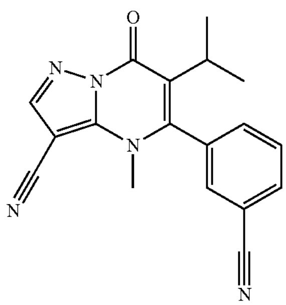 [SMILES: CC(C)c1c(-c2cccc(C#N)c2)n(C)c2c(C#N)cnn2c1=O] | A | 318.3 | E | 0.78 | $^1$H NMR (400 MHz, DMSO-d$_6$) δ 8.53 (s, 1H), 8.13-8.09 (m, 1H), 8.01 (s, 1H), 7.89-7.80 (m, 2H), 3.44 (s, 3H), 2.25-2.17 (m, 1H), 1.18 (d, J = 6.8 Hz, 6H). |
| 167 | 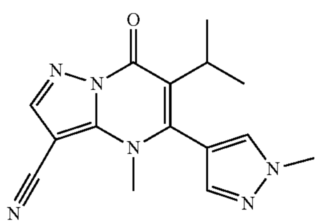 [SMILES: CC(C)c1c(-c2cnn(C)c2)n(C)c2c(C#N)cnn2c1=O] | A | 296.8 | E | 0.70 | $^1$H NMR (400 MHz, DMSO-d$_6$) δ 8.48 (s, 1H), 8.01 (s, 1H), 7.62 (s, 1H), 3.97 (s, 3H), 3.58 (s, 3H), 2.68-2.59 (m, 1H), 1.22 (d, J = 6.8 Hz, 6H). |
| 168 | 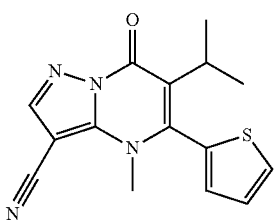 [SMILES: CC(C)c1c(-c2cccs2)n(C)c2c(C#N)cnn2c1=O] | A | 299.1 | A | 1.08 | $^1$H NMR (400 MHz, DMSO-d$_6$) δ 8.50 (s, 1H), 7.95 (d, J = 4.0 Hz, 1H), 7.39-7.27 (m, 2H), 3.54 (s, 3H), 1.22 (d, J = 7.2 Hz, 6H). |
| 169 | 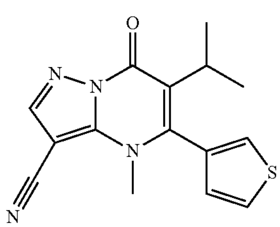 [SMILES: CC(C)c1c(-c2ccsc2)n(C)c2c(C#N)cnn2c1=O] | A | 299.0 | A | 1.07 | $^1$H NMR (400 MHz, DMSO-d$_6$) δ 8.49 (s, 1H), 7.88 (d, J = 4.4 Hz, 1H), 7.82 (s, 1H), 7.23 (d, J = 4.8 Hz, 1H), 3.49 (s, 3H), 2.47-2.37 (m, 1H), 1.20 (d, J = 7.2 Hz, 6H). |
| 170 | 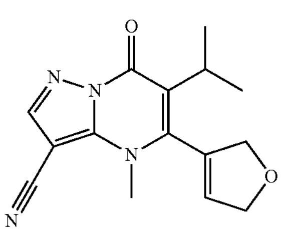 [SMILES: CC(C)c1c(C2=CCOC2)n(C)c2c(C#N)cnn2c1=O] | A | 284.9 | E | 0.71 | $^1$H NMR (400 MHz, DMSO-d$_6$) δ 8.46 (s, 1H), 6.39 (s, 1H), 4.91-4.56 (m, 4H), 3.78 (s, 3H), 2.86-2.79 (m, 1H), 1.29 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 171 | 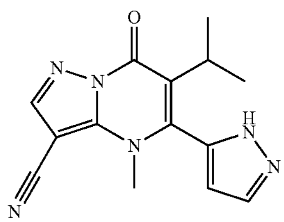 [SMILES: CC(C)c1c(-c2ccn[nH]2)n(C)c2c(C#N)cnn2c1=O] | A | 283.2 | C | 1.07 | $^1$H NMR (400 MHz, CD$_3$OD) δ 8.32 (s, 1H), 7.97 (d, J = 2.4 Hz, 1H), 6.60 (d, J = 2.0 Hz, 1H), 3.63 (s, 3H), 2.62-2.55 (m, 1H), 1.30 (d, J = 6.8 Hz, 6H) |
| 172 | 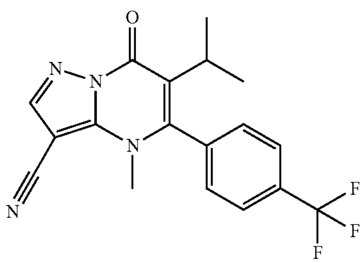 [SMILES: CC(C)c1c(-c2ccc(C(F)(F)F)cc2)n(C)c2c(C#N)cnn2c1=O] | A | 361.12 | E | 0.88 | $^1$H NMR (400 MHz, DMSO-d$_6$) δ 8.52 (s, 1H), 8.03 (d, J = 8.0 Hz, 2H), 7.73 (d, J = 7.6 Hz, 2H), 3.43 (s, 3H), 2.24-2.17 (m, 1H), 1.18 (d, J = 7.2 Hz, 6H). |
| 173 | 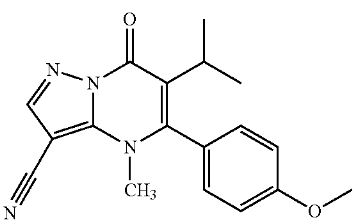 [SMILES: COc1ccc(-c2c(C(C)C)c(=O)n3ncc(C#N)c3n2C)cc1] | A | 323.1 | C | 1.34 | $^1$H NMR: (400 MHz, DMSO-d$_6$) δ 8.46 (s, 1H), 7.34 (d, J = 8.8 Hz, 2H), 7.14 (d, J = 8.4 Hz, 2H), 3.83 (s, 3H), 3.43 (s, 3H), 2.37-2.32 (m, 1H), 1.15 (d, J = 7.2 Hz, 6H), |
| 174 | 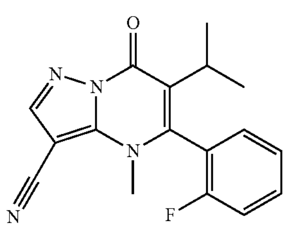 [SMILES: CC(C)c1c(-c2ccccc2F)n(C)c2c(C#N)cnn2c1=O] | A | 311.1 | E | 0.82 | $^1$H NMR (400 MHz, DMSO-d$_6$) δ 8.52 (s, 1H), 7.74-7.70 (m, 1H), 7.55-7.49 (m, 3H), 3.52 (s, 3H), 2.34-2.27 (m, 1H), 1.17, 1.21 (d, J = 6.8 Hz, 6H). |
| 175 | 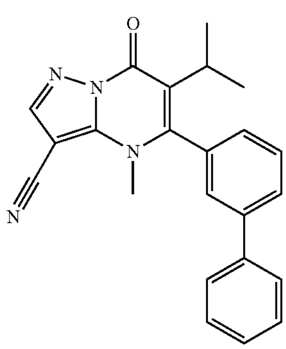 [SMILES: CC(C)c1c(-c2cccc(-c3ccccc3)c2)n(C)c2c(C#N)cnn2c1=O] | A | 369.2 | A | 1.25 | $^1$H NMR (400 MHz, CD$_3$OD) δ 8.30 (s, 1H), 7.89 (d, J = 8.0 Hz, 1H), 7.75-7.65 (m, 4H), 7.53-7.45 (m, 2H), 7.44-7.35 (m, 2H), 2.58-2.48 (m, 1H), 1.29 (d, J = 6.8 Hz, 6H). |

| Ex | Structure | Syn. Met. | LCMS (ESI) m/z | LCMS Method | R_T (min) | NMR |
|---|---|---|---|---|---|---|
| 176 | 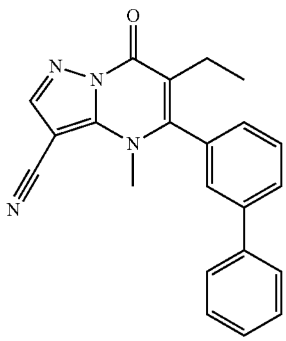 [SMILES: CCc1c(-c2cccc(-c3ccccc3)c2)n(C)c2c(C#N)cnn2c1=O] | A | 355.1 | A | 1.20 | $^1$H NMR (400 MHz, DMSO-d$_6$) δ 8.54 (s, 1H), 7.93 (d, J = 7.6 Hz, 1H), 7.81 (s, 1H), 7.78-7.69 (m, 3H), 7.56-7.38 (m, 4H), 3.55 (s, 3H), 2.20 (q, J = 7.2 Hz, 2H), 0.93 (t, J = 7.2 Hz, 3H) |
| 177 | 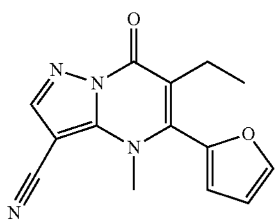 [SMILES: CCc1c(-c2ccco2)n(C)c2c(C#N)cnn2c1=O] | A | 269.2 | A | 0.94 | $^1$H NMR (400 MHz, CD$_3$OD) δ 8.31 (s, 1H), 7.86 (d, J = 1.6 Hz, 1H), 6.91 (d, J = 3.4 Hz, 1H), 6.72 (dd, J = 3.4, 1.6 Hz, 1H), 3.70 (s, 3H), 2.44 (q, J = 7.6 Hz, 2H), 1.08 (t, J = 7.6 Hz, 3H). |
| 178 | 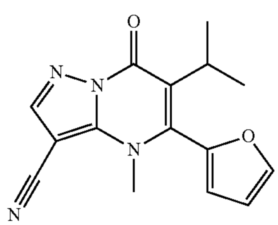 [SMILES: CC(C)c1c(-c2ccco2)n(C)c2c(C#N)cnn2c1=O] | A | 282.8 | E | 0.80 | $^1$H NMR (400 MHz, DMSO-d$_6$) δ 8.51 (s, 1H), 8.05 (d, J = 0.8 Hz, 1H), 6.93 (d, J = 2.8 Hz, 1H), 6.79 (dd, J = 2.8, 0.8 Hz, 1H), 3.53 (s, 3H), 2.60-2.54 (m, 1H), 1.22 (d, J = 7.2 Hz, 6H). |
| 179 | 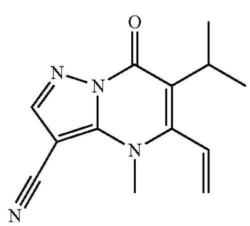 [SMILES: C=Cc1c(C(C)C)c(=O)n2ncc(C#N)c2n1C] | A | 243.2 | A | 0.92 | $^1$H NMR (400 MHz, CD$_3$OD) δ 8.27 (s, 1H), 6.74 (dd, J = 17.2, 12.0 Hz, 1H), 6.00 (d, J = 12.0 Hz, 1H), 5.70 (d, J = 17.2 Hz, 1H), 3.95 (s, 3H), 3.24-3.17 (m, 1H), 1.37 (d, J = 6.8 Hz, 6H). |
| 180 | 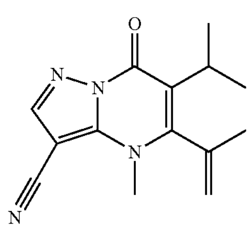 [SMILES: C=C(C)c1c(C(C)C)c(=O)n2ncc(C#N)c2n1C] | A | 257.1 | C | 1.23 | $^1$H NMR (400 MHz, DMSO-d$_6$) δ 8.13 (s, 1H), 5.60 (s, 1H), 5.21 (s, 1H), 3.76 (s, 3H), 2.86-2.48 (m, 1H), 1.99 (s, 3H), 1.21-1.29 (m, 6H). |
| 181 | 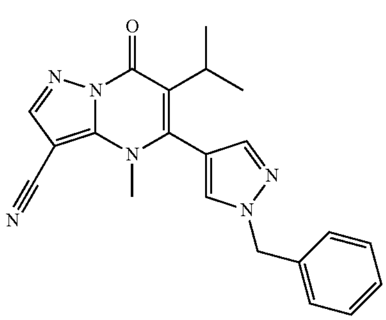 [SMILES: CC(C)c1c(-c2cnn(Cc3ccccc3)c2)n(C)c2c(C#N)cnn2c1=O] | A | 372.9 | E | 0.82 | $^1$H NMR (400 MHz, DMSO-d$_6$) δ 8.44 (s, 1H), 8.13 (s, 1H), 7.66 (s, 1H), 7.37-7.33 (m, 2H), 7.32-7.26 (m, 1H), 7.24-7.20 (m, 2H), 5.44 (s, 2H), 3.55 (s, 3H), 2.60-2.54 (m, 1H), 1.17 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 182 | 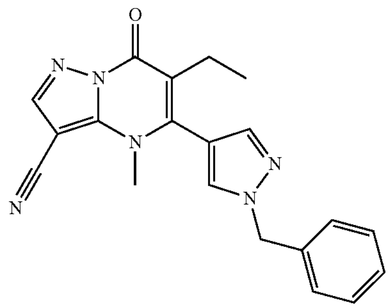 [SMILES: CCc1c(-c2cnn(Cc3ccccc3)c2)n(C)c2c(C#N)cnn2c1=O] | A | 358.9 | E | 0.79 | $^1$H NMR (400 MHz, DMSO-d$_6$) δ 8.46 (s, 1H), 8.18 (s, 1H), 7.69 (s, 1H), 7.40-7.33 (m, 2H), 7.32-7.28 (m, 1H), 7.25-7.19 (m, 2H), 5.45 (s, 2H), 3.60 (s, 3H), 2.25 (q, J = 7.2 Hz, 2H), 0.92 (t, J = 7.2 Hz, 3H). |
| 183 | 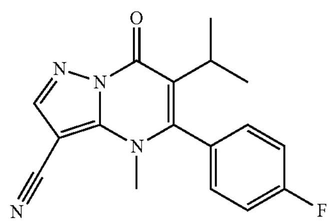 [SMILES: CC(C)c1c(-c2ccc(F)cc2)n(C)c2c(C#N)cnn2c1=O] | A | 310.9 | E | 0.84 | $^1$H NMR (400 MHz, DMSO-d$_6$) δ 8.47 (s, 1H), 7.52-7.42 (m, 4H), 3.41 (s, 3H), 2.30-2.22 (m, 1H), 1.14 (d, J = 7.2 Hz, 6H) |
| 184 | 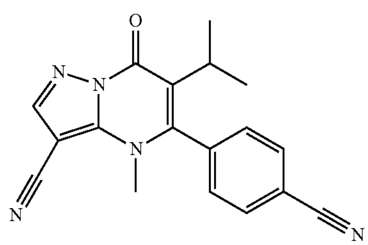 [SMILES: CC(C)c1c(-c2ccc(C#N)cc2)n(C)c2c(C#N)cnn2c1=O] | A | 318.1 | C | 1.25 | $^1$H NMR (400 MHz, DMSO-d$_6$) δ 8.49 (s, 1H), 8.10 (d, J = 8.0 Hz, 2H), 7.66 (d, J = 8.0 Hz, 2H), 3.39 (s, 3H), 2.14-2.17 (m, 1H), 1.14 (d, J = 7.2 Hz, 6H), |
| 185 | 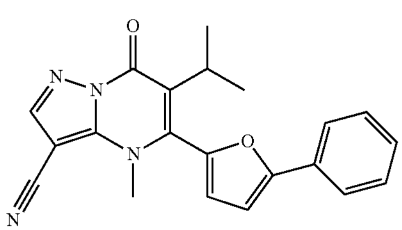 [SMILES: CC(C)c1c(-c2ccc(-c3ccccc3)o2)n(C)c2c(C#N)cnn2c1=O] | A | 359.1 | C | 1.47 | $^1$H NMR (400 MHz, DMSO-d$_6$) δ 8.50 (s, 1H), 7.78 (d, J = 7.6 Hz, 2H), 7.47 (t, J = 7.6 Hz, 2H), 7.37 (t, J = 7.6 Hz, 1H), 7.25 (d, J = 3.2 Hz, 1H), 7.06 (d, J = 3.6 Hz, 1H), 3.65 (s, 3H), 2.71-2.67 (m, 1H), 1.25 (d, J = 6.8 Hz, 6H). |
| 186 | 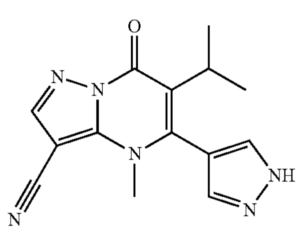 [SMILES: CC(C)c1c(-c2cn[nH]c2)n(C)c2c(C#N)cnn2c1=O] | A | 283.1 | A | 0.76 | $^1$H NMR (400 MHz, DMSO-d$_6$) δ 13.51 (s., 1H), 8.48 (s., 1H), 8.06 (s, 1H), 7.69 (s., 1H), 3.56 (s., 3H), 2.64-2.51 (m, 1H), 1.21 (d, J = 7.2 Hz, 6H). |

-continued

| Ex | Structure | Syn. Met. | LCMS (ESI) m/z | LCMS Method | R_T (min) | NMR |
|---|---|---|---|---|---|---|
| 187 | 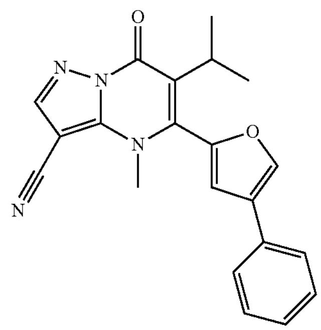 [SMILES: CC(C)c1c(-c2cc(-c3ccccc3)co2)n(C)c2c(C#N)cnn2c1=O] | A | 359.0 | A | 1.18 | $^1$H NMR (400 MHz, DMSO-d$_6$) δ 8.54 (s, 1H), 8.13 (d, J = 1.6 Hz, 1H), 7.48-7.43 (m, 2H), 7.41-7.32 (m, 3H), 7.20 (d, J = 1.6 Hz, 1H), 3.58 (s, 3H), 2.43-2.38 (m, 1H), 1.12 (d, J = 6.8 Hz, 3H), 0.81 (d, J = 7.2 Hz, 3H). |
| 188 | 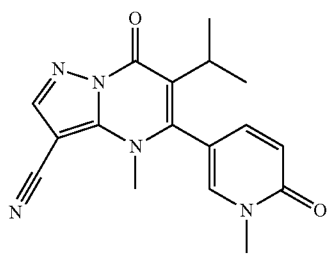 [SMILES: CC(C)c1c(-c2ccc(=O)n(C)c2)n(C)c2c(C#N)cnn2c1=O] | A | 323.1 | E | 0.61 | $^1$H NMR (400 MHz, CD$_3$OD) δ 8.30 (s, 1H), 7.86 (d, J = 2.4 Hz, 1H), 7.51 (dd, J = 9.2, 2.4 Hz, 1H), 6.73 (d, J = 9.2 Hz, 1H), 3.75 (s, 3H), 3.65 (s, 3H), 2.64-2.75 (m, 1H), 1.32 (2 d, J = 7.2 Hz, 6H) |
| 189 | 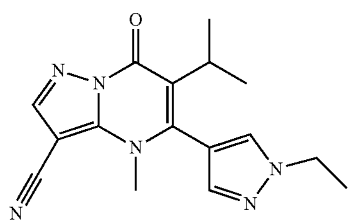 [SMILES: CCn1cc(-c2c(C(C)C)c(=O)n3ncc(C#N)c3n2C)cn1] | A | 310.9 | E | 0.71 | $^1$H NMR (400 MHz, CD$_3$OD) δ 8.28 (s, 1H), 7.94 (s, 1H), 7.64 (s, 1H), 4.32 (q, J = 7.6 Hz, 2H), 3.71 (s, 3H), 2.66-2.74 (m, 1H), 1.54 (t, J = 7.2 Hz, 3H), 1.29 (d, J = 7.2 Hz, 6H). |
| 190 | 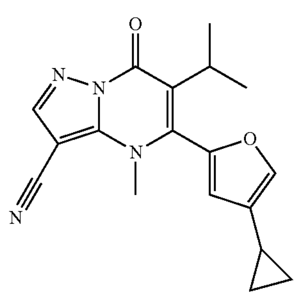 [SMILES: CC(C)c1c(-c2cc(C3CC3)co2)n(C)c2c(C#N)cnn2c1=O] | A | 323.1 | A | 1.15 | $^1$H NMR (400 MHz, DMSO-d$_6$) δ 8.49 (s, 1H), 7.83 (s, 1H), 6.74 (s, 1H), 3.53 (s, 3H), 2.61-2.55 (m, 1H), 1.85-1.76 (m, 1H), 1.22 (d, J = 7.2 Hz, 6H), 0.93-0.87 (m, 2H), 0.64-0.58 (m, 2H). |
| 191 | 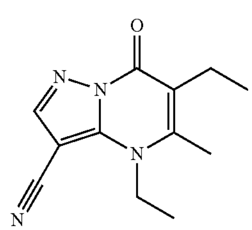 [SMILES: CCc1c(C)n(CC)c2c(C#N)cnn2c1=O] | A | 231.1 | F | 3.12 | $^1$H NMR (400 MHz, DMSO-d$_6$) δ 8.43 (s, 1H), 4.33 (q, J = 7.22 Hz, 2H), 2.58 (q, J = 7.42 Hz, 2H), 2.48 (s, 3H), 1.39 (t, J = 7.20 Hz, 3H), 1.03 (t, J = 7.41 Hz, 3H). |

| Ex | Structure | Syn. Met. | LCMS (ESI) m/z | LCMS Method | R$_T$ (min) | NMR |
|---|---|---|---|---|---|---|
| 192 | 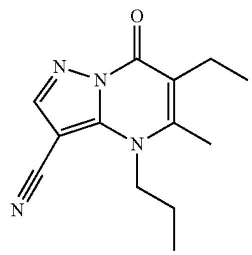 [SMILES: CCCn1c(C)c(CC)c(=O)n2ncc(C#N)c12] | A | 245.2 | F | 3.87 | $^1$H NMR (500 MHz, CDCl$_3$) δ 8.08 (s, 1H), 4.25-4.21 (m, 2H), 2.70 (q, J = 7.42 Hz, 2H), 2.47 (s, 3H), 1.94-1.86 (m, 2H), 1.15-1.08 (m, 6H). |
| 193 | 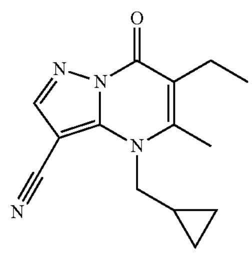 [SMILES: CCc1c(C)n(CC2CC2)c2c(C#N)cnn2c1=O] | A | 257.2 | F | 3.94 | $^1$H NMR (500 MHz, CDCl$_3$) δ 8.08 (s, 1H), 4.33 (d, J = 6.55 Hz, 2H), 2.72 (q, J = 7.42 Hz, 2H), 2.52 (s, 3H), 1.29-1.21 (m, 2H), 1.15 (t, J = 7.41 Hz, 3H), 0.76-0.71 (m, 2H), 0.61-0.55 (m, 2H). |
| 194 | 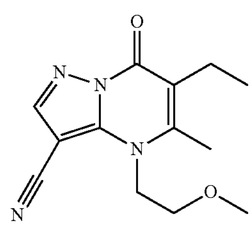 [SMILES: CCc1c(C)n(CCOC)c2c(C#N)cnn2c1=O] | A | 261.2 | F | 3.56 | $^1$H NMR (500 MHz, CDCl$_3$) δ 8.08 (s, 1H), 4.54 (t, J = 4.70 Hz, 2H), 3.81 (t, J = 4.70 Hz, 2H), 3.34 (s, 3H), 2.72 (q, J = 7.42 Hz, 2H), 2.52 (s, 3H), 1.14 (t, J = 7.50 Hz, 3H). |
| 195 | 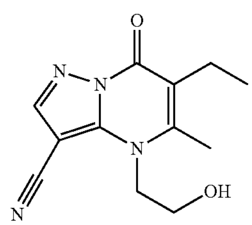 [SMILES: CCc1c(C)n(CCO)c2c(C#N)cnn2c1=O] | A | 247.2 | F | 2.70 | $^1$H NMR (400 MHz, DMSO-d$_6$) δ 8.42 (s, 1H), 5.14 (s, 1H), 4.41 (t, J = 5.12 Hz, 2H), 3.80 (s, 3H), 2.59 (q, J = 7.49 Hz, 4H), 1.03 (t, J = 7.40 Hz, 3H) |
| 196 | 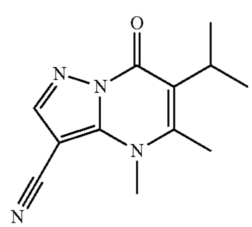 [SMILES: Cc1c(C(C)C)c(=O)n2ncc(C#N)c2n1C] | A | 231.1 | F | 3.22 | $^1$H NMR (400 MHz, DMSO-d$_6$) δ 8.39 (s, 1H), 3.88 (s, 3H), 3.26-3.17 (m, 1H), 2.45 (s, 3H), 1.29 (d, J = 7.01 Hz, 6H). |
| 197 | 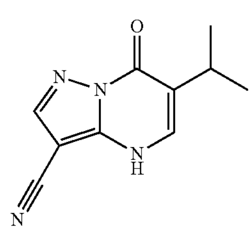 | A | 203.1 | F | 4.71 | $^1$H NMR (400 MHz, DMSO-d$_6$) δ 13.37 (s, 1H), 8.37 (s, 1H), 7.73 (d, J = 0.74 Hz, 1H), 3.01 (p, J = 6.92 Hz, 1H), 1.20 (d, J = 6.91 Hz, 6H). |

-continued

| Ex | Structure | Syn. Met. | LCMS (ESI) m/z | LCMS Method | $R_T$ (min) | NMR |
|---|---|---|---|---|---|---|
| 198 | 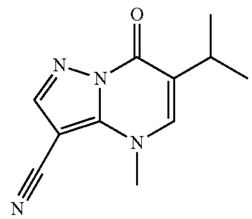 [SMILES: CC(C)c1cn(C)c2c(C#N)cnn2c1=O] | A | 217.1 | F | 2.58 | $^1$H NMR (400 MHz, DMSO-d$_6$) δ 8.43 (s, 1H), 7.87 (d, J = 0.66 Hz, 1H), 3.94 (s, 3H), 3.00 (pd, J = 0.75, 6.86 Hz, 1H), 1.19 (d, J = 6.88 Hz, 6H). |
| 199 | 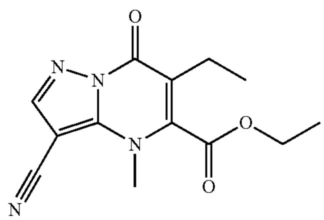 [SMILES: CCOC(=O)c1c(CC)c(=O)n2ncc(C#N)c2n1C] | A | 275.1 | F | 4.85 | $^1$H NMR (400 MHz, DMSO-d$_6$) δ 8.50 (s, 1H), 4.53 (q, J = 7.14 Hz, 2H), 3.82 (s, 3H), 2.41 (q, J = 7.38 Hz, 2H), 1.37 (t, J = 7.12 Hz, 3H), 1.09 (t, J = 7.34 Hz, 3H) |
| 200 | 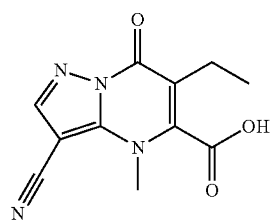 [SMILES: CCc1c(C(=O)O)n(C)c2c(C#N)cnn2c1=O] | A | 247.1 | F | 0.74 | $^1$H NMR (400 MHz, DMSO-d$_6$) δ 8.34 (s, 1H), 7.10 (s, 1H), 3.81 (s, 3H), 2.40 (q, J = 7.31 Hz, 2H), 1.04 (t, J = 7.33 Hz, 3H). |
| 201 | 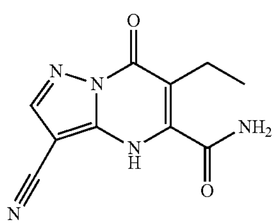 [SMILES: CCc1c(C(N)=O)[nH]c2c(C#N)cnn2c1=O] | A | 232.2 | F | 1.31 | $^1$H NMR (400 MHz, DMSO-d$_6$) δ 8.06 (s, 1H), 7.64 (brs, 1H), 7.28 (brs, 2H), 2.60 (q, J = 7.25 Hz, 2H), 1.03 (t, J = 7.25 Hz, 3H). |
| 202 | 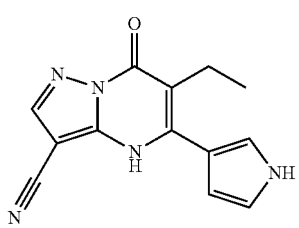 [SMILES: CCc1c(-c2cc[nH]c2)[nH]c2c(C#N)cnn2c1=O] | A | 254.1 | F | 4.42 | $^1$H NMR (400 MHz, DMSO-d$_6$) δ 8.05 (s, 1H), 7.93 (s, 1H), 7.09 (q, J = 1.92 Hz, 1H), 6.76 (q, J = 2.43 Hz, 1H), 6.43 (td, J = 1.52, 2.62 Hz, 1H), 2.66 (q, J = 7.24 Hz, 2H), 1.12-1.06 (m, 3H). |
| 203 | 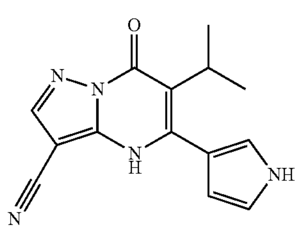 [SMILES: CC(C)c1c(-c2cc[nH]c2)[nH]c2c(C#N)cnn2c1=O] | A | 268.2 | F | 3.95 | $^1$H NMR (400 MHz, DMSO-d$_6$) δ 8.06 (s, 1H), 7.00 (s, 1H), 6.80 (s, 1H), 6.26 (t, J = 2.31 Hz, 1H), 3.30-3.25 (m, 2H), 1.30 (d, J = 6.91 Hz, 6H). |

| Ex | Structure | Syn. Met. | LCMS (ESI) m/z | LCMS Method | $R_T$ (min) | NMR |
|---|---|---|---|---|---|---|
| 204 | 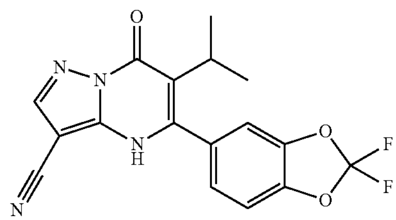 [SMILES: CC(C)c1c(-c2ccc3c(c2)OC(F)(F)O3)[nH]c2c(C#N)cnn2c1=O] | A | 359.2 | F | 5.32 | $^1$H NMR (400 MHz, DMSO-d$_6$) δ 13.36 (s, 1H), 8.36 (s, 1H), 7.66 (dt, J = 2.02, 3.57 Hz, 1H), 7.60 (d, J = 8.21 Hz, 1H), 7.37-7.32 (m, 1H), 2.60 (p, J = 6.94 Hz, 1H), 1.24 (d, J = 6.94 Hz, 6H). |
| 205 | 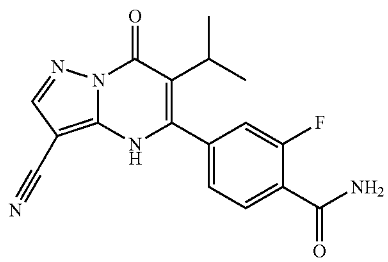 [SMILES: CC(C)c1c(-c2ccc(C(N)=O)c(F)c2)[nH]c2c(C#N)cnn2c1=O] | A | 340.2 | F | 3.73 | $^1$H NMR (400 MHz, DMSO-d$_6$) δ 13.48 (s, 1H), 8.40 (s, 1H), 7.87 (s, 1H), 7.80 (t, J = 7.63 Hz, 1H), 7.75 (s, 1H), 7.52 (d, J = 10.65 Hz, 1H), 7.40 (dd, J = 1.55, 7.89 Hz, 1H), 2.60-2.52 (m, 1H), 1.24 (d, J = 6.94 Hz, 6H). |
| 206 | 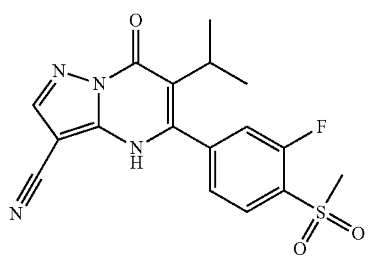 [SMILES: CC(C)c1c(-c2ccc(S(C)(=O)=O)c(F)c2)[nH]c2c(C#N)cnn2c1=O] | A | 375.2 | F | 4.21 | $^1$H NMR (400 MHz, DMSO-d$_6$) δ 8.40 (s, 1H), 8.09-8.00 (m, 1H), 7.80 (d, J = 10.34 Hz, 1H), 7.61 (d, J = 8.15 Hz, 1H), 3.43 (s, 3H), 2.58-2.52 (m, 2H), 1.25 (d, J = 6.90 Hz, 6H). |
| 207 | 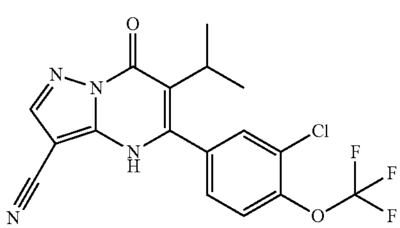 [SMILES: CC(C)c1c(-c2ccc(OC(F)(F)F)c(Cl)c2)[nH]c2c(C#N)cnn2c1=O] | A | 397.0 | F | 5.85 | $^1$H NMR (400 MHz, DMSO-d$_6$) δ 13.41 (s, 1H), 8.39 (s, 1H), 7.94 (s, 1H), 7.78 (d, J = 8.98 Hz, 1H), 7.63 (dd, J = 2.11, 8.40 Hz, 1H), 2.59-2.51 (m, 1H), 1.24 (d, J = 6.93 Hz, 6H). |
| 208 | 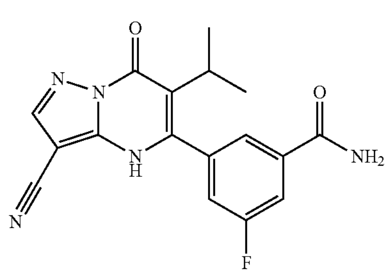 [SMILES: CC(C)c1c(-c2cc(F)cc(C(N)=O)c2)[nH]c2c(C#N)cnn2c1=O] | A | 340.1 | F | 4.90 | $^1$H NMR (400 MHz, DMSO-d$_6$) δ 13.46 (s, 1H), 8.36 (s, 1H), 8.14 (d, J = 5.12 Hz, 1H), 7.82 (s, 2H), 7.64 (s, 2H), 2.62-2.52 (m, 1H), 1.24 (d, J = 6.95 Hz, 6H). |
| 209 | 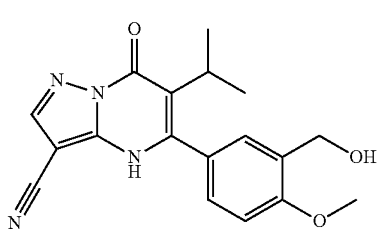 [SMILES: COc1ccc(-c2[nH]c3c(C#N)cnn3c(=O)c2C(C)C)cc1CO] | A | 339.1 | F | 5.18 | $^1$H NMR (400 MHz, DMSO-d$_6$) δ 13.27 (s, 1H), 8.36 (s, 1H), 7.51-7.45 (m, 1H), 7.36 (dd, J = 2.35, 8.41 Hz, 1H), 7.13 (d, J = 8.45 Hz, 1H), 5.19 (s, 1H), 4.57 (s, 2H), 3.87 (s, 3H), 2.71 (p, J = 6.92 Hz, 1H), 1.24 (d, J = 6.92 Hz, 6H). |

| Ex | Structure | Syn. Met. | LCMS (ESI) m/z | LCMS Method | R$_T$ (min) | NMR |
|---|---|---|---|---|---|---|
| 210 | 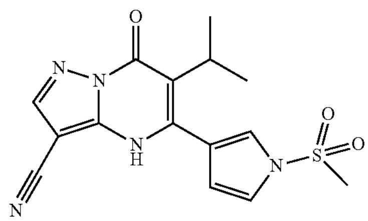 [SMILES: CC(C)c1c(-c2ccn(S(C)(=O)=O)c2)[nH]c2c(C#N)cnn2c1=O] | A | 346.1 | F | 5.41 | $^1$H NMR (400 MHz, DMSO-d$_6$) δ 13.11 (s, 1H), 8.35 (s, 1H), 7.64 (s, 1H), 7.45 (t, J = 2.72 Hz, 1H), 6.60 (dd, J = 1.66, 3.18 Hz, 1H), 3.61 (s, 3H), 2.98 (p, J = 6.95 Hz, 1H), 1.29 (d, J = 6.95 Hz, 6H). |
| 211 | 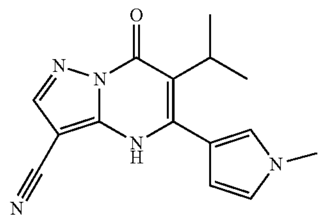 [SMILES: CC(C)c1c(-c2ccn(C)c2)[nH]c2c(C#N)cnn2c1=O] | A | 282.1 | F | 5.53 | $^1$H NMR (400 MHz, DMSO-d$_6$) δ 13.42 (s, 1H), 8.35 (s, 1H), 6.98 (s, 1H), 6.26 (s, 1H), 6.16 (s, 1H), 3.54 (s, 3H), 2.76-2.72 (m, 1H), 1.22 (d, J = 6.91 Hz, 6H). |
| 212 | 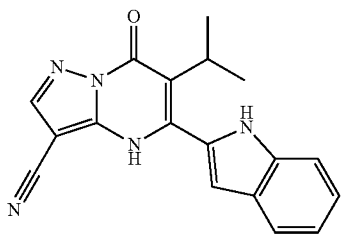 [SMILES: CC(C)c1c(-c2cc3ccccc3[nH]2)[nH]c2c(C#N)cnn2c1=O] | A | 318.2 | F | 5.01 | $^1$H NMR (400 MHz, DMSO-d$_6$) δ 13.55 (s, 1H), 11.73 (s, 1H), 8.40 (s, 1H), 7.67 (d, J = 7.98 Hz, 1H), 7.50 (dd, J = 0.99, 8.26 Hz, 1H), 7.22 (q, J = 7.25 Hz, 1H), 7.15-7.05 (m, 1H), 6.79 (s, 1H), 3.10-3.06 (m, 1H), 1.31 (d, J = 6.91 Hz, 6H). |
| 213 | 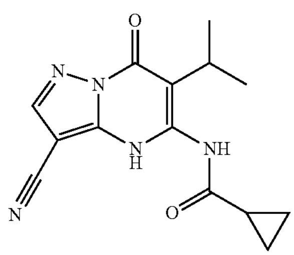 [SMILES: CC(C)c1c(NC(=O)C2CC2)[nH]c2c(C#N)cnn2c1=O] | D | 286.1 | F | 4.71 | $^1$H NMR (400 MHz, DMSO-d$_6$) δ 10.42 (s, 1H), 8.31 (s, 1H), 2.98 (p, J = 6.89 Hz, 1H), 1.96-1.83 (m, 1H), 1.26 (d, J = 6.98 Hz, 6H), 0.88 (dd, J = 4.49, 6.54 Hz, 4H). |
| 214 | 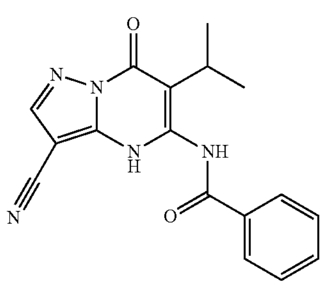 [SMILES: CC(C)c1c(NC(=O)c2ccccc2)[nH]c2c(C#N)cnn2c1=O] | D | 322.1 | F | 5.18 | $^1$H NMR (400 MHz, DMSO-d$_6$) δ 8.30 (s, 1H), 8.05-7.96 (m, 2H), 7.64 (t, J = 7.32 Hz, 1H), 7.56 (t, J = 7.53 Hz, 2H), 6.48 (s, 1H), 2.97 (s, 1H), 1.27 (d, J = 6.98 Hz, 6H). |
| 215 | 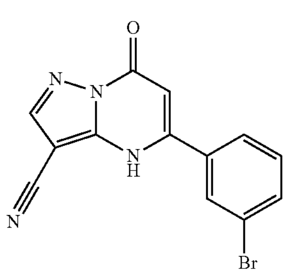 [SMILES: N#Cc1cnn2c(=O)cc(-c3cccc(Br)c3)[nH]c12] | B | 315.0 | F | 3.98 | $^1$H NMR (400 MHz, DMSO-d6) δ 8.41 (s, 1H), 8.07 (t, J = 1.9 Hz, 1H), 7.89-7.79 (m, 2H), 7.70 (s, 1H), 7.53 (t, J = 7.9 Hz, 1H), 6.30 (s, 1H). |

-continued

| Ex | Structure | Syn. Met. | LCMS (ESI) m/z | LCMS Method | R_T (min) | NMR |
|---|---|---|---|---|---|---|
| 216 | 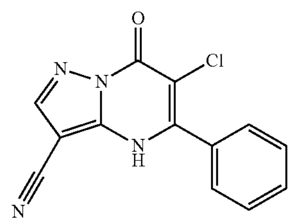 [SMILES: N#Cc1cnn2c(=O)c(Cl)c(-c3ccccc3)[nH]c12] | C | 271.0 | F | 3.50 | $^1$H NMR (400 MHz, DMSO-d6) δ 8.40 (s, 1H), 7.67-7.51 (m, 5 |
| 217 | 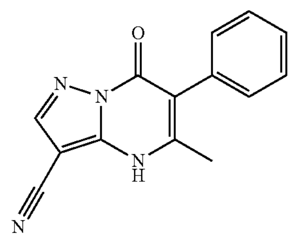 [SMILES: Cc1[nH]c2c(C#N)cnn2c(=O)c1-c1ccccc1] | C | 251.2 | F | 3.59 | $^1$H NMR (400 MHz, DMSO-d6) δ 13.36 (s, 1H), 8.40 (s, 1H), 7.49-7.35 (m, 3H), 7.33-7.26 (m, 2H), 2.20 (s, 3H). |
| 218 | 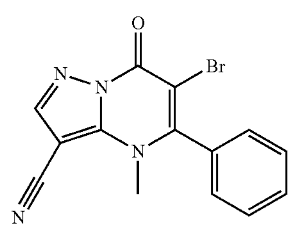 [SMILES: Cn1c(-c2ccccc2)c(Br)c(=O)n2ncc(C#N)c12] | C | 329.0 | F | 4.18 | $^1$H NMR (400 MHz, DMSO-d6) δ 8.59 (s, 1H), 7.70-7.58 (m, 3H), 7.53-7.41 (m, 2H), 3.57 (s, 3H). |
| 219 | 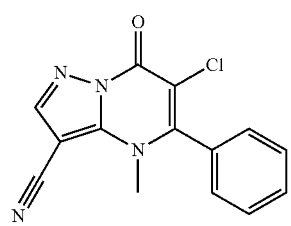 [SMILES: Cn1c(-c2ccccc2)c(Cl)c(=O)n2ncc(C#N)c12] | C | 285.1 | F | 3.92 | $^1$H NMR (400 MHz, DMSO-d6) δ 8.61 (s, 1H), 7.69-7.62 (m, 3H), 7.57-7.42 (m, 2H), 3.57 (s, 3H). |
| 220 | 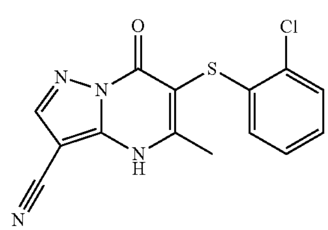 [SMILES: Cc1[nH]c2c(C#N)cnn2c(=O)c1Sc1ccccc1Cl] | C | 317.0 | F | 4.06 | $^1$H NMR (400 MHz, DMSO-d6) δ 8.43 (s, 1H), 7.60-7.33 (m, 1H), 7.22-7.09 (m, 2H), 7.09-6.93 (m, 1H), 2.53 (s, 3H). |
| 221 | 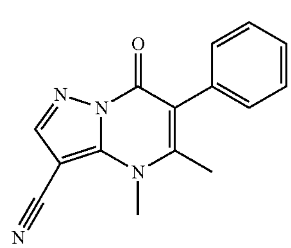 [SMILES: Cc1c(-c2ccccc2)c(=O)n2ncc(C#N)c2n1C] | C | 265.2 | F | 3.78 | $^1$H NMR (400 MHz, DMSO-d6) δ 8.49 (s, 1H), 7.50-7.37 (m, 3H), 7.30-7.22 (m, 2H), 3.95 (s, 3H), 2.26 (s, 3H). |

-continued

| Ex | Structure | Syn. Met. | LCMS (ESI) m/z | LCMS Method | $R_T$ (min) | NMR |
|---|---|---|---|---|---|---|
| 222 | 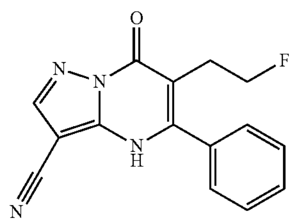 [SMILES: N#Cc1cnn2c(=O)c(CCF)c(-c3ccccc3)[nH]c12] | B | 283.0 | F | 3.99 | ¹H NMR (400 MHz, DMSO-d6) δ 13.67 (s, 1H), 8.43 (s, 1H), 7.66-7.53 (m, 5H), 4.49 (dt, J = 47.3, 6.6 Hz, 2H), 2.70 (dt, J = 19.9, 6.7 Hz, 2H). |
| 223 | 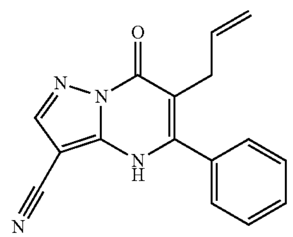 [SMILES: C=CCc1c(-c2ccccc2)[nH]c2c(C#N)cnn2c1=O] | B | 277.2 | F | 4.27 | ¹H NMR (400 MHz, DMSO-d6) δ 13.57 (s, 1H), 8.41 (s, 1H), 7.64-7.48 (m, 5H), 5.82 (ddt, J = 17.2, 10.2, 5.7 Hz, 1H), 5.03-4.77 (m, 2H), 3.04 (dt, J = 5.8, 1.7 Hz, 2H). |
| 224 | 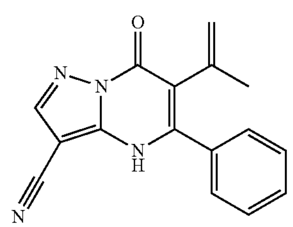 [SMILES: C=C(C)c1c(-c2ccccc2)[nH]c2c(C#N)cnn2c1=O] | C | 277.1 | F | 5.15 | ¹H NMR (400 MHz, DMSO-d6) δ 8.21 (s, 1H), 7.52-7.47 (m, 2H), 7.39 (d, J = 6.5 Hz, 3H), 4.96 (s, 1H), 4.57 (s, 1H), 1.90 (s, 3H). |
| 225 | 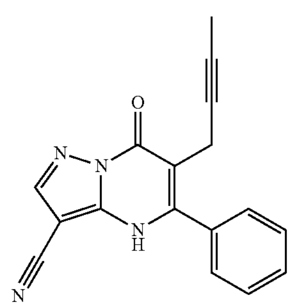 [SMILES: CC#CCc1c(-c2ccccc2)[nH]c2c(C#N)cnn2c1=O] | B | 289.2 | F | 4.35 | ¹H NMR (400 MHz, DMSO-d6) δ 8.42 (s, 1H), 7.68-7.54 (m, 5H), 3.12 (q, J = 2.5 Hz, 2H), 1.69 (t, J = 2.5 Hz, 3H). |
| 226 | 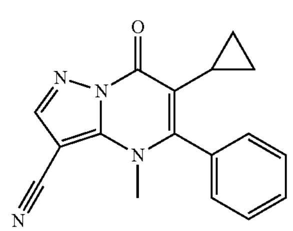 [SMILES: Cn1c(-c2ccccc2)c(C2CC2)c(=O)n2ncc(C#N)c12] | B | 291.1 | F | 4.28 | ¹H NMR (400 MHz, Chloroform-d) δ 7.87 (s, 1H), 7.74-7.67 (m, 2H), 7.51-7.39 (m, 3H), 4.48 (s, 3H), 1.78 (tt, J = 8.3, 5.5 Hz, 1H), 0.84-0.73 (m, 2H), 0.40-0.33 (m, 2H). |

| Ex | Structure | Syn. Met. | LCMS (ESI) m/z | LCMS Method | R_T (min) | NMR |
|---|---|---|---|---|---|---|
| 227 | 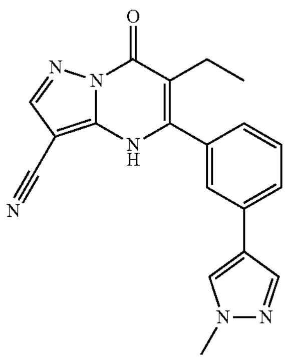 [SMILES: CCc1c(-c2cccc(-c3cnn(C)c3)c2)[nH]c2c(C#N)cnn2c1=O] | B | 345.1 | F | 5.19 | $^1$H NMR (400 MHz, DMSO-d6) δ 8.39 (s, 1H), 8.22 (s, 1H), 7.93 (s, 1H), 7.78-7.47 (m, 3H), 7.32 (d, J = 7.8 Hz, 1H), 3.87 (s, 3H), 2.34 (q, J = 7.2 Hz, 2H), 1.01 (t, J = 7.3 Hz, 3H). |
| 228 | 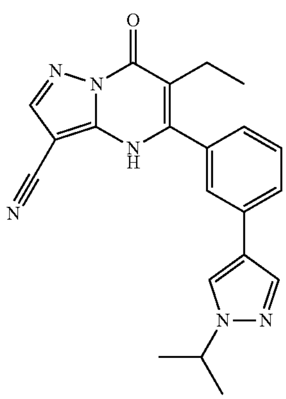 [SMILES: CCc1c(-c2cccc(-c3cnn(C(C)C)c3)c2)[nH]c2c(C#N)cnn2c1=O] | B | 373.2 | F | 4.63 | $^1$H NMR (400 MHz, DMSO-d6) δ 13.54 (s, 1H), 8.30 (s, 2H), 7.92 (s, 1H), 7.71 (s, 2H), 7.49 (s, 1H), 7.28 (s, 1H), 4.50 (h, J = 6.6 Hz, 1H), 2.35 (q, J = 7.4 Hz, 2H), 1.45 (d, J = 6.6 Hz, 6H), 1.00 (t, J = 7.3 Hz, 3H). |
| 229 | 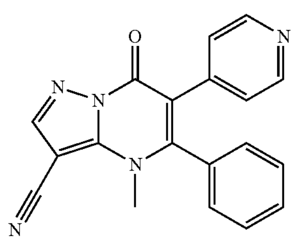 [SMILES: Cn1c(-c2ccccc2)c(-c2ccncc2)c(=O)n2ncc(C#N)c12] | C | 328.2 | F | 2.87 | $^1$H NMR (400 MHz, DMSO-d6) δ 8.61 (s, 1H), 8.45-8.28 (m, 2H), 7.49-7.27 (m, 4H), 7.14-6.95 (m, 2H), 3.60 (s, 3H). |
| 230 | 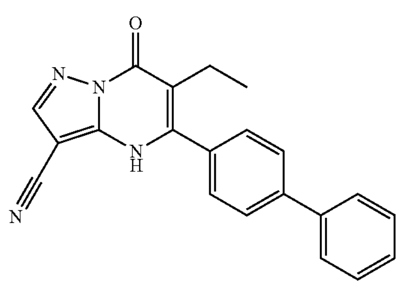 [SMILES: CCc1c(-c2ccc(-c3ccccc3)cc2)[nH]c2c(C#N)cnn2c1=O] | B | 341.1 | F | 6.15 | $^1$H NMR (400 MHz, DMSO-d6) δ 8.05 (s, 1H), 7.77-7.66 (m, 4H), 7.55-7.46 (m, 4H), 7.42-7.36 (m, 1H), 2.43 (q, J = 7.3 Hz, 2H), 1.02 (t, J = 7.2 Hz, 3H). |
| 231 | 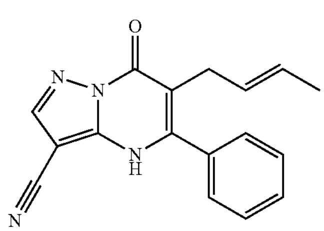 [SMILES: C/C=C/Cc1c(-c2ccccc2)[nH]c2c(C#N)cnn2c1=O] | B | 291.1 | F | 5.75 | $^1$H NMR (400 MHz, DMSO-d6) δ 13.53 (s, 1H), 8.37 (s, 1H), 7.61-7.48 (m, 5H), 5.49-5.34 (m, 1H), 5.31-5.17 (m, 1H), 3.03-2.91 (m, 2H), 1.61-1.47 (m, 3H). |

| Ex | Structure | Syn. Met. | LCMS (ESI) m/z | LCMS Method | R$_T$ (min) | NMR |
|---|---|---|---|---|---|---|
| 232 | 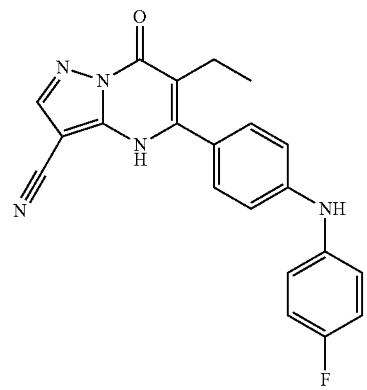 [SMILES: CCc1c(-c2ccc(Nc3ccc(F)cc3)cc2)[nH]c2c(C#N)cnn2c1=O] | B | 374.1 | F | 6.37 | $^1$H NMR (400 MHz, DMSO-d6) δ 13.28 (s, 1H), 8.43 (s, 1H), 8.28 (s, 1H), 7.43-7.30 (m, 2H), 7.20-7.04 (m, 6H), 2.41 (q, J = 7.2 Hz, 2H), 1.03 (t, J = 7.3 Hz, 3H). |
| 233 | 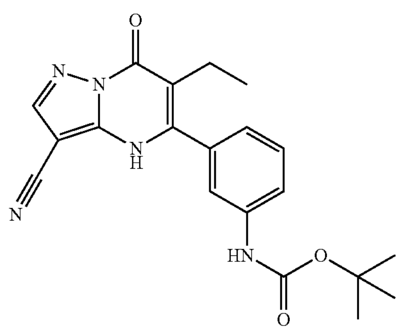 [SMILES: CCc1c(-c2cccc(NC(=O)OC(C)(C)C)c2)[nH]c2c(C#N)cnn2c1=O] | B | 380.2 | F | 5.75 | $^1$H NMR (400 MHz, DMSO-d6) δ 13.44 (s, 1H), 9.58 (s, 1H), 8.37 (s, 1H), 7.48 (d, J = 65.0 Hz, 3H), 7.07 (s, 1H), 2.31 (q, J = 7.2 Hz, 2H), 1.48 (s, 9H), 1.00 (t, J = 7.3 Hz, 3H). |
| 234 | 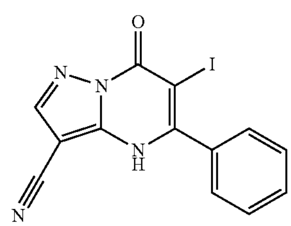 [SMILES: N#Cc1cnn2c(=O)c(I)c(-c3ccccc3)[nH]c12] | C | 363.0 | F | 4.97 | $^1$H NMR (400 MHz, DMSO-d6) δ 8.14 (s, 1H), 7.59-7.32 (m, 5H). |
| 235 | 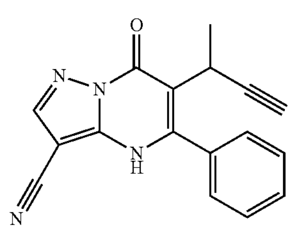 [SMILES: C#CC(C)c1c(-c2ccccc2)[nH]c2c(C#N)cnn2c1=O] | B | 289.2 | F | 4.23 | $^1$H NMR (400 MHz, DMSO-d6) δ 13.62 (s, 1H), 8.42 (s, 1H), 7.65-7.51 (m, 5H), 3.47 (qd, J = 7.0, 2.7 Hz, 1H), 2.84 (d, J = 2.6 Hz, 1H), 1.42 (d, J = 7.1 Hz, 3H). |
| 236 | 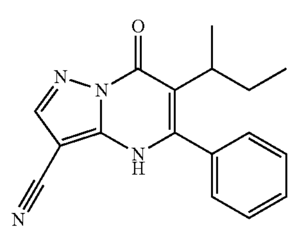 [SMILES: CCC(C)c1c(-c2ccccc2)[nH]c2c(C#N)cnn2c1=O] | B | 293.1 | F | 5.71 | $^1$H NMR (400 MHz, DMSO-d6) δ 13.49 (s, 1H), 8.40 (s, 1H), 7.60-7.45 (m, 5H), 2.30 (dq, J = 9.0, 6.7 Hz, 1H), 1.91 (ddq, J = 13.3, 9.1, 7.4 Hz, 1H), 1.48 (tt, J = 13.6, 7.3 Hz, 1H), 1.22 (d, J = 7.0 Hz, 3H), 0.65 (t, J = 7.5 Hz, 3H). |

-continued

| Ex | Structure | Syn. Met. | LCMS (ESI) m/z | LCMS Method | R_T (min) | NMR |
|---|---|---|---|---|---|---|
| 237 | 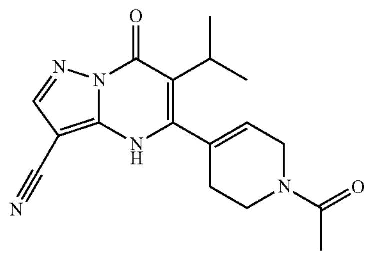 [SMILES: CC(=O)N1CC=C(c2[nH]c3c(C#N)cnn3c(=O)c2C(C)C)CC1] | A | 326.1 | C | 1.046 | ¹H NMR (400 MHz, MeOD) δ 8.19 (s, 1H), 6.03 (m, 1H), 4.23 (m, 2H), 3.74-3.85 (m, 2H), 2.88-2.98 (m, 1H), 2.49 (m, 1H), 2.41 (m, 1H), 2.17 (2s, 3H), 1.36 (d, J = 6.8 Hz, 6H). |
| 238 | 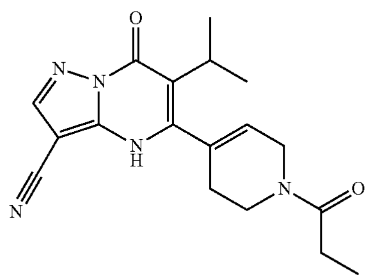 [SMILES: CCC(=O)N1CC=C(c2[nH]c3c(C#N)cnn3c(=O)c2C(C)C)CC1] | A | 339.1 | E | 0.732 | ¹H NMR (400 MHz, MeOD) δ 8.21 (s, 1H), 6.04 (m, 1H), 4.25 (s, 2H), 3.76-3.88 (m, 2H), 2.94 (m, 1H), 2.38-2.56 (m, 4H), 1.37 (d, J = 6.8 Hz, 6H), 1.13-1.22 (m, 3H). |
| 239 | 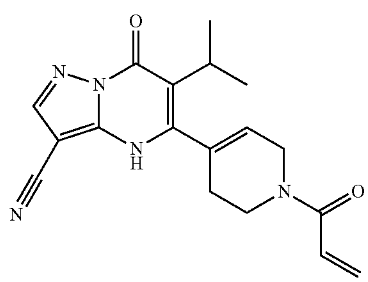 [SMILES: C=CC(=O)N1CC=C(c2[nH]c3c(C#N)cnn3c(=O)c2C(C)C)CC1] | A | 338.1 | E | 1.085 | ¹H NMR (400 MHz, MeOD) δ 8.21 (s, 1H), 6.74-6.92 (m, 1H), 6.27 (m, 1H), 6.06 (m Hz, 1H), 5.81 (m, 1H), 4.33 (m, 2H), 3.90 (m, 2H), 2.93 (s, 1H), 2.48 (m, 2H), 1.37 (d, J = 6.8 Hz, 6H). |
| 240 | 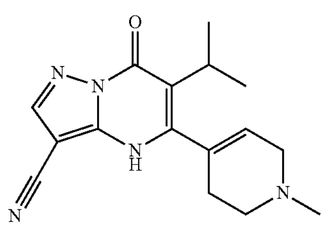 [SMILES: CC(C)c1c(C2=CCN(C)CC2)[nH]c2c(C#N)cnn2c1=O] | A | 298.2 | C | 1.544 | ¹H NMR (400 MHz, DMSO-d₆) δ 9.80 (s, 1H), 8.02 (s, 1H), 5.60 (m, 1H), 4.11 (m, 1H), 3.77 (s, 2H), 3.17 (m, 1H), 2.97-2.92 (m, 1H), 2.90 (2s, 3H), 2.60 (m, 2H), 1.27 (d, J = 6.8 Hz, 6H). |
| 241 | 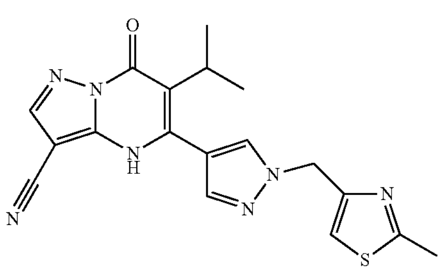 [SMILES: Cc1nc(Cn2cc(-c3[nH]c4c(C#N)cnn4c(=O)c3C(C)C)cn2)cs1] | A | 380.1 | E | 0.759 | ¹H NMR (400 MHz, CD₃OD) δ 8.21 (s, 1H), 8.13 (s, 1H), 7.78 (s, 1H), 7.36 (s, 1H), 5.49 (s, 2H), 3.13-3.03 (m, 1H), 2.68 (s, 3H), 1.37 (d, J = 6.8 Hz, 6H). |
| 242 | 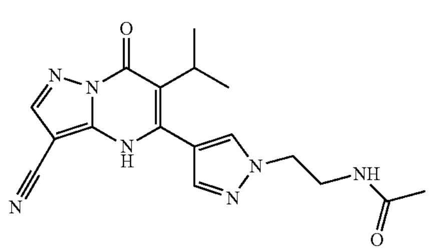 [SMILES: CC(=O)NCCn1cc(-c2[nH]c3c(C#N)cnn3c(=O)c2C(C)C)cn1] | A | 354.1 | E | 0.658 | ¹H NMR (400 MHz, CD₃OD) δ 8.21 (s, 1H), 8.23 (s, 1H), 8.02 (s, 1H), 7.79 (s, 1H), 4.36 (t, J = 6.0 Hz, 2H), 3.65 (t, J = 6.0 Hz, 2H), 3.12-3.05 (m, 1H), 1.93 (s, 3H), 1.39 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 243 | 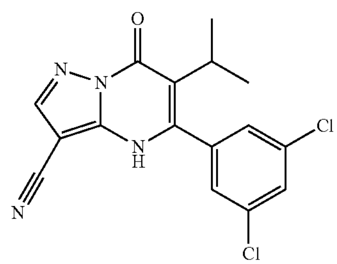 [SMILES: CC(C)c1c(-c2cc(Cl)cc(Cl)c2)[nH]c2c(C#N)cnn2c1=O] | A | 349.1 | A | 1.171 | $^1$H NMR (400 MHz, CD$_3$OD) δ 8.27 (s, 1H), 7.73 (m, 1H), 7.59-7.58 (m, 2H), 2.70-2.62 (m, 1H), 1.35 (d, J = 6.4 Hz, 6H). |
| 244 | 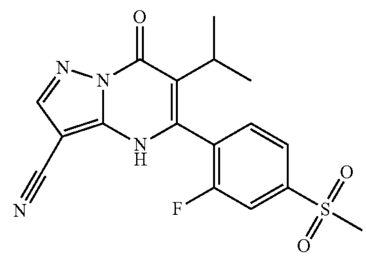 [SMILES: CC(C)c1c(-c2ccc(S(C)(=O)=O)cc2F)[nH]c2c(C#N)cnn2c1=O] | A | 375.2 | C | 1.161 | $^1$H NMR (400 MHz, DMSO-d$_6$) δ 13.67 (s, 1H), 8.43 (s, 1H), 8.06 (d, J = 8.4 Hz, 1H), 7.98 (d, J = 7.6 Hz, 1H), 7.91-7.87 (m, 1H), 3.39 (s, 3H), 2.44-2.43 (m, 1H), 1.26-1.21 (2q, J = 6.8 Hz, 6H). |
| 245 | 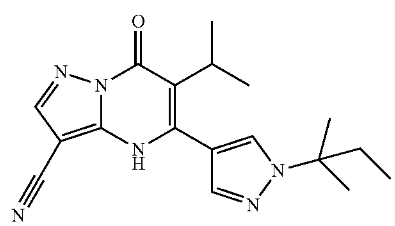 [SMILES: CCC(C)(C)n1cc(-c2[nH]c3c(C#N)cnn3c(=O)c2C(C)C)cn1] | A | 339.1 | C | 1.284 | $^1$H NMR (400 MHz, DMSO-d$_6$) δ 13.06 (s, 1H), 8.38 (s, 1H), 8.17 (s, 1H), 7.75 (s, 1H), 3.00-2.93 (m, 1H), 1.92-1.86 (m, 2H), 1.57 (s, 6H), 1.57 (d, J = 6.4 Hz, 6H), 0.67 (t, J = 7.2 Hz, 3H). |
| 246 | 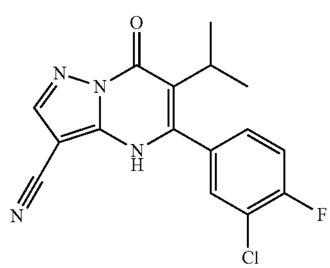 [SMILES: CC(C)c1c(-c2ccc(F)c(Cl)c2)[nH]c2c(C#N)cnn2c1=O] | A | 330.9 | C | 1.342 | $^1$H NMR (400 MHz, DMSO-d$_6$) δ 13.42 (s, 1H), 8.42 (s, 1H), 7.86 (m 1H), 7.64 (t, J = 9.2 Hz, 1H), 7.58-7.56 (m, 1H), 2.58-2.55 (m, 1H), 1.23 (d, J = 6.8 Hz, 6H). |
| 247 | 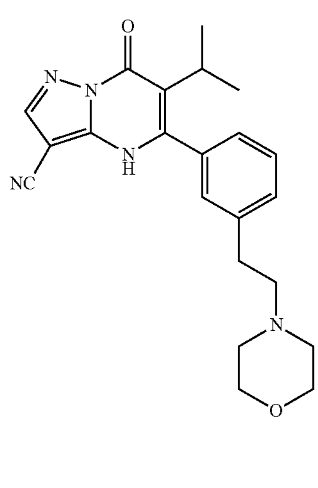 [SMILES: CC(C)c1c(-c2cccc(CCN3CCOCC3)c2)[nH]c2c(C#N)cnn2c1=O] | A | 392.2 | C | 0.982 | $^1$H NMR (400 MHz, DMSO-d$_6$) δ 8.20 (s, 1H), 7.45-7.42 (m, 1H), 7.36-7.26 (m, 3H), 3.71 (m, 4H), 2.95 (m, 4H), 2.67-2.62 (m, 2H), 1.24 (d, J = 6.4 Hz, 6H). |

| Ex | Structure | Syn. Met. | LCMS (ESI) m/z | LCMS Method | R$_T$ (min) | NMR |
|---|---|---|---|---|---|---|
| 248 | 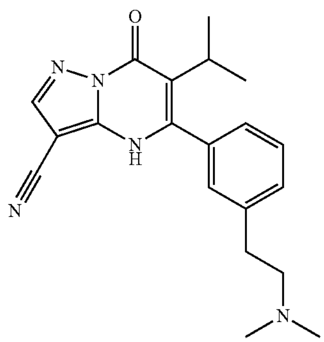 [SMILES: CC(C)c1c(-c2cccc(CCN(C)C)c2)[nH]c2c(C#N)cnn2c1=O] | A | 350.1 | C | 0.980 | $^1$H NMR (400 MHz, DMSO-d$_6$) δ 8.03 (s, 1H), 7.41-7.37 (m, 1H), 7.29-7.23 (m, 3H), 3.02-2.98 (m, 2H), 2.80 (s, 6H), 2.70-2.68 (m, 2H), 1.24 (d, J = 7.2 Hz, 6H). |
| 249 | 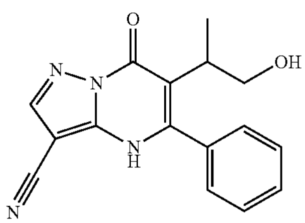 [SMILES: CC(CO)c1c(-c2ccccc2)[nH]c2c(C#N)cnn2c1=O] | B | 295.0 | C | 1.030 | $^1$H NMR (400 MHz, CD$_3$OD) δ 8.27 (s, 1H), 7.59 (m, 5H), 4.13-4.08 (m, 1H), 3.69-3.65 (m, 1H), 2.84-2.78 (m, 1H), 1.28 (d, J = 7.2 Hz, 3H). |
| 250 | 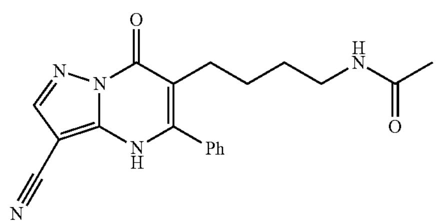 [SMILES: CC(=O)NCCCCc1c(-c2ccccc2)[nH]c2c(C#N)cnn2c1=O] | B | 350.1 | C | 1.041 | $^1$H NMR (400 MHz, CD$_3$OD) δ 8.28 (s, 1H), 7.61-7.55 (m, 5H), 3.05 (t, J = 6.8 Hz, 2H), 2.48 (t, J = 7.6 Hz, 2H), 1.91 (s, 3H), 1.57-1.49 (m, 2H), 1.43-1.38 (m, 2H). |
| 251 | 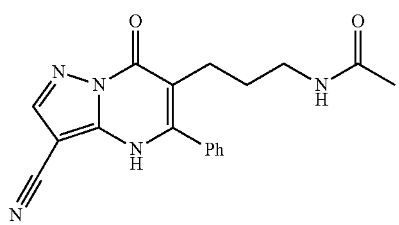 [SMILES: CC(=O)NCCCc1c(-c2ccccc2)[nH]c2c(C#N)cnn2c1=O] | B | 336.1 | C | 0.992 | $^1$H NMR (400 MHz, CD$_3$OD) δ 8.20 (s, 1H), 7.89 (s, 1H), 7.52-7.47 (m, 5H), 3.06-3.01 (m, 2H), 2.47 (m, 2H), 1.82 (s, 3H), 1.89-1.62 (m, 2H). |
| 252 | 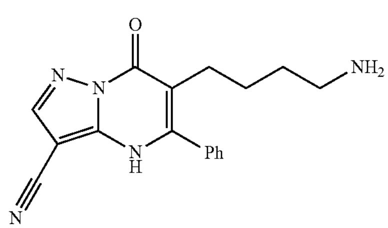 [SMILES: N#Cc1cnn2c(=O)c(CCCCN)c(-c3ccccc3)[nH]c12] | B | 308.1 | C | 1.390 | $^1$H NMR (400 MHz, DMSO-d$_6$) δ 13.59 (s, 1H), 8.42 (s, 1H), 7.76 (s, 3H), 7.59-7.54 (m, 5H), 2.65 (m, 2H), 2.31 (m, 2H), 1.28 (m, 4H). |
| 253 | 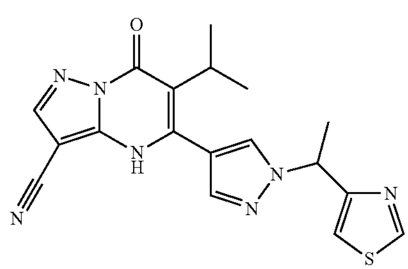 [SMILES: CC(C)c1c(-c2cnn(C(C)c3cscn3)c2)[nH]c2c(C#N)cnn2c1=O] | A | 380.0 | C | 1.152 | $^1$H NMR (400 MHz, DMSO-d$_6$) δ 13.06 (s, 1H), 9.08 (s, 1H), 8.34 (s, 1H), 8.21 (s, 1H), 7.73 (s, 1H), 7.59 (s, 1H), 5.93-5.88 (q, J = 6.8 Hz, 1H), 2.94 (m, 1H), 1.87 (d, J = 7.2 Hz, 3H), 1.26 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 254 | 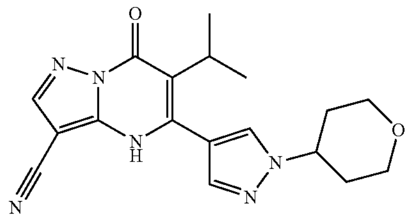 [SMILES: CC(C)c1c(-c2cnn(C3CCOCC3)c2)[nH]c2c(C#N)cnn2c1=O] | A | 353.1 | E | 0.648 | 1H NMR (400 MHz, CD$_3$CD) δ 8.21 (s, 1H), 8.13 (s, 1H), 7.78 (s, 1H), 4.53-4.57 (m, 1H), 4.08-4.11 (m, 2H), 3.57-3.64 (m, 2H), 3.44-3.80 (m, 1H), 2.11-2.17 (m, 4H), 1.37 (d, J = 6.8 Hz, 6H). |
| 255 | 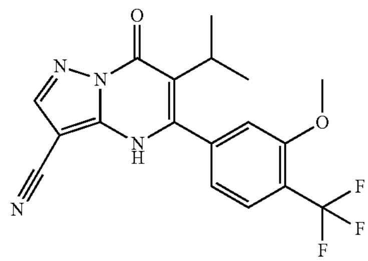 [SMILES: COc1cc(-c2[nH]c3c(C#N)cnn3c(=O)c2C(C)C)ccc1C(F)(F)F] | A | 376.9 | E | 0.873 | 1H NMR (400 MHz, CD$_3$CD) δ 8.26 (s, 1H), 7.80 (d, J = 8.0 Hz, 1H), 7.38 (s, 1H), 7.21 (d, J = 8.0 Hz, 1H), 3.98 (s, 3H), 2.65-2.72 (m, 1H), 1.34 (d, J = 7.2 Hz, 6H). |
| 256 | 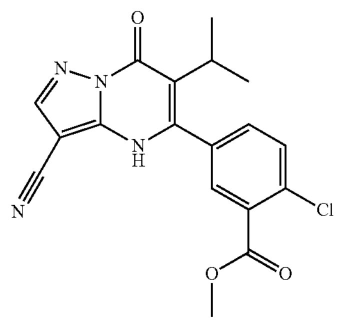 [SMILES: COC(=O)c1cc(-c2[nH]c3c(C#N)cnn3c(=O)c2C(C)C)ccc1Cl] | A | 370.8 | E | 0.814 | 1H NMR (400 MHz, CD$_3$CD) δ 8.25 (s, 1H), 7.99 (d, J = 2.0 Hz, 1H), 7.74 (d, J = 8.4 Hz, 1H), 7.66 (d, J = 8.4 Hz, 1H), 3.95 (s, 3H), 2.64-2.70 (m, 1H), 1.33 (d, J = 6.8 Hz, 6H). |
| 257 | 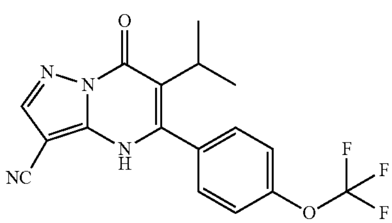 [SMILES: CC(C)c1c(-c2ccc(OC(F)(F)F)cc2)[nH]c2c(C#N)cnn2c1=O] | A | 362.9 | E | 0.866 | 1H NMR (400 MHz, CD$_3$OD) δ 8.25 (s, 1H), 7.65 (d, J = 8.8 Hz, 2H), 7.51 (d, J = 8.0 Hz, 2H), 2.64-2.74 (m, 1H), 1.33 (d, J = 6.8 Hz, 6H). |
| 258 | 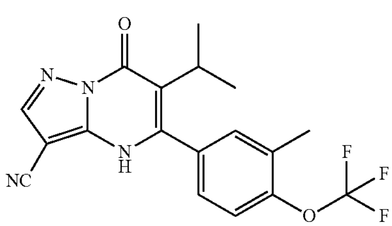 [SMILES: Cc1cc(-c2[nH]c3c(C#N)cnn3c(=O)c2C(C)C)ccc1OC(F)(F)F] | A | 376.9 | E | 0.897 | 1H NMR (400 MHz, CD$_3$CD) δ 8.24 (s, 1H), 7.43-7.53 (m, 3H), 2.67-2.74 (m, 1H), 2.42 (s, 3H), 1.33 (d, J = 7.2 Hz, 6H). |
| 259 | 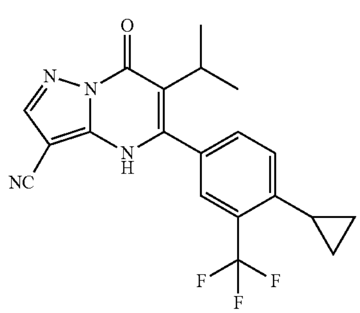 [SMILES: CC(C)c1c(-c2ccc(C3CC3)c(C(F)(F)F)c2)[nH]c2c(C#N)cnn2c1=O] | A | 386.9 | E | 0.964 | 1H NMR (400 MHz, CD$_3$CD) δ 8.24 (s, 1H), 7.81 (s, 1H), 7.65 (d, J = 8.0 Hz, 1H), 7.32 (d, J = 8.0 Hz, 1H), 2.64-2.71 (m, 1H), 2.28-2.31 (m, 1H), 1.32 (d, J = 6.4 Hz, 6H), 1.18-1.16 (m, 2H), 0.92 (m, 2H). |

| Ex | Structure | Syn. Met. | LCMS (ESI) m/z | LCMS Method | R_T (min) | NMR |
|---|---|---|---|---|---|---|
| 260 | 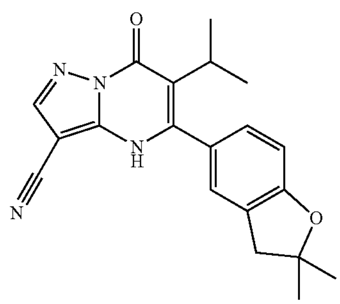 [SMILES: CC(C)c1c(-c2ccc3c(c2)CC(C)(C)O3)[nH]c2c(C#N)cnn2c1=O] | A | 348.9 | E | 0.892 | 1H NMR (400 MHz, CD₃CD) δ 8.21 (s, 1H), 7.30 (s, 1H), 7.23 (d, J = 8.8 Hz, 1H), 6.83 (d, J = 8.0 Hz, 1H), 3.13 (s, 2H), 2.83-2.90 (m, 1H), 1.50 (s, 6H), 1.33 (d, J = 7.2 Hz, 6H). |
| 261 | 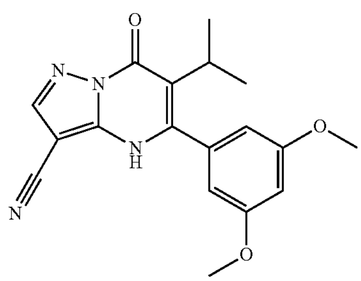 [SMILES: COc1cc(OC)cc(-c2[nH]c3c(C#N)cnn3c(=O)c2C(C)C)c1] | A | 338.9 | E | 0.855 | 1H NMR (400 MHz, CD₃CD) δ 8.22 (s, 1H), 6.66 (m, 3H), 3.85 (s, 6H), 2.76-2.83 (m, 1H), 1.33 (d, J = 7.2 Hz, 6H). |
| 262 | 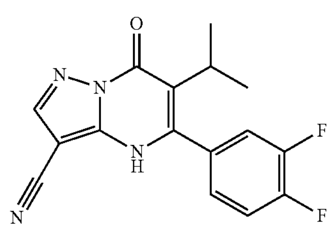 [SMILES: CC(C)c1c(-c2ccc(F)c(F)c2)[nH]c2c(C#N)cnn2c1=O] | A | 5 | E | 0.729 | 1H NMR (400 MHz, CD₃CD) δ 8.24 (s, 1H), 7.48-7.56 (m, 2H), 7.35-7.36 (m, 1H), 2.63-2.74 (m, 1H), 1.32 (d, J = 7.2 Hz, 6H). |
| 263 | 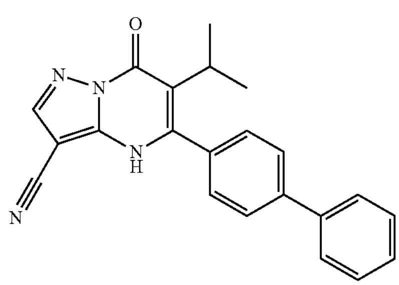 [SMILES: CC(C)c1c(-c2ccc(-c3ccccc3)cc2)[nH]c2c(C#N)cnn2c1=O] | A | 354.9 | E | 0.940 | 1H NMR (400 MHz, CD₃CD) δ 8.25 (s, 1H), 7.84 (d, J = 8.0 Hz, 2H), 7.71 (d, J = 7.2 Hz, 2H), 7.60 (d, J = 8.0 Hz, 2H), 7.49 (d, J = 8.0 Hz, 2H), 7.41 (m, 1H), 2.80-2.87 (m, 1H), 1.35 (d, J = 7.2 Hz, 6H) |
| 264 | 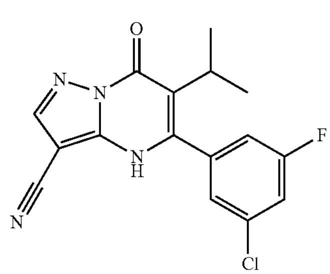 [SMILES: CC(C)c1c(-c2cc(F)cc(Cl)c2)[nH]c2c(C#N)cnn2c1=O] | A | 330.8 | E | 0.917 | 1H NMR (400 MHz, CD₃CD) δ 8.23 (s, 1H), 7.44-7.49 (m, 2H), 7.10 (d, J = 8.4 Hz, 1H), 2.62-2.69 (m, 1H), 1.33 (d, J = 6.8 Hz, 6H). |

-continued
| Ex | Structure | Syn. Met. | LCMS (ESI) m/z | LCMS Method | R_T (min) | NMR |
|---|---|---|---|---|---|---|
| 265 | 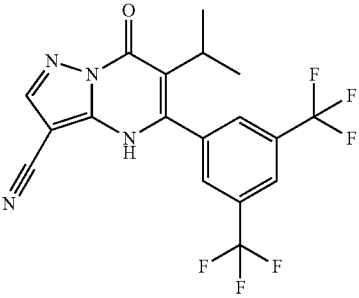 [SMILES: CC(C)c1c(-c2cc(C(F)(F)F)cc(C(F)(F)F)c2)[nH]c2c(C#N)cnn2c1=O] | A | 415.0 | E | 0.818 | 1H NMR (400 MHz, CD$_3$CD) δ 8.25 (s, 1H), 8.22 (s, 3H), 2.52-2.59 (m, 1H), 1.33 (d, J = 7.2 Hz, 6H). |
| 266 | 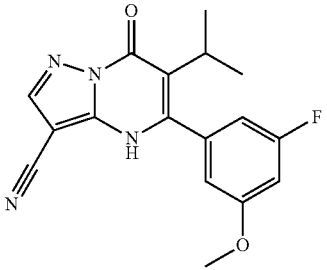 [SMILES: COc1cc(F)cc(-c2[nH]c3c(C#N)cnn3c(=O)c2C(C)C)c1] | A | 327.0 | E | 0.749 | 1H NMR (400 MHz, CD$_3$CD) δ 8.23 (s, 1H), 6.83-6.92 (m, 3H), 3.86 (s, 3H), 2.70-2.75 (m, 1H), 1.32 (d, J = 6.8 Hz, 6H). |
| 267 | 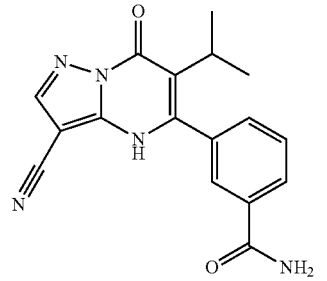 [SMILES: CC(C)c1c(-c2cccc(C(N)=O)c2)[nH]c2c(C#N)cnn2c1=O] | A | 321.9 | E | 0.564 | $^1$H NMR (400 MHz, CD$_3$CD) δ 8.25 (s, 1H), 8.10 (m, 1H), 8.03 (s, 1H), 7.69 (m, 2H), 2.66-2.73 (m, 1H), 1.33 (d, J = 6.8 Hz, 6H). |
| 268 | 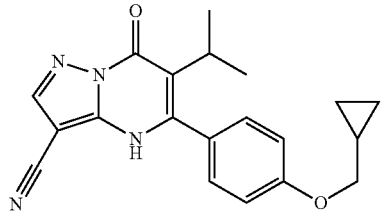 [SMILES: CC(C)c1c(-c2ccc(OCC3CC3)cc2)[nH]c2c(C#N)cnn2c1=O] | A | 348.9 | E | 0.746 | $^1$H NMR (400 MHz, CD$_3$CD) δ 8.24 (s, 1H), 7.44 (d, J = 8.4 Hz, 2H), 7.12 (d, J = 8.4 Hz, 2H), 3.93 (d, J = 6.4 Hz, 2H), 1.33 (d, J = 6.4 Hz, 6H), 0.66 (m, 2H), 0.41 (m, 2H). |
| 269 | 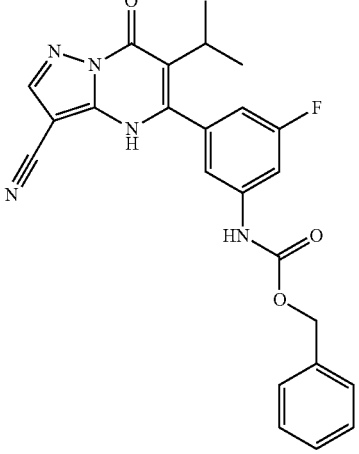 | A | 446.0 | E | 0.762 | $^1$H NMR (400 MHz, CD$_3$CD) δ 8.24 (s, 1H), 7.54 (d, J = 11.6 Hz, 1H), 7.30-7.46 (m, 7H), 6.95 (d, J = 8.0 Hz, 1H), 2.71-2.78 (m, 1H), 1.33 (d, J = 7.2 Hz, 6H) |

| Ex | Structure | Syn. Met. | LCMS (ESI) m/z | LCMS Method | R_T (min) | NMR |
|---|---|---|---|---|---|---|
| 270 | 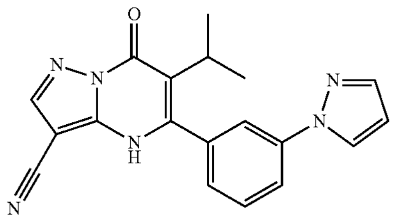 [SMILES: CC(C)c1c(-c2cccc(-n3cccn3)c2)[nH]c2c(C#N)cnn2c1=O] | A | 344.9 | E | 0.675 | ¹H NMR (400 MHz, CD₃CD) δ 8.23 (s, 1H), 8.34 (s, 1H), 7.99-8.01 (m, 2H), 7.78 (s, 1H), 7.71 (d, J = 8.0 Hz, 1H), 7.47 (d, J = 7.6 Hz, 1H), 6.58 (d, J = 2.0, 1H), 2.75-3.31 (m, 1H), 1.35 (d, J = 7.2 Hz, 6H). |
| 271 | 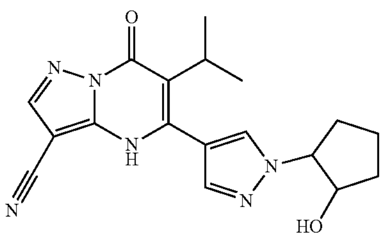 [SMILES: CC(C)c1c(-c2cnn(C3CCCC3O)c2)[nH]c2c(C#N)cnn2c1=O] | A | 352.9 | E | 0.601 | ¹H NMR (400 MHz, CD₃CD) δ 8.17 (s, 1H), 8.04 (s, 1H), 7.76 (s, 1H), 4.40-4.53 (m, 1H), 3.12-3.17 (m, 1H), 2.30-2.32 (m, 1H), 2.11-2.17 (m, 2H), 1.92-1.94 (m, 2H), 1.72-1.74 (m, 1H), 1.39 (d, J = 7.2 Hz, 6H). |
| 272 | 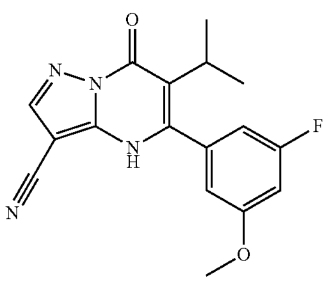 [SMILES: COc1cc(F)cc(-c2[nH]c3c(C#N)cnn3c(=O)c2C(C)C)c1] | A | 327.0 | E | 0.749 | ¹H NMR (400 MHz, CD₃CD) δ 8.23 (s, 1H), 6.83-6.92 (m, 3H), 3.86 (s, 3H), 2.70-2.75 (m, 1H), 1.32 (d, J = 6.8 Hz, 6H). |
| 273 | 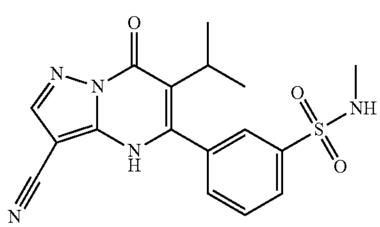 [SMILES: CNS(=O)(=O)c1cccc(-c2[nH]c3c(C#N)cnn3c(=O)c2C(C)C)c1] | A | 371.9 | E | 0.610 | ¹H NMR (400 MHz, CD₃CD) δ 8.25 (s, 1H), 8.07-8.04 (m, 1H), 7.98 (s, 1H), 7.81-7.79 (m, 2H), 2.68-2.61 (m, 1H), 2.59 (s, 3H), 1.32 (d, J = 7.2 Hz, 6H). |
| 274 | 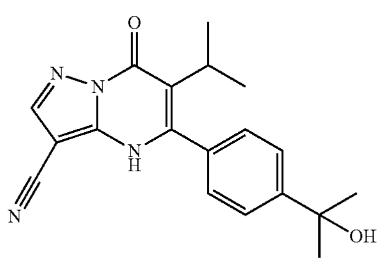 [SMILES: CC(C)c1c(-c2ccc(C(C)(C)O)cc2)[nH]c2c(C#N)cnn2c1=O] | A | 337.1 | E | 0.982 | ¹H NMR (400 MHz, CD₃CD) δ 8.23 (s, 1H), 7.70 (d, J = 8.0 Hz, 2H), 7.47 (d, J = 8.0 Hz, 2H), 2.73-2.79 (m, 1H), 1.58 (s, 6H), 1.31 (d, J = 6.8 Hz, 6H). |
| 275 | 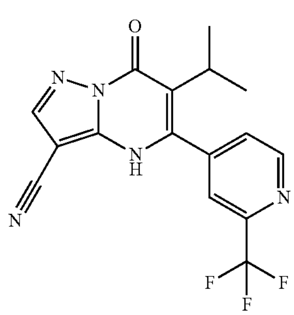 [SMILES: CC(C)c1c(-c2ccnc(C(F)(F)F)c2)[nH]c2c(C#N)cnn2c1=O] | A | 348.1 | E | 0.807 | ¹H NMR (400 MHz, CD₃CD) δ 8.88 (d, J = 4.4 Hz, 1H), 7.98 (s, 1H), 7.77 (d, J = 4.4 Hz, 1H), 2.61-2.64 (m, 1H), 1.33 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 276 | 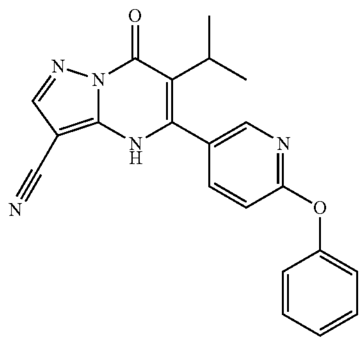 [SMILES: CC(C)c1c(-c2ccc(Oc3ccccc3)nc2)[nH]c2c(C#N)cnn2c1=O] | A | 372.0 | E | 0.866 | $^1$H NMR (400 MHz, CD$_3$CD) δ 8.26 (d, J = 3.2 Hz, 2H), 7.96 (s, 1H), 7.13-7.48 (m, 6H), 2.46-2.48 (m, 1H), 1.34 (d, J = 7.2 Hz, 6H). |
| 277 | 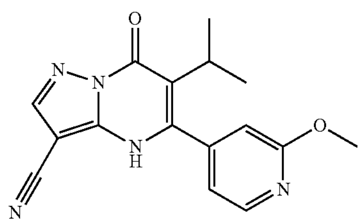 [SMILES: COc1cc(-c2[nH]c3c(C#N)cnn3c(=O)c2C(C)C)ccn1] | A | 310.2 | E | 0.782 | $^1$H NMR (400 MHz, CD$_3$CD) δ 8.34 (d, J = 5.2 Hz, 2H.), 8.25 (s, 1H), 7.08 (d, J = 4.8 Hz, 1H), 6.97 (s, 1H), 4.00 (s, 3H), 2.63-2.70 (m, 1H), 1.33 (d, J = 6.8 Hz, 6H). |
| 278 | 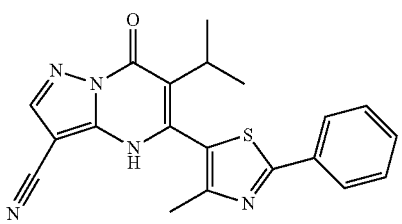 [SMILES: Cc1nc(-c2ccccc2)sc1-c1[nH]c2c(C#N)cnn2c(=O)c1C(C)C] | A | 375.8 | E | 0.771 | $^1$H NMR (400 MHz, CD$_3$CD) δ 8.27 (s, 1H), 8.00 (m, 2H), 7.52-7.54 (m, 3H), 2.78-2.84 (m, 1H), 2.45 (s, 3H), 1.38 (d, J = 7.2 Hz, 6H). |
| 279 | 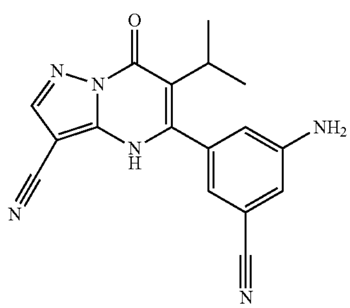 [SMILES: CC(C)c1c(-c2cc(N)cc(C#N)c2)[nH]c2c(C#N)cnn2c1=O] | A | 318.9 | E | 0.765 | $^1$H NMR (400 MHz, CD$_3$CD) δ 8.24 (s, 1H), 6.98-7.10 (m, 3H), 2.70-2.76 (m, 1H), 1.34 (d, J = 6.8 Hz, 6H). |
| 280 | 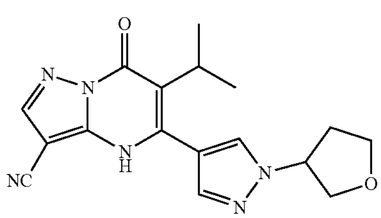 [SMILES: CC(C)c1c(-c2cnn(C3CCOC3)c2)[nH]c2c(C#N)cnn2c1=O] | A | 339.0 | E | 0.726 | $^1$H NMR (400 MHz, CD$_3$CD) δ 8.22 (s, 1H), 8.11 (s, 1H), 7.78 (s, 1H), 5.14-5.17 (m, 1H), 4.08-4.17 (m, 3H), 3.93-3.96 (m, 1H), 3.04-3.08 (m, 1H), 2.53-2.56 (m, 2H), 1.38 (d, J = 7.2 Hz, 6H). |
| 281 | 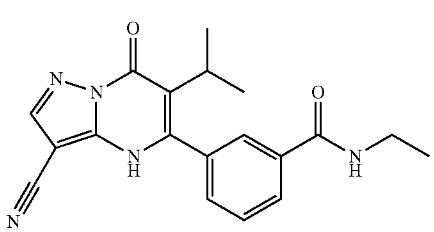 [SMILES: CCNC(=O)c1cccc(-c2[nH]c3c(C#N)cnn3c(=O)c2C(C)C)c1] | A | 349.9 | E | 1.077 | $^1$H NMR (400 MHz, CD$_3$CD) δ 8.25 (s, 1H), 8.02-8.04 (m, 1H), 7.97 (s, 1H), 7.68 (m, 2H), 3.45 (q, J = 7.2 Hz, 2H), 2.66-2.73 (m, 1H), 1.33 (d, J = 7.2 Hz, 6H), 1.24 (t, J = 7.2 Hz, 3H). |

| Ex | Structure | Syn. Met. | LCMS (ESI) m/z | LCMS Method | R_T (min) | NMR |
|---|---|---|---|---|---|---|
| 282 | 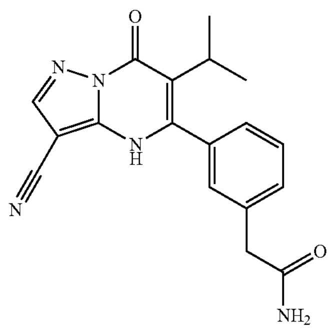 [SMILES: CC(C)c1c(-c2cccc(CC(N)=O)c2)[nH]c2c(C#N)cnn2c1=O] | A | 335.9 | E | 1.024 | ¹H NMR (400 MHz, CD₃OD) δ 8.24 (s, 1H), 7.40-7.56 (m, 4H), 3.64 (s, 2H), 2.73-2.80 (m, 1H), 1.32 (d, J = 6.8 Hz, 6H). |
| 283 | 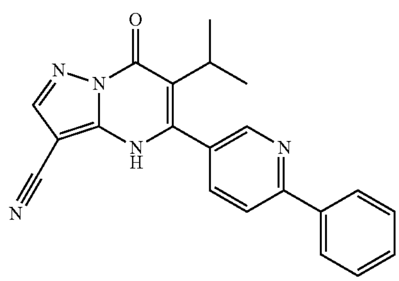 [SMILES: CC(C)c1c(-c2ccc(-c3ccccc3)nc2)[nH]c2c(C#N)cnn2c1=O] | A | 356.0 | E | 1.214 | ¹H NMR (400 MHz, CD₃OD) δ 8.99 (s, 1H), 8.43 (d, J = 2.4 Hz, 1H), 8.35 (d, J = 8.4 Hz, 1H), 8.29 (s, 1H), 8.09 (m, 2H), 7.65 (m 3H), 2.70-2.77 (m, 1H), 1.39 (d, J = 7.2 Hz, 6H). |
| 284 | 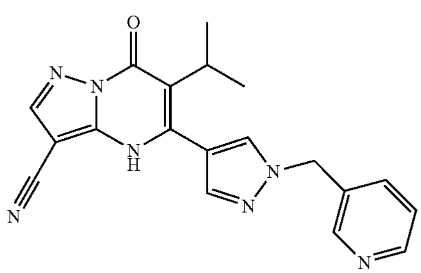 [SMILES: CC(C)c1c(-c2cnn(Cc3cccnc3)c2)[nH]c2c(C#N)cnn2c1=O] | A | 360.0 | E | 0.854 | ¹H NMR (400 MHz, CD₃OD) δ 8.53-8.58 (m, 2H), 8.21 (s, m, 2H), 7.81-7.87 (m, 2H), 7.47-7.51 (m, 1H), 5.55 (s, 2H), 3.01-3.12 (m, 1H), 1.37 (d, J = 6.8 Hz, 6H). |
| 285 | 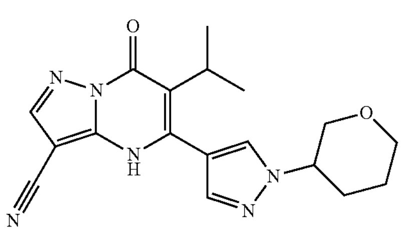 [SMILES: CC(C)c1c(-c2cnn(C3CCCOC3)c2)[nH]c2c(C#N)cnn2c1=O] | A | 352.9 | E | 1.079 | ¹H NMR (400 MHz, CD₃OD) δ 8.17 (s, 1H), 8.13 (s, 1H), 7.75 (s, 1H), 4.13-4.34 (m, 1H), 4.09-4.10 (m, 1H), 3.79-3.90 (m, 2H), 3.59-3.61 (m, 1H), 3.07-3.09 (m, 1H), 2.22-3.17 (m, 2H), 1.73-1.84 (m, 2H), 1.38 (d, J = 7.2 Hz, 6H). |
| 286 | 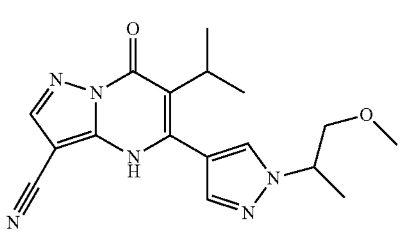 [SMILES: COCC(C)n1cc(-c2[nH]c3c(C#N)cnn3c(=O)c2C(C)C)cn1] | A | 340.9 | E | 1.068 | ¹H NMR (400 MHz, CD₃OD) δ 8.16 (s, 1H), 8.02 (s, 1H), 7.75 (s, 1H), 4.64-4.68 (m, 1H), 3.72-3.77 (m, 1H), 3.66-3.69 (m, 1H), 3.32 (s, 3H), 3.10-3.13 (m, 1H), 1.54 (d, J = 6.8 Hz, 3H), 1.38 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 287 | 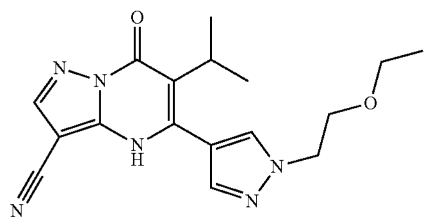 [SMILES: CCOCCn1cc(-c2[nH]c3c(C#N)cnn3c(=O)c2C(C)C)cn1] | A | 341.0 | E | 1.069 | $^1$H NMR (400 MHz, CD$_3$CD) δ 8.22 (s, 1H), 8.06 (s, 1H), 7.79 (s, 1H), 4.41 (t, J = 4.8 Hz, 2H), 3.84 (t, J = 5.2 Hz, 2H), 3.50 (q, J = 7.2 Hz, 2H), 1.37 (d, J = 7.2 Hz, 6H), 1.15 (t, J = 7.2 Hz, 3H). |
| 288 | 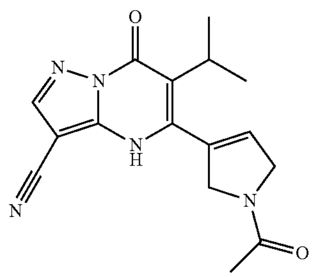 [SMILES: CC(=O)N1CC=C(c2[nH]c3c(C#N)cnn3c(=O)c2C(C)C)C1] | A | 312.1 | E | 0.684 | 1H NMR: (400 MHz, CD$_3$CD) δ 8.22 (s, 1H), 6.29 (m, 1H), 4.62 (m, 2H), 4.47 (m, 2H), 2.93-3.03 (m, 1H), 2.51 (s, 3H), 1.38 (m, 6H). |
| 289 | 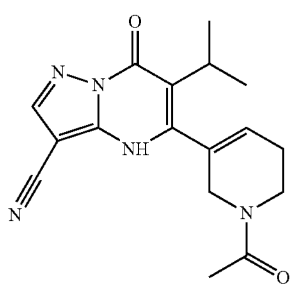 [SMILES: CC(=O)N1CCC=C(c2[nH]c3c(C#N)cnn3c(=O)c2C(C)C)C1] | A | 326.0 | E | 0.709 | $^1$H NMR (400 MHz, CD$_3$CD) δ 8.34 (s, 1H), 6.23-6.18 (m, 1H), 4.24 (s, 2H), 3.74 (m, 2H), 2.94 (m, 1H), 2.45 (m, 2H), 2.17 (2s, 3H), 1.38 (d, J = 7.2 Hz, 6H). |
| 290 | 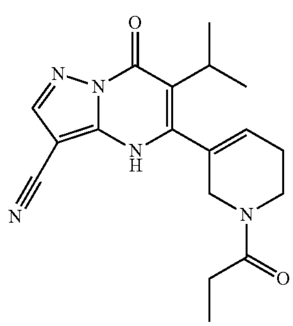 [SMILES: CCC(=O)N1CCC=C(c2[nH]c3c(C#N)cnn3c(=O)c2C(C)C)C1] | A | 340.1 | E | 0.753 | 1H NMR (400 MHz, CD$_3$CD) δ 8.21 (s, 1H), 6.23-6.17 (m, 1H), 4.25-4.22 (m, 2H), 3.78-3.72 (m, 2H), 2.89-2.96 (m, 1H), 2.33-2.43 (m, 4H), 1.30 (d, J = 7.2 Hz, 6H), 1.06 (t, J = 7.2 Hz, 3H). |
| 291 | 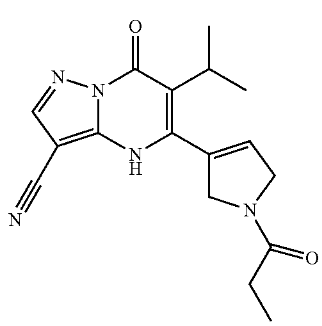 [SMILES: CCC(=O)N1CC=C(c2[nH]c3c(C#N)cnn3c(=O)c2C(C)C)C1] | A | 325.9 | E | 0.731 | 1H NMR (400 MHz, CD$_3$CD) δ 8.21 (s, 1H), 6.29 (m, 1H), 4.44-4.46 (m, 4H), 2.93-3.02 (m, 1H), 2.38-2.43 (m, 2H), 1.38 (m, 6H), 1.17 (m, 3H). |

-continued

| Ex | Structure | Syn. Met. | LCMS (ESI) m/z | LCMS Method | R_T (min) | NMR |
|---|---|---|---|---|---|---|
| 292 | 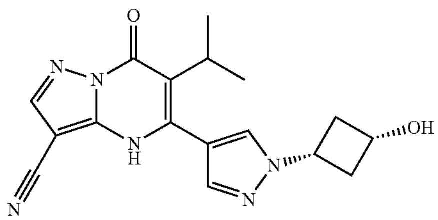 [SMILES: CC(C)c1c(-c2cnn([C@H]3C[C@@H](O)C3)c2)[nH]c2c(C#N)cnn2c1=O] | A | 325.9 | E | 0.731 | 1H NM: (400 MHz, CD$_3$CD) δ 8.21 (s, 1H), 8.10 (s, 1H), 7.79 (s, 1H), 4.50-4.56 (m, 1H), 4.15 (m, 1H), 3.06-3.08 (m, 1H), 2.90-2.92 (m, 2H), 2.50-2.53 (m, 2H), 1.38 (d, J = 7.2 Hz, 6H). |
| 293 | 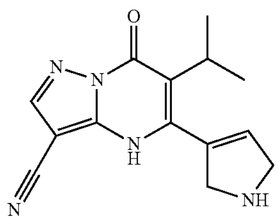 [SMILES: CC(C)c1c(C2=CCNC2)[nH]c2c(C#N)cnn2c1=O] | A | 269.9 | E | 0.621 | 1H NMR (400 MHz, CD$_3$CD) δ 9.15 (brs, 1H), 8.03 (s, 1H), 5.88 (s, 1H), 4.28 (s, 2H), 4.18 (s, 2H), 3.05-3.12 (m, 1H), 1.31 (d, J = 6.8 Hz, 6H). |
| 294 | 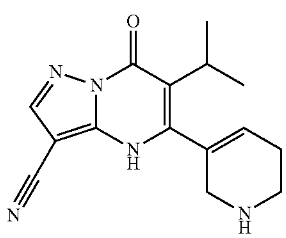 [SMILES: CC(C)c1c(C2=CCCNC2)[nH]c2c(C#N)cnn2c1=O] | A | 283.9 | E | 0.652 | 1H NMR (400 MHz, CD$_3$CD) δ 8.01 (s, 1H), 5.80 (s, 1H), 3.81 (s, 2H), 3.25 (m, 2H), 3.04-3.09 (m, 1H), 2.43 (m, 2H), 1.29 (d, J = 6.8 Hz, 6H). |
| 295 | 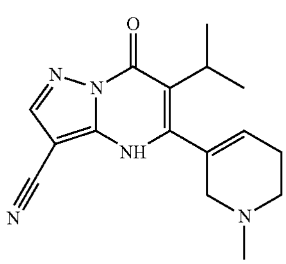 [SMILES: CC(C)c1c(C2=CCCN(C)C2)[nH]c2c(C#N)cnn2c1=O] | A | 298.0 | E | 0.650 | 1H NMR (400 MHz, CD$_3$CD) δ 9.86 (s, 1H), 8.01 (s, 1H), 5.79 (m, 1H), 3.85 (m, 2H), 3.24-3.25 (m, 2H), 3.01-3.07 (m, 1H), 2.86 (s, 3H), 2.40-2.42 (m, 2H), 1.29 (d, J = 6.4 Hz, 6H). |
| 296 | 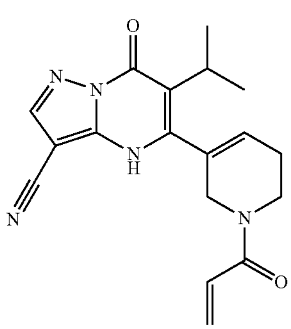 [SMILES: C=CC(=O)N1CCC=C(c2[nH]c3c(C#N)cnn3c(=O)c2C(C)C)C1] | A | 338.1 | E | 0.730 | 1H NMR (400 MHz, CD$_3$CD) δ 8.22 (s, 1H), 6.74-6.90 (m, 1H), 6.19-6.30 (m, 2H), 5.79-5.84 (m, 1H), 4.30 (s, 2H), 3.85 (m, 2H), 2.95-2.99 (m, 1H), 2.43 (m, 2H), 1.38 (d, J = 6.4 Hz, 6H). |

| Ex | Structure | Syn. Met. | LCMS (ESI) m/z | LCMS Method | R$_T$ (min) | NMR |
|---|---|---|---|---|---|---|
| 297 | 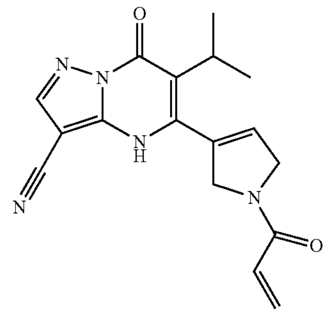 [SMILES: C=CC(=O)N1CC=C(c2[nH]c3c(C#N)cnn3c(=O)c2C(C)C)C1] | A | 324.1 | E | 0.712 | 1H NMR (400 MHz, CD$_3$CD) δ 8.23 (s, 1H), 6.30-6.60 (m, 1H), 6.28-6.39 (m, 2H), 5.83-5.85 (m, 1H), 4.72 (m, 2H), 4.55 (m, 2H), 2.97-3.04 (m, 1H), 1.39 (d, J = 7.2 Hz, 6H). |
| 298 | 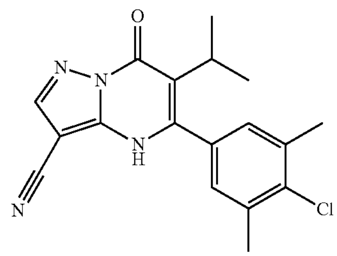 [SMILES: Cc1cc(-c2[nH]c3c(C#N)cnn3c(=O)c2C(C)C)cc(C)c1Cl] | A | 341.1 | A | 1.215 | 1H NMR (400 MHz, DMSO-d$_6$) δ 13.56 (s, 1H), 8.37 (s, 1H), 7.33 (s, 2H), 2.61-2.54 (m, 1H), 2.39 (s, 6H), 1.20 (d, J = 6.8 Hz, 6H). |
| 299 | 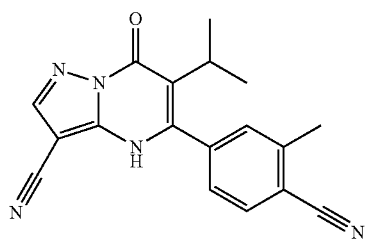 [SMILES: Cc1cc(-c2[nH]c3c(C#N)cnn3c(=O)c2C(C)C)ccc1C#N] | A | 318.1 | E | 0.797 | 1H NMR (400 MHz, DMSO-d$_6$) δ 13.49 (s, 1H), 8.43 (s, 1H), 8.00 (d, J = 8.4 Hz, 1H), 7.66 (s, 1H), 7.54 (d, J = 7.6 Hz, 1H), 2.58 (s, 3H), 1.23 (d, J = 7.2 Hz, 6H). |
| 300 | 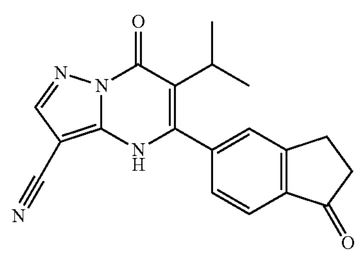 [SMILES: CC(C)c1c(-c2ccc3c(c2)CCC3=O)[nH]c2c(C#N)cnn2c1=O] | A | 333.1 | E | 0.760 | 1H NMR (400 MHz, DMSO-d$_6$) δ 13.53 (s, 1H), 8.43 (s, 1H), 7.82 (d, J = 8.0 Hz, 1H), 7.76 (s, 1H), 7.55 (d, J = 7.6 Hz, 1H), 3.20 (t, J = 6.0 Hz, 2H), 2.74 (t, J = 6.0 Hz, 2H), 2.56-2.54 (m, 1H), 1.24 (d, J = 6.8 Hz, 6H). |
| 301 | 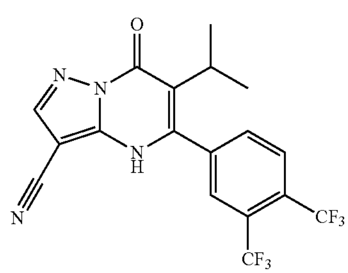 [SMILES: CC(C)c1c(-c2ccc(C(F)(F)F)c(C(F)(F)F)c2)[nH]c2c(C#N)cnn2c1=O] | A | 415.1 | E | 0.905 | 1H NMR (400 MHz, DMSO-d$_6$) δ 13.41 (s, 1H), 8.41 (s, 1H), 8.25 (d, J = 7.2 Hz, 1H), 8.24 (s, 1H), 8.06 (d, J = 8.0 Hz, 1H), 2.44-2.39 (m, 1H), 1.20 (d, J = 6.4 Hz, 6H). |
| 302 | 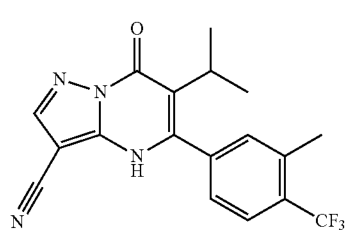 [SMILES: Cc1cc(-c2[nH]c3c(C#N)cnn3c(=O)c2C(C)C)ccc1C(F)(F)F] | A | 361.1 | A | 1.183 | 1H NMR (400 MHz, DMSO-d$_6$) δ 13.46 (s, 1H), 8.42 (s, 1H), 7.88 (d, J = 8.0 Hz, 1H), 7.64 (s, 1H), 7.55 (d, J = 7.2 Hz, 1H), 2.54 (s, 3H), 2.54 (m, 1H), 1.20 (d, J = 6.4 Hz, 6H). |

| Ex | Structure | Syn. Met. | LCMS (ESI) m/z | LCMS Method | $R_T$ (min) | NMR |
|---|---|---|---|---|---|---|
| 303 | 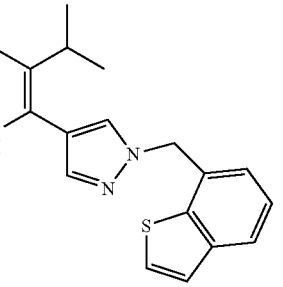 | A | 415.1 | A | 1.109 | 1H NMR (400 MHz, DMSO-d$_6$) δ 13.13 (s, 1H), 8.36 (2s, 2H), 7.89 (d, J = 8.0 Hz, 1H), 7.81 (d, J = 5.6 Hz, 1H), 7.79 (s, 1H), 7.53 (d, J = 5.6 Hz, 1H), 7.43 (t, J = 7.6 Hz, 1H), 7.28 (d, J = 6.8 Hz, 1H), 5.72 (s, 2H), 3.03-2.96 (m, 1H), 1.29 (d, J = 5.6 Hz, 6H). |
| 304 | 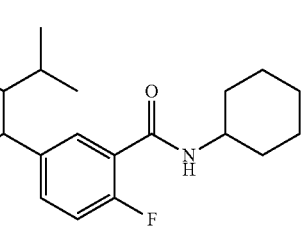 | A | 422.2 | A | 1.132 | 1H NMR (400 MHz, DMSO-d$_6$) δ 13.40 (s, 1H), 8.39 (s, 1H), 8.28 (d, J = 7.6 Hz, 1H), 7.70-7.63 (m, 2H), 7.48 (t, J = 8.8 Hz, 1H), 3.76 (m, 1H), 2.61-2.58 (m, 1H), 1.84 (m, 2H), 1.72 (m, 1H), 1.59 (m, 1H), 1.29 (m, 4H), 1.24 (d, J = 6.4 Hz, 6H), 1.16 (m, 1H). |
| 305 | 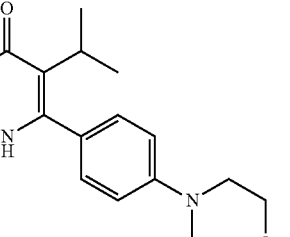 | GNT_E | 364.2 | A | 1.031 | 1H NMR (400 MHz, DMSO-d$_6$) δ 13.28 (s, 1H), 8.20 (s, 1H), 7.30 (d, J = 8.4 Hz, 2H), 7.04 (d, J = 8.4 Hz, 2H), 3.77 (t, J = 4.4 Hz, 4H), 3.19 (t, J = 4.4 Hz, 4H), 2.82-2.79 (m, 1H), 1.26 (d, J = 7.2 Hz, 6H). |
| 306 | 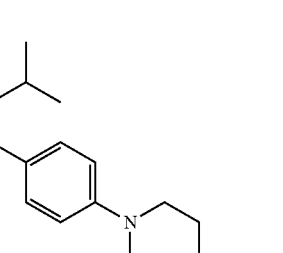 | A | 463.2 | A | 1.206 | 1H NMR (400 MHz, DMSO-d$_6$) δ 7.99 (s, 1H), 7.23 (d, J = 8.8 Hz, 2H), 6.98 (d, J = 8.4 Hz, 2H), 3.15 (m, 8H), 2.87-2.80 (m, 1H), 1.43 (s, 9H), 1.25 (d, J = 6.4 Hz, 6H). |
| 307 | 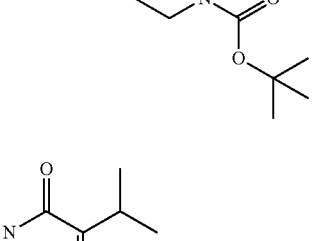 | A | 327.1 | A | 1.154 | 1H NMR (400 MHz, DMSO-d$_6$) δ 13.43 (s, 1H), 8.41 (s, 1H), 7.50 (s, 1H), 7.44 (s, 1H), 7.30 (s, 1H), 2.58-2.55 (m, 1H), 2.41 (s, 3H), 1.24 (d, J = 7.2 Hz, 6H). |

| Ex | Structure | Syn. Met. | LCMS (ESI) m/z | LCMS Method | $R_T$ (min) | NMR |
|---|---|---|---|---|---|---|
| 308 | 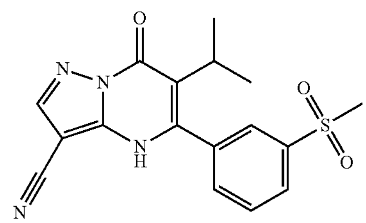 [SMILES: CC(C)c1c(-c2cccc(S(C)(=O)=O)c2)[nH]c2c(C#N)cnn2c1=O] | A | 357.40 | E | 0.751 | 1H NMR (400 MHz, CD₃OD) δ 8.20 (s, 1H), 8.13-8.09 (m, 2H), 7.84-7.80 (m, 2H), 3.18 (s, 3H), 2.69-2.62 (m, 1H), 1.31 (d, J = 6.8 Hz, 6H). |
| 309 | 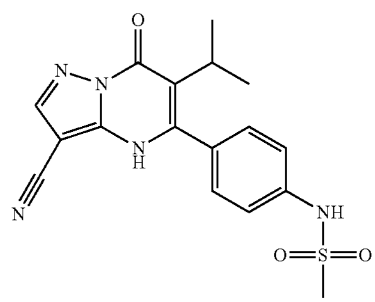 [SMILES: CC(C)c1c(-c2ccc(NS(C)(=O)=O)cc2)[nH]c2c(C#N)cnn2c1=O] | A | 372.41 | A | 0.926 | 1H NMR (400 MHz, DMSO-d₆) δ 13.36 (s, 1H), 10.02 (s, 1H), 8.25 (s, 1H), 7.42 (m, 2H), 7.31 (m, 2H), 3.09 (s, 3H), 2.73-2.67 (m, 1H), 1.25 (d, J = 6.4 Hz, 6H). |
| 310 | 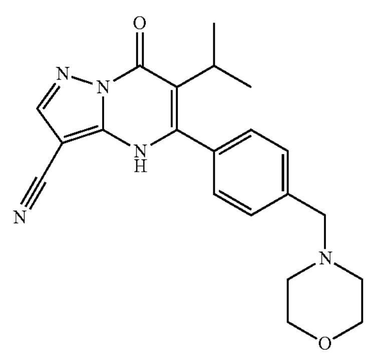 [SMILES: CC(C)c1c(-c2ccc(CN3CCOCC3)cc2)[nH]c2c(C#N)cnn2c1=O] | A | 378.44 | A | 1.014 | 1H NMR (400 MHz, CD₃OD) δ 8.74 (s, 1H), 7.61 (d, J = 8.0 Hz, 2H), 7.53 (d, J = 8.0 Hz, 2H), 3.87 (s, 2H), 3.79 (m, 4H), 2.75 (m, 5H), 1.33 (d, J = 6.8 Hz, 6H). |
| 311 | 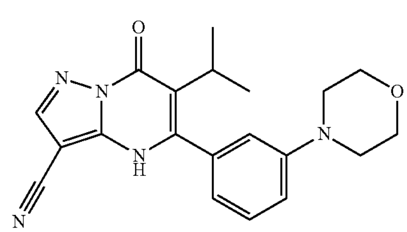 [SMILES: CC(C)c1c(-c2cccc(N3CCOCC3)c2)[nH]c2c(C#N)cnn2c1=O] | A | 364.41 | A | 1.015 | 1H NMR (400 MHz, CD₃OD) δ 8.19 (s, 1H), 7.41 (t, J = 7.6 Hz, 1H), 7.14-7.12 (m, 1H), 7.05 (s, 1H), 6.94 (d, J = 7.2 Hz, 1H), 3.87 (t, J = 4.8 Hz, 4H), 3.23 (t, J = 5.2 Hz, 4H), 2.85-2.78 (m, 1H), 1.34 (d, J = 6.8 Hz, 6H). |
| 312 | 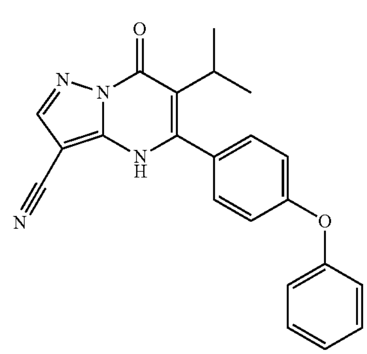 [SMILES: CC(C)c1c(-c2ccc(Oc3ccccc3)cc2)[nH]c2c(C#N)cnn2c1=O] | A | 371.40 | A | 1.190 | 1H NMR (400 MHz, DMSO-d₆) δ 13.37 (s, 1H), 8.39 (s, 1H), 7.53-7.46 (m, 4H), 7.24 (t, J = 6.8 Hz, 1H), 7.14 (t, J = 9.2 Hz, 4H), 2.70-2.66 (m, 1H), 1.25 (d, J = 7.2 Hz, 6H). |

| Ex | Structure | Syn. Met. | LCMS (ESI) m/z | LCMS Method | R_T (min) | NMR |
|---|---|---|---|---|---|---|
| 313 | 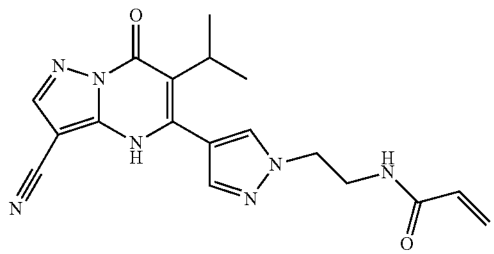 [SMILES: C=CC(=O)NCCn1cc(-c2[nH]c3c(C#N)cnn3c(=O)c2C(C)C)cn1] | A | 366.16 | E | 0.687 | 1H NMR (400 MHz, DMSO-$d_6$) δ 13.04 (s, 1H), 8.25 (s, 1H), 8.24 (s, 1H), 7.98 (s, 1H), 7.70 (s, 1H), 6.20-6.03 (m, 2H), 5.57 (d, J = 10.0 Hz, 1H), 4.26 (t, J = 6.0 Hz, 1H), 3.55 (t, J = 6.0 Hz, 1H), 3.02-2.98 (m, 1H), 1.26 (d, J = 7.2 Hz, 6H). |
| 314 | 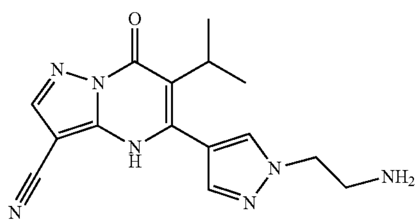 [SMILES: CC(C)c1c(-c2cnn(CCN)c2)[nH]c2c(C#N)cnn2c1=O] | A | 312.15 | E | 0.351 | 1H NMR (400 MHz, DMSO-$d_6$) δ 13.09 (s, 1H), 8.38 (s, 1H), 8.28 (s, 3H), 8.27 (s, 1H), 7.84 (s, 1H), 4.51 (d, J = 6.4 Hz, 2H), 3.32 (d, J = 6.0 Hz, 2H), 3.05-2.99 (m, 1H), 1.31 (d, J = 7.2 Hz, 6H). |
| 315 | 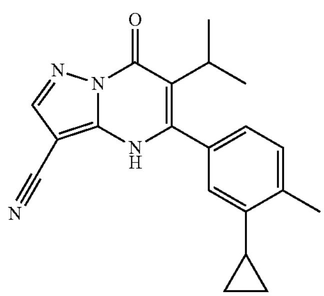 [SMILES: Cc1ccc(-c2[nH]c3c(C#N)cnn3c(=O)c2C(C)C)cc1C1CC1] | A | 333.2 | A | 1.176 | 1H NMR (400 MHz, CD$_3$OD) δ 8.25 (s, 1H), 7.36 (d, J = 7.6 Hz, 1H), 7.22 (d, J = 8.0 Hz, 1H), 7.11 (s, 1H), 2.77-2.74 (m, 1H), 2.54 (s, 3H), 2.06-2.02 (m, 1H), 1.32 (d, J = 6.8 Hz, 6H), 1.05-1.03 (m, 2H), 0.71-0.70 (m, 2H). |
| 316 | 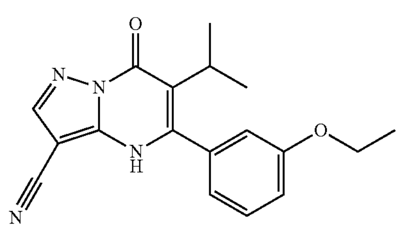 [SMILES: CCOc1cccc(-c2[nH]c3c(C#N)cnn3c(=O)c2C(C)C)c1] | A | 323.14 | A | 1.084 | 1H NMR (400 MHz, CD$_3$OD) δ 8.25 (s, 1H), 7.47 (t, J = 8.0 Hz, 1H), 7.15-7.13 (m, 1H), 7.07 (m, 2H), 4.16-4.10 (q, J = 6.8 Hz 2H), 2.80-2.76 (m, 1H), 1.44 (t, J = 6.8 Hz, 3H), 1.34 (d, J = 7.2 Hz, 6H). |
| 317 | 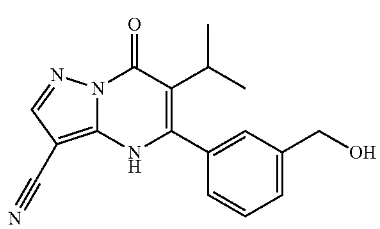 [SMILES: CC(C)c1c(-c2cccc(CO)c2)[nH]c2c(C#N)cnn2c1=O] | A | 309.1 | A | 0.888 | 1H NMR (400 MHz, CD$_3$OD) δ 8.26 (s, 1H), 7.59-7.58 (m, 2H), 7.53 (s, 1H), 7.43 (d, J = 6.8 Hz, 1H), 4.74 (s, 2H), 2.79-2.74 (m, 1H), 1.34 (d, J = 6.8 Hz, 6H). |
| 318 | 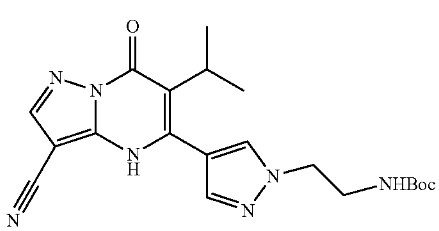 [SMILES: CC(C)c1c(-c2cnn(CCNC(=O)OC(C)(C)C)c2)[nH]c2c(C#N)cnn2c1=O] | A | 412.20 | E | 0.790 | 1H NMR (400 MHz, CD$_3$OD) δ 8.12 (s, 1H), 4.28 (t, J = 6.0 Hz, 2H), 3.50 (t, J = 6.0 Hz, 2H), 3.16-3.12 (m, 1H), 1.40-1.36 (m, 15H). |

| Ex | Structure | Syn. Met. | LCMS (ESI) m/z | LCMS Method | R$_T$ (min) | NMR |
|---|---|---|---|---|---|---|
| 319 | 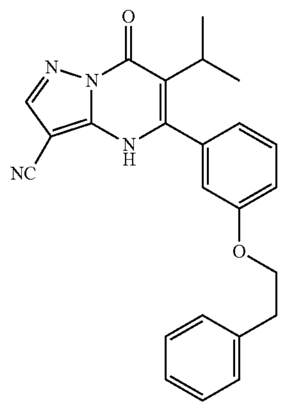 [SMILES: CC(C)c1c(-c2cccc(OCCc3ccccc3)c2)[nH]c2c(C#N)cnn2c1=O] | A | 399.2 | A | 1.223 | 1H NMR (400 MHz, DMSO-d$_6$) δ 13.42 (s, 1H), 8.40 (s, 1H), 7.46 (t, J = 8.0 Hz, 1H), 7.35-7.30 (m, 4H), 7.23 (m, 1H), 7.14 (m, 1H), 7.10 (s, 1H), 7.04 (m, 1H), 4.26 (t, J = 6.8 Hz, 2H), 3.07 (t, J = 6.4 Hz, 2H), 2.66-2.59 (m, 1H), 1.23 (d, J = 6.4 Hz, 6H). |
| 320 | 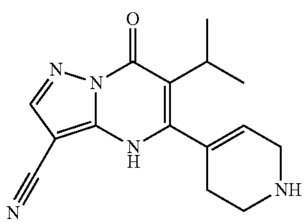 [SMILES: CC(C)c1c(C2=CCNCC2)[nH]c2c(C#N)cnn2c1=O] | A | 284.1 | 0-30CD | 1.355 | 1H NMR (400 MHz, DMSO-d$_6$) δ 13.11 (s, 1H), 9.19 (s, 1H), 8.38 (s, 1H), 5.99 (m, 1H), 3.75 (m, 2H), 3.27 (m, 2H), 3.01-2.94 (m, 1H), 2.54 (m, 2H), 1.28 (d, J = 7.2 Hz, 6H). |
| 321 | 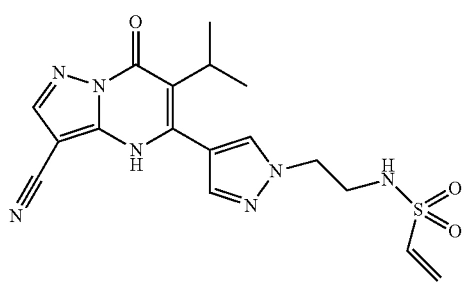 [SMILES: C=CS(=O)(=O)NCCn1cc(-c2[nH]c3c(C#N)cnn3c(=O)c2C(C)C)cn1] | A | 402.1 | E | 0.718 | 1H NMR (400 MHz, DMSO-d$_6$) δ 13.05 (s, 1H), 8.33 (s, 1H), 8.18 (s, 1H), 7.76 (s, 1H), 7.54 (s, H), 6.64 (dd, J = 16.4 Hz, 10 Hz, 1H), 6.02-5.92 (m, 2H), 4.27 (m, 2H), 3.28 (m, 2H) 2.99-2.96 (m, 1H), 1.26 (d, J = 6.8 Hz, 6H). |
| 322 | 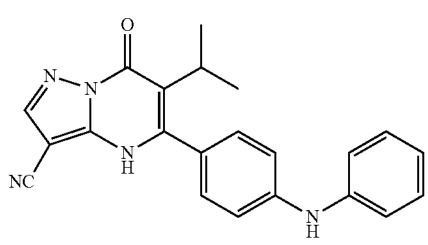 [SMILES: CC(C)c1c(-c2ccc(Nc3ccccc3)cc2)[nH]c2c(C#N)cnn2c1=O] | A | 370.2 | E | 0.884 | 1H NMR: (400 MHz, CD$_3$OD) δ 8.20 (s, 1H), 7.35-7.28 (m, 4H), 7.21-7.19 (m, 4H), 6.95 (t, J = 7.6 Hz, 1H), 2.92-2.97 (m, 1H), 1.37 (d, J = 6.4 Hz, 6H). |
| 323 | 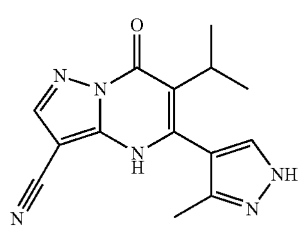 [SMILES: Cc1n[nH]cc1-c1[nH]c2c(C#N)cnn2c(=O)c1C(C)C] | A | 283.2 | A | 0.790 | $^1$H NMR (400 MHz, CD$_3$OD) δ 8.21 (s, 1H), 2.83-2.76 (m, 1H), 2.29 (s, 3H), 1.32 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 324 | 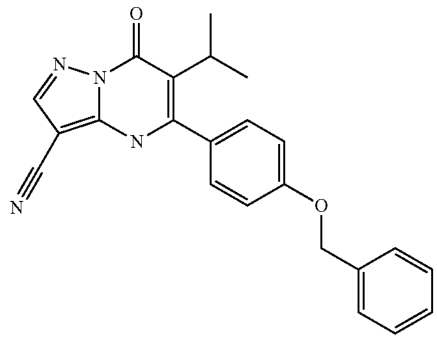 [SMILES: CC(C)c1c(-c2ccc(OCc3ccccc3)cc2)[nH]c2c(C#N)cnn2c1=O] | A | 385.3 | A | 1.208 | $^1$H NMR (400 MHz, CD$_3$OD) δ 8.24 (s, 1H), 7.53-7.32 (m, 8H), 7.21 (d, J = 8.4 Hz, 2H), 5.22 (s, 2H), 2.90-2.75 (m, 1H), 1.34 (d, J = 7.2 Hz, 6H). |
| 325 | 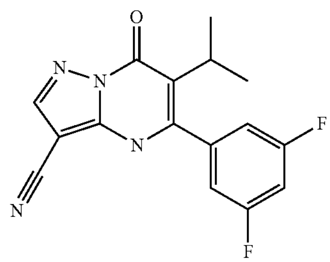 [SMILES: CC(C)c1c(-c2cc(F)cc(F)c2)[nH]c2c(C#N)cnn2c1=O] | A | 315.1 | A | 1.068 | $^1$H NMR (400 MHz, CD$_3$OD) δ 8.27 (s, 1H), 7.31-7.18 (m, 3H), 2.72-2.65 (m, 1H), 1.35 (d, J = 7.2 Hz, 6H). |
| 326 | 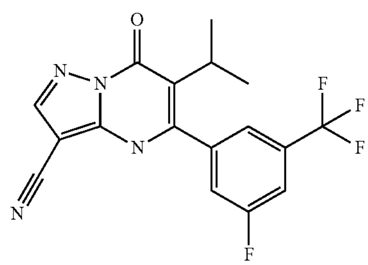 [SMILES: CC(C)c1c(-c2cc(F)cc(C(F)(F)F)c2)[nH]c2c(C#N)cnn2c1=O] | A | 365.1 | E | 0.875 | $^1$H NMR (400 MHz, CD$_3$OD) δ 8.28 (s, 1H), 7.81-7.74 (m, 2H), 7.69 (d, J = 8.4 Hz, 1H), 2.67-2.60 (m, 1H), 1.36 (d, J = 7.2 Hz, 6H). |
| 327 | 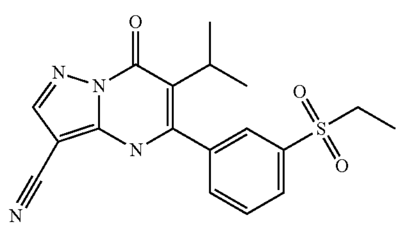 [SMILES: CCS(=O)(=O)c1cccc(-c2[nH]c3c(C#N)cnn3c(=O)c2C(C)C)c1] | A | 371.2 | A | 0.954 | $^1$H NMR (400 MHz, CD$_3$OD) δ 8.28 (s, 1H), 8.19-8.14 (m, 1H), 8.12 (s, 1H), 7.92-7.87 (m, 2H), 3.32-3.30 (m, 2H), 2.68-2.62 (m, 1H), 1.35 (d, J = 6.6 Hz, 6H), 1.28 (t, J = 7.2 Hz, 3H). |
| 328 | 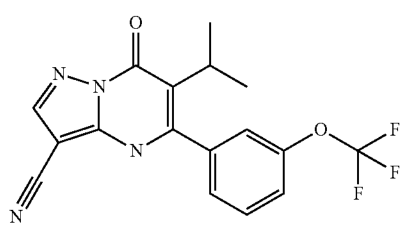 [SMILES: CC(C)c1c(-c2cccc(OC(F)(F)F)c2)[nH]c2c(C#N)cnn2c1=O] | A | 363.1 | A | 0.876 | $^1$H NMR (400 MHz, CD$_3$OD) δ 8.27 (s, 1H), 7.76-7.68 (m, 1H), 7.58-7.49 (m, 3H), 2.71-2.64 (m, 1H), 1.34 (d, J = 7.2 Hz, 6H). |
| 329 | 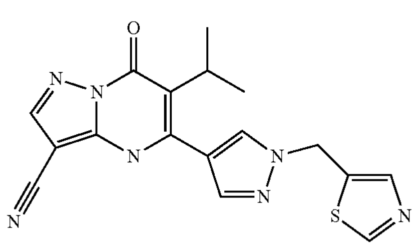 [SMILES: CC(C)c1c(-c2cnn(Cc3cncs3)c2)[nH]c2c(C#N)cnn2c1=O] | A | 366.1 | A | 0.879 | $^1$H NMR (400 MHz, DMSO-d$_6$) δ 13.11 (s, 1H), 9.09 (s, 1H), 8.37 (s, 1H), 8.30 (s, 1H), 7.97 (s, 1H), 7.81 (s, 1H), 5.76 (s, 2H), 2.98-2.91 (m, 1H), 1.29 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 330 | 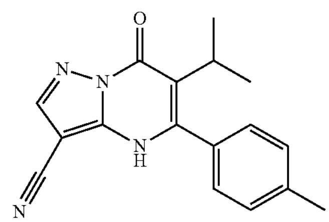 [SMILES: Cc1ccc(-c2[nH]c3c(C#N)cnn3c(=O)c2C(C)C)cc1] | A | 293.0 | C | 1.313 | $^1$H NMR (400 MHz, DMSO-d$_6$) δ 8.06 (s, 1H), 7.24-7.13 (m, 4H), 2.72 (m, 1H), 2.36 (s, 3H), 1.23 (d, J = 7.2 Hz, 6H) |
| 331 | 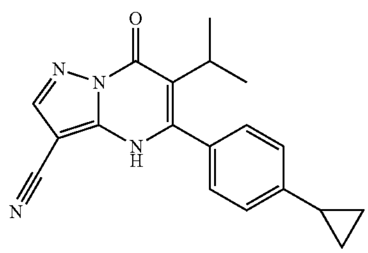 [SMILES: CC(C)c1c(-c2ccc(C3CC3)cc2)[nH]c2c(C#N)cnn2c1=O] | A | 319.2 | C | 1.380 | $^1$H NMR (400 MHz, DMSO-d$_6$) δ 13.36 (s, 1H), 8.35 (s, 1H), 7.35 (d, J = 8.0 Hz, 2H), 7.24 (d, J = 8.0 Hz, 2H), 2.52-2.50 (m, 1H), 2.03-1.99 (m, 1H), 1.23 (d, J = 6.8 Hz, 6H), 1.04-1.01 (m, 2H), 0.78-0.75 (m, 2H). |
| 332 | 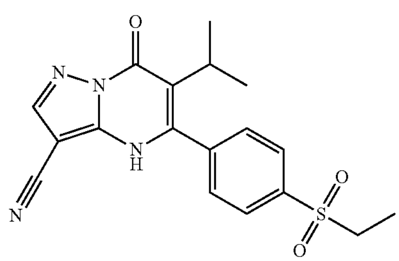 [SMILES: CCS(=O)(=O)c1ccc(-c2[nH]c3c(C#N)cnn3c(=O)c2C(C)C)cc1] | A | 371.1 | C | 1.152 | $^1$H NMR (400 MHz, DMSO-d$_6$) δ 13.47 (s, 1H), 8.42 (s, 1H), 8.08 (d, J = 8.0 Hz, 2H), 7.81 (d, J = 8.0 Hz, 2H), 3.42-3.35 (m, 2H), 2.52-2.50 (m, 1H), 1.23 (d, J = 6.8 Hz, 6H), 1.16 (t, J = 7.2 Hz, 3H). |
| 333 | 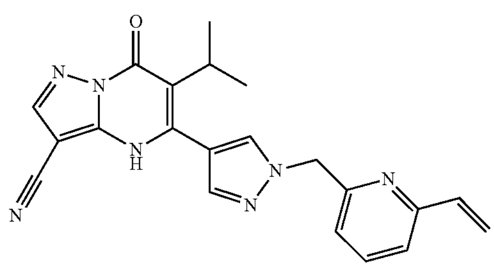 [SMILES: C=Cc1cccc(Cn2cc(-c3[nH]c4c(C#N)cnn4c(=O)c3C(C)C)cn2)n1] | A | 386.1 | C | 1.198 | $^1$H NMR (400 MHz, CD$_3$OD) δ 8.12 (d, J = 4.4 Hz, 2H), 7.77 (s, 1H), 7.74 (d, J = 7.6 Hz, 1H), 7.43 (d, J = 8.0 Hz, 1H), 7.04 (d, J = 7.6 Hz, 1H), 6.82 (dd, J = 17.2, 11.2 Hz, 1H), 6.23 (d, J = 16.4 Hz, 1H), 5.53 (s, 2H), 5.50 (dd, J = 11.2, 1.2 Hz, 1H), 3.18-3.12 (m, 1H), 1.38 (d, J = 7.2 Hz, 6H). |
| 334 | 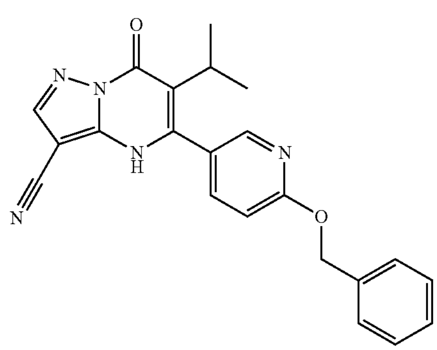 [SMILES: CC(C)c1c(-c2ccc(OCc3ccccc3)nc2)[nH]c2c(C#N)cnn2c1=O] | A | 386.1 | E | 0.912 | $^1$H NMR (400 MHz, DMSO-d$_6$) δ 13.39 (s, 1H), 8.41 (s, 1H), 8.33 (s, 1H), 7.87 (dd, J = 8.8, 2.0 Hz, 1H), 7.48 (m, 2H), 7.40-7.34 (m, 3H), 7.08 (d, J = 8.8 Hz, 1H), 5.44 (s, 2H), 2.62-2.58 (m, 1H), 1.25 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 335 | 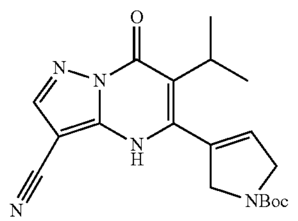 [SMILES: CC(C)c1c(C2=CCN(C(=O)OC(C)(C)C)C2)[nH]c2c(C#N)cnn2c1=O] | A | 313.9 | E | 0.841 | $^1$H NMR (400 MHz, CD$_3$OD) δ 8.11 (s, 1H), 5.97 (m, 1H), 4.404-4.327 (m, 4H), 3.05-3.00 (m, 1H), 1.55 (s, 9H), 1.38 (d, J = 6.8 Hz, 6H). |
| 336 | 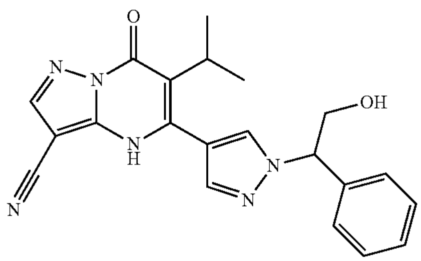 [SMILES: CC(C)c1c(-c2cnn(C(CO)c3ccccc3)c2)[nH]c2c(C#N)cnn2c1=O] | A | 388.8 | E | 0.767 | $^1$H NMR (400 MHz, DMSO-d$_6$) δ 13.08 (s, 1H), 8.34 (s, 1H), 8.31 (s, 1H), 7.78 (s, 1H), 7.39-7.27 (m, 5H), 5.78 (m, 1H), 5.20 (m, 1H), 4.25 (m, 1H), 3.95 (m, 1H), 2.99-2.95 (m, 1H), 1.29-1.26 (m, 6H). |
| 337 | 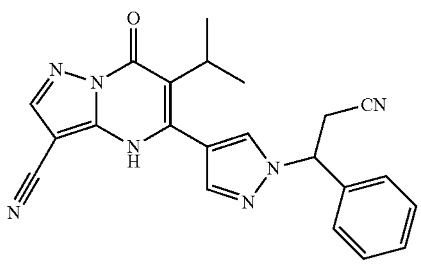 [SMILES: CC(C)c1c(-c2cnn(C(CC#N)c3ccccc3)c2)[nH]c2c(C#N)cnn2c1=O] | A | 398.1 | C | 1.267 | $^1$H NMR (400 MHz, CDCl$_3$) δ 13.16 (s, 1H), 8.36 (s, 1H), 7.87 (s, 1H), 7.46-7.38 (m, 5H), 6.08 (s, 1H), 3.73 (m, 1H), 3.58 (m, 1H), 2.65-2.62 (m, 1H), 1.30-1.27 (m, 6H). |
| 338 | 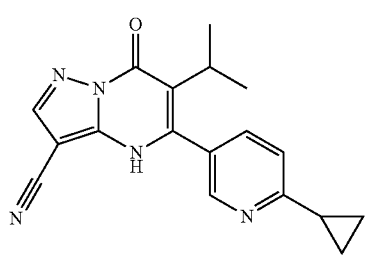 [SMILES: CC(C)c1c(-c2ccc(C3CC3)nc2)[nH]c2c(C#N)cnn2c1=O] | A | 320.1 | C | 1.120 | $^1$H NMR (400 MHz, DMSO-d$_6$) δ 13.43 (s, 1H), 8.51 (s, 1H), 8.39 (s, 1H), 7.78 (dd, J = 8.0, 2.0 Hz, 1H), 7.49 (d, J = 8.0 Hz, 1H), 2.61-2.56 (m, 1H), 2,23-2.20 (m, 1H), 1.23 (d, J = 6.4 Hz, 6H), 1.04-0.99 (m, 4H). |
| 339 | 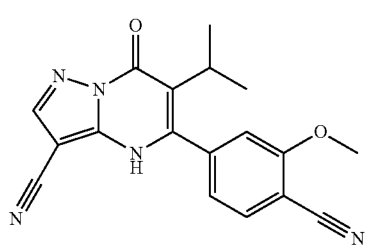 [SMILES: COc1cc(-c2[nH]c3c(C#N)cnn3c(=O)c2C(C)C)ccc1C#N] | A | 334.0 | C | 1.244 | $^1$H NMR (400 MHz, DMSO-d$_6$) δ 13.48 (s, 1H), 8.38 (s, 1H), 7.91 (d, J = 7.6 Hz, 1H), 7.42 (s, 1H), 7.21 (d, J = 7.6 Hz, 1H), 3.93 (s, 3H), 2.52-2.51 (m, 1H), 1.21 (d, J = 6.8 Hz, 6H) |
| 340 | 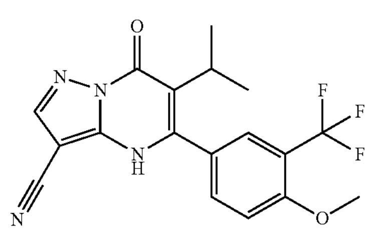 [SMILES: COc1ccc(-c2[nH]c3c(C#N)cnn3c(=O)c2C(C)C)cc1C(F)(F)F] | A | 377.0 | C | 1.364 | $^1$H NMR (400 MHz, DMSO-d$_6$) δ 13.30 (s, 1H), 8.38 (s, 1H), 7.77 (s, 1H), 7.75 (d, J = 8.8 Hz, 1H), 7.42 (d, J = 8.8 Hz, 1H), 3.93 (s, 1H), 2.56-2.53 (m, 1H), 1.20 (d, J = 6.8 Hz, 6H) |

| Ex | Structure | Syn. Met. | LCMS (ESI) m/z | LCMS Method | R$_T$ (min) | NMR |
|---|---|---|---|---|---|---|
| 341 | 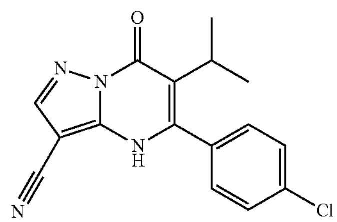 [SMILES: CC(C)c1c(-c2ccc(Cl)cc2)[nH]c2c(C#N)cnn2c1=O] | A | 313.0 | C | 1.328 | $^1$H NMR (400 MHz, DMSO-d$_6$) δ 13.39 (s, 1H), 8.38 (s, 1H), 7.62 (d, J = 8.4 Hz, 2H), 7.52 (d, J = 8.4 Hz, 2H), 2.54-2.51 (m, 1H), 1.19 (d, J = 6.8 Hz, 6H) |
| 342 | 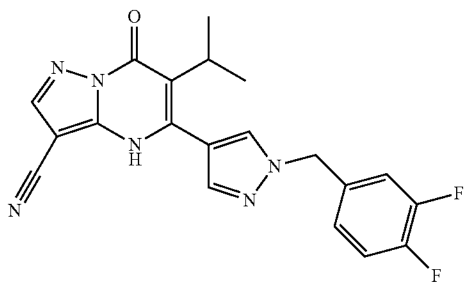 [SMILES: CC(C)c1c(-c2cnn(Cc3ccc(F)c(F)c3)c2)[nH]c2c(C#N)cnn2c1=O] | A | 394.9 | E | 0.822 | $^1$H NMR (400 MHz, DMSO-d$_6$) δ 13.05 (s, 1H), 8.34 (s, 1H), 8.29 (s, 1H), 7.77 (s, 1H), 7.47-7.35 (m, 2H), 7.18 (m, 1H), 5.41 (s, 2H), 2.96-2.89 (m, 1H), 1.26 (d, J = 6.8 Hz, 6H). |
| 343 | 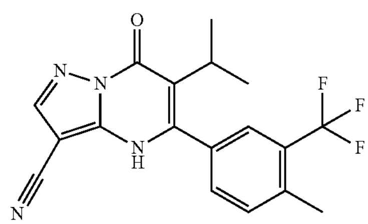 [SMILES: Cc1ccc(-c2[nH]c3c(C#N)cnn3c(=O)c2C(C)C)cc1C(F)(F)F] | A | 361.1 | E | 0.908 | $^1$H NMR (400 MHz, DMSO-d$_6$) δ 13.35 (s, 1H), 8.39 (s, 1H), 7.81 (s, 1H), 7.67 (d, J = 8.4 Hz, 1H), 7.61 (d, J = 8.0 Hz, 1H), 2.51 (s, 3H), 2.47-2.48 (m, 1H), 1.19 (d, J = 6.8 Hz, 6H). |
| 344 | 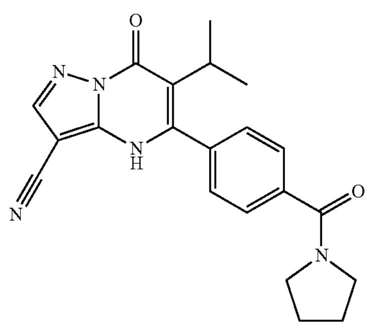 [SMILES: CC(C)c1c(-c2ccc(C(=O)N3CCCC3)cc2)[nH]c2c(C#N)cnn2c1=O] | A | 376.1 | E | 0.763 | $^1$H NMR (400 MHz, DMSO-d$_6$) δ 13.41 (s, 1H), 8.37 (s, 1H), 7.65 (d, J = 8.0 Hz, 2H), 7.53 (d, J = 8.0 Hz, 2H), 3.47 (t, J = 6.4 Hz, 2H), 3.39 (t, J = 6.4 Hz, 2H), 2.58-2.55 (m, 1H), 1.88-1.80 (m, 4H), 1.21 (d, J = 6.8 Hz, 6H). |
| 345 | 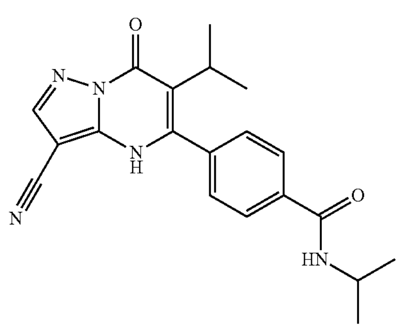 [SMILES: CC(C)NC(=O)c1ccc(-c2[nH]c3c(C#N)cnn3c(=O)c2C(C)C)cc1] | A | 364.1 | E | 0.764 | $^1$H NMR (400 MHz, DMSO-d$_6$) δ 13.45 (s, 1H), 8.38 (s, 1H), 7.96 (d, J = 8.0 Hz, 2H), 7.60 (d, J = 8.4 Hz, 2H), 4.14-4.05 (m, 1H), 2.53-2.51 (m, 1H), 1.19 (d, J = 6.8 Hz, 6H), 1.16 (d, J = 6.4 Hz, 6H). |

| Ex | Structure | Syn. Met. | LCMS (ESI) m/z | LCMS Method | R_T (min) | NMR |
|---|---|---|---|---|---|---|
| 346 | 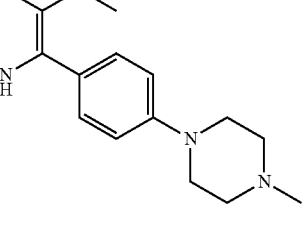 | A | 377.1 | E | 0.688 | $^1$H NMR (400 MHz, DMSO-d$_6$) δ 13.25 (s, 1H), 8.36 (s, 1H), 7.36 (d, J = 8.4 Hz, 2H), 7.13 (d, J = 8.4 Hz, 2H), 3.95 (m, 4H), 3.11 (m, 4H), 2.82 (s, 3H), 2.70-2.66 (m, 1H), 1.21 (d, J = 6.8 Hz, 6H). |
| 347 | 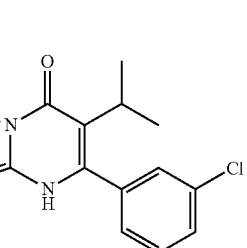 | A | 338.0 | E | 0.824 | $^1$H NMR (400 MHz, DMSO-d$_6$) δ 13.43 (s, 1H), 8.41 (s, 1H), 8.26 (s, 1H), 8.02, 8.04 (2s, 2H), 2.52-2.47 (m, 1H), 1.20 (d, J = 6.8 Hz, 6H). |
| 348 | 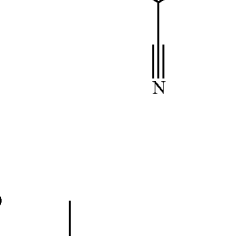 | A | 386.1 | C | 1.133 | H NMR (400 MHz, DMSO-d$_6$) δ 13.41 (s, 1H), 8.36 (s, 1H), 7.68-7.64 (m, 1H), 7.52 (m, 2H), 7.43-7.39 (m, 2H), 4.23 (d, J = 6.0 Hz, 2H), 2.87 (s, 3H), 2.58-2.55 (m, 1H), 1.20 (d, J = 6.8 Hz, 6H). |
| 349 | 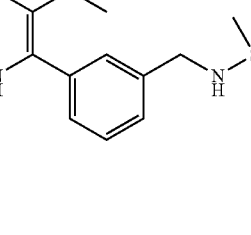 | A | 345.1 | C | 1.185 | $^1$H NMR (400 MHz, DMSO-d$_6$) δ 13.47 (s, 1H), 8.38 (s, 1H), 7.98 (d, J = 8.0 Hz, 1H), 7.92 (s, 1H), 7.76 (s, 1H), 7.58 (t, J = 8.0 Hz, 1H), 7.39 (d, J = 7.6 Hz, 1H), 6.79 (d, J = 2 Hz, 1H), 2.66-2.62 (m, 1H), 1.22 (d, J = 7.8 Hz, 6H). |
| 350 | 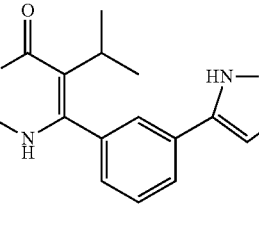 | A | 357.1 | C | 1.106 | $^1$H NMR (400 MHz, DMSO-d$_6$) δ 13.49 (s, 1H), 8.39 (s, 1H), 8.10 (d, J = 8.0 Hz, 2H), 7.78 (d, J = 8.0 Hz, 2H), 3.33 (s, 3H), 2.52-2.48 (m, 1H), 1.21 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 351 | 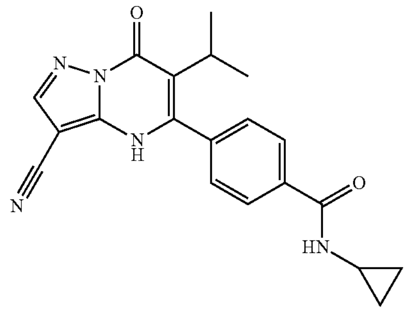 [SMILES: CC(C)c1c(-c2ccc(C(=O)NC3CC3)cc2)[nH]c2c(C#N)cnn2c1=O] | A | 362.1 | E | 0.762 | $^1$H NMR (400 MHz, DMSO-d$_6$) δ 13.45 (s, 1H), 8.55 (s, 1H), 8.36 (s, 1H), 7.92 (d, J = 8.0 Hz, 2H), 7.55 (d, J = 7.6 Hz, 2H), 2.88-2.83 (m, 1H), 1.19 (d, J = 6.8 Hz, 6H), 0.58-0.57 (m, 2H), 0.57-0.56 (m, 2H). |
| 352 | 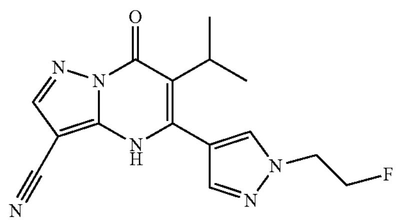 [SMILES: CC(C)c1c(-c2cnn(CCF)c2)[nH]c2c(C#N)cnn2c1=O] | A | 315.1 | C | 1.072 | $^1$H NMR (400 MHz, DMSO-d$_6$) δ 13.17 (s, 1H), 8.32 (s, 1H), 8.17 (s, 1H), 7.77 (s, 1H), 4.88-4.74 (dt, J = 51.6, 4.4 Hz, 2H), 4.57-4.49 (dt, J = 28.0, 4.4 Hz, 2H), 2.98-2.91 (m, 1H), 1.26 (d, J = 6.8 Hz, 6H). |
| 353 | 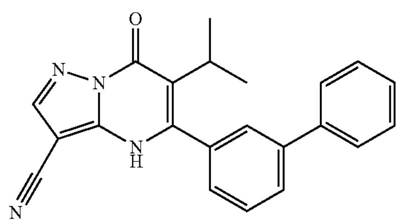 [SMILES: CC(C)c1c(-c2cccc(-c3ccccc3)c2)[nH]c2c(C#N)cnn2c1=O] | A | 355.1 | C | 1.424 | $^1$H NMR (400 MHz, DMSO-d$_6$) δ 13.48 (s, 1H), 8.39 (s, 1H), 7.85-7.64 (m, 5H), 7.51-7.39 (m, 4H), 2.68-2.65 (m, 1H), 1.23 (d, J = 6.8 Hz, 6H). |
| 354 | 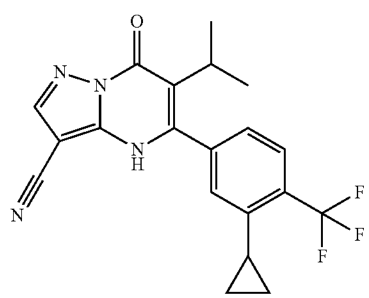 [SMILES: CC(C)c1c(-c2ccc(C(F)(F)F)c(C3CC3)c2)[nH]c2c(C#N)cnn2c1=O] | A | 387.1 | E | 0.926 | $^1$H NMR (400 MHz, DMSO-d$_6$) δ 13.39 (s, 1H), 8.38 (s, 1H), 7.83 (d, J = 8.4 Hz, 1H), 7.46 (d, J = 8.0 Hz, 1H), 7.26 (s, 1H), 2.48-2.41 (m, 1H), 2.16-2.17 (m, 1H), 1.19 (d, J = 6.8 Hz, 6H), 1.10-1.07 (m, 2H), 1.07-0.85 (m, 2H). |
| 355 | 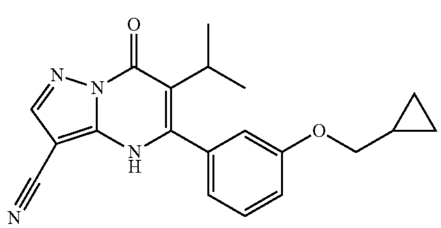 [SMILES: CC(C)c1c(-c2cccc(OCC3CC3)c2)[nH]c2c(C#N)cnn2c1=O] | A | 349.1 | E | 0.878 | $^1$H NMR (400 MHz, DMSO-d$_6$) δ 13.43 (s, 1H), 8.37 (s, 1H), 7.46-7.42 (m, 1H), 7.10-7.01 (m, 1H), 3.87 (d, J = 6.8 Hz, 2H), 2.64-2.62 (m, 1H), 1.23 (d, J = 7.2 Hz, 6H), 0.60-0.56 (m, 2H), 0.35-0.31 (m, 2H). |
| 356 | 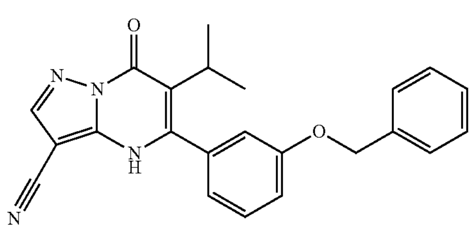 [SMILES: CC(C)c1c(-c2cccc(OCc3ccccc3)c2)[nH]c2c(C#N)cnn2c1=O] | A | 385.1 | E | 0.903 | $^1$H NMR (400 MHz, DMSO-d$_6$) δ 13.42 (s, 1H), 8.36 (s, 1H), 7.46-7.05 (m, 9H), 5.15 (s, 2H), 2.58-2.52 (m, 1H), 1.17 (d, J = 6.8 Hz, 6H) |

| Ex | Structure | Syn. Met. | LCMS (ESI) m/z | LCMS Method | R$_T$ (min) | NMR |
|---|---|---|---|---|---|---|
| 357 | 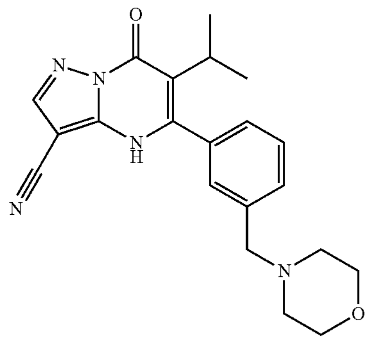 [SMILES: CC(C)c1c(-c2cccc(CN3CCOCC3)c2)[nH]c2c(C#N)cnn2c1=O] | A | 378.1 | E | 0.640 | $^1$H NMR (400 MHz, DMSO-d$_6$) δ 13.47 (s, 1H), 11.92 (s, 1H), 8.43 (s, 1H), 7.89-7.60 (m, 4H), 4.44 (s, 2H), 3.97-3.88 (m, 4H), 3.28-3.11 (m, 4H), 2.58-2.54 (m, 1H), 1.23 (d, J = 6.8 Hz, 6H). |
| 358 | 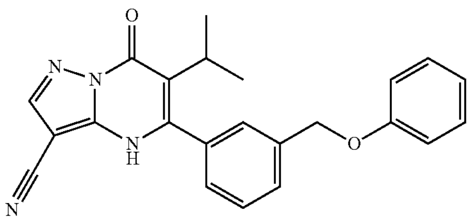 [SMILES: CC(C)c1c(-c2cccc(COc3ccccc3)c2)[nH]c2c(C#N)cnn2c1=O] | A | 385.1 | E | 0.905 | $^1$H NMR (400 MHz, DMSO-d$_6$) δ 13.45 (s, 1H), 8.37 (s, 1H), 7.62-6.92 (m, 9H) 5.18 (m, 2H), 2.56-2.52 (m, 1H), 1.17 (d, J = 7.2 Hz, 6H) |
| 359 | 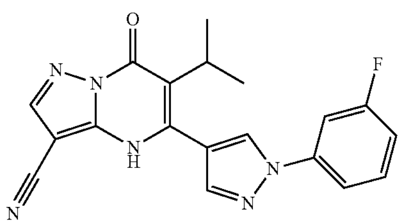 [SMILES: CC(C)c1c(-c2cnn(-c3cccc(F)c3)c2)[nH]c2c(C#N)cnn2c1=O] | A | 363.1 | C | 1.324 | $^1$H NMR (400 MHz, DMSO-d$_6$) δ 13.25 (s, 1H), 8.97 (s, 1H), 8.38 (s, 1H), 8.05 (s, 1H), 7.82-7.78 (m, 1H), 7.62-7.58 (m, 1H), 7.24-7.20 (m, 1H), 2.98-2.91 (m, 1H), 1.28 (d, J = 6.8 Hz, 6H). |
| 360 | 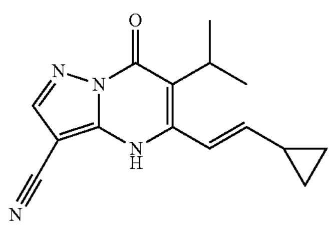 [SMILES: CC(C)c1c(/C=C/C2CC2)[nH]c2c(C#N)cnn2c1=O] | A | 269.1 | C | 1.242 | $^1$H NMR (400 MHz, DMSO-d$_6$) δ 12.47 (s, 1H), 8.29 (s, 1H), 6.69 (d, J = 15.6 Hz, 1H), 6.06 (dd, J = 15.6, 9.6 Hz, 1H), 3.19-3.13 (m, 1H), 1.77-1.73 (m, 1H), 1.25 (d, J = 7.6 Hz, 6H), 0.93-0.90 (m, 2H), 0.68-0.65 (m, 2H). |
| 361 | 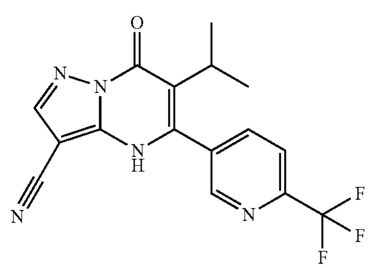 [SMILES: CC(C)c1c(-c2ccc(C(F)(F)F)nc2)[nH]c2c(C#N)cnn2c1=O] | A | 348.1 | C | 1.242 | $^1$H NMR (400 MHz, DMSO-d$_6$) δ 13.49 (s, 1H), 8.93 (s, 1H), 8.42 (s, 1H), 8.27 (d, J = 8.0 Hz, 1H), 8.13 (d, J = 8.0 Hz, 1H), 2.48-2.47 (m, 1H), 1.21 (d, J = 7.2 Hz, 6H). |
| 362 | 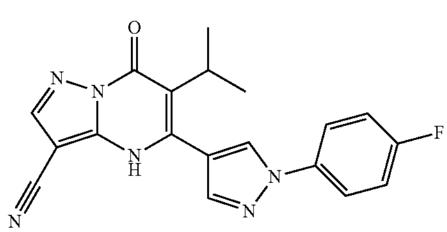 [SMILES: CC(C)c1c(-c2cnn(-c3ccc(F)cc3)c2)[nH]c2c(C#N)cnn2c1=O] | A | 363.1 | C | 1.303 | $^1$H NMR (400 MHz, DMSO-d$_6$) δ 13.25 (s, 1H), 8.89 (s, 1H), 8.38 (s, 1H), 8.03 (s, 1H), 7.98-7.95 (m, 2H), 7.44-7.40 (m, 2H), 3.02-2.97 (m, 1H), 1.32 (d, J = 6.8 Hz, 6H). |

-continued

| Ex | Structure | Syn. Met. | LCMS (ESI) m/z | LCMS Method | $R_T$ (min) | NMR |
|---|---|---|---|---|---|---|
| 363 | 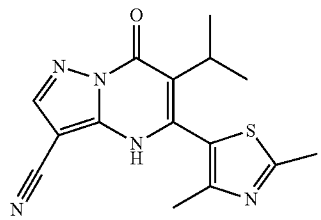 [SMILES: Cc1nc(C)c(-c2[nH]c3c(C#N)cnn3c(=O)c2C(C)C)s1] | A | 314.0 | C | 1.145 | $^1$H NMR (400 MHz, DMSO d$_6$) δ 13.46 (s, 1H), 8.34 (s, 1H), 2.67 (s, 3H), 2.62-2.59 (m, 1H), 2.22 (s, 3H), 1.21 (d, J = 6.4 Hz, 6H). |
| 364 | 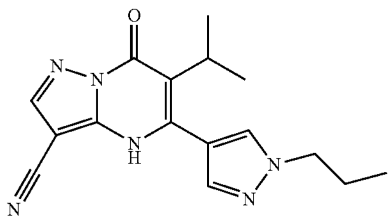 [SMILES: CCCn1cc(-c2[nH]c3c(C#N)cnn3c(=O)c2C(C)C)cn1] | A | 311.0 | E | 0.774 | $^1$H NMR (400 MHz, DMSO-d$_6$) δ 13.07 (s, 1H), 8.36 (s, 1H), 8.16 (s, 1H), 7.74 (s, 1H), 4.17 (t, J = 6.8 Hz, 2H) 2.99-2.96 (m, 1H), 1.81-1.82 (m, 2H), 1.29 (d, J = 6.8 Hz, 6H), 0.88 (t, J = 7.6 Hz, 3H) |
| 365 | 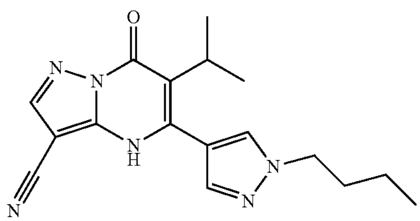 [SMILES: CCCCn1cc(-c2[nH]c3c(C#N)cnn3c(=O)c2C(C)C)cn1] | A | 324.9 | E | 0.812 | $^1$H NMR (400 MHz, DMSO-d$_6$) δ 8.23 (s, 1H), 8.06 (s, 1H), 7.78 (s, 1H), 4.28 (t, J = 6.4 Hz, 2H), 3.12 (m, 1H), 1.98-1.89 (m, 2H), 1.40-1.39 (m, 8H),. 1.00 (t, J = 7.2 Hz, 3H). |
| 366 | 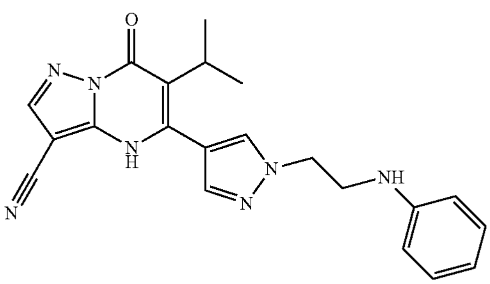 [SMILES: CC(C)c1c(-c2cnn(CCNc3ccccc3)c2)[nH]c2c(C#N)cnn2c1=O] | A | 388.1 | C | 1.235 | $^1$H NMR (400 MHz, DMSO-d$_6$) δ 13.07 (s, 1H), 8.34 (s, 1H), 8.14 (s, 1H), 7.79 (s, 1H), 7.10-7.06 (m, 2H), 6.59-6.53 (m, 3H), 5.75 (s, 1H), 4.37 (t, J = 6.0 Hz, 2H). 3.51 (m, 2H), 2.99-2.93 (m, 1H), 1.27 (d, J = 7.2 Hz, 6H). |
| 367 | 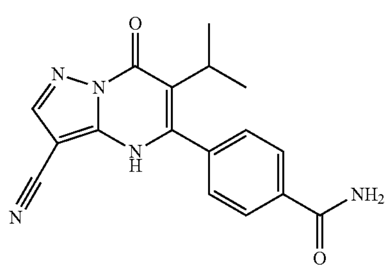 [SMILES: CC(C)c1c(-c2ccc(C(N)=O)cc2)[nH]c2c(C#N)cnn2c1=O] | A | 322.0 | E | 1.036 | $^1$H NMR (400 MHz, DMSO-d$_6$) δ 13.48 (s, 1H), 8.40 (s, 1H), 8.14 (s, 1H), 8.04 (d, J = 8.0 Hz, 2H), 7.60 (d, J = 8.0 Hz, 2H), 7.55 (s, 1H), 2.58-2.50 (m, 1H), 1.23 (d, J = 6.8 Hz, 6H). |
| 368 | 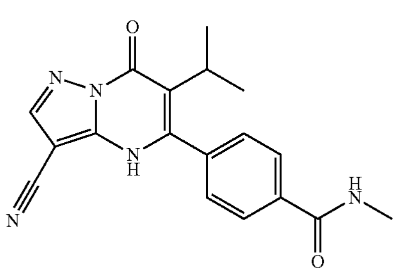 [SMILES: CNC(=O)c1ccc(-c2[nH]c3c(C#N)cnn3c(=O)c2C(C)C)cc1] | A | 336.1 | E | 1.080 | $^1$H NMR (400 MHz, DMSO-d$_6$) δ 13.48 (s, 1H), 8.60 (s, 1H), 8.40 (s, 1H), 7.98 (d, J = 8.0 Hz, 2H), 7.60 (d, J = 8.0 Hz, 2H), 2.82 (d, J = 4.4 Hz, 2H), 2.57-2.54 (m, 1H), 1.22 (d, J = 6.8 Hz, 6H). |

| Ex | Structure | Syn. Met. | LCMS (ESI) m/z | LCMS Method | R$_T$ (min) | NMR |
|---|---|---|---|---|---|---|
| 369 | 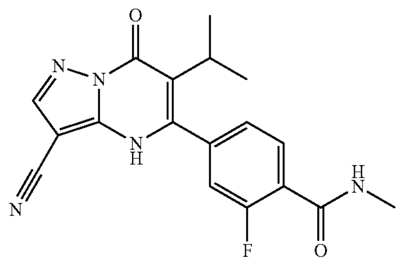 [SMILES: CNC(=O)c1ccc(-c2[nH]c3c(C#N)cnn3c(=O)c2C(C)C)cc1F] | A | 354.1 | E | 0.737 | $^1$H NMR (400 MHz, DMSO-d$_6$) δ 13.52 (s, 1H), 8.42 (s, 1H), 7.77 (t, J = 7.6 Hz, 1H), 7.55 (d, J = 10.4 Hz, 1H), 7.42 (d, J = 8.0 Hz, 1H), 2.81 (d, J = 4.4 Hz, 3H), 2.65-2.60 (m, 1H), 1.24 (d, J = 6.8 Hz, 6H). |
| 370 | 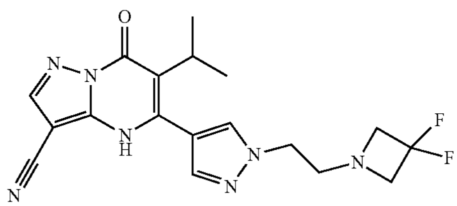 [SMILES: CC(C)c1c(-c2cnn(CCN3CC(F)(F)C3)c2)[nH]c2c(C#N)cnn2c1=O] | A | 388.1 | C | 0.947 | $^1$H NMR (400 MHz, DMSO-d$_6$) δ 8.26 (s, 1H), 8.20 (s, 1H), 7.91 (s, 1H), 4.88-4.83 (m, 4H), 4.71 (m, 2H), 4.03-3.99 (m, 2H), 3.14-3.04 (m, 1H), 1.39 (d, J = 6.4 Hz, 6H). |
| 371 | 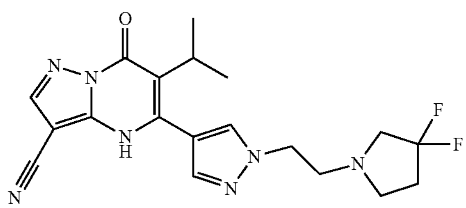 [SMILES: CC(C)c1c(-c2cnn(CCN3CCC(F)(F)C3)c2)[nH]c2c(C#N)cnn2c1=O] | A | 402.1 | C | 0.958 | $^1$H NMR (400 MHz, DMSO-d$_6$) δ 8.28 (s, 1H), 8.12 (s, 1H), 7.72 (s, 1H), 4.32 (t, J = 6.0 Hz, 2H). 2.96-2.93 (m, 1H), 2.92-2.89 (m, 4H), 2.75 (t, J = 6.8 Hz, 2H). 2.23-2.17 (m, 2H), 1.29 (d, J = 7.2 Hz, 6H). |
| 372 | 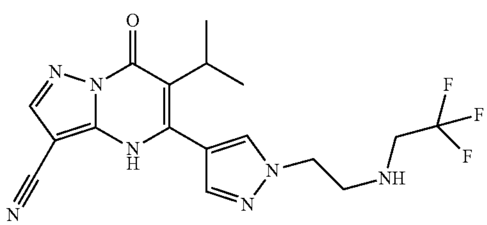 [SMILES: CC(C)c1c(-c2cnn(CCNCC(F)(F)F)c2)[nH]c2c(C#N)cnn2c1=O] | A | 394.1 | C | 1.057 | $^1$H NMR (400 MHz, DMSO-d$_6$) δ 8.26 (s, 1H), 8.19 (s, 1H), 7.92 (s, 1H), 4.71 (m 2H). 4.20-4.14 (m, 2H), 3.78 (m, 2H), 3.12-3.05 (m, 1H), 1.40 (d, J = 7.2 Hz, 6H). |
| 373 | 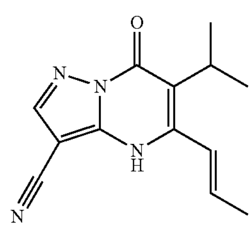 [SMILES: C/C=C/c1[nH]c2c(C#N)cnn2c(=O)c1C(C)C] | A | 242.8 | E | 0.753 | $^1$H NMR (400 MHz, CD$_3$OD) δ 8.18 (s, 1H), 7.71 (s, 1H), 6.70 (m, 1H), 6.63-6.56 (m, 1H), 3.29-3.22 (m, 1H), 2.02 (d, J = 5.6 Hz, 1H), 1.39 (d, J = 7.2 Hz, 6H). |
| 374 | 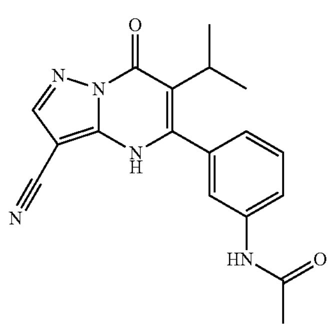 [SMILES: CC(=O)Nc1cccc(-c2[nH]c3c(C#N)cnn3c(=O)c2C(C)C)c1] | A | 336.1 | E | 0.740 | $^1$H NMR (400 MHz, CD$_3$OD) δ 8.24 (s, 1H), 7.82 (s, 1H), 7.69 (d, J = 8.4 Hz, 1H), 7.54-7.49 (m, 1H), 7.23 (d, J = 7.6 Hz, 1H), 2.84-2.77 (m, 1H), 2.18 (s, 3H), 1.35 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 375 | 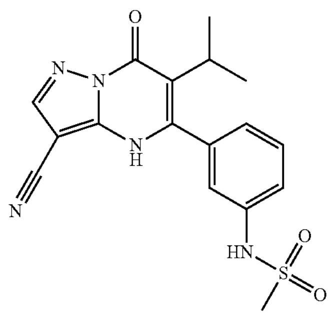 [SMILES: CC(C)c1c(-c2cccc(NS(C)(=O)=O)c2)[nH]c2c(C#N)cnn2c1=O] | A | 372.0 | E | 0.737 | $^1$H NMR (400 MHz, CD$_3$OD) δ 8.21 (s, 1H), 7.55-7.50 (m, 1H), 7.41 (d, J = 8.0 Hz, 1H), 7.37 (s, 1H), 7.25 (d, J = 7.6 Hz, 1H), 3.04 (s., 3H), 2.81-2.75 (m, 1H), 1.34 (d, J = 6.8 Hz, 6H). |
| 376 | 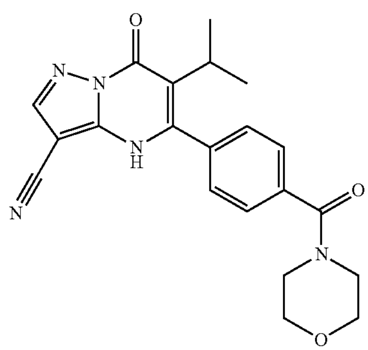 [SMILES: CC(C)c1c(-c2ccc(C(=O)N3CCOCC3)cc2)[nH]c2c(C#N)cnn2c1=O] | A | 392.1 | A | 1.063 | $^1$H NMR (400 MHz, CD$_3$OD) δ 8.25 (s, 1H), 7.66-7.60 (m, 4H), 3.81-3.76 (m, 4H), 3.68-3.62 (m, 2H), 3.51-3.48 (m, 2H), 2.74-2.68 (m, 1H), 1.32 (d, J = 7.2 Hz, 6H). |
| 377 | 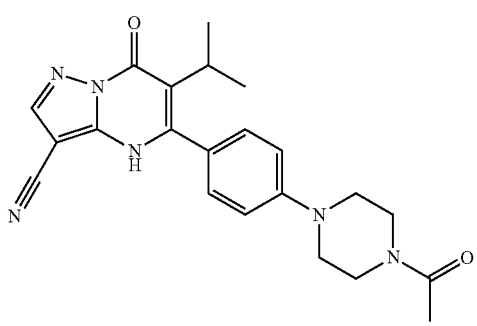 [SMILES: CC(=O)N1CCN(c2ccc(-c3[nH]c4c(C#N)cnn4c(=O)c3C(C)C)cc2)CC1] | A | 405.2 | A | 0.975 | $^1$H NMR (400 MHz, CD$_3$OD) δ 8.26 (s, 1H), 7.57 (d, J = 8.8 Hz, 2H), 7.48 (d, J = 8.0 Hz, 2H), 3.93-3.89 (m, 4H), 3.60-3.57 (m, 2H), 3.54-3.50 (m, 2H), 2.83-2.75 (m, 1H), 2.22 (s, 3H), 1.34 (d, J = 6.4 Hz, 6H). |
| 378 | 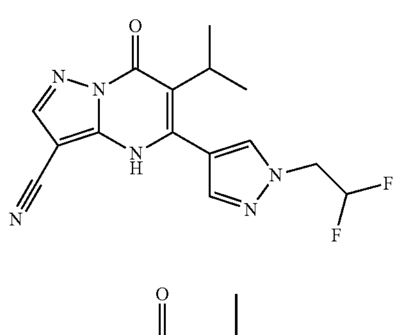 | A | 332.9 | A | 1.049 | $^1$H NMR (400 MHz, CD$_3$OD) δ 8.18 (s., 1H), 8.07 (s, 1H), 7.82 (s, 1H), 6.28 (tt, J = 55.2 Hz, J = 4.0 Hz, 1H), 4.70 (td, J = 14 Hz, J = 3.6 Hz, 2H), 3.14-3.06 (m, 1H), 1.40 (d, J = 7.2 Hz, 6H) |
| 379 | 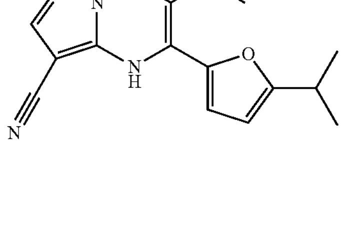 | A | 311.1 | E | 0.882 | $^1$H NMR (400 MHz, CD$_3$OD) δ 8.25 (s, 1H), 6.95 (d, J = 2.8 Hz, 2H), 6.36 (d, J = 3.2 Hz, 2H), 3.33-3.25 (m, 1H), 3.13-3.08 (m, 1H), 1.43 (d, J = 6.8 Hz, 6H), 1.36 (d, J = 6.8 Hz, 6H). |

-continued

| Ex | Structure | Syn. Met. | LCMS (ESI) m/z | LCMS Method | R$_T$ (min) | NMR |
|---|---|---|---|---|---|---|
| 380 | 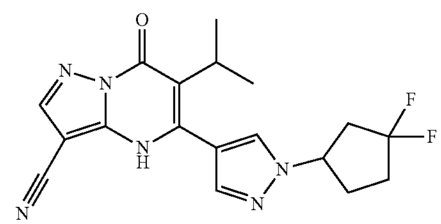 [SMILES: CC(C)c1c(-c2cnn(C3CCC(F)(F)C3)c2)[nH]c2c(C#N)cnn2c1=O] | A | 373.1 | A | 1.024 | $^1$H NMR (400 MHz, CD$_3$OD) δ 8.23 (s, 1H), 8.14 (s, 1H), 7.82 (s, 1H), 5.11-5.03 (m, 1H), 3.10-3.06 (m, 1H), 2.80-2.73 (m., 2H), 2.50-2.47 (m., 2H), 2.46-2.32 (m, 2H), 1.40 (d, J = 6.8 Hz, 6H). |
| 381 | 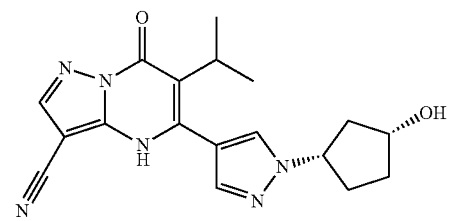 [SMILES: CC(C)c1c(-c2cnn([C@H]3CC[C@@H](O)C3)c2)[nH]c2c(C#N)cnn2c1=O] | A | 353.1 | A | 0.875 | $^1$H NMR (400 MHz, CD$_3$OD) δ 8.20 (s, 1H), 8.15 (s, 1H), 7.77 (s, 1H), 4.43-4.37 (m, 1H), 3.16-3.11 (m, 1H), 2.57-2.53 (m., 1H), 2.33-2.31 (m., 1H), 2.25-2.23 (m, 1H), 2.10-2.08 (m, 1H), 1.97-1.93 (m, 2H), 1.41 (d, J = 7.2 Hz, 6H). |
| 382 | 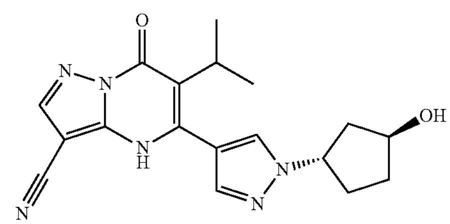 [SMILES: CC(C)c1c(-c2cnn([C@H]3CC[C@H](O)C3)c2)[nH]c2c(C#N)cnn2c1=O] | A | 353.1 | A | 0.855 | $^1$H NMR (400 MHz, CD$_3$OD) δ 8.09 (s, 1H), 7.95 (s, 1H), 7.69 (s, 1H), 5.07-5.01 (m, 1H), 4.55-4.52 (m, 1H), 3.22-3.17 (m, 1H), 2.45-2.42 (m, 1H), 2.32-2.24 (m, 3H), 2.09-2.06 (m, 1H), 1.77-1.75 (m, 1H), 1.41 (d, J = 7.2 Hz, 6H). |
| 383 | 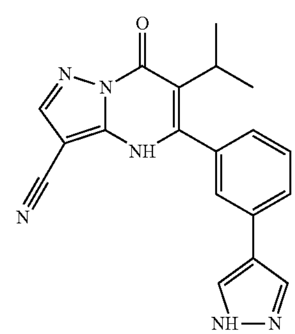 [SMILES: CC(C)c1c(-c2cccc(-c3cn[nH]c3)c2)[nH]c2c(C#N)cnn2c1=O] | A | 345.1 | A | 0.962 | $^1$H NMR (400 MHz, DMSO-d$_6$) δ 13.53 (s, 1H),. 8.42 (s, 1H), 8.17 (s, 2H), 7.82 (d, J = 8.0 Hz, 1H), 7.78 (s, 1H), 7.54 (t, J = 8.0 Hz, 1H), 7.30 (d, J = 7.6 Hz, 1H), 2.70-2.64 (m, 1H), 1.25 (d, J = 7.2 Hz, 6H). |
| 384 | 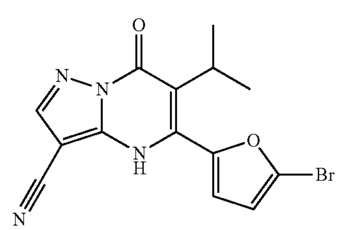 [SMILES: CC(C)c1c(-c2ccc(Br)o2)[nH]c2c(C#N)cnn2c1=O] | A | 347.0 | A | 1.049 | $^1$H NMR (400 MHz, CD$_3$OD) δ 8.19 (s, 1H), 6.83 (d, J = 3.6 Hz, 1H), 6.61 (d, J = 3.6 Hz, 1H), 3.19-3.16 (m, 1H), 1.38 (d, J = 6.8 Hz, 6H). |

| Ex | Structure | Syn. Met. | LCMS (ESI) m/z | LCMS Method | $R_T$ (min) | NMR |
|---|---|---|---|---|---|---|
| 385 | 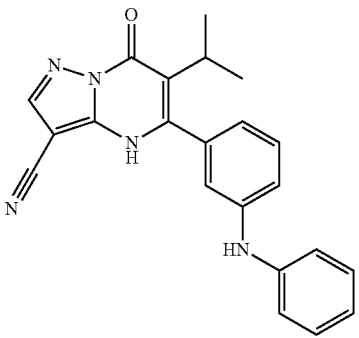 [SMILES: CC(C)c1c(-c2cccc(Nc3ccccc3)c2)[nH]c2c(C#N)cnn2c1=O] | A | 370.1 | A | 1.146 | ¹H NMR (400 MHz, CD₃OD) δ 8.24 (s, 1H), 7.42-7.38 (m, 1H), 7.30-7.24 (m, 3H), 7.19-7.16 (m, 3H), 6.95-6.91 (m, 2H), 2.93-2.86 (m, 1H), 1.36 (d, J = 6.8 Hz, 6H). |
| 386 | 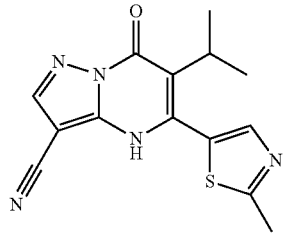 [SMILES: Cc1ncc(-c2[nH]c3c(C#N)cnn3c(=O)c2C(C)C)s1] | A | 300.0 | A | 0.908 | ¹H NMR (400 MHz, CD₃OD) δ 8.26 (s, 1H), 7.90 (s, 1H), 2.94-2.86 (m, 1H), 2.83 (s, 3H), 1.37 (d, J = 6.8 Hz, 6H). |
| 387 | 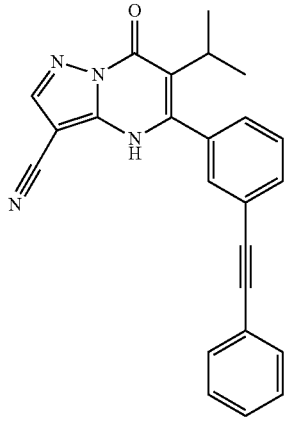 [SMILES: CC(C)c1c(-c2cccc(C#Cc3ccccc3)c2)[nH]c2c(C#N)cnn2c1=O] | A | 379.1 | A | 1.245 | ¹H NMR (400 MHz, CD₃OD) δ 8.33 (s, 1H), 7.67 (d, J = 7.2 Hz, 1H), 7.62 (s, 1H), 7.57-7.53 (m, 3H), 7.46 (d, J = 7.6 Hz, 1H), 7.42-7.38 (m, 3H), 2.83-2.78 (m, 1H), 1.37 (d, J = 7.2 Hz, 6H). |
| 388 | 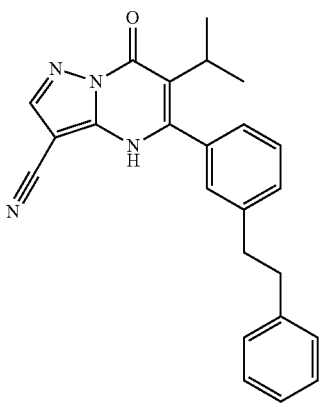 [SMILES: CC(C)c1c(-c2cccc(CCc3ccccc3)c2)[nH]c2c(C#N)cnn2c1=O] | A | 383.1 | A | 1.240 | ¹H NMR (400 MHz, DMSO-d₆) δ 13.40 (s, 1H),. 8.39 (s, 1H), 7.50 7.42 (m, 2H), 7.34-7.30 (m, 2H), 7.28-7.21 (m, 4H), 7.19-7.15 (m, 1H), 3.00-2.94 (m., 4H), 2.58-2.53 (m, 1H), 1.21 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 389 | 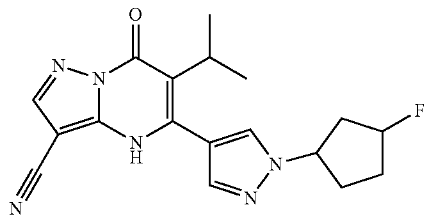 [SMILES: CC(C)c1c(-c2cnn(C3CCC(F)C3)c2)[nH]c2c(C#N)cnn2c1=O] | A | 355.1 | A | 1.005 | $^1$H NMR (400 MHz, CD$_3$OD) δ 8.18 (s, 1H), 8.07 (s, 1H), 7.75 (s, 1H), 5.34 (2m, J = 54 Hz, 1H), 5.10-5.04 (m, 1H), 3.11-3.05 (m, 1H), 2.54-2.41 (m, 4H), 2.12-2.08 (m, 2H), 1.38 (d, J = 6.8 Hz, 6H). |
| 390 | 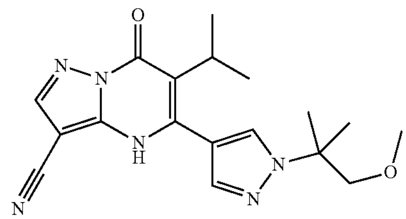 [SMILES: COCC(C)(C)n1cc(-c2[nH]c3c(C#N)cnn3c(=O)c2C(C)C)cn1] | A | 355.1 | A | 1.005 | $^1$H NMR (400 MHz, CD$_3$OD) δ 8.21 (s, 1H), 8.13 (s, 1), 7.77 (s, 1H), 3.67 (s, 2H), 3.30 (s, 3H), 3.12-3.05 (m, 1H), 1.64 (s, 6H), 1.38 (d, J = 7.2 Hz, 6H). |
| 391 | 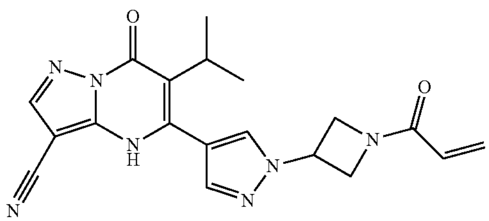 [SMILES: C=CC(=O)N1CC(n2cc(-c3[nH]c4c(C#N)cnn4c(=O)c3C(C)C)cn2)C1] | A | 378.1 | A | 0.864 | $^1$H NMR (400 MHz, CD$_3$OD) δ 8.22 (s, 1H), 8.19 (s, 1H), 7.90 (s, 1H), 6.45 6.32 (m, 2H), 5.82 (dd, J = 10.4, 2.0 Hz, 1H), 5.48-5.42 (m, 1H), 4.88-4.83 (m, 1H), 4.76-4.72 (m, 1H), 4.63-4.58 (m, 1H), 4.50-4.46 (m, 1H), 3.10-3.03 (m, 1H), 1.38 (d, J = 7.2 Hz, 6H). |
| 392 | 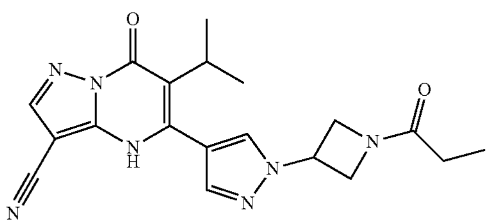 [SMILES: CCC(=O)N1CC(n2cc(-c3[nH]c4c(C#N)cnn4c(=O)c3C(C)C)cn2)C1] | A | 380.2 | A | 0.874 | $^1$H NMR (400 MHz, CD$_3$OD) δ 8.24 (s, 1H), 8.20 (s, 1H), 7.92 (s, 1H), 5.44-5.37 (m, 1H), 4.74 (m, 1H), 4.66-4.62 (m, 1H), 4.51 (m, 1H), 4.41-4.36 (m, 1H), 3.11-3.04 (m, 1H), 2.27 (q, J = 7.6 Hz, 2H), 1.39 (d, J = 6.8 Hz, 6H), 1.16 (t, J = 7.6 Hz, 3H). |
| 393 | 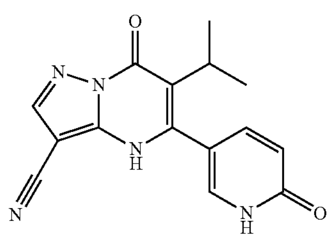 [SMILES: CC(C)c1c(-c2ccc(=O)[nH]c2)[nH]c2c(C#N)cnn2c1=O] | A | 296.0 | A | 0.637 | $^1$H NMR (400 MHz, CD$_3$OD) δ 8.14 (s, 1H), 7.70 (dd, J = 9.6, 2.4 Hz, 1H), 7.58 (d, J = 2.0 Hz, 1H), 6.64 (d, J = 8.8 Hz, 1H), 2.95-2.87 (m, 1H), 1.39 (d, J = 6.8 Hz, 6H). |
| 394 | 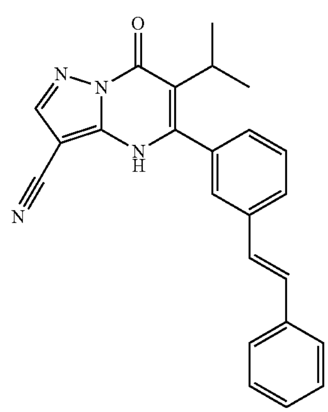 [SMILES: CC(C)c1c(-c2cccc(/C=C/c3ccccc3)c2)[nH]c2c(C#N)cnn2c1=O] | A | 381.1 | D | 1.007 | $^1$H NMR (400 MHz, CD$_3$OD) δ 8.13 (s, 1H), 7.64-7.25 (m, 11H), 2.87-2.80 (m, 1H), 1.34 (d, J = 7.2 Hz, 6H). |

-continued

| Ex | Structure | Syn. Met. | LCMS (ESI) m/z | LCMS Method | R$_T$ (min) | NMR |
|---|---|---|---|---|---|---|
| 395 | 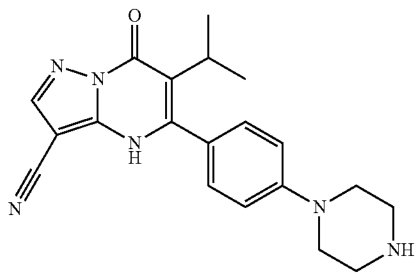 [SMILES: CC(C)c1c(-c2ccc(N3CCNCC3)cc2)[nH]c2c(C#N)cnn2c1=O] | A | 363.1 | C | 0.950 | $^1$H NMR (400 MHz, DMSO-d$_6$) δ 13.28 (s, 1H), 9.33 (s, 2H), 8.38 (s, 1H), 7.38 (d, J = 8.8 Hz, 2H), 7.15 (d, J = 8.4 Hz, 2H), 3.53-3.50 (m, 4H), 3.25-3.20 (m, 4H), 2.74-2.67 (m, 1H), 1.24 (d, J = 7.2 Hz, 6H). |
| 396 | 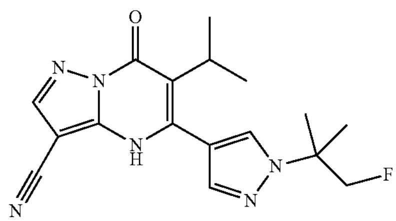 [SMILES: CC(C)c1c(-c2cnn(C(C)(C)CF)c2)[nH]c2c(C#N)cnn2c1=O] | A | 343.2 | A | 0.960 | $^1$H NMR (400 MHz, DMSO-d$_6$) δ 13.11 (s, 1H), 8.34 (s, 1H), 8.05 (s, 1H), 7.77 (s, 1H), 4.44 (d, J = 20.4 Hz, 1H), 2.99-2.93 (m, 1H), 1.36 (s, 3H), 1.31 (s, 3H), 1.29 (d, J = 7.2 Hz, 6H). |
| 397 | 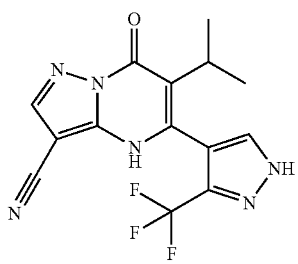 [SMILES: CC(C)c1c(-c2c[nH]nc2C(F)(F)F)[nH]c2c(C#N)cnn2c1=O] | A | 337.2 | A | 0.950 | $^1$H NMR (400 MHz, CD$_3$OD) δ 8.24 (s, 1H), 8.13 (s, 1H), 2.65-2.58 (m, 1H), 1.30 (d, J = 7.2 Hz, 6H). |
| 398 | 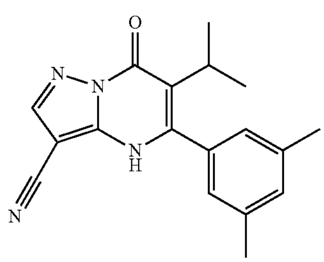 [SMILES: Cc1cc(C)cc(-c2[nH]c3c(C#N)cnn3c(=O)c2C(C)C)c1] | A | 307.0 | A | 1.147 | $^1$H NMR (400 MHz, CD$_3$OD) δ 8.24 (s, 1H), 7.25 (s, 1H), 7.13 (s, 2H), 2.82-2.75 (m, 1H), 2.43 (s, 6H), 1.33 (d, J = 6.8 Hz, 6H). |
| 399 | 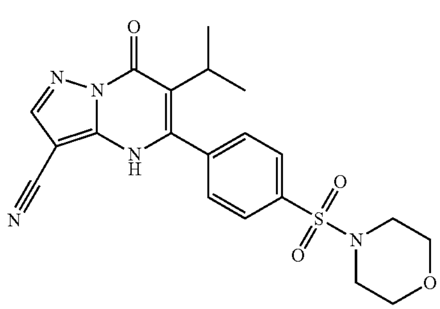 [SMILES: CC(C)c1c(-c2ccc(S(=O)(=O)N3CCOCC3)cc2)[nH]c2c(C#N)cnn2c1=O] | A | 428.2 | A | 1.007 | $^1$H NMR (400 MHz, CD$_3$OD) δ 8.26 (s, 1H), 7.98 (d, J = 8.0 Hz, 2H), 7.80 (d, J = 8.0 Hz, 2H), 3.74 (t, J = 4.4 Hz, 4H), 3.03 ((t, J = 4.4 Hz, 4H), 2.69-2.63 (m, 1H), 1.34 (d, J = 6.4 Hz, 6H) |
| 400 | 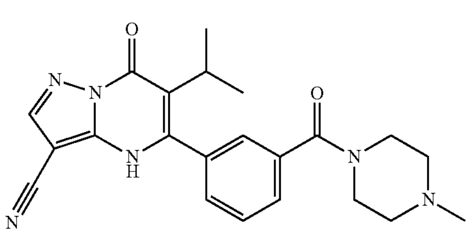 [SMILES: CC(C)c1c(-c2cccc(C(=O)N3CCN(C)CC3)c2)[nH]c2c(C#N)cnn2c1=O] | A | 405.3 | C | 0.937 | $^1$H NMR (400 MHz, CD$_3$OD) δ 8.17 (s, 1H), 7.66-7.60 (m, 1H), 7.59-7.54 (m, 2H), 7.50 (s, 1H), 3.30 (brs, 4H), 2.89-2.73 (m, 4H), 2.71 (m, 1H), 2.54 (s, 3H), 1.31 (d, J = 7.2 Hz, 6H). |

| Ex | Structure | Syn. Met. | LCMS (ESI) m/z | LCMS Method | R$_T$ (min) | NMR |
|---|---|---|---|---|---|---|
| 401 | 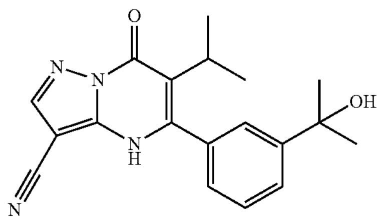 [SMILES: CC(C)c1c(-c2cccc(C(C)(C)O)c2)[nH]c2c(C#N)cnn2c1=O] | A | 337.2 | A | 0.990 | $^1$H NMR (400 MHz, CD$_3$OD) δ 8.24 (s, 1H), 7.71 (d, J = 7.6 Hz, 1H), 7.63 (s, 1H), 7.56-7.52 (m, 1H), 7.37 (d, J = 7.6 Hz, 1H), 2.77-2.70 (m, 1H), 1.58 (s, 6H), 1.32 (d, J = 7.2 Hz, 6H). |
| 402 | 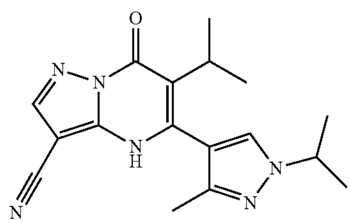 [SMILES: Cc1nn(C(C)C)cc1-c1[nH]c2c(C#N)cnn2c(=O)c1C(C)C] | A | 325.1 | A | 0.960 | $^1$H NMR (400 MHz, CD$_3$OD) δ 8.20 (s, 1H), 7.87 (s, 1H), 4.57-4.50 (m, 1H), 2.83-2.76 (m, 1H), 2.23 (s, 3H), 1.52 (d, J = 6.8 Hz, 6H), 1.32 (d, J = 6.8 Hz, 6H). |
| 403 | 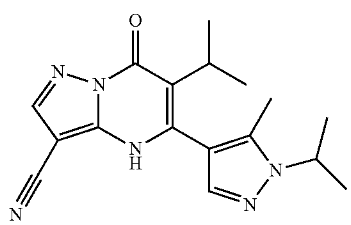 [SMILES: Cc1c(-c2[nH]c3c(C#N)cnn3c(=O)c2C(C)C)cnn1C(C)C] | A | 325.1 | A | 0.974 | $^1$H NMR (400 MHz, CD$_3$OD) δ 8.21 (s, 1H), 7.59 (s, 1H), 4.67-4.61 (m, 1H), 2.84-2.77 (m, 1H), 2.31 (s, 3H), 1.50 (d, J = 6.4 Hz, 6H), 1.32 (d, J = 6.8 Hz, 6H). |
| 404 | 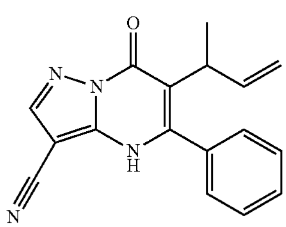 [SMILES: C=CC(C)c1c(-c2ccccc2)[nH]c2c(C#N)cnn2c1=O] | B | 291.0 | A | 1.019 | $^1$H NMR (400 MHz, DMSO-d$_6$) δ 13.54 (s, 1H), 8.41 (s, 1H), 7.63-7.56 (m, 3H), 7.52-7.51 (m, 2H), 6.19-6.11 (m, 1H), 4.93-4.79 (m, 2H), 3.17-3.10 (m, 1H), 1.31 (d, J = 7.2 Hz, 3H) |
| 405 | 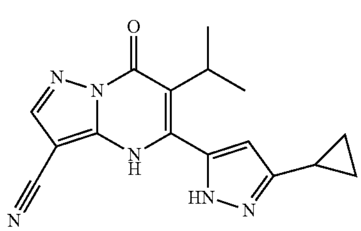 [SMILES: CC(C)c1c(-c2cc(C3CC3)n[nH]2)[nH]c2c(C#N)cnn2c1=O] | A | 309.2 | F | 4.20 | $^1$H NMR (DMSO-d$_6$) δ: 13.17 (s, 2H), 8.35 (s, 1H), 6.31 (s, 1H), 3.22-3.07 (m, 1H), 2.05-1.95 (m, 1H), 1.27 (d, J = 6.9 Hz, 6H), 1.06-0.94 (m, 2H), 0.84-0.72 (m, 2H) |
| 406 | 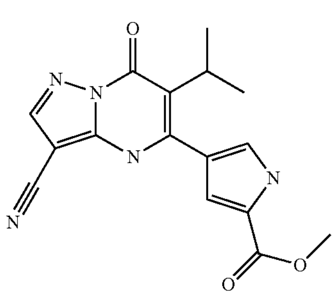 [SMILES: COC(=O)c1cc(-c2[nH]c3c(C#N)cnn3c(=O)c2C(C)C)c[nH]1] | A | 326.2 | F | 4.11 | $^1$H NMR (DMSO-d$_6$) δ: 13.01 (s, 1H), 12.50 (s, 1H), 8.32 (s, 1H), 7.38 (s, 1H), 7.01 (dd, J = 2.5, 1.6 Hz, 1H), 3.82 (s, 3H), 3.06 (p, J = 6.9 Hz, 1H), 1.29 (d, J = 6.9 Hz, 6H) |

-continued

| Ex | Structure | Syn. Met. | LCMS (ESI) m/z | LCMS Method | R_T (min) | NMR |
|---|---|---|---|---|---|---|
| 407 | 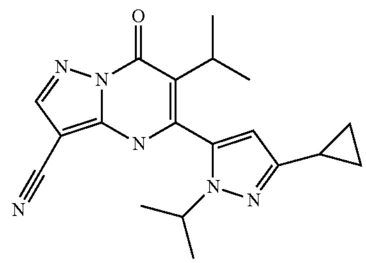 [SMILES: CC(C)c1c(-c2cc(C3CC3)nn2C(C)C)[nH]c2c(C#N)cnn2c1=O] | A | 351.2 | F | 4.85 | $^1$H NMR (DMSO-d$_6$) δ: 13.63 (s, 1H), 8.38 (s, 1H), 6.17 (s, 1H), 4.28 (p, J = 6.5 Hz, 1H), 2.48-2.39 (m, 1H), 2.02-1.88 (m, 1H), 1.46-1.12 (m, 12H), 0.90 (dd, J = 8.4, 2.4 Hz, 2H), 0.74-0.60 (m, 2H) |
| 408 | 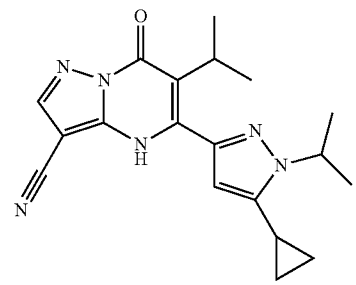 [SMILES: CC(C)c1c(-c2cc(C3CC3)n(C(C)C)n2)[nH]c2c(C#N)cnn2c1=O] | A | 351.2 | F | 5.20 | $^1$H NMR (DMSO-d$_6$) δ: 13.01 (s, 1H), 8.34 (s, 1H), 6.32-6.18 (m, 1H), 4.86 (p, J = 6.6 Hz, 1H), 3.21-3.06 (m, 1H), 2.06-1.96 (m, 1H), 1.46 (d, J = 6.6 Hz, 6H), 1.26 (d, J = 7.0 Hz, 6H), 1.06-0.97 (m, 2H), 0.75-0.67 (m, 2H) |
| 409 | 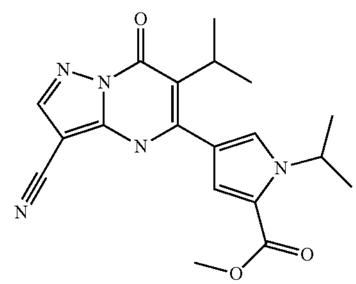 [SMILES: COC(=O)c1cc(-c2[nH]c3c(C#N)cnn3c(=O)c2C(C)C)cn1C(C)C] | A | 368.2 | F | 4.98 | $^1$H NMR (DMSO-d$_6$) δ: 12.97 (s, 1H), 8.36 (s, 1H), 7.95 (s, 0H), 7.68 (d, J = 2.0 Hz, 1H), 7.07 (d, J = 1.9 Hz, 1H), 5.39 (p, J = 6.7 Hz, 1H), 3.80 (s, 3H), 3.02 (p, J = 6.9 Hz, 1H), 1.46 (d, J = 6.7 Hz, 6H), 1.29 (d, J = 6.9 Hz, 6H) |
| 410 | 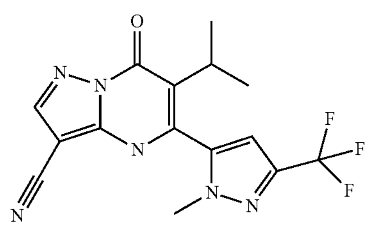 [SMILES: CC(C)c1c(-c2cc(C(F)(F)F)nn2C)[nH]c2c(C#N)cnn2c1=O] | A | 351.1 | F | 4.83 | $^1$H NMR (DMSO-d$_6$) δ: 8.38 (s, 1H), 7.06 (s, 1H), 3.86 (s, 3H), 2.50-2.43 (m, 1H), 1.23 (d, J = 7.0 Hz, 6H) |
| 411 | 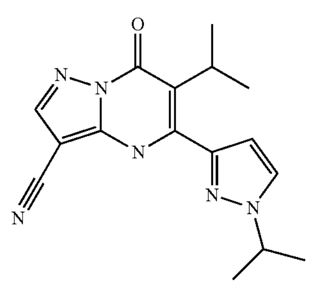 [SMILES: CC(C)c1c(-c2ccn(C(C)C)n2)[nH]c2c(C#N)cnn2c1=O] | A | 311.2 | F | 4.45 | $^1$H NMR (DMSO-d$_6$) δ: 13.14 (s, 1H), 8.33 (s, 1H), 7.97 (s, 1H), 6.58 (d, J = 2.4 Hz, 1H), 4.62 (p, J = 6.7 Hz, 1H), 3.16-3.07 (m, 1H), 1.48 (d, J = 6.6 Hz, 6H), 1.27 (d, J = 6.9 Hz, 6H) |

| Ex | Structure | Syn. Met. | LCMS (ESI) m/z | LCMS Method | R$_T$ (min) | NMR |
|---|---|---|---|---|---|---|
| 412 | 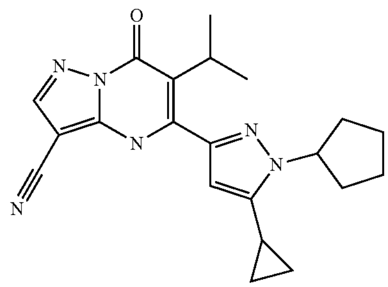 [SMILES: CC(C)c1c(-c2cc(C3CC3)n(C3CCCC3)n2)[nH]c2c(C#N)cnn2c1=O] | A | 377.2 | F | 5.73 | $^1$H NMR (DMSO-d$_6$) δ: 13.00 (s, 1H), 8.33 (s, 1H), 6.27 (s, 1H), 5.05 (q, J = 6.7 Hz, 1H), 3.23-3.08 (m, 1H), 2.18-2.07 (m, 2H), 2.06-1.94 (m, 2H), 1.91-1.78 (m, 2H), 1.73-1.61 (m, 2H), 1.26 (d, J = 7.0 Hz, 6H), 1.06-0.97 (m, 2H), 0.75-0.66 (m, 2H) |
| 413 | 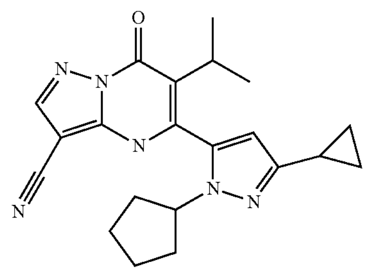 [SMILES: CC(C)c1c(-c2cc(C3CC3)nn2C2CCCC2)[nH]c2c(C#N)cnn2c1=O] | A | 377.2 | F | 5.42 | $^1$H NMR (DMSO-d$_6$) δ: 13.64 (s, 1H), 8.37 (s, 1H), 6.18 (s, 1H), 4.59-4.36 (m, 1H), 2.08-1.68 (m, 8H), 1.64-1.42 (m, 2H), 1.36-1.12 (m, 6H), 0.99-0.78 (m, 2H), 0.77-0.57 (m, 2H) |
| 414 | 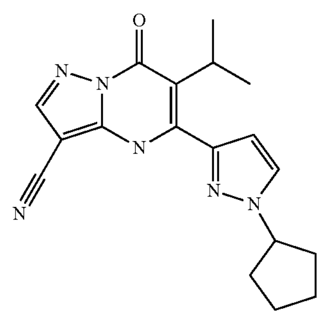 [SMILES: CC(C)c1c(-c2ccn(C3CCCC3)n2)[nH]c2c(C#N)cnn2c1=O] | A | 337.2 | F | 4.99 | $^1$H NMR (DMSO-d$_6$) δ: 13.14 (s, 1H), 8.30 (s, 1H), 8.00-7.88 (m, 1H), 6.62-6.51 (m, 1H), 4.81 (p, J = 6.9 Hz, 1H), 3.22-3.07 (m, 1H), 2.19-2.06 (m, 2H), 2.05-1.92 (m, 2H), 1.90-1.75 (m, 2H), 1.74-1.60 (m, 2H), 1.33-1.21 (m, 6H) |
| 415 | 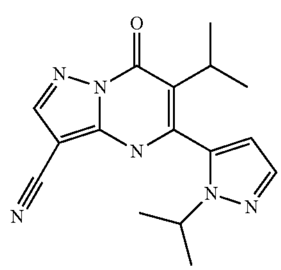 [SMILES: CC(C)c1c(-c2ccnn2C(C)C)[nH]c2c(C#N)cnn2c1=O] | A | 311.2 | F | 4.19 | $^1$H NMR (DMSO-d$_6$) δ: 13.65 (s, 1H), 8.38 (s, 1H), 7.65 (s, 1H), 6.49 (s, 1H), 4.41 (p, J = 6.5 Hz, 1H), 2.44-2.36 (m, 1H), 1.48-1.30 (m, 6H), 1.30-1.14 (m, 6H) |
| 416 | 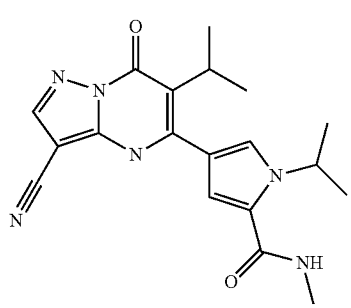 [SMILES: CNC(=O)c1cc(-c2[nH]c3c(C#N)cnn3c(=O)c2C(C)C)cn1C(C)C] | A | 367.2 | F | 4.55 | $^1$H NMR (DMSO d$_6$) δ: 8.04 (s, 1H), 7.94 (s, 1H), 7.19 (s, 1H), 6.84 (s, 1H), 5.51 (p, J = 6.7 Hz, 1H), 3.26-3.19 (m, 1H), 2.71 (d, J = 4.5 Hz, 3H), 1.39 (d, J = 6.7 Hz, 6H), 1.32 (d, J = 6.9 Hz, 6H) |

| Ex | Structure | Syn. Met. | LCMS (ESI) m/z | LCMS Method | R$_T$ (min) | NMR |
|---|---|---|---|---|---|---|
| 417 | 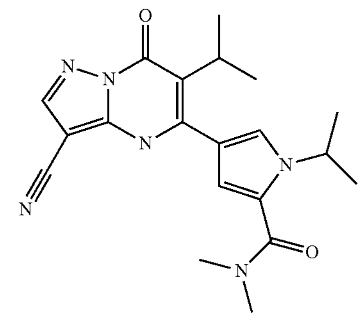 [SMILES: CC(C)c1c(-c2cc(C(=O)N(C)C)n(C(C)C)c2)[nH]c2c(C#N)cnn2c1=O] | A | 381.2 | F | 4.61 | $^1$H NMR (DMSO-d$_6$) δ: 12.90 (s, 1H), 8.34 (s, 1H), 7.44 (s, 1H), 6.49 (s, 1H), 4.72 (p, J = 6.7 Hz, 1H), 3.30 (s, 6H), 3.15-3.03 (m, 1H), 1.42 (d, J = 6.7 Hz, 6H), 1.30 (d, J = 6.9 Hz, 6H) |
| 418 | 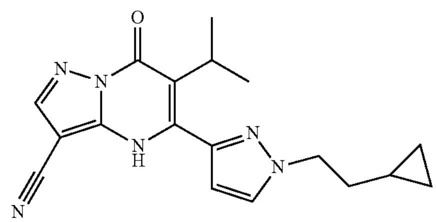 [SMILES: CC(C)c1c(-c2ccn(CCC3CC3)n2)[nH]c2c(C#N)cnn2c1=O] | A | 337.2 | F | 5.11 | $^1$H NMR (DMSO d$_6$) δ: 13.18 (s, 1H), 8.35 (s, 1H), 7.96 (s, 1H), 6.59 (s, 1H), 4.28 (t, J = 6.9 Hz, 2H), 3.20-3.02 (m, 1H), 1.74 (q, J = 6.9 Hz, 2H), 1.26 (d, J = 7.0 Hz, 6H), 0.74-0.59 (m, 1H), 0.46-0.33 (m, 2H), 0.06-0.01 (m, 2H) |
| 419 | 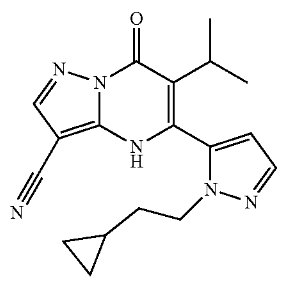 [SMILES: CC(C)c1c(-c2ccnn2CCC2CC2)[nH]c2c(C#N)cnn2c1=O] | A | 337.2 | F | 4.81 | $^1$H NMR (DMSO-d$_6$) δ: 13.59 (s, 1H), 8.35 (s, 1H), 7.52 (s, 1H), 6.49 (s, 1H) 4.10 (t, J = 7.2 Hz, 2H), 1.77-1.49 (m, 2H), 1.23 (d, J = 6.9 Hz, 6H), 0.68-0.50 (m, 1H), 0.30 (d, J = 7.9 Hz, 2H), −0.03--0.13 (m, 2H) |
| 420 | 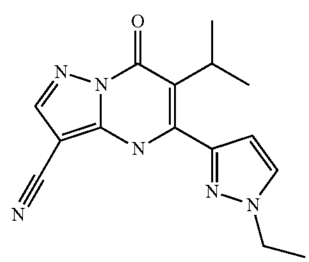 [SMILES: CCn1ccc(-c2[nH]c3c(C#N)cnn3c(=O)c2C(C)C)n1] | A | 297.2 | F | 4.30 | $^1$H NMR (DMSO-d$_6$) δ: 13.21 (s, 1H), 8.24 (s, 1H), 7.25 (d, J = 8.6 Hz, 1H), 6.92 (d, J = 8.7 Hz, 1H), 4.23 (q, J = 7.3 Hz, 2H), 3.27-3.14 (m, 1H), 1.43 (t, J = 7.3 Hz, 3H), 1.27 (d, J = 7.0, 6H) |
| 421 | 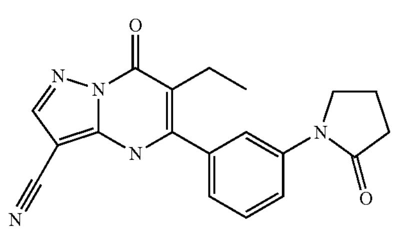 [SMILES: CCc1c(-c2cccc(N3CCCC3=O)c2)[nH]c2c(C#N)cnn2c1=O] | A | 348.2 | F | 3.97 | $^1$H NMR (DMSO-d$_6$) δ: 13.49 (s, 1H), 8.38 (s, 1H), 7.88 (s, 1H), 7.81 (d, J = 8.2 Hz, 1H), 7.56 (t, J = 8.0 Hz, 1H), 7.28 (d, J = 7.6 Hz, 1H), 3.89 (t, J = 7.0 Hz, 2H), 2.58-2.51 (m, 2H), 2.32 (q J = 7.3 Hz, 2H), 2.16-2.03 (m, 2H), 1.01 (t, J = 7.3 Hz, 3H). |
| 422 | 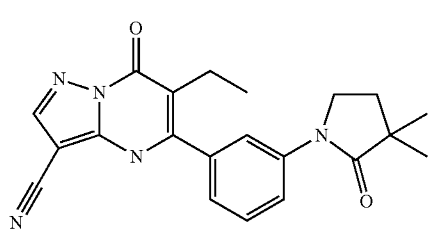 [SMILES: CCc1c(-c2cccc(N3CCC(C)(C)C3=O)c2)[nH]c2c(C#N)cnn2c1=O] | A | 376.2 | F | 4.56 | $^1$H NMR (Chloroform-d) δ: 8.03 (s, 1H), 7.97-7.91 (m, 1H), 7.60-7.42 (m, 2H), 7.31-7.27 (m, 1H), 3.82 (dt, J = 13.2, 6.9 Hz, 2H), 2.56 (q, J = 7.3 Hz, 2H), 2.06 (dd, J = 8.0, 5.8 Hz, 2H), 1.26 (s, 6H), 1.15 (t, J = 7.3 Hz, 3H) |

| Ex | Structure | Syn. Met. | LCMS (ESI) m/z | LCMS Method | R$_T$ (min) | NMR |
|---|---|---|---|---|---|---|
| 423 | 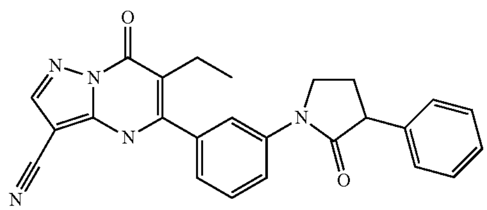 [SMILES: CCc1c(-c2cccc(N3CCC(c4ccccc4)C3=O)c2)[nH]c2c(C#N)cnn2c1=O] | A | 424.18 | F | 4.84 | ¹H NMR (DMSO-d$_6$) δ: 13.50 (s, 1H), 8.37 (s, 1H), 7.95-7.81 (m, 2H), 7.58 (t, J = 7.9 Hz, 1H), 7.42-7.24 (m, 6H), 4.05-3.93 (m, 3H), 2.67-2.55 (m, 1H), 2.39-2.29 (m, 2H), 2.23 (dq, J = 12.5, 8.6 Hz, 1H), 1.01 (t, J = 7.3 Hz, 3H) |
| 424 | 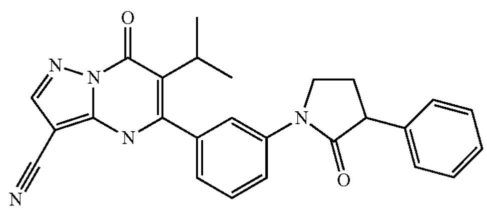 | A | 438.2 | F | 5.27 | ¹H NMR (DMSO-d$_6$) δ: 13.43 (s, 1H), 8.29 (s, 1H), 7.92-7.77 (m, 2H), 7.55 (t, J = 7.9 Hz, 1H), 7.42-7.21 (m, 6H), 4.04-3.90 (m, 3H), 2.74-2.54 (m, 2H), 2.29-2.16 (m, 1H), 1.24 (dd, J = 6.9, 1.1 Hz, 6H) |
| 425 | 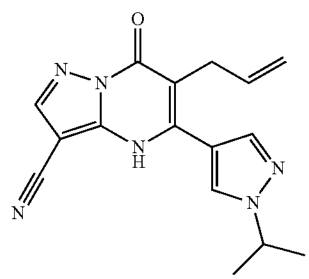 [SMILES: C=CCc1c(-c2cnn(C(C)C)c2)[nH]c2c(C#N)cnn2c1=O] | B | 309.1 | F | 4.95 | 1H NMR (400 MHz, DMSO-d6) δ 8.11 (s, 1H), 8.05 (s, 1H), 7.76 (s, 1H), 6.05-5.88 (m, 1H), 5.04-4.87 (m, 2H), 4.58 (h, J = 6.7 Hz, 1H), 3.38 (d, J = 5.3 Hz, 2H), 1.45 (d, J = 6.6 Hz, 6H). |
| 426 | 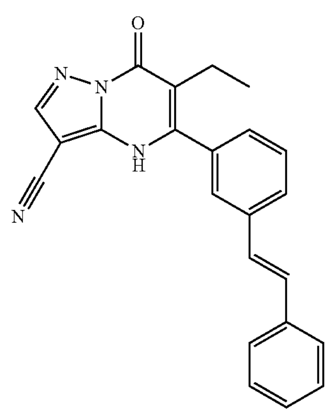 [SMILES: CCc1c(-c2cccc(/C=C/c3ccccc3)c2)[nH]c2c(C#N)cnn2c1=O] | B | 367.2 | F | 6.94 | 1H NMR (400 MHz, DMSO-d6) δ 13.54 (s, 1H), 8.35 (s, 1H), 7.77 (s, 2H), 7.70-7.51 (m, 3H), 7.46-7.22 (m, 6H), 2.35 (q, J = 7.1 Hz, 2H), 1.01 (t, J = 7.3 Hz, 3H). |
| 427 | 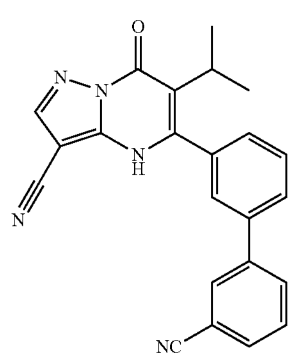 [SMILES: CC(C)c1c(-c2cccc(-c3cccc(C#N)c3)c2)[nH]c2c(C#N)cnn2c1=O] | B | 380.2 | F | 5.42 | 1H NMR (400 MHz, DMSO-d6) δ 13.46 (s, 1H), 8.41 (s, 1H), 8.25 (t, J = 1.8 Hz, 1H), 8.16-8.04 (m, 1H), 8.02-7.91 (m, 2H), 7.88 (dt, J = 7.8, 1.3 Hz, 1H), 7.76-7.66 (m, 2H), 7.59-7.55 (m, 1H), 2.67 (p, J = 6.9 Hz, 1H), 1.26 |

| Ex | Structure | Syn. Met. | LCMS (ESI) m/z | LCMS Method | R_T (min) | NMR |
|---|---|---|---|---|---|---|
| 428 | 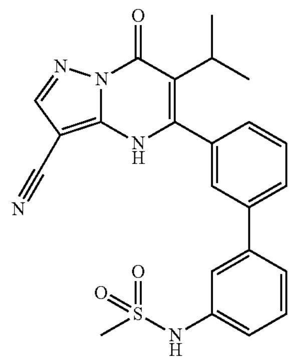 [SMILES: CC(C)c1c(-c2cccc(-c3cccc(NS(C)(=O)=O)c3)c2)[nH]c2c(C#N)cnn2c1=O] | B | 448.2 | F | 4.90 | 1H NMR (400 MHz, DMSO-d6) δ 13.47 (s, 1H), 9.85 (s, 1H), 8.39 (s, 1H), 7.86-7.64 (m, 3H), 7.58-7.44 (m, 4H), 7.31-7.21 (m, 1H), 3.04 (s, 3H), 2.68 (p, J = 7.0 Hz, 1H), 1.26 (d, J = 6.9 Hz, 6H). |
| 429 | 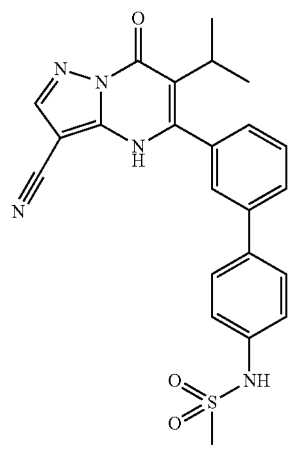 [SMILES: CC(C)c1c(-c2cccc(-c3ccc(NS(C)(=O)=O)cc3)c2)[nH]c2c(C#N)cnn2c1=O] | B | 448.2 | F | 4.85 | 1H NMR (400 MHz, DMSO-d6) δ 13.46 (s, 1H), 9.88 (s, 1H), 8.39 (s, 1H), 7.86-7.56 (m, 5H), 7.46 (d, J = 7.7 Hz, 1H), 7.37-7.27 (m, 2H), 3.04 (s, 3H), 2.68 (p, J = 7.0 Hz, 1H), 1.26 (d, J = 6.9 Hz, 6H). |
| 430 | 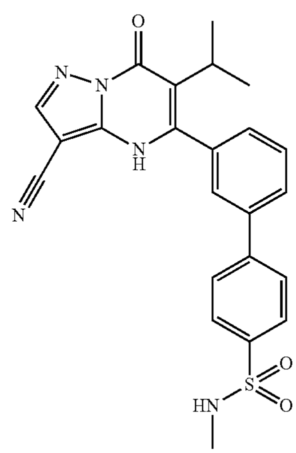 [SMILES: CNS(=O)(=O)c1ccc(-c2cccc(-c3[nH]c4c(C#N)cnn4c(=O)c3C(C)C)c2)cc1] | B | 448.2 | F | 4.88 | 1H NMR (400 MHz, DMSO-d6) δ 13.47 (s, 1H), 8.39 (s, 1H), 8.04-7.82 (m, 5H), 7.70 (t, J = 7.6 Hz, 1H), 7.59-7.47 (m, 2H), 2.75-2.62 (m, 1H), 2.46 (d, J = 5.0 Hz, 3H), 1.30-1.20 (m, 6H). |
| 431 | 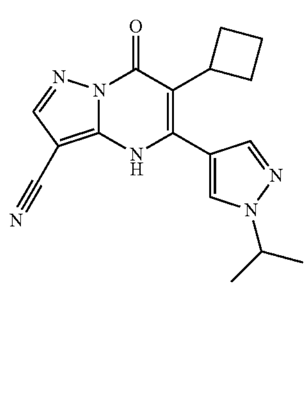 [SMILES: CC(C)n1cc(-c2[nH]c3c(C#N)cnn3c(=O)c2C2CCC2)cn1] | B | 323.2 | F | 4.38 | 1H NMR (400 MHz, DMSO-d6) δ 13.00 (s, 1H), 8.33 (s, 1H), 8.15 (s, 1H), 7.72 (s, 1H), 4.62 (hept, J = 6.7 Hz, 1H), 3.59 (p, J = 9.1 Hz, 1H), 2.67-2.54 (m, 2H), 2.04-1.96 (m, 2H), 1.86-1.73 (m, 2H), 1.48 (d, J = 6.7 Hz, 6H). |

| Ex | Structure | Syn. Met. | LCMS (ESI) m/z | LCMS Method | R_T (min) | NMR |
|---|---|---|---|---|---|---|
| 432 | 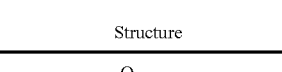 | B | 337.2 | F | 4.23 | 1H NMR (400 MHz, DMSO-d6) δ 13.01 (s, 1H), 8.31 (s, 1H), 8.02 (s, 1H), 7.63 (s, 1H), 4.59 (p, J = 6.7 Hz, 1H), 1.85 (d, J = 6.7 Hz, 3H), 1.69 (d, J = 6.9 Hz, 2H), 1.58 (s, 3H), 1.45 (d, J = 6.7 Hz, |

Example 433

Synthesis of ethyl 2-acetylpentanoate

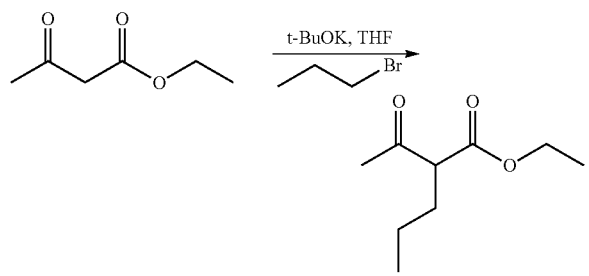

Ethyl 2-acetylpentanoate was synthesized according to Beddow et al, Org. Biomol. Chem. 5: 2812-2825 (2007). To a solution of t-BuOK (11.8 g, 0.11 mol) in THF (150 mL) was added ethyl 3-oxobutanoate (13 g, 0.1 mol) dropwise at 0° C., after stirred for 30 minutes, 1-bromopropane (12.3 g, 0.1 mmol) was added dropwise and the mixture was refluxed for 16 h. The reaction mixture was quenched by water, extracted with EtOAc (100 mL×2), combined organic layer was dried over anhydrous Na$_2$SO$_4$, evaporated, purified by column chromatography to give the expected compound ethyl 2-acetylpentanoate (8.5 g, 49%) as colorless oil. m/z (ESI) 173 [M+H]$^+$.

Example 434

By a similar method to Example 433, using the appropriate starting materials, the compounds in Table 2 were prepared.

TABLE 2

| Compound name | Structure | Data |
|---|---|---|
| ethyl 2-acetyl-4-methylpentanoate | 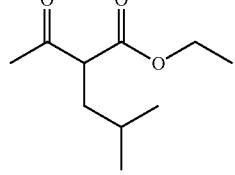 | m/z (ESI) 187 [M + H]$^+$ |
| ethyl 2-acetylpent-4-enoate | 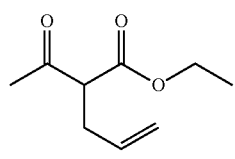 | m/z (ESI) 171 [M + H]$^+$ |
| ethyl 2-acetyl-4-methoxybutanoate | 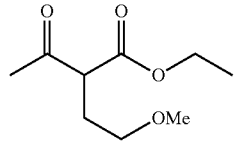 | m/z (ESI) 189 [M + H]$^+$ |

TABLE 2-continued

| Compound name | Structure | Data |
|---|---|---|
| ethyl 2-acetylpent-4-ynoate | 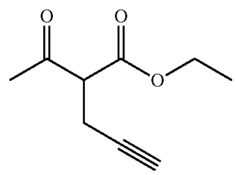 | m/z (ESI) 169 [M + H]$^+$ |
| ethyl 2-ethyl-4,4,4-trifluoro-3-oxobutanoate | 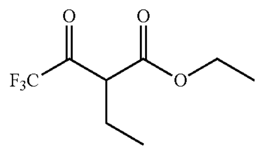 | m/z (ESI) 213 [M + H]$^+$ |
| ethyl 4-ethoxy-2-ethyl-3-oxobutanoate | 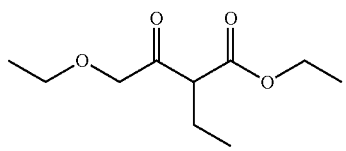 | m/z (ESI) 203 [M + H]$^+$ |
| ethyl 2-(2-methoxyacetyl)pent-4-enoate | 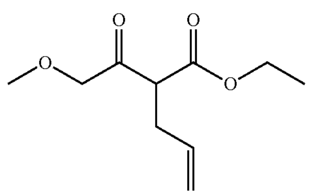 | m/z (ESI) 201 [M + H]$^+$ |
| ethyl 2-benzoylbutanoate | 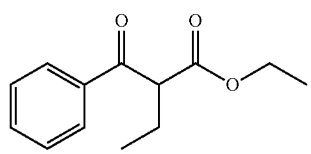 [SMILES: CCOC(=O)C(CC)C(=O)c1ccccc1] | m/z (ESI) 221 [M + H]$^+$ |
| ethyl 2-(furan-2-carbonyl)butanoate | 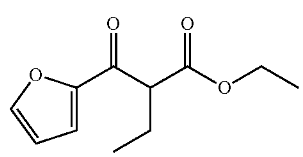 | m/z (ESI) 211 [M + H]$^+$ |
| 3-ethylpentane-2,4-dione | 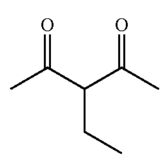 | m/z (ESI) 129 [M + H]$^+$ |

Example 435

Synthesis of ethyl 2-ethyl-4-methoxy-3-oxobutanoate

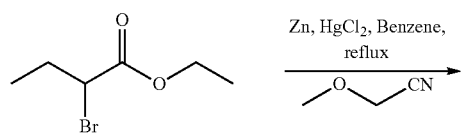

-continued

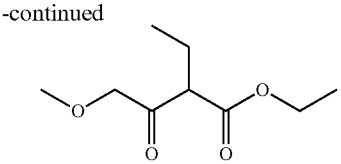

Ethyl 2-ethyl-4-methoxy-3-oxobutanoate was prepared according to WO 98/43968. Zinc (2 g, 30 mmol), methoxyacetonitrile (1.42 g, 20 mmol) and a catalytic amount of mercuric chloride in toluene (50 mL) were heated to reflux. Ethyl 2-bromobutanoate (5.85 g, 30 mmol) was added dropwise, then reflux continued for a hour, and cooled to a room temperature. 10% Aqueous sulfuric solution (16.5 mL) was added, and the organic layer was separated. The aqueous layer was further extracted with ethyl ether and the combined organic layers washed with water and saturated sodium bicarbonate solution, then dried over anhydrous magnesium sulfate and concentrated in vacuo. The residue was purified by column chromatography to give the product as yellow oil (1.7 g, 45%). $^1$H NMR (300 MHz, CDCl$_3$) δ 4.14 (q, J=7.2 Hz, 2H), 4.07 (d, J=3.6 Hz, 2H), 3.45 (t, J=7.2 Hz, 1H), 3.37 (s, 3H), 1.85 (m, 2H), 1.22 (t, J=7.2 Hz, 3H). 0.90 (t, J=7.5 Hz, 3H); m/z (ESI) 189 [M+H]$^+$.

Example 436

By a similar method to Example 435, using the appropriate starting materials, the compounds in Table 3 were prepared and isolated.

TABLE 3

| Compound name | Structure | Data |
|---|---|---|
| ethyl 2-(2-methoxyacetyl)pentanoate | 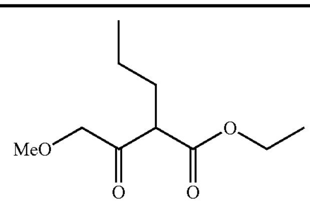 | m/z (ESI) 225 [M + Na$^+$] |
| ethyl 2-ethyl-3-oxo-4-phenylbutanoate | 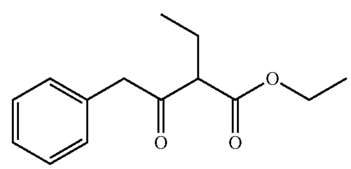 [SMILES: CCOC(=O)C(CC)C(=O)Cc1ccccc1] | m/z (ESI) 257 [M + Na$^+$] |

Example 437

Synthesis of diethyl 2-ethyl-3-oxosuccinate

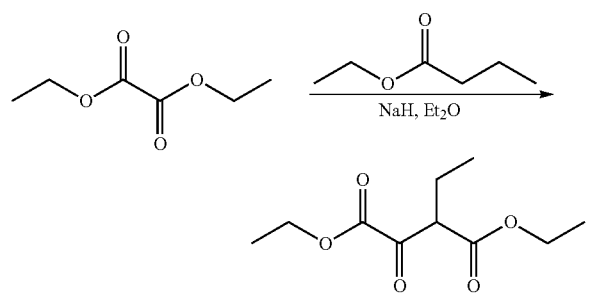

Diethyl-2-ethyl-3-oxosuccinate was prepared according to Soloway et al, J. Org. Chem. 69: 2677-2678 (1947). To a mixture of NaH (60%, 12 g, 300 mmol) and diethyl oxalate (43.8 g, 300 mmol) in ether (100 mL), ethyl butyrate (18 g, 150 mmol) was added. The reaction mixture was refluxed over night. After cooling to room temperature water was added, the mixture was extracted with EtOAc. The organic layer was dried over with Na$_2$SO$_4$ and evaporated in vacuo. The residue was purified by column chromatography to give diethyl-2-ethyl-3-oxosuccinate (8 g, 24%) as light oil. m/z (ESI) 217 [M+H]$^+$.

Example 438

Synthesis of ethyl 2-ethyl-6-methoxy-3-oxohexanoate

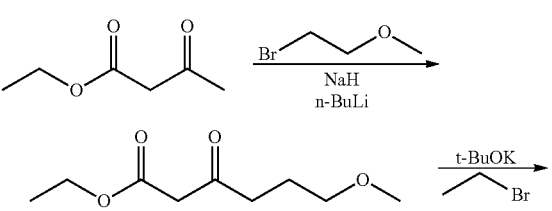

-continued

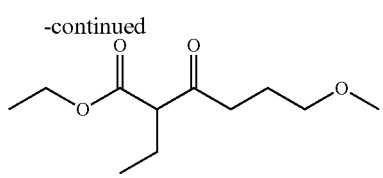

Ethyl 2-ethyl-6-methoxy-3-oxohexanoate was prepared according to WO2006124490.

Synthesis of ethyl 6-methoxy-3-oxohexanoate

To a solution of ethyl 3-oxobutanoate (1.3 g, 10 mol) in THF (50 mL) was added NaH (60%, 480 mg, 12 mmol) at 0° C. After stirring under N$_2$ at 0° C. for 0.5 h, n-BuLi (4 mL, 10 mmol) was added at 0° C. and then the solution of the mixture was cooled to −25° C. After 1-bromo-2-methoxyethane (1.39 g, 10 mmol) was added, the solution of the mixture was stirring for overnight at room temperature. The mixture was evaporated in vacuo, purified by column chromatography to give ethyl 6-methoxy-3-oxohexanoate (0.65 g, 34.5%). m/z (ESI) 211 [M+Na]$^+$.

Synthesis of ethyl 2-ethyl-6-methoxy-3-oxohexanoate

To a solution of ethyl 6-methoxy-3-oxohexanoate (650 mg, 3.45 mmol) in THF (50 mL), $^t$BuOK (406 mg, 3.63 mmol) was added at 0° C. and then the solution of the

Example 439

Synthesis of 6-cyclopropyl-5-methyl-7-oxo-4,7-dihydropyrazolo[1,5-a]pyrimidine-3-carbonitrile

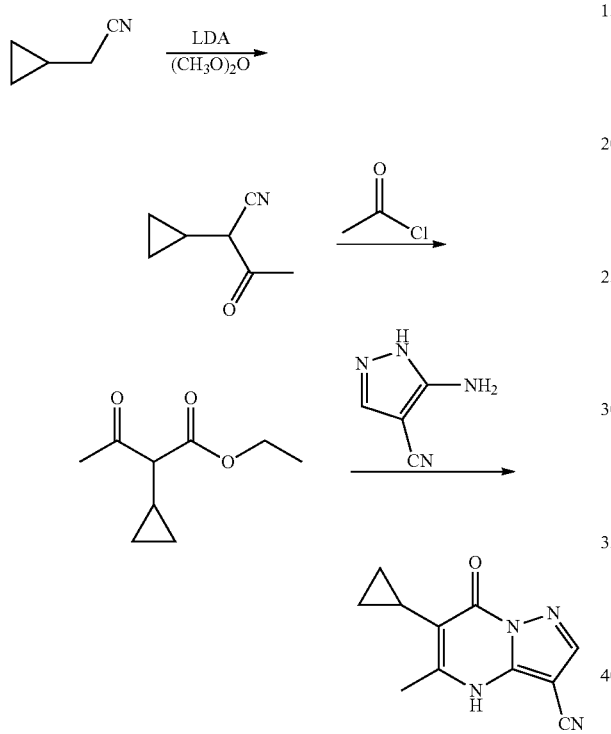

Synthesis of 2-cyclopropyl-3-oxobutanenitrile

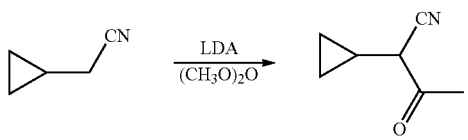

To a solution of 2-cyclopropylacetonitrile (1.17 g, 14.4 mmol) in THF (10 mL) was added LDA (8.7 ml, 17.3 mmol) dropwise at −78° C. under N₂. After stirred for 60 mins, (CH₃O)₂O (1.12 g, 14.4 mmol) was added dropwise at −78° C. and the mixture was stirred for 2 h at ambient temperature. The reaction mixture was quenched by the aqueous of HCl (2N), extracted with ethyl acetate (30 ml×3), combined organic layer was dried over anhydrous Na₂SO₄ and evaporated, purified by column chromatography to give 2-cyclopropyl-3-oxobutanenitrile as yellow oil. m/z (ESI) 124 [M+H]⁺.

mixture was stirring for 30 min at 0° C., followed by refluxing overnight. The mixture was evaporated in vacuo, purified by column chromatography to give ethyl 2-ethyl-6-methoxy-3-oxohexanoate (400 mg, 53.6%). m/z (ESI) 217 [M+H]⁺.

Synthesis of ethyl 2-cyclopropyl-3-oxobutanoate

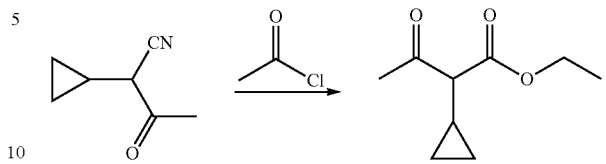

To a solution of 2-cyclopropyl-3-oxobutanenitrile (600 mg, 5 mmol) in EtOH (10 mL) was added acetyl chloride (3 mL) dropwise at 0° C. After stirred for 16 h, EtOH was removed, the mixture was added concentrated HCl (1 mL) and EtOH (10 mL), and stirred for 4 h at 40° C. The mixture was quenched by water and extracted with ethyl acetate (20 mL×3), combined organic layer was dried over anhydrous Na₂SO₄ and evaporated, purified by column chromatography to give ethyl 2-cyclopropyl-3-oxobutanoate (30 mg, 10%) as yellow oil. m/z (ESI) 171 [M+H]⁺.

Example 440

Synthesis of 5-amino-3-ethyl-1H-pyrazole-4-carbonitrile

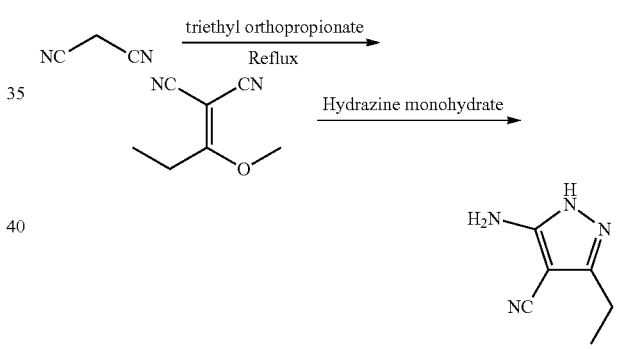

5-Amino-3-ethyl-1H-pyrazole-4-carbonitrile was prepared in a manner substantially similar to that described in WO2005070916 and US2006135526.

Synthesis of 2-(1-methoxypropylidene)malononitrile

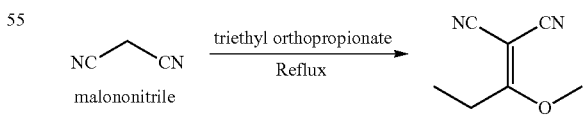

A mixture of malononitrile (180 g, 1.02 mol) and triethyl orthopropionate (66 g, 1 mol) was refluxed for 3 h. The reaction mixture was distilled under vacuum to give the expected compound 12-1-a (60 g, 40%) as pale yellow oil. ¹H NMR (300 MHz, CDCl₃) δ 4.46 (q, J=6.9 Hz, 2H), 2.65 (q, J=7.5 Hz, 2H), 1.45 (t, J=6.9 Hz, 3H), 1.26 (t, J=7.5 Hz, 3H).

Synthesis of 5-amino-3-ethyl-1H-pyrazole-4-carbonitrile

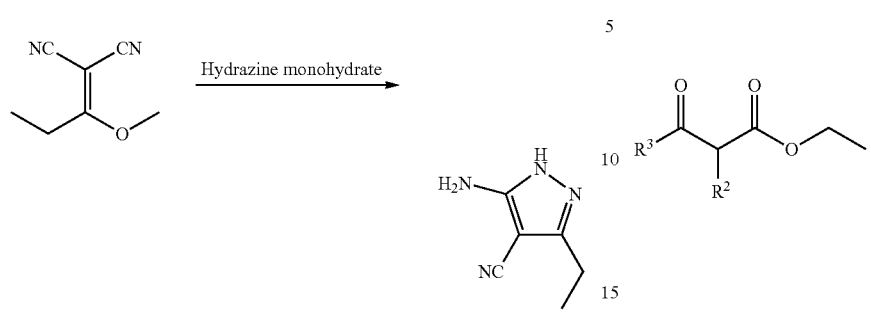

A solution of 2-(1-methoxypropylidene)malononitrile (10 g, 0.067 mol) in EtOH (50 mL) was added dropwise into the solution of hydrazine monohydrate (6.8 ml, 0.134 mol) in EtOH (100 mL) at 0° C. for 30 min. After stirred for 3 h at 90° C., the mixture was concentrated and purified by column chromatography to give the expected compound 5-amino-3-ethyl-1H-pyrazole-4-carbonitrile (5 g, 60% yield) as yellow solid. $^1$H NMR (300 MHz, CDCl$_3$) δ 4.40 (s, 2H), 2.69 (q, J=7.5 Hz, 2H), 1.29 (t, J=7.5 Hz, 3H).

Example 441

General Procedure

A mixture of a cyanopyrazole (0.86 mmol), a beta-ketoester (293 mg, 1.72 mmol) and acetic acid (3 mL) is stirred at 80° C. for 1.5 hours. The mixture is cooled to room temperature. The solvent is removed in vacuo. The residue is purified by silica gel column chromatography to yield the desired compound.

Using the general procedure above in Example 441 and the appropriate starting materials, the compounds in Table 4 were prepared.

TABLE 4

| Compound Name | Structure | Data |
|---|---|---|
| 2-ethyl-9-oxo-4,5,6,7,8,9-hexahydropyrazolo[5,1-b]quinazoline-3-carbonitrile | 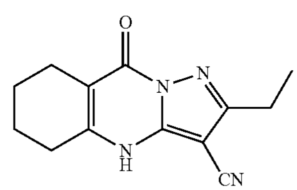 [SMILES: CCc1nn2c(=O)c3c([nH]c2c1C#N)CCCC3] | $^1$H NMR (300 MHz, DMSO) δ 12.84 (brs, 1H), 2.74 (q, J = 6.9 Hz, 2H,), 2.62 (m, 2H), 2.40 (m, 2H) 1.71 (m, 4H), 1.26 (t, J = 6.9 Hz, 3H); m/z (ESI) 243 [M + H]$^+$. |
| 2-methyl-9-oxo-4,5,6,7,8,9-hexahydropyrazolo[5,1-b]quinazoline-3-carbonitrile | 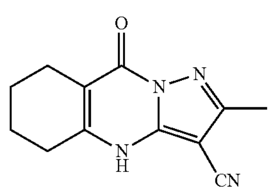 [SMILES: Cc1nn2c(=O)c3c([nH]c2c1C#N)CCCC3] | $^1$H NMR (300 MHz, CD$_3$OD) δ 2.72 (m, 2H), 2.60 (m, 2H), 2.43 (s, 3H), 1.81 (m, 4H). m/z (ESI) 229 [M + H]$^+$. |
| 9-oxo-4,5,6,7,8,9-hexahydropyrazolo[5,1-b]quinazoline-3-carbonitrile | 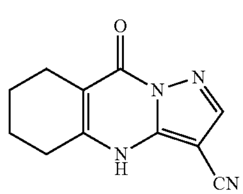 [SMILES: N#Cc1cnn2c(=O)c3c([nH]c12)CCCC3] | $^1$H NMR (300 MHz, DMSO-d6) δ 13.07 (s, 1H), 8.32 (s, 1H), 2.66 (m, 2H), 2.42 (m, 2H), 1.72 (m, 4H). |
| 6-isopropyl-2,5-dimethyl-7-oxo-4,7-dihydropyrazolo[1,5-a]pyrimidine-3-carbonitrile | 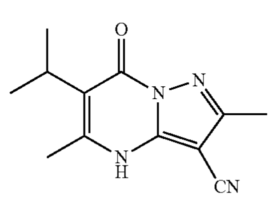 [SMILES: Cc1nn2c(=O)c(C(C)C)c(C)[nH]c2c1C#N] | $^1$H-NMR (300 MHz, CD$_3$COCD$_3$) δ 3.11 (m, 1H), 2.49 (s, 3H), 2.36 (s, 1H) 1.34 (d, J = 6.9 Hz, 6H); m/z (ESI) 231 [M + H]$^+$. |

TABLE 4-continued

| Compound Name | Structure | Data |
|---|---|---|
| 6-propyl-2,5-dimethyl-7-oxo-4,7-dihydropyrazolo[1,5-a]pyrimidine-3-carbonitrile | 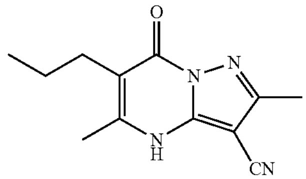 [SMILES: CCCc1c(C)[nH]c2c(C#N)c(C)nn2c1=O] | $^1$H NMR (300 MHz, CD$_3$COCD$_3$) δ 2.54 (t, J = 7.5 Hz, 2H), 2.49 (s, 3H), 2.36 (s, 3H), 2.06 (m, 2H), 1.55 (m, 2H), 0.96 (t, J = 7.5 Hz, 3H); m/z (ESI) 231 [M + H]$^+$. |
| 6-isopropyl-5-methyl-7-oxo-4,7-dihydropyrazolo[1,5-a]pyrimidine-3-carbonitrile | 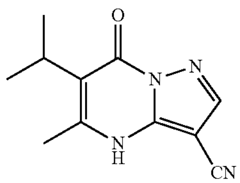 [SMILES: Cc1[nH]c2c(C#N)cnn2c(=O)c1C(C)C] | $^1$H NMR (300 MHz, DMSO-d6) δ 7.93 (s, 1H), 3.02 (m, 1H), 2.26 (s, 3H), 1.27 (d, J = 7.2 Hz, 6H); m/z (ESI) 217 [M + H]$^+$. |
| 6-propyl-5-methyl-7-oxo-4,7-dihydropyrazolo[1,5-a]pyrimidine-3-carbonitrile | 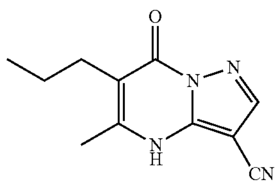 [SMILES: CCCc1c(C)[nH]c2c(C#N)cnn2c1=O] | $^1$H NMR (300 MHz, DMSO-d6) δ 13.07 (s, 1H), 8.35 (s, 1H), 2.47 (m, 2H), 2.38 (s, 3H), 1.46 (q, J = 7.5 Hz, 2H), 0.92 (t, J = 7.5 Hz, 3H); m/z (ESI) 217 [M + H]$^+$. |
| 6-ethyl-5-(methoxymethyl)-2-methyl-7-oxo-4,7-dihydropyrazolo[1,5-a]pyrimidine-3-carbonitrile | 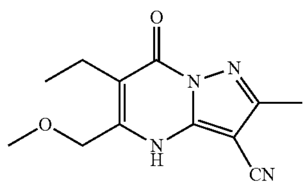 | $^1$H NMR (300 MHz, DMSO) δ 4.26 (s, 2H), 3.27 (s, 3H), 2.48 (m, 2H), 2.29 (s, 3H), 1.01 (t, J = 7.2 Hz, 3H); m/z (ESI) 247 [M + H]$^+$. |
| 6-ethyl-5-(methoxymethyl)-7-oxo-4,7-dihydropyrazolo[1,5-a]pyrimidine-3-carbonitrile | 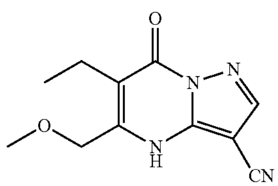 [SMILES: CCc1c(COC)[nH]c2c(C#N)cnn2c1=O] | $^1$H NMR (300 MHz, CD$_3$COCD$_3$) δ 7.93 (s, 1H), 4.40 (s, 2H), 3.34 (s, 3H), 2.65 (q, J = 7.5 Hz, 2H), 1.12 (t, J = 7.5 Hz, 3H); m/z (ESI) 233 [M + H]$^+$. |
| ethyl 3-cyano-6-ethyl-2-methyl-7-oxo-4,7-dihydropyrazolo[1,5-a]pyrimidine-5-carboxylate | 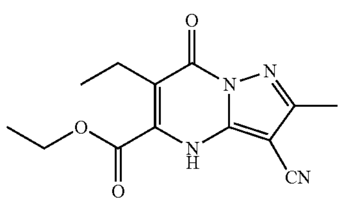 [SMILES: CCOC(=O)c1[nH]c2c(C#N)c(C)nn2c(=O)c1CC] | $^1$H NMR (300 MHz, CD$_3$OD) δ 4.52 (q, J = 7.2 Hz, 2H), 2.82 (q, J = 7.2 Hz, 2H), 2.50 (s, 3H), 1.47 (t, J = 7.2 Hz, 3H), 1.21 (t, J = 7.5 Hz, 3H); m/z (ESI) 275 [M + H]$^+$. |
| ethyl 3-cyano-6-ethyl-7-oxo-4,7-dihydropyrazolo[1,5-a]pyrimidine-5-carboxylate | 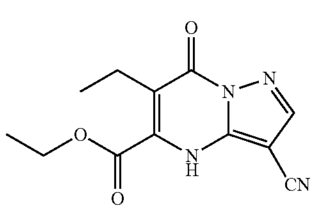 [SMILES: CCOC(=O)c1[nH]c2c(C#N)cnn2c(=O)c1CC] | $^1$H NMR (300 MHz, CD$_3$OD) δ 8.26 (s, 1H), 4.44 (q, J = 7.2 Hz, 2H), 2.70 (q, J = 6.9 Hz, 2H), 1.42 (t, J = 7.2 Hz, 3H), 1.17 (t, J = 7.2 Hz, 3H); m/z (ESI) 262 [M + H]$^+$. |
| 6-ethyl-5-methyl-7-oxo-4,7-dihydro-[1,2,3]triazolo[1,5-a]pyrimidine-3-carbonitrile | 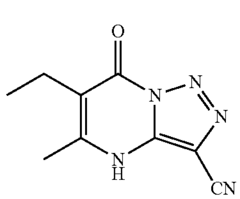 | $^1$H NMR (300 MHz, CD$_3$OD) δ 2.82 (s, 3H), 2.69 (q, J = 7.5 Hz, 2H), 1.20 (t, J = 7.5 Hz, 3H); m/z (ESI) 204 [M + H]$^+$. |

TABLE 4-continued

| Compound Name | Structure | Data |
| --- | --- | --- |
| 5-methyl-7-oxo-6-propyl-4,7-dihydro-[1,2,3]triazolo[1,5-a]pyrimidine-3-carbonitrile | 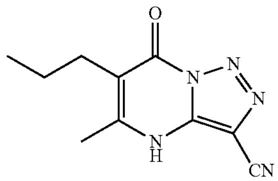 | $^1$H NMR (300 MHz, CD$_3$OD) δ 2.82 (s, 3H), 2.65 (t, J = 7.5 Hz, 3H), 1.63 (m, 2H), 1.06 (t, J = 7.2 Hz, 3H); m/z (ESI) 218 [M + H]$^+$. |
| 5-(methoxymethyl)-7-oxo-6-propyl-4,7-dihydropyrazolo[1,5-a]pyrimidine-3-carbonitrile | 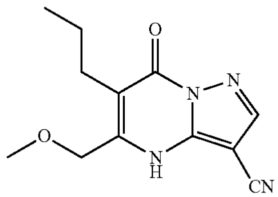 [SMILES: CCCc1c(COC)[nH]c2c(C#N)cnn2c1=O] | $^1$H NMR (300 MHz, CD$_3$OD) δ 8.29 (s, 1H), 4.78 (s, 2H), 3.59 (s, 3H), 2.63 (m, 2H), 1.64 (m, 2H), 1.05 (t, J = 7.5 Hz, 3H); m/z (ESI) 247 [M + H]$^+$. |
| 5-(ethoxymethyl)-6-ethyl-7-oxo-4,7-dihydropyrazolo[1,5-a]pyrimidine-3-carbonitrile | 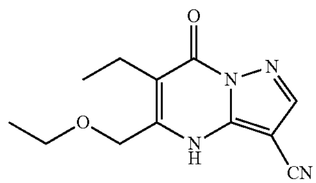 [SMILES: CCOCc1[nH]c2c(C#N)cnn2c(=O)c1CC] | $^1$HNMR (300 MHz, CD$_3$OD) δ 8.27 (s, 1H), 4.64 (s, 2H), 3.71 (q, J = 7.2 Hz, 2H), 2.69 (q, J = 7.5 Hz, 2H), 1.32 (t, J = 7.2 Hz, 3H), 1.20 (t, J = 7.5 Hz, 3H); m/z (ESI) 247 [M + H]$^+$. |
| 6-(2-methoxyethyl)-5-methyl-7-oxo-4,7-dihydropyrazolo[1,5-a]pyrimidine-3-carbonitrile | 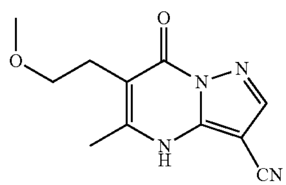 [SMILES: COCCc1c(C)[nH]c2c(C#N)cnn2c1=O] | $^1$H NMR (300 MHz, CD$_3$OD) δ 8.26 (s, 1H), 3.62 (t, J = 6.6 Hz, 2H), 3.39 (s, 3H), 2.93 (t, J = 6.6 Hz, 2H), 2.55 (s, 3H); m/z (ESI) 233 [M + H]$^+$. |
| 6-ethyl-5-(3-methoxypropyl)-7-oxo-4,7-dihydropyrazolo[1,5-a]pyrimidine-3-carbonitrile | 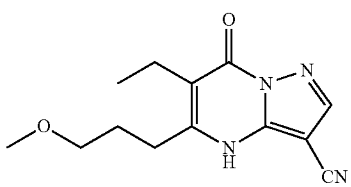 [SMILES: CCc1c(CCCOC)[nH]c2c(C#N)cnn2c1=O] | $^1$H NMR (300 MHz, CD$_3$Cl) δ 11.87 (brs, 1H), 8.01 (s, 1H), 3.65 (m, 2H), 3.63 (s, 3H), 2.96 (m, 2H), 2.66 (q, J = 7.5 Hz, 2H), 2.08 (m, 2H), 1.13 (t, J = 7.5 Hz, 3H); m/z (ESI) 261 [M + H]$^+$. |
| 5-methyl-7-oxo-6-(prop-2-ynyl)-4,7-dihydropyrazolo[1,5-a]pyrimidine-3-carbonitrile | 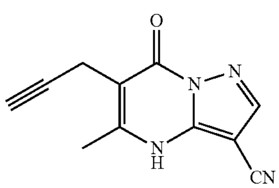 [SMILES: C#CCc1c(C)[nH]c2c(C#N)cnn2c1=O] | $^1$HNMR (300 MHz, CD$_3$OD) δ 8.26 (s, 1H), 3.58 (d, J = 2.7 Hz, 2H), 2.59 (s, 3H), 2.37 (t, J = 2.7 Hz, 1H); m/z (ESI) 235 [M + Na]$^+$. |
| 6-allyl-5-(methoxymethyl)-7-oxo-4,7-dihydropyrazolo[1,5-a]pyrimidine-3-carbonitrile | 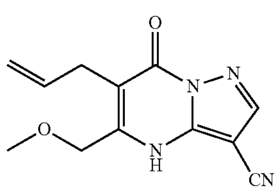 [SMILES: C=CCc1c(COC)[nH]c2c(C#N)cnn2c1=O] | $^1$HNMR (300 MHz, CD$_3$Cl) δ 9.38 (brs, 1H), 8.07 (s, 1H), 5.83 (m, 1H), 5.08 (m, 2H), 4.55 (s, 2H), 3.63 (s, 3H), 3.29 (d, J = 6.3 Hz, 2H); m/z (ESI) 267 [M + Na]$^+$. |
| 6-ethyl-7-oxo-5-phenyl-4,7-dihydropyrazolo[1,5-a]pyrimidine-3-carbonitrile | 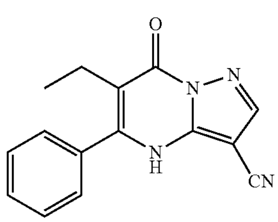 [SMILES: CCc1c(-c2ccccc2)[nH]c2c(C#N)cnn2c1=O] | $^1$HNMR (300 MHz, CD$_3$OD) δ 8.30 (s, 1H), 7.64-7.57 (5H), 2.49 (q, J = 7.2 Hz, 2H), 1.14 (t, J = 7.2 Hz, 3H); m/z (ESI) 265 [M + H]$^+$. |

TABLE 4-continued

| Compound Name | Structure | Data |
|---|---|---|
| 5-benzyl-6-ethyl-7-oxo-4,7-dihydropyrazolo[1,5-a]pyrimidine-3-carbonitrile | 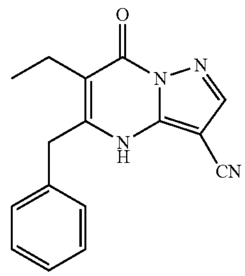 [SMILES: CCc1c(Cc2ccccc2)[nH]c2c(C#N)cnn2c1=O] | ¹HNMR (300 MHz, CD₃OD) δ 8.26 (s, 1H), 7.39-7.27 (5H), 4.20 (s, 2H), 2.65 (q, J = 7.5 Hz, 2H), 1.03 (t, J = 7.5 Hz, 3H); m/z (ESI) 279 [M + H]⁺. |
| benzyl 3-cyano-6-ethyl-7-oxo-4,7-dihydropyrazolo[1,5-a]pyrimidine-5-carboxylate | 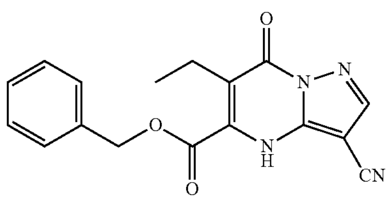 | ¹HNMR (300 MHz, CD₃OD) δ 8.22 (s, 1H), 7.56-7.42 (5H), 5.51 (s, 2H), 2.79 (q, J = 7.2 Hz, 2H), 1.12 (t, J = 7.2 Hz, 3H); m/z (ESI) 245 [M + Na]⁺. |
| ethyl 3-cyano-7-oxo-6-propyl-4,7-dihydropyrazolo[1,5-a]pyrimidine-5-carboxylate | 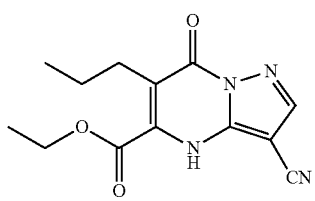 [SMILES: CCCc1c(C(=O)OCC)[nH]c2c(C#N)cnn2c1=O] | ¹HNMR (300 MHz, CD₃OD) δ 8.17 (s, 1H), 4.43 (q, J = 7.2 Hz, 2H), 2.62 (t, J = 7.5 Hz, 2H), 1.62 (m, 2H), 1.44 (t, J = 7.2 Hz, 3H), 0.97 (t, J = 7.5 Hz, 3H); m/z (ESI) 275 [M + H]⁺. |
| 6-ethyl-7-oxo-5-(trifluoromethyl)-4,7-dihydropyrazolo[1,5-a]pyrimidine-3-carbonitrile | 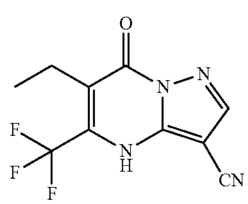 [SMILES: CCc1c(C(F)(F)F)[nH]c2c(C#N)cnn2c1=O] | ¹HNMR (300 MHz, CD₃OD) δ 8.08 (s, 1H), 2.63 (q, J = 7.2 Hz, 2H), 1.06 (t, J = 7.2 Hz, 3H); m/z (ESI) 257 [M + H]⁺. |
| 6-allyl-5-methyl-7-oxo-4,7-dihydropyrazolo[1,5-a]pyrimidine-3-carbonitrile | 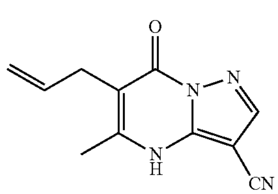 [SMILES: C=CCc1c(C)[nH]c2c(C#N)cnn2c1=O] | ¹H NMR (300 MHz, DMSO) δ 13.18 (s, 1H), 8.37 (s, 1H), 5.83 (m, 1H), 5.02 (m, 2H), 3.29 (m, 2H), 2.35 (s, 3H); m/z (ESI) 215 [M + H]⁺. |
| 6-isobutyl-5-methyl-7-oxo-4,7-dihydropyrazolo[1,5-a]pyrimidine-3-carbonitrile | 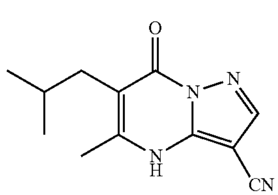 [SMILES: Cc1[nH]c2c(C#N)cnn2c(=O)c1CC(C)C] | ¹H NMR (300 MHz, DMSO-d₆) δ 13.16 (brs, 1H), 8.30 (s, 1H), 2.39-2.34 (5H), 1.86 (m, 1H), 0.85 (d, J = 6.6 Hz, 6H); m/z (ESI) 231 [M + H]⁺. |

TABLE 4-continued

| Compound Name | Structure | Data |
|---|---|---|
| 6-ethyl-5-(furan-3-yl)-7-oxo-4,7-dihydropyrazolo[1,5-a]pyrimidine-3-carbonitrile | 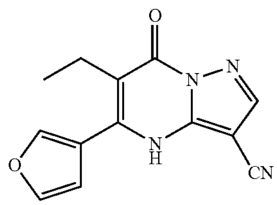 [SMILES: CCc1c(-c2ccoc2)[nH]c2c(C#N)cnn2c1=O] | ¹HNMR (300 MHz, CD₃OD) δ 8.28 (s, 1H), 8.05 (dd, J = 1.8 Hz, 0.9 Hz, 1H), 7.79 (m, 1H), 6.84 (dd, J = 1.8 Hz, 0.9 Hz, 1H), 2.66 (q, J = 7.5 Hz, 2H), 1.20 (t, J = 7.2 Hz, 3H); m/z (ESI) 277 [M + Na]⁺. |
| 7-oxo-5-(trifluoromethyl)-4,7-dihydropyrazolo[1,5-a]pyrimidine-3-carbonitrile | 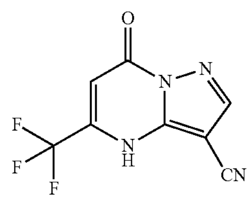 [SMILES: N#Cc1cnn2c(=O)cc(C(F)(F)F)[nH]c12] | ¹HNMR (300 MHz, CD₃OD) δ 8.36 (s, 1H), 6.53 (s, 1H); m/z (ESI) 251 [M + Na]⁺. |
| 6-cyclopropyl-5-methyl-7-oxo-4,7-dihydropyrazolo[1,5-a]pyrimidine-3-carbonitrile | 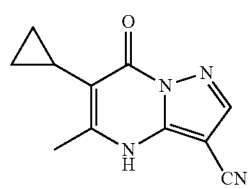 [SMILES: Cc1[nH]c2c(C#N)cnn2c(=O)c1C1CC1] | ¹HNMR (300 MHz, CD₃OD) δ 8.19 (s, 1H), 2.59 (s, 3H), 1.33 (m, 1H), 1.01 (m, 2H), 0.73 (m, 2H); m/z (ESI) 237 [M + Na]⁺. |

Example 442

Synthesis of 4-methyl-9-oxo-4,5,6,7,8,9-hexahydropyrazolo[5,1-b]quinazoline-3-carbonitrile

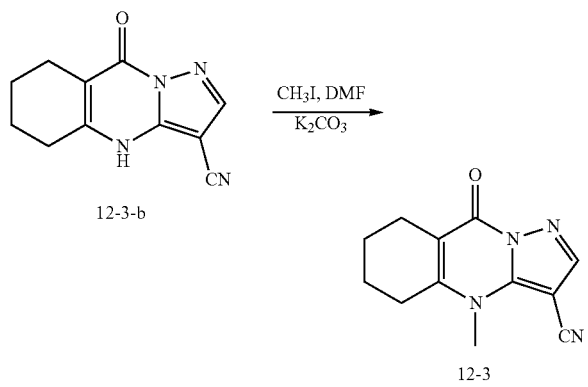

9-Oxo-4,5,6,7,8,9-hexahydropyrazolo[5,1-b]quinazoline-3-carbonitrile (50 mg, 0.23 mmol) was dissolved in DMF (1 mL), potassium carbonate (63 mg, 0.46 mmol) was added followed by iodomethane (36 mg, 0.26 mmol). The mixture was stirred at room temperature overnight, then diluted with water (10 mL) and extracted with EtOAc (5 mL×3). The combined organic layer was dried and concentrated to dryness. The residue was recrystallized from methanol to afford 12-3 (25 mg, 47%). ¹H NMR (300 MHz, CDCl₃) δ 8.07 (s, 1 H), 3.94 (s, 3 H), 2.69 (m, 4 H), 1.92 (m, 2 H), 1.76 (m, 2 H); m/z (ESI) 229 [M+H]⁺.

By a similar method to Example 442, using the appropriate starting material, 6-ethyl-4,5-dimethyl-7-oxo-4,7-dihydropyrazolo[1,5-a]pyrimidine-3-carbonitrile was prepared and isolated.

| Compound Name | Structure | Data |
|---|---|---|
| 6-ethyl-4,5-dimethyl-7-oxo-4,7-dihydropyrazolo[1,5-a]pyrimidine-3-carbonitrile | 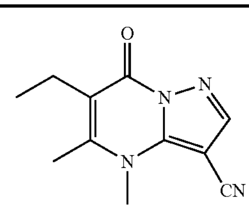 | ¹H NMR (300 MHz, CDCl₃) δ 8.09 (s, 1H), 4.00 (s, 3H), 2.71 (q, J = 7.5 Hz, 2H), 2.48 (s, 3H), 1.14 (t, J = 7.5 Hz, 3H); m/z (ESI) 217 [M + H]⁺. |

Example 443

Synthesis of 4-(2-bromoethyl)-6-ethyl-5-methyl-7-oxo-4,7-dihydropyrazolo[1,5-a]pyrimidine-3-carbonitrile

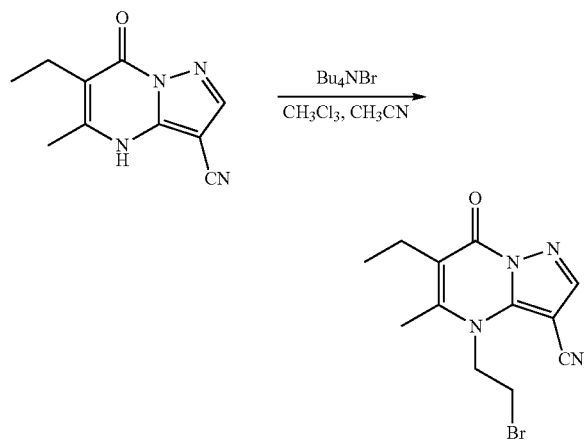

To a solution of tetrabutylammoniunbromide (557 mg, 1.73 mmol) in water (20 mL), NaOH (76 mg, 1.9 mmol) was added at ambient temperature, followed by 6-ethyl-5-methyl-7-oxo-4,7-dihydropyrazolo[1,5-a]pyrimidine-3-carbonitrile (350 mg, 1.73 mmol) in CHCl₃ (20 mL), the mixture continued to stir for 10 min. The organic phase was separated, the aqueous phase was extracted with CHCl₃ (10 mL). The combined organic phase was dried over anhydrous Na₂SO₄, evaporated to give white solid. The solid was dissolved in CH₃CN (10 mL), followed by 1,2-dibromoethane (360 mg, 2 mmol). The mixture continued to stir for 16 h at refluxing temperature, followed by concentration and purification with column chromatography to give 4-(2-bromoethyl)-6-ethyl-5-methyl-7-oxo-4,7-dihydropyrazolo[1,5-a]pyrimidine-3-carbonitrile (200 mg, 40%). m/z (ESI) 309 [M+H]⁺.

Example 444

Synthesis of 4-(2-(dimethylamino)ethyl)-6-ethyl-5-methyl-7-oxo-4,7-dihydropyrazolo[1,5-a]pyrimidine-3-carbonitrile

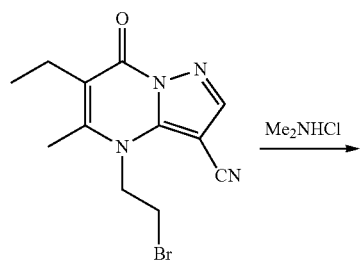

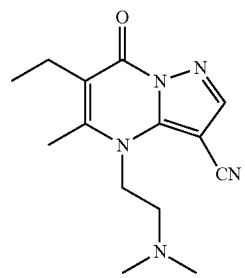

To a solution of 4-(2-bromoethyl)-6-ethyl-5-methyl-7-oxo-4,7-dihydropyrazolo[1,5-a]pyrimidine-3-carbonitrile (200 mg, 0.65 mmol) in DMF (10 mL) were added potassium carbonate (446 mg, 3.24 mmol) and dimethylamine hydrochloride (155 mg, 1.94 mmol) consequently. The mixture was stirred at room temperature overnight, then diluted with water (10 mL) and extracted with EtOAc (10 mL×3). The combined organic layer was dried with Na₂SO₄, concentrated and purified by column chromatography to afford 4-(2-(dimethylamino)ethyl)-6-ethyl-5-methyl-7-oxo-4,7-dihydropyrazolo[1,5-a]pyrimidine-3-carbonitrile (12 mg, 10%). ¹H NMR (300 MHz, CD₃OD) δ 8.29 (s, 1 H), 4.52 (t, J=7.2 Hz, 2 H), 2.83 (t, J=7.2 Hz, 2H), 2.72 (q, J=7.5 Hz, 2 H), 2.61 (s, 3 H), 2.39 (s, 6H) 1.15 (t, J=7.5 Hz, 3 H); m/z (ESI) 274 [M+H]⁺.

Example 445

Synthesis of 9-methoxy-5,6,7,8-tetrahydropyrazolo[5,1-b]quinazoline-3-carbonitrile

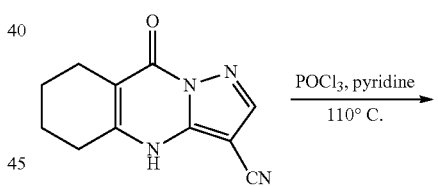

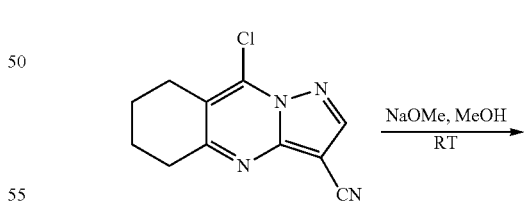

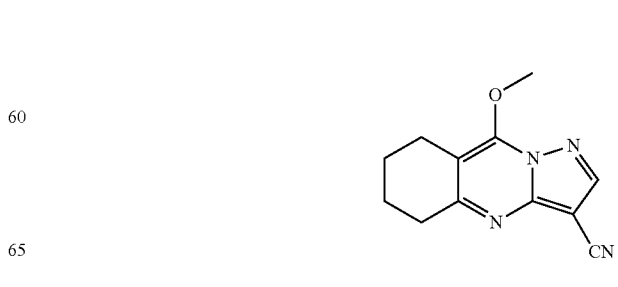

Synthesis of 9-chloro-5,6,7,8-tetrahydropyrazolo[5,1-b]quinazoline-3-carbonitrile

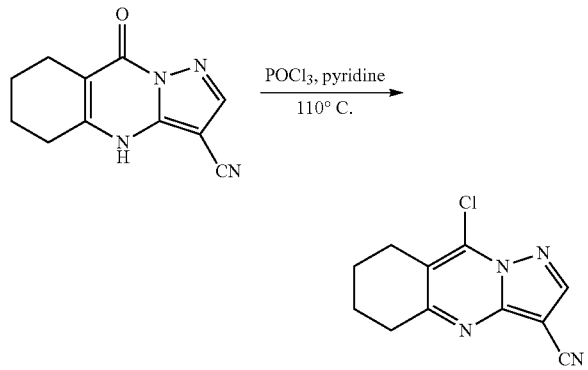

To a solution of 9-oxo-4,5,6,7,8,9-hexahydropyrazolo[5,1-b]quinazoline-3-carbonitrile (1.0 g, 4.6 mmol) in dry POCl₃ (20 mL) was added pyridine (0.2 mL) under a nitrogen atmosphere, the mixture was heated to 110° C. overnight. After cooling down to room temperature, the solvent was removed in vacuo, and the residue was purified by silica gel column chromatography to yield the desired compound 9-chloro-5,6,7,8-tetrahydropyrazolo[5,1-b]quinazoline-3-carbonitrile (0.6 g, yield 56%). $^1$H NMR (300 MHz, CDCl₃) δ 8.36 (s, 1H), 3.10 (m, 2H), 2.93 (m, 2H), 1.96 (m, 4H).

Synthesis of 9-methoxy-5,6,7,8-tetrahydropyrazolo[5,1-b]quinazoline-3-carbonitrile

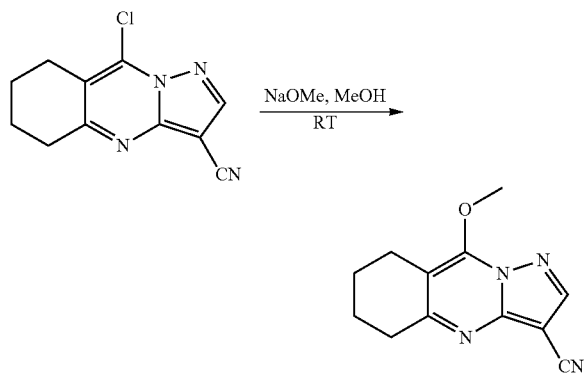

A mixture of 9-chloro-5,6,7,8-tetrahydropyrazolo[5,1-b]quinazoline-3-carbonitrile (100 mg, 0.43 mmol) and MeONa (48 mg, 0.86 mmol) in MeOH (4 mL) was stirred at room temperature for 1.5 hour, and the reaction was quenched by saturated NH₄Cl, and extracted with DCM (50 mL×3). The organic layer was washed by brine, dried over Na₂SO₄, concentrated in vacuo, and crude product was purified by preparation thick layer chromatography to yield the desired compound 9-methoxy-5,6,7,8-tetrahydropyrazolo[5,1-b]quinazoline-3-carbonitrile (20 mg, yield 21%) as a white solid. $^1$H NMR (300 MHz, CDCl₃) δ 8.25 (s, 1H), 4.44 (s, 3H), 3.02 (t, J=6.3 Hz, 2H), 2.80 (t, J=6.3 Hz, 2H), 1.89 (m, 4H); m/z (ESI) 229 [M+H]⁺.

By a similar method to Example 445, using the appropriate starting material, 6-ethyl-7-methoxy-5-methylpyrazolo[1,5-a]pyrimidine-3-carbonitrile was prepared and isolated.

| Compound Name | Structure | Data |
|---|---|---|
| 6-ethyl-7-methoxy-5-methylpyrazolo[1,5-a]pyrimidine-3-carbonitrile | ![structure] | $^1$H NMR (300 MHz, CDCl₃) δ 8.28 (s, 1H), 4.43 (s, 3H), 2.77 (q, J = 7.8 Hz, 2H), 2.70 (s, 3H), 1.23 (t, J = 7.5 Hz, 3H); m/z (ESI) 217 [M]⁺ |

Example 446

Synthesis of 9-(2-hydroxyethoxy)-5,6,7,8-tetrahydropyrazolo[5,1-b]quinazoline-3 carbonitrile

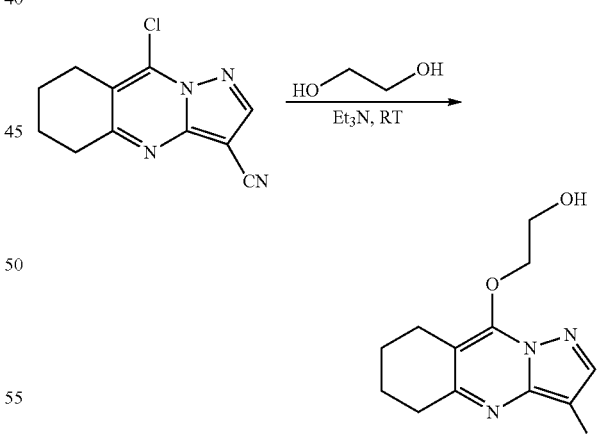

A mixture of 9-chloro-5,6,7,8-tetrahydropyrazolo[5,1-b]quinazoline-3-carbonitrile (100 mg, 0.43 mmol), Et₃N (0.7 mL) in ethane-1,2-diol (2 mL) was stirred at room temperature overnight. The reaction was diluted with EtOAc (2.0 mL). The addition of hexane (2 mL) led to the precipitation of the product. The product was filtered, washed with EtOAc to yield the desired compound 9-(2-hydroxyethoxy)-5,6,7,8-tetrahydropyrazolo[5,1-b]quinazoline-3 carbonitrile (2.0 mg, yield 2%) as a white solid. $^1$H NMR (300 MHz, CDCl₃)

δ 8.69 (s, 1H), 4.94 (t, J=5.1 Hz, 1H), 4.79 (t, J=4.5 Hz, 2H), 3.73 (m, 2H), 2.94 (t, J=5.7 Hz, 2H), 2.82 (t, J=6.3 Hz, 2H), 1.83 (m, 4H); m/z (ESI) 259 [M+H]⁺.

Example 447

Synthesis of 9-(2-methoxyethoxy)-5,6,7,8-tetrahydropyrazolo[5,1-b]quinazoline-3-carbonitrile

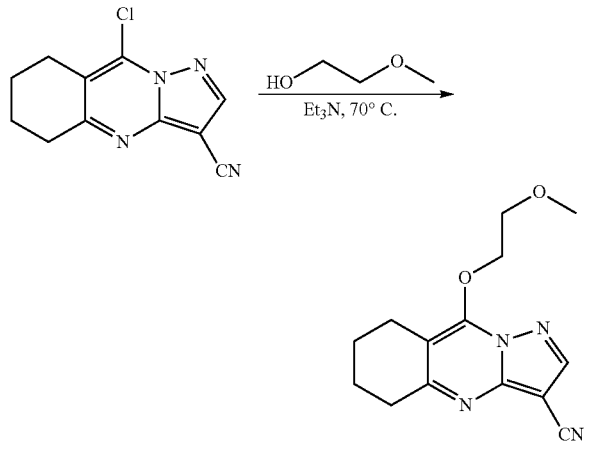

A mixture of 9-chloro-5,6,7,8-tetrahydropyrazolo[5,1-b]quinazoline-3-carbonitrile (100 mg, 0.43 mmol), Et₃N (0.7 mL) in 2-methoxyethanol (2 mL) was stirred at 70° C. overnight. The solvent was removed in vacuo, and the crude product was purified by preparation thin layer chromatography to yield the desired compound 9-(2-methoxyethoxy)-5,6,7,8-tetrahydropyrazolo[5,1-b]quinazoline-3-carbonitrile (10.0 mg, yield 9%) as a white solid. ¹H NMR (300 MHz, CDCl₃) δ 8.24 (s, 1H), 4.92 (m, 2H), 3.75 (m, 2H), 3.37 (s, 3H), 3.03 (t, J=6.0 Hz, 2H), 2.84 (t, J=6.0 Hz, 2H), 1.91 (m, 4H); m/z (ESI) 273 [M+H]⁺.

Example 448

Synthesis of 3-cyano-6-ethyl-N-methyl-7-oxo-4,7-dihydropyrazolo[1,5-a]pyrimidine-5-carboxamide

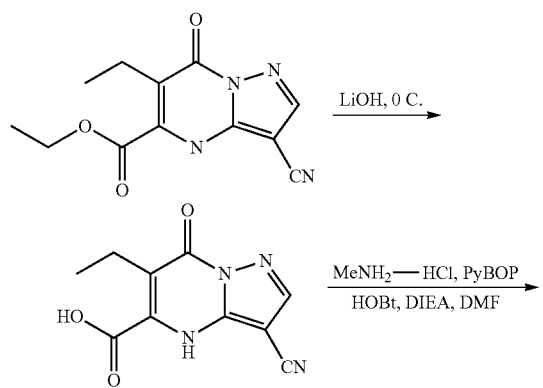

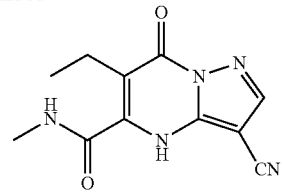

Synthesis of 3-cyano-6-ethyl-7-oxo-4,7-dihydropyrazolo[1,5-a]pyrimidine-5-carboxylic acid

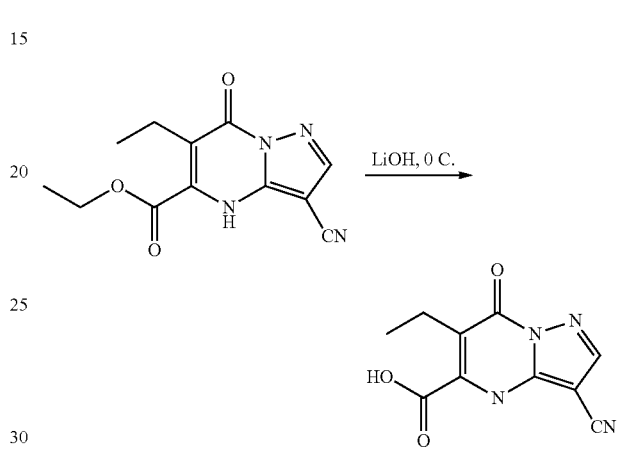

To a solution of ethyl 3-cyano-6-ethyl-7-oxo-4,7-dihydropyrazolo[1,5-a]pyrimidine-5-carboxylate (500 mg, 1.92 mmol) in EtOH (50 mL) and H₂O (5 mL) at 0° C., LiOH (230 mg, 9.6 mmol) was added in portions. The reaction mixture was stirred at room temperature for 2 h. After removal of EtOH in vacuo, water (5 mL) was added, and the mixture was filtered to produce 3-cyano-6-ethyl-7-oxo-4,7-dihydropyrazolo[1,5-a]pyrimidine-5-carboxylic acid (380 mg, 89%) as off-white solid. ¹H NMR (300 MHz, DMSO-d6) δ 8.41 (s, 1 H), 2.67 (q, J=6.9 Hz, 2H), 1.09 (t, J=6.9 Hz, 3H).

Synthesis of 3-cyano-6-ethyl-N-methyl-7-oxo-4,7-dihydropyrazolo[1,5-a]pyrimidine-5-carboxamide

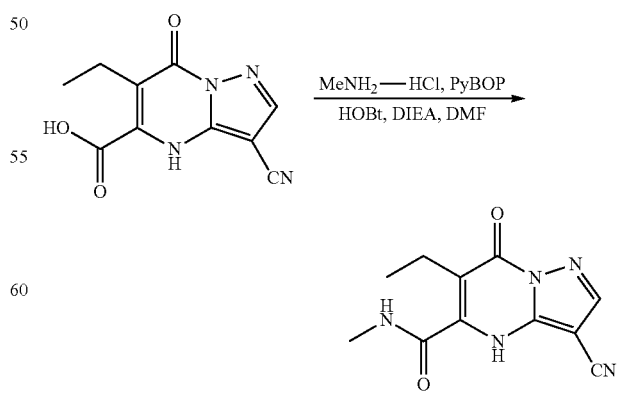

To a solution of 3-cyano-6-ethyl-7-oxo-4,7-dihydropyrazolo[1,5-a]pyrimidine-5-carboxylic acid (50 mg, 0.21 mmol), methanamine hydrochloride (15 mg, 0.21 mmol), PyBOP (105.20 mg, 0.21 mmol) and HOBT (41.85 mg, 0.31 mmol) in DMF (2 mL) was added DIEA (129 mg, 1 mmol). The reaction mixture was stirred at room temperature overnight. The mixture was diluted with $CH_2Cl_2$ and purified by column chromatography to produce 3-cyano-6-ethyl-N-methyl-7-oxo-4,7-dihydropyrazolo[1,5-a]pyrimidine-5-carboxamide (16 mg, 31%) as off-white solid. $^1$HNMR (300 MHz, $CD_3OD$) δ 8.16 (s, 1H), 2.95 (s, 3H), 2.79 (q, J=7.5 Hz, 2H), 1.20 (t, J=7.5 Hz, 3H); m/z (ESI) 246 $[M+H]^+$.

By a similar method to Example 448 above, using the ethanamine hydrochloride as reagent, 3-cyano-N,6-diethyl-7-oxo-4,7-dihydropyrazolo[1,5-a]pyrimidine-5-carboxamide was prepared and isolated.

| Compound Name | Structure | Data |
|---|---|---|
| 3-cyano-N,6-diethyl-7-oxo-4,7-dihydropyrazolo[1,5-a]pyrimidine-5-carboxamide | 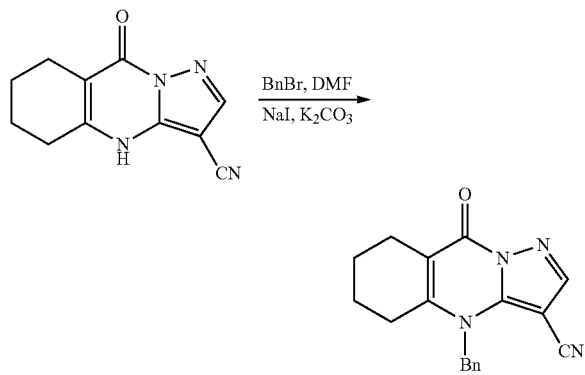 | $^1$HNMR (300 MHz, $CD_3OD$) δ 8.16 (s, 1H), 3.43 (q, J = 7.2 Hz, 2H), 2.77 (q, J = 7.5 Hz, 2H), 1.31 (t, J = 7.5 Hz, 3H), 1.21 (t, J = 7.2 Hz, 3H); m/z (ESI) 260 $[M + H]^+$. |

Example 449

Synthesis of 4-benzyl-9-oxo-4,5,6,7,8,9-hexahydropyrazolo[5,1-b]quinazoline-3-carbonitrile To solution of 9-oxo-4,5,6,7,8,9-hexahydropyrazolo[5,1-b]quinazoline-3-carbonitrile (50 mg, 0.23 mmol) in DMF (1 mL), potassium carbonate (63 mg, 0.46 mmol) and sodium iodide (5 mg, 3 mmol) were added followed by benzyl bromide (43 mg, 0.25 mmol). The mixture was stirred at room temperature overnight, then diluted with water (10 mL) and extracted with EtOAc (5 mL×3). The combined organic layer was dried and concentrated to dryness. The residue was purified by thick layer chromatography on silica gel to afford 4-benzyl-9-oxo-4,5,6,7,8,9-hexahydropyrazolo[5,1-b]quinazoline-3-carbonitrile (25 mg, 35%). $^1$H NMR (300 MHz, $CDCl_3$) δ 8.03 (s, 1 H), 7.38 (m, 3 H), 7.04 (d, J=5.6 Hz, 2 H), 5.56 (s, 2 H), 2.68 (m, 4 H), 1.79 (m, 4 H); m/z (ESI) 305 $[M+H]^+$.

Example 450

Synthesis of 9-oxo-4-phenyl-4,5,6,7,8,9-hexahydropyrazolo[5,1-b]quinazoline-3-carbonitrile

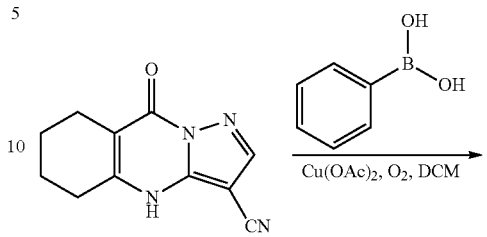

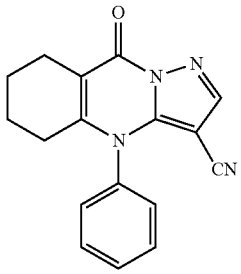

To a solution of 9-oxo-4,5,6,7,8,9-hexahydropyrazolo[5,1-b]quinazoline-3-carbonitrile (645 mg, 3 mmol) in $CH_2Cl_2$ (20 mL) was added $Cu(OAc)_2$, 4 A molecular sieve, $Et_3N$ (607 mg, 6 mmol) and pyridine (474 mg, 6 mmol) consequently, the solution was stirred for 2 days under $O_2$. To the mixture was added $NH_3H_2O$ and adjusted to PH>8. After filtration, the solution was concentrated and purified by column chromatography to give 9-oxo-4-phenyl-4,5,6,7,8,9-hexahydropyrazolo[5,1-b]quinazoline-3-carbonitrile (60 mg, 10%) as white solid. $^1$H NMR (300 MHz, $CD_3Cl$) δ 7.99 (s, 1H), 7.52-7.36 (5H), 2.81 (m, 2H), 2.52 (m, 2H), 1.80 (m, 4H); m/z (ESI) 291 $[M+H]^+$.

Example 451

Synthesis of 6-ethyl-5-(hydroxymethyl)-2-methyl-7-oxo-4,7-dihydropyrazolo[1,5-a]pyrimidine-3-carbonitrile

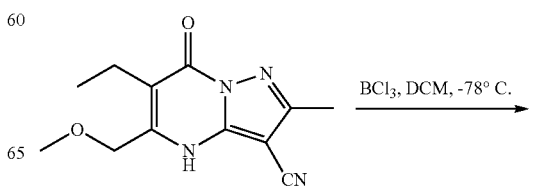

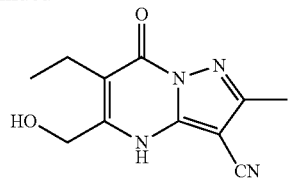

To a solution of 6-ethyl-5-(methoxymethyl)-2-methyl-7-oxo-4,7-dihydropyrazolo[1,5-a]pyrimidine-3-carbonitrile (50 mg, 0.2 mmoL) in CH$_2$Cl$_2$ (20 mL) at −78° C., BCl$_3$ (1 mL, 1 mmol) was added dropwise, the mixture continued to stir at −78° C. for 2 h, then allowed to room temperature for 16 h. The mixture was quenched by water, and the aqueous phase was washed by CH$_2$Cl$_2$ (20 mL×3). After removal of water, the residue was washed with CH$_2$Cl$_2$/MeOH (50 mL, V/V=20/1) and filtered. The solution was concentrated and purified by column chromatography to give 6-ethyl-5-(hydroxymethyl)-2-methyl-7-oxo-4,7-dihydropyrazolo[1,5-a]pyrimidine-3-carbonitrile (10 mg, 23% yield) as off-white solid. $^1$H NMR (300 MHz, CD$_3$OD) δ 4.71 (s, 2H), 2.61 (m, 2H), 2.49 (s, 3H), 1.56 (t, J=7.2 Hz, 3H); m/z (ESI) 233 [M+H]$^+$.

By a similar method to Example 451 above, using the appropriate starting materials, the compounds in Table 5 were prepared and isolated.

TABLE 5

| Compound Name | Structure | Data |
|---|---|---|
| 6-ethyl-5-(hydroxymethyl)-7-oxo-4,7-dihydropyrazolo[1,5-a]pyrimidine-3-carbonitrile | 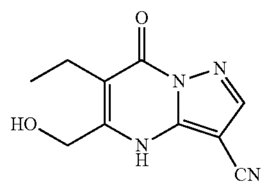 [SMILES: CCc1c(CO)[nH]c2c(C#N)cnn2c1=O] | $^1$H NMR (300 MHz, CD$_3$OD) δ 8.24 (s, 1H), 4.73 (s, 2H), 2.64 (m, 2H), 1.17 (t, J = 7.5 Hz, 3H); m/z (ESI) 219 [M + H]$^+$ |
| 5-(hydroxymethyl)-7-oxo-6-propyl-4,7-dihydropyrazolo[1,5-a]pyrimidine-3-carbonitrile | 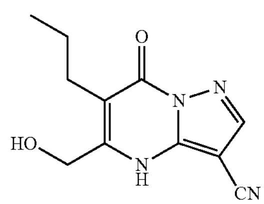 [SMILES: CCCc1c(CO)[nH]c2c(C#N)cnn2c1=O] | $^1$H NMR (300 MHz, CD$_3$OD) δ 8.30 (s, 1H), 4.78 (s, 2H), 2.63 (m, 2H), 1.64 (m, 2H), 1.06 (t, J = 7.5 Hz, 3H); m/z (ESI) 233 [M + H]$^+$ |
| 6-(2-hydroxyethyl)-5-methyl-7-oxo-4,7-dihydropyrazolo[1,5-a]pyrimidine-3-carbonitrile | 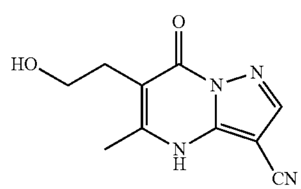 [SMILES: Cc1[nH]c2c(C#N)cnn2c(=O)c1CCO] | $^1$H NMR (300 MHz, DMSO-d6) δ 13.08 (s, 1H), 8.35 (s, 1H), 4.61 (brs, 1H), 3.50 (m, 2H), 2.63 (t, J = 6.6 Hz, 2H), 2.39 (s, 3H); m/z (ESI) 219 [M + H]$^+$. |
| 6-ethyl-5-(3-hydroxypropyl)-7-oxo-4,7-dihydropyrazolo[1,5-a]pyrimidine-3-carbonitrile | 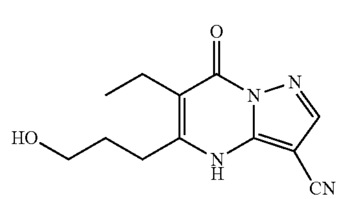 [SMILES: CCc1c(CCCO)[nH]c2c(C#N)cnn2c1=O] | $^1$H NMR (300 MHz, CD$_3$OD) δ 8.22 (s, 1H), 3.70 (t, J = 6.0 Hz, 2H), 2.86 (m, 2H), 2.65 (q, J = 7.5 Hz, 2H), 1.93 (m, 2H), 1.19 (t, J = 7.5 Hz, 3H); m/z (ESI) 247 [M + H]$^+$ |
| 6-allyl-5-(hydroxymethyl)-7-oxo-4,7-dihydropyrazolo[1,5-a]pyrimidine-3-carbonitrile | 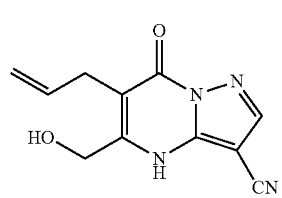 [SMILES: C=CCc1c(CO)[nH]c2c(C#N)cnn2c1=O] | $^1$HNMR (300 MHz, CD$_3$OD) δ 8.26 (s, 1H), 5.94 (m, 1H), 5.08 (m, 2H), 4.71 (s, 2H), 3.41 (d, J = 6.0 Hz, 2H); m/z (ESI) 253 [M + Na]$^+$. |

Example 452

Synthesis of 6-ethyl-5-oxo-5,7,8,9-tetrahydropyrazolo[1,5-a]pyrrolo[1,2-]pyrimidine-1-carbonitrile

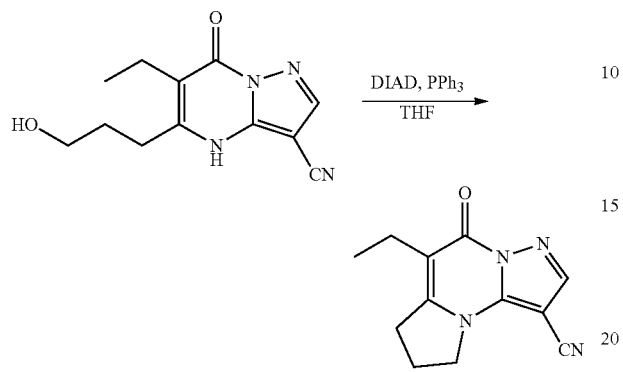

To a solution of 6-ethyl-4,7-dihydro-5-(3-hydroxypropyl)-7-oxopyrazolo[1,5-a]pyrimidine-3-carbonitrile (12 mg, 0.05 mmol) in THF (10 mL) was added DIAD (10 mg, 0.06 mmol) and PPh₃ (16 mg, 0.06 mmol) at 0° C. The mixture was allowed to room temperature and stirred for overnight. The mixture was evaporated in vacuo, purified by column chromatography to give 6-ethyl-5-oxo-5,7,8,9-tetrahydropyrazolo[1,5-a]pyrrolo[1,2-c]pyrimidine-1-carbonitrile (5 mg, 43.8%). $^1$H NMR (300 MHz, CD₃OD) δ 8.24 (s, 1 H), 4.55 (t, J=7.5 Hz, 2 H), 3.23 (t, J=7.8 Hz, 2 H), 2.60 (q, J=7.5 Hz, 2 H), 2.47 (m, 2 H), 1.18 (t, J=7.5 Hz, 3H); m/z (ESI) 229 [M+H]⁺.

Example 453

Synthesis of 6-ethyl-5-formyl-7-oxo-4,7-dihydropyrazolo[1,5-a]pyrimidine-3-carbonitrile

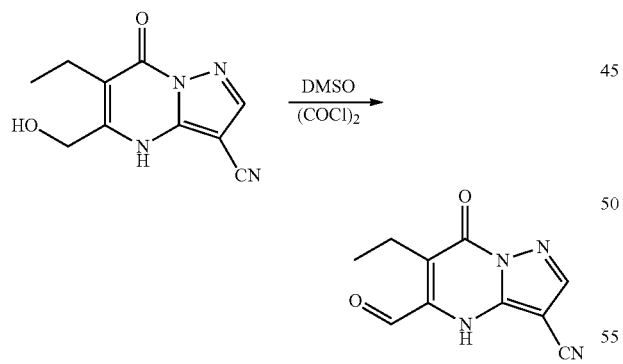

To a solution of DMSO (780 mg, 5 mmol) in CH₂Cl₂ (20 mL) was added dropwise oxalyl dichloride (127 mg, 5 mmol) at −78° C., then continued to stir for 30 min. 6-ethyl-5-(hydroxymethyl)-7-oxo-4,7-dihydropyrazolo[1,5-a]pyrimidine-3-carbonitrile (110 mg, 0.5 mmol) in CH₂Cl₂ (5 mL) was added dropwise. After stirring for 1 h, Et₃N (1.5 g, 15 mmol) was added dropwise and allowed to ambient temperature. The mixture was quenched by water, extracted with CH₂Cl₂ (10 mL×3), combined organic layer was dried over anhydrous Na₂SO₄ and evaporated. The crude was purified by column chromatography to give 6-ethyl-5-formyl-7-oxo-4,7-dihydropyrazolo[1,5-a]pyrimidine-3-carbonitrile (50 mg, 50%) as yellow solid. $^1$H NMR (300 MHz, CD₃Cl) δ 10.12 (s, 1H), 8.32 (s, 1H), 3.04 (q, J=7.2 Hz, 2H), 1.23 (t, J=7.2 Hz, 3H); m/z (ESI) 217 [M+H]⁺.

Example 454

Synthesis of 6-ethyl-5-(1-hydroxyethyl)-7-oxo-4,7-dihydropyrazolo[1,5-a]pyrimidine-3-carbonitrile

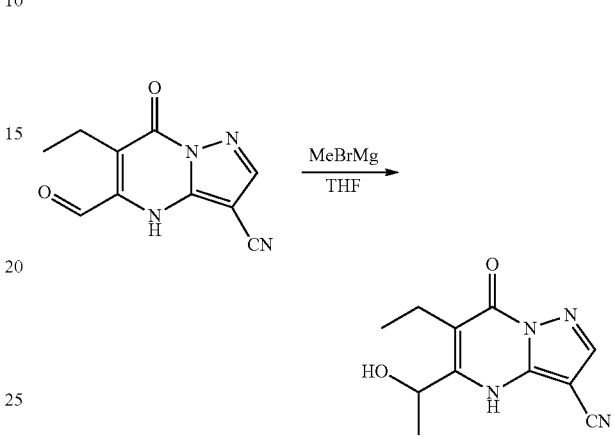

To a solution of 6-ethyl-5-formyl-7-oxo-4,7-dihydropyrazolo[1,5-a]pyrimidine-3-carbonitrile (50 mg, 0.23 mmol) in THF (10 mL) at −60° C., CH₃MgBr (0.7 mL, 0.68 mmol) was added dropwise, and continued to stir for 1 h. The mixture was quenched by saturated NH₄Cl, and extracted by CH₂Cl₂ (20 mL×5). Combined organic layer was dried over anhydrous Na₂SO₄ and evaporated. The residue was purified by column chromatography to give 6-ethyl-5-(1-hydroxyethyl)-7-oxo-4,7-dihydropyrazolo[1,5-a]pyrimidine-3-carbonitrile (5 mg, 15%) as white solid. $^1$H NMR (300 MHz, CD₃OD) δ 8.29 (s, 1H), 5.22 (m, 1H), 2.65 (m, 2H), 1.59 (d, J=6.6 Hz, 3H), 1.24 (t, J=7.5 Hz, 3H); m/z 233 [M+H]⁺.

Example 455

Synthesis of 9-oxo-4,9-dihydropyrazolo[5,1-b]quinazoline-3-carbonitrile

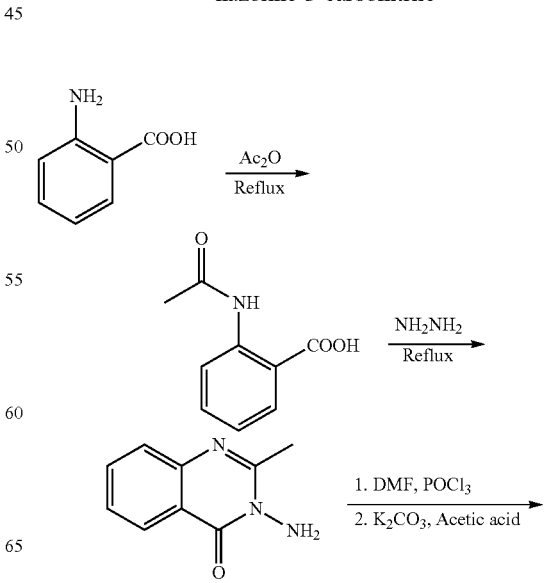

287
-continued

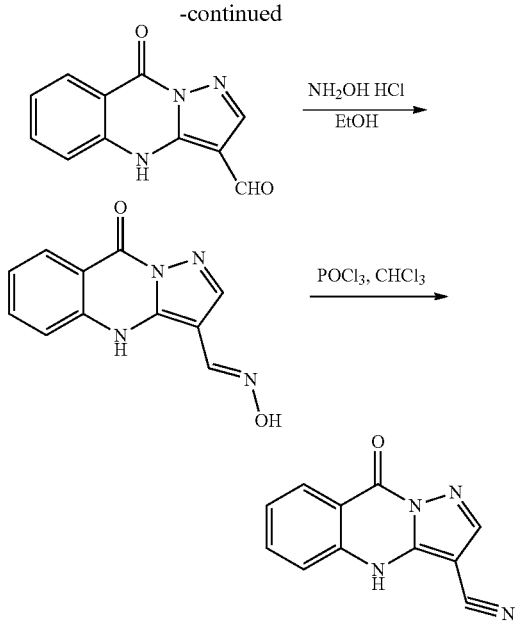

Synthesis of 2-acetamidobenzoic acid

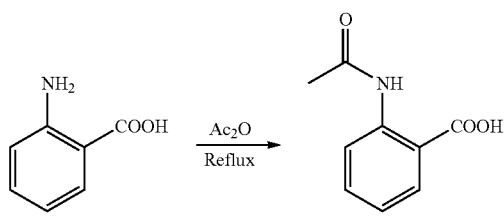

Anthranilic acid (100 g, 0.73 mol) in Ac$_2$O (1000 mL) was heated at 100° C. for 2 h. The Ac$_2$O was evaporated in vacuo and the residue was washed with hexane to give the product 2-acetamidobenzoic acid (130 g, 100%) as off-white solid. $^1$H NMR (300 MHz, CDCl$_3$) δ 8.19 (m, 1 H), 7.79 (m, 1 H), 7.54 (m, 2 H), 2.48 (s, 3 H).

Synthesis of 3-amino-2-methylquinazolin-4(3H)-one

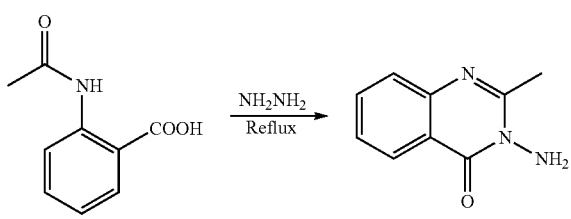

A mixture of 2-acetamidobenzoic acid (6.0 g, 33.5 mmol) and NH$_2$NH$_2$.H$_2$O (5.9 g, 100 mmol) was stirred at 0° C. for 10 min and heated to reflux for 30 min. After removal of solvent, the residue was washed with ethanol to give 3-amino-2-methylquinazolin-4(3H)-one as off-white solid (1 g, 12.5%). $^1$H NMR (300 MHz, CD$_3$OD) δ 8.24 (m, 1H), 7.75 (m, 2H), 7.46 (m, 1H), 2.72 (s, 3H).

288
Synthesis of 9-oxo-4,9-dihydropyrazolo[5,1-b]quinazoline-3-carbaldehyde

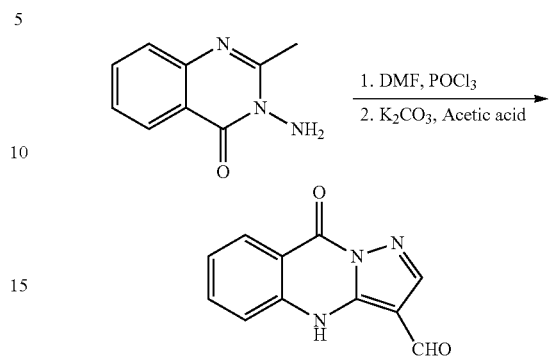

The Vilsmeier-Haack reaction was performed according to Pandit, R. S.; Seshadri, S. Vilsmeier-Haack reaction. Indian. J. Chem. 1973, 11(6), 532-537. To a solution of POCl$_3$ (2.7 mL, 29 mmol) in DMF (5 mL), was added 3-amino-2-methylquinazolin-4(3H)-one (1.0 g, 5.7 mmol) in DMF (10 mL) at 0° C. Then the mixture was heated at 70° C. for 5 h and poured into crushed ice. The resulting creamy solution was basified with NaHCO$_3$ to pH=8 at 0° C. when a bright yellow crystalline compound separated out. It was filtered, washed with water. The solid was taken in potassium carbonate solution (10%, 10 mL) and warmed at 60° C. for half an hour when a clear yellow solution was obtained. The solution was neutralized to pH=5 with HCl (1N), and filtered to give 9-oxo-4,9-dihydropyrazolo[5,1-b]quinazoline-3-carbaldehyde as off-white solid (800 mg, 82.5%). $^1$H NMR (300 MHz, DMSO-d6) δ 9.90 (s, 1H), 8.44 (s, 1H), 8.24 (m, 1H), 7.86 (m, 2H), 7.42 (m, 1H).

Synthesis of 9-oxo-4,9-dihydropyrazolo[5,1-b]quinazoline-3-carbaldehyde oxime

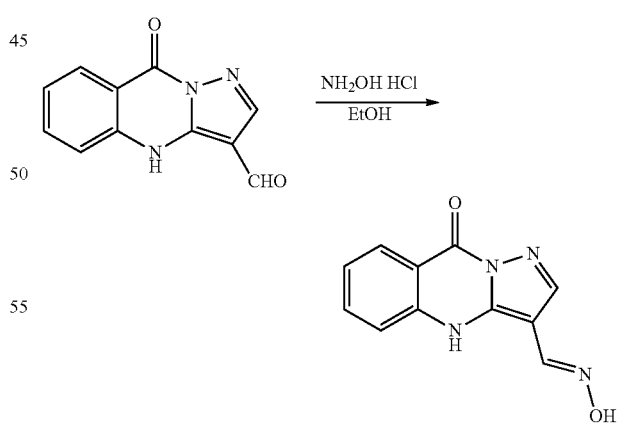

9-Oxo-4,9-dihydropyrazolo[5,1-b]quinazoline-3-carbaldehyde (800 mg, 3.75 mmol) and hydroxylamine hydrochloride (250 mg, 3.6 mmol) were taken in EtOH (50 mL) and reflux for 3 h. The solvent was removed in vacuo to give the crude product 9-oxo-4,9-dihydropyrazolo[5,1-b]quinazoline-3-carbaldehyde oxime (700 mg, 82%) as off-white solid. ¹H NMR (300 MHz, DMSO-d6) δ 12.48 (s, 1H), 11.35 (s, 1H), 8.57 (s, 1H), 8.21 (m, 1H), 7.82 (m, 1H), 7.52 (m, 1H), 7.34 (m, 1H).

Synthesis of 9-oxo-4,9-dihydropyrazolo[5,1-b]quinazoline-3-carbonitrile

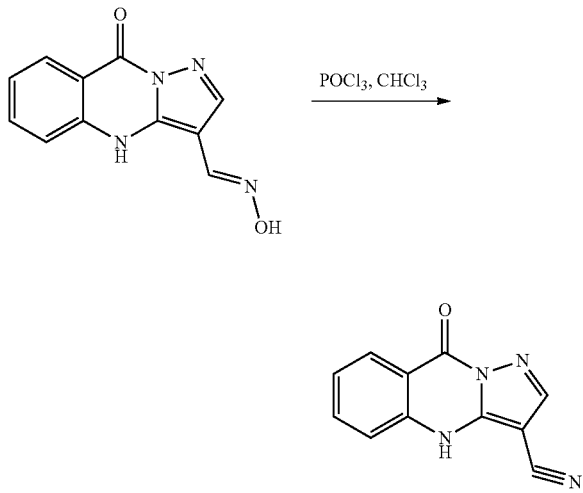 [SMILES: O=c1c2ccccc2[nH]c2c(/C=N/O)cnn12 ; N#Cc1cnn2c(=O)c3ccccc3[nH]c12]

To a solution of 9-oxo-4,9-dihydropyrazolo[5,1-b]quinazoline-3-carbaldehyde oxime (600 mg, 2.63 mmol) in dry CHCl₃ (10 mL) was added phosphorus oxychloride (0.5 mL, 5.5 mmol) and the mixture refluxed for 2 h. After removal of CH₃Cl, ice-cooled water was added followed by sodium bicarbonate to adjust to pH around 8. Precipitate was filtered, washed with water to give 9-oxo-4,9-dihydropyrazolo[5,1-b]quinazoline-3-carbonitrile (200 mg, 30%) as off-white solid. ¹H NMR (300 MHz, DMSO-d6) δ 13.33 (s, 1H), 8.43 (s, 1H), 8.23 (d, J=8.1 Hz, 1H), 7.86 (dd, J=8.4 Hz, 6.9 Hz, 1H), 7.58 (d, J=8.1 Hz, 1H), 7.41 (dd, J=8.1 Hz, 7.2 Hz, 1H); m/z (ESI) 211 [M+H]⁺.

Example 456

Synthesis of 3-ethyl-2-methyl-4-oxo-3,4-dihydropyrazolo[1,5-a][1,3,5]triazine-8-carbonitrile

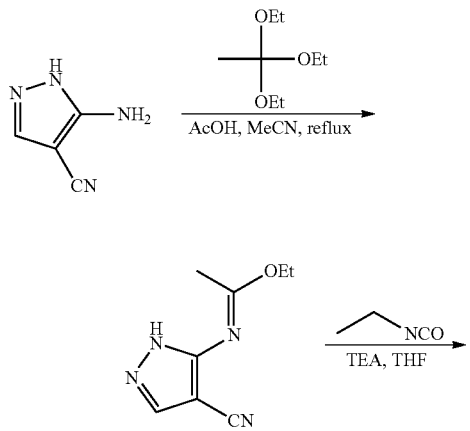

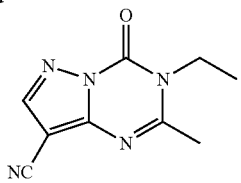

Synthesis of (E)-ethyl N-4-cyano-1H-pyrazol-5-ylacetimidate

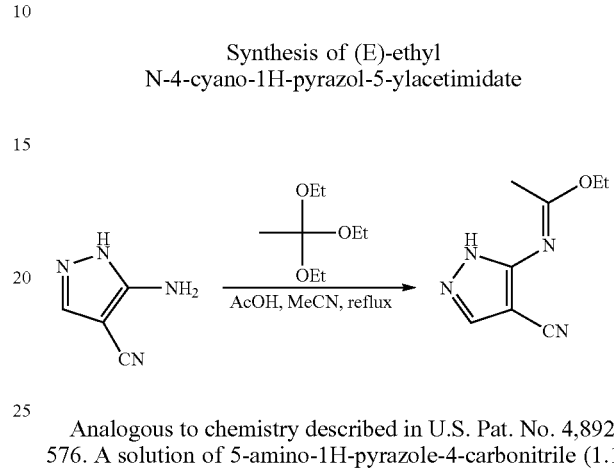

Analogous to chemistry described in U.S. Pat. No. 4,892,576. A solution of 5-amino-1H-pyrazole-4-carbonitrile (1.1 g, 10 mmol), 1,1,1-triethoxyethane (2 g, 12 mmol) and AcOH (3 drops) in MeCN (74 mL) was refluxed for 16 h. The resulting mixture was cooled down to room temperature, evaporated under vacuo. The residue was purified with column chromatography to yield (E)-ethyl N-4-cyano-1H-pyrazol-5-ylacetimidate (400 mg, 22%). ¹H NMR (300 MHz, CDCl₃) δ 7.80 (s, 1H), 4.33 (q, J=7.2 Hz, 2H), 2.10 (s, 3H), 1.38 (t, J=7.2 Hz, 3H).

Synthesis of 3-ethyl-2-methyl-4-oxo-3,4-dihydropyrazolo[1,5-a][1,3,5]triazine-8-carbonitrile

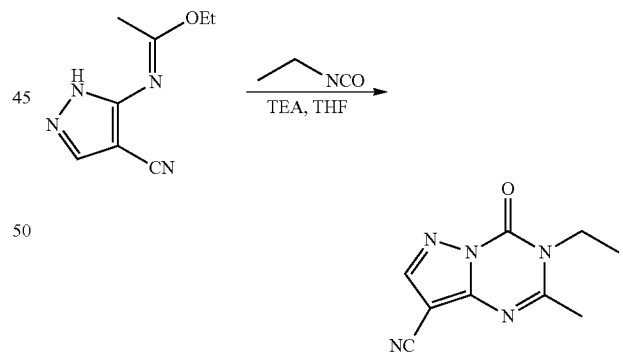

To a solution of (E)-ethyl N-4-cyano-1H-pyrazol-5-ylacetimidate (100 mg, 0.56 mmol) in anhydrous THF (5 mL) was added TEA (57 mg, 0.56 mmol) and isocyanatoethane (50 mg, 0.7 mmol) at 0° C. The mixture was warmed to ambient temperature and stirred for 18 h. The solvent was removed at reduced pressure, and the residue was purified with column chromatography to yield 3-ethyl-2-methyl-4-oxo-3,4-dihydropyrazolo[1,5-a][1,3,5]triazine-8-carbonitrile (10 mg, yield 8.8%). ¹H NMR (300 MHz, CD₃OD) δ 8.32 (s, 1H), 4.23 (q, J=7.2 Hz, 2H), 2.73 (s, 3H), 1.42 (t, J=7.2 Hz, 3H); m/z (ESI) 204 [M+H]⁺.

Example 457

Synthesis of 6-ethyl-5-((methylamino)methyl)-7-oxo-4,7-dihydropyrazolo[1,5-a]pyrimidine-3-carbonitrile

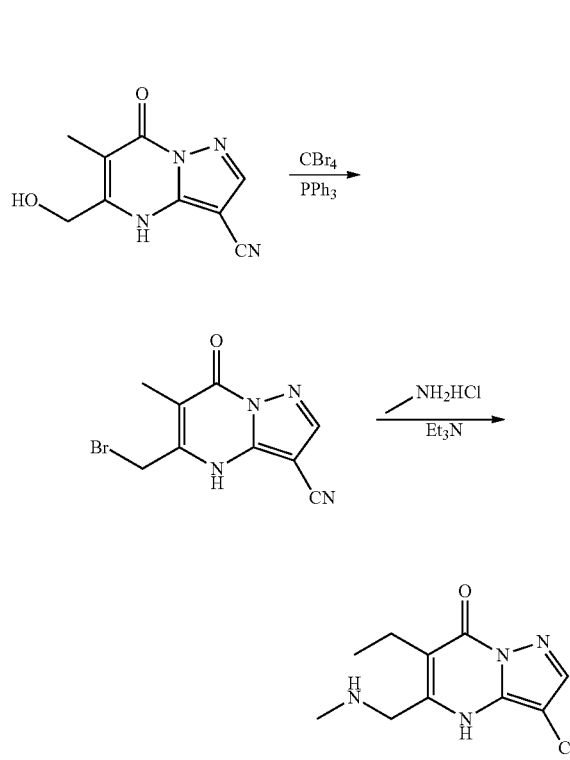

Synthesis of 5-(bromomethyl)-6-ethyl-7-oxo-4,7-dihydropyrazolo[1,5-a]pyrimidine-3-carbonitrile

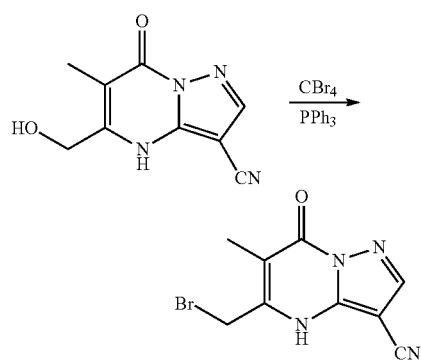

To a solution of 6-ethyl-5-(hydroxymethyl)-7-oxo-4,7-dihydropyrazolo[1,5-a]pyrimidine-3-carbonitrile (50 mg, 0.228 mmol) and PPh$_3$ (120 mg, 0.456 mmol) in CH$_2$Cl$_2$ (10 mL) was added CBr$_4$ (152 mg, 0.456 mmol) at ambient temperature. The reaction mixture was stirred for 16 h. The residue was concentrated and purified by column chromatography to give 5-(bromomethyl)-6-ethyl-7-oxo-4,7-dihydropyrazolo[1,5-a]pyrimidine-3-carbonitrile (30 mg, 50%). m/z (ESI) 281/283 [M+H]$^+$.

Synthesis of 6-ethyl-5-((methylamino)methyl)-7-oxo-4,7-dihydropyrazolo[1,5-a]pyrimidine-3-carbonitrile

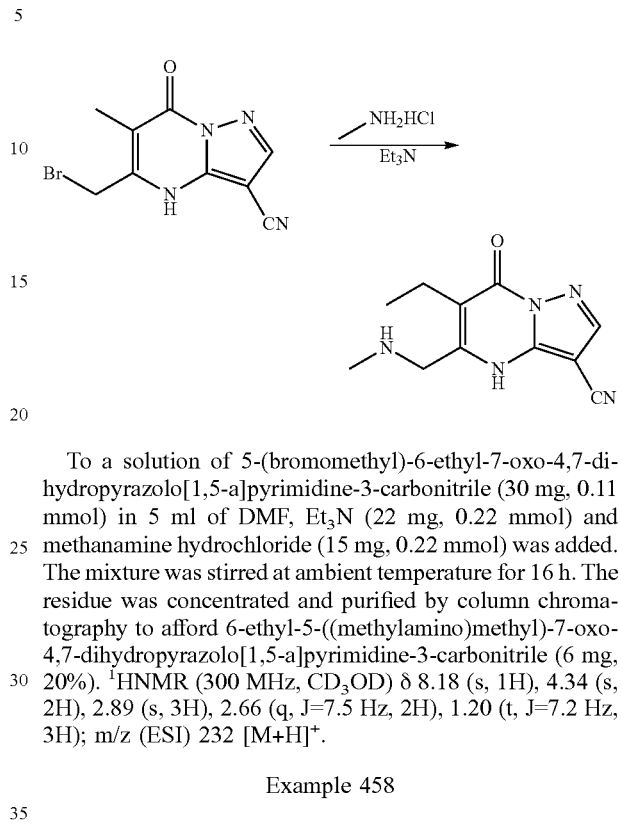

To a solution of 5-(bromomethyl)-6-ethyl-7-oxo-4,7-dihydropyrazolo[1,5-a]pyrimidine-3-carbonitrile (30 mg, 0.11 mmol) in 5 ml of DMF, Et$_3$N (22 mg, 0.22 mmol) and methanamine hydrochloride (15 mg, 0.22 mmol) was added. The mixture was stirred at ambient temperature for 16 h. The residue was concentrated and purified by column chromatography to afford 6-ethyl-5-((methylamino)methyl)-7-oxo-4,7-dihydropyrazolo[1,5-a]pyrimidine-3-carbonitrile (6 mg, 20%). $^1$HNMR (300 MHz, CD$_3$OD) δ 8.18 (s, 1H), 4.34 (s, 2H), 2.89 (s, 3H), 2.66 (q, J=7.5 Hz, 2H), 1.20 (t, J=7.2 Hz, 3H); m/z (ESI) 232 [M+H]$^+$.

Example 458

Assessment of Inhibitory Effect of Test Compounds on GASC1 Demethylase Activity on Histone 3 Lysine 9 Trimethyl Peptide (H3K9Me3)

GASC1 Demethylation Assay

6×His tagged recombinant GASC1 (N 350aa) was purified from *E. Coli* BL21(DE3) to near homogeneity. The demethylation reaction buffer contained 50 mM TrisCl pH 7.5, 0.01% Triton X-100, 5% glycerol, 1 mM ascorbate (Cat# A4034, Sigma Aldrich), 5 μM α-ketoglutarate (# K2010, Sigma Aldrich) and 20 μM Fe$_2$(NH$_4$)$_2$(SO$_4$)$_2$ (Cat# F1543, Sigma Aldrich). In 25 μL demethylation reaction system, 400 nM recombinant GASC1 and 20 μM H3K9me3 peptide (1-21 aa) were incubated with compounds for 10 minutes, and then α-ketoglutarate and Fe$_2$(NH$_4$)$_2$(SO$_4$)$_2$ were added to initiate the reaction. All of the reactions were incubated for 45 minutes at room temperature, and then 25 μl of 1 N HCl was added to quench the reactions. After termination, plates were sealed and frozen at −80° C. and shipped on dry ice to BioTrove Inc. (Woburn, Mass.) for analysis.

High Throughput Mass Spectrometry (HT-MS) Analysis

All the reactions were read by RapidFire™ HT-MS platform developed in BioTrove Inc, and the method has been described in detail previously (Assay and Drug Development Technologies, 2004; 2(4): 373-381). Briefly, at BioTrove, plates were thawed and immediately analyzed using RapidFire™ system coupled to a Sciex API4000 triple quadrapole mass spectrometer. The samples were delivered directly from the plate to a clean-up cartridge (BioTrove column A) to remove nonvolatile assay components with 0.1% formic acid in a 3-sec wash cycle. The peptide substrate and demethylated product were coeluted to the mass spectrometer with 80% acetonitrile, 0.1% formic acid. Both the substrate and product signals were read at their +5 charge species, and the conversion from substrate to product is assessed by [H3K9me2 Read]/[H3K9me2 Read+ H3K9me3 Read].

Example 459

Table 6 shows the activity of selected compounds of this invention in the GASC1 inhibition assay. The compound numbers correspond to the compound numbers in Table 1. Compounds having an activity designated as "A" provided an $IC_{50} \leq 1$ µM; compounds having an activity designated as "B" provided an $IC_{50}$ 1-10 µM; compounds having an activity designated as "C" provided an $IC_{50}$ of 10-50 µM; and compounds having an activity designated as "D" provided an $IC_{50} \geq 50$ µM.

TABLE 6

GASC1 Inhibition Data

| Compound # | GASC1 Inhibition |
|---|---|
| I-1 | D |
| I-2 | D |
| I-3 | B |
| I-4 | A |
| I-5 | B |
| I-6 | D |
| I-12 | C |
| I-13 | D |
| I-14 | D |
| I-15 | B |
| I-16 | B |
| I-17 | A |
| I-18 | D |
| I-19 | D |
| I-20 | B |
| I-21 | A |
| I-22 | B |
| I-23 | B |
| I-24 | B |
| I-25 | A |
| I-26 | B |
| I-27 | D |
| I-28 | D |
| I-29 | D |
| I-30 | B |
| I-31 | B |
| I-32 | B |
| I-33 | B |
| I-34 | A |
| I-35 | B |
| I-36 | D |
| I-37 | D |
| I-38 | A |
| I-39 | B |
| I-40 | B |
| I-41 | A |
| I-42 | A |
| I-43 | B |
| I-44 | A |
| I-45 | A |
| I-46 | A |
| I-47 | A |
| I-48 | B |
| I-49 | B |
| I-50 | B |
| I-51 | A |
| I-52 | B |
| I-53 | B |
| I-54 | B |
| I-55 | B |

Example 460

Assessment of Inhibitory Effect of Test Compounds on JARID1A and PLU-1 Demethylase Activity on Histone 3 Lysine 4 Trimethyl Peptide (H3K4Me3)

JARID1A/PLU1 Demethylase Assays

FLAG tagged full length recombinant JARID1A and PLU1 proteins were purified from Sf9 insect cells to near homogeneity. The demethylation reaction buffer contained 50 mM TrisCl pH 7.5, 0.01% Triton X-100, 0.005% BSA, 1 mM ascorbate (Cat# A4034, Sigma Aldrich), 1.7 µM α-ketoglutarate (# K2010, Sigma Aldrich) and 20 µM $Fe_2(NH_4)_2(SO_4)_2$ (Cat# F1543, Sigma Aldrich). In a 25 µL demethylation reaction system, 20 nM recombinant JARID1A or PLU1 proteins and 4 µM H3K4me3 peptide (1-21 aa), which can be biotinylated or unlabelled, were incubated with compounds for 10 minutes, and then α-ketoglutarate and $Fe_2(NH_4)_2(SO_4)_2$ were added to initiate the reaction. All of the reactions were incubated for 45 minutes at room temperature, and then 25 µl of 1 N HCl was added to quench the reactions. After termination, plates were sealed and frozen at −80° C. for analysis.

High Throughput Mass Spectrometry (HT-MS) Analysis

All the reactions were read by RapidFire™ HT-MS platform developed in BioCius Inc, and described in detail (Assay and Drug Development Technologies, 2004; 2(4): 373-381). Briefly, plates were thawed and immediately analyzed using RapidFire™ system coupled to a Sciex API4000 triple quadrapole mass spectrometer. The samples were delivered directly from the plate to a clean-up cartridge (BioCius column A) to remove nonvolatile assay components with 0.1% formic acid in a 3-sec wash cycle. The peptide substrate and demethylated product were coeluted to the mass spectrometer with 80% acetonitrile, 0.1% formic acid. Both the substrate and product signals were read at their +5 charge species, and the conversion from substrate to product assessed by [H3K4me2 Read]/[H3K4me2 Read+ H3K4me3 Read].

Example 461

Table 7 shows the activity of selected compounds of this invention in the JARID1A and PLU-1 inhibition assays. The compound numbers correspond to the compound numbers in Table 1. Compounds having an activity designated as "A" provided an $IC_{50} \leq 1$ µM; compounds having an activity designated as "B" provided an $IC_{50}$ 1-10 µM; compounds having an activity designated as "C" provided an $IC_{50}$ of 10-50 µM; and compounds having an activity designated as "D" provided an $IC_{50} \geq 50$ µM.

TABLE 7

JARID1A and PLU-1 Inhibition Data

| Compound # | JARID1A | PLU-1 |
|---|---|---|
| I-4 | B | B |
| I-21 | A | A |
| I-23 | A | A |
| I-25 | A | A |
| I-29 | B | B |
| I-30 | A | A |
| I-49 | A | B |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Example 462

Assessment of Inhibitory Effect of Test Compounds on KDM5A Demethylase Activity KDM5A Demethylase Assay (MassSpec Assay—A)

Full length recombinant Flag tagged KDM5A protein was purified from Sf9 insect cells. The demethylation reaction buffer contained 50 mM TrisCl pH 7.4, 0.01% Triton X-100, 0.025 mg/mL BSA, 1 mM ascorbate (Cat# A4034, Sigma Aldrich), 2 mM TCEP (Cat# D9779, Sigma Aldrich), 2.0 µM α-ketoglutarate (# K2010, Sigma Aldrich) and 50 µM $Fe_2(NH_4)_2(SO_4)_2$ (Cat# F1543, Sigma Aldrich). In a 25 µL demethylation reaction system, 20 nM recombinant KDM5A and was incubated with compounds for 10 minutes in the above buffer, and then 2.0 α-ketoglutarate (# K2010, Sigma Aldrich), 4.0 µM biotinylated H3K9me1 peptide (1-21 aa), and $Fe_2(NH_4)_2(SO_4)_2$ were added to initiate the reaction. (All reagent concentrations are final reagent concentrations.) Reactions were incubated for 30 minutes at room temperature, and then quenched by addition of an equal volume of 1% formic acid. After termination, plates were sealed and frozen at −80° C. for analysis.

KDM5A Demethylase Assays (TR-FRET Assay—B)

Full length recombinant Flag tagged KDM5A protein was purified from Sf9 insect cells. The demethylation reaction buffer contained 50 mM TrisCl pH 7.4, 0.01% Triton X-100, 0.025 mg/mL BSA, 1 mM ascorbate, 2 mM TCEP, 3.0 µM α-ketoglutarate, and 50 µM $Fe_2(NH_4)_2(SO_4)_2$. In a 10 µL demethylation reaction system, 2 nM recombinant KDM5A and was incubated with compounds for 15 minutes in the above buffer ($V_t$ 5 uL) in a 384 well Proxi Plate (Perkin Elmer Corp.), and then 0.1 µM biotinylated H3K9me1 peptide (1-21 aa, New England Peptide, $V_t$ 5 uL) was added to initiate the reaction ($V_t$ 10 uL). (All protein/reagent concentrations are final concentrations.) Reactions were incubated for 25 minutes at room temperature, and then quenched by addition of 5 uL of detection reagents (buffer as above with addition of 0.3 mM EDTA, 150 mM NaCl, 150 nM SA-SurelightAPC and 1.5 nM Eu(W1024)-K3K4Me1/2 antibody (TR-FRET reagents both Perkin-Elmer)). After a one hour incubation assays were read on a Perkin-Elmer Envision equipped with a laser source and appropriate filters. $IC_{50}$s were calculated using standard dose-response equations and relative to a Max (no inhibition) and Min (no enzyme or quenched enzyme) controls.

KDM5A Demethylase Assays (TR-FRET Assay—C)

Full length recombinant Flag tagged KDM5A protein was purified from Sf9 insect cells. The demethylation reaction buffer contained 50 mM HEPES pH 7.0, 0.01% Triton X-100, 0.5 mM ascorbate, 2 mM DTT, 1 µM α-ketoglutarate, and 100 µM $Fe_2(NH_4)_2(SO_4)_2$. In a 10 µL demethylation reaction system, 2 nM recombinant KDM5A was added to compounds in the above buffer ($V_t$ 5 uL) in a 384 well Proxi Plate (Perkin Elmer Corp.) and then 0.1 µM biotinylated H3K9me1 peptide (1-21 aa, New England Peptide, $V_t$ 5 uL) was added to initiate the reaction ($V_t$ 10 uL). (All protein/reagent concentrations are final concentrations.) Reactions were incubated for 30 minutes at room temperature, and then quenched by addition of 5 uL stop buffer (3 mM EDTA, 50 mM TrisCl pH 7.5, 0.01% Triton X-100, 0.01 mg/mL BSA) followed by addition of 5 uL of detection reagents (buffer as above without EDTA but with addition of 200 nM SA-XL665 (CisBio) and 2 nM Eu(W1024)-anti-H3K4Me1-2 antibody (PerkinElmer)). After a 30 minute incubation assays were read on a Perkin-Elmer Envision equipped with appropriate filters. $IC_{50}$s were calculated using standard dose-response equations and relative to a Max (no inhibition) and Min (no enzyme or quenched enzyme) controls.

Example 463

KDM5 Enzyme Assay Procedure

Full length KDM5A enzyme was expressed and purified inhouse. Biotin-H3K4me3 peptide was purchased from New England Biolabs. HTRF reagents (containing Eu-labeled H3K4me1-2 antibody, and streptavidin-XL665) were purchased from Cis-Bio International. Plates were read on an Envision multi-label plate reader Perkin Elmer).

The HTRF assay mixture contained 2 nM full length KDM5A enzyme, 100 nM H3K4Me3 peptide substrate, 1 uM 2-OG, 100 uM $Fe^{2+}$, 500 uM ascorbate. 50 mM HEPES pH 7.0 buffer, 0.01% Triton-X 100, 2 mM DTT. 0.25% DMSO at a final volume of 10 uL. The enzyme reaction was carried out at room temperature in black Proxiplate 384-Plus plate (Corning, Costar) within 30 minutes, in the presence of varying concentration of a test compound. At the end of enzyme reaction, 5 uL of 1 mM EDTA were added to quench the reaction and then the detection reagents (5 uL) were added to give final concentrations of 0.5 nM Eu-labeled H3K4me1-2 antibody, and 50 nM streptavidin-XL665. The plates were incubated at room temperature for 60 minutes and then read in the Envision plate reader. The readouts were transformed into % inhibition, and IC50 value of a test compounds was generated by using four parameters curve fitting (Model 205 in XLFIT5, iDBS).

Example 464

KDM5 Cell Assay Procedure

PC9 cells were seeded in a 384 well plate (2000 cells/well) with a test compound and incubated for 120 hours at 37° C. H3K4Me3 mark. level was assessed using AlphaLISA reagents from Perkin Elmer. Briefly, cells were lysed in 5 µL of Histone cell lysis buffer for 30 min on ice. Then histones were extracted by addition of 10 µL of Histone extraction buffer to each well for 20 minutes. 10 µL of acceptor beads and 10 µL of donor beads were added sequentially one hour apart, and the mixture was incubated at 26° C. for 30 minutes. Assay plate was read subsequently on Envision (Perkin Elmer). Each compound was run in duplicate. Data were normalized to DMSO treated wells as the low response and $EC_{50}$'s were calculate using a four-parameter fit.

Data for the compounds of Examples 1-432 from the assay described in Example 463 is provided in the following table.

| Compound (Example Number) | Example 463 Assay KDM5A HTRF $IC_{50}$ (uM) |
|---|---|
| 1 | 0.0043 |
| 2 | 0.003 |
| 3 | 0.0038 |

| Compound (Example Number) | Example 463 Assay KDM5A HTRF IC$_{50}$ (uM) |
|---|---|
| 4 | 0.065 |
| 5 | 0.0055 |
| 6 | 0.013 |
| 7 | 0.03 |
| 8 | 0.022 |
| 9 | 0.04 |
| 10 | 0.024 |
| 11 | 0.014 |
| 12 | 0.018 |
| 13 | 0.023 |
| 14 | 0.0053 |
| 15 | 0.047 |
| 16 | 0.011 |
| 17 | 0.041 |
| 18 | 0.021 |
| 19 | 0.055 |
| 20 | 0.037 |
| 21 | 0.038 |
| 22 | 0.0095 |
| 23 | 0.0098 |
| 24 | 0.007 |
| 25 | 0.22 |
| 26 | 4.4 |
| 27 | 3.9 |
| 28 | 0.018 |
| 29 | 0.016 |
| 30 | 0.012 |
| 31 | 0.025 |
| 32 | 0.015 |
| 33 | 0.0093 |
| 34 | 0.0095 |
| 35 | 0.03 |
| 36 | 0.0104 |
| 37 | 0.024 |
| 38 | 0.036 |
| 39 | 0.128 |
| 40 | 0.01 |
| 41 | 0.019 |
| 42 | 0.021 |
| 43 | 0.083 |
| 44 | 0.368 |
| 45 | 0.03 |
| 46 | 2.9 |
| 47 | 0.024 |
| 48 | 0.084 |
| 49 | 0.025 |
| 50 | 0.02 |
| 51 | 0.0083 |
| 52 | 0.0058 |
| 53 | 0.017 |
| 54 | 0.006 |
| 55 | 0.011 |
| 56 | 0.016 |
| 57 | 0.0057 |
| 58 | 0.0073 |
| 59 | 0.034 |
| 60 | 0.019 |
| 61 | 0.01 |
| 62 | 0.012 |
| 63 | 0.015 |
| 64 | 0.021 |
| 65 | 0.014 |
| 66 | 0.014 |
| 67 | 0.01 |
| 68 | 0.013 |
| 69 | 0.021 |
| 70 | 0.0078 |
| 71 | 0.0045 |
| 72 | 0.01 |
| 73 | 0.0073 |
| 74 | 0.004 |
| 75 | 0.01 |
| 76 | 0.006 |
| 77 | 0.012 |
| 78 | 0.0077 |
| 79 | 0.013 |
| 80 | 0.0068 |
| 81 | 0.0065 |
| 82 | 0.012 |
| 83 | 0.012 |
| 84 | 0.0083 |
| 85 | 0.012 |
| 86 | 0.0045 |
| 87 | 0.0075 |
| 88 | 0.014 |
| 89 | 0.01 |
| 90 | 0.009 |
| 91 | 0.012 |
| 92 | 0.0055 |
| 93 | 0.013 |
| 94 | 0.012 |
| 95 | 0.011 |
| 96 | 0.034 |
| 97 | 0.038 |
| 98 | 0.037 |
| 99 | 0.006 |
| 100 | 0.008 |
| 101 | 0.0085 |
| 102 | 0.01 |
| 103 | 0.0055 |
| 104 | 0.021 |
| 105 | 0.008 |
| 106 | 0.018 |
| 107 | 0.019 |
| 108 | 0.028 |
| 109 | 0.011 |
| 110 | 0.007 |
| 111 | 0.015 |
| 112 | 0.33 |
| 113 | 0.006 |
| 114 | 0.0055 |
| 115 | 0.006 |
| 116 | 0.008 |
| 117 | 0.014 |
| 118 | 0.015 |
| 119 | 0.019 |
| 120 | 0.019 |
| 121 | 0.01 |
| 122 | 0.013 |
| 123 | 0.008 |
| 124 | 0.011 |
| 125 | 0.03 |
| 126 | 0.008 |
| 127 | 0.013 |
| 128 | 0.016 |
| 129 | 0.023 |
| 130 | 0.0045 |
| 131 | 0.018 |
| 132 | 0.0072 |
| 133 | 0.011 |
| 134 | 0.0055 |
| 135 | 0.0058 |
| 136 | 0.009 |
| 137 | 0.012 |
| 138 | 0.015 |
| 139 | 0.013 |
| 140 | 0.012 |
| 141 | 0.0093 |
| 142 | 0.012 |
| 143 | 0.025 |
| 144 | 0.019 |
| 145 | 0.017 |
| 146 | 0.0075 |
| 147 | 0.0095 |
| 148 | 0.016 |
| 149 | 0.006 |
| 150 | 0.014 |
| 151 | 0.017 |
| 152 | 0.014 |
| 153 | 0.013 |

-continued

| Compound (Example Number) | Example 463 Assay KDM5A HTRF IC$_{50}$ (uM) |
|---|---|
| 154 | 0.006 |
| 155 | 0.0098 |
| 156 | 0.022 |
| 157 | 0.007 |
| 158 | 0.015 |
| 159 | 0.035 |
| 160 | 0.019 |
| 161 | 0.013 |
| 162 | 0.064 |
| 163 | 0.097 |
| 164 | 0.15 |
| 165 | 0.061 |
| 166 | 0.2 |
| 167 | 0.1 |
| 168 | 0.046 |
| 169 | 0.047 |
| 170 | 0.21 |
| 171 | 0.037 |
| 172 | 0.14 |
| 173 | 0.039 |
| 174 | 0.081 |
| 175 | 0.043 |
| 176 | 0.052 |
| 177 | 0.038 |
| 178 | 0.043 |
| 179 | 0.035 |
| 180 | 0.061 |
| 181 | 0.06 |
| 182 | 0.13 |
| 183 | 0.033 |
| 184 | 0.056 |
| 185 | 0.02 |
| 186 | 0.049 |
| 187 | 0.75 |
| 188 | 0.24 |
| 189 | 0.16 |
| 190 | 0.057 |
| 191 | 0.76 |
| 192 | 1.5 |
| 193 | 0.86 |
| 194 | 2.3 |
| 195 | 2.2 |
| 196 | 0.047 |
| 197 | 0.029 |
| 198 | 0.61 |
| 199 | 0.18 |
| 200 | 0.9 |
| 201 | 0.029 |
| 202 | 0.006 |
| 203 | 0.011 |
| 204 | 0.019 |
| 205 | 0.023 |
| 206 | 0.021 |
| 207 | 0.033 |
| 208 | 0.009 |
| 209 | 0.018 |
| 210 | 0.012 |
| 211 | 0.024 |
| 212 | 0.008 |
| 213 | 0.018 |
| 214 | 0.026 |
| 215 | 0.41 |
| 216 | 0.02 |
| 217 | 2.1 |
| 218 | 8 |
| 219 | 4.3 |
| 220 | 21 |
| 221 | 25 |
| 222 | 0.012 |
| 223 | 0.009 |
| 224 | 0.025 |
| 225 | 5.4 |
| 226 | 0.37 |
| 227 | 0.013 |
| 228 | 0.023 |

-continued

| Compound (Example Number) | Example 463 Assay KDM5A HTRF IC$_{50}$ (uM) |
|---|---|
| 229 | 9.6 |
| 230 | 0.009 |
| 231 | 0.17 |
| 232 | 0.019 |
| 233 | 0.02 |
| 234 | 0.015 |
| 235 | 0.014 |
| 236 | 0.018 |
| 237 | 0.078 |
| 238 | 0.049 |
| 239 | 0.021 |
| 240 | 0.05 |
| 241 | 0.013 |
| 242 | 0.027 |
| 243 | 0.02 |
| 244 | 0.021 |
| 245 | 0.046 |
| 246 | 0.022 |
| 247 | 0.015 |
| 248 | 0.069 |
| 249 | 0.03 |
| 250 | 5.7 |
| 251 | 8 |
| 252 | 7.63 |
| 253 | 0.013 |
| 254 | 0.033 |
| 255 | 0.035 |
| 256 | 0.015 |
| 257 | 0.037 |
| 258 | 0.044 |
| 259 | 0.043 |
| 260 | 0.036 |
| 261 | 0.031 |
| 262 | 0.021 |
| 263 | 0.028 |
| 264 | 0.021 |
| 265 | 0.04 |
| 266 | 0.029 |
| 267 | 0.0098 |
| 268 | 0.023 |
| 269 | 0.019 |
| 270 | 0.013 |
| 271 | 0.024 |
| 272 | 0.029 |
| 273 | 0.023 |
| 274 | 0.073 |
| 275 | 0.034 |
| 276 | 0.035 |
| 277 | 0.032 |
| 278 | 0.076 |
| 279 | 0.024 |
| 280 | 0.015 |
| 281 | 0.032 |
| 282 | 0.008 |
| 283 | 0.037 |
| 284 | 0.016 |
| 285 | 0.023 |
| 286 | 0.03 |
| 287 | 0.022 |
| 288 | 0.012 |
| 289 | 0.035 |
| 290 | 0.039 |
| 291 | 0.055 |
| 292 | 0.009 |
| 293 | 0.019 |
| 294 | 0.062 |
| 295 | 0.039 |
| 296 | 0.047 |
| 297 | 0.028 |
| 298 | 0.024 |
| 299 | 0.025 |
| 300 | 0.018 |
| 301 | 0.17 |
| 302 | 0.052 |
| 303 | 0.015 |

| Compound (Example Number) | Example 463 Assay KDM5A HTRF IC$_{50}$ (uM) |
|---|---|
| 304 | 0.052 |
| 305 | 0.047 |
| 306 | 0.2 |
| 307 | 0.025 |
| 308 | 0.017 |
| 309 | 0.037 |
| 310 | 0.019 |
| 311 | 0.028 |
| 312 | 0.028 |
| 313 | 0.018 |
| 314 | 0.0052 |
| 315 | 0.024 |
| 316 | 0.034 |
| 317 | 0.025 |
| 318 | 0.021 |
| 319 | 0.046 |
| 320 | 0.02 |
| 321 | 0.023 |
| 322 | 0.01 |
| 323 | 0.031 |
| 324 | 0.026 |
| 325 | 0.019 |
| 326 | 0.014 |
| 327 | 0.048 |
| 328 | 0.03 |
| 329 | 0.011 |
| 330 | 0.023 |
| 331 | 0.027 |
| 332 | 0.02 |
| 333 | 0.012 |
| 334 | 0.025 |
| 335 | 0.06 |
| 336 | 0.032 |
| 337 | 0.025 |
| 338 | 0.034 |
| 339 | 0.033 |
| 340 | 0.031 |
| 341 | 0.021 |
| 342 | 0.009 |
| 343 | 0.036 |
| 344 | 0.093 |
| 345 | 0.14 |
| 346 | 0.04 |
| 347 | 0.024 |
| 348 | 0.014 |
| 349 | 0.014 |
| 350 | 0.02 |
| 351 | 0.027 |
| 352 | 0.027 |
| 353 | 0.014 |
| 354 | 0.077 |
| 355 | 0.04 |
| 356 | 0.044 |
| 357 | 0.022 |
| 358 | 0.025 |
| 359 | 0.02 |
| 360 | 0.028 |
| 361 | 0.052 |
| 362 | 0.024 |
| 363 | 0.025 |
| 364 | 0.018 |
| 365 | 0.018 |
| 366 | 0.018 |
| 367 | 0.025 |
| 368 | 0.075 |
| 369 | 0.085 |
| 370 | 0.008 |
| 371 | 0.011 |
| 372 | 0.015 |
| 373 | 0.024 |
| 374 | 0.038 |
| 375 | 0.019 |
| 376 | 0.019 |
| 377 | 0.022 |
| 378 | 0.014 |
| 379 | 0.011 |
| 380 | 0.048 |
| 381 | 0.03 |
| 382 | 0.048 |
| 383 | 0.031 |
| 384 | 0.013 |
| 385 | 0.021 |
| 386 | 0.012 |
| 387 | 0.13 |
| 388 | 0.025 |
| 389 | 0.033 |
| 390 | 0.055 |
| 391 | 0.011 |
| 392 | 0.02 |
| 393 | 0.012 |
| 394 | 0.02 |
| 395 | 0.01 |
| 396 | 0.034 |
| 397 | 0.032 |
| 398 | 0.041 |
| 399 | 0.054 |
| 400 | 0.035 |
| 401 | 0.039 |
| 402 | 0.058 |
| 403 | 0.057 |
| 404 | 0.018 |
| 405 | 0.012 |
| 406 | 0.015 |
| 407 | 0.048 |
| 408 | 0.15 |
| 409 | 0.044 |
| 410 | 0.039 |
| 411 | 0.035 |
| 412 | 0.046 |
| 413 | 0.11 |
| 414 | 0.014 |
| 415 | 0.077 |
| 416 | 0.048 |
| 417 | 0.031 |
| 418 | 0.013 |
| 419 | 0.088 |
| 420 | 0.023 |
| 421 | 0.019 |
| 422 | 0.029 |
| 423 | 0.02 |
| 424 | 0.008 |
| 425 | 0.016 |
| 426 | 0.023 |
| 427 | 0.039 |
| 428 | 0.014 |
| 429 | 0.027 |
| 430 | 0.032 |
| 431 | 0.021 |
| 432 | 0.056 |

Data for representative compounds of formulae I-1 to I-65 from the assay described in Example 463 is provided in the following table.

| Compound (Example Number) | Example 463 Assay KDM5A HTRF IC$_{50}$ (uM) |
|---|---|
| I-3 | 286 |
| I-4 | 832 |
| I-9 | 564 |
| I-10 | 227 |
| I-12 | 9300 |
| I-13 | 16000 |
| I-14 | 15700 |
| I-15 | 119 |
| I-16 | 2100 |
| I-17 | 54 |

-continued

| Compound (Example Number) | Example 463 Assay KDM5A HTRF IC$_{50}$ (uM) |
|---|---|
| I-18 | 842 |
| I-19 | 7400 |
| I-22 | 875 |
| I-24 | 2600 |
| I-25 | 7.5 |
| I-27 | 2500 |
| I-28 | 6200 |
| I-29 | 176 |
| I-30 | 163 |
| I-31 | 339 |
| I-33 | 284 |
| I-34 | 54.5 |
| I-36 | 3100 |
| I-37 | 469 |
| I-38 | 21.7 |
| I-39 | 2200 |
| I-40 | 227 |
| I-41 | 12 |
| I-42 | 6.6 |
| I-43 | 55.9 |
| I-44 | 21.8 |
| I-45 | 40 |
| I-46 | 25.4 |
| I-47 | 15.6 |
| I-48 | 66.5 |
| I-49 | 52 |
| I-50 | 265 |
| I-51 | 130 |
| I-52 | 457 |
| I-53 | 10.9 |
| I-54 | 1300 |
| I-55 | 1700 |
| I-56 | 6.3 |
| I-57 | 726 |
| I-58 | 146 |
| I-60 | 219 |
| I-62 | 25000 |
| I-64 | 218 |
| I-65 | 1200 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

What is claimed is:

1. A compound of formula I:

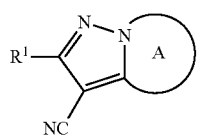

or a pharmaceutically acceptable salt thereof, wherein:

$R^1$ is —R, halogen, —OR, —SR, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(═N(R'))N(R')$_2$, —C═NN(R')$_2$, —C═NOR, —C(═N(R'))N(R')$_2$, —OC(O)R, or —OC(O)N(R')$_2$;

each R is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-3 heteroatoms independently selected from nitrogen, oxygen, or sulfur, a 4-7 membered saturated or partially unsaturated heterocyclic ring having 1-2 heteroatoms independently selected from nitrogen, oxygen, or sulfur, a 7-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;

each R' is independently —R, —C(O)R, —CO$_2$R, or two R' on the same nitrogen are taken together with their intervening atoms to form a 4-7 membered heterocyclic ring having 1-2 heteroatoms independently selected from nitrogen, oxygen, and sulfur;

Ring A is

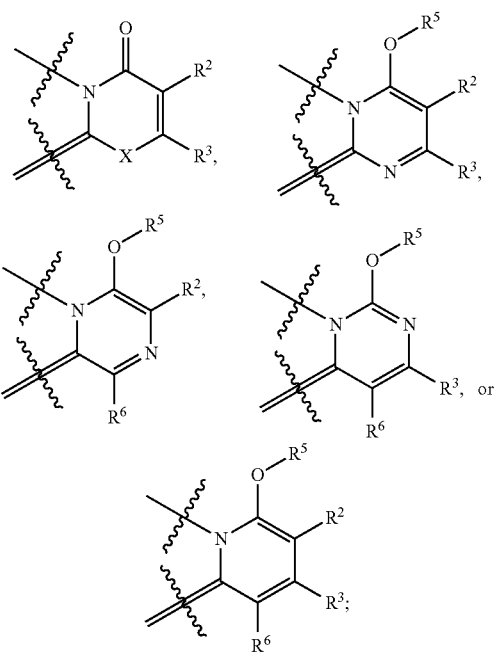

$R^2$ is C$_{1-6}$ alkenyl, C$_{1-6}$ alkynyl, cyclopropyl, or cyclobutyl; wherein the C$_{1-6}$ alkyl, C$_{1-6}$ alkenyl, C$_{1-6}$ alkynyl, cyclopropyl, or cyclobutyl are optionally substituted by one or more of groups consisting of halogen, —(CH$_2$)$_{0-4}$R°; —O—(CH$_2$)$_{0-4}$C(O)OR°, —(CH$_2$)$_{0-4}$CH(OR°)$_2$, —(CH$_2$)$_{0-4}$SR°, —C═CHPh which may be substituted with R°, —NO$_2$, —CN, —N$_3$, —(CH$_2$)$_{0-4}$N(R°)$_2$, —(CH$_2$)$_{0-4}$N(R°)C(O)R°, —N(R°)C(S)R°, —(CH$_2$)$_{0-4}$N(R°)C(O)NR°$_2$, —N(R°)C(S)NR°$_2$, —(CH$_2$)$_{0-4}$N(R°)C(O)OR°, —N(R°)N(R°)C(O)R°, —N(R°)N(R°)C(O)NR°$_2$, —N(R°)N(R°)C(O)OR°, —(CH$_2$)$_{0-4}$C(O)R°, —C(S)R°, —(CH$_2$)$_{0-4}$C(O)SR°, —(CH$_2$)$_{0-4}$C(O)OSiR°$_3$, —OC(O)(CH$_2$)$_{0-4}$SR—, SC(S)SR°, —(CH$_2$)$_{0-4}$SC(O)R°, —(CH$_2$)$_{0-4}$C(O)NR°$_2$, —C(S)NR°$_2$, —C(S)SR°, —SC(S)SR°, —(CH$_2$)$_{0-4}$C(O)NR°$_2$, —C(O)N(OR°)R°, —C(O)C(O)R°, —C(O)CH$_2$C(O)R°, —C(NOR°)R°, —(CH$_2$)$_{0-4}$SSR°, —(CH$_2$)$_{0-4}$S(O)$_2$R°, —(CH$_2$)$_{0-4}$S(O)$_2$OR°, —(CH$_2$)$_{0-4}$OS(O)$_2$R°, —S(O)$_2$NR°$_2$, —(CH$_2$)$_{0-4}$S(O)R°, —N(R°)S(O)$_2$NR°$_2$, —N(R°)S(O)$_2$R°, —N(OR°)R°, —C(NH)

NR°$_2$, —P(O)$_2$R°, —P(O)R°$_2$, —OP(O)R°$_2$, —OP(O)(OR°)$_2$, —SiR°$_3$, —(C$_{1-4}$ straight or branched alkylene)O—N(R°)$_2$ and —(C$_{1-4}$ straight or branched alkylene)C(O)O—N(R°)$_2$;

each R° may be optionally substituted and is independently hydrogen, or C$_{1-6}$ aliphatic, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur; and wherein the optional substituent on R° is independently halogen or =O;

R$^3$ is —R, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; or:

R$^2$ and R$^3$ are taken together with their intervening atoms to form an optionally substituted 5-7 membered partially unsaturated or aromatic fused ring having 0-4 heteroatoms independently selected from nitrogen, oxygen, and sulfur;

X is —N(R$^4$)—, —O—, or —S—;

R$^4$ is —R, —C(O)R, —CO$_2$R, or —S(O)$_2$R; or:

R$^4$ and R$^3$ are taken together with their intervening atoms to form an optionally substituted 5-7 membered saturated, partially unsaturated, or aromatic fused ring having 1-4 heteroatoms independently selected from nitrogen, oxygen, and sulfur;

R$^5$ is R, —C(O)R, —CO$_2$R, —C(O)N(R')$_2$, —C(O)C(O)R, or —C(O)CH$_2$C(O)R; or:

R$^5$ and R$^2$ are taken together with their intervening atoms to form an optionally substituted 5-7 membered partially unsaturated or aromatic fused ring having 1-4 heteroatoms independently selected from nitrogen, oxygen, and sulfur; and R$^6$ is —R, halogen, —OR, —SR, —N(R')$_2$, —CN, —NO$_2$, —C(O)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; or:

R$^6$ and R$^3$ are taken together with their intervening atoms to form an optionally substituted 5-7 membered partially unsaturated or aromatic fused ring having 0-4 heteroatoms independently selected from nitrogen, oxygen, and sulfur;

provided that the compound is other than any one of the following:

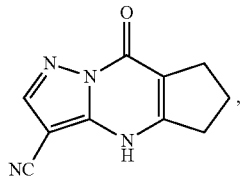

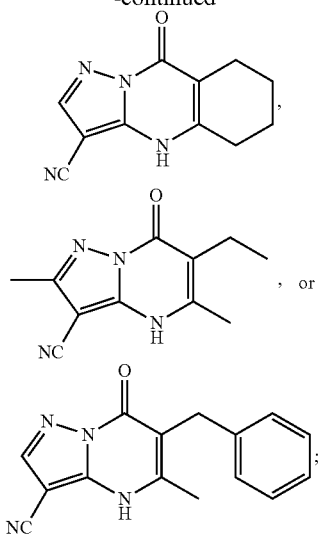

and provided the compound is not a compound of formula (II):

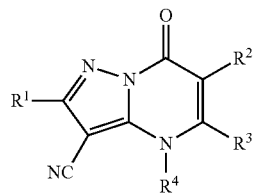

wherein:
R$^1$ is H, when R$^2$ is ethyl, or 2-choropropyl, or and R$^3$methyl;
R$^1$ is H, when R$^2$ is 2-choroethyl, and R$^3$ is ethoxycarbonyl;
R$^1$ is H, when R$^2$ and R$^3$ taken together form a fused benzo ring;
R$^1$ is methyl, when R$^2$ is ethyl, and R$^3$ is methyl;
R$^1$ is methyl, when R$^2$ and R$^3$ taken together form a fused cyclopentyl ring; or
R$^1$ is H, when R$^2$ and R$^3$ taken together form a fused cyclohexyl ring;

and provided that the compound is other than any one of the following:

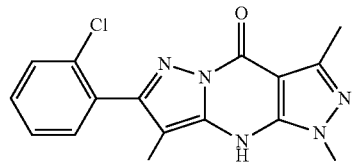

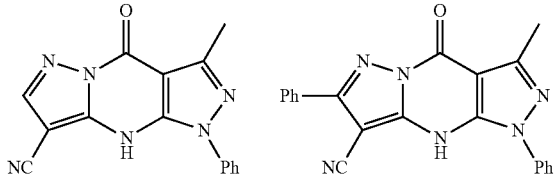

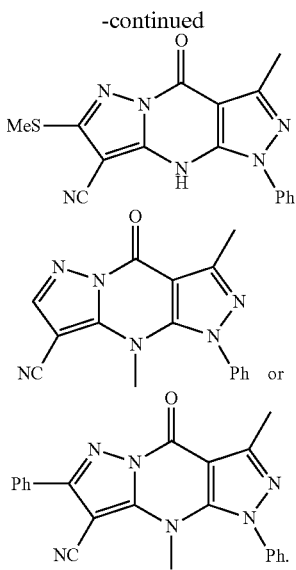

2. The compound according to claim 1, wherein said compound is of formula II:

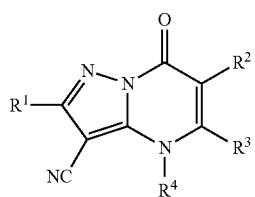

or a pharmaceutically acceptable salt thereof.

3. The compound according to claim 1, wherein said compound is of formula IV:

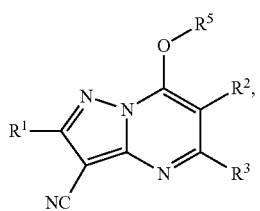

wherein $R^5$ is optionally substituted $C_{1-6}$ aliphatic.

4. The compound of claim 1, which is a compound of formula (II):

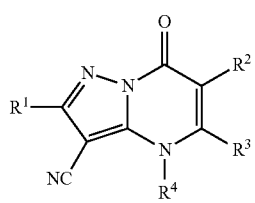

or a salt thereof, wherein:

$R^1$ is H, $C_{1-6}$alkyl, trifluoromethyl, 3-6 membered carbocyclyl, 6 membered aryl, 3-6 membered heterocyclyl, 5-6 membered heteroaryl, halo, —$OR^f$, —$N(R^f)_2$, —CN, or —$NO_2$, wherein said alkyl, carbocyclyl, aryl, heteroaryl, and heterocyclyl are optionally substituted with one or more groups independently selected from oxo, halo, $C_{1-3}$alkoxy and $C_{1-3}$alkyl;

$R^2$ is $C_{1-6}$alkyl, $C_{2-12}$alkenyl, $C_{2-12}$alkynyl, cyclopropyl, or cyclobutyl, wherein any $C_{1-6}$alkyl cyclopropyl, and cyclobutyl is optionally substituted with one or more groups independently selected from $C_{1-3}$alkyl, carbocyclyl, halo, and —CN;

$R^3$ is H, $C_{1-12}$alkyl, $C_{2-12}$alkenyl, $C_{2-12}$alkynyl, carbocyclyl, aryl, heterocyclyl, heteroaryl, —$OR^a$, —$SR^a$, —$N(R^a)_2$, —CN, —$NO_2$, —$C(O)R^a$, —$CO_2R^a$, —$C(O)N(R^a)_2$, —$C(O)SR^a$, —$C(O)C(O)R^a$, —$C(O)CH_2C(O)R^a$, —$C(S)N(R^a)_2$, —$C(S)OR^a$, —$S(O)R^a$, —$SO_2R^a$, —$SO_2N(R^a)_2$, —$N(R^a)C(O)R^a$, —$N(R^a)C(O)N(R^a)_2$, —$N(R^a)SO_2 R^a$, —$N(R^a)SO_2N(R^a)_2$, —$N(R^a)N(R^a)_2$, —$N(R^a)C(=N(R^a))N(R^a)_2$, —$C(=N)N(R^a)_2$, —$C=NOR^a$, —$C(=N(R^a))N(R^a)_2$, —$OC(O)R^a$, or —$OC(O)N(R^a)_2$, wherein each $C_1$-$12$ alkyl, $C_{2-12}$alkenyl, $C_{2-12}$alkynyl, carbocyclyl, aryl, heteroaryl, and heterocyclyl of $R^3$ is independently optionally substituted with one or more groups $R^x$; and wherein $R^2$ and $R^3$ are not each H; or $R^2$ and $R^3$ taken together with the atoms to which they are attached form a 4, 5, 6, 7, or 8 membered carbocyclyl or aryl, which carbocyclyl or aryl is optionally substituted with one or more groups $R^x$;

$R^4$ is H, $C_{1-12}$alkyl, $C_{2-12}$alkenyl, $C_{2-12}$alkynyl, carbocyclyl, aryl, heteroaryl, and heterocyclyl, wherein each $C_{1-12}$alkyl, $C_{2-12}$alkenyl, $C_{2-12}$alkynyl, carbocyclyl, aryl, heteroaryl, and heterocyclyl is optionally substituted with one or more groups independently selected from oxo, $C_{1-12}$ alkyl, $C_{1-12}$haloalkyl, carbocyclyl, aryl, heterocyclyl, heteroaryl, halo, —CN, —$NO_2$, —$NR^mR^m$, —$OR^m$, —$C(=O)OR^m$, and —$OC(=O)R^m$; or $R^4$ and $R^3$ taken together with the atoms to which they are attached form a heterocyclyl;

each $R^a$ is independently selected from H, $C_{1-6}$alkyl, $C_{2-6}$alkenyl, $C_{2-6}$alkynyl, carbocyclyl, aryl, heteroaryl, and heterocyclyl, wherein each $C_{1-6}$alkyl, $C_{3-6}$alkenyl, $C_{3-6}$alkynyl, carbocyclyl, aryl, heteroaryl, and heterocyclyl is optionally substituted with one or more groups $R^x$;

each $R^f$ is independently selected from H, $C_{1-3}$ alkyl, trifluoromethyl, 3-6 membered carbocyclyl, 6 membered aryl, 3-6 membered heterocyclyl, and 5-6 membered heteroaryl, or two $R^f$ groups together with the nitrogen to which they are attached form a 3-6 membered heterocyle;

each $R^m$ is independently selected from H, $C_{1-6}$alkyl, $C_{2-6}$alkenyl, $C_{2-6}$alkynyl, $C_{1-6}$haloalkyl, carbocyclyl, $C_{1-6}$ alkanoyl, phenyl, and benzyl, wherein any $C_{1-6}$alkyl, $C_{2-6}$alkenyl, $C_{2-6}$alkynyl, $C_{1-6}$ haloalkyl, carbocyclyl, $C_{1-6}$ alkanoyl, phenyl, or benzyl is optionally substituted with one or more groups independently selected from halo, —CN, —$NO_2$, —$NR^yR^z$, and —$OR^w$; or two $R^m$ groups together with the nitrogen to which they are attached form a 3-6 membered heterocyle;

each $R^v$ is independently hydrogen, $C_{1-6}$alkyl, $C_{2-6}$alkenyl, $C_{2-6}$alkynyl, carbocyclyl, aryl, heteroaryl, and heterocyclyl, wherein each $C_{1-6}$alkyl, $C_{2-6}$alkenyl, $C_{2-6}$alkynyl, carbocyclyl, aryl, heteroaryl, and heterocyclyl is optionally substituted with one or more groups independently selected from oxo, halo, amino, hydroxyl, aryl, carbocyclyl, and $C_1$-$C_6$ alkyl that is optionally substituted with one or more groups independently selected from oxo and halo; or two $R^v$ are taken together with the nitrogen to which they are attached to form a heterocyclyl that is optionally substituted with one or more groups independently selected from oxo, halo and $C_{1-3}$alkyl that is optionally substituted with one or more groups independently selected from oxo and halo;

each $R^w$ is independently selected from H, $C_{1-4}$alkyl, $C_{1-4}$alkanoyl, phenyl, benzyl, and phenethyl;

each $R^x$ is independently selected from oxo, $C_{1-6}$alkyl, $C_{2-6}$alkenyl, $C_{2-6}$alkynyl, carbocyclyl, aryl, heteroaryl, heterocycle, —F, —Cl, —Br, —I, —$NO_2$, —$N(R^v)_2$, —CN, —C(O)—$N(R^v)_2$, —S(O)—$N(R^v)_2$, —$S(O)_2$—$N(R^v)_2$, —S—$R^v$, —O—C(O)—$R^v$, —C(O)—$R^v$, —C(O)—O—$R^v$, —S(O)—$R^v$, —$S(O)_2$—, —$R^v$, —O—C(O)—$N(R^v)_2$, —$N(R^v)$—C(O)—$OR^v$, —$N(R^v)$—C(O)—$N(R^v)_2$, —$S(O)_2$—$N(R^v)_2$, —$N(R^v)$—C(O)—$R^v$, —$N(R^v)$—S(O)—$R^v$, —$N(R^v)$—$S(O)_2$—$R^v$, —$N(R^v)$—S(O)—$N(R^v)_2$, and —$N(R^v)$—$S(O)_2$—$N(R^v)_2$, wherein any $C_{1-6}$alkyl, $C_{2-6}$alkenyl, $C_{2-6}$alkynyl, carbocyclyl, aryl, heteroaryl, and heterocycle is optionally substituted with one or more groups independently selected from $R^{xa}$, oxo, halo, —$NO_2$, —$N(R^v)_2$, —CN, —C(O)—$N(R^v)_2$, —S(O)—$N(R^v)_2$, —$S(O)_2$—$N(R^v)_2$, —O—$R^v$; —S—$R^v$, —O—C(O)—$R^v$, —C(O)—$R^v$, —C(O)—O—$R^v$, —S(O)—$R^v$, —$S(O)_2$—$R^v$, —C(O)—$N(R^v)_2$, —$S(O)_2$—$N(R^v)_2$, —$N(R^v)$—C(O)—$R^v$, —$N(R^v)$—C(O)—$OR^v$, —$N(R^v)$—S(O)—$R^v$, —$N(R^v)$—$S(O)_2$—$R^v$, and $C_{1-6}$alkyl that is optionally substituted with one or more groups independently selected from oxo and halo;

each $R^y$ and $R^z$ is independently selected from H, $C_{1-4}$alkyl, $C_{1-4}$alkanoyl, $C_{1-4}$alkoxycarbonyl, phenyl, benzyl, and phenethyl, or $R^y$ and $R^z$ together with the nitrogen to which they are attached form a heterocyclyl;

each $R^{xa}$ is independently selected from aryl, heteroaryl, heterocycle, and carbocycle, wherein any aryl, heteroaryl, heterocycle, and carbocycle is optionally substituted with one or more groups independently selected from $C_{1-6}$alkyl, $C_{2-6}$alkenyl, $C_{2-6}$alkynyl, —F, —Cl, —Br, —I, —$NO_2$, —$N(R^v)_2$, —CN, carbocycle, aryl, —C(O)—$N(R^v)_2$, —S(O)—$N(R^v)_2$, —$S(O)_2$—$N(R^v)_2$, —O—$R^v$, —S—$R^v$, —O—C(O)—$R^v$, —C(O)—$R^v$, —C(O)—O—$R^v$, —S(O)—$R^v$, —$S(O)_2$—$R^v$, —O—C(O)—$N(R^v)_2$, —$N(R^v)$—C(O)—$OR^v$, —$N(R^v)$—C(O)—$N(R^v)_2$, —$S(O)_2$—$N(R^v)_2$, —$N(R^v)$—C(O)—$R^v$, —$N(R^v)$—S(O)—$R^v$, —$N(R^v)$—$S(O)_2$, —$R^v$, and —$N(R^v)$—S(O)—$N(R^v)_2$, wherein any $C_{1-6}$alkyl, $C_{2-6}$alkenyl, and $C_{2-6}$alkynyl is optionally substituted with one or more groups independently selected from oxo, halo, —$NO_2$, —$N(R^v)_2$, —CN, —C(O)—$N(R^v)_2$, —S(O)—$N(R^v)_2$, —$S(O)_2$—$N(R^v)_2$, —O—C(O)—$R^v$, —C(O)—$R^v$, —C(O)—O—$R^v$, —S(O)—$R^v$, —$S(O)_2$, —$R^v$, —C(O)—$N(R^v)_2$, —$S(O)_2$, —$N(R^v)_2$, —$N(R^v)$—C(O)—$R^v$, —$N(R^v)$—S(O)—$R^v$, and —$N(R^v)$—$S(O)_2$—$R^v$.

5. The compound of claim 4 wherein $R^1$ is H, methyl, or ethyl.

6. The compound of claim 4 wherein $R^2$ is isopropyl, ethyl, tert-butyl, 2,2-difluoroethyl, cyclobutyl, 2-propyn-1-yl, vinyl, 2-fluoroethyl, 2-propenyl, 1-methylvinylcyclopropyl, 2-buten-1-yl, 1-methyl-2-propyn-1-yl, 1-methylprop-1-yl, 1-(cyclopropyl)ethyl, 2-butynyl, 1 methyl-2-propenyl, 1-methylcyclobutyl, propyl, and 2-methylpropyl.

7. The compound of claim 4 wherein $R^2$ and $R^3$ taken together with the atoms to which they are attached form a 4, 5, 6, 7, or 8 membered carbocyclyl or aryl, which carbocyclyl or aryl is optionally substituted with one or more groups $R^x$.

8. The compound of claim 4 wherein $R^3$ is H, $C_{1-12}$alkyl, $C_{2-12}$alkenyl, $C_{2-12}$alkynyl, aryl, heterocyclyl, heteroaryl, —$OR^a$, —$N(R^a)_2$, —C(O)$R^a$, -$CO_2R^a$, —C(O)$N(R^a)_2$, or —$N(R^a)$C(O)$R^a$, wherein each $C_{1-12}$alkyl, $C_{2-12}$alkenyl, $C_{2-12}$alkynyl, aryl, heteroaryl, and heterocyclyl of $R^3$ is independently optionally substituted with one or more groups $R^x$.

9. The compound of claim 4 wherein $R^3$ is H, methyl, carboxy, formyl, aminocarbonyl, furan-3-yl, phenyl, benzyl, phenethyl, phenoxy, 1H-pyrazol-4-yl, 1-(cyclopropylmethyl)-1H-pyrazol-4-yl, 1-(1-methylcyclopropyl)-1H-pyrazol-4-yl, 5-fluoro-1H-pyrazol-4-yl, 1-(2-phenylpropan-2-yl)-1H-pyrazol-4-yl, 1-(pyridin-3-yl)-1H-pyrazol-4-yl, 1-(pyridin-4-yl)-1H-pyrazol-4-yl, 1-(pyridin-2-yl)-1H-pyrazol-4-yl, 1-[1-(N-methylaminocarbonyl)-1,1-dimethylmethyl]- 1H-pyrazol-4-yl, 5-fluoro-1-isopropyl-1H-pyrazol-4-yl, 1-(cyclopropylmethyl)-1H-pyrazol-5-yl, 1-(cyclopropylmethyl)-1H-pyrazol-3-yl, 1-(tetrahydro-2H-thiopyran-4-yl)-1H-pyrazol-4-yl, 1-(1,1-dioxidotetrahydro-2H-thiopyran-4-yl)-1H-pyrazol-4-yl, 1-((6-(3-oxobut-1-en-1-yl)pyridin-2-yl)methyl)-1H-pyrazol-4-yl, 3-iodophenyl, methylaminocarbonyl, 3-methyl-1,2,4-oxadiazol-5-yl, 5-methyl-1,3,4-oxadiazol-2-yl, 1H-imidazol-2-yl, N-(benzoylmethyl)aminocarbonyl, 5-phenyloxazol-2-yl, 1-cyclohexylpyrazol-4-yl, 1-isopropylpyrazol-4-yl, biphenyl-3-yl, 3-((4-fluorophenyl)amino)phenyl, 3-(2-oxopyrrolidin-1-yl)phenyl, 3-(methylcarbonylamino)-5-phenylphenyl, phenyl amino, piperidin-1-yl, methoxymethyl, ethoxymethyl, ethoxycarbonyl, 3-methoxypropyl, benzyloxycarbonyl, trifluoromethyl, 3-furyl, ethylaminocarbonyl, hydroxymethyl, 3-hydroxypropyl, 2-hydroxyethyl, methylaminomethyl, benzofuran-3-yl, 1-phenyl-1H-pyrazol-3-yl, 5-cyclopropyl-furan-2-yl, 2-methylfuran-3-yl, 1-phenyl-1H-pyrazol-4-yl, 1-ethyl-1H-pyrazol-4-yl, 1-methyl-6-oxo-1,6-dihydropyridin-3-yl, furan-2-yl, 5-phenylfuran-2-yl, 1-isopropyl-1H-pyrazol-4-yl, pyrimidin-5-yl, 5-methylpyridin-3-yl, 1-methyl-1H-pyrazol-3-yl, 4-phenylfuran-2-yl, 2-fluorophenyl, 4-cyanophenyl, 4-methoxyphenyl, 4-(trifluoromethyl) phenyl, 4-fluorophenyl, 1-benzyl-1H-pyrazol-4-yl, 5-chloropyridin-3-yl, 5-fluoropyridin-3-yl, prop-1-en-2-yl, vinyl, 1-methyl-1H-pyrazol-5-yl, 4-(hydroxymethyl)furan-2-yl, 3-cyanophenyl, 1H-pyrazol-5-yl, 2,5-dihydrofuran-3-yl, thiophen-3-yl, thiophen-2-yl, 1-methyl-1H-pyrazol-4-yl, 5-methylfuran-2-yl, 5-(hydroxymethyl)furan-2-yl, 3-(trifluoromethyl)phenyl, 3-methoxyphenyl, 3-fluorophenyl, pyridin-3-yl, 1-(methylsulfonyl)-1H-pyrazol-4-yl, 1-cyclopentyl-1H-pyrazol-4-yl, 1-(thiophen-3-ylmethyl)-1H-pyrazol-4-yl, 4-chloro-3-(morpholine-4-carbonyl)phenyl, 3-chlor-4-(cyclopropylaminocarbonyl)phenyl, 1-(1-hydroxy-2-methylpropan-2-yl)-1H-pyrazol-4-yl, 1-(3-methoxybenzyl)-1H-pyrazol-4-yl, 1-(pyridin-4-ylmethyl)-1H-pyrazol-4-yl, 1-(2-chlorobenzyl)-1H-pyrazol-4-yl, 1-(3-phenoxybenzyl)-1H-pyrazol-4-yl, 1-(4-phenoxybenzyl)-1H-pyrazol-4-yl, 1-cyclohexyl-1H-pyrazol-4-yl, 1-(1-phenylethyl)-1H-pyrazol-4-yl, 1-cyclobutyl-1H-pyrazol-4-yl, 1-(sec-butyl)-1H-pyrazol-4-yl, 4-fluoro-3-(pyrrolidine-1-carbonyl)phenyl, 1-(cyclopropylsulfonyl)-1H-pyrazol-3-yl, 1-(cyclopropanecarbonyl)-1H-pyrazol-3-yl, 1-(2-cyclopropylethyl)-1H-pyrazol-4-yl, 1-([1,1'-biphenyl]-3-ylmethyl)-1H-pyrazol-4-yl, 1-phenethyl-1H-pyrazol-4-yl, 1-(2-methoxybenzyl)-1H-pyrazol-4-yl, 1-(4-methoxybenzyl)-1H-pyrazol-4-yl, 1-(tert-butyl)-1H-pyrazol-4-yl, 3,4-dimethylphenyl, 3-chloro-4-ethoxyphenyl, 4-methoxy-3-methylphenyl, 2-methylbenzo[d]thiazol-5-yl, 1-(2-phenoxybenzyl)-1H-pyrazol-4-yl, 1-(phenylsulfonyl)-1H-pyrazol-4-yl, 1-benzoyl-1H-pyrazol-4-yl, 1-benzhydryl-1H-pyrazol-4-yl, 1-([1,1'-biphenyl]-2-ylmethyl)-1H-pyrazol-4-yl, 1-(cyclohexylmethyl)-1H-pyrazol-4-yl, 1-(pyridin-3-ylmethyl)-1H-pyrazol-4-yl, benzofuran-2-yl, (E)-styryl, 5-ethylfuran-2-yl, 1-(2-methoxyethyl)-1H-pyrazol-4-yl, 1-(naphthalen-1-ylmethyl)-1H-pyrazol-4-yl, 1-([1,1'-biphenyl]-4-ylmethyl)-1H-pyrazol-4-yl, 3-phenoxyphenyl, phenyl ethynyl, 3,4-dichlorophenyl, 3-chloro-4-methoxyphenyl, 3-methoxy-4-methylphenyl, 1-(thiazol-4-ylmethyl)-1H-pyrazol-4-yl, 1H-indazol-5-yl, 3,4-dimethoxyphenyl, 4-methoxy-3,5-dimethylphenyl, 1-(oxetan-3-yl)-1H-pyrazol-4-yl, 1-(2-fluorobenzyl)-1H-pyrazol-4-yl, 1-(4-fluorobenzyl)-1H-pyrazol-4-yl, 1-(methoxycarbonylmethyl) -1H-pyrazol-4-yl, 1-(2-(dimethylamino)ethyl)-1H-pyrazol-4-yl, 3-cyano-4-methylphenyl, benzo[d][1,3]dioxol-5-yl, 2,3-dihydrobenzofuran-5-yl, 1-(3-fluorobenzyl)-1H-pyrazol-4-yl, 1-(thiophen-2-ylmethyl)-1H-pyrazol-4-yl, 1-(2,2,2-trifluoroethyl)-1H-pyrazol-4-yl, 1-(3-chlorobenzyl)-1H-pyrazol-4-yl, 1-isobutyl-1H-pyrazol-4-yl, 1-(3,3,3-trifluoropropyl)-1H-pyrazol-4-yl, 1-(difluoromethyl)-1H-pyrazol-4-yl, 1-(2-cyanoethyl)-1H-pyrazol-4-yl, 4-cyclopropylfuran-2-yl, 1H-pyrrol-3-yl, 2,2-difluorobenzo[d][1,3]dioxol-5-yl, 3-fluoro-4-(aminocarbonyl)phenyl, 3-fluoro-4-(methylsulfonyl)phenyl, 3-chloro-4-(trifluoromethoxy)phenyl, 5-fluoro-3-(aminocarbonyl)phenyl, 3-(hydroxymethyl)-4-methoxyphenyl, 1-(methylsulfonyl)-1H-pyrrol-3-yl, 1-methyl-1H-pyrrol-3-yl, 1H-indol-2-yl, cyclopropylcarbonylamino, benzoyl amino, 3-bromophenyl, 3-(1-methylpyrazol-4-yl)phenyl, 3-(1-isopropylpyrazol-4-yl)phenyl, 4-phenylphenyl, 4-(4-fluoroanilino)phenyl, 3-(tert-butoxycarbonylamino)phenyl, 1-acetyl-1,2,3,6-tetrahydropyridin-4-yl, 1-propionyl-1,2,3,6-tetrahydropyridin-4-yl, 1-acryloyl-1,2,3,6-tetrahydropyridin-4-yl, 1-methyl-1,2,3,6-tetrahydropyridin-4-yl, 14(2-methylthiazol-4-yl) methyl)-1H-pyrazol-4-yl, 1-(2-(acetylamino)ethyl) -1H-pyrazol-4-yl, 3,5-dichlorophenyl, 2-fluoro-4-(methylsulfonyl)phenyl, 1-(tert-pentyl)-1H-pyrazol-4-yl, 3-(2-morpholinoethyl)phenyl, 3-(2-(dimethylamino)ethyl) phenyl, 1-(1-(thiazol-4-yl)ethyl)-1H-pyrazol-4-yl, 1-(tetrahydro-2H-pyran-4-yl)-1H-pyrazol-4-yl, 3-methoxy-4-(trifluoromethyl)phenyl, 3-methoxycarbonyl-4-chlorophenyl, 4-(trifluoromethoxy)phenyl, 3-methyl-4-(trifluoromethoxy) phenyl, 4-cyclopropyl-3-(trifluoromethyl)phenyl, 2,2-dimethyl-2,3-dihydrobenzofuran-5-yl, 3,5-dimethoxyphenyl, 3,4-difluorophenyl, 4-biphenyl, 3-chloro-5-fluorophenyl, 3,5-bis(trifluoromethyl)phenyl, 3-fluoro-5-methoxyphenyl, 3-(aminocarbonyl)phenyl, 4-(cyclopropylmethoxy)phenyl, 2-fluoro-5-(benzyloxycarbonyl)phenyl, 3-(1H-pyrazol-1-yl) phenyl, 1-(2-hydroxycyclopentyl)-1H-pyrazol-4-yl, 3 -(N-methylaminosulfonyl)phenyl, 4-(2-hydroxypropan-2-yl) phenyl, 2-(trifluoromethyl)pyridin-4-yl, 6-phenoxypyridin-3-yl, 2-methoxypyridin-4-yl, 4-methyl-2-phenylthiazol-5-yl, 3-amino-5-cyanophenyl, 1-(tetrahydrofuran-3-yl, 3-(N-ethylaminocarbonyl)phenyl, 3-(aminocarbonylmethyl) phenyl, 6-phenylpyridin-3-yl, 1-(tetrahydro-2H-pyran-3-yl)-1H-pyrazol-4-yl, 1-(1-methoxypropan-2-yl)-1H-pyrazol-4-yl, 1-(2-ethoxyethyl)-1H-pyrazol-4-yl, 1-acetyl-2,5-dihydro-1H-pyrrol-3-yl, 1-acetyl-1,2,5,6-tetrahydropyridin-3-yl, 1-propionyl-1,2,5,6-tetrahydropyridin-3-yl, 1-propionyl-2,5-dihydro-1H-pyrrol-3-yl, 1-((1S,3S)-3-hydroxycyclobutyl)-1H-pyrazol-4-yl, 2,5-dihydro-1H-pyrrol-3-yl, 1,2,5,6-tetrahydropyridin-3-yl, 1-methyl-1,2,5,6-tetrahydropyridin-3-yl, 1-acryloyl-1,2,5,6-tetrahydropyridin-3-yl, 1-acryloyl-2,5-dihydro-1H-pyrrol-3-yl, 4-chloro-3,5-dimethylphenyl, 4-cyano-3-methylphenyl, 1-oxo-2,3-dihydro-1H-inden-5-yl, 3,4-bis (trifluoromethyl)phenyl, 3-methyl-4-(trifluoromethyl) phenyl, 1-(benzo[b]thiophen-7-ylmethyl)-1H-pyrazol-4-yl, 4-fluoro-3-(N-cyclohexylaminocarbonyl)phenyl, 4-morpholinophenyl, 4-(4-(tert-butoxycarbonyl)piperazin-1-yl) phenyl, 3-chloro-5-methylphenyl, 3-(methylsulfonyl)phenyl, 4-(methyl sulfonylamino)phenyl, 4-(morpholinomethyl)phenyl, 3-morpholinophenyl, 1-(2-(vinylcarbonyl amino)ethyl)-1H-pyrazol-4-yl, 1-(2-aminoethyl)-1H-pyrazol-4-yl, 3-cyclopropyl-4-methylphenyl, 3-ethoxyphenyl, 3-(hydroxymethyl)phenyl, 1-(2-(tert-butoxycarbonylamino)ethyl)-1H-pyrazol-4-yl, 3-phenethoxyphenyl, 1,2,3,6-tetrahydropyridin-4-yl, 1-(2-(vinylsulfonylamino)ethyl)-1H-pyrazol-4-yl, 4-(phenylamino)phenyl, 3-methyl-1H-pyrazol-4-yl, 4-(benzyloxy)phenyl, 3,5-difluorophenyl, 3-fluoro-5-trifluoromethylphenyl, 3-(ethylsulfonyl)phenyl, 3-(trifluoromethoxy)phenyl, 1-(thiazol-5-ylmethyl)-1H-pyrazol-4-yl, p-tolyl, 4-cyclopropylphenyl, 4-(ethyl sulfonyl)phenyl, 1-(6-vinylpyridin-2-yl)methyl)-1H-pyrazol-4-yl, 6-(benzyloxy)pyridin-3-yl, 1-(tert-butoxycarbonyl)-2,5-dihydro-1H-pyrrol-3-yl, 1-(2-hydroxy-1-phenyl ethyl)-1H-pyrazol-4-yl, 1-(2-cyano-1-phenylethyl)-1H-pyrazol-4-yl, 6-cyclopropylpyridin-3-yl, 4-cyano-3-methoxyphenyl, 4-methoxy-3-(trifluoromethyl)phenyl, 4-chlorophenyl, 1-(3,4-difluorobenzyl)-1H-pyrazol-4-yl, 4-methyl-3-(trifluoromethyl)phenyl, 4-(pyrrolidine-1-carbonyl)phenyl, 4-(isopropylaminocarbonyl)phenyl, 4-(4-methylpiperazin-1-yl)phenyl, 3-chloro-5-cyanophenyl, 3-(pyrrolidine-1-carbonyl)phenyl, 3-(methylsulfonylaminomethyl) phenyl, 3-(1H-pyrazol-5-yl)phenyl, 4-(methylsulfonyl) phenyl, 4-(cyclopropylaminocarbonyl)phenyl, 1-(2-fluoroethyl)-1H-pyrazol-4-yl, 3-(cyclopropylmethoxy) phenyl, 3-(benzyloxy)phenyl, 3-(morpholinomethyl)phenyl, 3-(phenoxymethyl)phenyl, 1-(3-fluorophenyl)-1H-pyrazol-4-yl, 2-cyclopropylvinyl, 6-(trifluoromethyl)pyridin-3-yl, 1-(4-fluorophenyl)-1H-pyrazol-4-yl, 2,4-dimethylthiazol-5-yl, 1-propyl-1H-pyrazol-4-yl, 1-butyl-1H-pyrazol-4-yl, 1-(2-(phenylamino)ethyl)-1H-pyrazol-4-yl, 4-(aminocarbonyl)phenyl, 4-(N-methylaminocarbonyl)phenyl, 3-fluor-4-(N-methylaminocarbonyl)phenyl, 1-(2-(3,3-difluoroazetidin-1-yl)ethyl)-1H-pyrazol-4-yl, 1-(2-(3,3-difluoropyrrolidin-1-yl)ethyl)-1H-pyrazol-4-yl, 1-(2-((2,2,2-trifluoroethyl)amino)ethyl)-1H-pyrazol-4-yl, 1-propenyl, 3-(methylcarbonylamino)phenyl, 4-(methyl sulfonylamino) phenyl, 4-(morpholine-4-carbonyl)phenyl, 4-(4-acetylpiperazin-1-yl)phenyl, 1-(2,2-difluoroethyl)-1H-pyrazol-4-yl, 5-isopropylfuran-2-yl, 1-(3,3-difluorocyclopentyl)-1H-pyrazol-4-yl, 1-((1S,3R)-3-hydroxycyclopentyl)-1H-pyrazol-4-yl, 1-((1S,3S)-3-hydroxycyclopentyl)-1H-pyrazol-4-yl, 3-(1H-pyrazol-4-yl)phenyl, 5-bromofuran-2-yl, 3-(phenylamino)phenyl, 2-methylthiazol-5-yl, 3-(phenylethynyl)phenyl, 3-phenethylphenyl, 1-(3-fluorocyclopentyl)-1H-pyrazol-4-yl, 1-(1-methoxy-2-methylpropan-2-yl)-1H-pyrazol-4-yl, 1-(1-acryloylazetidin-3-yl)-1H-pyrazol-4-yl, 1-(1-propionylazetidin-3-yl)-1H-pyrazol-4-yl, 6-oxo-1,6-dihydropyridin-3-yl, 4-(piperazin-1-yl)phenyl, 1-(1-fluoro-2-methylpropan-2-yl)-1H-pyrazol-4-yl, 3-(trifluoromethyl)-1H-pyrazol-4-yl, 3,5-dimethylphenyl, 4-(morpholinosulfonyl)phenyl, 3-(4-methylpiperazine-1-carbonyl)phenyl, 3-(2-hydroxypropan-2-yl)phenyl, 1-isopropyl-3-methyl-1H-pyrazol-4-yl, 1-isopropyl-5-methyl-1H-pyrazol-4-yl, 3-cyclopropyl-1H-pyrazol-5-yl, 5-methoxycarbonylpyrrol-3-yl, 3-cyclopropyl-1-isopropyl-1H-pyrazol-5-yl, 5-cyclopropyl-1-isopropyl-1H-pyrazol-3- yl, 1-isopropyl-5-(methoxycarbonyl)pyrrol-3-yl, 1-methyl-3-(trifluoromethyl)-1H-pyrazol-5-yl, 1-isopropyl-1H-pyrazol-3-yl, 1-cyclopentyl-5-cyclopropyl-1H-pyrazol-3-yl, 1-cyclopentyl-3-cyclopropyl-1H-pyrazol-5-yl, 1-cyclopentyl-1H-pyrazol-3-yl, 1-isopropyl-1H-pyrazol-5-yl, 1-isopropyl-5-(N-methylaminocarbonyl)pyrrol-3-yl, 1-isopropyl-5-(N,N-dimethylaminocarbonyl)pyrrol-3-yl, 1-(2-cyclopropylethyl)-1H-pyrazol-3-yl, 1-(2-cyclopropylethyl)-1H-pyrazol-5-yl, 1-ethyl-1H-pyrazol-3-yl, 3-(3,3-dimethyl-2-oxopyrrolidin-1-yl)phenyl, 3-(2-oxo-3-phenylpyrrolidin-1-yl)phenyl, 3-((E)-styryl)phenyl, 3-(3-cyanophenyl)phenyl, 3-(3-(methylsulfonylamino)phenyl)phenyl, 3-(4-(methylsulfonylamino)phenyl)phenyl, or 3-(4-(N-methylaminosulfonyl)phenyl)phenyl.

10. The compound of claim 4 wherein $R^4$ is H, methyl, ethyl, propyl, cyclopropylmethyl, 2-hydroxyethyl, 2-(dimethylmino)ethyl, phenyl, benzyl, or 2-methoxyethyl.

11. The compound of claim 1 which is selected from the group consisting of:

I-12

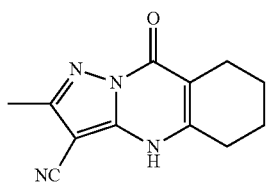

I-13

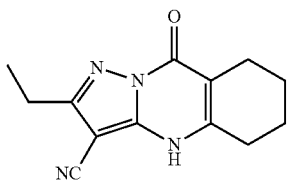

I-14

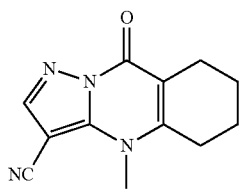

I-15

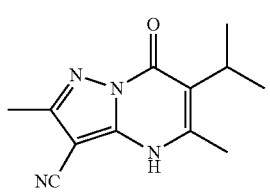

I-16

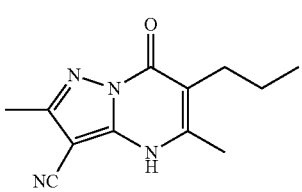

I-17

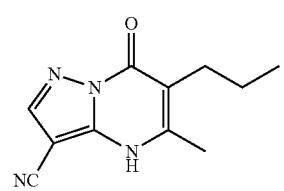

I-18

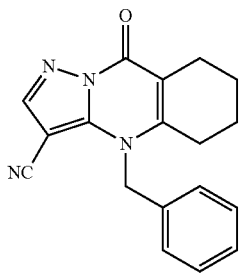

I-19

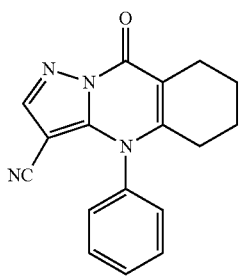

I-20

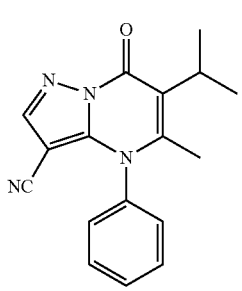

I-21

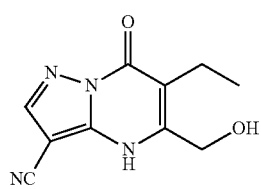

I-22

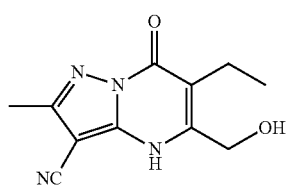

I-23

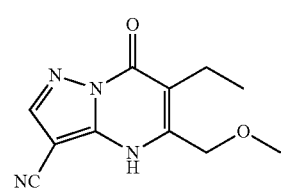

I-24

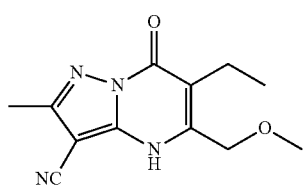

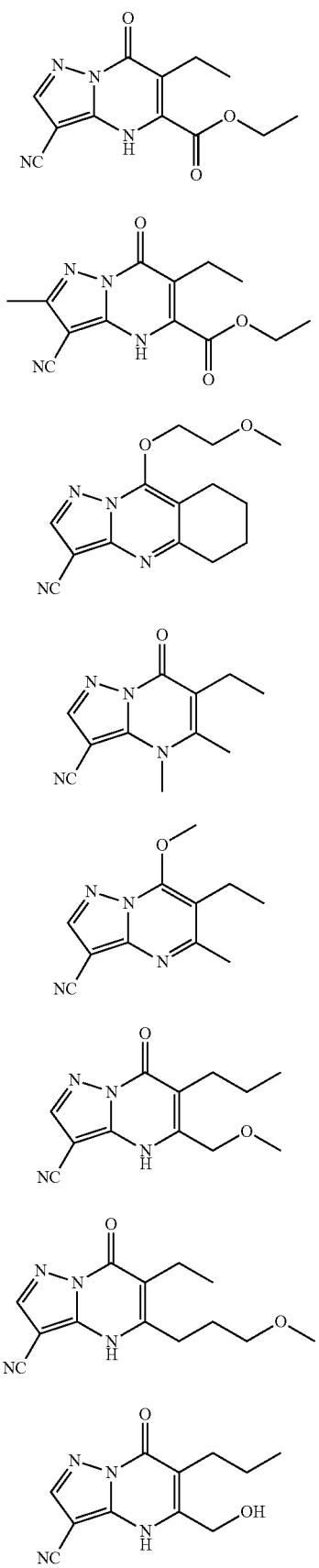
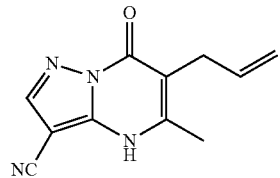
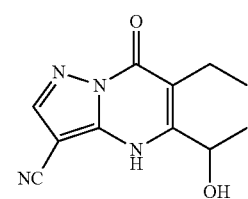
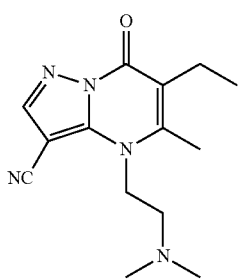
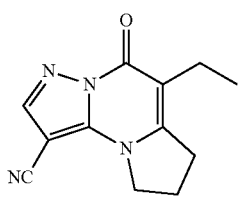
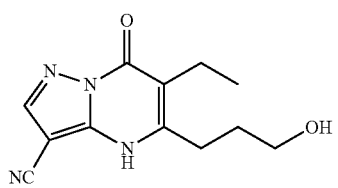
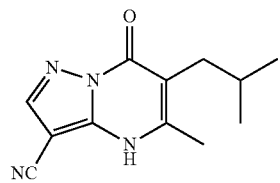
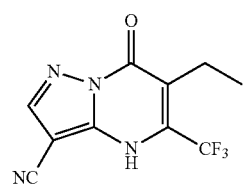

-continued
I-42
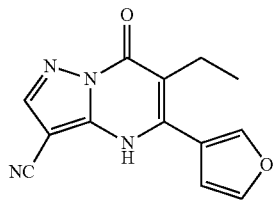
I-43
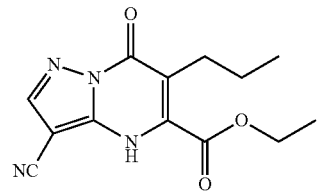
I-44
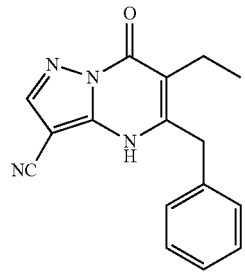
I-45
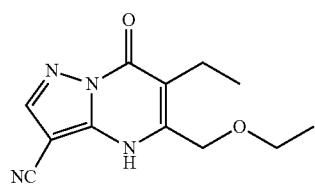
I-46
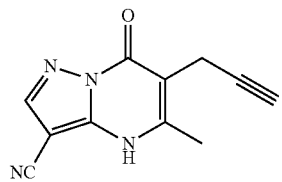
I-47
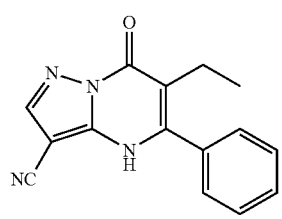
I-48
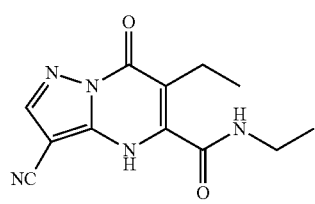
-continued
I-49
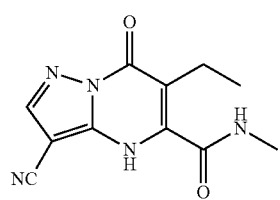
I-50
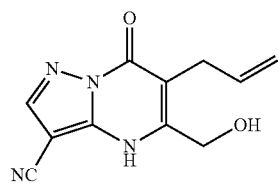
I-51
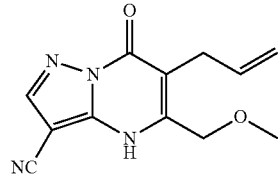
I-52
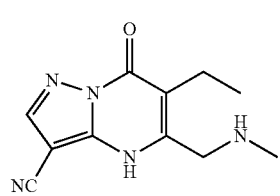
I-53
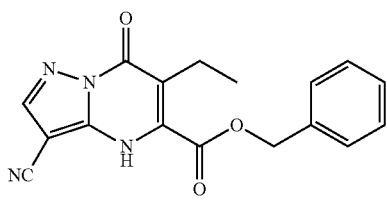
I-54
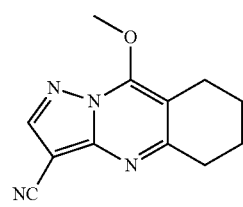
I-56
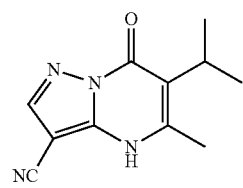
I-57
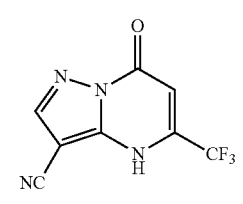

I-58 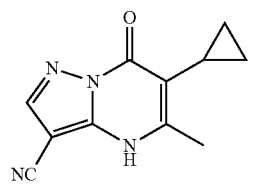
I-59 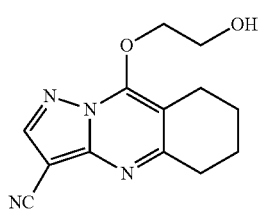
I-60 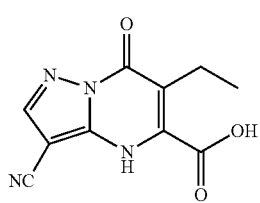
I-61 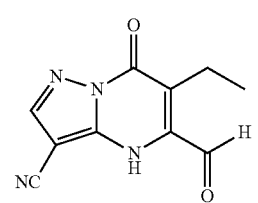
I-63 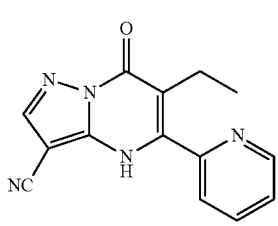
I-64 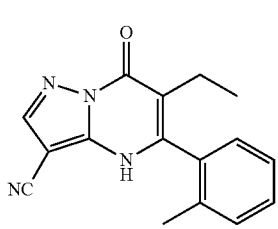
I-65 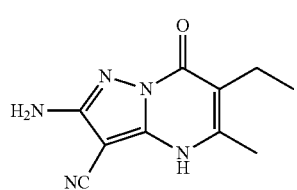
I-66 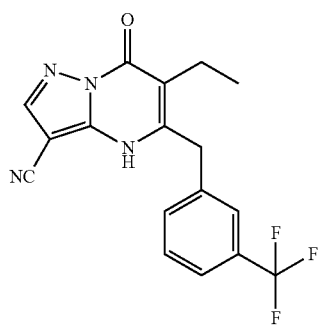
I-67 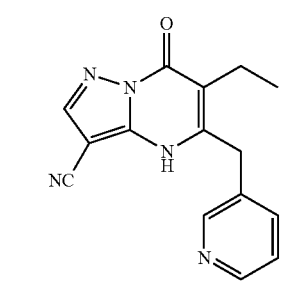
I-68 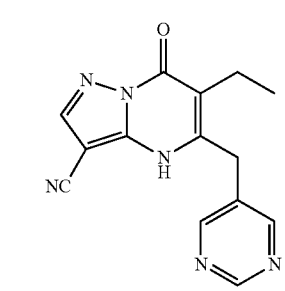
I-69 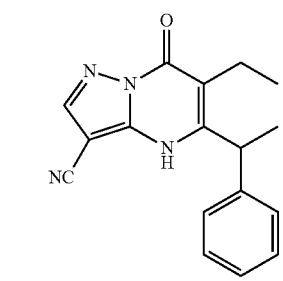
I-70 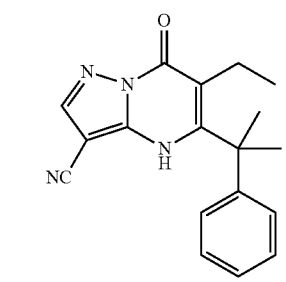

321
-continued
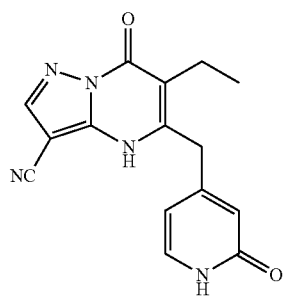
I-71
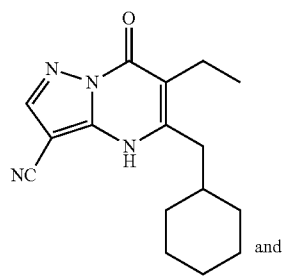
I-72
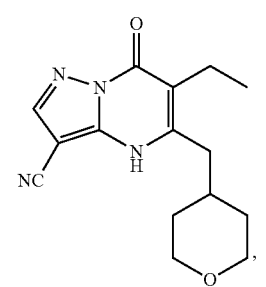
and
or a salt thereof.
12. The compound of claim 1 which is selected from the group consisting of:
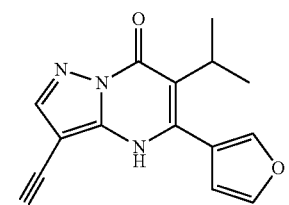
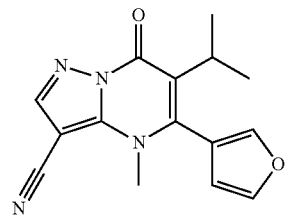
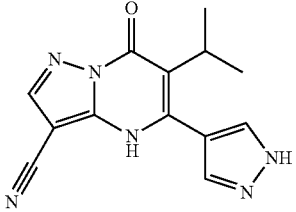
322
-continued
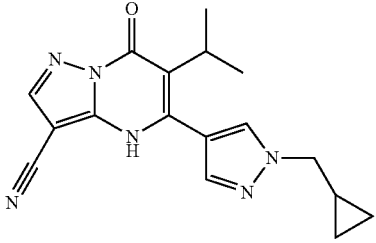
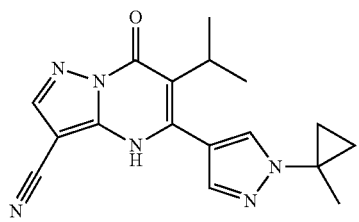
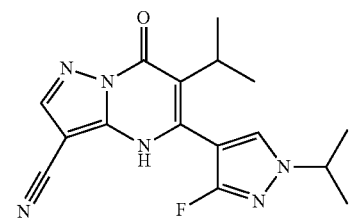
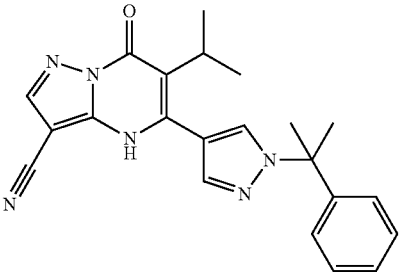
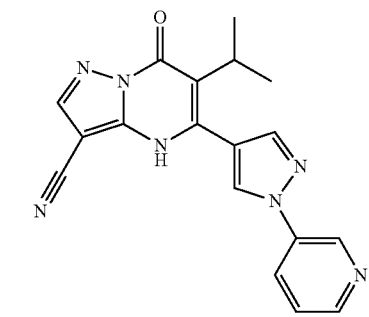
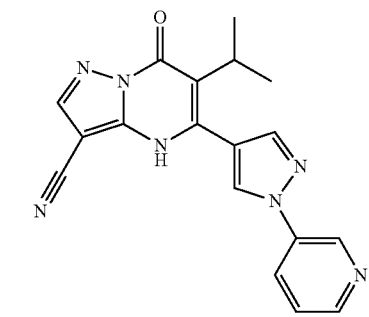

323
-continued
324
-continued
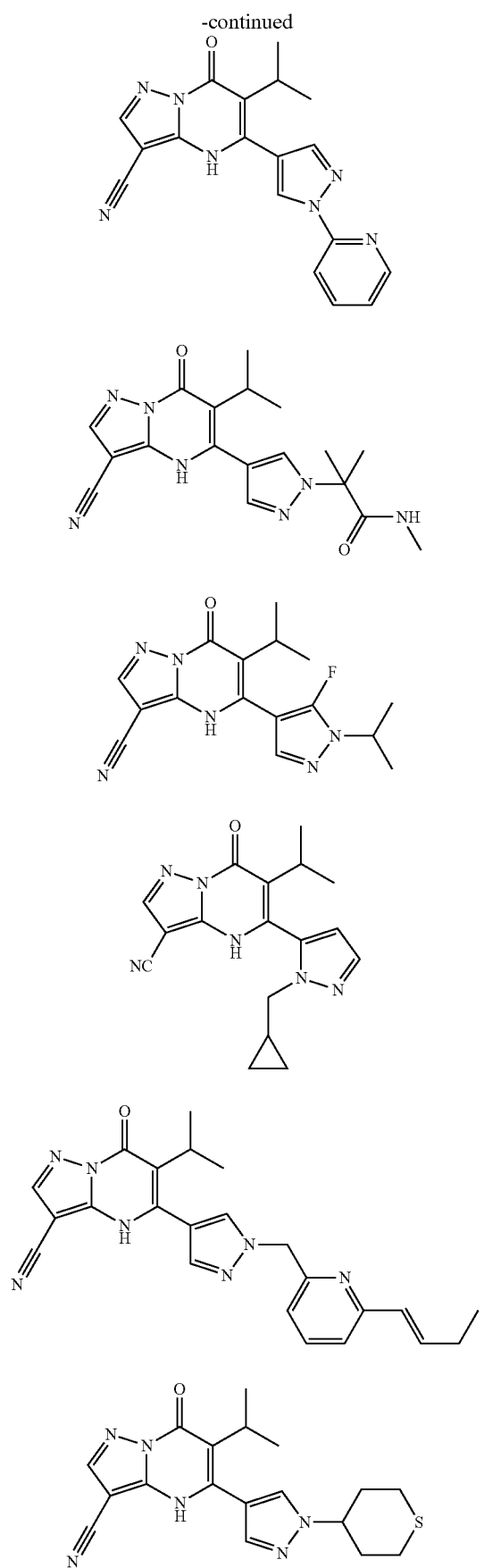
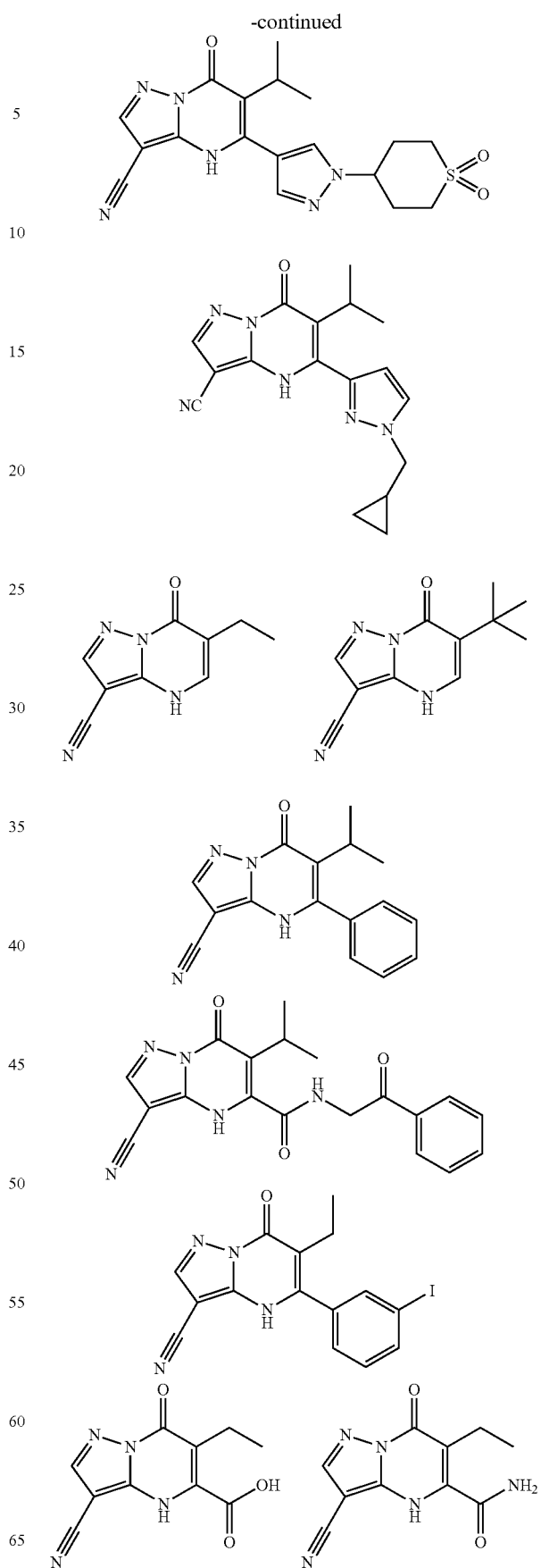

-continued
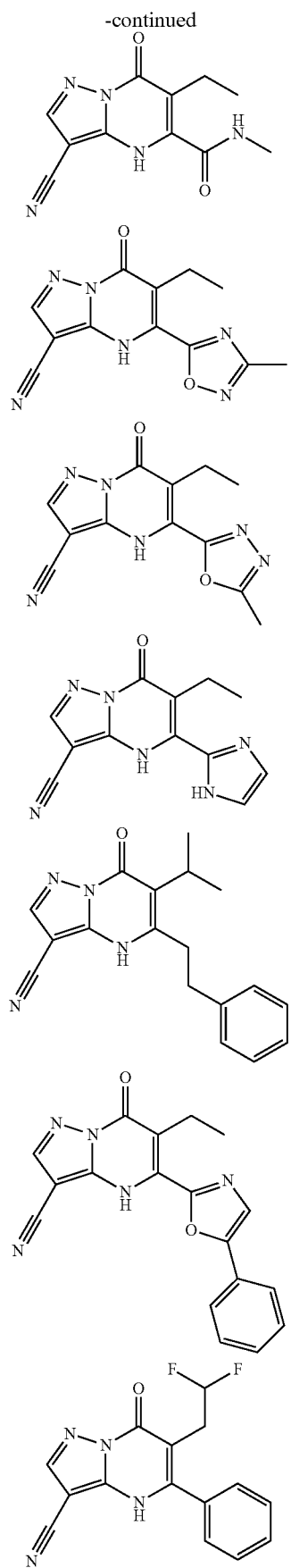
-continued
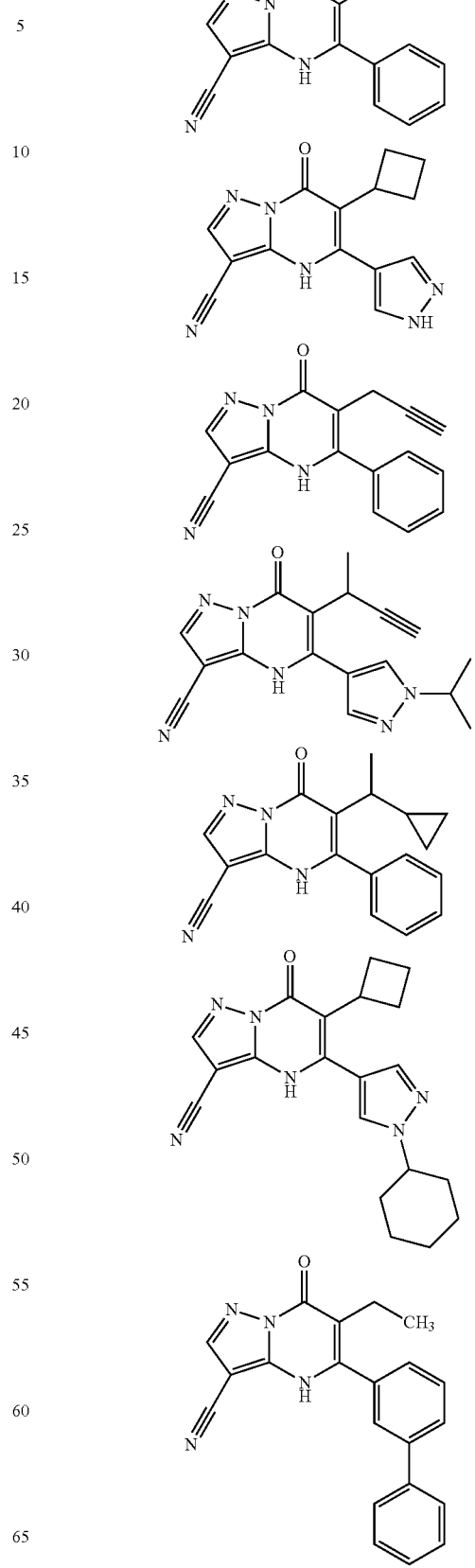

327
-continued
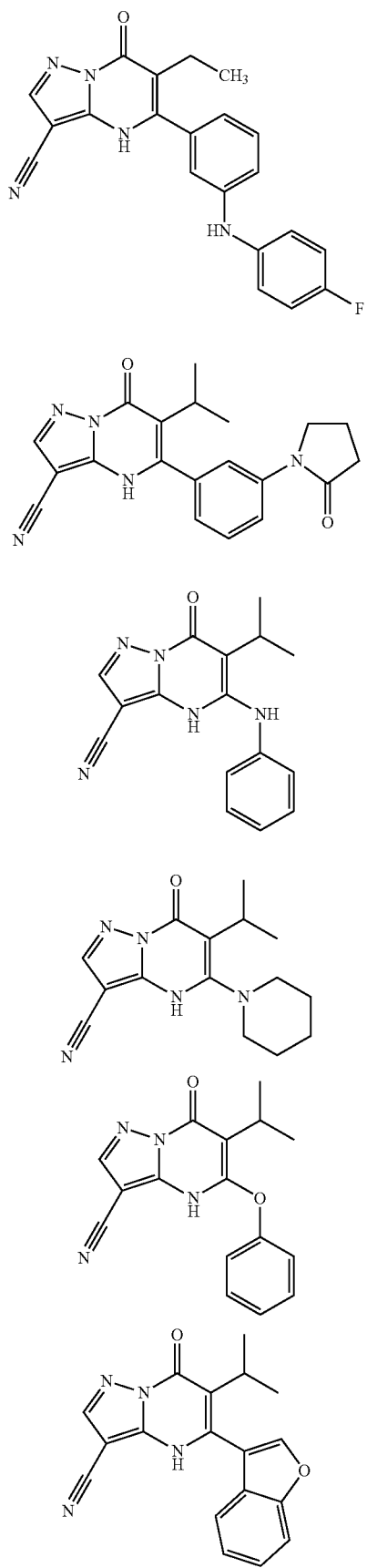
328
-continued
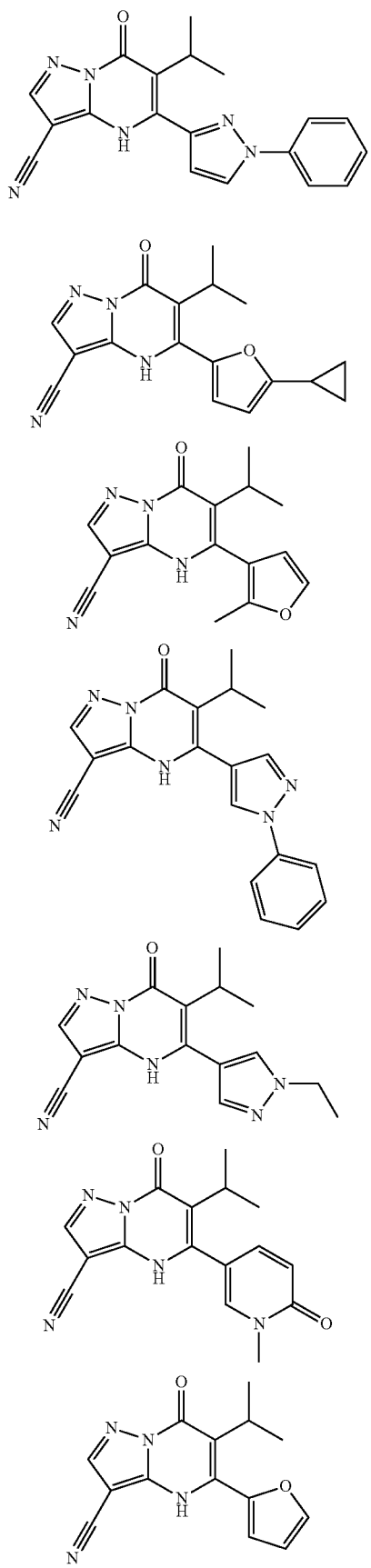

329
-continued
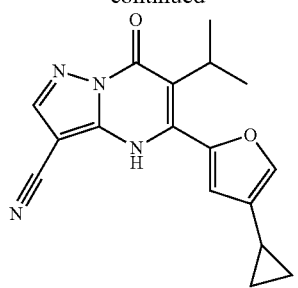
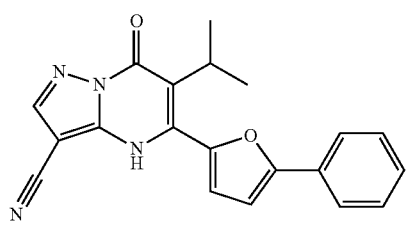
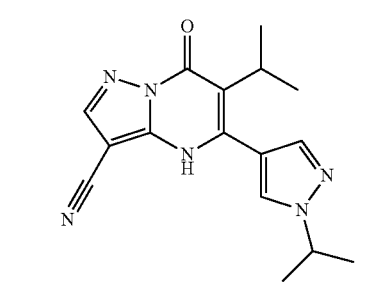
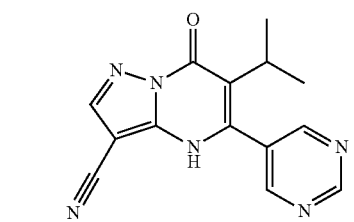
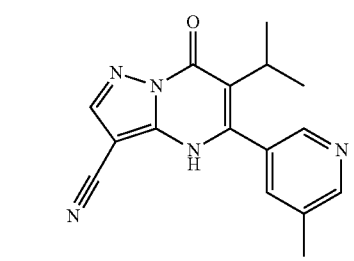
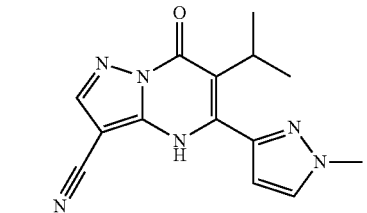
330
-continued
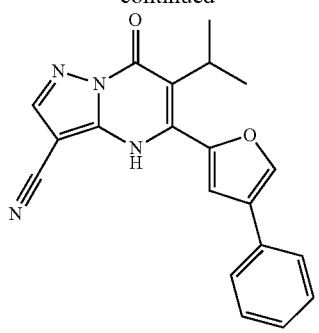
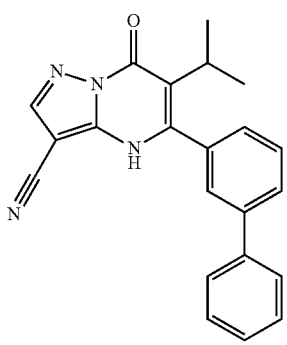
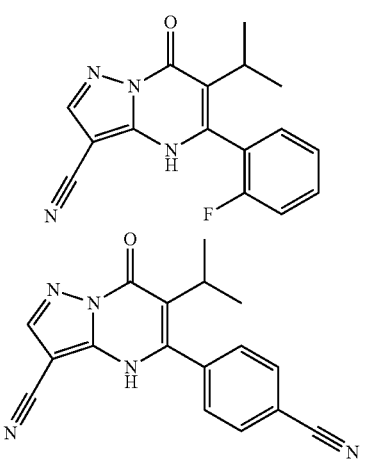
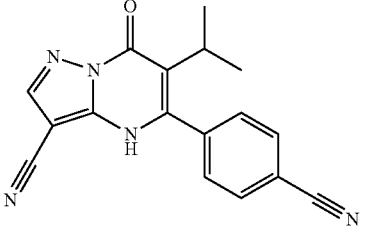
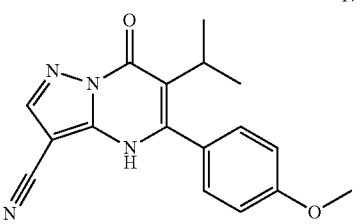
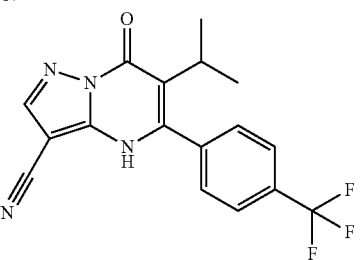

| 331 | 332 |
|---|---|
| -continued | -continued |
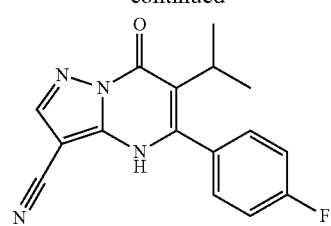
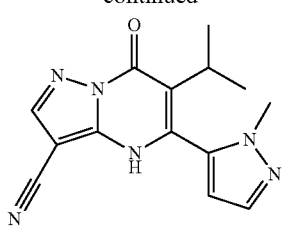
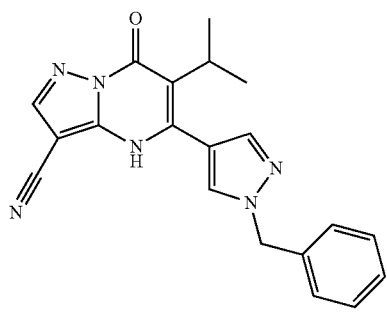
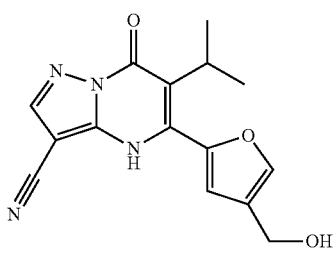
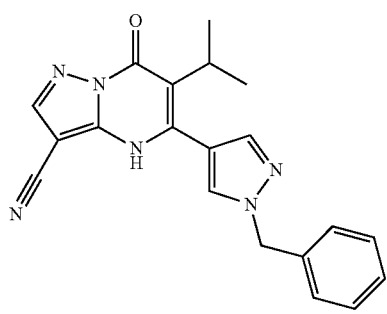
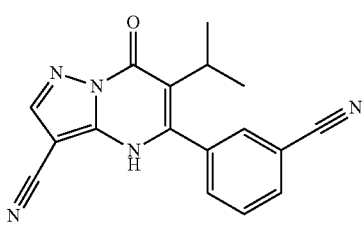
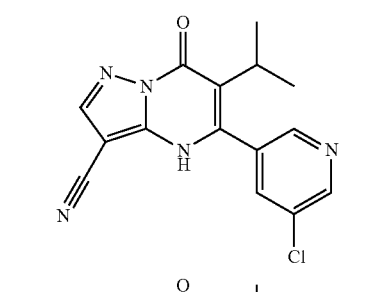
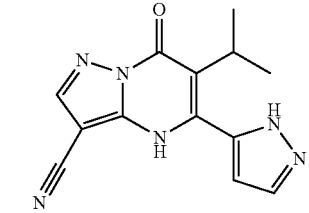
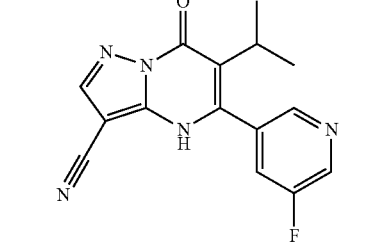
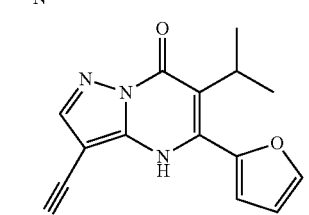
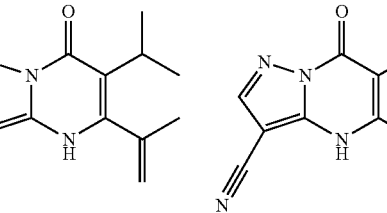
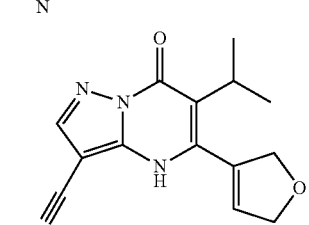
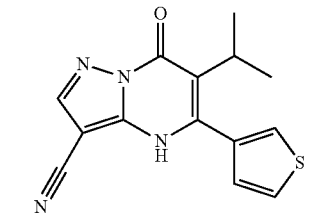

333
-continued
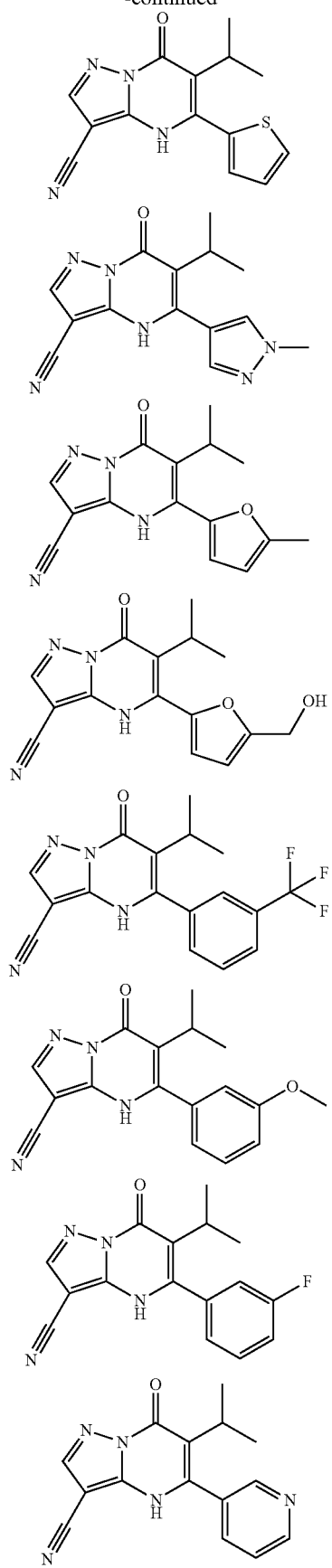
334
-continued
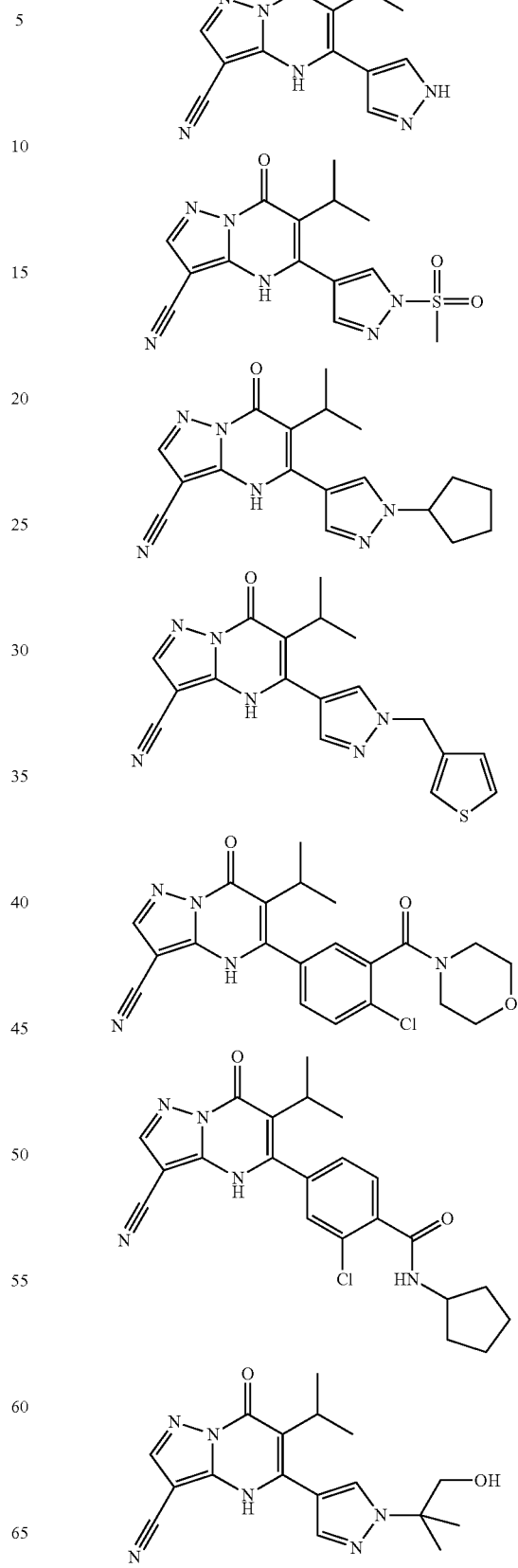

335
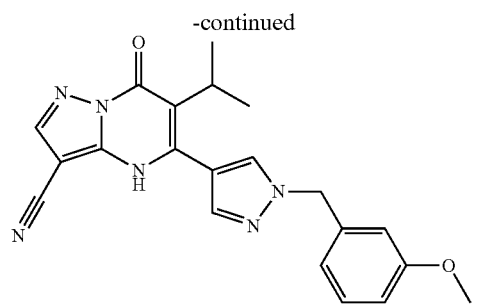
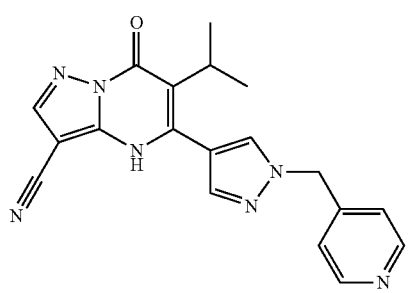
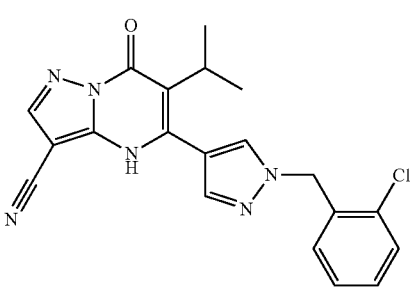
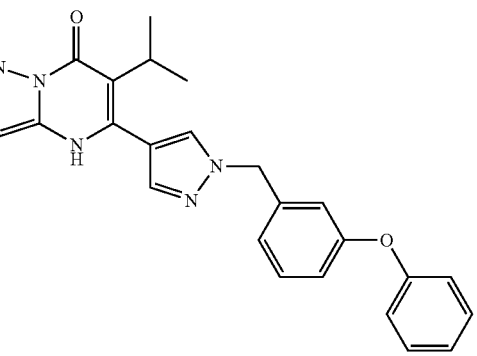
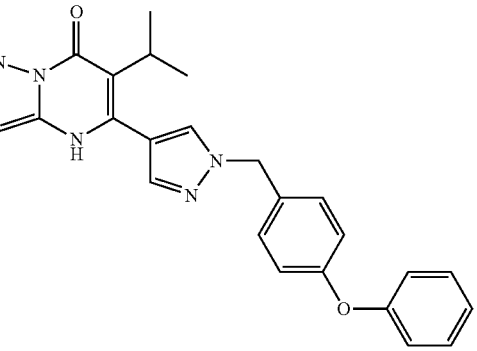
336
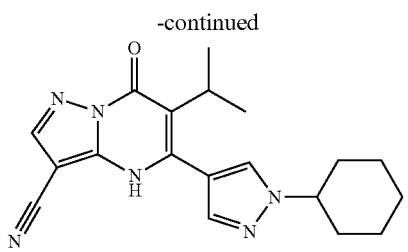
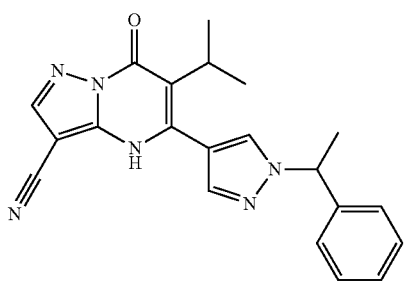
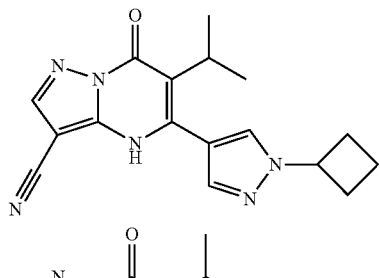
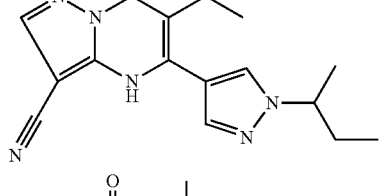
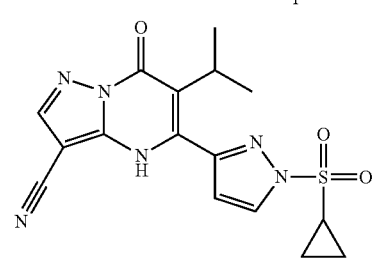
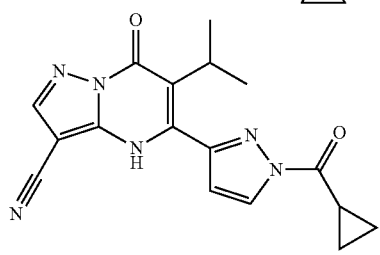

337
-continued
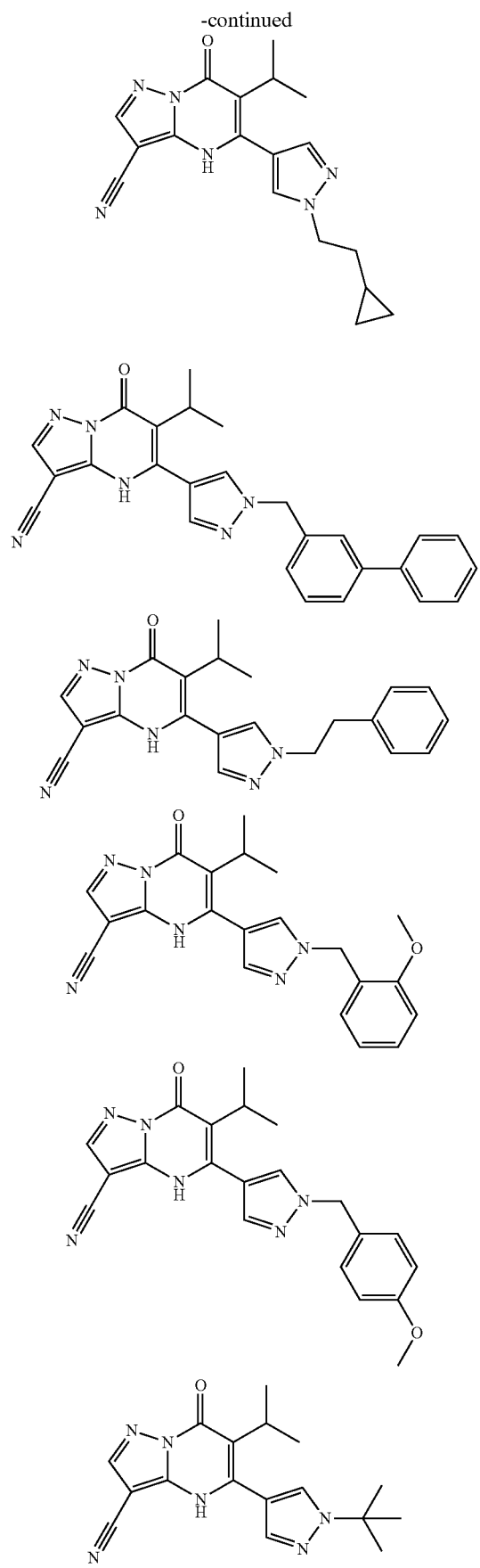
338
-continued
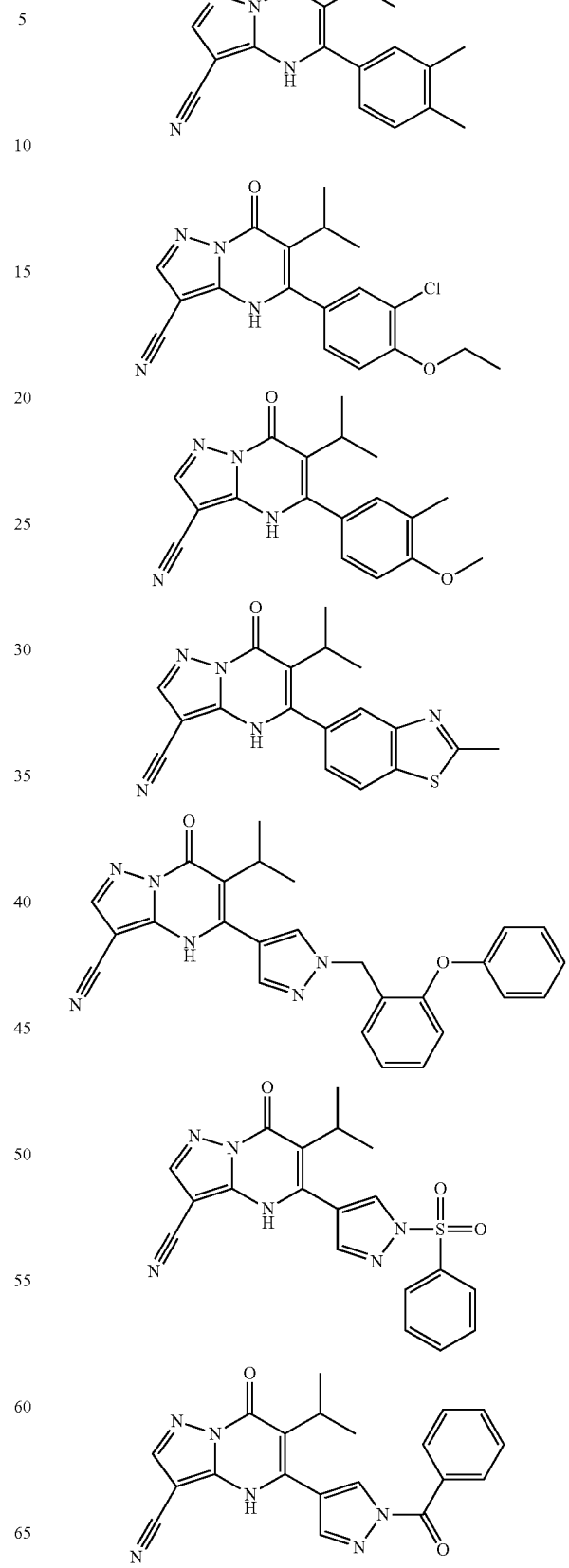

339
-continued
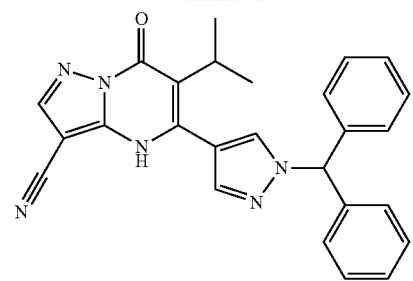
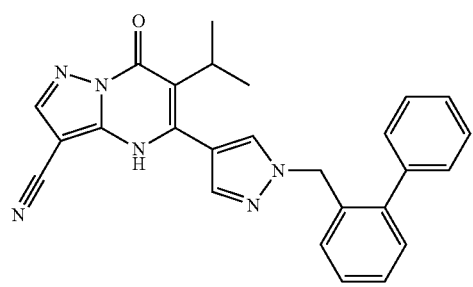
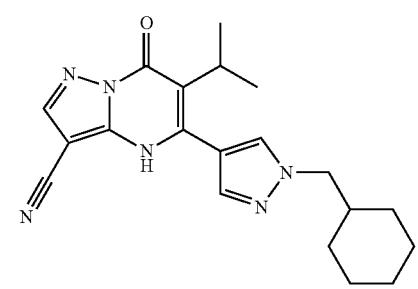
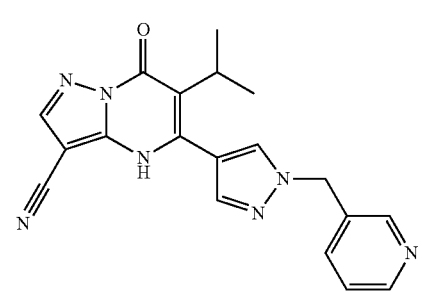
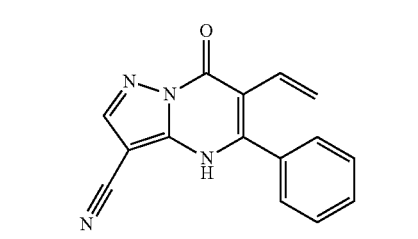
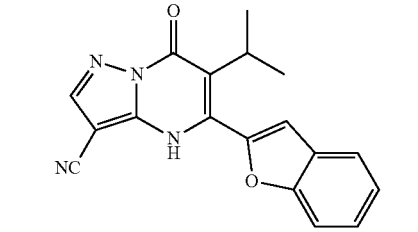
340
-continued
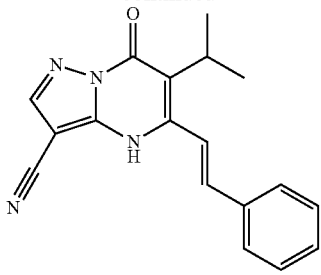
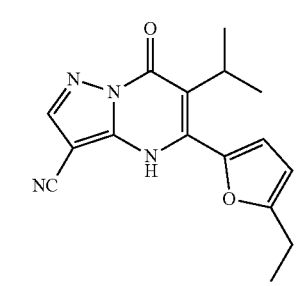
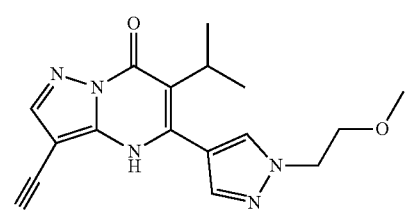
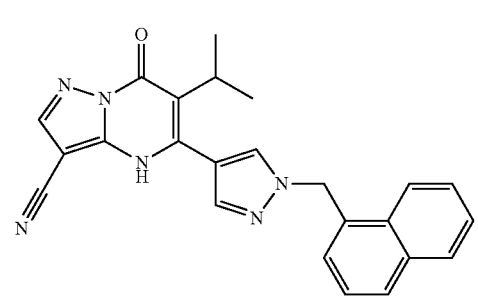
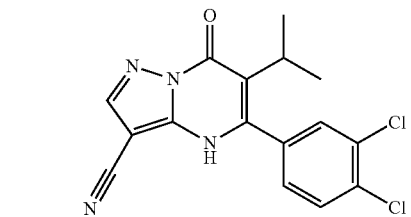
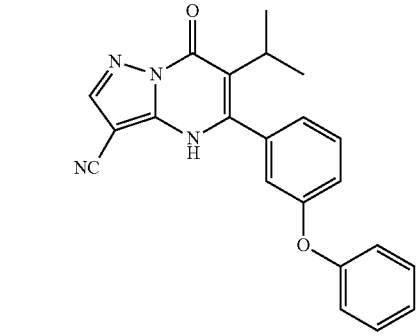

341
-continued
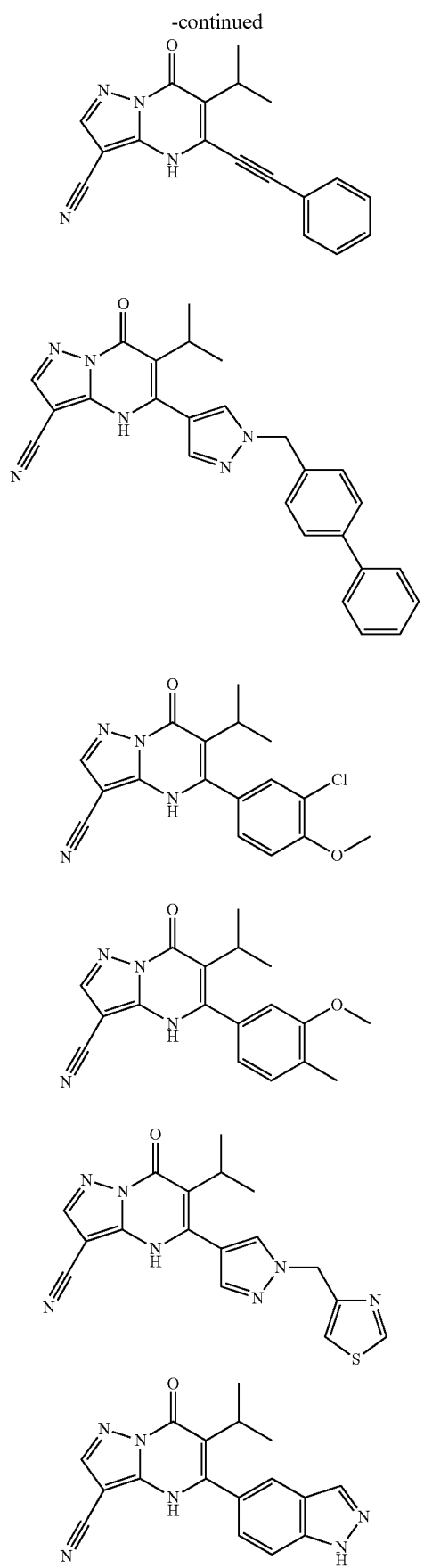
342
-continued
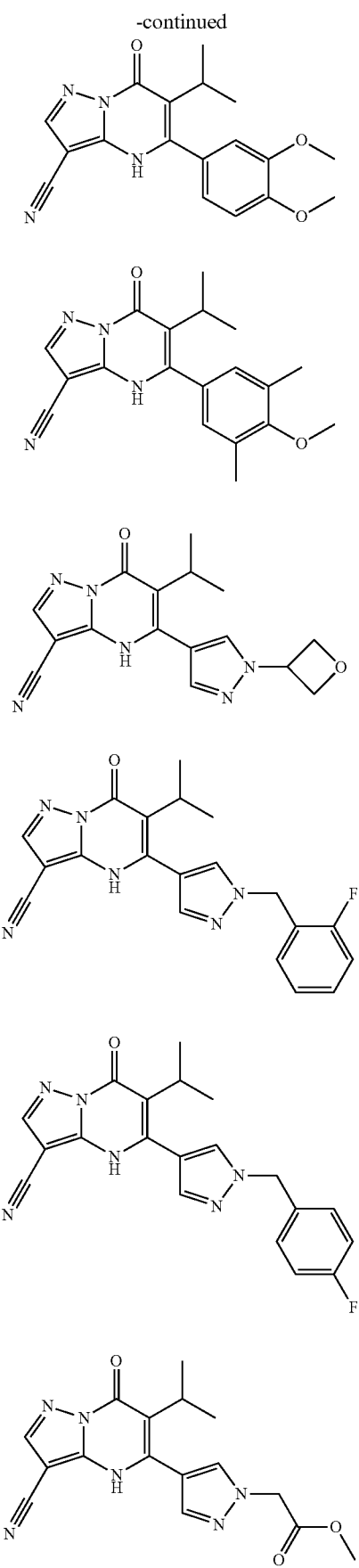

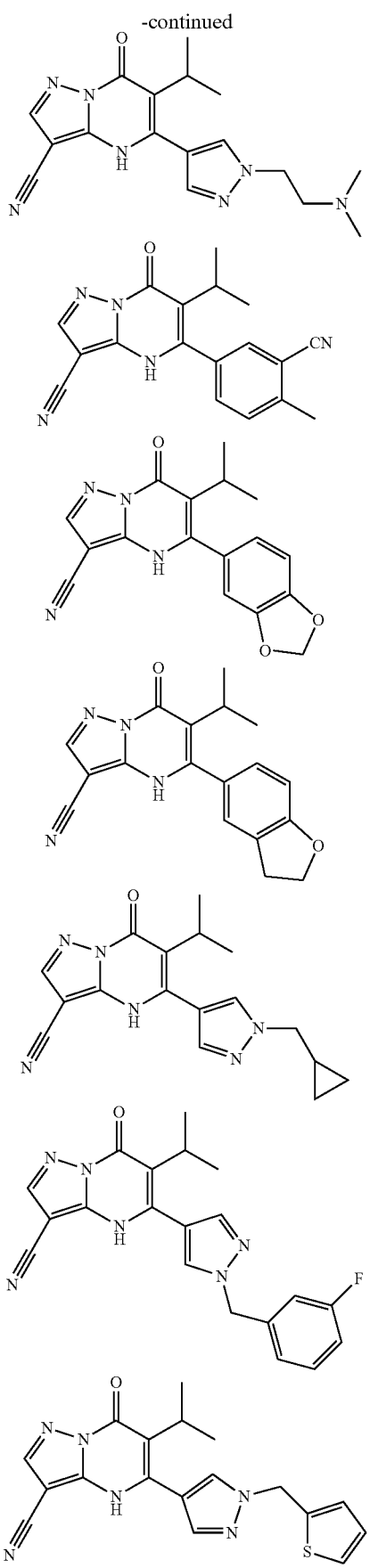
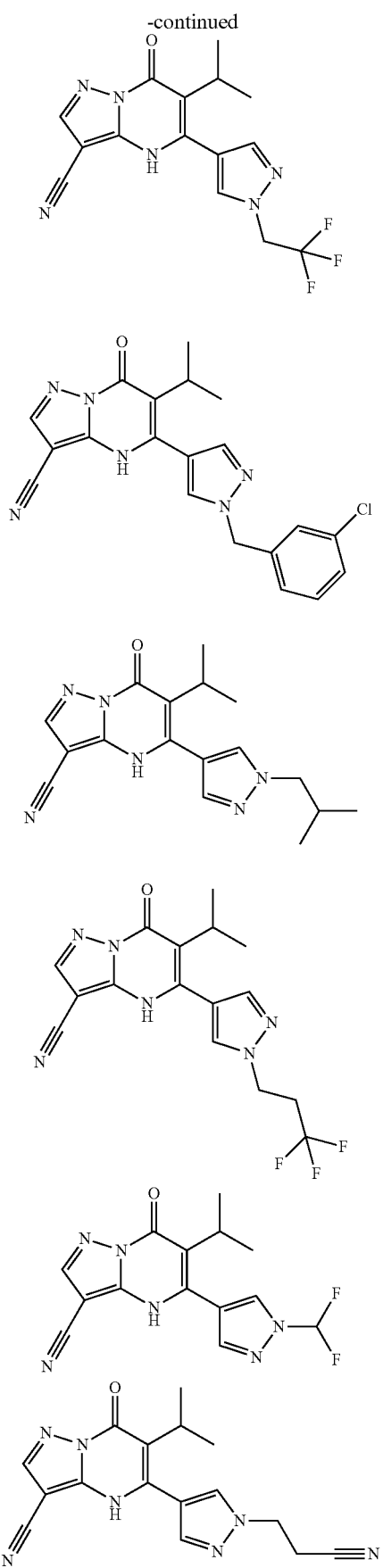

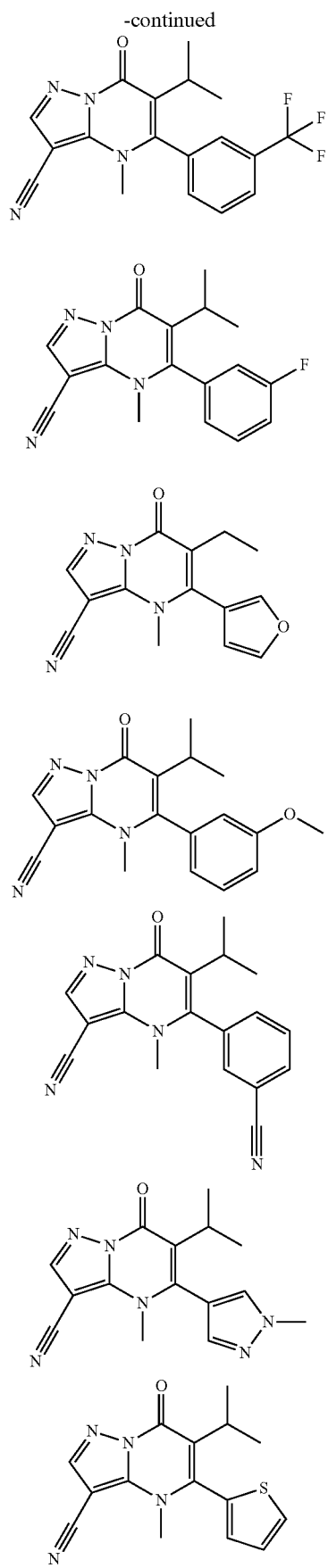
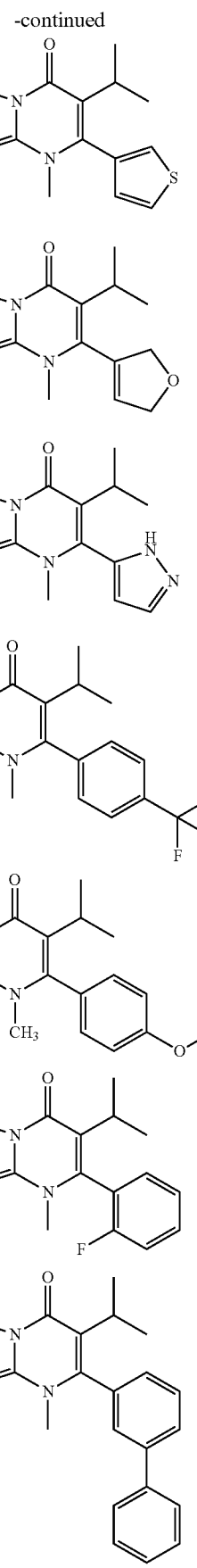

347
-continued
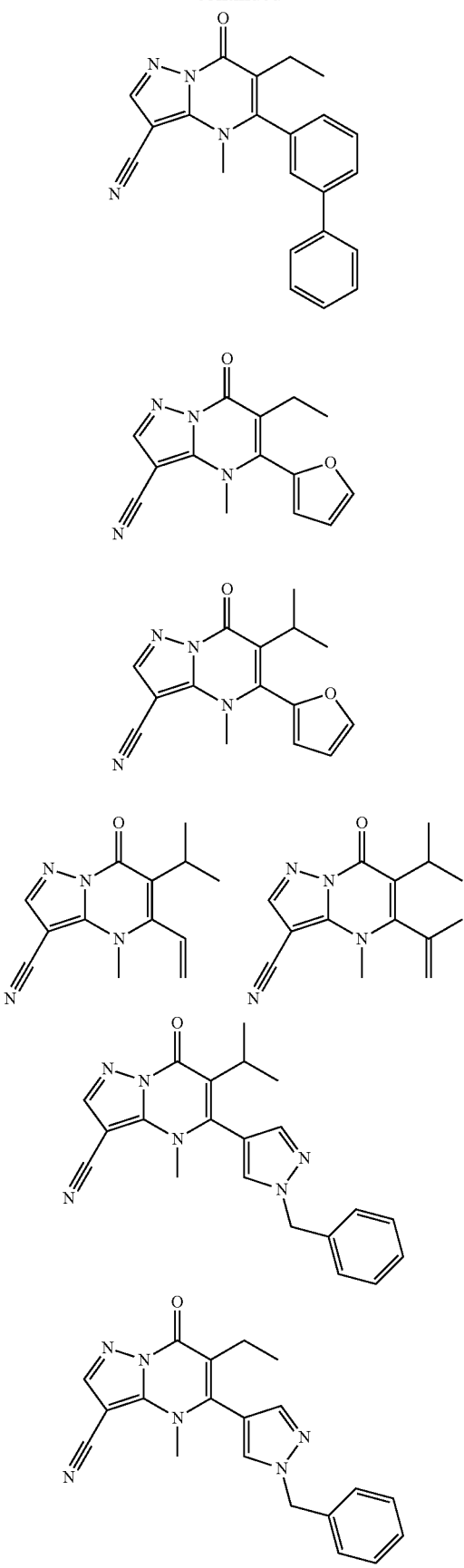
348
-continued
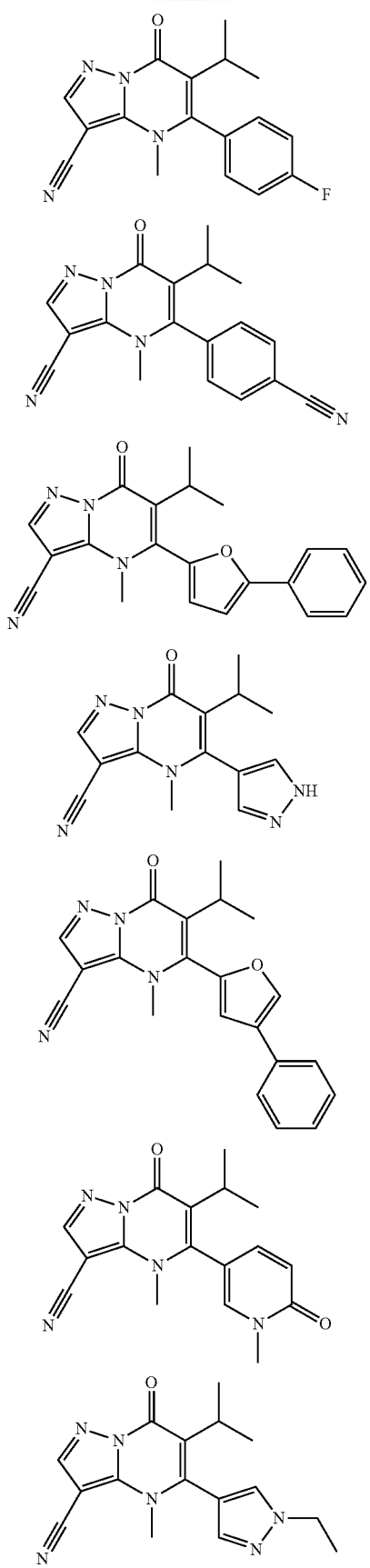

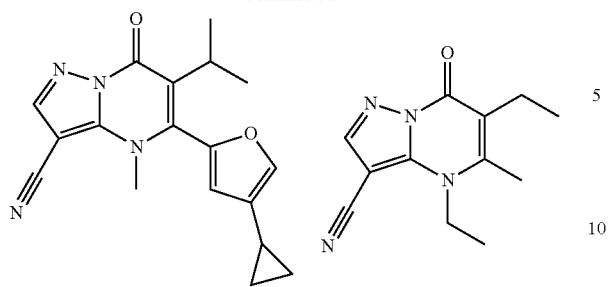
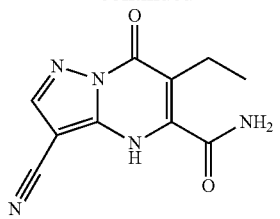
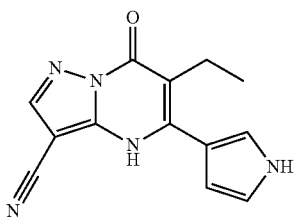
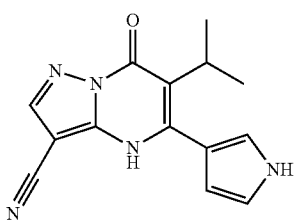
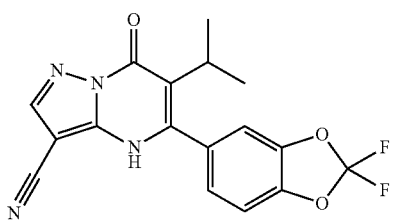
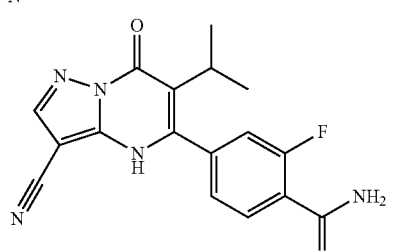
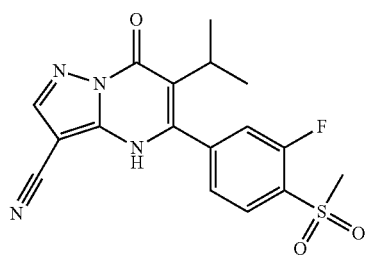
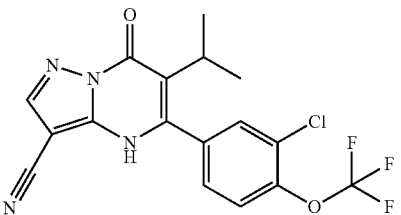

-continued
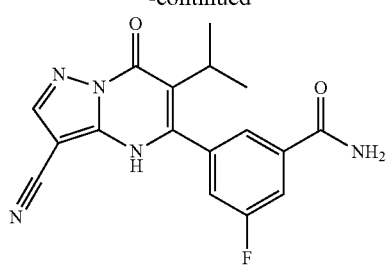
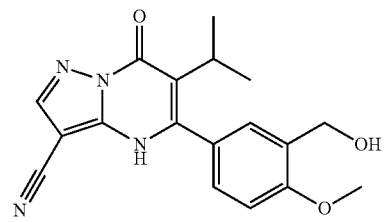
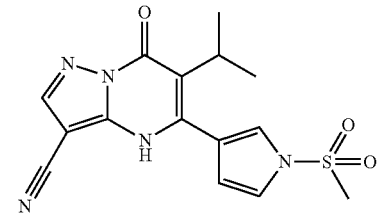
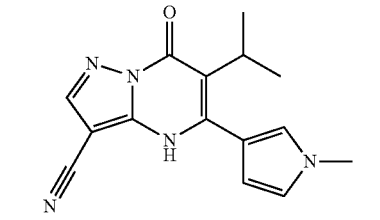
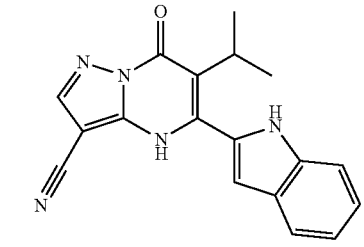
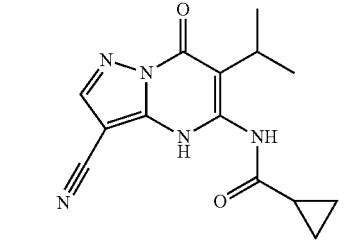
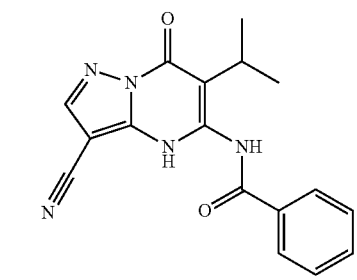
-continued
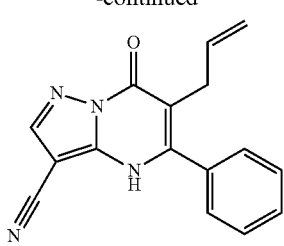
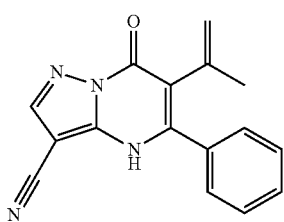
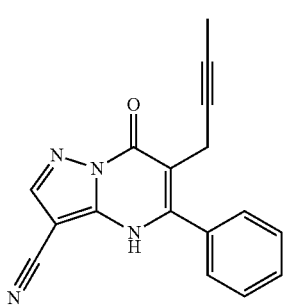
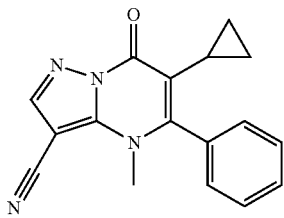
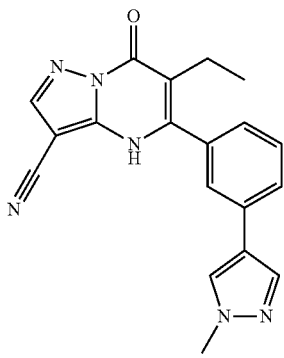
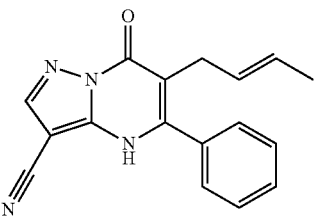

353
-continued
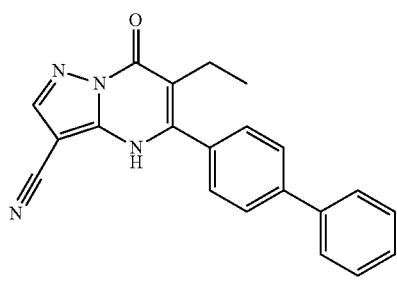
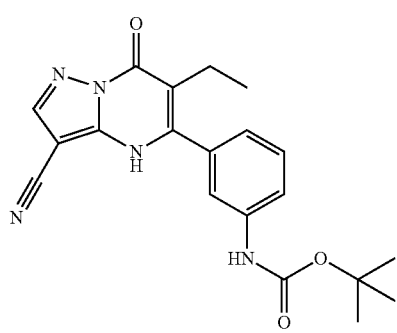
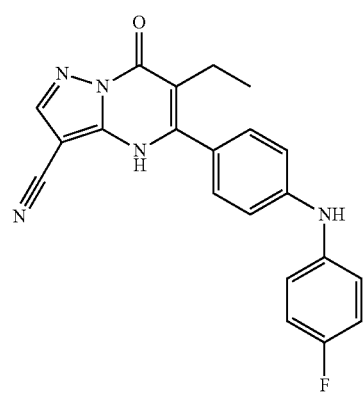
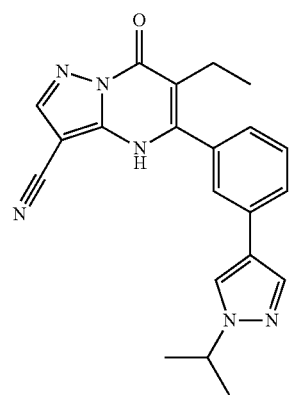
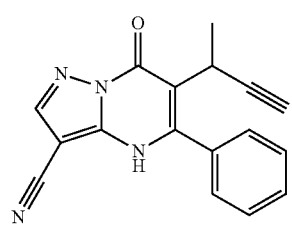
354
-continued
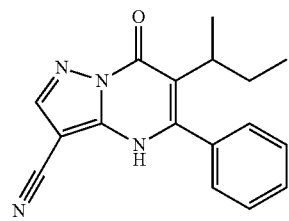
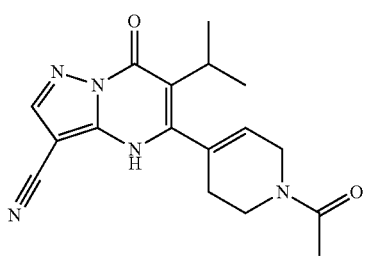
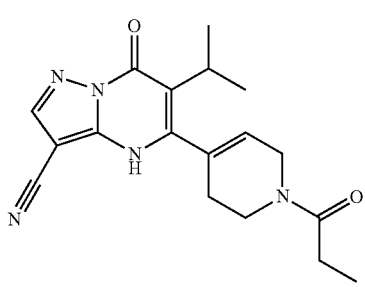
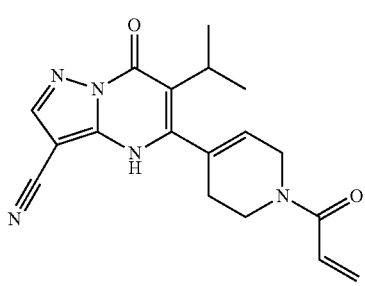
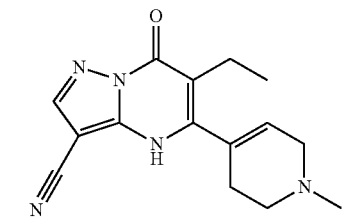
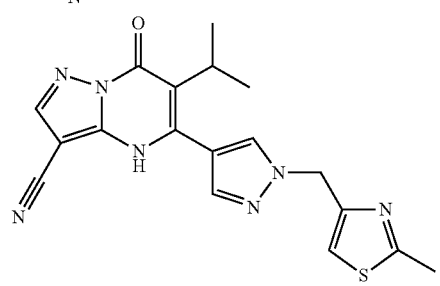

355
-continued
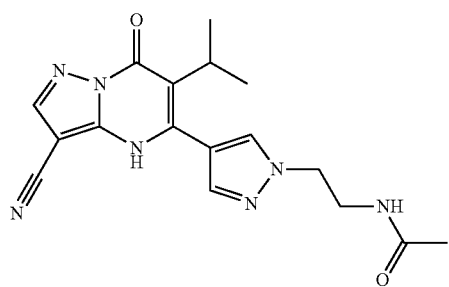
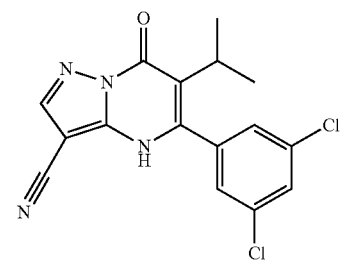
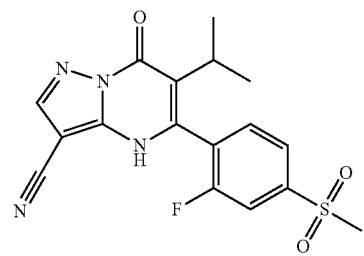
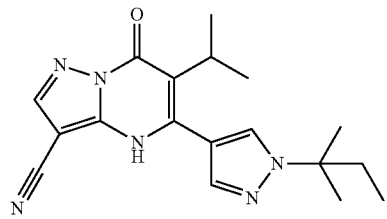
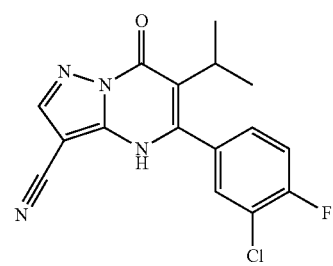
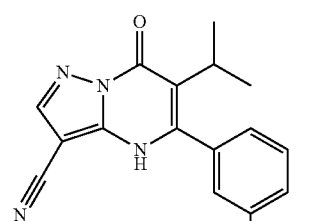
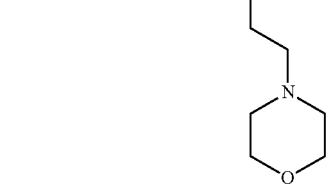
356
-continued
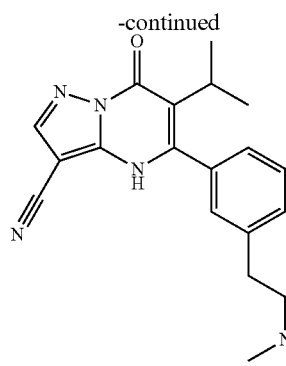
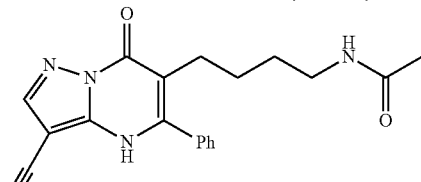
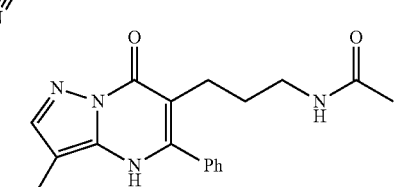
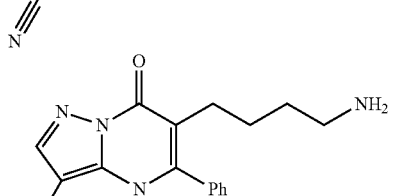
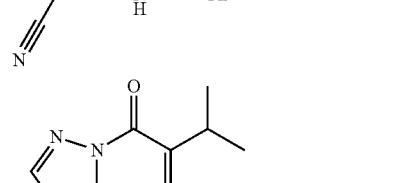
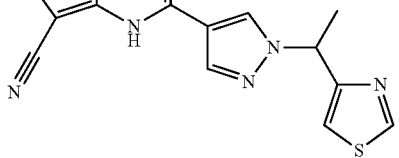
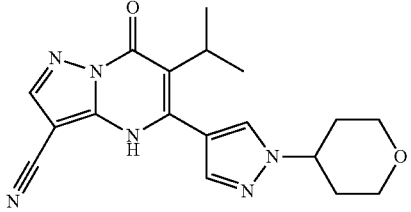
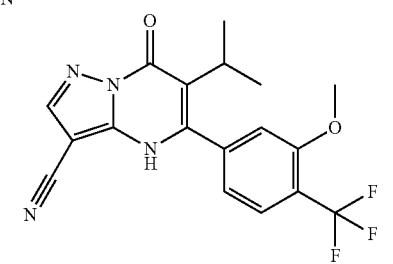

357
-continued
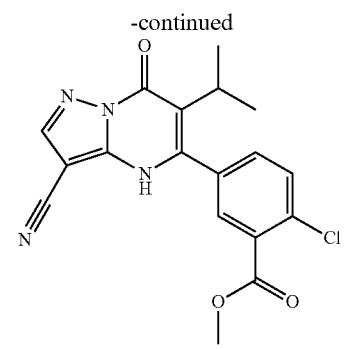
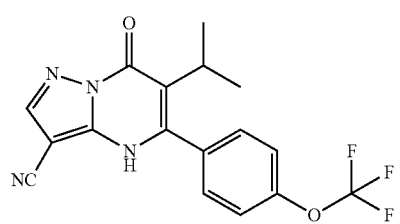
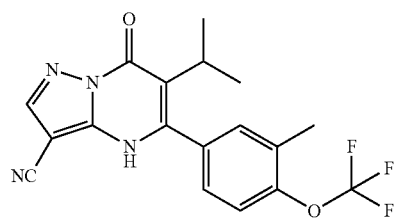
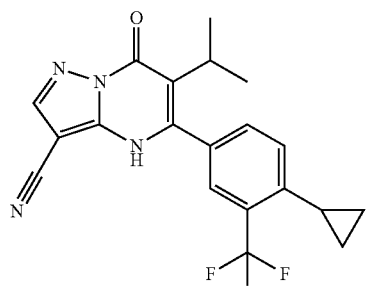
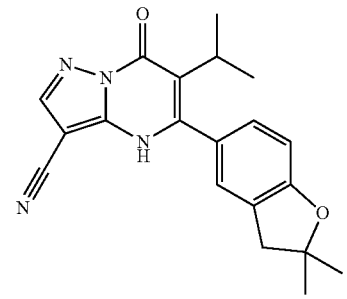
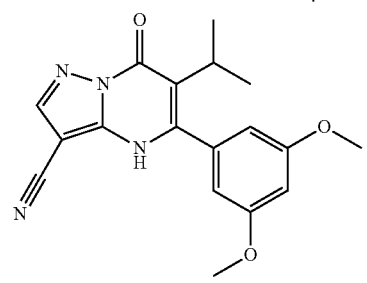
358
-continued
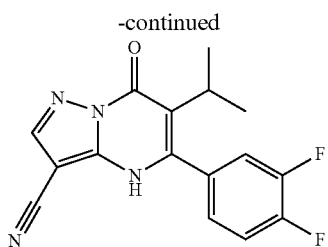
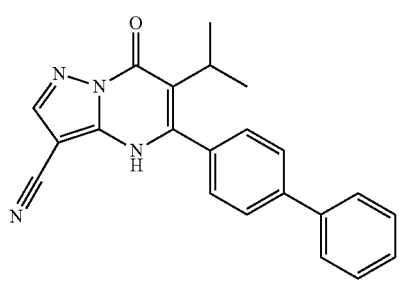
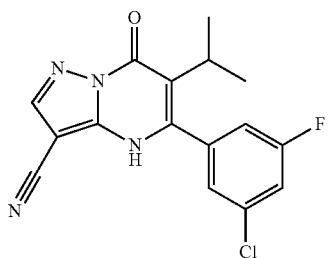
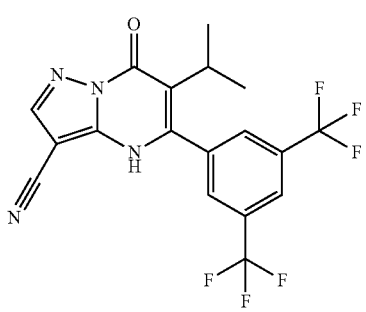
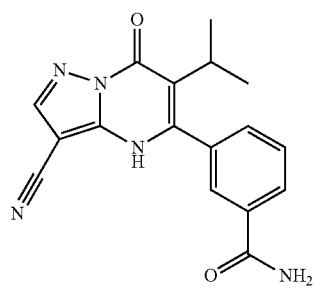

359
-continued
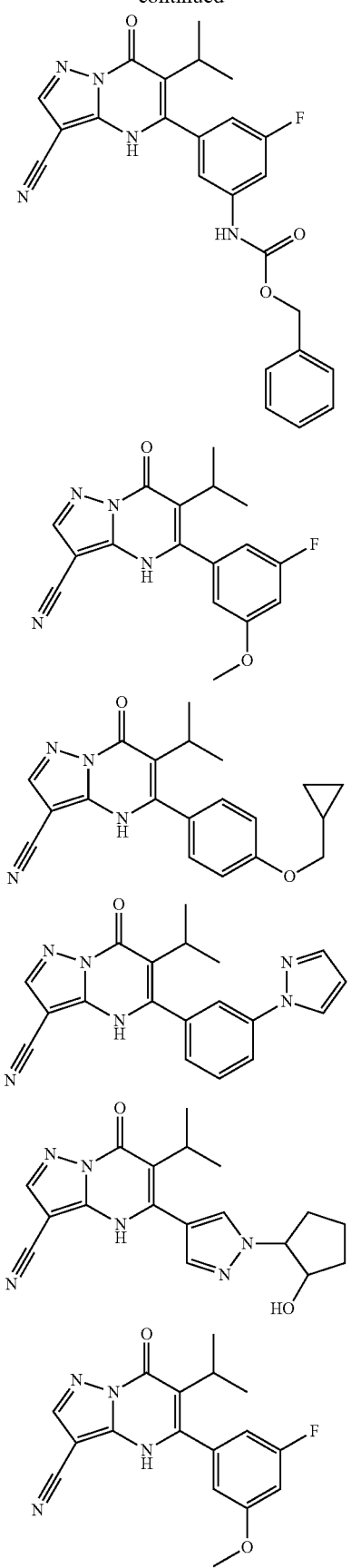
360
-continued
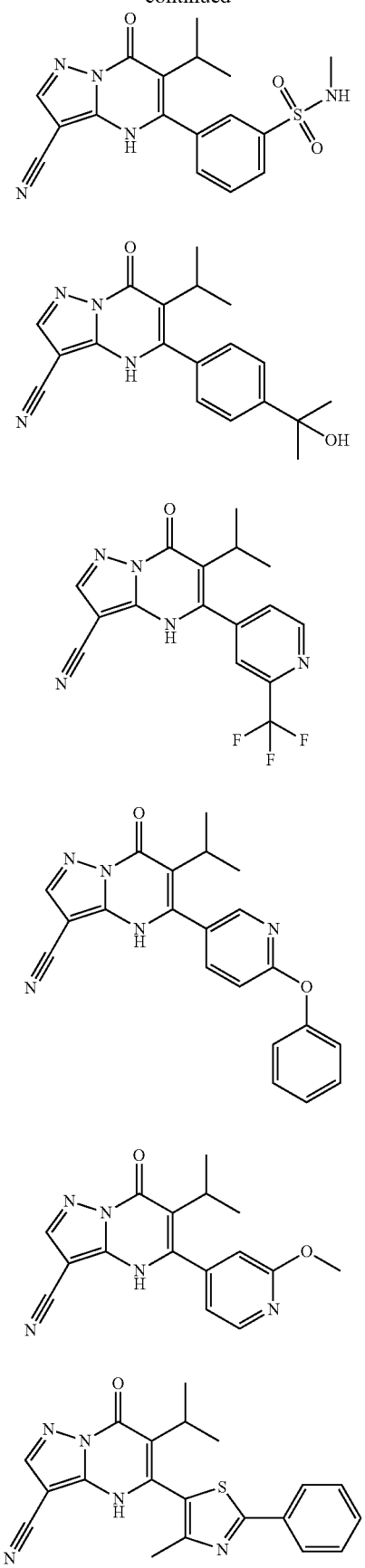

361
-continued
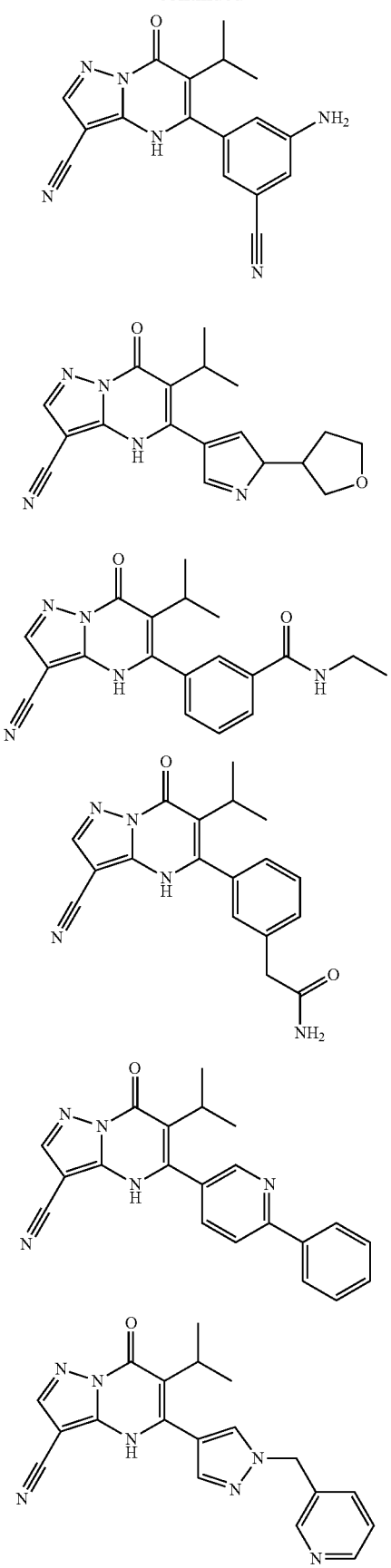
362
-continued
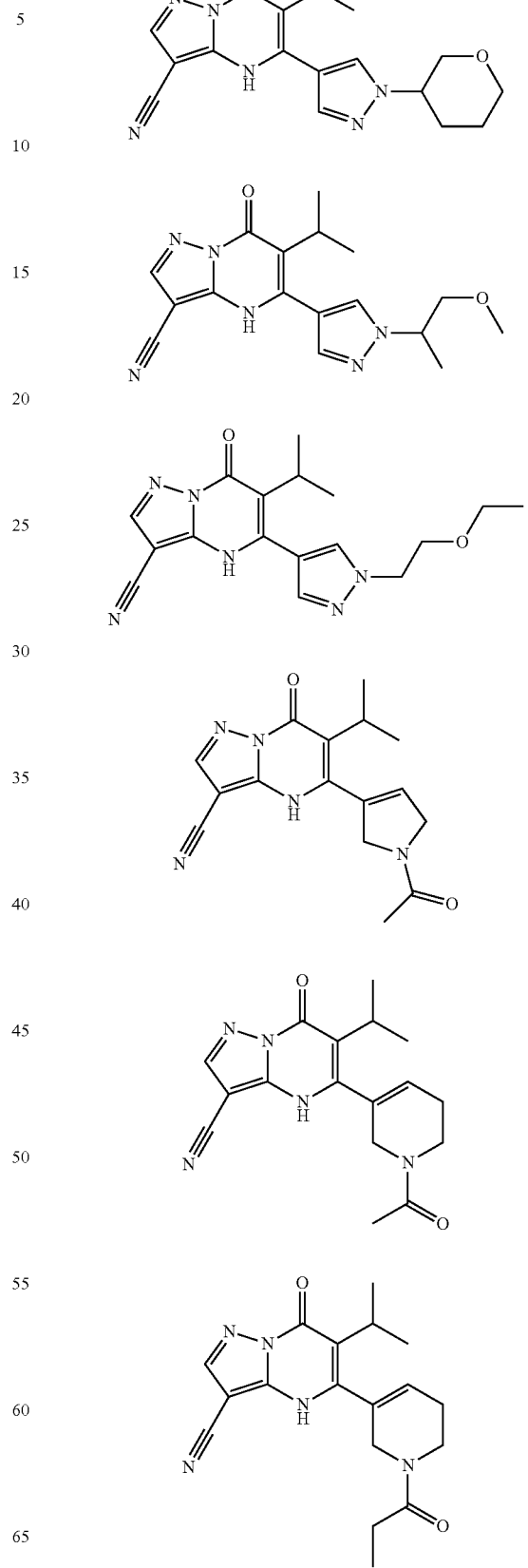

363
-continued
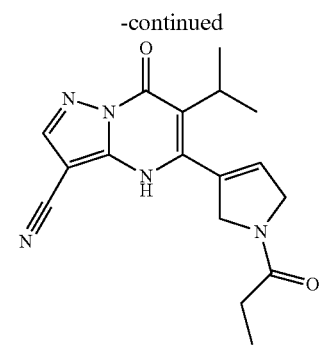
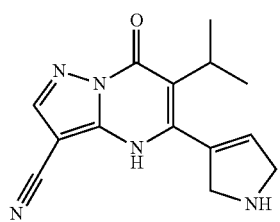
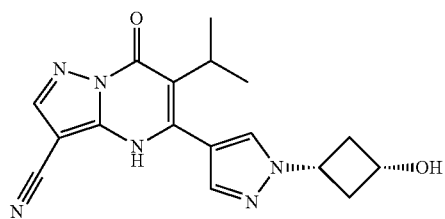
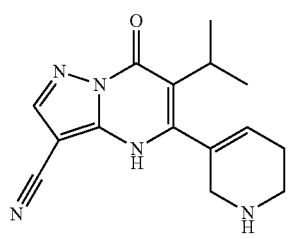
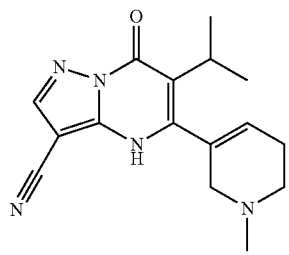
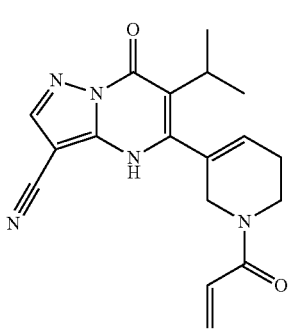
364
-continued
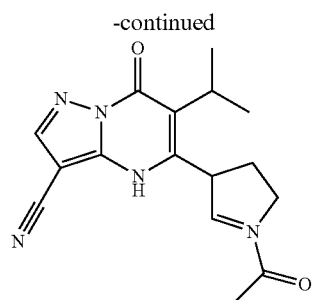
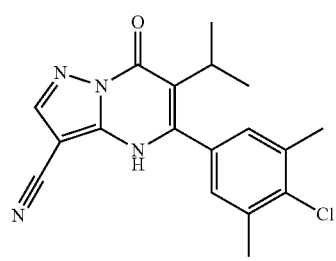
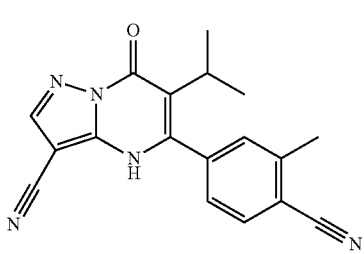
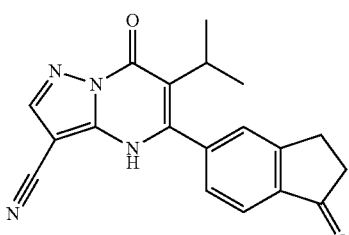
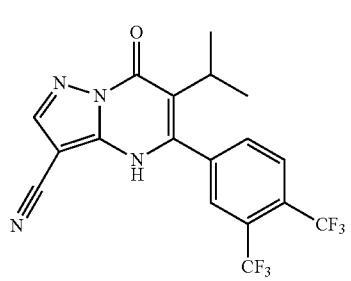
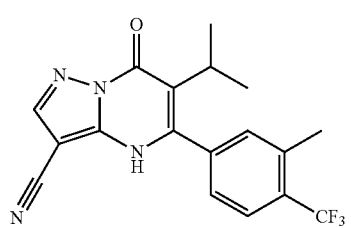

365
-continued
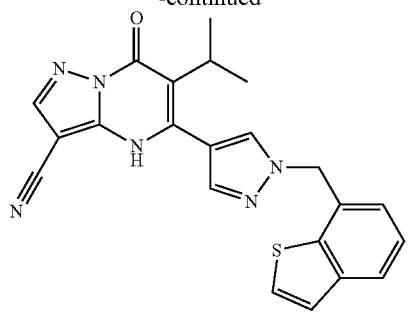
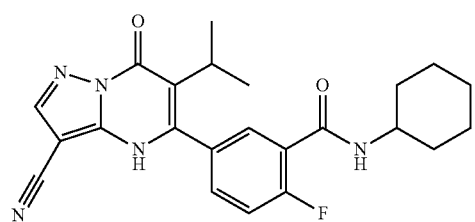
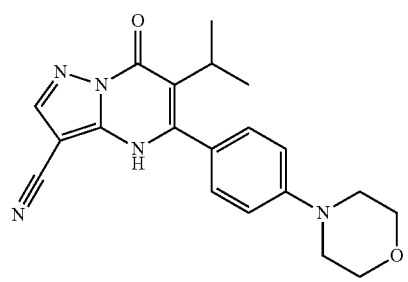
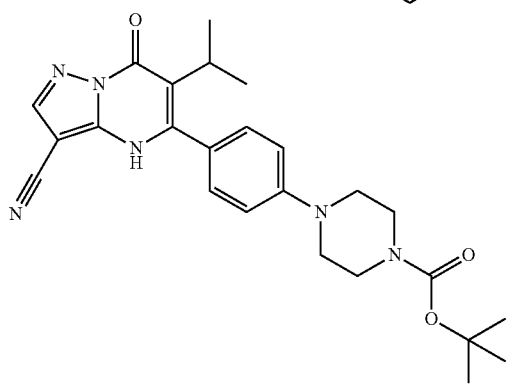
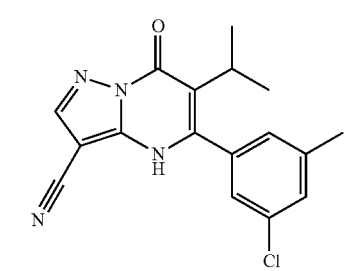
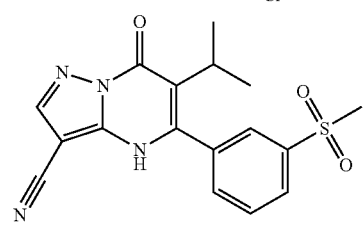
366
-continued
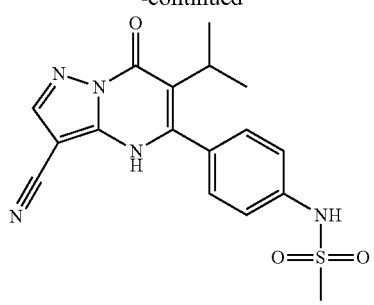
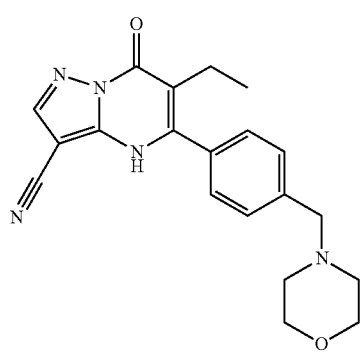
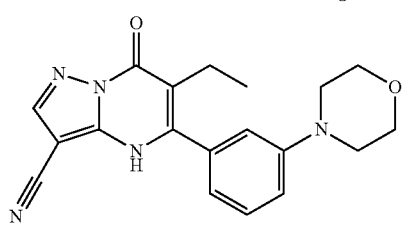
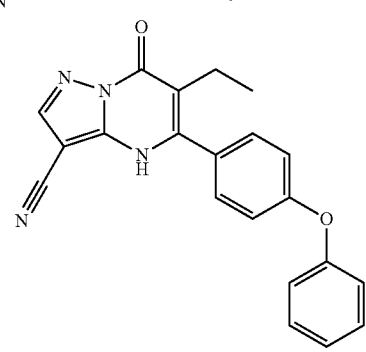
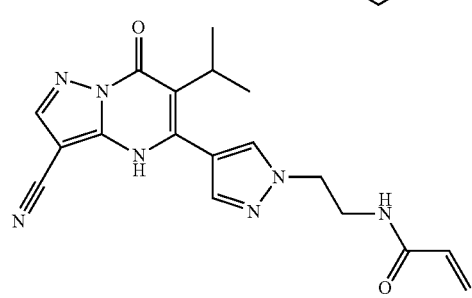
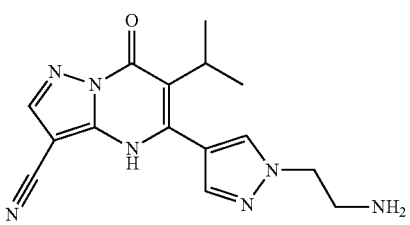

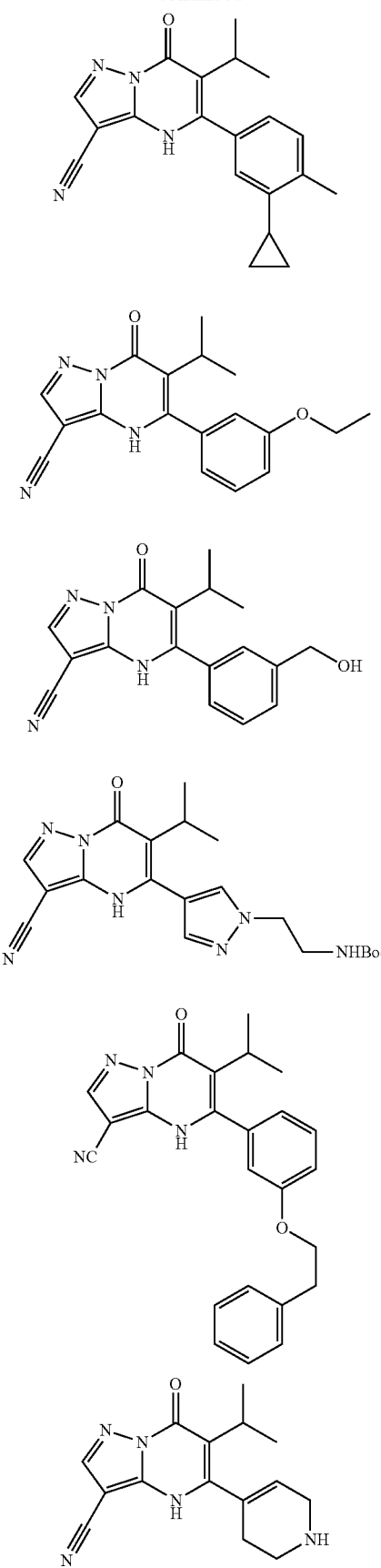
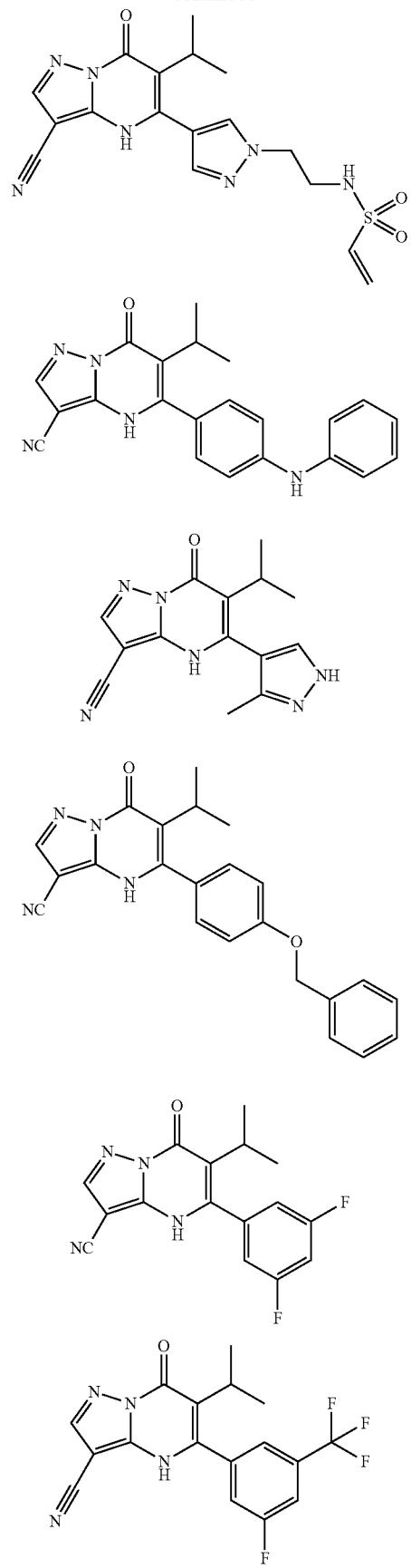

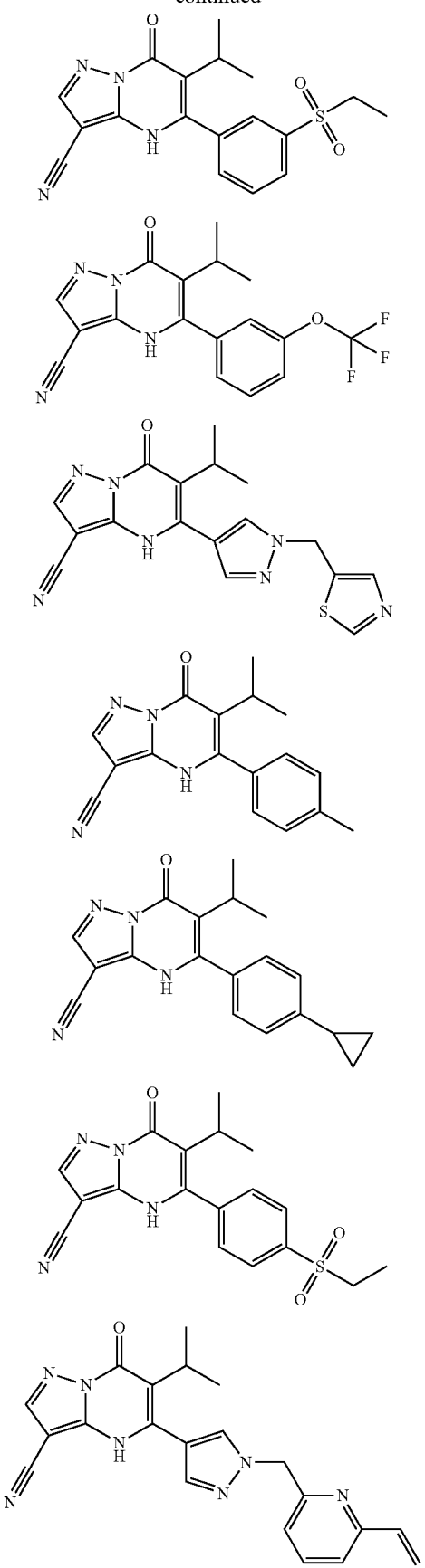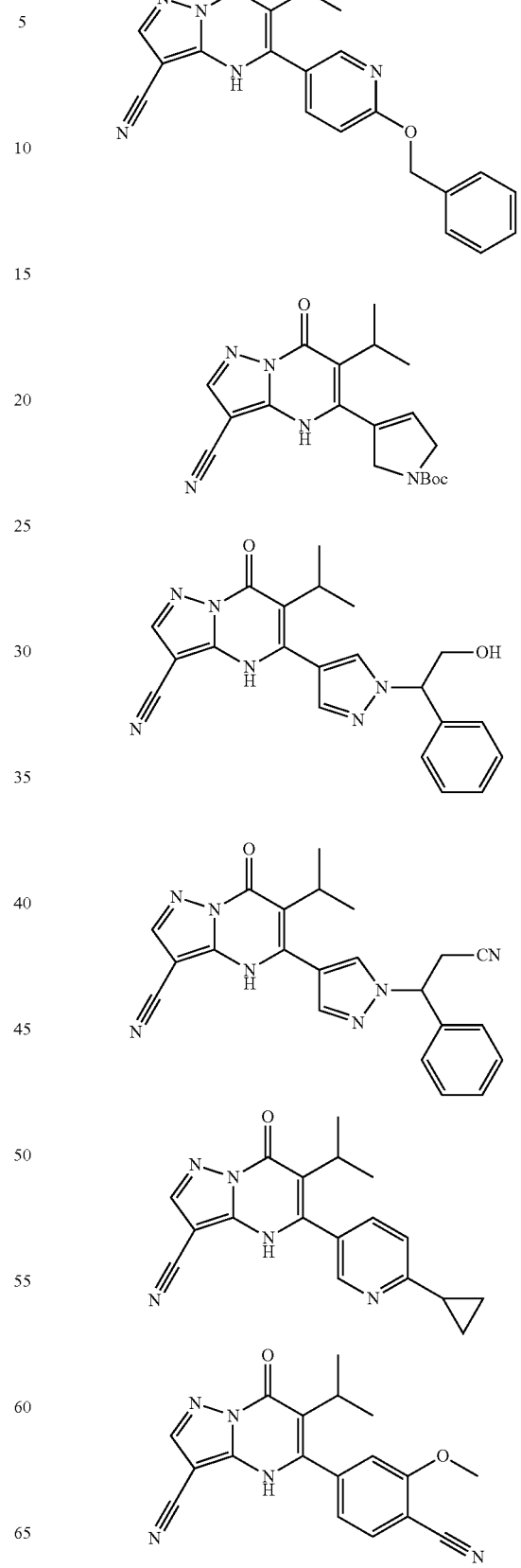

371
-continued
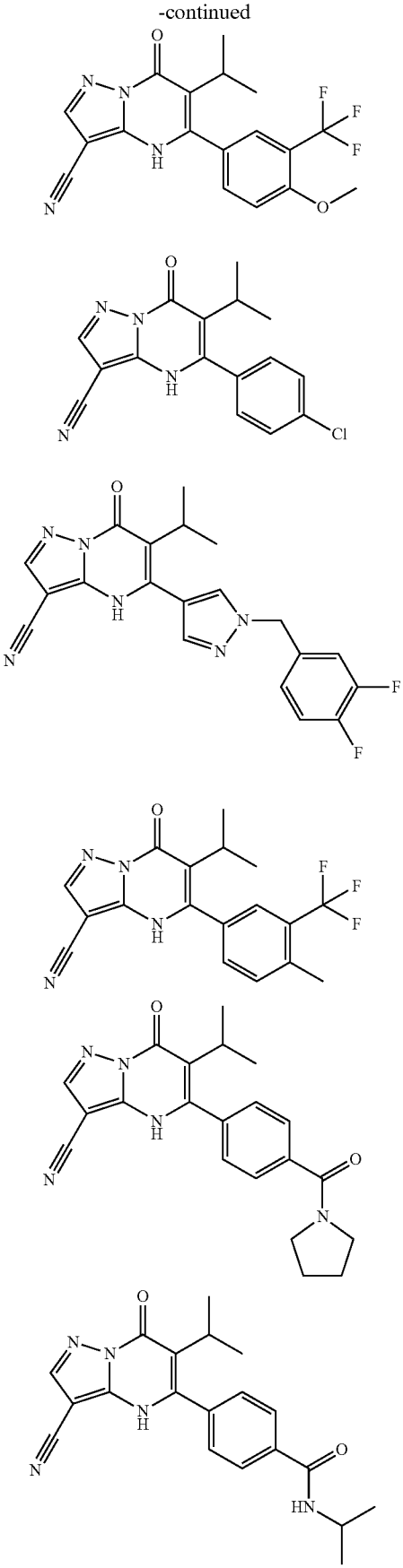
372
-continued
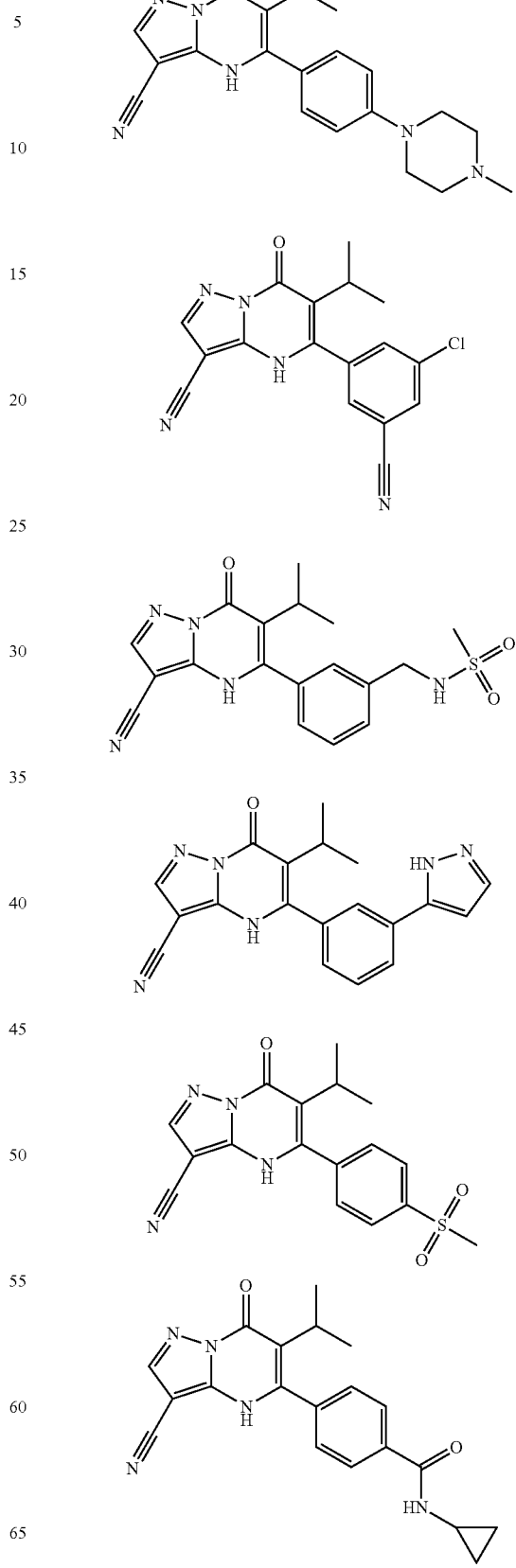

373
-continued
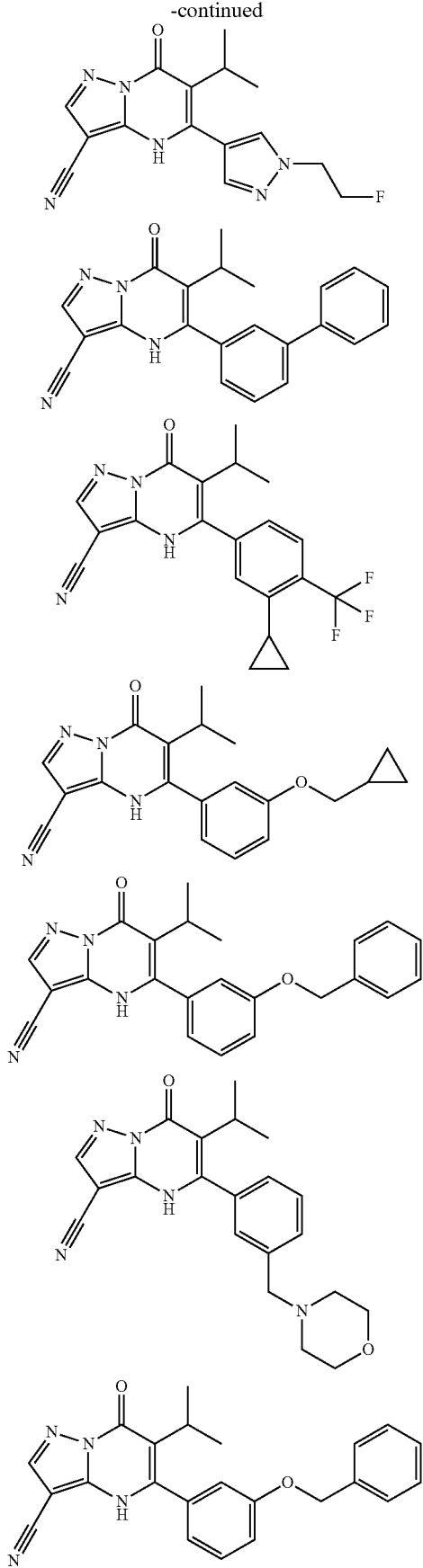
374
-continued
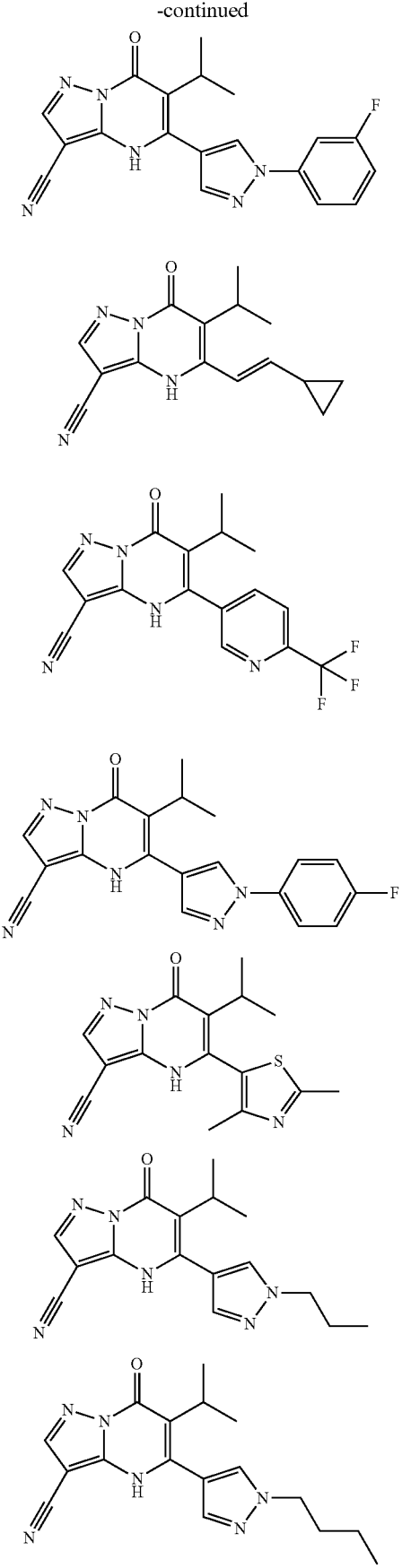

375
-continued
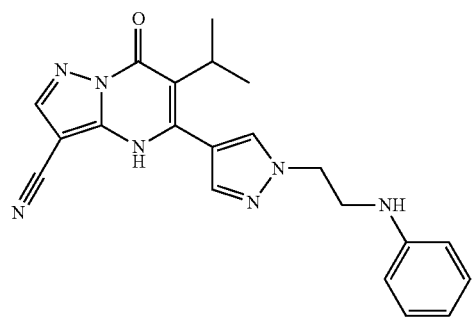
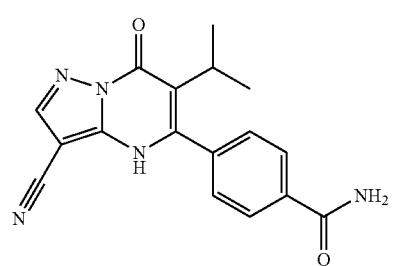
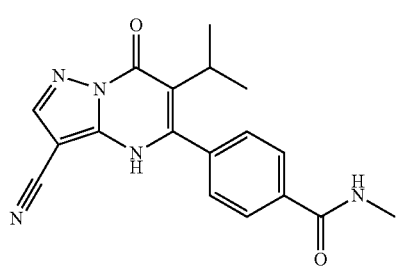
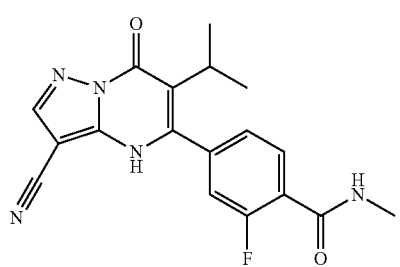
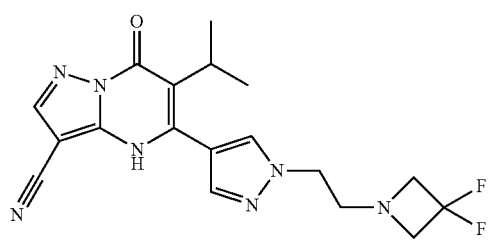
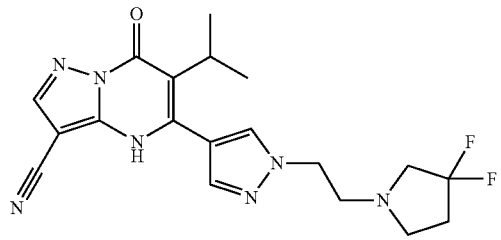
376
-continued
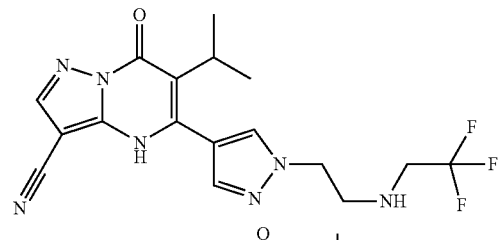
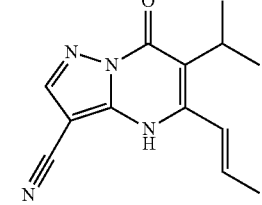
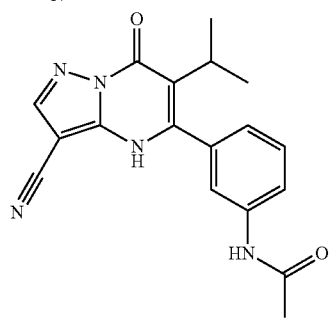
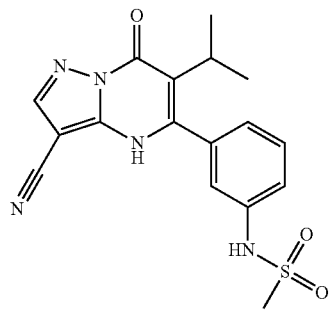
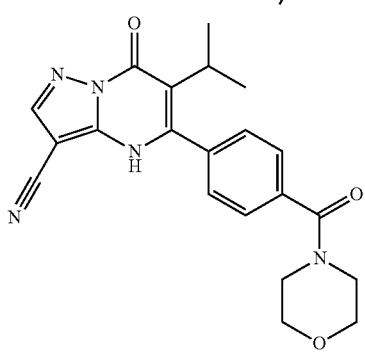
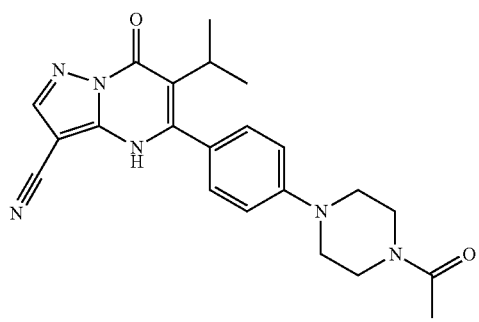

377
-continued
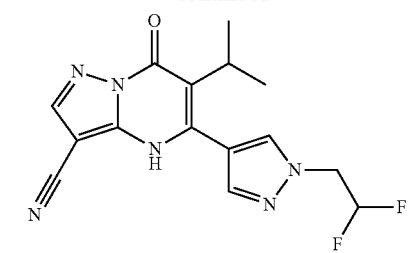
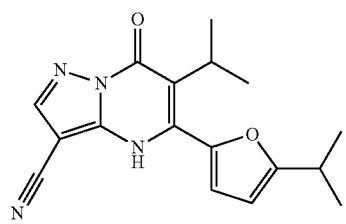
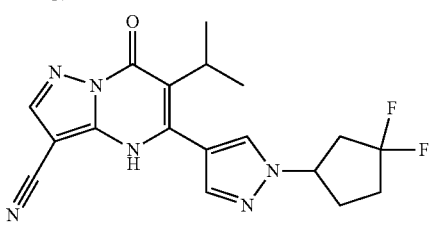
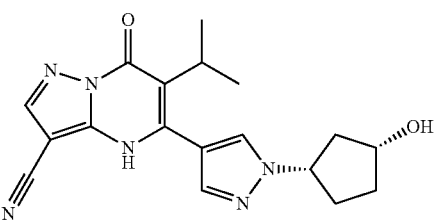
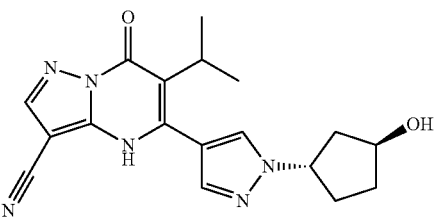
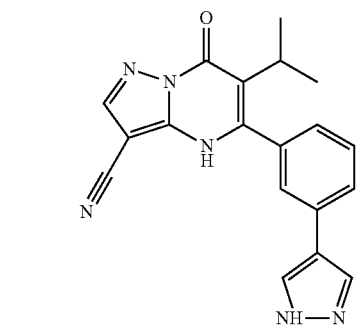
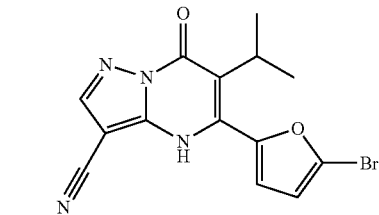
378
-continued
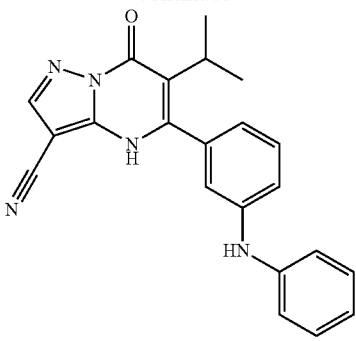
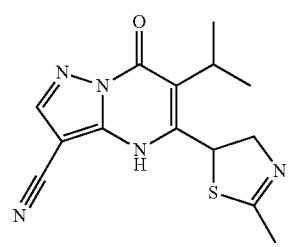
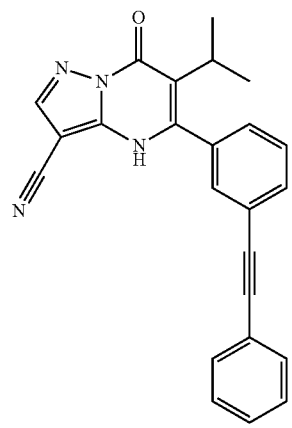
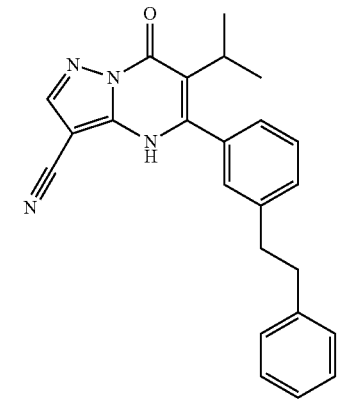
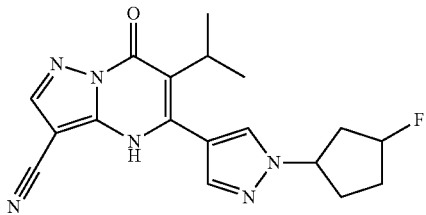

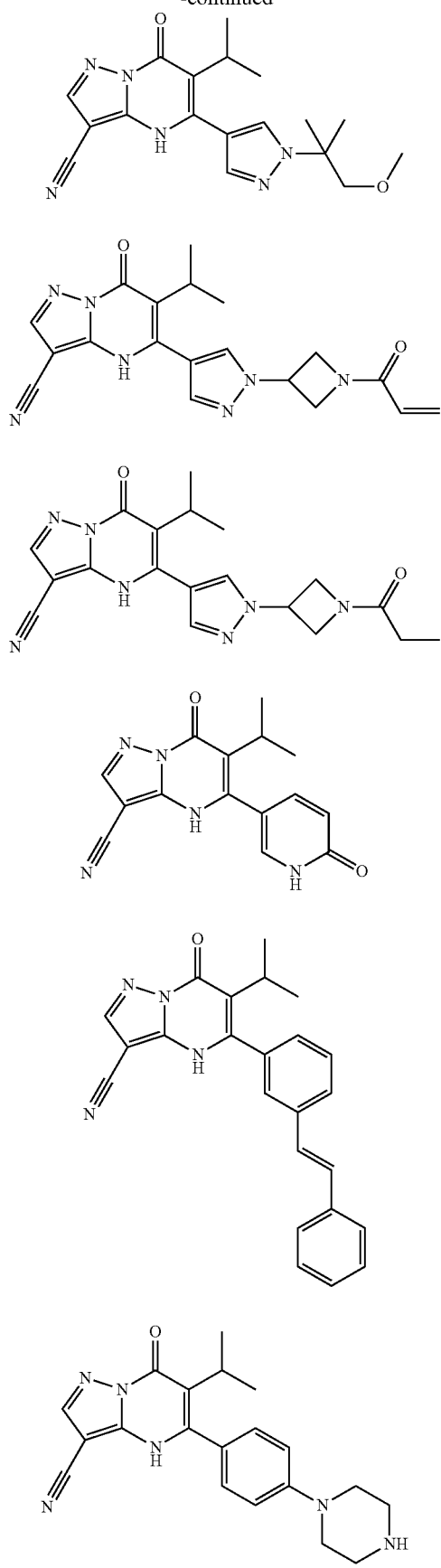
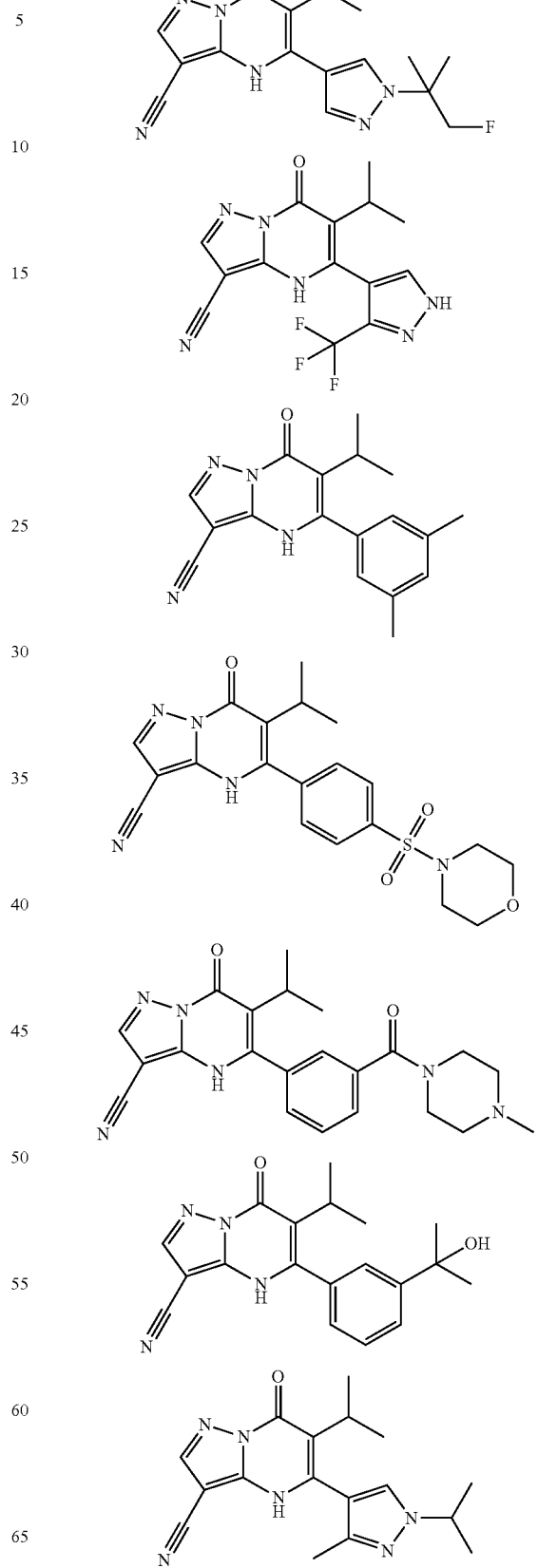

381
-continued
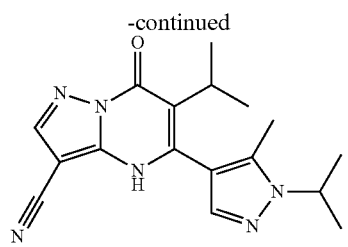
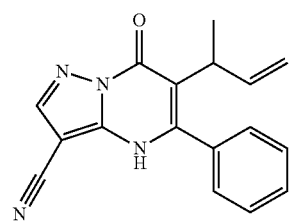
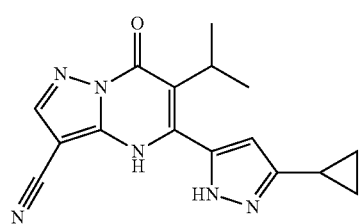
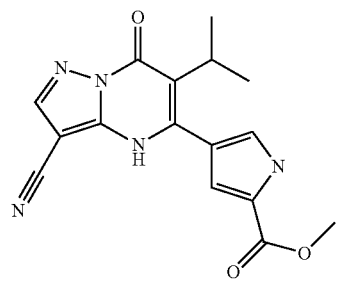
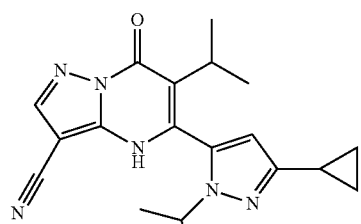
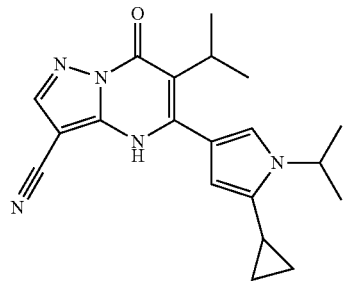
382
-continued
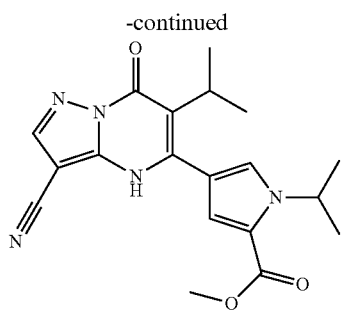
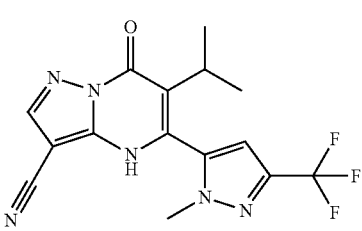
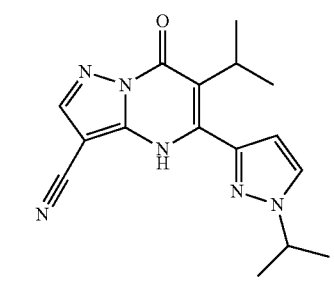
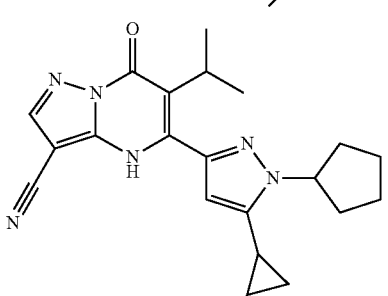
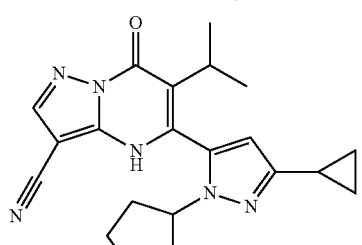
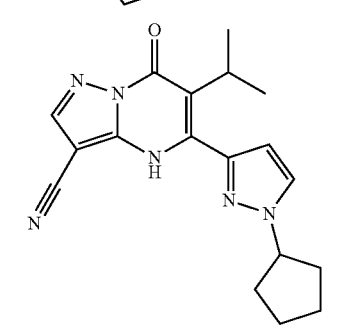

383
-continued
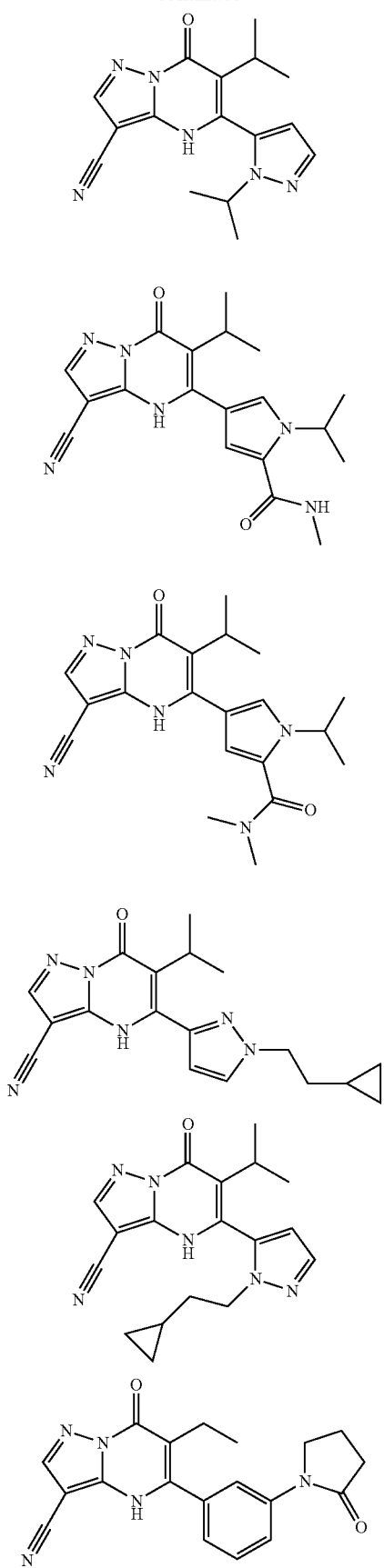
384
-continued
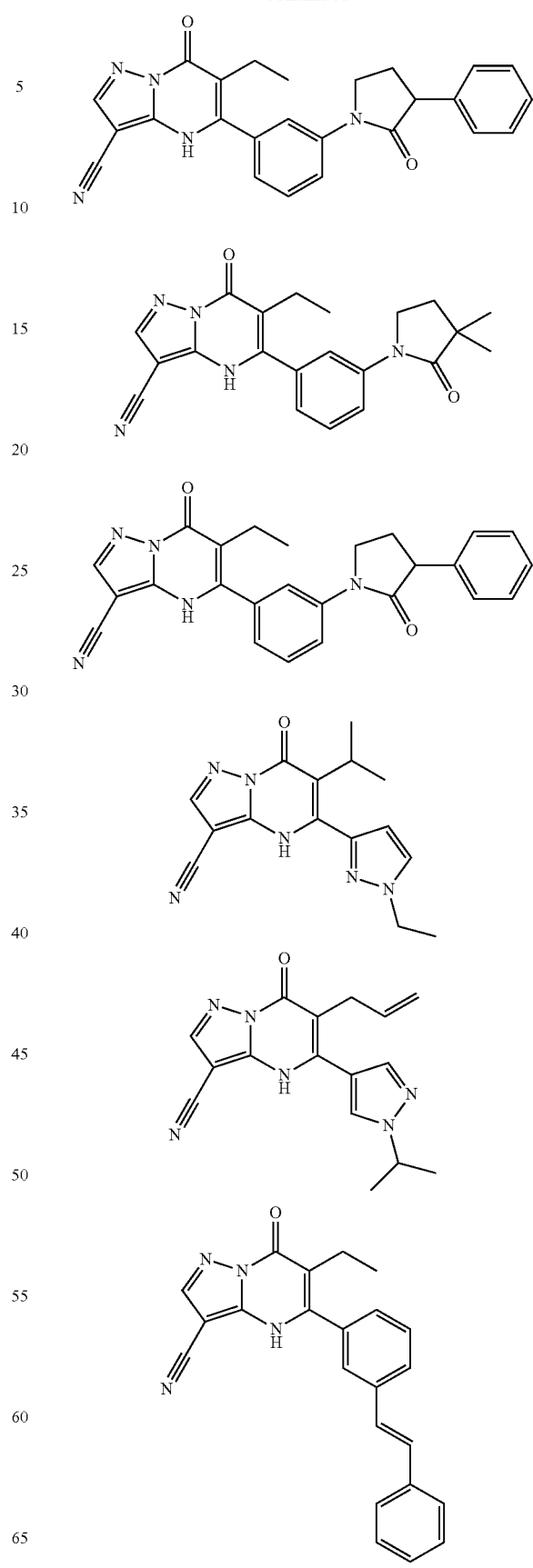

385
-continued
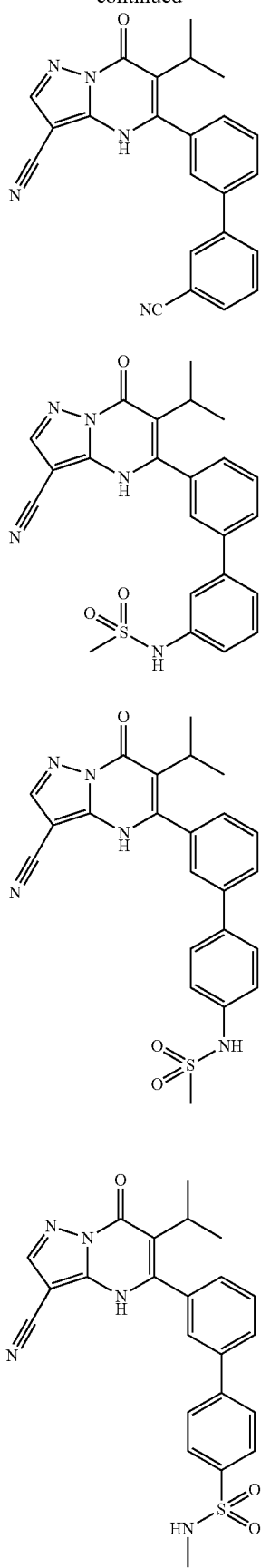
386
-continued
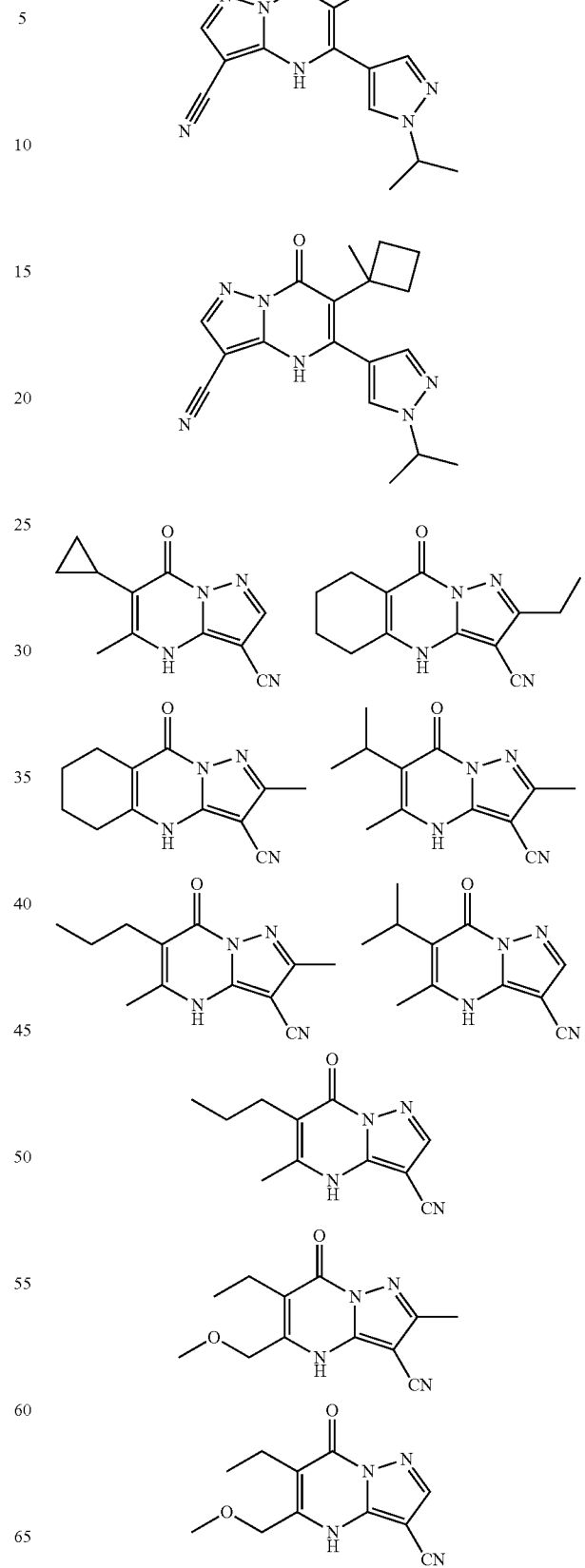

387
-continued
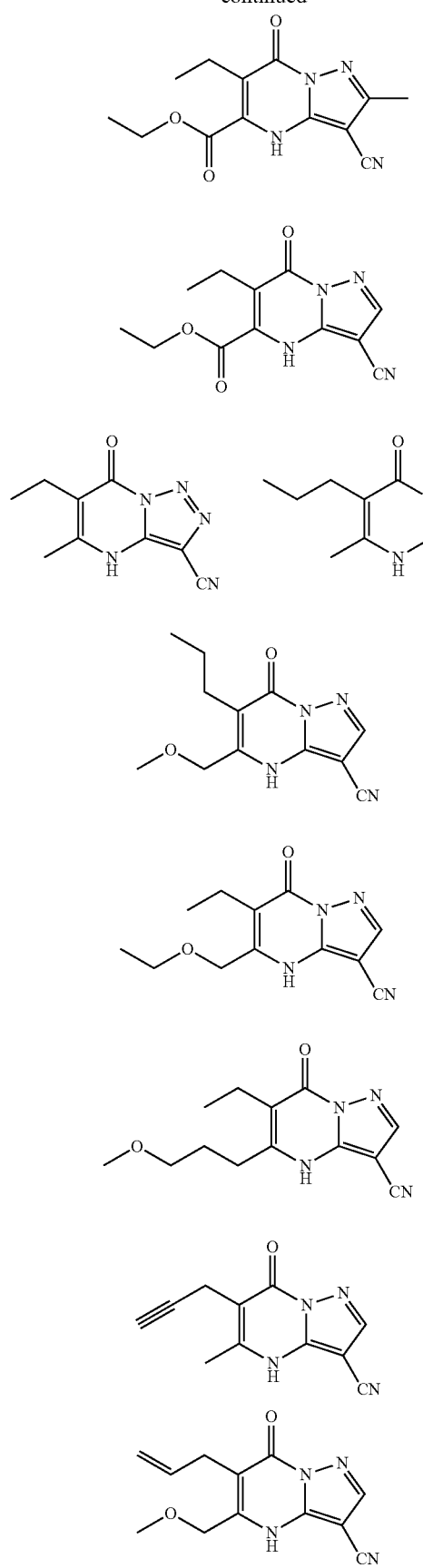
388
-continued
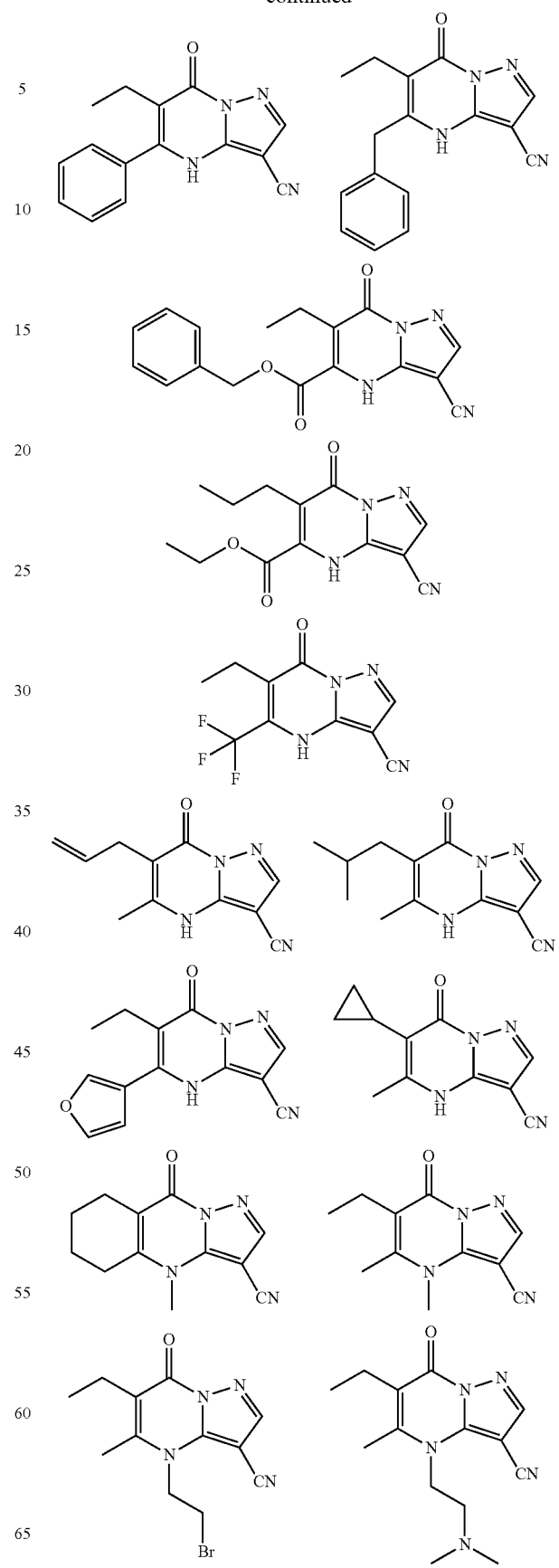

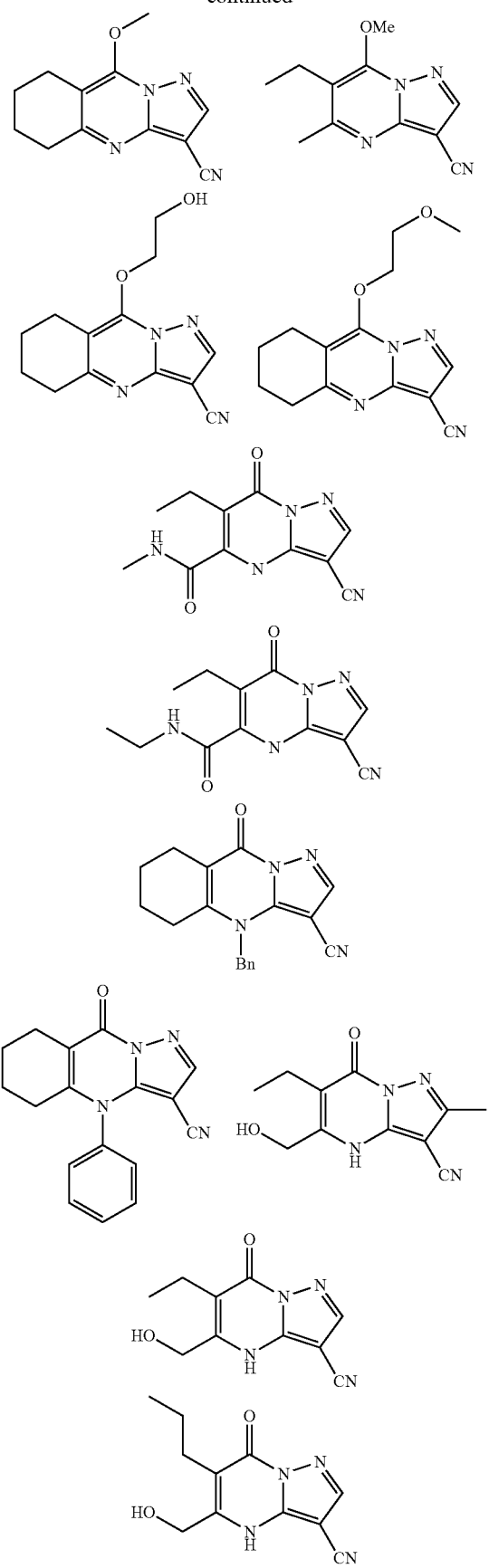

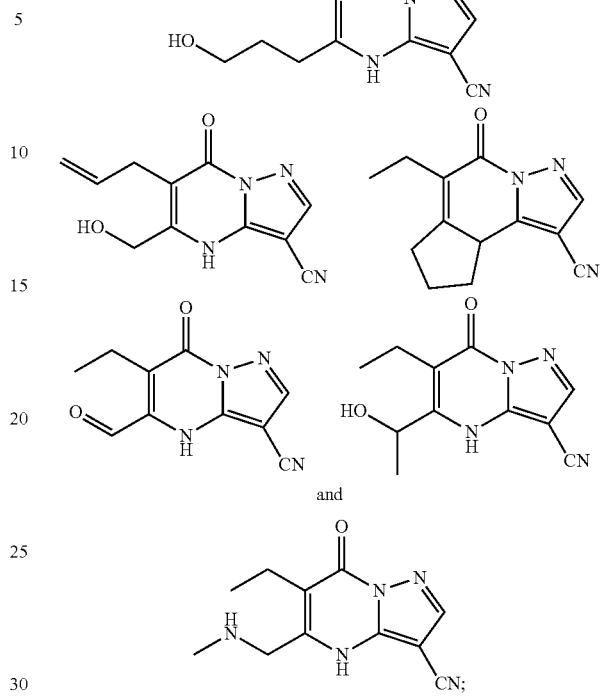

or a salt thereof.

13. The compound of claim 1, wherein $R^2$ is $C_{1-6}$ alkyl, $C_{1-6}$ alkenyl, or $C_{1-6}$ alkynyl; wherein the $C_{1-6}$ alkyl, $C_{1-6}$ alkenyl, or $C_{1-6}$ alkynyl, are optionally substituted by one or more of groups consisting of halogen, —$(CH_2)_{0-4}R°$, —O—$(CH_2)_{0-4}C(O)OR°$, —$(CH_2)_{0-4}CH(OR°)_2$, —$(CH_2)_{0-4}SR°$, —CH=CHPh which may be substituted with $R°$, —$NO_2$, —CN, —$N_3$, —$(CH_2)_{0-4}N(R°)_2$, —$(CH_2)_{0-4}N(R°)C(O)R°_2$, —$N(R°)C(S)R°_2$, —$(CH_2)_{0-4}N(R°)C(O)NR°_2$, —$N(R°)C(S)NR°_2$, —$(CH_2)_{0-4}N(R°)C(O)OR°_2$, —$N(R°)N(R°)C(O)R°_2$, —$N(R°)N(R°)C(O)NR°_2$, —$N(R°)N(R°)C(O)OR°$, —$(CH_2)_{0-4}C(O)R°$, —$C(S)R°$, —$(CH_2)_{0-4}C(O)SR°$, —$(CH_2)_{0-4}C(O)OSiR°_3$, —$OC(O)(CH_2)_{0-4}SR$—, $SC(S)SR°$, —$(CH_2)_{0-4}SC(O)R°$, —$(CH_2)_{0-4}C(O)NR°_2$, —$C(S)NR°_2$, —$C(S)SR°$, —$SC(S)SR°$, —$(CH_2)_{0-4}C(O)NR°_2$, —$C(O)N(OR°)R°$, —$C(O)C(O)R°$, —$C(O)CH_2C(O)R°_2$, —$C(NOR°)R°$, —$(CH_2)_{0-4}S$ $SR°$, —$(CH_2)_{0-4}S(O)_2R°$, —$(CH_2)_{0-4}S(O)_2OR°$, —$(CH_2)_{0-4}S(O)_2R°$, —$S(O)_2NR°_2$, —$(CH_2)_{0-4}S(O)R°_2$, —$N(R°)S(O)_2NR°_2$, —$N(R°)S(O)_2R°_2$, —$N(OR°)R°$, —$C(NH)NR°_2$, —$P(O)_2R°$, —$P(O)R°_2$, —$OP(O)R°_2$, —$OP(O)(OR°)_2$, —$SiR°_3$, —$(C_{1-4}$ straight or branched)alkylene)O—$N(R°)_2$ and —$(C_{1-4}$ straight or branched)alkylene)C(O)O—$N(R°)_2$; and each $R°$ may be optionally substituted and is independently hydrogen, or $C_{1-6}$ aliphatic-or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur; and wherein the optional substituent on $R°$ is independently halogen or =O.

14. The compound of claim 4, wherein $R^2$ is $C_{1-6}$alkyl, $C_{2-12}$alkenyl, or $C_{2-12}$alkynyl, wherein any $C_{1-6}$alkyl is optionally substituted with one or more groups independently selected from $C_{1-3}$alkyl, carbocyclyl, halo, and —CN.

15. The compound:
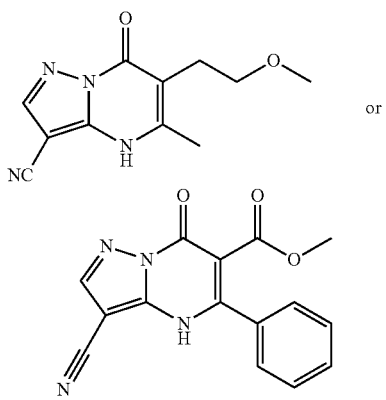
or
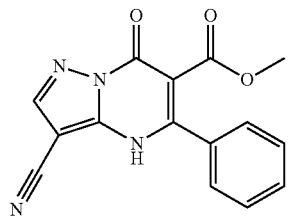
or a salt thereof.

UNITED STATES PATENT AND TRADEMARK OFFICE
CERTIFICATE OF CORRECTION

PATENT NO. : 10,035,801 B2
APPLICATION NO. : 14/775405
DATED : July 31, 2018
INVENTOR(S) : Brian K. Albrecht et al.

Page 1 of 5

It is certified that error appears in the above-identified patent and that said Letters Patent is hereby corrected as shown below:

In the Claims

Column 304, Line 47, Claim 1, please delete "$R^2$ is $C_{1-6}$ alkenyl" and insert
-- $R^2$ is $C_{1-6}$ alkyl, $C_{1-6}$ alkenyl --;

Column 304, Line 62, Claim 1, please delete "-$(CH_2)_{0-4}C(O)NR^O{}_2$," and insert
-- -$(CH_2)_{0-4}OC(O)NR^O{}_2$, --;

Column 306, Line 28-34, Claim 1, please delete the following structure:

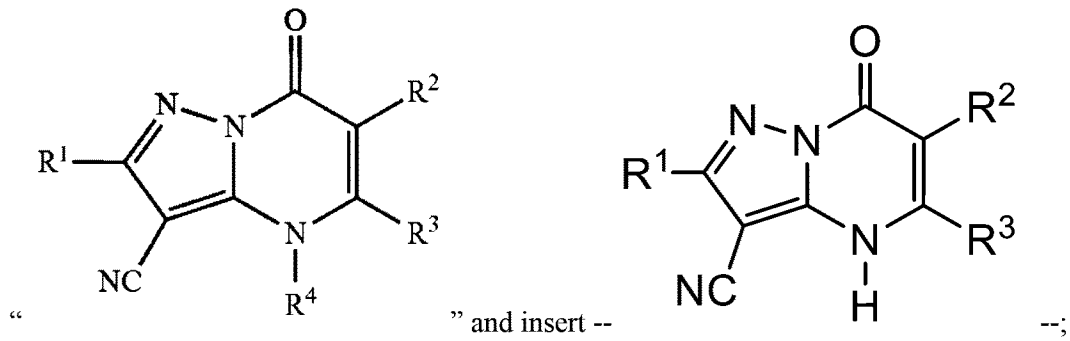

Column 306, Lines 38-39, Claim 1, please delete "2-choropropyl, or and $R^3$methyl;" and insert
-- 2-chloropropyl, and $R^3$ is methyl; --;

Column 308, Lines 22-23, Claim 4, please delete "wherein each $C_1$-12 alkyl" and insert
-- where each $C_{1-12}$ alkyl --;

Column 309, Line 18, Claim 4, please delete "-$S(O)_2$-$N(R^v)_2$, -S-$R^{v'}$" and insert
-- -$S(O)_2$-$N(R^v)_2$, -O-$R^v$, -S-$R^v$, --;

Column 309, Line 19, Claim 4, please delete "-$S(O)_2$, -$R^v$," and insert -- -$S(O)_2$-$R^v$, --;

Signed and Sealed this
Twenty-ninth Day of January, 2019

Andrei Iancu
*Director of the United States Patent and Trademark Office*

Column 309, Line 48, Claim 4, please delete "-S-R',"  and insert -- -S-R$^v$, --;

Column 309, Line 48, Claim 4, please delete "-O-C(O)-R$^v$, -C(O)—R$^v$," and insert
-- -O-C(O)-R$^v$, -O-C(O)-O-R$^v$, -C(O)—R$^v$, --;

Column 309, Line 53, Claim 4, please delete "-S(O)$_2$, -R$^v$," and insert -- -S(O)$_2$-R$^v$, --;

Column 309, Lines 57-58, Claim 4, please delete "-S(O)$_2$-N(R$^v$)$_2$, -O-C(O)-R$^v$," and insert
-- -S(O)$_2$-N(R$^v$)$_2$, -O-R$^v$, -S-R$^v$, -O-C(O)-R$^v$, --;

Column 309, Line 59, Claim 4, please delete "-S(O)$_2$, -R$^v$," and insert -- -S(O)$_2$-R$^v$, --;

Column 309, Line 60, Claim 4, please delete "-S(O)$_2$, -N(R$^v$)$_2$," and insert -- -S(O)$_2$-N(R$^v$)$_2$, --;

Column 310, Line 56, Claim 9, please delete "3-chlor-4-" and insert -- 3-chloro-4- --;

Column 311, Lines 12-13, Claim 9, please delete "phenyl ethynyl" and insert -- phenylethynyl --;

Column 311, Line 33, Claim 9, please delete "benzoyl amino" and insert -- benzoylamino --;

Column 311, Line 33, Claim 9, please delete "14(2-methylthiazol-4-" and insert
-- 1-((2-methylthiazol-4- --;

Column 312, Line 10, Claim 9, please delete "methyl sulfonylamino" and insert
-- methylsulfonylamino --;

Column 312, Line 12, Claim 9, please delete "(vinylcarbonyl amino)" and insert
-- (vinylcarbonylamino) --;

Column 312, Line 22, Claim 9, please delete "(ethyl sulfonyl)" and insert -- (ethylsulfonyl) --;

Column 312, Lines 24-25, Claim 9, please delete "-phenyl ethyl)" and insert -- -phenylethyl) --;

Column 312, Line 47, Claim 9, please delete "(methyl sulfonylamino)" and insert
-- (methylsulfonylamino) --;

Column 341, Lines 14-27, Claim 12, please delete the following compound:
" 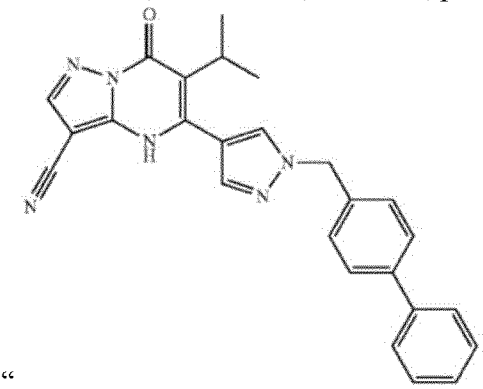 " and insert -- 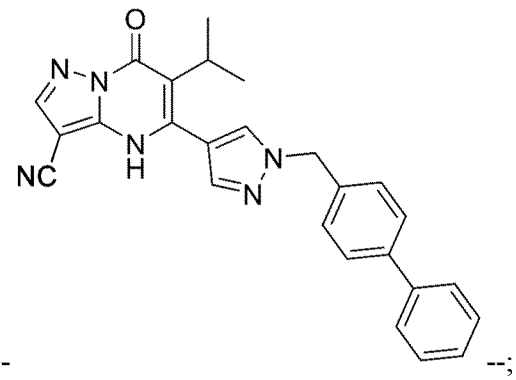 --;
Column 344, Lines 50-3, Claim 12, please delete the following compound:
" 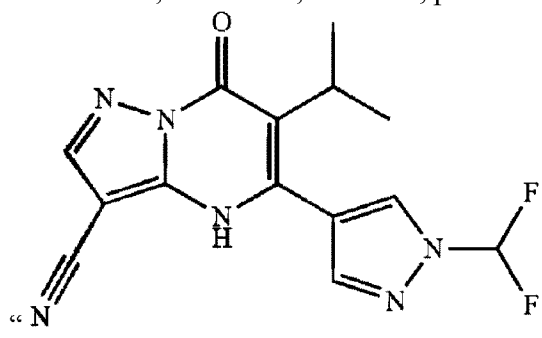 " and insert -- 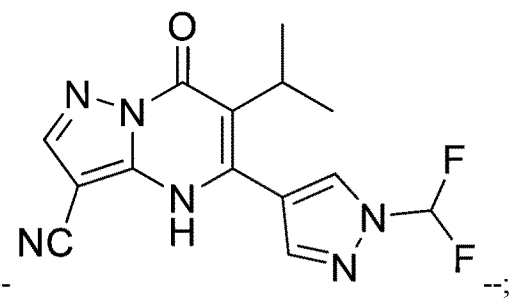 --;
Column 355, Lines 51-66, Claim 12, please delete the following compound:
" 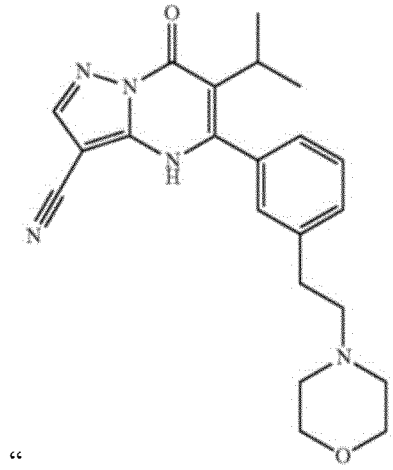 " and insert -- 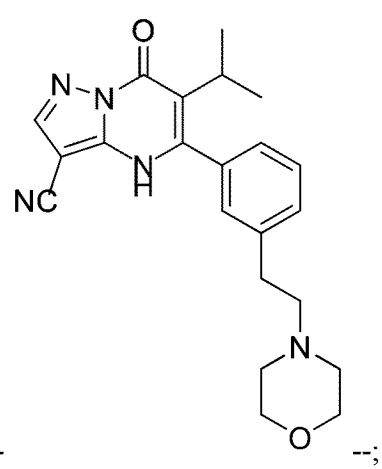 --;

Column 357, Lines 34-45, Claim 12, please delete the following compound:
" 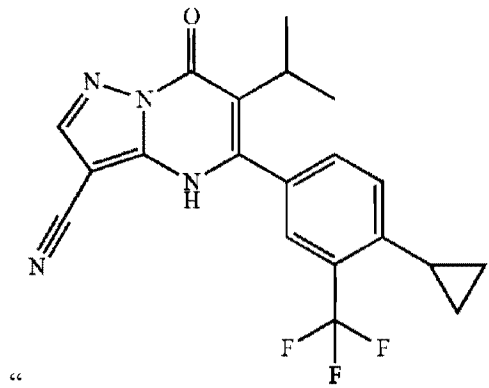 " and insert -- 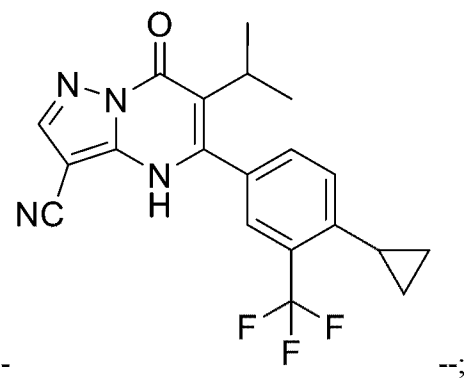 --;
Column 361, Lines 15-27, Claim 12, please delete the following compound:
" 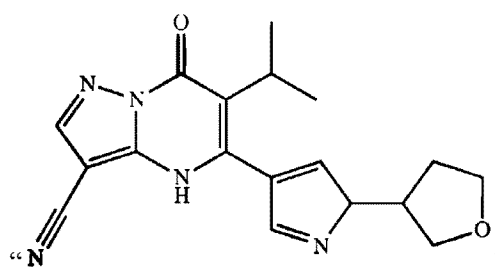 " and insert -- 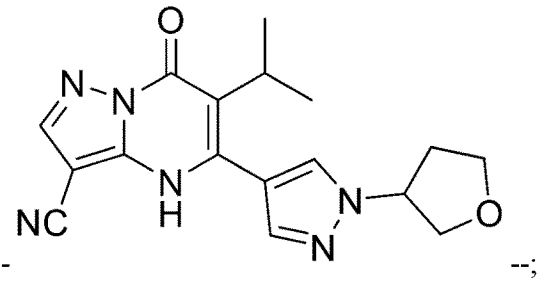 --;
Column 368, Lines 33-45, Claim 12, please delete the following compound:
" 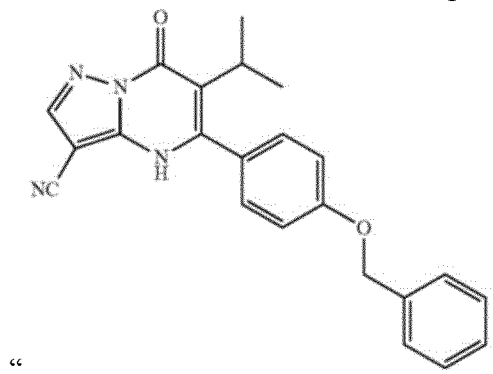 " and insert -- 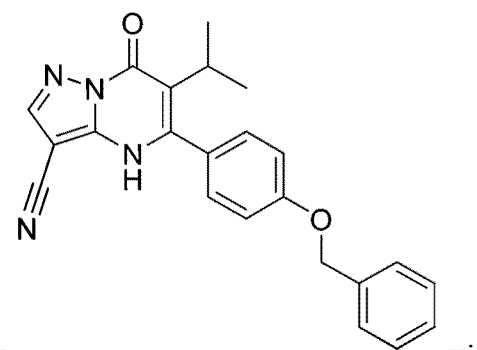 --;
Column 368, Lines 47-56, Claim 12, please delete the following compound:
" 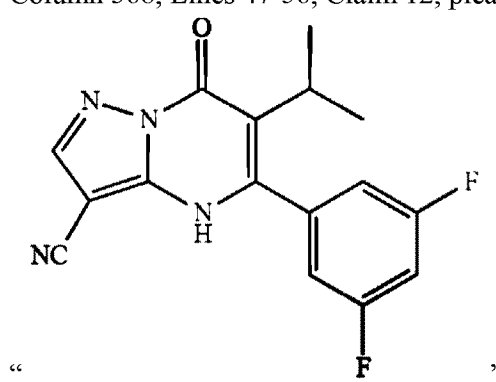 " and insert -- 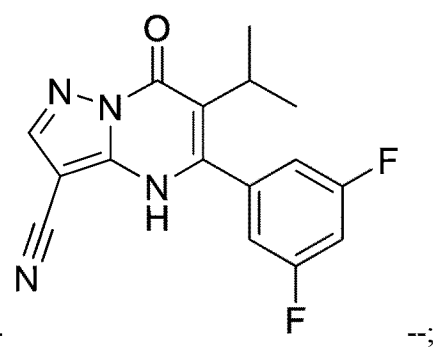 --;

Column 373, Lines 5-66, Claim 12, please delete the following compound:

" 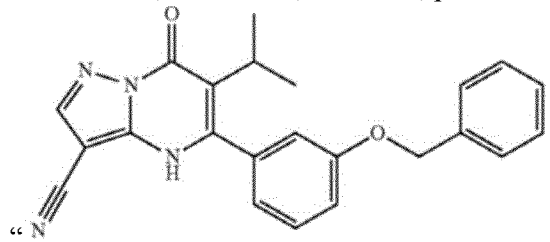 " and insert -- 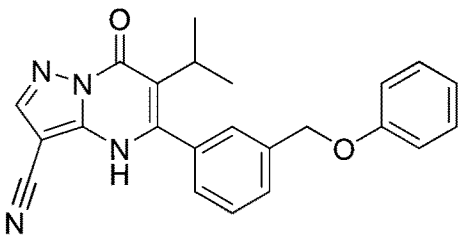 --;

Column 381, Lines 56-66, Claim 12, please delete the following compound:

" 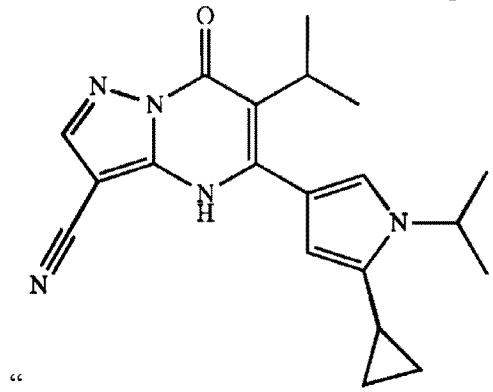 " and insert -- 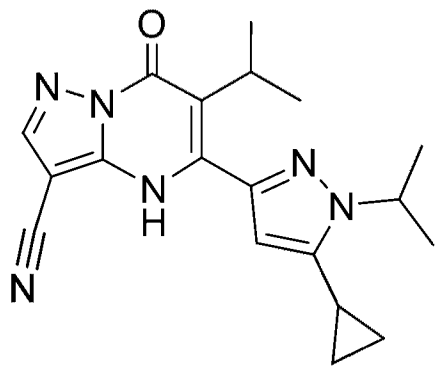 --;

Column 390, Line 40, Claim 13, please delete "-(CH$_2$)$_{0-4}$N(R$^o$)C(O)R$^o_2$," and insert -- -(CH$_2$)$_{0-4}$N(R$^o$)C(O)R$^o$, --;

Column 390, Line 41, Claim 13, please delete "-N(R$^o$)C(S)R$^o_2$," and insert -- -N(R$^o$)C(S)R$^o$, --;

Column 390, Line 42, Claim 13, please delete "-(CH$_2$)$_{0-4}$N(R$^o$)C(O)OR$^o_2$," and insert -- -(CH$_2$)$_{0-4}$N(R$^o$)C(O)OR$^o$, --;

Column 390, Lines 42-43, Claim 13, please delete "-N(R$^o$)N(R$^o$)C(O)R$^o_2$," and insert -- -N(R$^o$)N(R$^o$)C(O)R$^o$, --;

Column 390, Line 48, Claim 13, please delete "-C(O)CH$_2$C(O)R$^o_2$," and insert -- -C(O)CH$_2$C(O)R$^o$, --;

Column 390, Line 49, Claim 13, please delete "-(CH$_2$)$_{0-4}$S SR$^o$," and insert -- -(CH$_2$)$_{0-4}$SSR$^o$, --;

Column 390, Line 50, Claim 13, please delete "-(CH$_2$)$_{0-4}$S(O)$_2$R$^o$," and insert -- -(CH$_2$)$_{0-4}$OS(O)$_2$R$^o$, --;

Column 390, Line 51, Claim 13, please delete "-(CH$_2$)$_{0-4}$S(O)R$^o_2$," and insert -- -(CH$_2$)$_{0-4}$S(O)R$^o$, --;

Column 390, Lines 51-52, Claim 13, please delete "-N(R$^o$)S(O)$_2$R$^o_2$," and insert -- -N(R$^o$)S(O)$_2$R$^o$, -- therefor.